US012622959B2

(12) United States Patent　　　(10) Patent No.:　US 12,622,959 B2
Kang et al.　　　　　　　　　　(45) Date of Patent:　　May 12, 2026

(54) CORONAVIRUS RECOMBINANT SPIKE PROTEIN, POLYNUCLEOTIDE ENCODING SAME, VECTOR COMPRISING POLYNUCLEOTIDE, AND VACCINE FOR PREVENTING OR TREATING CORONAVIRUS INFECTION, COMPRISING VECTOR

(71) Applicant: CELLID CO., LTD., Seoul (KR)

(72) Inventors: Chang-Yuil Kang, Seoul (KR);
Seung-Phil Shin, Seoul (KR);
Kwang-Soo Shin, Seoul (KR);
Tae-Gwon Oh, Seoul (KR)

(73) Assignee: CELLID CO., LTD., Seoul (KR)

( * ) Notice: Subject to any disclaimer, the term of this patent is extended or adjusted under 35 U.S.C. 154(b) by 587 days.

(21) Appl. No.: 18/042,913

(22) PCT Filed: Aug. 27, 2021

(86) PCT No.: PCT/KR2021/011512
§ 371 (c)(1),
(2) Date: Feb. 24, 2023

(87) PCT Pub. No.: WO2022/045827
PCT Pub. Date: Mar. 3, 2022

(65) Prior Publication Data
US 2023/0293670 A1　　Sep. 21, 2023

(30) Foreign Application Priority Data

Aug. 27, 2020　(KR) ........................ 10-2020-0108276
Nov. 13, 2020　(KR) ........................ 10-2020-0152184

(51) Int. Cl.
A61K 39/00　　　(2006.01)
A61K 39/12　　　(2006.01)
A61K 39/215　　(2006.01)
A61P 31/14　　　(2006.01)
A61P 37/04　　　(2006.01)

(52) U.S. Cl.
CPC ............ A61K 39/215 (2013.01); A61P 31/14 (2018.01); A61P 37/04 (2018.01); A61K 2039/53 (2013.01)

(58) Field of Classification Search
CPC .............. A61K 39/215; A61K 2039/53; A61K 2039/575; A61K 39/12; A61K 2039/545
See application file for complete search history.

(56) References Cited

FOREIGN PATENT DOCUMENTS

| | | | |
|---|---|---|---|
| CN | 111 218 459 | A | 6/2020 |
| EP | 1693459 | A1 | 8/2006 |
| JP | H11 513249 | A1 | 11/1999 |
| JP | 2019 505512 | A1 | 8/2006 |
| JP | 2018 512863 | A1 | 5/2018 |
| JP | 2020503891 | A | 2/2020 |
| WO | WO 2006/009011 | A1 | 1/2006 |
| WO | WO 2018/104562 | A1 | 6/2018 |
| WO | WO 2021/194826 | A2 | 9/2021 |
| WO | WO 2021/226436 | A1 | 11/2021 |
| WO | WO 2021/229448 | A1 | 11/2021 |

OTHER PUBLICATIONS

James et al., "Proteolytic Cleavage on the SARS-CoV-2 Spike Protein and the Role of the Novel S/S2 site", iScience, Jun. 2020:1-7.*
Supplementary European Search Report for EP application No. 21862123.3, mailed May 2, 2024.
Walls Alexandra et al.: "Structure, Function, and Antigenicity of the SARS-CoV-2 Spike Glycoprotein", Cell, Elsevier, Amsterdam NL, vol. 180, No. 2, Apr. 16, 2020 (Apr. 16, 2020), pp. 281-292.
Xing Yue et al: "Natural Polymorphisms Are Present in the Furin Cleavage Site of the SARS-CoV-2 Spike Glycoprotein", Frontiers in Genetics, vol. 11, Jul. 17, 2020 (Jul. 17, 2020), pp. 1-4.
Bos et al. (Jul. 2020) "Ad26-vector based COVID-19 vaccine encoding a prefusion stabilized SARSCoV-2 Spike immunogen induces potent humoral and cellular immune responses," bioRxiv preprint doi: https:// doi.org/ 10.1101/2020.07.30.227470.
Chen et al. (Jul. 2020) "Bioinformatics analysis of epitope-based vaccine design against the novel SARS-CoV-2," Infectious Diseases of Poverty, electronic publication Jul. 10, 2020, 9, 88, 1-10. https:// doi.org/10.1186/s40249-020-00713-3.
Follis et al. (2006) "Furin cleavage of the SARS coronavirus spike glycoprotein enhances cell-cell fusion but does not affect virion entry," Virology, 350, 358-369.
International Search Report dated Dec. 6, 2021, corresponding to International Application No. PCT/KR2021/011512, from which the present application claims priority, 11 pp.
Johnson et al. (Aug. 2020) "Furin Cleavage Site is Key to SARS-CoV-2 Pathogenesis," bioRxiv, electronic publication Aug. 26, 2020, pp. 1-31.

(Continued)

*Primary Examiner* — Barry A Chestnut
(74) *Attorney, Agent, or Firm* — LEYDIG, VOIT & MAYER, LTD.

(57)　　　　ABSTRACT

The present invention relates to a novel coronavirus recombinant spike protein, a polynucleotide encoding the same, a vector comprising the polynucleotide, and a vaccine for preventing or treating coronavirus infection, comprising the vector. The coronavirus recombinant spike protein of the present invention is stable and thereby not easily decomposed in cells, and effectively activates immune cells thereby resulting in a high antibody production amount and T cell reactivity. It was confirmed that the vector of the present invention exhibits a high antigen expression level and thereby has a high antibody production amount and T cell reactivity, has a long antibody production period and expression period, and does not show liver toxicity. Accordingly, the vector of the present invention can be helpfully used as a vaccine for preventing or treating coronavirus infection.

14 Claims, 20 Drawing Sheets

Specification includes a Sequence Listing.

(56)  References Cited

OTHER PUBLICATIONS

Kim et al. (2014) "Immunogenicity of an adenoviral-based Middle East Respiratory Syndrome coronavirus vaccine in BALB/c mice," Vaccine, 32, 5975-5982.

Qian et al. (2013) "Role of the Spike Glycoprotein of Human Middle East Respiratory Syndrome Coronavirus (MERS-CoV) in Virus Entry and Syncytia Formation," PLoS ONE, 8, 10, e76469, pp. 1-12.

Office Action mailed Mar. 5, 2024 in corresponding Japanese Application No. 2023-513777, 8 pages.

Xu, Meng et al., "Nasopharyngeal Viral Load Is the Major Driver of Incident Antibody Immune Response to SARS-CoV-2 Infection," Open Forum Infectious Diseases, Dec. 2, 2023, pp. 1-9.

Chen, X., et al., "Fusion Protein Linkers: Property, Design and Functionality," Adv Drug Deliv Rev. Oct. 15, 2013; 65(10): 1357-1369.

* cited by examiner

SARS-CoV-2 Spike gene

Fig. 5

IFN-γ ELISpot in mouse after 10 weeks
of AdCLD-CoV19 treatment

CORONAVIRUS RECOMBINANT SPIKE PROTEIN, POLYNUCLEOTIDE ENCODING SAME, VECTOR COMPRISING POLYNUCLEOTIDE, AND VACCINE FOR PREVENTING OR TREATING CORONAVIRUS INFECTION, COMPRISING VECTOR

CROSS-REFERENCE TO RELATED APPLICATIONS

This application is a U.S. National Stage Application filed under 35 U.S.C. § 371 of International Application No. PCT/KR2021/011512, filed Aug. 27, 2021, which claims the benefit of and priority to Korean Application No. 10-2020-0108276, filed Aug. 27, 2020, and Korean Application No. 10-2020-0152184, filed Nov. 13, 2020, all of which are hereby incorporated by reference in their entireties to the extent not inconsistent herewith.

REFERENCE TO AN ELECTRONIC SEQUENCE LISTING

The contents of the electronic sequence listing ("3-23 revised seq listing 2026 ST25. txt"; Size: 545,662 bytes; and Date of Creation: Feb. 6, 2026) is herein incorporated by reference in its entirety.

BACKGROUND OF THE INVENTION

1. Field of the Invention

The present invention relates to a novel coronavirus recombinant spike protein, a polynucleotide encoding the same, a vector comprising the polynucleotide, and a vaccine for preventing or treating coronavirus infection comprising the vector.

2. Description of the Related Art

Coronavirus, which causes severe respiratory disease and causes death, is classified as RNA virus belonging to Coronaviridae, and coronavirus infection is defined as respiratory syndrome caused by infection with coronavirus. Among the viruses belonging to Coronaviridae, there are a total of seven types of viruses known to infect humans, including four types that cause colds (229E, OC43, NL63 and HKU1), two types that cause severe pneumonia (SARS-CoV and MERS-CoV), and SARS-CoV-2, the virus responsible for this pandemic. The three types of viruses that cause severe pneumonia (SARS-CoV, MERS-CoV and SARS-CoV-2) are spreading worldwide, starting with SARS-CoV in 2002, followed by MERS-CoV in 2012, and the current SARS-CoV-2, which has high gene sequence homology with SARS-CoV.

Coronaviruses (Coronaviridae) have unstable RNAs as their genomes, so mutations easily occur, and due to these characteristics, there is a possibility of transmission in both animals and humans. Studies to date have shown that SARS-CoV has been transmitted from civets to humans, and MERS-CoV has been transmitted from dromedaries to humans. Judging from these cases, coronaviruses of other species that use animals as hosts have the potential to evolve into mutant viruses that infect humans.

SARS-CoV-2 was first reported in late 2019. Compared to SARS-CoV that occurred in China in 2002, SARS-CoV has a higher severity, but SARS-CoV-2 has a higher transmissibility, which is attributed to mutations in spike protein, the cell receptor binding site of SARS-CoV-2. This resulted in a worldwide pandemic. Common signs of infection include respiratory symptoms, fever, cough, shortness of breath, and dyspne. In more severe cases, infection can cause pneumonia, severe acute respiratory syndrome, kidney failure and even death.

Currently, numerous countries and institutions are striving to develop vaccines to eradicate the COVID-19 pandemic. The types of preventive vaccines are classified into inactivated vaccines, attenuated vaccines, protein subunit vaccines, viral vector-based vaccines, DNA vaccines, and mRNA vaccines depending on the production method. Inactivated vaccines and attenuated live vaccines, which have traditionally been widely used as vaccine formulations, have the advantage of a simple production process, but the inactivated vaccines do not induce a high level of immune response, and the live attenuated vaccines have a risk of reacquiring pathogenicity through mutations. Since the protein subunit vaccines do not induce an immune response well, there is a problem that an immune enhancer must be used together.

With the development of biotechnology, vaccine formulations based on new platforms have begun to be developed, one of which is a viral vector-based vaccine. Vector-based vaccines activate the immune response by delivering vaccine antigen genes to human cells with high efficiency to produce antigen proteins on their own in the body. Viral vector-based vaccines are safe and induce a high level of immune response, so efficient immunization is possible only with a single administration without the need for repeated administration. Viral vector-based vaccines also have the advantage of efficiently inducing cytotoxic T cell immunity as well as antibody production based on the virus structurally. Many viruses are being studied as gene vectors, and among them, adenovirus is widely used in the field of gene therapy because it is easy to manipulate and safety has been verified through a lot of research. Adenovirus has high competitiveness compared to other viral vectors because it can deliver relatively large antigens (9-35 kb).

Adenovirus is a linear, double-stranded DNA virus, 70-90 nm in diameter, has no envelope, and has an icosahedral capsid, which is formed by 240 hexons, 12 pentons, and fibers extending from each vertex of the icosahedron. These hexons, pentons and fibers determine the major adenovirus antigen and its serotype. The adenovirus genome is approximately 30-45 kb in size and has 4 early regions (E1, E2, E3 and E4) and 5 late regions (L1-L5). Adenovirus is a good candidate as a recombinant vector for vaccine production because it is highly infectious and many of them are not pathogenic. In addition, adenovirus vectors can efficiently translate large genes and prolong immune responses in animals. The adenovirus vector is mainly used in a form in which the E1 gene responsible for self-replication is removed, and the adenovirus vector from which the E1 gene is removed is safe because it does not cause pathogenicity in the body because self-replication is impossible in human cells.

Ad5/35 vector is a form in which the knob gene of the non-replicable adenovirus serotype 5 (Ad5) is substituted with the knob gene of the adenovirus serotype 35 (Ad35). Through this modification, the Ad5/35 vector can be introduced into cells through the CD46 receptor, which is highly expressed in human immune cells, rather than the existing cell receptor of Ad5. That is, Ad5/35 is efficiently introduced into human antigen presenting cells, and thus can be an efficient vaccine platform to maximize the production of antigens. In addition, it has been reported that the Ad5/35 vector has a significantly lower risk of inducing hepatotoxicity compared to the Ad5 vector. In fact, the present inventors have confirmed in preclinical and clinical trials that a high level of immune response is induced when a cancer antigen gene is delivered to a cancer patient using an adenovirus vector. In addition, it was confirmed that there were no problems related to stability and toxicity when administered to a large number of patients in clinical trials.

A consideration in preparing vaccine candidate substances is the stability of the antigen to be expressed. It is important that a large amount of vaccine antigens is secreted, but even if they are expressed, if they are quickly decomposed in the early stages, they may not effectively activate immune cells. Therefore, it is important to stably maintain the antigen for a long period of time.

Therefore, in order to develop a vaccine for preventing or treating coronavirus disease-19 (COVID-19), the present inventors prepared a preventive or therapeutic vaccine by introducing a polynucleotide in which a cleavage site located between S1 gene and S2 gene encoding a spike protein, which plays a key role in cell infection of SARS-CoV-2 was substituted with a linker sequence into a vector. And the present inventors have completed the present invention by confirming that the vaccine has high antibody production and T cell reactivity against SARS-CoV-2.

SUMMARY OF THE INVENTION

It is an object of the present invention to provide a novel coronavirus recombinant spike protein, a polynucleotide encoding the same, a vector comprising the polynucleotide, and a vaccine for preventing or treating coronavirus infection comprising the vector.

To achieve the above object, the present invention provides a recombinant spike protein in which a cleavage site between S1 and S2 genes of a coronavirus spike protein is removed and a linker sequence is introduced.

The present invention also provides a recombinant spike protein in which a cleavage site between S1 and S2 genes of a SARS-CoV-2 spike protein is removed and a linker sequence is introduced.

The present invention also provides a polynucleotide encoding a recombinant spike protein in which a cleavage site between S1 and S2 genes of a coronavirus spike protein is removed and a linker sequence is introduced.

The present invention also provides a polynucleotide encoding a recombinant spike protein in which a cleavage site between S1 and S2 genes of a SARS-CoV-2 spike protein is removed and a linker sequence is introduced.

The present invention also provides a vector comprising a polynucleotide encoding a recombinant spike protein in which a cleavage site between S1 and S2 genes of a coronavirus spike protein is removed and a linker sequence is introduced.

The present invention also provides a vector comprising a polynucleotide encoding a recombinant spike protein in which a cleavage site between S1 and S2 genes of a SARS-CoV-2 spike protein is removed and a linker sequence is introduced.

The present invention also provides a vector characterized by introducing a polynucleotide encoding a recombinant spike protein in which a cleavage site between S1 and S2 genes of a coronavirus spike protein is removed and a linker sequence is introduced into adenovirus.

The present invention also provides a vector characterized by introducing a polynucleotide encoding a recombinant spike protein in which a cleavage site between S1 and S2 genes of a coronavirus spike protein is removed and a linker sequence is introduced into Ad5/35 virus.

The present invention also provides a vector characterized by introducing a polynucleotide encoding a recombinant spike protein in which a cleavage site between S1 and S2 genes of a SARS-CoV-2 spike protein is removed and a linker sequence is introduced into Ad5/35 virus.

The present invention also provides a vaccine for preventing or treating coronavirus infection comprising a vector containing a polynucleotide of S1 and S2 genes of a coronavirus spike protein.

The present invention also provides a vaccine for preventing or treating coronavirus infection comprising a vector containing a polynucleotide of S1 and S2 genes of a SARS-CoV-2 spike protein.

The present invention also provides a vaccine for preventing or treating coronavirus infection characterized by introducing a polynucleotide of S1 and S2 genes of a SARS-CoV-2 spike protein into adenovirus.

The present invention also provides a vaccine for preventing or treating coronavirus infection characterized by introducing a polynucleotide of S1 and S2 genes of a SARS-CoV-2 spike protein into Ad5/35 virus.

In addition, the present invention provides a vaccine for preventing or treating coronavirus disease-19 (COVID-19) comprising a vector characterized by introducing a polynucleotide in which a cleavage site between S1 and S2 genes of a SARS-CoV-2 spike protein is removed and a linker sequence is introduced into Ad5/35 virus.

Advantageous Effect

The present invention relates to a novel coronavirus recombinant spike protein, a polynucleotide encoding the same, a vector comprising the polynucleotide, and a vaccine for preventing or treating coronavirus infection, comprising the vector. The coronavirus recombinant spike protein of the present invention is stable and thereby not easily decomposed in cells, and effectively activates immune cells thereby resulting in a high antibody production amount and T cell reactivity. It was confirmed that the vector of the present invention exhibits a high antigen expression level and thereby has a high antibody production amount and T cell reactivity, has a long antibody production period and expression period, and does not show liver toxicity. Accordingly, the vector of the present invention can be helpfully used as a vaccine for preventing or treating coronavirus infection.

BRIEF DESCRIPTION OF THE DRAWINGS

FIG. 5 is a schematic diagram showing the adenovirus vectors #1 to #4 loaded with spike protein antigens, which are antigen expression genes.

DESCRIPTION OF THE PREFERRED EMBODIMENTS

Figure 1:
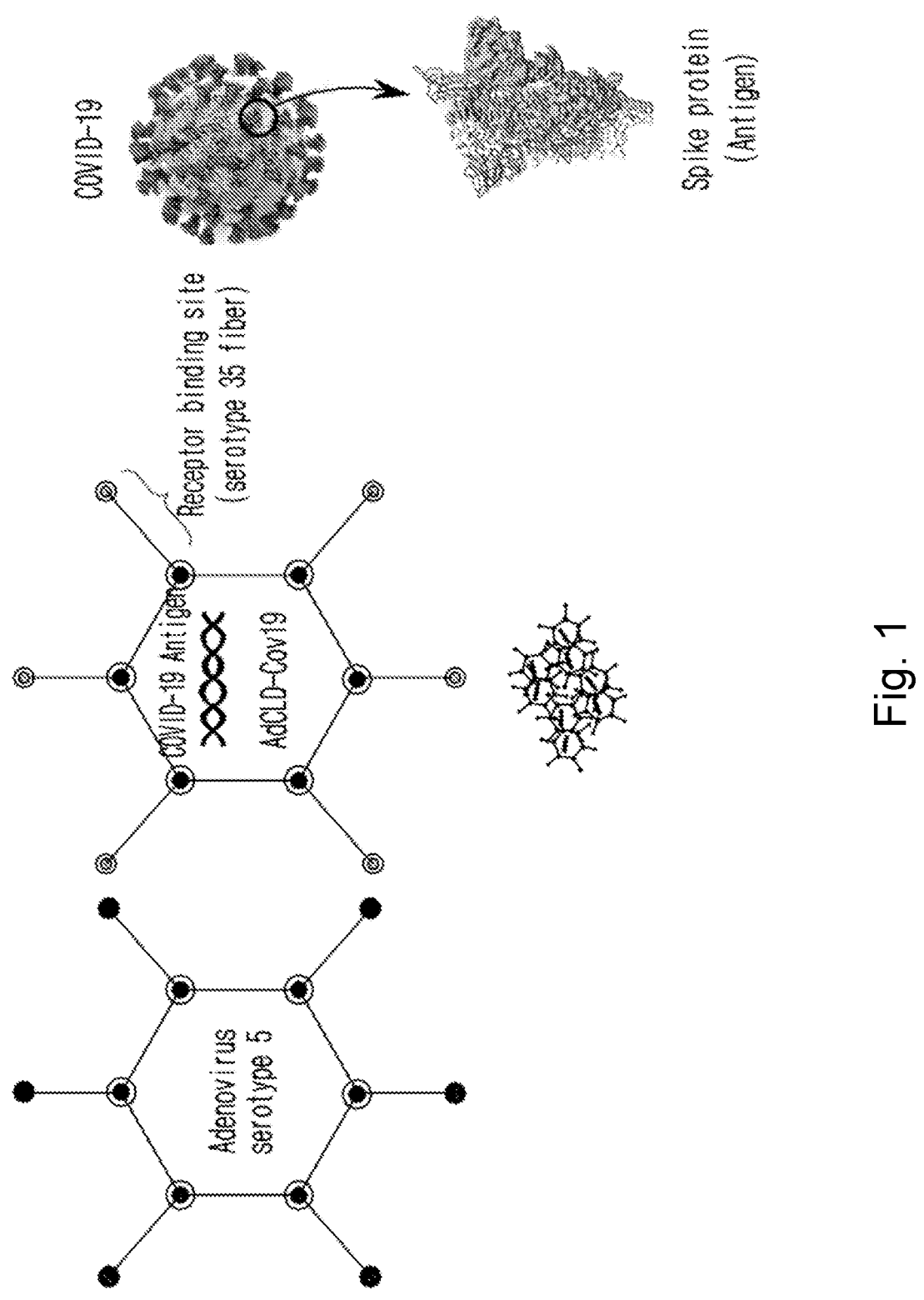
FIG. 1 is a schematic diagram showing the vaccine for preventing or treating COVID-19 according to the present invention, in which the E3 gene region, a receptor binding site, is replaced with a fiber gene of adenovirus serotype 35 based on adenovirus serotype 5, and a spike protein, which plays a key role in cell infection of SARS-CoV-2 is loaded as an antigen.
Figure 2:
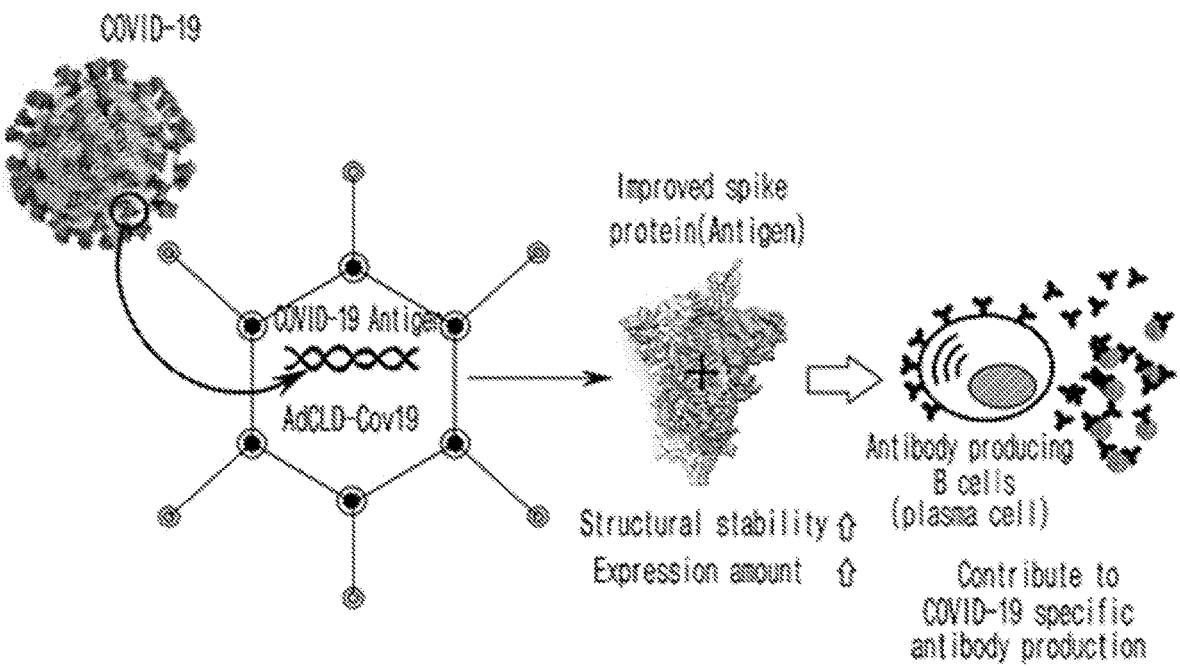
FIG. 2 is a schematic diagram showing that the vaccine for preventing or treating COVID-19 of the present invention comprising a recombinant spike protein in which a cleavage site of a gene encoding a spike protein is substituted with a linker sequence as an antigen has high structural stability and high antigen expression, and excellent ability to produce neutralizing antibodies in antibody-producing B cells.
Figure 3:
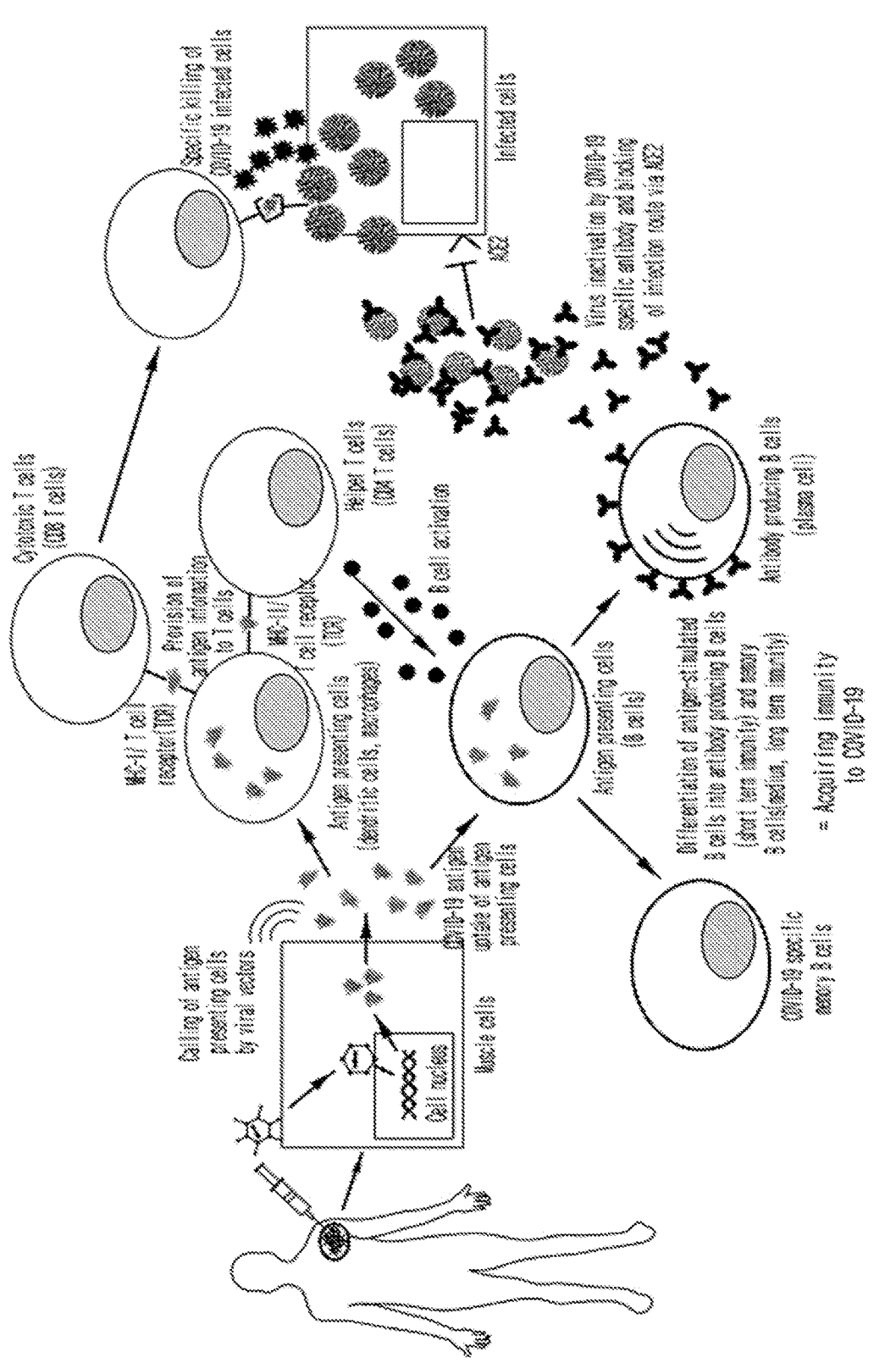
FIG. 3 is a schematic diagram showing the working mechanism of the vaccine for preventing or treating coronavirus disease-19 of the present invention.

Hereinafter, the present invention is described in detail.

The present invention provides a recombinant spike protein in which a cleavage site between S1 and S2 genes of a coronavirus spike protein is removed and a linker sequence is introduced.

The said coronavirus is characterized in that it is SARS-CoV, MERS-CoV or SARS-CoV-2 belonging to *Betacoronaviruses.*

The genome homology between SARS-CoV-2 and SARS-CoV is 79.6%, and the genome homology between SARS-CoV-2 and MERS-CoV is as high as 50%. In particular, while the homology of the spike protein, which is the target of the present invention, is similar at 35% between SARS-CoV-2 and MERS-CoV, the spike protein homology between SARS-CoV-2 and SARS-CoV is very high at 76%.

The present invention also provides a recombinant spike protein in which a cleavage site between S1 and S2 genes of a SARS-CoV-2 spike protein is removed and a linker sequence is introduced.

In vaccines, it is important that antigens are secreted in large amounts, but even if they are expressed in large amounts, if they are initially degraded, they do not stimulate immune cells to sufficiently induce immune responses, so it is very important that the stability of the expressed antigen is high. The recombinant spike protein of the present invention, in which a linker sequence is linked between S1 and S2, has high antigen expression and improved stability, and thus has excellent ability to generate neutralizing antibodies and to induce T cell reactivity.

The term "immune response" can include humoral and cellular immune responses, such as CD4+ or CD8+ cell activation, but not always limited thereto.

The spike protein antigen linked by the linker sequence is characterized in that the antigen expression increases.

The spike protein (S protein) covers the surface of the coronavirus particle. It is a spike-shaped protein used by coronavirus to invade human cells and consists of subunits of S1 and S2. Coronavirus infects the human body in such a way that the spike protein binds to the angiotensin converting enzyme 2 (ACE-2) receptor of human cells, penetrates into the cells, inserts its genetic material (RNA) into the cells, and replicates itself.

The recombinant protein is characterized in that a cleavage site between S1 and S2 genes, which are subunits of the spike protein, is removed.

The protein is characterized in that a cleavage site between S1 and S2 genes is removed and linked with a linker sequence.

The linker is characterized in that it consists of (GGGGS (SEQ ID NO: 31))n, wherein n is an integer of 1 to 5.

The domains constituting each protein have a distance (length of the linker sequence) optimized for interaction according to their unique characteristics, and the structural stability of a protein is expressed according to the length of the linker sequence. Therefore, n of the protein may preferably be 1 to 3, and most preferably 1.

When n exceeds 4, a large number of repetitive sequences are generated, and the linker sequence may be deleted by unintentional homologous recombination, and the stability of the protein is reduced.

The spike protein antigen linked by the linker sequence is characterized in that stability is increased.

The linker sequence is characterized by consisting of SEQ. ID. NO: 19 or SEQ. ID. NO: 20.

All coronaviruses have a spike protein in common, and the spike protein is composed of S1 and S2 subunits, so all spike proteins of coronavirus can be used.

All spike proteins in which a cleavage site between S1 and S2 genes of the spike protein is removed and linked by a linker belong to this invention.

Coronaviruses include 229E, OC43, NL63 and HKU1, which cause colds, and SARS-CoV, MERS-CoV and SARS-CoV-2, which cause severe pneumonia. All spike proteins of these coronaviruses can be used.

Preferably, it is a recombinant spike protein in which a cleavage site between S1 and S2 genes of a spike protein of SARS-CoV-2 is removed and a linker sequence is introduced.

The recombinant spike protein can additionally contain an adjuvant to improve immunogenicity. The adjuvant can be at least one selected from the group consisting of GM-CSF, IL-17, IFNNg, IL-15, IL-5, JNK, NFkB, NKKKKLIGAND, PD1/2, NKKKKG2B, NKG2C, NKKKKG2E, NKKKK2F, TAPAPAP2 and a functional fragment thereof, E-selectin, IL-α, IL-6, INF-γ, lymphotoxin α, hGH-1, MIPPP1, IL-7, IL-8, APP, IRARAK, IkB, KILILUX, TRAIL-1, IL-1, AIR, and ICAM-1, ICAM-1, TAP2, a functional fragment of CD40, TAP1, TRAILrecDRC5, CD34, CD40L, DR3, Gly-CAM1, p55, CD2, Ox40, TRAF6, DR4, ICAM3, DR5, MyD88, p65Rel, pl5095, p38, CPG and TLR.

The adjuvant can be linked to the C-terminal of the recombinant spike protein.

The present invention also provides a polynucleotide encoding a recombinant spike protein in which a cleavage site between S1 and S2 genes of a coronavirus spike protein is removed and a linker sequence is introduced.

The coronavirus is characterized in that it is SARS-CoV, MERS-CoV or SARS-CoV-2.

The present invention also provides a polynucleotide encoding a recombinant spike protein in which a cleavage site between S1 and S2 genes of a SARS-CoV-2 spike protein is removed and a linker sequence is introduced.

The linker is characterized in that it consists of 9 to 45 nucleotides, preferably consists of 9 to 21 nucleotides, and more preferably consists of 15 nucleotides.

The polynucleotide encoding the spike protein linked by the linker sequence is characterized by the increased stability.

The polynucleotide encoding the spike protein linked by the linker sequence is characterized by the increased antigen expression.

The linker sequence is characterized by consisting of SEQ. ID. NO: 11 or SEQ. ID. NO: 15.

The polynucleotide can be SEQ. ID. NO: 12 or NO: 16.

The present invention also provides a vector comprising a polynucleotide encoding a recombinant spike protein in which a cleavage site between S1 and S2 genes of a coronavirus spike protein is removed and a linker sequence is introduced.

The coronavirus is characterized in that it is SARS-CoV, MERS-CoV or SARS-CoV-2.

The present invention also provides a vector comprising a polynucleotide encoding a recombinant spike protein in which a cleavage site between S1 and S2 genes of a SARS-CoV-2 spike protein is removed and a linker sequence is introduced.

The present invention also provides a vector characterized by introducing a polynucleotide encoding a recombinant spike protein in which a cleavage site between S1 and S2 genes of a coronavirus spike protein is removed and a linker sequence is introduced into adenovirus.

The present invention also provides a vector characterized by introducing a polynucleotide encoding a recombinant spike protein in which a cleavage site between S1 and S2 genes of a SARS-CoV-2 spike protein is removed and a linker sequence is introduced into adenovirus.

The vector prepared by introducing a polynucleotide encoding a recombinant spike protein in which a cleavage site between S1 and S2 genes of a SARS-CoV-2 spike protein is removed and a linker sequence is introduced into adenovirus can be SEQ. ID. NO: 27 or NO: 29.

The present invention also provides a vector characterized by introducing a polynucleotide encoding a recombinant spike protein in which a cleavage site between S1 and S2 genes of a coronavirus spike protein is removed and a linker sequence is introduced into Ad5/35 virus.

The present invention also provides a vector characterized by introducing a polynucleotide encoding a recombinant spike protein in which a cleavage site between S1 and S2 genes of a SARS-CoV-2 spike protein is removed and a linker sequence is introduced into Ad5/35 virus.

In the present invention, the term "vector" means a transporter carrying cloned genes (or other fragments of cloned DNA) and transporting thereof to target cells.

The vector can be any one selected from the group consisting of plasmids and viruses.

Specific examples of the plasmid DNA include commercial plasmids such as pCMV3, pET28a and pET. Other examples of the plasmid that can be used in the present invention include *Escherichia coli*-derived plasmids (pCMV3, pET28a, pET, pGEX, pQE, pDEST and pCOLD), *Bacillus subtilis*-derived plasmids (pUB110 and pTP5) and yeast-derived plasmids (YEp13, YEp24 and YCp50). Since these plasmids show different amounts of protein expression and modification depending on the host cell, a host cell most suitable for the purpose can be selected and used.

The virus can be any known virus that can be used as a vector, and can be any one selected from the group consisting of adenovirus, retrovirus, lentivirus, adeno-associated virus (AAV), modified vaccinia virus ankara (MVA), herpes simplex virus and baculovirus, but not always limited thereto. According to a specific embodiment of the present invention, it is preferable that the virus is adenovirus.

The term "adenovirus vector" used herein refers to adenovirus that has been manipulated so that the adenovirus genome has a nucleic acid sequence that is non-native with respect to the adenovirus genome. Therefore, the "recombinant adenovirus vector" used herein typically comprises an expression cassette containing at least one foreign nucleic acid sequence encoding the adenovirus genome and the required protein (for example, a recombinant spike protein in which a cleavage site between S1 and S2 of a SARS-CoV-2 spike protein is substituted with a linker sequence).

An adenoviral vector preferably contains at least a portion of each terminal repeat sequence required to support replication of viral DNA, preferably at least about 90% of a completely inverted terminal repeat (ITR) sequence, and DNA required to encapsulate the genome into the viral capsid. Adenoviruses from a variety of origins can be used as a source of viral genome for adenoviral vectors. Human adenovirus such as subgroup A (eg, serotypes 12, 18 and 31), subgroup B (eg, serotypes 3, 7, 11, 14, etc.), subgroup C (eg, serotypes 1, 2, 5 and 6), subgroup D (eg, serotype 8, 9, 10, 13, 15, 17, 19, 20, etc.), subgroup E (eg, serotype 4), subgroup F (eg, serotypes 40 and 41) and others are preferred. Preferably, the adenovirus vector is a vector of human subgroup C, in particular serotype 2, and more preferably serotype 5.

The adenovirus vector can be a replication competent vector. Typically, the adenovirus vector is a replication-defective vector in host cells. The term "replication-defective" means that an adenovirus vector has a deficiency in one or more gene functions or regions (eg, E1, E3 or E4 region) of the adenovirus genome for replication, so that the vector maintains some low level of replication or does not replicate in normal host cells, especially human cells infected by the adenovirus vector. The replication-defective adenovirus vector ensures the safety of vaccines. In one embodiment of the present invention, the adenovirus vector is a vector from which E1 or E3 or both have been removed. Deficiency in a gene is defined as a mutation or deletion to completely eliminate or impair the function of a gene, for example, so that the function of a gene product is reduced by at least about 2-fold, 5-fold, 10-fold, 20-fold, or more than that of a natural gene. The resulting replication-defective adenovirus vector is capable of accommodating one or more exogenous nucleic acid sequences at appropriate sites within the adeno-virus genome for the expression of one or more desired proteins, while retaining the ability to be packaged into the adenovirus capsid. For the purpose of generating high titer of viral vectors for stock solutions, the replication-defective adenovirus vector is typically produced in complementing cell lines, such as HEK293 or HEK293R cells, which provide gene functions not present in the replication-defec-tive adenovirus vector.

The adenovirus can be adenovirus serotype 2 (Ad2), adenovirus serotype 4 (Ad4), adenovirus serotype 5 (Ad5), adenovirus serotype 11 (Ad11), adenovirus serotype 26 (Ad26), adenovirus serotype 35 (Ad35), chimpanzee adeno-virus serotype 68 (ChAd68), fowl adenovirus serotype 9 (FAd9) or porcine adenovirus serotype 3 (PAd3).

The adenovirus can have a modified form based on Ad5.

The adenovirus can be an adenovirus (Ad5/35) in which the knob gene of adenovirus serotype 5 (Ad5) is replaced with the knob gene of adenovirus serotype 35 (Ad35).

The adenovirus is characterized in that the E1 gene and the E3 gene are deleted.

The adenovirus can have a form in which some or whole of the E4 gene is deleted and the E4 gene is relocated to the E1 region in addition to the deletion of the E1 gene and the E3 gene.

The adenovirus is characterized in that it is introduced into cells through a CD46 receptor that is highly expressed in human immune cells.

The adenovirus is characterized in that the effect of inducing hepatotoxicity is low.

The adenovirus is characterized in that the degree of antigen expression is high.

The present invention also provides a vaccine for pre-venting or treating coronavirus infection comprising a vector containing a polynucleotide of S1 and S2 genes of a coro-navirus spike protein.

The coronavirus can be any one selected from the group consisting of SARS-CoV, MERS-CoV and SARS-CoV-2.

The vector can be any known virus that can be used as a vector, and can be any one selected from the group consist-ing of adenovirus, retrovirus, lentivirus, adeno-associated virus (AAV) and modified vaccinia virus ankara (MVA), but not always limited thereto. According to a specific embodi-ment of the present invention, it is preferable that the virus is adenovirus.

The adenovirus can be adenovirus serotype 2 (Ad2), adenovirus serotype 4 (Ad4), adenovirus serotype 5 (Ad5), adenovirus serotype 11 (Ad11), adenovirus serotype 26 (Ad26), adenovirus serotype 35 (Ad35), chimpanzee adeno-virus serotype 68 (ChAd68), fowl adenovirus serotype 9 (FAd9) or porcine adenovirus serotype 3 (PAd3).

The adenovirus can have a modified form based on Ad5.

The adenovirus can be an adenovirus (Ad5/35) in which the knob gene of adenovirus serotype 5 (Ad5) is replaced with the knob gene of adenovirus serotype 35 (Ad35).

The adenovirus is characterized in that the E1 gene and the E3 gene are deleted.

The adenovirus can have a form in which some or whole of the E4 gene is deleted and the E4 gene is relocated to the E1 region in addition to the deletion of the E1 gene and the E3 gene.

The adenovirus is characterized in that it is introduced into cells through a CD46 receptor that is highly expressed in human immune cells.

The present invention also provides a vaccine for pre-venting or treating coronavirus infection comprising a vector containing a polynucleotide of S1 and S2 genes of a SARS-CoV-2 spike protein.

The present invention also provides a vaccine for pre-venting or treating coronavirus infection characterized by introducing a polynucleotide of S1 and S2 genes of a SARS-CoV-2 spike protein into adenovirus.

The present invention also provides a vaccine for pre-venting or treating coronavirus infection characterized by introducing a polynucleotide of S1 and S2 genes of a SARS-CoV-2 spike protein into Ad5/35 virus.

In addition, the vaccine of the present invention can be prepared as an oral or parenteral formulation, and can be administered by intradermal, intramuscular or intranasal route, preferably intramuscular route.

The vaccine of the present invention is characterized in that a cleavage site between S1 and S2 is removed.

The vaccine is characterized in that a cleavage site between S1 and S2 of a spike protein is removed and linked with a linker sequence.

The linker is characterized in that it consists of 9 to 45 nucleotides, preferably consists of 9 to 21 nucleotides, and more preferably consists of 15 nucleotides.

In addition, the present invention provides a method for preventing or treating coronavirus infection, including coro-navirus disease-19, severe acute respiratory syndrome (SARS) or Middle East respiratory syndrome (MERS), by administering the vaccine to a subject.

In the present invention, the term "subject" means all animals including humans that can be infected with coro-navirus. By administering the vaccine of the present inven-tion to a subject, the above diseases can be effectively prevented. For example, the vaccine of the present invention can prevent humans from coronavirus.

In the present invention, the term "prevention" means any action that suppresses or delays the onset of coronavirus infection by administering a vaccine.

In the present invention, the term "treatment" means any action that removes coronavirus or alleviates the symptoms caused by coronavirus by administering a vaccine.

The vaccine of the present invention is administered in a pharmaceutically effective dose. The term "pharmaceuti-cally effective dose" means an amount sufficient to treat a disease with a reasonable benefit/risk ratio applicable to medical treatment or improvement. The effective dose level depends on the factors including subject type and severity, age, gender, type of infected virus, drug activity, sensitivity to drug, time of administration, administration route, excre-tion rate, duration of treatment, concomitant drugs, and other factors well known in the medical field. The vaccine of the present invention can be administered alone or in com-bination with other therapeutic agents. In combination administration, the administration can be sequential or simultaneous. And the vaccine can be administered single or multiple times. It is important to administer an amount that can obtain the maximum effect with the minimum amount without side effects considering all of the above factors, which can be easily determined by those skilled in the art.

The term "effective amount" refers to a dose sufficient to provide the desired therapeutic effect to the subject being treated, for example, sufficient to generate or induce an immune response against a pathogen or antigen in its receptor. The effective amount may vary depending on various reasons such as the route of administration, the frequency of administration, the body weight and species of the individual receiving the drug, and the purpose of administration. Those skilled in the art can determine the dosage in each case based on the disclosure herein, established methods and their own experience. For example, in a certain embodiment of the present invention, the recombinant adenovirus vector of the present invention can be administered at a dose of $1 \times 10^9$ to $1 \times 10^{12}$ virus particles (VP), for example, can be administered at a dose of $1 \times 10^9$, $1 \times 10^{10}$, $1 \times 10^{11}$, or $1 \times 10^{12}$ VP.

In a specific embodiment of the present invention, the present inventors constructed a vector by introducing a polynucleotide in which a cleavage site between S1 and S2 of the polynucleotide encoding a spike protein of SARS-CoV-2 belonging to coronavirus was substituted with a linker sequence was introduced into adenovirus in which the E1 and E3 genes were deleted, and the fiber, which is the cell receptor binding site of adenovirus serotype 5, was replaced with the fiber of serotype 35 (see FIG. 4), and confirmed that the vector had high antigen expression, antibody production and T cell reactivity, long antibody production expression period, and did not show hepatotoxicity (see FIGS. 6, 7A and 7B, 9A and 9B, 12A and 12B, 13A and 13B, and 14). In addition, a vaccine prepared by loading an antigen into a vector in which some or whole of the E4 gene was deleted and the E4 gene was relocated to the E1 region in addition to the deletion of the E1 gene and the E3 gene was administered to mice and monkeys. As a result, it was confirmed that the amount of neutralizing antibody production was similar to that of a vaccine prepared by loading an antigen into the Ad5/35 vector (see FIGS. 15 and 16).

The coronavirus recombinant spike protein of the present invention is stable and thereby not easily decomposed in cells, and effectively activates immune cells thereby resulting in a high antibody production amount and T cell reactivity. It was confirmed that the vector of the present invention exhibits a high antigen expression level and thereby has a high antibody production amount and T cell reactivity, has a long antibody production period and expression period, and does not show liver toxicity. Accordingly, the vector of the present invention can be helpfully used as a vaccine for preventing or treating coronavirus infection.

Hereinafter, the present invention will be described in detail by the following examples and experimental examples.

However, the following examples and experimental examples are only for illustrating the present invention, and the contents of the present invention are not limited thereto.

<Example 1> Construction of Control Expression Vector (Plasmid Vector #1)

A plasmid containing an adenovirus sequence (SEQ. ID. NO: 21) that does not contain a spike protein antigen was named pAdk35F (SEQ. ID. NO: 1, 34,030 bp) and was constructed using the genome of adenovirus type 5 (Ad5). The pAdk35F includes adenovirus in which the E1 and E3 genes were deleted, and the fiber, which is the cell receptor binding site of adenovirus serotype 5, was replaced with the fiber of serotype 35. The E1 gene deletion site of pAdk35F is loaded with CMV (cytomegalovirus) promoter, tetracycline operator (Tet O), restriction enzyme SwaI site, and SV40 poly A sequence.

Figure 4:
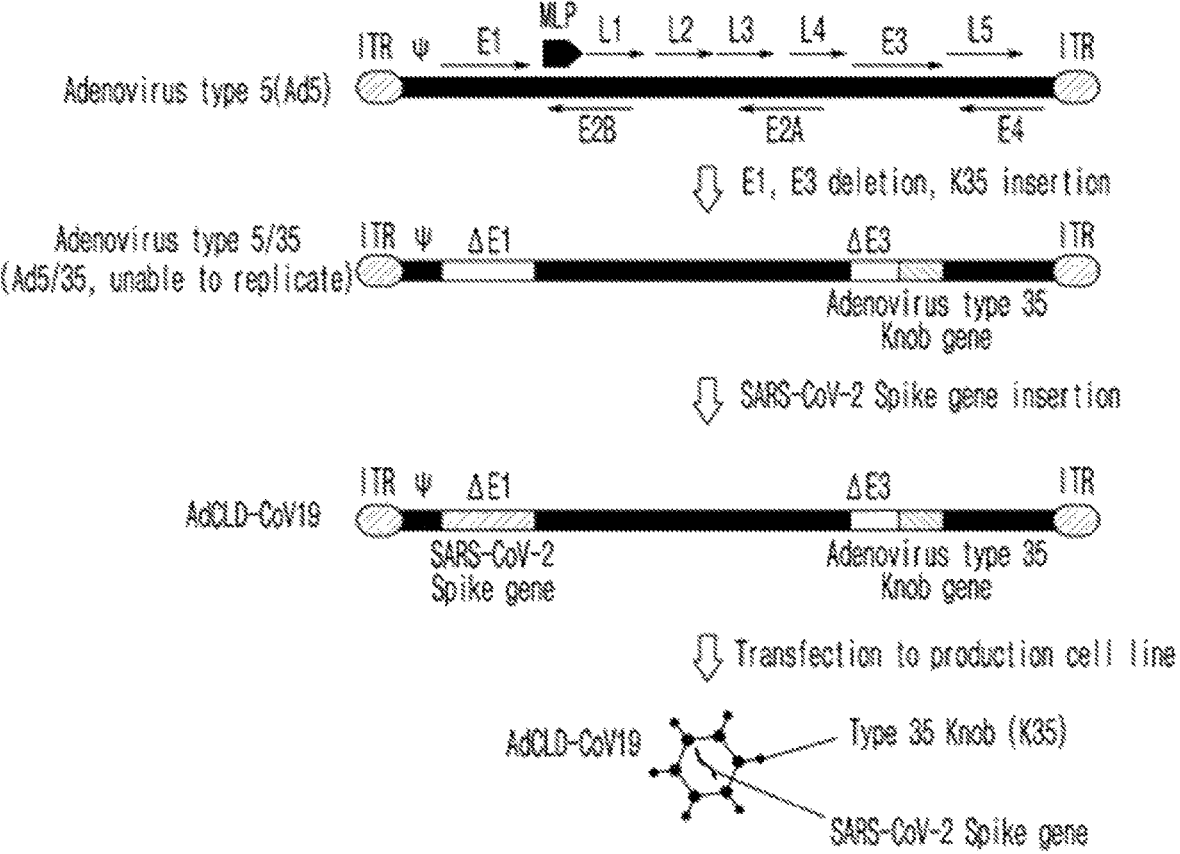
FIG. 4 is a schematic diagram showing the control expression vector prepared using the genome of adenovirus type 5 (Ad5).

As shown in FIG. 4, the extracellular domain of a spike protein antigen gene was amplified with the primer set for the spike protein antigen amplification listed in Table 1 below using pCMV3-SARS-CoV-2 (Spike ORF) vector (Sino Biological, Cat. #: VG40589-UT, SEQ. ID. NO: 2, 9,858 bp) loaded with a polynucleotide encoding the spike protein, an antigen expression gene, as a template, and then the plasmid vector #1 (SEQ. ID. NO: 22), a control expression vector, was constructed by in-fusion cloning ligation (Clontech, Cat. #: 639648) with the pAdk35F vector digested with SwaI. The region encoding the spike protein in the plasmid vector #1 is represented by SEQ. ID. NO: 3, and the nucleotide sequence of the adenovirus into which the spike protein is introduced is represented by SEQ. ID. NO: 23.

TABLE 1

|  | Sequence (5'→3') | SEQ. ID. NO |
|---|---|---|
| Forward primer | TCC AGC CTC CGA TTT GCC ACC ATG TTT GTG TTC CTG G | 4 |
| Reverse primer | GAT TAT GAT CAA TTT TCA TGG CCA CTT GAT GTA TTG TTC | 5 |

As shown in FIG. 4, the extracellular domain of a spike protein antigen gene was amplified with the primer set for the spike protein antigen amplification listed in Table 1 below using pCMV3-SARS-CoV-2 (Spike ORF) vector (Sino Biological, Cat. #: VG40589-UT, SEQ. ID. NO: 2, 9,858 bp) loaded with a polynucleotide encoding the spike protein, an antigen expression gene, as a template, and then the plasmid vector #1 (SEQ. ID. NO: 22), a control expression vector, was constructed by in-fusion cloning ligation (Clontech, Cat. #: 639648) with the pAdk35F vector digested with SwaI. The region encoding the spike protein in the plasmid vector #1 is represented by SEQ. ID. NO: 3, and the nucleotide sequence of the adenovirus into which the spike protein is introduced is represented by SEQ. ID. NO: 23.

<Example 2> Construction of Improved Spike Antigen Expression Vector

<2-1> Construction of Improved Spike Antigen Expression Vector (Plasmid Vector #2)

Figure 5:
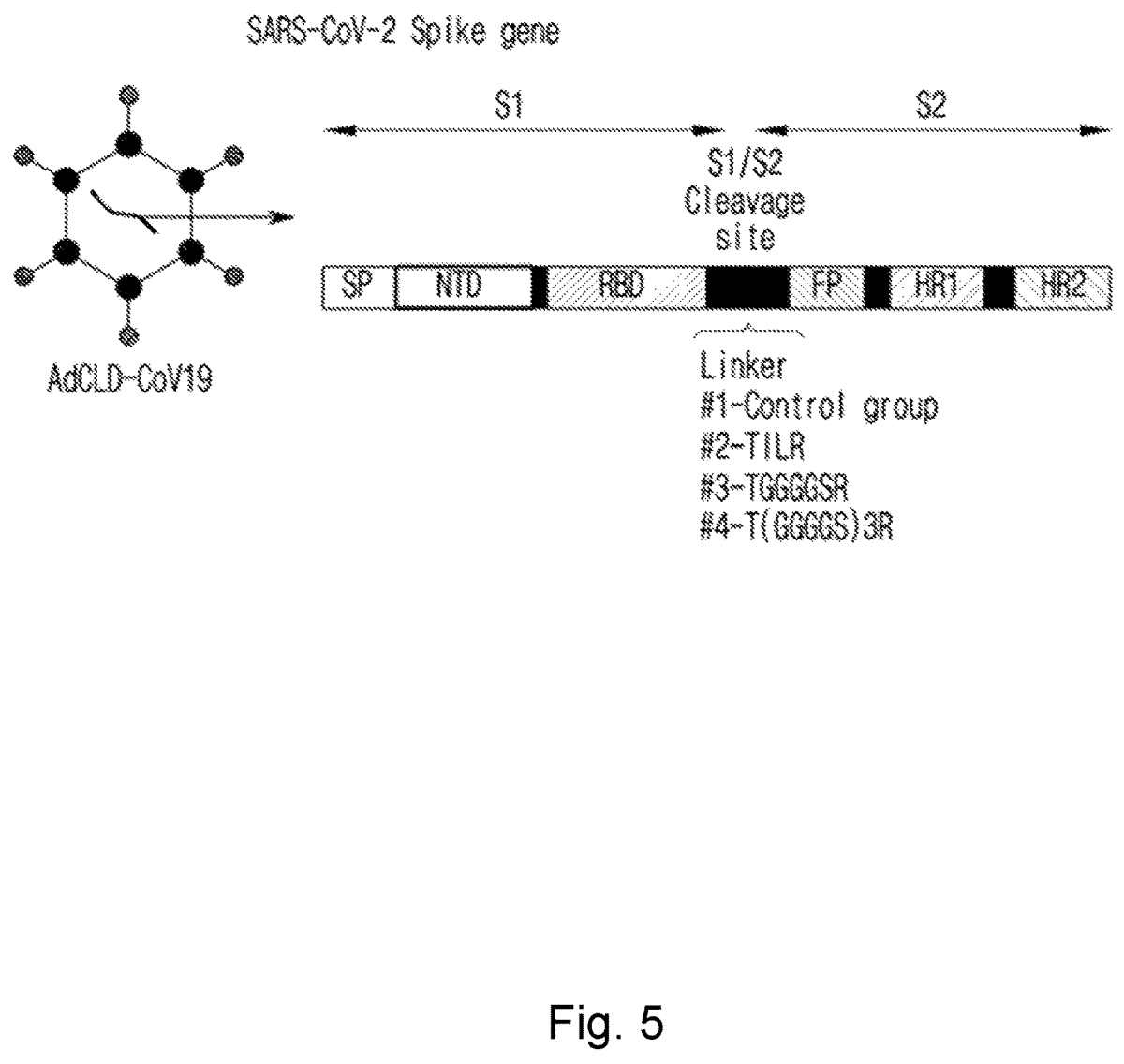

A cleavage site (having a nucleotide sequence of SEQ. ID. NO: 6, and an amino acid sequence of SEQ ID NO: 32: TNSPRRAR) of the domains S1 and S2 of a spike protein antigen of the pCMV3-SARS-COV-2 (Spike ORF) vector used as a template for polymerase chain reaction in Example 1 was substituted with TILR (Thr-11e-Arg-Leu) sequence (SEQ. ID. NO: 33) using the primer set listed in Table 2 below by site directed mutagenesis to prepare pCMV3-SARS-COV-2 (Spike IL) vector as shown in FIG. 5.

Subsequently, the vector substituted with the TILR sequence was amplified using the same primer set for the spike antigen amplification listed in Table 1 as the plasmid vector #1, and then the plasmid vector #2 (SEQ. ID. NO: 24), an improved spike antigen expression vector, was constructed by in-fusion cloning ligation (Clontech, Cat. #: 639648) with the pAdk35F vector digested with SwaI. The region encoding the spike protein in the plasmid vector #2 is represented by SEQ. ID. NO: 8, and the nucleotide sequence of the adenovirus into which the spike protein is introduced is represented by SEQ. ID. NO: 25.

TABLE 2

| | Sequence (5'→3') | SEQ. ID. NO |
|---|---|---|
| Forward primer | AGA CCA TCC TCA GGT CTG TGG CAA GCC AGA G | 9 |
| Reverse primer | CCT CCT ACC AGA CCC AGA CCA TCC TCA GGT | 10 |

<2-2> Construction of Improved Spike Antigen Expression Vector (Plasmid Vector #3; pAdCLD-CoV19 Vector)

A cleavage site (having a nucleotide sequence of SEQ. ID. NO: 6, and an amino acid sequence of SEQ ID NO: 32: TNSPRRAR) of the domains S1 and S2 of a spike protein antigen of the pCMV3-SARS-COV-2 (Spike ORF) vector used as a template for polymerase chain reaction in Example 1 was substituted with TGGGGSGR linker sequence (SEQ. ID. NO: 19) using the primer set listed in Table 3 below by site directed mutagenesis to prepare pCMV3-SARS-Co V-2 (Spike GGGGS, SEQ. ID. NO: 31) vector. Subsequently, the vector substituted with the TGGGGSR sequence (SEQ. ID. NO: 19) was amplified using the same primer set for the spike antigen amplification listed in Table 1 as the plasmid vector #1, and then the plasmid vector #3 (pAdCLD-CoV19 vector) (SEQ. ID. NO: 26), an improved spike antigen expression vector, was constructed by in-fusion cloning ligation (Clontech, Cat. #: 639648) with the pAdk35F vector digested with SwaI. The region encoding the spike protein in the plasmid vector #3 is represented by SEQ. ID. NO: 12, and the nucleotide sequence of the adenovirus into which the spike protein is introduced is represented by SEQ. ID. NO: 27.

TABLE 3

| | Sequence (5'→3') | SEQ. ID. NO |
|---|---|---|
| Forward primer | CGG TGG CGG TGG GTC GAG GTC TGT GGC AAG CCA GAG | 13 |
| Reverse primer | GAC CCA CCG CCA CCG GTC TGG GTC TGG TAG GAG G | 14 |

<2-3> Construction of Improved Spike Antigen Expression Vector (Plasmid Vector #4)

A cleavage site (amino acid sequence of SEQ ID NO: 32: TNSPRRAR) of the domains S1 and S2 of a spike protein antigen of the pCMV3-SARS-COV-2 (Spike ORF) vector used as a template for polymerase chain reaction in Example 1 was substituted with TGGGGSGGGGSGGGGSR sequence (SEQ. ID. NO: 34) using the primer set listed in Table 4 below by site directed mutagenesis to prepare pCMV3-SARS-Co V-2 (Spike GGGGS (SEQ. ID. NO: 31)×3) vector. Subsequently, the vector substituted with the TGGGGSGGGGSGGGGSR (SEQ. ID. NO: 34) sequence was amplified using the same primer set for the spike antigen amplification as the plasmid vector #1, and then the plasmid vector #4 (SEQ. ID. NO: 28), an improved spike antigen expression vector, was constructed by infusion cloning ligation (Clontech, Cat. #: 639648) with the pAdk35F vector digested with SwaI. The region encoding the spike protein in the plasmid vector #4 is represented by SEQ. ID. NO: 16, and the nucleotide sequence of the adenovirus into which the spike protein is introduced is represented by SEQ. ID. NO: 29.

TABLE 4

| | Sequence (5'→3') | SEQ. ID. NO |
|---|---|---|
| Forward primer | GGG CGG TGG TGG GTC GGG TGG CGG CGG TTC CAG GTC TGT GGC AAG CCA GAG | 17 |
| Reverse primer | GAC CCA CCA CCG CCC GAC CCA CCG CCA CCG GTC TGG GTC TGG TAG GAG G | 18 |

<Example 3> Construction of Adenovirus Vectors Loaded with Spike Antigens (Vectors #1 to #4)

Adenovirus vectors (vectors #1 to #4) were prepared from the vectors of Examples 1 and 2 above (plasmid vectors #1 to #4) using HEK293R cells. Initial adenovirus vectors were produced by transfecting HEK293R cells, which were approximately 80% confluent in T25 plates, with 12.5 μg of each vector along with 25 μℓ of lipofectamine 2000 (ThermoFisher, Cat. #: 11668027). Each initially produced adenovirus was amplified by infecting 20 T175 flasks containing $4 \times 10^7$ HEK293R cells.

The amplified adenovirus vectors #1 to #4 were purified through the first (1.2 g/mℓ CsCl+1.4 g/mL CsCl, 32,000 RPM, 90 minutes) and the second (1.35 g/mℓ CsCl, 32,000 RPM, 18 hours) cesium chloride (CsCl) density gradient centrifugation. The final adenoviruses were produced by dialysis (20 mM Tris-HCl, 25 mM sodium chloride, 2.5% glycerol).

<Example 4> Comparison of Antigen Expression Levels of Antigen Expression Vectors In Vitro <4-1> Comparison of Intracellular Antigen Expression According to Antigen Expression Vector Injection In order to compare the intracellular antigen expression levels of the vectors #1 to #4 prepared in Example 3, the antigen expression level in the THP-1 cell line derived from mononuclear cells was measured by flow cytometry (FACS).

Particularly, for flow cytometry, THP-1 cells were placed in a 96-well culture dish at the density of $2.5 \times 10^5$ cells per well, and each vector was inoculated into the cells at a multiplicity of infection (MOI) of 10, followed by culture for 24 hours. Then, the cells in each well were transferred to a 1.5 mℓ tube, and 500 μℓ of FACS buffer was added and centrifuged (5000 rpm, 3 minutes, 4° C.). After eliminating the supernatant, 50 μℓ of viability indicator dye (eFluor™450, ebioscience, cat #: 65-0863-14) diluted 1:1000 was added to each well, and surface staining was performed at 4° C. for 30 minutes.

To detect antigens expressed inside cells, the cell fixation/permeabilization concentrate (ebioscience, Cat. #: 00-5123-43) was diluted 1:4 in the cell fixation/permeabilization diluents (ebioscience, Cat. #: 00-5223-56), and 100 μℓ of

US 12,622,959 B2

15                                                                                                    16 the solution was added to each well, followed by cell fixation/permeabilization at 4° C. for 30 minutes. Spike antigen staining was performed with a solution (antibody concentration: 0.4 µg/ ml) of SARS-CoV-2 spike protein antibody (GeneTex, Cat. #: GTX632604) diluted 1:2500 in a permeabilization buffer (ebioscience, Cat. #: 00-8333-56) at 4° C. for 1 hour, followed by washing, and then antigen staining was performed (4° C., 30 minutes) with a solution (antibody concentration: 2 µg/ ml) of APC goat anti-mouse IgG antibody (Biolegend, Cat: 405308), a secondary antibody, diluted 1:100. After the staining reaction, 300 µℓ of buffer was added per sample and the degree of antigen expression was measured by flow cytometry (BD bioscience, LSRFORESSA).

Figure 6:
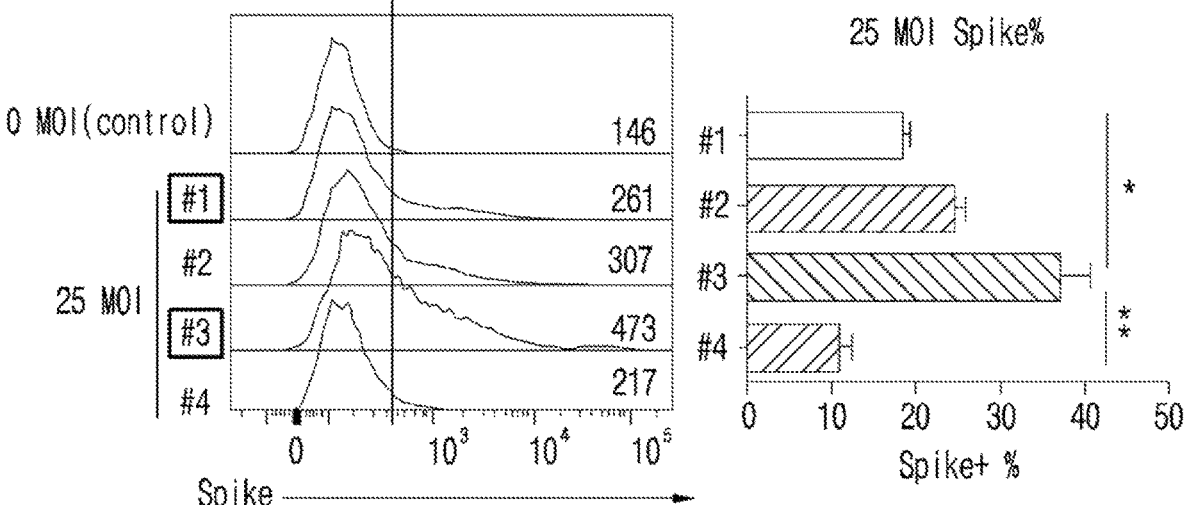
FIG. 6 is a diagram showing the expression levels of antigens when the adenovirus vectors #1 to #4 loaded with spike protein antigens, which are antigen expression genes, were introduced into a cultured cell line.

As a result, as shown in FIG. 6, it was confirmed that the adenovirus vector #3 prepared in Example 3 had the highest antigen expression level, which is the ability to produce proteins.

<4-2> Comparison of Extracellular Antigen Expression According to Antigen Expression Vector Injection To compare the expression levels of extracellular antigens of the vectors #1 to #4 prepared in Example 3, the antigen expression levels in mononuclear cell-derived THP-1 and muscle cell-derived RD cells were measured by Western blotting.

Particularly, the western blotting method for measuring the expression level of the spike protein antigen discharged out of cells is as follows. THP-1 and RD cells were distributed in 6-well culture dishes at the density of $5×10^5$ cells per well, and then each vector was inoculated to the cells to be 50 MOI, followed by culture for 24 hours. Thereafter, the culture medium was harvested through centrifugation, and then the culture medium was concentrated using Microcon (Millipore, 50,000 MWCO, Cat. #: UFC805024), and the cultured cells were decomposed into protein units using RIPA buffer (ThermoFisher, Cat. #: 89901). The total amount of protein in the concentrated culture medium was measured using a BCA protein assay kit (Thermo Fisher, Cat. #: 23225).

In order to confirm the spike protein (trimer, about 250 kDa or more) in the concentrated culture medium sample, the sample (60 µg/well) was electrophoresed at 180 V using Bolt™ Bis-Tris 4-12% plus gel (ThermoFisher, Cat. #: NW04120BOX).

The electrophoresed gel was transferred to a PVDF membrane for 10 minutes at 20 V using the iBlot 2 Dry blotting system (Invitrogen, Cat. #: IB21001). Then, the membrane was reacted with rabbit SARS-CoV-2 spike antibody (GeneTex, Cat. #: GTX135360) and goat anti-rabbit IgG H&L (HRP), respectively, and the trimeric spike protein of SARS-CoV-2 was detected with an ECL prime western blotting detection reagent (Amersham, Cat. #: RPN2232).

Figure 7A:
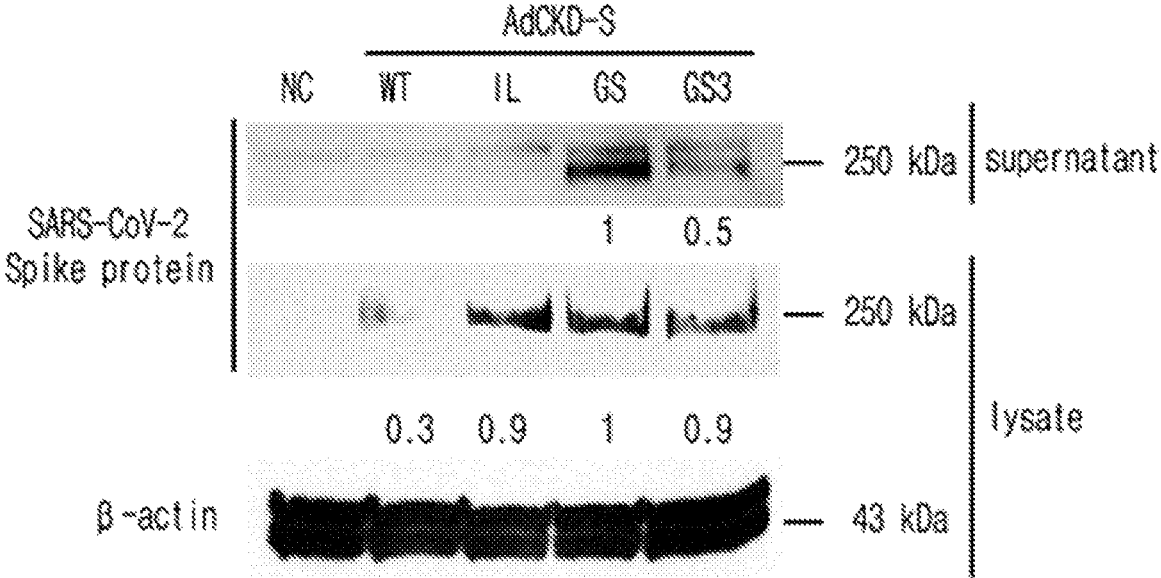
FIGS. 7A and 7B are diagrams showing the expression levels of antigens excreted out of cells when the adenovirus vectors #1 to #4 loaded with spike protein antigens, which are antigen expression genes, were introduced into a cultured cell line.
Figure 7B:
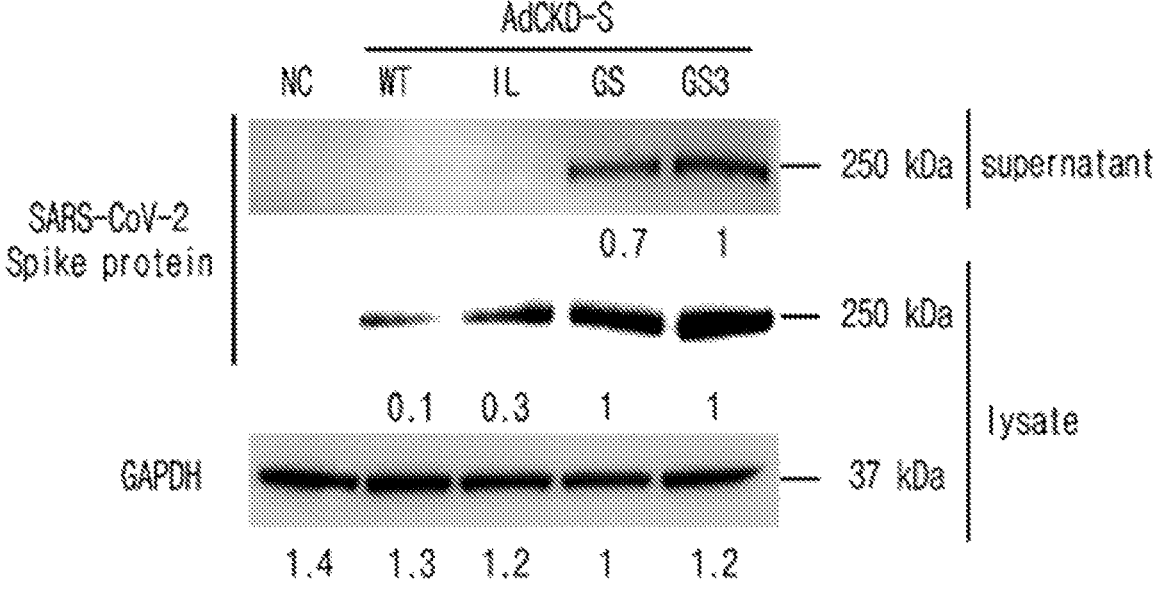

As a result, as shown in FIGS. 7A and 7B, it was confirmed that the adenovirus vector #3 prepared in Example 3 had the highest antigen expression for generating and discharging proteins.

<Example 5> Comparison of Antibody Production in Mice According to Antigen Expression Vector Injection <5-1> Comparison of Antibody Production in Mice According to Injection of Antigen Expression Vectors #1 to #4

After injecting the vectors #1 to #4 prepared in Example 3 into mice, the amount of antibody production was compared.

Particularly, the spike antigen expression vectors prepared in Example 3 (vectors #1~#4) were intramuscularly injected into 6-7-week-old BALB/c mice at a dose of $2×10^8$ IFU/mouse, 6 mice per group. About 300 µℓ of blood sample was collected by orbital blood sampling at 2-3 weeks after the administration. Then, the plasma was separated by centrifugation (8000 rpm, 10 minutes, 20° C.), and the amount of neutralizing antibodies present in the blood was measured by enzyme-linked immunosorbent assay (ELISA).

For the enzyme-linked immunosorbent assay, a 96-well plate was coated with a spike protein (Acro Biosystems, Cat. #: SPN-052H84) dissolved in PBSN (PBS 1 L+sodium azide 0.01 g) at 100 ng/well, followed by cold-reaction at 4° C. for 16 hours. After 16 hours of coating the 96-well plate, the coating protein was removed, washed three times with PBS, and then 150 µℓ of blocking buffer (PBSN+BSA 1%) was added to each well, followed by reaction (37° C., 90 minutes). During the reaction time, the plasma was diluted 6400-fold in dilution buffer (PBSN+0.1% BSA+0.05% Tween-20), and after the blocking reaction, the plate was washed three times with PBS, and then 50 µℓ of the diluted plasma sample was added to each well, followed by reaction (37° C., 3 hours). Upon completion of the reaction, the plate was washed three times with PBS, and 50 µℓ of secondary antibodies, GAM-IgG-HRP (Southernbiotech, Cat. #: 1030-05) and GAM-IgM-HRP (Southernbiotech, Cat. #: 1020-05), diluted 1000 times in dilution buffer was added to each well, followed by reaction (37° C., 2 hours). Then, the secondary antibodies were eliminated, the plate was washed 5 times with PBS, and 50 µℓ of a chromogenic reagent (TMB Peroxidase Substrate buffer, ROCKLAND, Cat. #: TMBE-1000) was added to each well, followed by color development for 15 minutes. The color development was stopped by adding 50 µℓ of 0.25 N HCl to each well, and the sample was analyzed at a wavelength of 450 nm with a microreader.

Figure 8A:
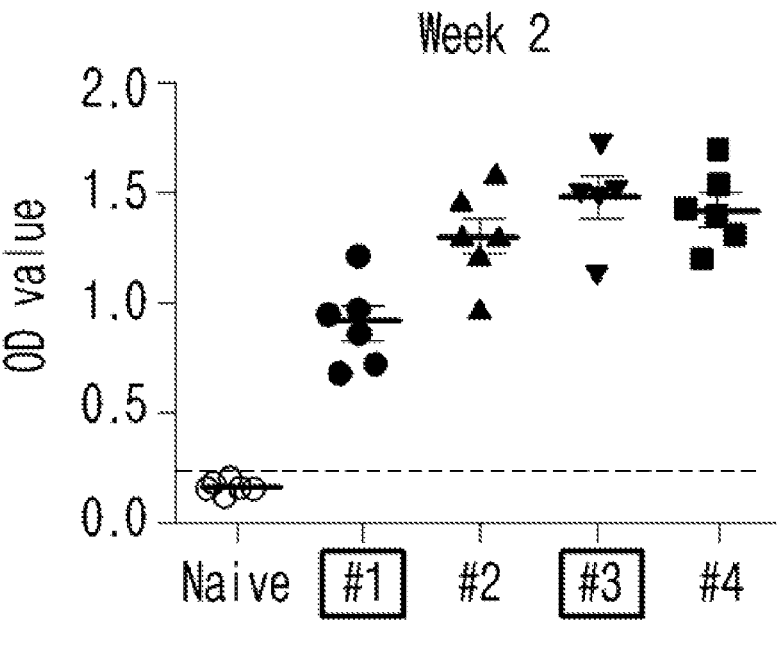
FIGS. 8A and 8B are diagrams showing the amount of antibody production after the adenovirus vectors #1 to #4 loaded with spike protein antigens, which are antigen expression genes, were injected into mice.
Figure 8B:
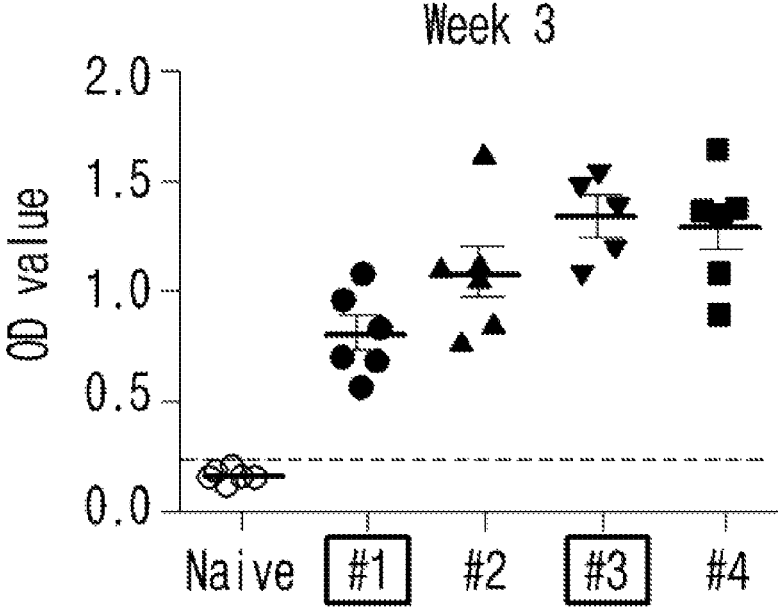

As a result, as shown in FIGS. 8A and 8B, it was found that the amount of antibody production of the adenovirus vector #3 prepared in Example 3 was the highest.

<5-2> Comparison of Mouse Antibody Production Expression Periods According to Antigen Expression Vector Injection In addition, the adenovirus vectors prepared in Example 3 (vectors #1~#3) were intramuscularly injected into 8-week-old BALB/c mice at a dose of $1×10^9$ VP/mouse or $2×10^8$ VP/mouse, 6 mice per group. About 300 µℓ of blood sample was collected by orbital blood sampling at 2-4 weeks after the administration. Then, the plasma was separated by centrifugation (8000 rpm, 10 minutes, 20° C.), and the amount of antigen-specific antibodies present in the blood was measured by enzyme-linked immunosorbent assay (ELISA) according to Example 5-1.

Figure 9A:
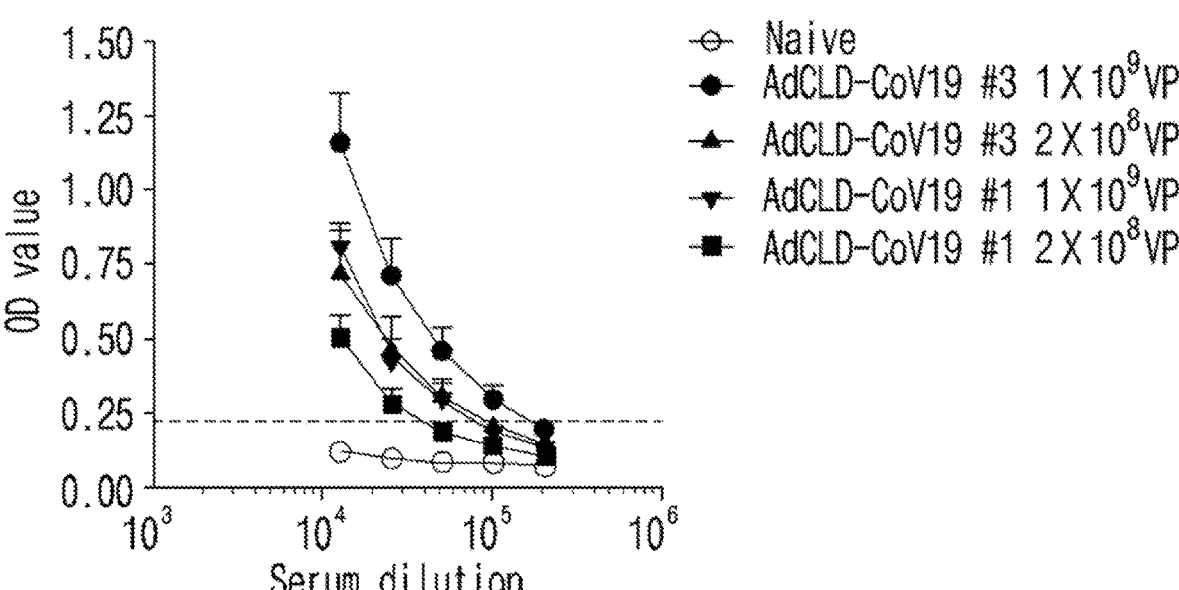
FIGS. 9A and 9B are diagrams showing the amount of antigen-specific antibodies present in the blood after the adenovirus vector #3 loaded with spike protein antigens, which are antigen expression genes, was injected into mice.
Figure 9B:
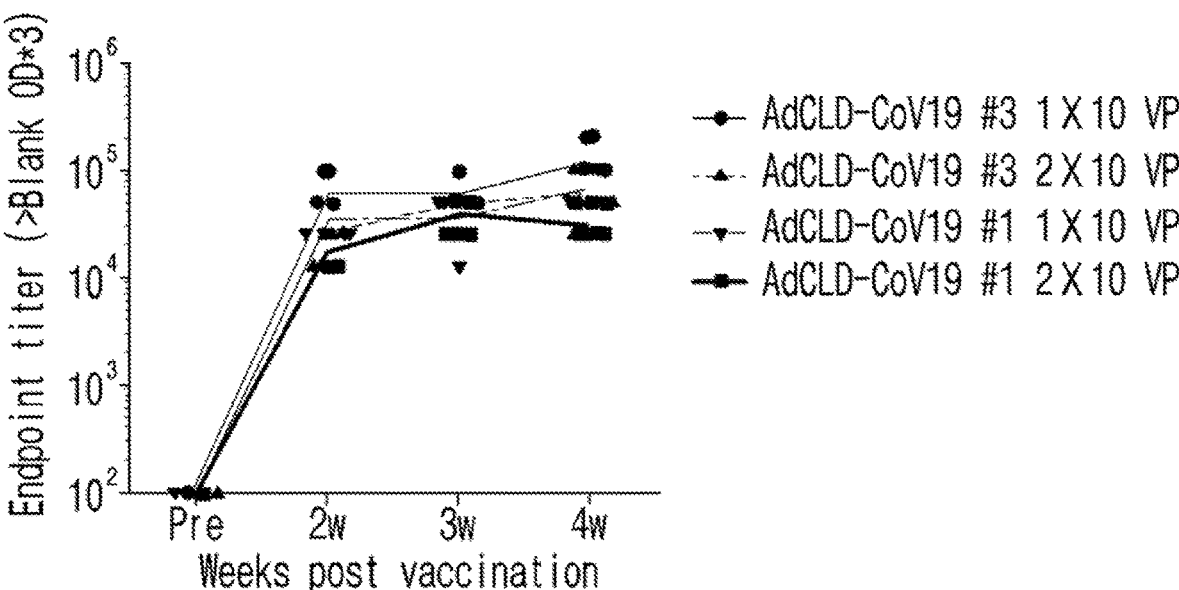

As a result, as shown in FIGS. 9A and 9B, it was found that the amount of antigen-specific antibodies present in the blood of mice injected with the adenovirus vector #3 prepared in Example 3 was maintained at a higher level than that of the vector #2 for 4 weeks or longer.

<Example 6> Comparison of Antibody Production and Hepatotoxicity in Monkeys According to Antigen Expression Vector Injection <6-1> Comparison of Antibody Production in Monkeys According to Antigen Expression Vector Injection The amount of antibody production in monkeys following the injection of the adenovirus vectors (vectors #1 and #3) prepared in Example 3 was compared.

Particularly, the adenovirus vectors #1 and #3 prepared in Example 3 were intramuscularly injected into 6-7-week-old monkeys (cynomolgus monkeys) at a dose of $1\times10^{11}$ VP/monkey, 2 monkeys per group. At 2 and 3 weeks after the immunization, blood samples were collected from the monkeys through intravenous blood sampling. Then, the plasma was separated by centrifugation (8000 rpm, 10 minutes, 20° C.), and the amount of antibodies present in the blood was measured by enzyme-linked immunosorbent assay (ELISA) and pseudovirus neutralization assay.

For the enzyme-linked immunosorbent assay, a 96-well plate was coated with a spike protein (Acro Biosystems, Cat. #: SPN-052H84) dissolved in PBSN at 100 ng/well, followed by cold-reaction at 4° C. for 16 hours. After 16 hours of coating the 96-well plate, the coating protein was removed, washed three times with PBS, and then 150 μℓ of blocking buffer was added to each well, followed by reaction (37° C., 90 minutes). During the reaction time, the plasma was diluted 1600-fold in dilution buffer, and after the blocking reaction, the plate was washed three times with PBS, and then 50 μℓ of the diluted plasma sample was added to each well, followed by reaction (37° C., 3 hours). Upon completion of the reaction, the plate was washed three times with PBS, and 50 μℓ of secondary antibody, human total Ig-HRP (Southernbiotech, Cat. #: 1010-05), diluted 1000 times in dilution buffer was added to each well, followed by reaction (37° C., 2 hours). Then, the secondary antibody was eliminated, the plate was washed 5 times with PBS, and 50 μℓ of a chromogenic reagent (TMB Peroxidase Substrate buffer, ROCKLAND, Cat. #: TMBE-1000) was added to each well, followed by color development for 15 minutes. The color development was stopped by adding 50 μℓ of 0.25 N HCl to each well, and the sample was analyzed at a wavelength of 450 nm with a microreader.

For the pseudovirus neutralization assay, HEK293T-hACE2 (human angiotensin converting enzyme 2; hACE2) cell line was placed in a 96-well plate at the density of $1\times10^4$ cells/well and cultured for 10 hours (37° C., 5% $CO_2$). The plasma collected from monkeys through intravenous sampling at 2 and 3 weeks after the immunization was diluted 4-fold from 100 to 6400 times and reacted with $7\times10^5$ TU/ mℓ of pseudovirus (lentivirus expressing spike protein and luciferase) for 1 hour (37° C.) The plasma was inoculated in the 96-well plate containing HEK293T-hACE2 cells being cultured along with 2 μg/well (200 μℓ) of polybrene (Merck, Cat. #: TR-1003-G) and cultured for 2 days. Then, the presence of neutralizing antibodies in the plasma binding to the spike protein was confirmed by measuring the degree of luciferase protein expression induced by infection of the HEK293T-hACE2 cell line with pseudovirus. The cells cultured for 2 days were washed with DPBS and then lysed with 25 μg of cell lysis reagent (Promega, Cat. #: E153A). After the lysed sample was transferred to an opaque 96-well plate, 100 μg of luciferase detection indicator (Promega, Cat. #: E151A) was added to each well and the level of luminescence was measured (detection indicator injection—5 seconds mixing—2 seconds delay—10 seconds measurement) using a luminometer (Luminometer Centro XS3 LB960, Berthold Technologies, Cat. #: LB960, software: Mikro 2000 program).

Figure 10A:
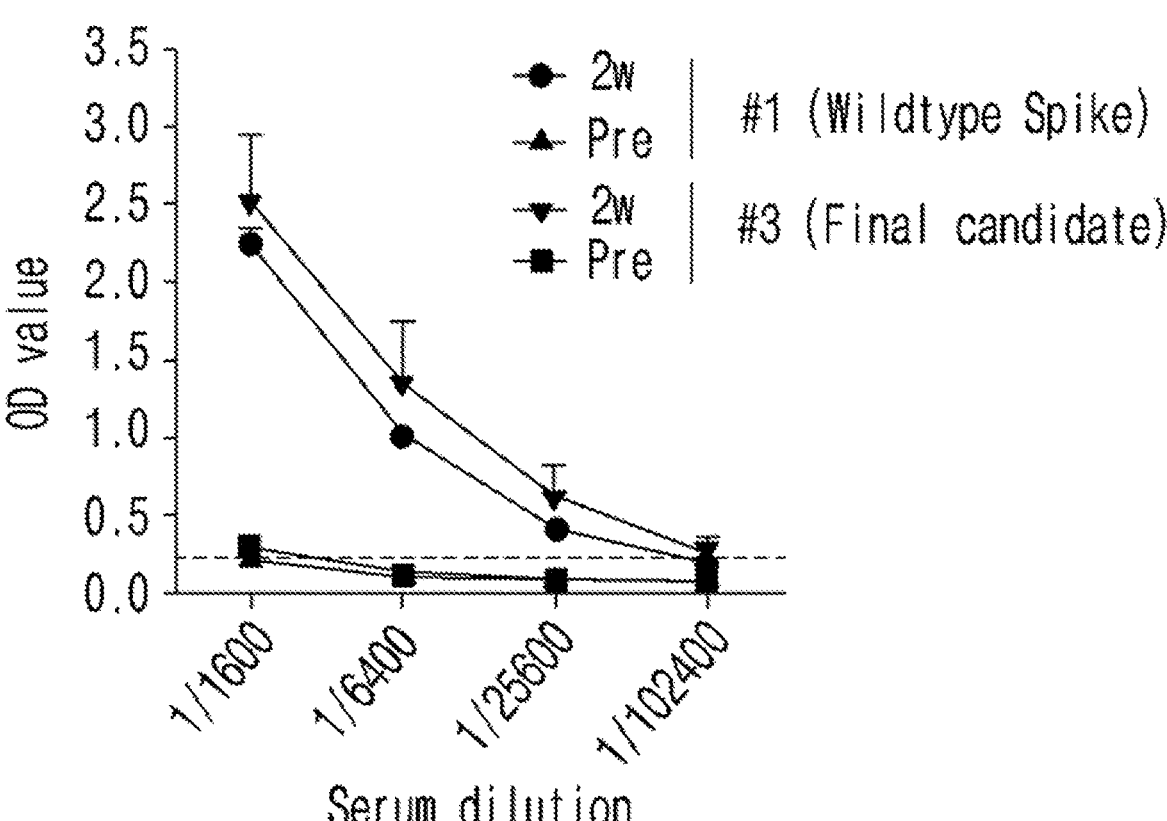
FIGS. 10A and 10B are diagrams showing the amount of antigen-specific antibodies present in the blood after the adenovirus vector #3 loaded with spike protein antigens, which are antigen expression genes, was injected into monkeys.
Figure 10B:
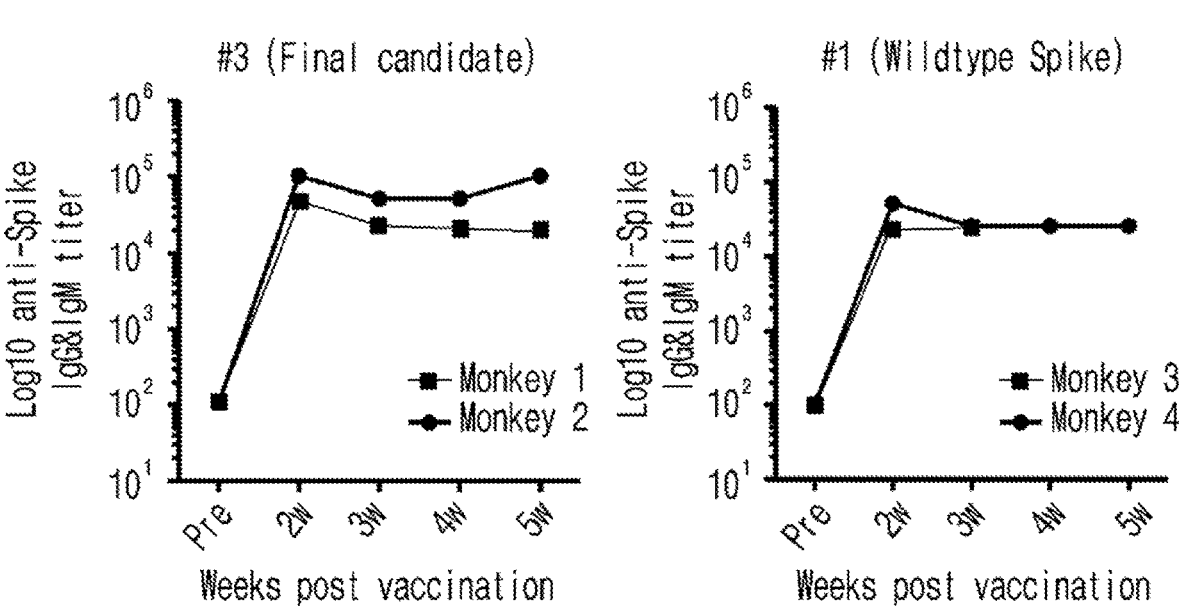
Figure 11:
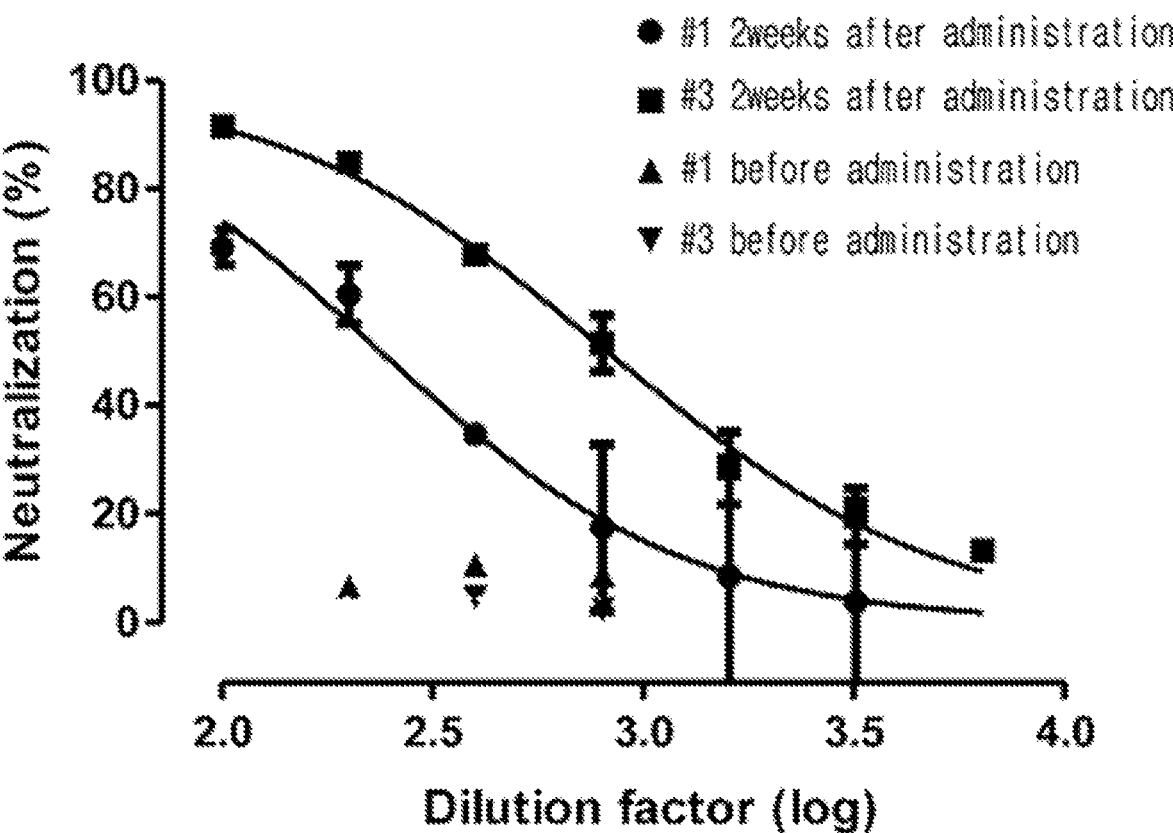
FIG. 11 is a diagram showing the concentration of neutralizing antibodies after the adenovirus vector #3 loaded with spike protein antigens, which are antigen expression genes, was injected into monkeys.

As a result, as shown in FIGS. 10A and 10B, it was confirmed that the amount of antibody production was excellent when the vector was injected, and the antibody titer was maintained even after 5 weeks after the vector injection. In addition, as shown in FIG. 11, it was confirmed that the neutralizing antibody concentration was high when the vector #3 was injected. These results suggest that a large amount of neutralizing antibodies start to be produced 2 weeks the after vaccine administration, effectively blocking viral infection of cells.

<6-2> Comparison of Hepatotoxicity in Monkeys According to Antigen Expression Vector Injection Due to the nature of adenoviruses, most of them move to the liver and may cause hepatotoxicity. Since hepatotoxicity is fatal to the human body, it is very important to prepare a vaccine that does not exhibit hepatotoxicity even when a high dose of viral particles is administered. Accordingly, hepatotoxicity was compared in monkeys according to the injection of the adenovirus vectors (vectors #1 and #3) prepared in Example 3.

The adenovirus vectors #1 and #3 prepared in Example 3 were intramuscularly injected into 6-7-week-old monkeys (cynomolgus monkeys) at a dose of $1\times10^{11}$ VP/monkey, 2 monkeys per group. Blood was collected from all animals before (pre) and 9, 22, and 36 days after the administration. All blood collection was performed in a fasting state (free intake of drinking water), and about 3 mℓ of blood was collected from the femoral vein using a disposable syringe (3 mℓ, 23G, KOREAVACCINE, KOR).

About 0.6 ml of blood collected for blood biochemical tests was dispensed into a SSTTM tube (Vacutainer®, BD, USA), and the serum was separated by centrifugation at 13,000 rpm for 5 minutes (5424R, Eppendorf, USA). Then, the hepatotoxicity levels, aspartate aminotransferase (AST) and alanine aminotransferase (ALT), were measured using a biochemical analyzer (7180, HITACHI, JPN).

Figure 12A:
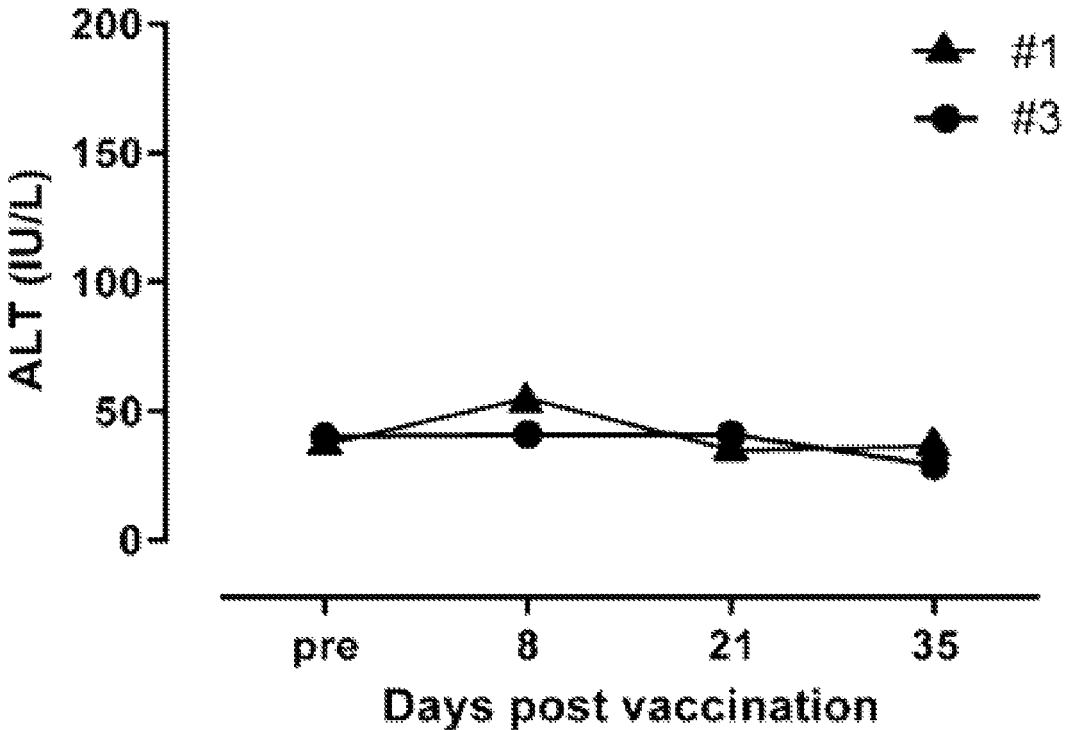
FIGS. 12A and 12B are diagrams showing the levels of liver toxicity in the blood after the adenovirus vectors #1 to #4 loaded with spike protein antigens, which are antigen expression genes, were injected into monkeys.
Figure 12B:
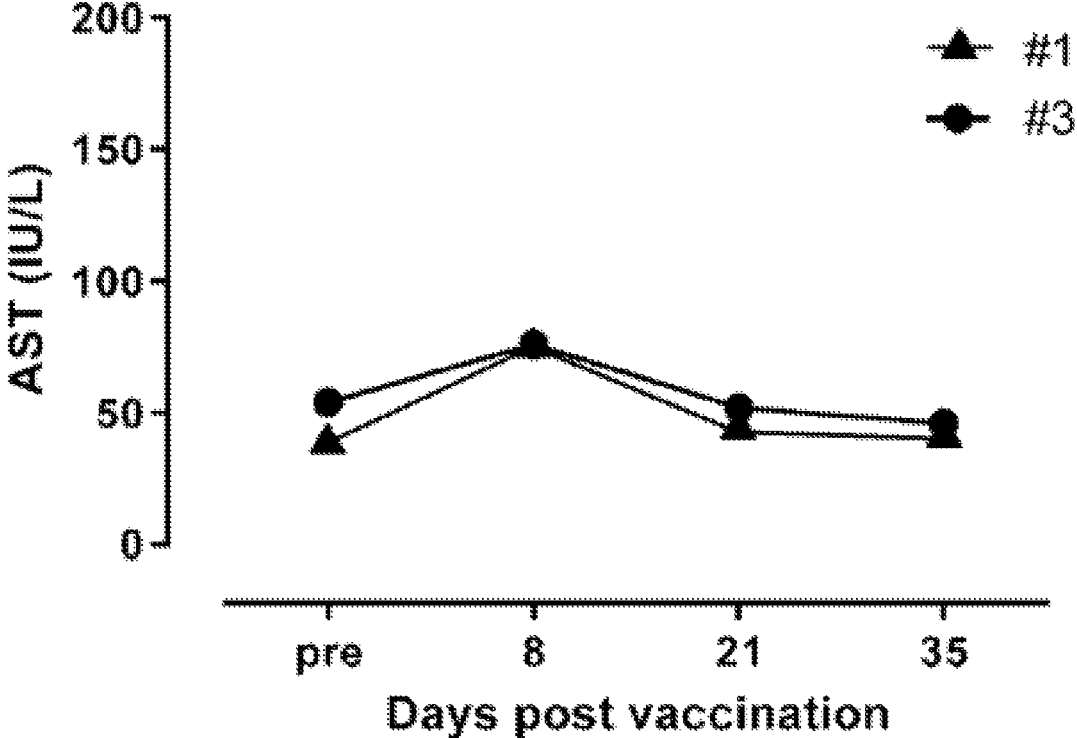

As a result, as shown in FIGS. 12A and 12B, it was confirmed that monkeys injected with the vectors #1 and #3 using the same adenovirus vector platform did not show severe hepatotoxicity even though high doses of virus particles were administered.

<Example 7> Measurement of T Cell Reactivity when Antigen Expression Vectors were Injected into Mice and Monkeys <7-1> Measurement of T Cell Reactivity in Spleen Cells and Peripheral Blood Mononuclear Cells (PBMC) in Mice T cell reactivity was measured in mice following injection of the spike antigen expression vectors (vectors #1 and #3) prepared in Example 3 as follows.

Particularly, the mice administered with the vaccine (vectors #1 and #3) of Example 5 were sacrificed at 10 weeks of administration, blood was collected through orbital blood sampling, and the spleen was separated. The spleen cells were pulverized using a 70 μm cell strainer (BD Bioscience, Cat. #: 352350) to form single cells, and then red blood cells were removed using an ACK lysis buffer (Gibco, Cat. #: A1049201). Peripheral blood mononuclear cells (PBMC) were isolated from blood samples by density gradient centrifugation using Histopaque®-1077 (Sigma-Aldrich, Cat. #: 10771). The separated spleen cells and PBMCs were counted and suspended in RF10 culture medium (RPMI1640+10% FBS+1% penicillin/streptomycin) at a concentration of $2\times10^6$ cells/ mℓ.

Peptivator SARS-CoV-2 Prot_S (Miltenyi Biotec, Cat. #: 130-126-701) was added to the preheated RF10 culture medium at a concentration of 50 μg/ mℓ and each well of the coated plate in the mouse IFN-γ ELISPOT kit (CTL, Cat. #: MIFNgp-2M/10) was filled with 100 μℓ of the mixture and stored in a 37° C. $CO_2$ incubator for 20 minutes (Wells for each group were performed in duplicate). Thereafter, 100 μℓ of the culture medium containing the resuspended mouse spleen cells and PBMCs was added to each well and cultured in a 37° C. CO2 incubator. Anti-CD3 mAb (1 μg/ mℓ, Biolegend, Cat. #: 100331) was added to the positive control well, and only RF10 was added to the negative control well without putting cells. After culturing for 24 hours, ELISPOT development was performed according to manufacturer's protocol included in the mouse IFN-γ ELISPOT kit. After color development, the plate was dried at room temperature for 24 hours by blocking light, and then analyzed using an immunospot S6 micro analyzer (CTL). The results were converted into units of $1 \times 10^6$ PBMC.

Figure 13A:
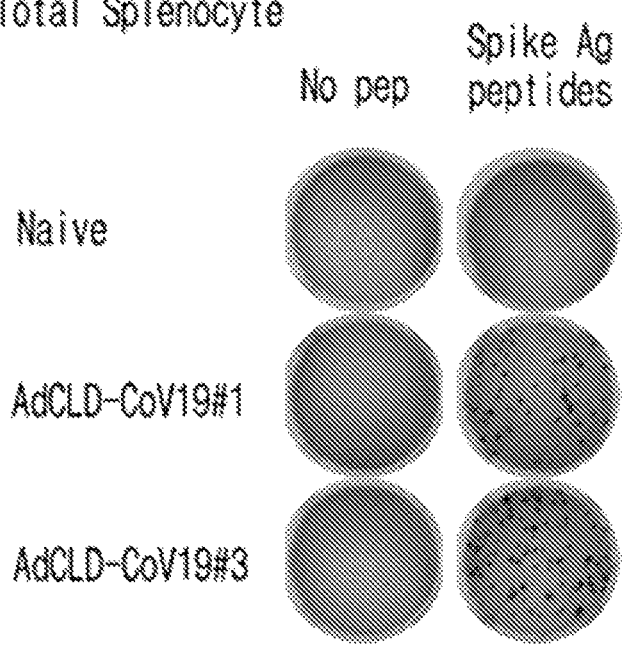
FIGS. 13A and 13B are diagrams showing the T cell reactivity in spleen cells and peripheral blood mononuclear cells (PBMC) after the adenovirus vectors #1 to #3 loaded with spike protein antigens, which are antigen expression genes, were injected into mice.
Figure 13A:
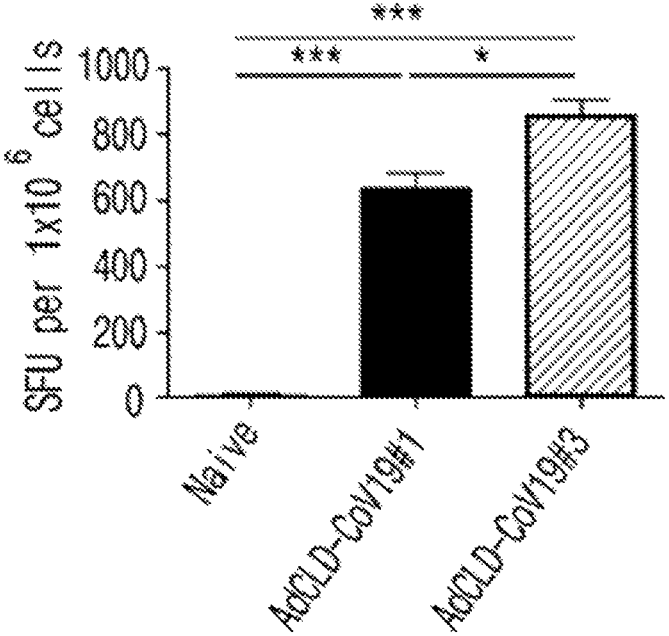
Figure 13B:
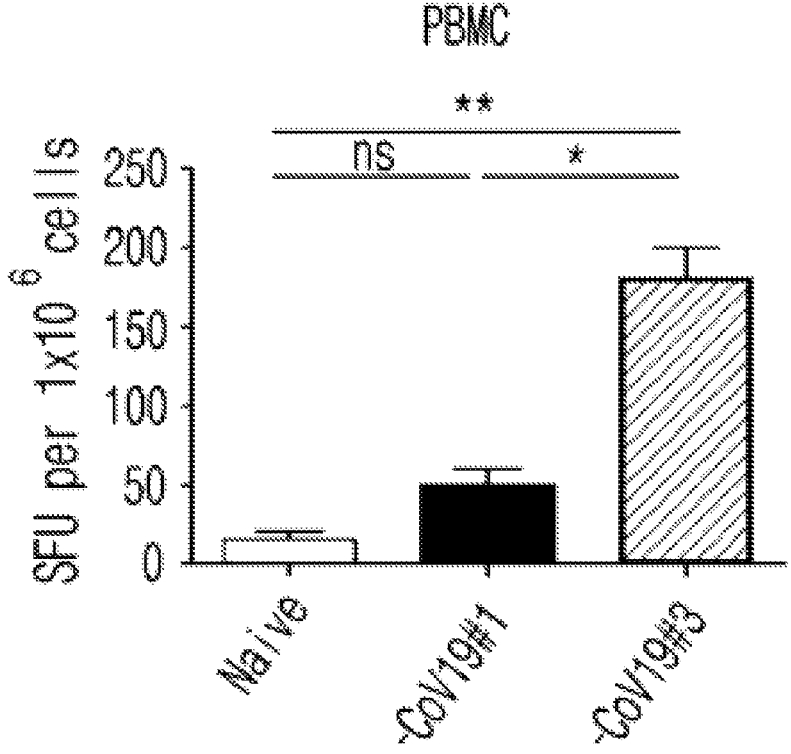

As a result, as shown in FIGS. 13A and 13B, it was confirmed that the T cell reactivity was significantly increased in the spleen cells and peripheral blood mononuclear cells (PBMC) of the mice injected with the vector #3, compared to the group not injected with the vector and the group injected with the vector #1. The above results suggest that the vaccine composition of the present invention can actively induce memory immune responses by T cells as well as antibody production when reinfected with SARS-CoV-2.

<7-2> Measurement of T Cell Reactivity in Peripheral Blood Mononuclear Cells (PBMC) in Monkeys T cell reactivity was measured in monkeys following injection of the adenovirus vectors (vectors #1 and #3) prepared in Example 3 as follows.

Blood (5 mℓ) was collected from the monkey administered with the vaccine of Example 6 (vector #3) through intravenous blood sampling at 4 weeks of administration. Peripheral blood mononuclear cells (PBMC) were isolated from blood samples by density gradient centrifugation using Histopaque®-1077 (Sigma-Aldrich, Cat. #: 10771), and then red blood cells were removed using an ACK lysis buffer (Gibco, Cat. #: A1049201). The separated PBMCs were counted and suspended in RF10 culture medium (RPMI1640+10% FBS+1% penicillin/streptomycin) at a concentration of $2 \times 10^6$ cells/ mℓ.

Peptivator SARS-CoV-2 Prot_S (Miltenyi Biotec, Cat. #: 130-126-701) was added to the preheated RF10 culture medium at a concentration of 100 μg/ mℓ, and each well of the coated plate in the human IFN-γ ELISPOT kit (CTL, Cat. #: HIFNgp-2M/10) was filled with 100 μℓ of the mixture and stored in a 37° C. CO₂ incubator for 20 minutes (Wells for each group were performed in duplicate). Thereafter, 100 μℓ of the culture medium containing the resuspended PBMCs was added to each well and cultured in a 37° C. CO2 incubator. PMA (10 ng/ mℓ) and ionomycin (1 μg/ mℓ) were added to the positive control well, and only RF10 was added to the negative control well without putting cells. After culturing for 24 hours, ELISPOT development was performed according to manufacturer's protocol included in the human IFN-γ ELISPOT kit. After color development, the plate was dried at room temperature for 24 hours by blocking light, and then analyzed using an immunospot S6 micro analyzer (CTL). The results were converted into units of $1 \times 10^6$ PBMC.

Figure 14:
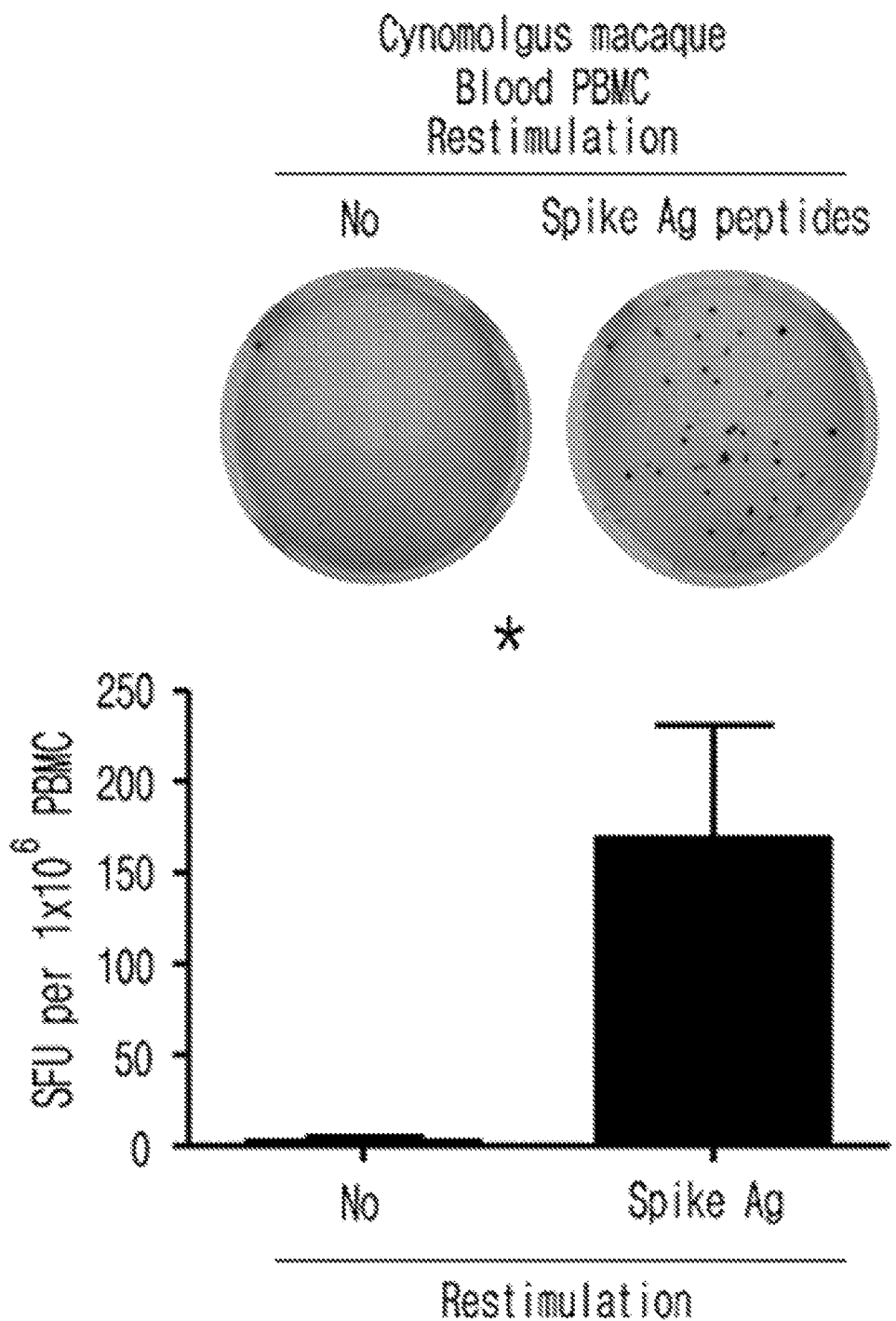
FIG. 14 is a diagram showing the T cell reactivity in peripheral blood mononuclear cells (PBMC) after the adenovirus vector #3 loaded with spike protein antigens, which are antigen expression genes, were injected primates.

As a result, as shown in FIG. 14, it was confirmed that the T cell reactivity was significantly increased in the peripheral blood mononuclear cells (PBMC) of the monkey injected with the vector #3, compared to the group not injected with the vector. The above results suggest that the vaccine composition of the present invention can actively induce memory immune responses by T cells as well as antibody production when reinfected with SARS-CoV-2.

<Example 8> Comparison of Antigen-Specific Neutralizing Antibody Production Equivalence in Mice and Monkeys According to Injection of Antigen Expression Vector #3 and Antigen Hetero Vector #3

<8-1> Comparison of Antigen-Specific Neutralizing Antibody Production Equivalence in Mice According to Injection of Antigen Expression Vector #3 and Antigen Hetero Vector #3

The amount of antibody production was compared after injecting the vector #3 prepared in Example 3 and the hetero vector #3 (SEQ. ID. NO: 30) prepared as an equivalence comparison group into mice. The hetero vector #3 is a form in which the E4 gene among the adenovirus genes of the vector #3 used in Example 3 was relocated into the E1 region of the virus genome. Specifically, the vector is a form in which 711 bp of E4orf6 of the Ad5/35 vector in which the E3 knob gene was substituted with Ad35 in the E1/E3-deleted Ad5 was deleted, and the recombinant spike protein (fusion protein in which S1 domain and S2 domain of SARS-CoV-2 were connected by GGGGS (SEQ ID NO: 31) linker) and the E4orf6 gene were forwardly inserted into the E1 deletion site. The vector was prepared in the same manner as in Example 3.

Particularly, the spike antigen expression vectors (vector #3 and hetero vector #3) were intramuscularly injected into 6-7-week-old BALB/c mice at a dose of $1 \times 10^9$ VP/mouse, 5 mice per group. About 300 μℓ of blood was collected from the mouse by orbital blood sampling at 9 weeks after the administration. Then, the plasma was separated by centrifugation (8000 rpm, 10 minutes, 20° C.), and the amount of neutralizing antibodies present in the blood was measured by pseudovirus neutralization assay.

For the pseudovirus neutralization assay, HEK293T-hACE2 (human angiotensin converting enzyme 2; hACE2) cell line was placed in a 96-well plate at the density of $1 \times 10^4$ cells/well and cultured for 10 hours (37° C., 5% CO₂). The plasma collected from mice through intravenous sampling at 8 weeks after the immunization was diluted 4-fold from 100 to 6400 times and reacted with $7 \times 10^5$ TU/mℓ of pseudovirus (lentivirus expressing spike protein and luciferase) for 1 hour (37° C.), followed by culture in the 96-well plate containing HEK293T-hACE2 cells being cultured for 3 days. Then, the presence of neutralizing antibodies in the plasma binding to the spike protein was confirmed by measuring the degree of luciferase protein expression induced by infection of the HEK293T-hACE2 cell line with pseudovirus. The cells cultured for 3 days were washed with DPBS and then lysed with 25 μg of cell lysis reagent (Promega, Cat. #: E153A). After the lysed sample was transferred to an opaque 96-well plate, 100 μg of luciferase detection indicator (Promega, Cat. #: E151A) was added to each well and the level of luminescence was measured (detection indicator injection—5 seconds mixing—2 seconds delay—10 seconds measurement) using a luminometer (Luminometer Centro XS3 LB960, Berthold Technologies, Cat. #: LB960, software: Mikro 2000 program).

Figure 15:
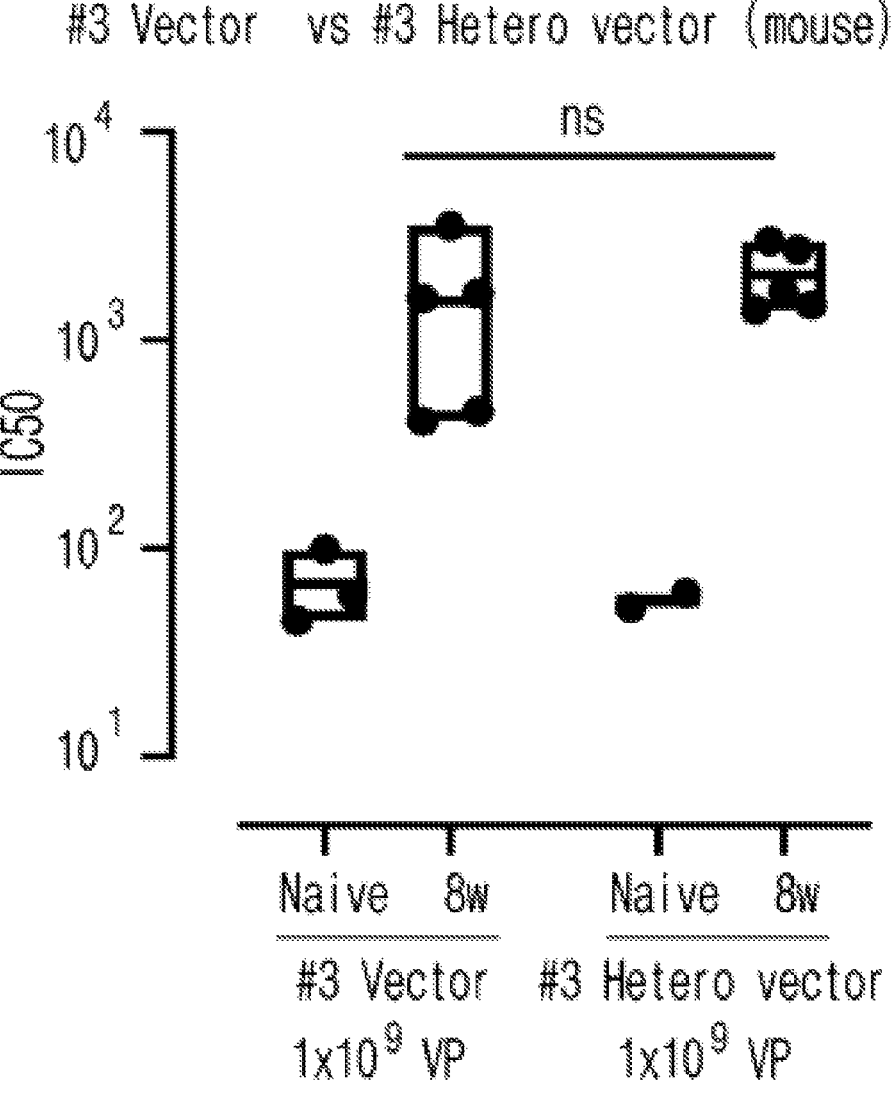
FIG. 15 is a diagram confirming that a similar level of neutralizing antibodies was produced when the vector #3 expressing spike antigens prepared in Example 3 or the vector in which the E4 gene among the adenovirus genes of the vector #3 was rearranged into the E1 region of the viral genome was injected into mice.

As a result, as shown in FIG. 15, the antigen vector #3 and the antigen hetero vector #3 showed excellent antibody production, and there was no difference between the two groups. The above results suggest that the antigen #3 has an equivalent level of neutralizing antibody activity even when loaded on different platform vectors.

<8-2> Comparison of Antigen-Specific Neutralizing Antibody Production Equivalence in Monkeys According to Injection of Antigen Expression Vector #3 and Antigen Hetero Vector #3

The amount of antigen-specific neutralizing antibody production was compared after injecting the vector #3 and the hetero vector #3 prepared as an equivalence comparison group of Example 8-1 into monkeys (cynomolgus monkey).

Particularly, the spike antigen expression vectors (vector #3 and hetero vector #3) were intramuscularly injected into 6-7-week-old monkeys at a dose of $2 \times 10^{10}$ VP/monkey, 2 monkeys per group. Blood was collected from the monkey by intravenous blood sampling at 9 weeks after the immunization. Then, the plasma was separated by centrifugation (8000 rpm, 10 minutes, 20° C.), and the amount of neutralizing antibodies present in the blood was measured by pseudovirus neutralization assay.

For the pseudovirus neutralization assay, HEK293T-hACE2 (human angiotensin converting enzyme 2; hACE2) cell line was placed in a 96-well plate at the density of $1 \times 10^4$ cells/well and cultured for 10 hours (37° C., 5% $CO_2$). The plasma collected from monkeys through intravenous blood sampling at 9 weeks after the immunization was diluted 4-fold from 100 to 6400 times and reacted with $7 \times 10^5$ TU/mℓ of pseudovirus (lentivirus expressing spike protein and luciferase) for 1 hour (37° C.), followed by culture in the 96-well plate containing HEK293T-hACE2 cells being cultured for 3 days. Then, the presence of neutralizing antibodies in the plasma binding to the spike protein was confirmed by measuring the degree of luciferase protein expression induced by infection of the HEK293T-hACE2 cell line with pseudovirus. The cells cultured for 3 days were washed with DPBS and then lysed with 25 μg of cell lysis reagent (Promega, Cat. #: E153A). After the lysed sample was transferred to an opaque 96-well plate, 100 μg of luciferase detection indicator (Promega, Cat. #: E151A) was added to each well and the level of luminescence was measured (detection indicator injection—5 seconds mixing—2 seconds delay—10 seconds measurement) using a luminometer (Luminometer Centro XS3 LB960, Berthold Technologies, Cat. #: LB960, software: Mikro 2000 program).

Figure 16:
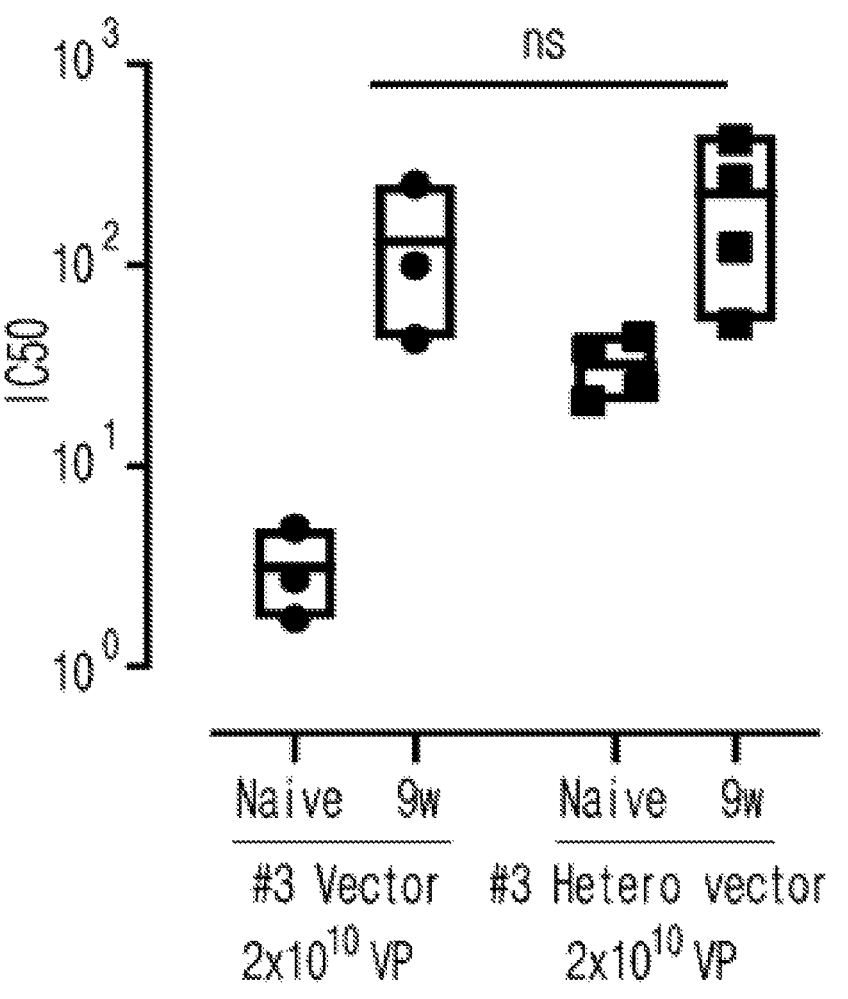
FIG. 16 is a diagram confirming that a similar level of neutralizing antibodies was produced when the vector #3 expressing spike antigens prepared in Example 3 or the vector in which the E4 gene among the adenovirus genes of the vector #3 was rearranged into the E1 region of the viral genome was injected into monkeys.

As a result, as shown in FIG. 16, the vector #3 and the hetero vector #3 showed excellent antibody production, and there was no difference in the expression level.

<Example 9> Comparison of Antibody Production in Mice According to Recombinant Spike Protein Injection <9-1> Comparison of Mouse Antibody Production by Injection of Recombinant Spike Protein After injecting the recombinant spike proteins (recombinant protein #2 and recombinant protein #3) derived from the vectors #1 to #3 prepared in Example 3 into mice, the amount of antibody production was compared.

Particularly, the recombinant spike proteins derived from the vectors #1 to #3 were intramuscularly injected into 6-7-week-old BALB/c mice, 6 mice per group. 10 μg of each recombinant spike protein (#1 to #3) was diluted in 150 μℓ of PBS (pH 7.4) and administered by intramuscular injection. About 300 μℓ of blood sample was collected by orbital blood sampling at 2-4 weeks after the administration. Then, the plasma was separated by centrifugation (8000 rpm, 10 minutes, 20° C.), and the amount of neutralizing antibodies present in the blood was measured by enzyme-linked immunosorbent assay (ELISA) and pseudovirus neutralization assay.

For the enzyme-linked immunosorbent assay, a 96-well plate was coated with a spike protein (Acro Biosystems, Cat. #: SPN-052H84) dissolved in PBSN (PBS 1 L+sodium azide 0.01 g) at 100 ng/well, followed by cold-reaction at 4° C. for 16 hours. After 16 hours of coating the 96-well plate, the coating protein was removed, washed three times with PBS, and then 150 μℓ of blocking buffer (PBSN+BSA 1%) was added to each well, followed by reaction (37° C., 90 minutes). During the reaction time, the plasma was diluted 6400-fold in dilution buffer (PBSN+0.1% BSA+0.05% Tween-20), and after the blocking reaction, the plate was washed three times with PBS, and then 50 μℓ of the diluted plasma sample was added to each well, followed by reaction (37° C., 3 hours). Upon completion of the reaction, the plate was washed three times with PBS, and 50 μℓ of secondary antibodies, GAM-IgG-HRP (Southernbiotech, Cat. #: 1030-05) and GAM-IgM-HRP (Southernbiotech, Cat. #: 1020-05), diluted 1000 times in dilution buffer was added to each well, followed by reaction (37° C., 2 hours). Then, the secondary antibodies were eliminated, the plate was washed 5 times with PBS, and 50 μℓ of a chromogenic reagent (TMB Peroxidase Substrate buffer, ROCKLAND, Cat. #: TMBE-1000) was added to each well, followed by color development for 15 minutes. The color development was stopped by adding 50 μℓ of 0.25 N HCl to each well, and the sample was analyzed at a wavelength of 450 nm with a microreader.

For the pseudovirus neutralization assay, HEK293T-hACE2 (human angiotensin converting enzyme 2; hACE2) cell line was placed in a 96-well plate at the density of $1 \times 10^4$ cells/well and cultured for 10 hours (37° C., 5% $CO_2$). The plasma collected from mice through intravenous sampling at 2 to 4 weeks after the immunization was diluted 4-fold from 100 to 6400 times and reacted with $7 \times 10^5$ TU/mℓ of pseudovirus (lentivirus expressing spike protein and luciferase) for 1 hour (37° C.), followed by culture in the 96-well plate containing HEK293T-hACE2 cells being cultured for 3 days. Then, the presence of neutralizing antibodies in the plasma binding to the spike protein was confirmed by measuring the degree of luciferase protein expression induced by infection of the HEK293T-hACE2 cell line with pseudovirus. The cells cultured for 3 days were washed with DPBS and then lysed with 25 μg of cell lysis reagent (Promega, Cat. #: E153A). After the lysed sample was transferred to an opaque 96-well plate, 100 μg of luciferase detection indicator (Promega, Cat. #: E151A) was added to each well and the level of luminescence was measured (detection indicator injection—5 seconds mixing—2 seconds delay—10 seconds measurement) using a luminometer (Luminometer Centro XS3 LB960, Berthold Technologies, Cat. #: LB960, software: Mikro 2000 program).

<Example 10> Comparison of Antibody Production in Mice According to Spike Antigen Plasmid Injection <10-1> Comparison of Mouse Antibody Production According to Spike Antigen Plasmid Injection After injecting the vectors #1 to #3 prepared in Examples 1 and 2 in the form of plasmids (plasmid vector #1 and plasmid vector #3) into mice, the amount of antibody production was compared.

Particularly, the plasmid vectors #2 and #3 prepared in Examples 1 and 2 were introduced into *E. coli* and cultured in 200 mL of LB culture medium for one day. The cultured plasmids were harvested using QIAGEN Endofree Plasmid Maxi kit (Cat. #12362) and then administered to 6-7-week-old BALB/c mice, 6 mice per group. 100 µg of each vector (##2 and #3) was diluted in 50 µℓ of PBS (pH 7.4) and administered by intramuscular injection. About 300 µℓ of blood sample was collected by orbital blood sampling at 2-4 weeks after the administration. Then, the plasma was separated by centrifugation (8000 rpm, 10 minutes, 20° C.), and the amount of neutralizing antibodies present in the blood was measured by enzyme-linked immunosorbent assay (ELISA) and pseudovirus neutralization assay.

For the enzyme-linked immunosorbent assay, a 96-well plate was coated with a spike protein (Acro Biosystems, Cat. #: SPN-052H84) dissolved in PBSN (PBS 1 L+sodium azide 0.01 g) at 100 ng/well, followed by cold-reaction at 4° C. for 16 hours. After 16 hours of coating the 96-well plate, the coating protein was removed, washed three times with PBS, and then 150 µℓ of blocking buffer (PBSN+BSA 1%) was added to each well, followed by reaction (37° C., 90 minutes). During the reaction time, the plasma was diluted 6400-fold in dilution buffer (PBSN+0.1% BSA+0.05% Tween-20), and after the blocking reaction, the plate was washed three times with PBS, and then 50 µℓ of the diluted plasma sample was added to each well, followed by reaction (37° C., 3 hours). Upon completion of the reaction, the plate was washed three times with PBS, and 50 µℓ of secondary antibodies, GAM-IgG-HRP (Southernbiotech, Cat. #: 1030-05) and GAM-IgM-HRP (Southernbiotech, Cat. #: 1020-05), diluted 1000 times in dilution buffer was added to each well, followed by reaction (37° C., 2 hours). Then, the secondary antibodies were eliminated, the plate was washed 5 times with PBS, and 50 µℓ of a chromogenic reagent (TMB Peroxidase Substrate buffer, ROCKLAND, Cat. #: TMBE-1000) was added to each well, followed by color development for 15 minutes. The color development was stopped by adding 50 µℓ of 0.25 N HCl to each well, and the sample was analyzed at a wavelength of 450 nm with a microreader.

For the pseudovirus neutralization assay, HEK293T-hACE2 (human angiotensin converting enzyme 2; hACE2) cell line was placed in a 96-well plate at the density of $1 \times 10^4$ cells/well and cultured for 10 hours (37° C., 5% $CO_2$). The plasma collected from mice through intravenous sampling at 2 to 4 weeks after the immunization was diluted 4-fold from 100 to 6400 times and reacted with $7 \times 10^5$ TU/mℓ of pseudovirus (lentivirus expressing spike protein and luciferase) for 1 hour (37° C.), followed by culture in the 96-well plate containing HEK293T-hACE2 cells being cultured for 3 days. Then, the presence of neutralizing antibodies in the plasma binding to the spike protein was confirmed by measuring the degree of luciferase protein expression induced by infection of the HEK293T-hACE2 cell line with pseudovirus. The cells cultured for 3 days were washed with DPBS and then lysed with 25 µg of cell lysis reagent (Promega, Cat. #: E153A). After the lysed sample was transferred to an opaque 96-well plate, 100 µg of luciferase detection indicator (Promega, Cat. #: E151A) was added to each well and the level of luminescence was measured (detection indicator injection—5 seconds mixing—2 seconds delay—10 seconds measurement) using a luminometer (Luminometer Centro XS3 LB960, Berthold Technologies, Cat. #: LB960, software: Mikro 2000 program).

What is claimed is:

1. A vector expressing a recombinant spike protein derived from a coronavirus, wherein the vector comprises a polynucleotide encoding the recombinant spike protein in which an amino acid sequence TNSPRRAR (SEQ ID NO: 32) of a cleavage site between S1 and S2 genes of a coronavirus spike protein is replaced by a linker sequence comprising an amino acid sequence of TGGGGSR (SEQ ID NO: 19), wherein the vector is derived from an adenoviral vector comprising the sequence as set forth in SEQ ID NO: 21, wherein E1 and E3 regions of the adenoviral vector are deleted, and wherein the polynucleotide encoding the recombinant spike protein is inserted in the deleted E1 region.

2. The vector according to claim 1, wherein the coronavirus is SARS-COV, MERS-COV or SARS-COV-2.

3. The vector according to claim 2, wherein the coronavirus is SARS-COV-2.

4. The vector according to claim 1, wherein the spike protein linked by the linker sequence has an increased stability.

5. The according to claim 1, wherein the spike protein linked by the linker sequence has an increased antigen expression level.

6. The vector according to claim 1, wherein the coronavirus is SARS-COV, MERS-COV or SARS-COV-2.

7. The vector according to claim 1, wherein the coronavirus is SARS-COV-2.

8. The vector according to claim 1, wherein the vector is a virus or a plasmid.

9. The vector according to claim 8, wherein the virus is adenovirus, retrovirus, lentivirus, modified vaccinia virus ankara (MVA), adeno-associated virus (AAV), herpes simplex virus or baculovirus.

10. The vector according to claim 9, wherein the adenovirus is Ad2, Ad4, Ad5, Ad11, Ad26, Ad35, ChAd68, FAd9 or PAd3.

11. The vector according to claim 9, wherein the adenovirus has a high antigen expression level.

12. The vector according to claim 10, wherein the adeno-virus has a high antigen expression level.

13. A method for preventing or treating coronavirus infection comprising a step of administering to a subject a vector of claim 1.

14. The method for preventing or treating coronavirus infection according to claim 13, wherein the coronavirus infection is SARS, MERS or COVID-19.

\* \* \* \* \*

SEQUENCE LISTING

<160> NUMBER OF SEQ ID NOS: 34

<210> SEQ ID NO 1
<211> LENGTH: 34030
<212> TYPE: DNA
<213> ORGANISM: Artificial Sequence
<220> FEATURE:
<223> OTHER INFORMATION: pAdk35F

<400> SEQUENCE: 1

```
ttaattaaca tgcatggatc catatgcggt gtgaaatacc gcacagatgc gtaaggagaa        60
aataccgcat caggcgctct tccgcttcct cgctcactga ctcgctgcgc tcggtcgttc       120
ggctgcggcg agcggtatca gctcactcaa aggcggtaat acggttatcc acagaatcag       180
gggataacgc aggaaagaac atgtgagcaa aaggccagca aaaggccagg aaccgtaaaa       240
aggccgcgtt gctggcgttt ttccataggc tccgcccccc tgacgagcat cacaaaaatc       300
gacgctcaag tcagaggtgg cgaaacccga caggactata aagataccag gcgtttcccc       360
ctggaagctc cctcgtgcgc tctcctgttc cgaccctgcc gcttaccgga tacctgtccg       420
cctttctccc ttcgggaagc gtggcgcttt ctcatagctc acgctgtagg tatctcagtt       480
cggtgtaggt cgttcgctcc aagctgggct gtgtgcacga accccccgtt cagcccgacc       540
gctgcgcctt atccggtaac tatcgtcttg agtccaaccc ggtaagacac gacttatcgc       600
cactggcagc agccactggt aacaggatta gcagagcgag gtatgtaggc ggtgctacag       660
agttcttgaa gtggtggcct aactacggct acactagaag gacagtattt ggtatctgcg       720
ctctgctgaa gccagttacc ttcggaaaaa gagttggtag ctcttgatcc ggcaaacaaa       780
```

```
ccaccgctgg tagcggtggt ttttttgttt gcaagcagca gattacgcgc agaaaaaaag     840
gatctcaaga agatcctttg atcttttcta cggggtctga cgctcagtgg aacgaaaact     900
cacgttaagg gattttggtc atgagattat caaaaaggat cttcacctag atccttttaa     960
attaaaaatg aagtttttaaa tcaatctaaa gtatatatga gtaaacttgg tctgacagtt    1020
accaatgctt aatcagtgag gcacctatct cagcgatctg tctatttcgt tcatccatag    1080
ttgcctgact ccccgtcgtg tagataacta cgatacggga gggcttacca tctggcccca    1140
gtgctgcaat gataccgcga gacccacgct caccggctcc agatttatca gcaataaacc    1200
agccagccgg aagggccgag cgcagaagtg gtcctgcaac tttatccgcc tccatccagt    1260
ctattaattg ttgccgggaa gctagagtaa gtagttcgcc agttaatagt ttgcgcaacg    1320
ttgttgccat tgctgcagcc atgagattat caaaaaggat cttcacctag atccttttca    1380
cgtagaaagc cagtccgcag aaacggtgct gaccccggat gaatgtcagc tactgggcta    1440
tctggacaag ggaaaacgca agcgcaaaga gaaagcaggt agcttgcagt gggcttacat    1500
ggcgatagct agactgggcg gttttatgga cagcaagcga accggaattg ccagctgggg    1560
cgccctctgg taaggttggg aagccctgca aagtaaactg gatggctttc ttgccgccaa    1620
ggatctgatg gcgcaggggaa tcaagctctg atcaagagac aggatgagga tcgtttcgca    1680
tgattgaaca agatggattg cacgcaggtt ctccggccgc ttgggtggag aggctattcg    1740
gctatgactg ggcacaacag acaatcggct gctctgatgc cgccgtgttc cggctgtcag    1800
cgcaggggcg cccggttctt tttgtcaaga ccgacctgtc cggtgccctg aatgaactgc    1860
aagacgaggc agcgcggcta tcgtggctgg ccacgacggg cgttccttgc gcagctgtgc    1920
tcgacgttgt cactgaagcg ggaagggact ggctgctatt gggcgaagtg ccggggcagg    1980
atctcctgtc atctcacctt gctcctgccg agaaagtatc catcatggct gatgcaatgc    2040
ggcggctgca tacgcttgat ccggctacct gcccattcga ccaccaagcg aaacatcgca    2100
tcgagcgagc acgtactcgg atggaagccg gtcttgtcga tcaggatgat ctggacgaag    2160
agcatcaggg gctcgcgcca gccgaactgt tcgccaggct caaggcgagc atgcccgacg    2220
gcgaggatct cgtcgtgacc catggcgatg cctgcttgcc gaatatcatg gtggaaaatg    2280 gccgctttttc tggattcatc gactgtggcc ggctgggtgt ggcggaccgc tatcaggaca    2340
tagcgttggc tacccgtgat attgctgaag agcttggcgg cgaatgggct gaccgcttcc    2400
tcgtgcttta cggtatcgcc gctcccgatt cgcagcgcat cgccttctat cgccttcttg    2460
acgagttctt ctgaatttttg ttaaaatttt tgttaaatca gctcattttt taaccaatag    2520
gccgaaatcg gcaaaatccc ttataaatca aaagaataga ccgagatagg gttgagtgtt    2580
gttccagttt ggaacaagag tccactatta agaacgtgg actccaacgt caaagggcga    2640
aaaaccgtct atcagggcga tggcccacta cgtgaaccat caccctaatc aagttttttg    2700
gggtcgaggt gccgtaaagc actaaatcgg aaccctaaag ggagccccg atttagagct    2760 tgacggggaa agccggcgaa cgtggcgaga aaggaaggga agaaagcgaa aggagcgggc    2820 gctaggcgc tggcaagtgt agcggtcacg ctgcgcgtaa ccaccacacc cgccgcgctt    2880
aatgcgccgc tacaggggcgc gtccattcgc cattcaggat cgaattaatt cttaattaac    2940
atcatcaata atataccttaa ttttggattg aagccaatat gataatgagg gggtggagtt    3000
tgtgacgtgg cgcggggcgt gggaacgggg cgggtgacgt agtagtgtgg cggaagtgtg    3060
atgttgcaag tgtggcggaa cacatgtaag cgacggatgt ggcaaaagtg acgtttttgg    3120
```

-continued

```
tgtgcgccgg tgtacacagg aagtgacaat tttcgcgcgg ttttaggcgg atgttgtagt   3180
aaatttgggc gtaaccgagt aagatttggc cattttcgcg ggaaaactga ataagaggaa   3240
gtgaaatctg aataattttg tgttactcat agcgcgtaat actgtaatag taatcaatta   3300
cggggtcatt agttcatagc ccatatatgg agttccgcgt tacataactt acggtaaatg   3360
gcccgcctgg ctgaccgccc aacgaccccc gcccattgac gtcaataatg acgtatgttc   3420
ccatagtaac gccaataggg actttccatt gacgtcaatg ggtggagtat ttacggtaaa   3480
ctgcccactt ggcagtacat caagtgtatc atatgccaag tacgcccct attgacgtca   3540 atgacggtaa atggcccgcc tggcattatg cccagtacat gaccttatgg actttcctta   3600
cttggcagta catctacgta ttagtcatcg ctattaccat ggtgatgcgg ttttggcagt   3660
acatcaatgg gcgtggatag cggtttgact cacggggatt ccaagtctc caccccattg   3720 acgtcaatgg gagtttgttt tggcaccaaa atcaacggga ctttccaaaa tgtcgtaaca   3780
actccgcccc attgacgcaa atgggcggta ggcgtgtacg gtgggaggtc tatataagca   3840
gagctctccc tatcagtgat agagatctcc ctatcagtga tagagatcgt cgacgagctc   3900
gtttagtgaa ccgtcagatc gcctggagac gccatccacg ctgttttgac ctccatagaa   3960
gacaccggga ccgatccagc ctccgattta aattgatcat aatcagccat accacatttg   4020
tagaggtttt acttgcttta aaaaacctcc cacacctccc cctgaacctg aaacataaaa   4080
tgaatgcaat tgttgttgtt aacttgttta ttgcagctta taatggttac aaataaagca   4140
atagcatcac aaatttcaca ataaagcat tttttcact gcattctagt tgtggtttgt   4200
ccaaactcat caatgtatct taacgcggat ctgggcgtgg ttaagggtgg gaaagaatat   4260
ataaggtggg ggtcttatgt agttttgtat ctgttttgca gcagccgccg ccgccatgag   4320
caccaactcg tttgatggaa gcattgtgag ctcatatttg acaacgcgca tgccccatg   4380 ggccgggggtg cgtcagaatg tgatgggctc cagcattgat ggtcgccccg tcctgcccgc   4440
aaactctact accttgacct acgagaccgt gtctggaacg ccgttggaga ctgcagcctc   4500
cgccgccgct tcagccgctg cagccaccgc ccgcgggatt gtgactgact ttgctttcct   4560
gagcccgctt gcaagcagtg cagcttcccg ttcatccgcc cgcgatgaca agttgacggc   4620 tctttggca caattggatt ctttgacccg ggaacttaat gtcgtttctc agcagctgtt   4680
ggatctgcgc cagcaggttt ctgccctgaa ggcttcctcc cctcccaatg cggtttaaaa   4740
cataaataaa aaaccagact ctgtttggat ttggatcaag caagtgtctt gctgtcttta   4800
tttaggggtt ttgcgcgcgc ggtaggcccg ggaccagcgg tctcggtcgt tgagggtcct   4860 gtgtatttt tccaggacgt ggtaaaggtg actctggatg ttcagataca tgggcataag   4920
cccgtctctg gggtggaggt agcaccactg cagagcttca tgctgcgggg tggtgttgta   4980
gatgatccag tcgtagcagg agcgctgggc gtggtgccta aaaatgtctt tcagtagcaa   5040
gctgattgcc aggggcaggc ccttggtgta agtgtttaca aagcggttaa gctgggatgg   5100
gtgcatacgt ggggatatga gatgcatctt ggactgtatt tttaggttgg ctatgttccc   5160
agccatatcc ctccggggat tcatgttgtg cagaaccacc agcacagtgt atccggtgca   5220
cttgggaaat ttgtcatgta gcttagaagg aaatgcgtgg aagaacttgg agacgccctt   5280
gtgacctcca agattttcca tgcattcgtc cataatgatg gcaatgggcc cacgggcggc   5340
ggcctgggcg aagatatttc tgggatcact aacgtcatag ttgtgttcca ggatgagatc   5400
gtcataggcc attttttacaa agcgcgggcg gaggtgccaa gactgcggta taatggttcc   5460
atccggccca ggggcgtagt taccctcaca gatttgcatt tcccacgctt tgagttcaga   5520
```

```
tgggggatc atgtctacct gcggggcgat gaagaaaacg gtttccgggg taggggagat    5580
cagctgggaa gaaagcaggt tcctgagcag ctgcgactta ccgcagccgg tgggcccgta    5640
aatcacacct attaccggct gcaactggta gttaagagag ctgcagctgc cgtcatccct    5700 gagcagggg gccacttcgt taagcatgtc cctgactcgc atgtttccc tgaccaaatc      5760 cgccagaagg cgctcgccgc ccagcgatag cagttcttgc aaggaagcaa agtttttcaa    5820
cggtttgaga ccgtccgccg taggcatgct tttgagcgtt tgaccaagca gttccaggcg    5880
gtcccacagc tcggtcacct gctctacggc atctcgatcc agcatatctc ctcgtttcgc    5940 gggttgggc ggctttcgct gtacggcagt agtcggtgct cgtccagacg ggccagggtc     6000
atgtctttcc acgggcgcag ggtcctcgtc agcgtagtct gggtcacggt gaaggggtgc    6060
gctccgggct gcgcgctggc cagggtgcgc ttgaggctgg tcctgctggt gctgaagcgc    6120
tgccggtctt cgccctgcgc gtcggccagg tagcatttga ccatggtgtc atagtccagc    6180
ccctccgcgg cgtggccctt ggcgcgcagc ttgcccttgg aggaggcgcc gcacgagggg    6240
cagtgcagac ttttgagggc gtagagcttg ggcgcgagaa ataccgattc cggggagtag    6300
gcatccgcgc cgcaggcccc gcagacggtc tcgcattcca cgagccaggt gagctctggc    6360
cgttcggggt caaaaaccag gtttccccca tgctttttga tgcgtttctt acctctggtt    6420
tccatgagcc ggtgtccacg ctcggtgacg aaaaggctgt ccgtgtcccc gtatacagac    6480
ttgagaggcc tgtcctcgag cggtgttccg cggtcctcct cgtatagaaa ctcggaccac    6540
tctgagacaa aggctcgcgt ccaggccagc acgaaggagg ctaagtggga ggggtagcgg    6600
tcgttgtcca ctaggggtc cactcgctcc agggtgtgaa gacacatgtc gccctcttcg     6660
gcatcaagga aggtgattgg tttgtaggtg taggccacgt gaccgggtgt tcctgaaggg    6720
gggctataaa aggggtggg ggcgcgttcg tcctcactct cttccgcatc gctgtctgcg     6780
agggccagct gttggggtga gtactccctc tgaaaagcgg gcatgacttc tgcgctaaga    6840
ttgtcagttt ccaaaaacga ggaggatttg atattcacct ggcccgcggt gatgcctttg    6900
agggtggccg catccatctg gtcagaaaag acaatctttt tgttgtcaag cttggtggca    6960
aacgacccgt agagggcgtt ggacagcaac ttggcgatgg agcgcaggt ttggttttttg     7020 tcgcgatcgg cgcgctcctt ggccgcgatg tttagctgca cgtattcgcg cgcaacgcac    7080
cgccattcgg gaaagacggt ggtgcgctcg tcgggcacca ggtgcacgcg ccaaccgcgg    7140
ttgtgcaggg tgacaaggtc aacgctggtg gctacctctc cgcgtaggcg ctcgttggtc    7200
cagcagaggc ggccgcccctt gcgcgagcag aatggcggta gggggtctag ctgcgtctcg    7260
tccggggggt ctgcgtccac ggtaaagacc ccgggcagca ggcgcgcgtc gaagtagtct    7320
atcttgcatc cttgcaagtc tagcgcctgc tgccatgcgc gggcggcaag cgcgcgctcg    7380
tatgggttga gtgggggacc ccatggcatg gggtgggtga gcgcggaggc gtacatgccg    7440
caaatgtcgt aaacgtagag gggctctctg agtattccaa gatatgtagg gtagcatctt    7500
ccaccgcgga tgctggcgcg cacgtaatcg tatagttcgt gcgagggagc gaggaggtcg    7560
ggaccgaggt tgctacggc gggctgctct gctcggaaga ctatctgcct gaagatggca    7620
tgtgagttgg atgatatggt tggacgctgg aagacgttga agctggcgtc tgtgagacct    7680
accgcgtcac gcacgaagga ggcgtaggag tcgcgcagct tgttgaccag ctcggcggtg    7740
acctgcacgt ctagggcgca gtagtccagg gtttccttga tgatgtcata cttatcctgt    7800
cccttttttt tccacagctc gcggttgagg acaaactctt cgcggtcttt ccagtactct    7860
```

-continued

```
tggatcggaa acccgtcggc ctccgaacgg taagagccta gcatgtagaa ctggttgacg    7920
gcctggtagg cgcagcatcc cttttctacg ggtagcgcgt atgcctgcgc ggccttccgg    7980
agcgaggtgt gggtgagcgc aaaggtgtcc ctgaccatga ctttgaggta ctggtatttg    8040
aagtcagtgt cgtcgcatcc gccctgctcc cagagcaaaa agtccgtgcg cttttttggaa   8100 cgcggatttg gcagggcgaa ggtgacatcg ttgaagagta tctttcccgc gcgaggcata    8160
aagttgcgtg tgatgcggaa gggtcccggc acctcggaac ggttgttaat tacctgggcg    8220
gcgagcacga tctcgtcaaa gccgttgatg ttgtggccca caatgtaaag ttccaagaag    8280
cgcgggatgc ccttgatgga aggcaatttt ttaagttcct cgtaggtgag ctcttcaggg    8340
gagctgagcc cgtgctctga aagggcccag tctgcaagat gagggttgga agcgacgaat    8400
gagctccaca ggtcacgggc cattagcatt tgcaggtggt cgcgaaaggt cctaaactgg    8460
cgacctatgg ccattttttc tggggtgatg cagtagaagg taagcgggtc ttgttcccag    8520
cggtcccatc caaggttcgc ggctaggtct cgcgcggcag tcactagagg ctcatctccg    8580
ccgaacttca tgaccagcat gaagggcacg agctgcttcc caaaggcccc catccaagta    8640
taggtctcta catcgtaggt gacaaagaga cgctcggtgc gaggatgcga gccgatcggg    8700
aagaactgga tctcccgcca ccaattggag gagtggctat tgatgtggtg aaagtagaag    8760
tccctgcgac gggccgaaca ctcgtgctgg cttttgtaaa aacgtgcgca gtactggcag    8820
cggtgcacgg gctgtacatc ctgcacgagg ttgacctgac gaccgcgcac aaggaagcag    8880
agtgggaatt tgagcccctc gcctggcggg tttggctggt ggtcttctac ttcggctgct    8940
tgtccttgac cgtctggctg ctcgagggga gttacggtgg atcggaccac cacgccgcgc    9000
gagcccaaag tccagatgtc cgcgcgcggc ggtcggagct tgatgacaac atcgcgcaga    9060
tgggagctgt ccatggtctg gagctcccgc ggcgtcaggt caggcgggag ctcctgcagg    9120
tttacctcgc atagacgggt cagggcgcgg gctagatcca ggtgatacct aatttccagg    9180
ggctggttgg tggcggcgtc gatggcttgc aagaggccgc atccccgcgg cgcgactacg    9240
gtaccgcgcg gcgggcggtg ggccgcgggg gtgtccttgg atgatgcatc taaaagcggt    9300
gacgcgggcg agcccccgga ggtaggggg gctccggacc cgccgggaga gggggcaggg    9360
gcacgtcggc gccgcgcgcg ggcaggagct ggtgctgcgc gcgtaggttg ctggcgaacg    9420
cgacgacgcg gcggttgatc tcctgaatct ggcgcctctg cgtgaagacg acgggcccgg    9480
tgagcttgaa cctgaaagag agttcgacag aatcaatttc ggtgtcgttg acggcggcct    9540
ggcgcaaaat ctcctgcacg tctcctgagt tgtcttgata ggcgatctcg gccatgaact    9600
gctcgatctc ttcctcctgg agatctccgc gtccggctcg ctccacggtg cggcgaggt    9660 cgttggaaat gcgggccatg agctgcgaga aggcgttgag gcctccctcg ttccagacgc    9720
ggctgtagac cacgcccct tcggcatcgc gggcgcgcat gaccacctgc gcgagattga    9780
gctccacgtg ccgggcgaag acggcgtagt ttcgcaggcg ctgaaagagg tagttgaggg    9840
tggtggcggt gtgttctgcc acgaagaagt acataaccca gcgtcgcaac gtggattcgt    9900
tgatatcccc caaggcctca aggcgctcca tggcctcgta gaagtccacg gcgaagttga    9960
aaaactggga gttgcgcgcc gacacggtta actcctcctc cagaagacgg atgagctcgg    10020
cgacagtgtc gcgcacctcg cgctcaaagg ctacaggggc ctcttcttct tcttcaatct    10080
cctcttccat aagggcctcc ccttcttctt cttctggcgg cggtggggga ggggggacac    10140
ggcggcgacg acgcgcacc gggaggcggt cgacaaagcg ctcgatcatc tccccgcggc     10200
gacggcgcat ggtctcggtg acggcgcggc cgttctcgcg ggggcgcagt tggaagacgc    10260
```

-continued

```
cgcccgtcat gtcccggtta tgggttggcg gggggctgcc atgcggcagg gatacggcgc   10320
taacgatgca tctcaacaat tgttgtgtag gtactccgcc gccgagggac ctgagcgagt   10380
ccgcatcgac cggatcggaa aacctctcga gaaaggcgtc taaccagtca cagtcgcaag   10440
gtaggctgag caccgtggcg ggcggcagcg ggcggcggtc ggggttgttt ctggcggagg   10500
tgctgctgat gatgtaatta aagtaggcgg tcttgagacg gcggatggtc gacagaagca   10560
ccatgtcctt gggtccggcc tgctgaatgc gcaggcggtc ggccatgccc caggcttcgt   10620
tttgacatcg gcgcaggtct ttgtagtagt cttgcatgag cctttctacc ggcacttctt   10680
cttctccttc ctcttgtcct gcatctcttg catctatcgc tgcggcggcg gcggagtttg   10740
gccgtaggtg gcgccctctt cctcccatgc gtgtgacccc gaagcccctc atcggctgaa   10800
gcagggctag gtcggcgaca acgcgctcgg ctaatatggc ctgctgcacc tgcgtgaggg   10860
tagactggaa gtcatccatg tccacaaagc ggtggtatgc gcccgtgttg atggtgtaag   10920
tgcagttggc cataacggac cagttaacgg tctggtgacc cggctgcgag agctcggtgt   10980
acctgagacg cgagtaagcc ctcgagtcaa atacgtagtc gttgcaagtc cgcaccaggt   11040
actggtatcc caccaaaaag tgcggcggcg gctggcggta gaggggccag cgtagggtg   11100 ccggggctcc gggggcgaga tcttccaaca taaggcgatg atatccgtag atgtacctgg   11160
acatccaggt gatgccggcg gcggtggtgg aggcgcgcgg aaagtcgcgg acgcggttcc   11220
agatgttgcg cagcggcaaa aagtgctcca tggtcgggac gctctggccg gtcaggcgcg   11280
cgcaatcgtt gacgctctag cgtgcaaaag gagagcctgt aagcgggcac tcttccgtgg   11340
tctggtggat aaattcgcaa gggtatcatg gcggacgacc ggggttcgag ccccgtatcc   11400
ggccgtccgc cgtgatccat gcggttaccg cccgcgtgtc gaacccaggt gtgcgacgtc   11460
agacaacggg ggagtgctcc tttttggcttc cttccaggcg cggcggctgc tgcgctagct   11520
tttttggcca ctggccgcgc gcagcgtaag cggttaggct ggaaagcgaa agcattaagt   11580
ggctcgctcc ctgtagccgg agggttattt tccaagggtt gagtcgcggg accccggtt   11640 cgagtctcgg accggccgga ctgcggcgaa cgggggtttg cctccccgtc atgcaagacc   11700
ccgcttgcaa attcctccgg aaacagggac gagccccttt tttgctttc ccagatgcat   11760 ccggtgctgc ggcagatgcg ccccccctcct cagcagcggc aagagcaaga gcagcggcag   11820
acatgcaggg caccctcccc tcctcctacc gcgtcaggag gggcgacatc cgcggttgac   11880
gcggcagcag atggtgatta cgaaccccccg cggcgccggg cccggcacta cctggacttg   11940
gaggagggcg agggcctggc gcggctagga gcgccctctc ctgagcggca cccaagggtg   12000
cagctgaagc gtgatacgcg tgaggcgtac gtgccgcggc agaacctgtt tcgcgaccgc   12060
gagggagagg agcccgagga gatgcgggat cgaaagttcc acgcagggcg cgagctgcg   12120 catggcctga atcgcgagcg gttgctgcgc gaggaggact ttgagcccga cgcgcgaacc   12180
gggattagtc ccgcgcgcgc acacgtggcg gccgccgacc tggtaaccgc atacgagcag   12240
acggtgaacc aggagattaa ctttcaaaaa agctttaaca accacgtgcg tacgcttgtg   12300
gcgcgcgagg aggtggctat aggactgatg catctgtggg actttgtaag cgcgctggag   12360
caaaacccaa atagcaagcc gctcatggcg cagctgttcc ttatagtgca gcacagcagg   12420
gacaacgagg cattcaggga tgcgctgcta aacatagtag agcccgaggg ccgctggctg   12480
ctcgatttga taaacatcct gcagagcata gtggtgcagg agcgcagctt gagcctggct   12540
gacaaggtgg ccgccatcaa ctattccatg cttagcctgg gcaagtttta cgcccgcaag   12600
```

-continued

```
atataccata ccccttacgt tcccatagac aaggaggtaa agatcgaggg gttctacatg   12660
cgcatggcgc tgaaggtgct taccttgagc gacgacctgg gcgtttatcg caacgagcgc   12720
atccacaagg ccgtgagcgt gagccggcgg cgcgagctca gcgaccgcga gctgatgcac   12780
agcctgcaaa gggccctggc tggcacgggc agcggcgata gagaggccga gtcctacttt   12840
gacgcgggcg ctgacctgcg ctgggcccca agccgacgcg ccctggaggc agctggggcc   12900
ggacctgggc tggcggtggc acccgcgcgc gctggcaacg tcggcggcgt ggaggaatat   12960
gacgaggacg atgagtacga gccagaggac ggcgagtact aagcggtgat gtttctgatc   13020
agatgatgca agacgcaacg gacccggcgg tgcgggcggc gctgcagagc cagccgtccg   13080
gccttaactc cacggacgac tggcgccagg tcatggaccg catcatgtcg ctgactcgc   13140 gcaatcctga cgcgttccgg cagcagccgc aggccaaccg gctctccgca attctggaag   13200
cggtggtccc ggcgcgcgca aaccccacgc acgagaaggt gctggcgatc gtaaacgcgc   13260
tggccgaaaa cagggccatc cggcccgacg aggccggcct ggtctacgac gcgctgcttc   13320
agcgcgtggc tcgttacaac agcggcaacg tgcagaccaa cctggaccgg ctggtggggg   13380
atgtgcgcga ggccgtggcg cagcgtgagc gcgcgcagca gcagggcaac ctgggctcca   13440
tggttgcact aaacgccttc ctgagtacac agcccgccaa cgtgccgcgg ggacaggagg   13500
actacaccaa ctttgtgagc gcactgcggc taatggtgac tgagacaccg caaagtgagg   13560
tgtaccagtc tgggccagac tattttttcc agaccagtag acaaggcctg cagaccgtaa   13620
acctgagcca ggctttcaaa aacttgcagg ggctgtgggg ggtgcgggct cccacaggcg   13680
accgcgcgac cgtgtctagc ttgctgacgc ccaactcgcg cctgttgctg ctgctaatag   13740
cgcccttcac ggacagtggc agcgtgtccc gggacacata cctaggtcac ttgctgacac   13800
tgtaccgcga ggccataggt caggcgcatg tggacgagca tactttccag gagattacaa   13860
gtgtcagccg cgcgctgggg caggaggaca cgggcagcct ggaggcaacc ctaaactacc   13920
tgctgaccaa ccggcggcag aagatccccct cgttgcacag tttaaacagc gaggaggagc   13980
gcattttgcg ctacgtgcag cagagcgtga gccttaacct gatgcgcgac ggggtaacgc   14040
ccagcgtggc gctggacatg accgcgcgca acatggaacc gggcatgtat gcctcaaacc   14100
ggccgtttat caaccgccta atggactact tgcatcgcgc ggccgccgtg aaccccgagt   14160
atttcaccaa tgccatcttg aacccgcact ggctaccgcc ccctggtttc tacaccgggg   14220
gattcgaggt gcccgagggt aacgatggat tcctctggga cgacatagac gacagcgtgt   14280
tttccccgca accgcagacc ctgctagagt tgcaacagcg cgagcaggca gaggcggcgc   14340
tgcgaaagga aagcttccgc aggccaagca gcttgtccga tctaggcgct gcggccccgc   14400
ggtcagatgc tagtagccca tttccaagct tgataggggtc tcttaccagc actcgcacca   14460
cccgcccgcg cctgctgggc gaggaggagt acctaaacaa ctcgctgctg cagccgcagc   14520
gcgaaaaaaa cctgcctccg gcatttccca acaacgggat agagagccta gtggacaaga   14580
tgagtagatg gaagacgtac gcgcaggagc acagggacgt gccaggcccg cgcccgccca   14640
cccgtcgtca aaggcacgac cgtcagcggg gtctggtgtg ggaggacgat gactcggcag   14700
acgacagcag cgtcctggat ttgggaggga gtggcaaccc gtttgcgcac cttcgcccca   14760
ggctggggag aatgtttttaa aaaaaaaaaa gcatgatgca aaataaaaaa ctcaccaagg   14820
ccatggcacc gagcgttggt tttcttgtat tcccccttagt atgcggcgcg cggcgatgta   14880
tgaggaaggt cctcctccct cctacgagag tgtggtgagc gcggcgccag tggcggcggc   14940
gctgggttct cccttcgatg ctccctggga cccgccgttt gtgcctccgc ggtacctgcg   15000
```

-continued

```
gcctaccggg gggagaaaca gcatccgtta ctctgagttg gcacccctat tcgacaccac    15060
ccgtgtgtac ctggtggaca acaagtcaac ggatgtggca tccctgaact accagaacga    15120
ccacagcaac tttctgacca cggtcattca aaacaatgac tacagcccgg gggaggcaag    15180
cacacagacc atcaatcttg acgaccggtc gcactggggc ggcgacctga aaaccatcct    15240
gcataccaac atgccaaatg tgaacgagtt catgtttacc aataagttta aggcgcgggt    15300
gatggtgtcg cgcttgccta ctaaggacaa tcaggtggag ctgaaatacg agtgggtgga    15360
gttcacgctg cccgagggca actactccga gaccatgacc atagacctta tgaacaacgc    15420
gatcgtggag cactacttga aagtgggcag acagaacggg gttctggaaa gcgacatcgg    15480
ggtaaagttt gacacccgca acttcagact ggggtttgac cccgtcactg gtcttgtcat    15540
gcctggggta tatacaaacg aagccttcca tccagacatc attttgctgc caggatgcgg    15600
ggtggacttc acccacagcc gcctgagcaa cttgttgggc atccgcaagc ggcaaccctt    15660
ccaggagggc tttaggatca cctacgatga tctggagggt ggtaacattc ccgcactgtt    15720
ggatgtggac gcctaccagg cgagcttgaa agatgacacc gaacagggcg ggggtggcgc    15780
aggcggcagc aacagcagtg gcagcggcgc ggaagagaac tccaacgcgg cagccgcggc    15840
aatgcagccg gtggaggaca tgaacgatca tgccattcgc ggcgacacct ttgccacacg    15900
ggctgaggag aagcgcgctg aggccgaagc agcggccgaa gctgccgccc ccgctgcgca    15960
acccgaggtc gagaagcctc agaagaaacc ggtgatcaaa cccctgacag aggacagcaa    16020
gaaacgcagt tacaacctaa taagcaatga cagcaccttc acccagtacc gcagctggta    16080
ccttgcatac aactacggcg accctcagac cggaatccgc tcatggaccc tgctttgcac    16140
tcctgacgta acctgcggct cggagcaggt ctactggtcg ttgccagaca tgatgcaaga    16200
ccccgtgacc ttccgctcca cgcgccagat cagcaacttt ccggtggtgg cgccgagct    16260 gttgcccgtg cactccaaga gcttctacaa cgaccaggcc gtctactccc aactcatccg    16320
ccagtttacc tctctgaccc acgtgttcaa tcgctttccc gagaaccaga tttttggcgcg    16380 cccgccagcc cccaccatca ccaccgtcag tgaaaacgtt cctgctctca cagatcacgg    16440
gacgctaccg ctgcgcaaca gcatcggagg agtccagcga gtgaccatta ctgacgccag    16500
acgccgcacc tgcccctacg tttacaaggc cctgggcata gtctcgccgc gcgtcctatc    16560
gagccgcact ttttgagcaa gcatgtccat ccttatatcg cccagcaata acacaggctg    16620
gggcctgcgc ttcccaagca agatgtttgg cggggccaag aagcgctccg accaacaccc    16680
agtgcgcgtg cgcgggcact accgcgcgcc ctggggcgcg cacaaacgcg gccgcactgg    16740
gcgcaccacc gtcgatgacg ccatcgacgc ggtggtggag gaggcgcgca actacacgcc    16800
cacgccgcca ccagtgtcca cagtggacgc ggccattcag accgtggtgc gcggagcccg    16860
gcgctatgct aaaatgaaga acggcggag gcgcgtagca cgtcgccacc gccgccgacc    16920
cggcactgcc gcccaacgcg cggcggcggc cctgcttaac cgcgcacgtc gcaccggccg    16980
acgggcggcc atgcgggccg ctcgaaggct ggccgcgggt attgtcactg tgcccccag    17040 gtccaggcga cgagcggccg ccgcagcagc cgcggccatt agtgctatga ctcagggtcg    17100
caggggcaac gtgtattggg tgcgcgactc ggttagcggc ctgcgcgtgc ccgtgcgcac    17160 ccgcccccg cgcaactaga ttgcaagaaa aaactactta gactcgtact gttgtatgta    17220
tccagcggcg gcggcgcgca acgaagctat gtccaagcgc aaaatcaaag aagagatgct    17280
ccaggtcatc gcgccggaga tctatggccc cccgaagaag gaagagcagg attacaagcc    17340
```

```
ccgaaagcta aagcgggtca aaaagaaaaa gaaagatgat gatgatgaac ttgacgacga  17400
ggtggaactg ctgcacgcta ccgcgcccag gcgacgggta cagtggaaag gtcgacgcgt  17460
aaaacgtgtt ttgcgacccg gcaccaccgt agtctttacg cccggtgagc gctccacccg  17520
cacctacaag cgcgtgtatg atgaggtgta cggcgacgag gacctgcttg agcaggccaa  17580
cgagcgcctc ggggagtttg cctacggaaa gcggcataag gacatgctgg cgttgccgct  17640
ggacgagggc aacccaacac ctagcctaaa gcccgtaaca ctgcagcagg tgctgcccgc  17700
gcttgcaccg tccgaagaaa agcgcggcct aaagcgcgag tctggtgact tggcacccac  17760
cgtgcagctg atggtaccca agcgccagcg actggaagat gtcttggaaa aaatgaccgt  17820
ggaacctggg ctggagcccg aggtccgcgt gcggccaatc aagcaggtgg cgccgggact  17880
gggcgtgcag accgtggacg ttcagatacc cactaccagt agcaccagta ttgccaccgc  17940
cacagagggc atggagacac aaacgtcccc ggttgcctca gcggtggcgg atgccgcggt  18000
gcaggcggtc gctgcggccg cgtccaagac ctctacggag gtgcaaacgg acccgtggat  18060
gtttcgcgtt tcagcccccc ggcgcccgcg ccgttcgagg aagtacggcg ccgccagcgc  18120
gctactgccc gaatatgccc tacatccttc cattgcgcct accccggct atcgtggcta  18180 cacctaccgc cccagaagac gagcaactac ccgacgccga accaccactg gaacccgccg  18240
ccgccgtcgc cgtcgccagc ccgtgctggc cccgatttcc gtgcgcaggg tggctcgcga  18300
aggaggcagg accctggtgc tgccaacagc gcgctaccac cccagcatcg tttaaaagcc  18360
ggtctttgtg gttcttgcag atatggccct cacctgccgc ctccgtttcc cggtgccggg  18420
attccgagga agaatgcacc gtaggagggg catggccggc cacggcctga cgggcggcat  18480
gcgtcgtgcg caccaccggc ggcggcgcgc gtcgcaccgt cgcatgcgcg cggtatcct  18540 gcccctcctt attccactga tcgccgcggc gattggcgcc gtgcccggaa ttgcatccgt  18600
ggccttgcag gcgcagagac actgattaaa aacaagttgc atgtggaaaa atcaaaataa  18660
aaagtctgga ctctcacgct cgcttggtcc tgtaactatt ttgtagaatg gaagacatca  18720
actttgcgtc tctggccccg cgacacggct cgcgcccgtt catgggaaac tggcaagata  18780
tcggcaccag caatatgagc ggtggcgcct tcagctgggg ctcgctgtgg agcggcatta  18840
aaaatttcgg ttccaccgtt aagaactatg gcagcaaggc ctggaacagc agcacaggcc  18900
agatgctgag ggataagttg aaagagcaaa atttccaaca aaaggtggta gatggcctgg  18960
cctctggcat tagcggggtg gtggacctgg ccaaccaggc agtgcaaaat aagattaaca  19020
gtaagcttga tccccgccct cccgtagagg agcctccacc ggccgtggag acagtgtctc  19080
cagaggggcg tggcgaaaag cgtccgcgcc ccgacaggga agaaactctg gtgacgcaaa  19140
tagacgagcc tccctcgtac gaggaggcac taaagcaagg cctgcccacc acccgtccca  19200
tcgcgcccat ggctaccgga gtgctgggcc agcacacacc cgtaacgctg gacctgcctc  19260 ccccgccga cacccagcag aaacctgtgc tgccaggccc gaccgccgtt gttgtaaccc  19320
gtcctagccg cgcgtccctg cgccgcgccg ccagcggtcc gcgatcgttg cggcccgtag  19380
ccagtggcaa ctggcaaagc acactgaaca gcatcgtggg tctgggggtg caatccctga  19440 agcgccacg atgcttctga tagctaacgt gtcgtatgtg tgtcatgtat gcgtccatgt  19500
cgccgccaga ggagctgctg agccgccgcg cgcccgcttt ccaagatggc tacccttcg  19560 atgatgccgc agtggtctta catgcacatc tcgggccagg acgcctcgga gtacctgagc  19620
cccgggctgt gcagtttgc ccgcgccacc gagacgtact tcagcctgaa taacaagttt  19680 agaaaccca cggtggcgcc tacgcacgac gtgaccacag accggtccca gcgtttgacg  19740
```

-continued

```
ctgcggttca tccctgtgga ccgtgaggat actgcgtact cgtacaaggc gcggttcacc   19800
ctagctgtgg gtgataaccg tgtgctggac atggcttcca cgtactttga catccgcggc   19860
gtgctggaca ggggccctac tttaagccc tactctggca ctgcctacaa cgccctggct   19920
cccaagggtg ccccaaatcc ttgcgaatgg gatgaagctg ctactgctct tgaaataaac   19980
ctagaagaag aggacgatga caacgaagac gaagtagacg agcaagctga gcagcaaaaa   20040
actcacgtat ttgggcaggc gccttattct ggtataaata ttacaaagga gggtattcaa   20100
ataggtgtcg aaggtcaaac acctaaatat gccgataaaa catttcaacc tgaacctcaa   20160
ataggagaat ctcagtggta cgaaacagaa attaatcatg cagctgggag agtcctaaaa   20220
aagactaccc caatgaaacc atgttacggt tcatatgcaa aacccacaaa tgaaaatgga   20280
gggcaaggca ttcttgtaaa gcaacaaat ggaaagctag aaagtcaagt ggaaatgcaa   20340
tttttctcaa ctactgaggc agccgcaggc aatggtgata acttgactcc taaagtggta   20400
ttgtacagtg aagatgtaga tatagaaacc ccagacactc atatttctta catgcccact   20460
attaaggaag gtaactcacg agaactaatg ggccaacaat ctatgcccaa caggcctaat   20520
tacattgctt ttagggacaa ttttattggt ctaatgtatt acaacagcac gggtaatatg   20580
ggtgttctgg cgggccaagc atcgcagttg aatgctgttg tagatttgca agacagaaac   20640
acagagcttt cataccagct tttgcttgat tccattggtg atagaaccag gtacttttct   20700
atgtggaatc aggctgttga cagctatgat ccagatgtta gaattattga aaatcatgga   20760
actgaagatg aacttccaaa ttactgcttt ccactgggag gtgtgattaa tacagagact   20820
cttaccaagg taaaacctaa aacaggtcag gaaaatggat gggaaaaaga tgctacagaa   20880
ttttcagata aaaatgaaat aagagttgga aataattttg ccatggaaat caatctaaat   20940
gccaacctgt ggagaaattt cctgtactcc aacatagcgc tgtatttgcc cgacaagcta   21000
aagtacagtc cttccaacgt aaaaatttct gataacccaa acacctacga ctacatgaac   21060
aagcgagtgg tggctcccgg gctagtggac tgctacatta accttggagc acgctggtcc   21120
cttgactata tggacaacgt caacccattt aaccaccacc gcaatgctgg cctgcgctac   21180
cgctcaatgt tgctgggcaa tggtcgctat gtgcccttcc acatccaggt gcctcagaag   21240
ttctttgcca ttaaaaacct ccttctcctg ccgggctcat acacctacga gtggaacttc   21300
aggaaggatg ttaacatggt tctgcagagc tccctaggaa atgacctaag ggttgacgga   21360
gccagcatta gtttgatag catttgcctt tacgccacct tcttccccat ggcccacaac   21420
accgcctcca cgcttgaggc catgcttaga aacgacacca cgaccagtc ctttaacgac   21480 tatctctccg ccgccaacat gctctaccct atacccgcca acgctaccaa cgtgcccata   21540
tccatcccct cccgcaactg ggcggctttc cgcggctggg ccttcacgcg ccttaagact   21600
aaggaaaccc catcactggg ctcgggctac gacccttatt acacctactc tggctctata   21660
ccctacctag atggaacctt ttacctcaac cacaccttta agaaggtggc cattaccttt   21720
gactcttctg tcagctggcc tggcaatgac cgcctgctta cccccaacga gtttgaaatt   21780
aagcgctcag ttgacgggga gggttacaac gttgcccagt gtaacatgac caaagactgg   21840
ttcctggtac aaatgctagc taactataac attggctacc agggcttcta tatcccagag   21900
agctacaagg accgcatgta ctccttcttt agaaacttcc agcccatgag ccgtcaggtg   21960
gtggatgata ctaaatacaa ggactaccaa caggtgggca tcctacacca acacaacaac   22020
tctggatttg ttggctacct tgcccccacc atgcgcgaag acaggccta ccctgctaac   22080
```

-continued

```
ttcccctatc cgcttatagg caagaccgca gttgacagca ttacccagaa aaagtttctt  22140
tgcgatcgca ccctttggcg catcccattc tccagtaact ttatgtccat gggcgcactc  22200
acagacctgg gccaaaacct tctctacgcc aactccgccc acgcgctaga catgactttt  22260
gaggtggatc ccatggacga gcccaccctt ctttatgttt tgtttgaagt ctttgacgtg  22320
gtccgtgtgc accagccgca ccgcggcgtc atcgaaaccg tgtacctgcg cacgcccttc  22380
tcggccggca acgccacaac ataaagaagc aagcaacatc aacaacagct gccgccatgg  22440
gctccagtga gcaggaactg aaagccattg tcaaagatct tggttgtggg ccatattttt  22500
tgggcaccta tgacaagcgc tttccaggct ttgtttctcc acacaagctc gcctgcgcca  22560
tagtcaatac ggccggtcgc gagactgggg gcgtacactg gatggccttt gcctggaacc  22620
cgcactcaaa aacatgctac ctctttgagc cctttggctt ttctgaccag cgactcaagc  22680
aggtttacca gtttgagtac gagtcactcc tgcgccgtag cgccattgct tcttcccccg  22740
accgctgtat aacgctggaa aagtccaccc aaagcgtaca ggggcccaac tcggccgcct  22800
gtggactatt ctgctgcatg tttctccacg cctttgccaa ctggccccaa actcccatgg  22860
atcacaaccc caccatgaac cttattaccg gggtacccaa ctccatgctc aacagtcccc  22920
aggtacagcc caccctgcgt cgcaaccagg aacagctcta cagcttcctg gagcgccact  22980
cgccctactt ccgcagccac agtgcgcaga ttaggagcgc cacttctttt tgtcacttga  23040
aaaacatgta aaaataatgt actagagaca ctttcaataa aggcaaatgc ttttatttgt  23100
acactctcgg gtgattattt acccccaccc ttgccgtctg cgccgtttaa aaatcaaagg  23160
ggttctgccg cgcatcgcta tgcgccactg gcagggacac gttgcgatac tggtgtttag  23220
tgctccactt aaactcaggc acaaccatcc gcggcagctc ggtgaagttt tcactccaca  23280
ggctgcgcac catcaccaac gcgtttagca ggtcgggcgc cgatatcttg aagtcgcagt  23340
tggggcctcc gccctgcgcg cgcgagttgc gatacacagg gttgcagcac tggaacacta  23400
tcagcgccgg gtggtgcacg ctggccagca cgctcttgtc ggagatcaga tccgcgtcca  23460
ggtcctccgc gttgctcagg gcgaacggag tcaactttgg tagctgcctt cccaaaaagg  23520
gcgcgtgccc aggctttgag ttgcactcgc accgtagtgg catcaaaagg tgaccgtgcc  23580
cggtctgggc gttaggatac agcgcctgca taaaagcctt gatctgctta aaagccacct  23640
gagcctttgc gccttcagag aagaacatgc cgcaagactt gccggaaaac tgattggccg  23700
gacaggccgc gtcgtgcacg cagcaccttg cgtcggtgtt ggagatctgc accacatttc  23760
ggccccaccg gttcttcacg atcttggcct tgctagactg ctccttcagc gcgcgctgcc  23820
cgttttcgct cgtcacatcc atttcaatca cgtgctcctt atttatcata atgcttccgt  23880
gtagacactt aagctcgcct tcgatctcag cgcagcggtg cagccacaac gcgcagcccg  23940
tgggctcgtg atgcttgtag gtcacctctg caaacgactg caggtacgcc tgcaggaatc  24000
gccccatcat cgtcacaaag gtcttgttgc tggtgaaggt cagctgcaac ccgcggtgct  24060
cctcgttcag ccaggtcttg catacggccg ccagagcttc cacttggtca ggcagtagtt  24120
tgaagttcgc ctttagatcg ttatccacgt ggtacttgtc catcagcgcg cgcgcagcct  24180
ccatgccctt ctcccacgca gacacgatcg gcacactcag cgggttcatc accgtaattt  24240
cactttccgc ttcgctgggc tcttcctctt cctcttgcgt ccgcatacca cgcgccactg  24300
ggtcgtcttc attcagccgc cgcactgtgc gcttacctcc tttgccatgc ttgattagca  24360 ccggtgggt gctgaaaccc accatttgta gcgccacatc ttctctttct tcctcgctgt  24420
ccacgattac ctctggtgat ggcgggcgct cgggcttggg agaagggcgc ttcttttttct  24480
```

-continued

```
tcttgggcgc aatggccaaa tccgccgccg aggtcgatgg ccgcgggctg ggtgtgcgcg   24540
gcaccagcgc gtcttgtgat gagtcttcct cgtcctcgga ctcgatacgc cgcctcatcc   24600
gcttttttgg gggcgcccgg ggaggcggcg gcgacgggga cggggacgac acgtcctcca   24660
tggttggggg acgtcgcgcc gcaccgcgtc cgcgctcggg ggtggtttcg cgctgctcct   24720
cttcccgact ggccatttcc ttctcctata ggcagaaaaa gatcatggag tcagtcgaga   24780
agaaggacag cctaaccgcc ccctctgagt tcgccaccac cgcctccacc gatgccgcca   24840
acgcgcctac caccttcccc gtcgaggcac ccccgcttga ggaggaggaa gtgattatcg   24900
agcaggaccc aggtttttgta agcgaagacg acgaggaccg ctcagtacca acagaggata   24960
aaaagcaaga ccaggacaac gcagaggcaa acgaggaaca agtcgggcgg ggggacgaaa   25020
ggcatggcga ctacctagat gtgggagacg acgtgctgtt gaagcatctg cagcgccagt   25080
gcgccattat ctgcgacgcg ttgcaagagc gcagcgatgt gcccctcgcc atagcggatg   25140
tcagccttgc ctacgaacgc cacctattct caccgcgcgt accccccaaa cgccaagaaa   25200
acggcacatg cgagcccaac ccgcgcctca acttctaccc cgtatttgcc gtgccagagg   25260
tgcttgccac ctatcacatc ttttttccaaa actgcaagat acccctatcc tgccgtgcca   25320
accgcagccg agcggacaag cagctggcct tgcggcaggg cgctgtcata cctgatatcg   25380
cctcgctcaa cgaagtgcca aaaatctttg agggtcttgg acgcgacgag aagcgcgcgg   25440
caaacgctct gcaacaggaa aacagcgaaa atgaaagtca ctctggagtg ttggtggaac   25500
tcgagggtga caacgcgcgc ctagccgtac taaaacgcag catcgaggtc acccactttg   25560
cctacccggc acttaaccta ccccccaagg tcatgagcac agtcatgagt gagctgatcg   25620
tgcgccgtgc gcagcccctg gagagggatg caaatttgca agaacaaaca gaggagggcc   25680
tacccgcagt tggcgacgag cagctagcgc gctggcttca aacgcgcgag cctgccgact   25740
tggaggagcg acgcaaacta atgatggccg cagtgctcgt taccgtggag cttgagtgca   25800
tgcagcggtt ctttgctgac ccggagatgc agcgcaagct agaggaaaca ttgcactaca   25860
cctttcgaca gggctacgta cgccaggcct gcaagatctc caacgtggag ctctgcaacc   25920
tggtctccta ccttggaatt ttgcacgaaa accgccttgg gcaaaacgtg cttcattcca   25980
cgctcaaggg cgaggcgcgc cgcgactacg tccgcgactg cgtttactta tttctatgct   26040
acacctggca gacggccatg ggcgtttggc agcagtgctt ggaggagtgc aacctcaagg   26100
agctgcagaa actgctaaag caaaacttga aggacctatg gacggccttc aacgagcgct   26160
ccgtggccgc gcacctggcg gacatcattt tccccgaacg cctgcttaaa accctgcaac   26220
agggtctgcc agacttcacc agtcaaagca tgttgcagaa ctttaggaac tttatcctag   26280
agcgctcagg aatcttgccc gccacctgct gtgcacttcc tagcgacttt gtgcccatta   26340
agtaccgcga atgccctccg ccgctttggg gccactgcta ccttctgcag ctagccaact   26400
accttgccta ccactctgac ataatggaag acgtgagcgg tgacggtcta ctggagtgtc   26460
actgtcgctg caacctatgc acccccgcacc gctccctggt ttgcaattcg cagctgctta   26520
acgaaagtca aattatcggt acctttgagc tgcagggtcc ctcgcctgac gaaaagtccg   26580
cggctccggg gttgaaactc actccggggc tgtggacgtc ggcttacctt cgcaaatttg   26640
tacctgagga ctaccacgcc cacgagatta ggttctacga agaccaatcc cgcccgccta   26700
atgcggagct taccgcctgc gtcattaccc agggccacat tcttggccaa ttgcaagcca   26760
tcaacaaagc ccgccaagag tttctgctac gaaagggacg ggggtttac ttggacccccc   26820
```

-continued

```
agtccggcga ggagctcaac ccaatccccc cgccgccgca gccctatcag cagcagccgc   26880
gggcccttgc ttcccaggat ggcacccaaa aagaagctgc agctgccgcc gccacccacg   26940
gacgaggagg aatactggga cagtcaggca gaggaggttt tggacgagga ggaggaggac   27000
atgatggaag actgggagag cctagacgag gaagcttccg aggtcgaaga ggtgtcagac   27060
gaaacaccgt caccctcggt cgcattcccc tcgccggcgc cccagaaatc ggcaaccggt   27120
tccagcatgg ctacaacctc cgctcctcag gcgccgccgg cactgcccgt tcgccgaccc   27180
aaccgtagat gggacaccac tggaaccagg gccggtaagt ccaagcagcc gccgccgtta   27240
gcccaagagc aacaacagcg ccaaggctac cgctcatggc gcgggcacaa gaacgccata   27300
gttgcttgct tgcaagactg tggggggcaac atctccttcg cccgccgctt tcttctctac   27360
catcacggcg tggccttccc ccgtaacatc ctgcattact accgtcatct ctacagccca   27420
tactgcaccg gcggcagcgg cagcaacagc agcggccaca cagaagcaaa ggcgaccgga   27480
tagcaagact ctgacaaagc ccaagaaatc cacagcggcg gcagcagcag gaggaggagc   27540
gctgcgtctg gcgcccaacg aacccgtatc gacccgcgag cttagaaaca ggatttttcc   27600
cactctgtat gctatatttc aacagagcag gggccaagaa caagagctga aaataaaaaa   27660
caggtctctg cgatccctca cccgcagctg cctgtatcac aaaagcgaag atcagcttcg   27720
gcgcacgctg gaagacgcgg aggctctctt cagtaaatac tgcgcgctga ctcttaagga   27780
ctagtttcgc gccctttctc aaatttaagc gcgaaaacta cgtcatctcc agcggccaca   27840
cccggcgcca gcacctgttg tcagcgccat tatgagcaag gaaattccca cgccctacat   27900
gtggagttac cagccacaaa tgggacttgc ggctggagct gcccaagact actcaacccg   27960
aataaactac atgagcgcgg gaccccacat gatatcccgg gtcaacggaa tacgcgccca   28020
ccgaaaccga attctcctgg aacaggcggc tattaccacc acacctcgta ataaccttaa   28080
tccccgtagt tggcccgctg ccctggtgta ccaggaaagt cccgctccca ccactgtggt   28140
acttcccaga gacgcccagg ccgaagttca gatgactaac tcaggggcgc agcttgcggg   28200
cggctttcgt cacagggtgc ggtcgcccgg gcagggtata actcacctga caatcagagg   28260
gcgaggtatt cagctcaacg acgagtcggt gagctcctcg cttggtctcc gtccggacgg   28320
gacatttcag atcggcggcg ccggccgctc ttcattcacg cctcgtcagg caatcctaac   28380
tctgcagacc tcgtcctctg agccgcgctc tggaggcatt ggaactctgc aatttattga   28440
ggagtttgtg ccatcggtct actttaaccc cttctcggga cctcccggcc actatccgga   28500
tcaatttatt cctaactttg acgcggtaaa ggactcggcg gacggctacg actgaatgtt   28560
aagtggagag gcagagcaac tgcgcctgaa acacctggtc cactgtcgcc gccacaagtg   28620
ctttgcccgc gactccggtg agttttgcta ctttgaattg cccgaggatc atatcgaggg   28680
cccggcgcac ggcgtccggc ttaccgccca gggagagctt gcccgtagcc tgattcggga   28740
gtttacccag cgcccctgc tagttgagcg ggacagggga ccctgtgttc tcactgtgat   28800
ttgcaactgt cctaaccctg gattacatca agatcctcta gttaatgtca ggtcgcctaa   28860
gtcgattaac tagagtaccc ggggatctta ttccctttaa ctaataaaaa aaataataa   28920 agcatcactt acttaaaatc agttagcaaa tttctgtcca gttattcag cagcacctcc   28980 ttgccctcct cccagctctg gtattgcagc ttcctcctgg ctgcaaactt tctccacaat   29040
ctaaatggaa tgtcagtttc ctcctgttcc tgtccatccg cacccactat cttcatgttg   29100
ttgcagatga agcgcgcaag accgtctgaa gataccttca accccgtgta tccatatgac   29160
acggaaaccg gtcctccaac tgtgcctttt cttactcctc cctttgtatc ccccaatggg   29220
```

-continued

```
tttcaagaga gtccccctgg ggtactctct ttgcgcctat ccgaacctct agttacctcc   29280
aatggcatgc ttgcgctcaa aatgggcaac ggcctctctc tggacgaggc cggcaacctt   29340
acctcccaaa atgtaaccac tgtgagccca cctctcaaaa aaaccaagtc aaacataaac   29400
ctggaaatat ctgcacccct cacagttacc tcagaagccc taactgtggc tgccgccgca   29460
cctctaatgg tcgcgggcaa cacactcacc atgcaatcac aggccccgct aaccgtgcac   29520
gactccaaac ttagcattgc cacccaagga cccctcacag tgtcagaagg aaagctagcc   29580
ctgcaaacat caggcccccct caccaccacc gatagcagta cccttactat cactgcctca   29640 cccccctctaa ctactgccac tggtagcttg ggcattgact tgaaagagcc catttataca   29700
caaaatggaa aactaggact aaagtacggg gctcctttgc atgtaacaga cgacctaaac   29760
actttgaccg tagcaactgg tccaggtgtg actattaata atacttcctt gcaaactaaa   29820
gttactggag ccttgggttt tgattcacaa ggcaatatgc aacttaatgt agcaggagga   29880
ctaaggattg attctcaaaa cagacgcctt atacttgatg ttagttatcc gtttgatgct   29940
caaaaccaac taaatctaag actaggacag ggccctcttt ttataaactc agcccacaac   30000
ttggatatta actacaacaa aggcctttac ttgtttacag cttcaaacaa ttccaaaaag   30060
cttgaggtta acctaagcac tgccaagggg ttgatgtttg acgctacagc catagccatt   30120
aatgcaggag atgggcttga atttggttca cctaatgcac caaacacaaa tccccctcaaa   30180 acaaaaattg gccatggcct agaatttgat tcaaacaagg ctatggttcc taaactagga   30240
actggcctta gttttgacag cacaggtgcc attacagtag gaaacaaaaa taatgataag   30300
ctaactttgt ggaccggaat aaaccctcca cctaactgtc aaattgtgga aaacactaat   30360
acaaatgatg gcaaacttac tttagtatta gtaaaaaatg gagggcttgt taatggctac   30420
gtgtctctag ttggtgtatc agacactgtg aaccaaatgt tcacacaaaa gacagcaaac   30480
atccaattaa gattatattt tgactcttct ggaaatctat taactgagga atcagactta   30540
aaaattccac ttaaaaataa atcttctaca gcgaccagtg aaactgtagc cagcagcaaa   30600
gcctttatgc caagtactac agcttatccc ttcaacacca ctactaggga tagtgaaaac   30660
tacattcatg gaatatgtta ctacatgact agttatgata gaagtctatt tcccttgaac   30720
atttctataa tgctaaacag ccgtatgatt tcttccaatg ttgcctatgc catacaattt   30780
gaatggaatc taaatgcaag tgaatctcca gaaagcaaca tagctacgct gaccacatcc   30840
ccctttttct tttcttacat tacagaagac gacaactaaa gaatcgtttg tgttatgttt   30900
caacgtgttt atttttcaat tgcagaaaat ttcaagtcat ttttcattca gtagtatagc   30960
cccaccacca catagcttat acagatcacc gtaccttaat caaactcaca gaaccctagt   31020
attcaacctg ccacctccct cccaacacac agagtacaca gtcctttctc cccggctggc   31080
cttaaaaagc atcatatcat gggtaacaga catattctta ggtgttatat tccacacggt   31140
ttcctgtcga gccaaacgct catcagtgat attaataaac tccccgggca gctcacttaa   31200
gttcatgtcg ctgtccagct gctgagccac aggctgctgt ccaacttgcg gttgcttaac   31260
gggcggcgaa ggagaagtcc acgcctacat gggggtagag tcataatcgt gcatcaggat   31320
agggcggtgg tgctgcagca gcgcgcgaat aaactgctgc cgccgccgct ccgtcctgca   31380
ggaatacaac atggcagtgg tctcctcagc gatgattcgc accgcccgca gcataaggcg   31440
ccttgtcctc cgggcacagc agcgcaccct gatctcactt aaatcagcac agtaactgca   31500
gcacagcacc acaatattgt tcaaaatccc acagtgcaag gcgctgtatc caaagctcat   31560
```

```
ggcggggacc acagaaccca cgtggccatc ataccacaag cgcaggtaga ttaagtggcg    31620
acccctcata aacacgctgg acataaacat tacctctttt ggcatgttgt aattcaccac    31680
ctcccggtac catataaacc tctgattaaa catggcgcca tccaccacca tcctaaacca    31740
gctggccaaa acctgcccgc cggctataca ctgcagggaa ccgggactgg aacaatgaca    31800
gtggagagcc caggactcgt aaccatggat catcatgctc gtcatgatat caatgttggc    31860
acaacacagg cacacgtgca tacacttcct caggattaca agctcctccc gcgttagaac    31920
catatcccag ggaacaaccc attcctgaat cagcgtaaat cccacactgc agggaagacc    31980
tcgcacgtaa ctcacgttgt gcattgtcaa agtgttacat tcgggcagca gcggatgatc    32040
ctccagtatg gtagcgcggg tttctgtctc aaaaggaggt agacgatccc tactgtacgg    32100
agtgcgccga gacaaccgag atcgtgttgg tcgtagtgtc atgccaaatg gaacgccgga    32160
cgtagtcata tttcctgaag caaaaccagg tgcgggcgtg acaaacagat ctgcgtctcc    32220
ggtctcgccg cttagatcgc tctgtgtagt agttgtagta tatccactct ctcaaagcat    32280
ccaggcgccc cctggcttcg ggttctatgt aaactccttc atgcgccgct gccctgataa    32340
catccaccac cgcagaataa gccacaccca gccaacctac acattcgttc tgcgagtcac    32400
acacgggagg agcgggaaga gctggaagaa ccatgttttt tttttattc caaaagatta    32460 tccaaaacct caaaatgaag atctattaag tgaacgcgct cccctccggt ggcgtggtca    32520
aactctacag ccaaagaaca gataatggca tttgtaagat gttgcacaat ggcttccaaa    32580
aggcaaacgg ccctcacgtc caagtggacg taaaggctaa acccttcagg gtgaatctcc    32640
tctataaaca ttccagcacc ttcaaccatg cccaaataat tctcatctcg ccaccttctc    32700
aatatatctc taagcaaatc ccgaatatta agtccggcca ttgtaaaaat ctgctccaga    32760
gcgccctcca ccttcagcct caagcagcga atcatgattg caaaaattca ggttcctcac    32820
agacctgtat aagattcaaa agcggaacat taacaaaaat accgcgatcc cgtaggtccc    32880
ttcgcagggc cagctgaaca taatcgtgca ggtctcacg gaccagcgcg gccacttccc    32940
cgccaggaac catgacaaaa gaacccacac tgattatgac acgcatactc ggagctatgc    33000
taaccagcgt agccccgatg taagcttgtt gcatgggcgg cgatataaaa tgcaaggtgc    33060
tgctcaaaaa atcaggcaaa gcctcgcgca aaaagaaag cacatcgtag tcatgctcat    33120
gcagataaag gcaggtaagc tccggaacca ccacagaaaa agacaccatt tttctctcaa    33180
acatgtctgc gggtttctgc ataaacacaa aataaaataa caaaaaaaca tttaaacatt    33240
agaagcctgt cttacaacag gaaaaacaac ccttataagc ataagacgga ctacggccat    33300
gccggcgtga ccgtaaaaaa actggtcacc gtgattaaaa agcaccaccg acagctcctc    33360
ggtcatgtcc ggagtcataa tgtaagactc ggtaaacaca tcaggttgat tcacatcggt    33420
cagtgctaaa aagcgaccga aatagcccgg gggaatacat acccgcaggc gtagagacaa    33480
cattacagcc cccataggag gtataacaaa attaatagga gagaaaaaca cataaacacc    33540
tgaaaaaccc tcctgcctag gcaaaatagc accctcccgc tccagaacaa catacagcgc    33600
ttccacagcg gcagccataa cagtcagcct taccagtaaa aagaaaaacc tattaaaaaa    33660
acaccactcg acacggcacc agctcaatca gtcacagtgt aaaaaagggc caagtgcaga    33720
gcgagtatat ataggactaa aaaatgacgt aacggttaaa gtccacaaaa aacacccaga    33780
aaaccgcacg cgaacctacg cccagaaacg aaagccaaaa aacccacaac ttcctcaaat    33840
cgtcacttcc gttttcccac gttacgtcac ttcccatttt aagaaaacta caattcccaa    33900
cacatacaag ttactccgcc ctaaaaccta cgtcacccgc cccgttccca cgccccgcgc    33960
```

-continued

```
cacgtcacaa actccacccc ctcattatca tattggcttc aatccaaaat aaggtatatt    34020
attgatgatg                                                           34030

<210> SEQ ID NO 2
<211> LENGTH: 9858
<212> TYPE: DNA
<213> ORGANISM: Artificial Sequence
<220> FEATURE:
<223> OTHER INFORMATION: pCMV3-SARS-CoV2(Spike ORF)

<400> SEQUENCE: 2
gacggatcgg gagatctccc gatcccctat ggtgcactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg agtacattta tattggctca tgtccaatat     240
gaccgccatg ttgacattga ttattgacta gttattaata gtaatcaatt acggggtcat     300
tagttcatag cccatatatg gagttccgcg ttacataact tacggtaaat ggcccgcctg     360
gctgaccgcc caacgacccc cgcccattga cgtcaataat gacgtatgtt cccatagtaa     420
cgccaatagg gactttccat tgacgtcaat gggtggagta tttacggtaa actgcccact     480
tggcagtaca tcaagtgtat catatgccaa gtccgccccc tattgacgtc aatgacggta     540
aatggcccgc ctggcattat gcccagtaca tgaccttacg gactttcct acttggcagt     600 acatctacgt attagtcatc gctattacca tggtgatgcg gttttggcag tacaccaatg     660
ggcgtggata gcggtttgac tcacggggat ttccaagtct ccaccccatt gacgtcaatg     720
ggagtttgtt ttggcaccaa aatcaacggg actttccaaa atgtcgtaat aaccccgccc     780
cgttgacgca aatgggcggt aggcgtgtac ggtgggaggt ctatataagc agagctcgtt     840
tagtgaaccg tcagatcctc actctcttcc gcatcgctgt ctgcgagggc cagctgttgg     900
gctcgcggtt gaggacaaac tcttcgcggt ctttccagta ctcttggatc ggaaacccgt     960
cggcctccga acggtactcc gccaccgagg acctgagcg agtccgcatc gaccggatcg    1020
gaaaacctct cgagaaaggc gtctaaccag tcacagtcgc aaggtaggct gagcaccgtg    1080
gcgggcggca gcgggtggcg gtcggggttg tttctggcgg aggtgctgct gatgatgtaa    1140
ttaaagtagg cggtcttgag acggcggatg tcgaggtga ggtgtggcag gcttgagatc    1200
cagctgttgg ggtgagtact ccctctcaaa agcgggcatt acttctgcgc taagattgtc    1260
agtttccaaa aacgaggagg atttgatatt cacctggccc gatctggcca tacacttgag    1320
tgacaatgac atccactttg cctttctctc cacaggtgtc cactcccagg tccaagttta    1380
aactttaata cgactcacta tagggccgc caccaagctt ggtaccatgt ttgtgttcct    1440
ggtgctgctg ccactggtgt ccagccagtg tgtgaacctg accaccagga cccaacttcc    1500
tcctgcctac accaactcct tcaccagggg agtctactac cctgacaagg tgttcaggtc    1560
ctctgtgctg cacagcaccc aggacctgtt cctgccattc ttcagcaatg tgacctggtt    1620
ccatgccatc catgtgtctg gcaccaatgg caccaagagg tttgacaacc ctgtgctgcc    1680
attcaatgat ggagtctact ttgccagcac agagaagagc aacatcatca ggggctggat    1740
ttttggcacc accctggaca gcaagaccca gtccctgctg attgtgaaca atgccaccaa    1800
tgtggtgatt aaggtgtgtg agttccagtt ctgtaatgac ccattcctgg agtctactata   1860 ccacaagaac aacaagtcct ggatggagtc tgagttcagg gtctactcct ctgccaacaa    1920
```

-continued

```
ctgtaccttt gaatatgtga gccaaccatt cctgatggac ttggagggca agcagggcaa    1980
cttcaagaac ctgagggagt ttgtgttcaa gaacattgat ggctacttca agatttacag    2040
caaacacaca ccaatcaacc tggtgaggga cctgccacag ggcttctctg ccttggaacc    2100
actggtggac ctgccaattg gcatcaacat caccaggttc cagaccctgc tggctctgca    2160
caggtcctac ctgacacctg gagactcctc ctctggctgg acagcaggag cagcagccta    2220
ctatgtgggc tacctccaac caaggacctt cctgctgaaa tacaatgaga atggcaccat    2280
cacagatgct gtggactgtg ccctggaccc actgtctgag accaagtgta ccctgaaatc    2340
cttcacagtg gagaagggca tctaccagac cagcaacttc agggtccaac caacagagag    2400
cattgtgagg tttccaaaca tcaccaacct gtgtccattt ggagaggtgt tcaatgccac    2460
caggtttgcc tctgtctatg cctggaacag gaagaggatt agcaactgtg tggctgacta    2520
ctctgtgctc tacaactctg cctccttcag caccttcaag tgttatggag tgagcccaac    2580
caaactgaat gacctgtgtt tcaccaatgt ctatgctgac tcctttgtga ttaggggaga    2640
tgaggtgaga cagattgccc ctggacaaac aggcaagatt gctgactaca actacaaact    2700
gcctgatgac ttcacaggct gtgtgattgc ctggaacagc aacaacctgg acagcaaggt    2760
gggaggcaac tacaactacc tctacagact gttcaggaag agcaacctga aaccatttga    2820
gagggacatc agcacagaga tttaccaggc tggcagcaca ccatgtaatg gagtggaggg    2880
cttcaactgt tactttccac tccaatccta tggcttccaa ccaaccaatg gagtgggcta    2940
ccaaccatac agggtggtgg tgctgtcctt tgaactgctc catgcccctg ccacagtgtg    3000
tggaccaaag aagagcacca acctggtgaa gaacaagtgt gtgaacttca acttcaatgg    3060
actgacaggc acaggagtgc tgacagagag caacaagaag ttcctgccat tccaacagtt    3120
tggcagggac attgctgaca ccacagatgc tgtgagggac ccacagacct ggagattct    3180 ggacatcaca ccatgttcct ttggaggagt gtctgtgatt acacctggca ccaacaccag    3240
caaccaggtg gctgtgctct accaggatgt gaactgtact gaggtgcctg tggctatcca    3300
tgctgaccaa cttacaccaa cctggagggt ctacagcaca ggcagcaatg tgttccagac    3360
cagggctggc tgtctgattg gagcagagca tgtgaacaac tcctatgagt gtgacatccc    3420
aattggagca ggcatctgtg cctcctacca gacccagacc atcctcaggt ctgtggcaag    3480
ccagagcatc attgcctaca caatgagtct gggagcagag aactctgtgg cttacagcaa    3540
caacagcatt gccatcccaa ccaacttcac catctctgtg accacagaga ttctgcctgt    3600
gagtatgacc aagacctctg tggactgtac aatgtatatc tgtggagaca gcacagagtg    3660
tagcaacctg ctgctccaat atggctcctt ctgtacccaa cttaacaggg ctctgacagg    3720
cattgctgtg gaacaggaca agaacaccca ggaggtgttt gcccaggtga agcagattta    3780
caagacacct ccaatcaagg actttggagg cttcaacttc agccagattc tgcctgaccc    3840
aagcaagcca agcaagaggt ccttcattga ggacctgctg ttcaacaagg tgaccctggc    3900
tgatgctggc ttcatcaagc aatatggaga ctgtctggga gacattgctg ccaggacct    3960 gatttgtgcc cagaagttca atggactgac agtgctgcct ccactgctga cagatgagat    4020
gattgcccaa tacacctctg ccctgctggc tggcaccatc acctctggct ggacctttgg    4080
agcaggagca gccctccaaa tcccatttgc tatgcagatg gcttacaggt tcaatggcat    4140
tggagtgacc cagaatgtgc tctatgagaa ccagaaactg attgccaacc agttcaactc    4200
tgccattggc aagattcagg actccctgtc cagcacagcc tctgccctgg gcaaactcca    4260
agatgtggtg aaccagaatg cccaggctct gaacaccctg gtgaagcaac tttccagcaa    4320
```

-continued

```
ctttggagcc atctcctctg tgctgaatga catcctgagc agactggaca aggtggaggc    4380
tgaggtccag attgacagac tgattacagg cagactccaa tccctccaaa cctatgtgac    4440
ccaacaactt atcagggctg ctgagattag ggcatctgcc aacctggctg ccaccaagat    4500
gagtgagtgt gtgctgggac aaagcaagag ggtggacttc tgtggcaagg gctaccacct    4560
gatgagtttt ccacagtctg cccctcatgg agtggtgttc ctgcatgtga cctatgtgcc    4620
tgcccaggag aagaacttca ccacagcccc tgccatctgc catgatggca aggctcactt    4680
tccaagggag ggagtgtttg tgagcaatgg cacccactgg tttgtgaccc agaggaactt    4740
ctatgaacca cagattatca ccacagacaa cacctttgtg tctggcaact gtgatgtggt    4800
gattggcatt gtgaacaaca cagtctatga cccactccaa cctgaactgg actccttcaa    4860
ggaggaactg gacaaatact tcaagaacca caccagccct gatgtggacc tgggagacat    4920
ctctggcatc aatgcctctg tggtgaacat ccagaaggag attgacagac tgaatgaggt    4980
ggctaagaac ctgaatgagt ccctgattga cctccaagaa ctgggcaaat atgaacaata    5040
catcaagtgg ccatggtaca tctggctggg cttcattgct ggactgattg ccattgtgat    5100
ggtgaccata atgctgtgtt gtatgacctc ctgttgttcc tgtctgaaag gctgttgttc    5160
ctgtggctcc tgttgtaagt ttgatgagga tgactctgaa cctgtgctga aaggagtgaa    5220
actgcactac acctgatcta gagcggccgc cgaattcggg cccgtttaaa cccgctgatc    5280
agcctcgact gtgccttcta gttgccagcc atctgttgtt tgcccctccc ccgtgccttc    5340
cttgaccctg gaaggtgcca ctcccactgt cctttcctaa taaaatgagg aaattgcatc    5400
gcattgtctg agtaggtgtc attctattct ggggggtggg gtggggcagg acagcaaggg    5460
ggaggattgg gaagacaata gcaggcatgc tggggatgcg gtgggctcta tggcttctga    5520
ggcggaaaga accagctggg gctctagggg gtatccccac gcgccctgta gcggcgcatt    5580
aagcgcggcg ggtgtggtgg ttacgcgcag cgtgaccgct acacttgcca gcgccctagc    5640
gcccgctcct ttcgctttct tcccttcctt tctcgccacg ttcgccggct ttccccgtca    5700
agctctaaat cggggctcc ctttagggtt ccgatttagt gctttacggc acctcgaccc    5760
caaaaaactt gattagggtg atggttcacg tagtgggcca tcgccctgat agacggtttt    5820 tcgcccttg acgttggagt ccacgttctt taatagtgga ctcttgttcc aaactggaac    5880
aacactcaac cctatctcgg tctattcttt tgatttataa gggattttgc cgatttcggc    5940
ctattggtta aaaaatgagc tgatttaaca aaaatttaac gcgaattaat tctgtggaat    6000
gtgtgtcagt tagggtgtgg aaagtcccca ggctccccag caggcagaag tatgcaaagc    6060
atgcatctca attagtcagc aaccaggtgt ggaaagtccc caggctcccc agcaggcaga    6120
agtatgcaaa gcatgcatct caattagtca gcaaccatag tcccgcccct aactccgccc    6180
atcccgcccc taactccgcc cagttccgcc cattctccgc cccatggctg actaattttt    6240
tttatttatg cagaggccga ggccgcctct gcctctgagc tattccagaa gtagtgagga    6300
ggcttttttg gaggcctagg cttttgcaaa aagctcccgg gagcttgtat atccattttc    6360
ggatctgatc agcacgtgat gaaaaagcct gaactcaccg cgacgtctgt cgagaagttt    6420
ctgatcgaaa agttcgacag cgtctccgac ctgatgcagc tctcggaggg cgaagaatct    6480
cgtgctttca gcttcgatgt aggagggcgt ggatatgtcc tgcgggtaaa tagctgcgcc    6540
gatggtttct acaaagatcg ttatgtttat cggcactttg catcggccgc gctcccgatt    6600
ccggaagtgc ttgacattgg ggaattcagc gagagcctga cctattgcat ctcccgccgt    6660
```

-continued

```
gcacagggtg tcacgttgca agacctgcct gaaaccgaac tgcccgctgt tctgcagccg    6720
gtcgcggagg ccatggatgc gatcgctgcg gccgatctta gccagacgag cgggttcggc    6780
ccattcggac cgcaaggaat cggtcaatac actacatggc gtgatttcat atgcgcgatt    6840
gctgatcccc atgtgtatca ctggcaaact gtgatggacg acaccgtcag tgcgtccgtc    6900
gcgcaggctc tcgatgagct gatgctttgg gccgaggact gccccgaagt ccggcacctc    6960
gtgcacgcgg atttcggctc caacaatgtc ctgacggaca atggccgcat aacagcggtc    7020
attgactgga gcgaggcgat gttcggggat tcccaatacg aggtcgccaa catcttcttc    7080
tggaggccgt ggttggcttg tatggagcag cagacgcgct acttcgagcg gaggcatccg    7140
gagcttgcag gatcgccgcg gctccgggcg tatatgctcc gcattggtct tgaccaactc    7200
tatcagagct tggttgacgg caatttcgat gatgcagctt gggcgcaggg tcgatgcgac    7260
gcaatcgtcc gatccggagc cgggactgtc gggcgtacac aaatcgcccg cagaagcgcg    7320
gccgtctgga ccgatggctg tgtagaagta ctcgccgata gtggaaaccg acgccccagc    7380
actcgtccga gggcaaagga atagcacgtg ctacgagatt tcgattccac cgccgccttc    7440
tatgaaaggt tgggcttcgg aatcgttttc cgggacgccg gctggatgat cctccagcgc    7500
ggggatctca tgctggagtt cttcgcccac cccaacttgt ttattgcagc ttataatggt    7560
tacaaataaa gcaatagcat cacaaatttc acaaataaag catttttttc actgcattct    7620
agttgtggtt tgtccaaact catcaatgta tcttatcatg tctgtatacc gtcgacctct    7680
agctagagct tggcgtaatc atggtcatag ctgtttcctg tgtgaaattg ttatccgctc    7740
acaattccac acaacatacg agccggaagc ataaagtgta aagcctgggg tgcctaatga    7800
gtgagctaac tcacattaat tgcgttgcgc tcactgcccg ctttccagtc gggaaacctg    7860
tcgtgccagc tgcattaatg aatcggccaa cgcgcgggga gaggcggttt gcgtattggg    7920
cgctcttccg cttcctcgct cactgactcg ctgcgctcgg tcgttcggct gcggcgagcg    7980
gtatcagctc actcaaaggc ggtaatacgg ttatccacag aatcagggga taacgcagga    8040
aagaacatgt gagcaaaagg ccagcaaaag gccaggaacc gtaaaaaggc cgcgttgctg    8100
gcgtttttcc ataggctccg cccccctgac gagcatcaca aaaatcgacg ctcaagtcag    8160
aggtggcgaa acccgacagg actataaaga taccaggcgt ttccccctgg aagctccctc    8220
gtgcgctctc ctgttccgac cctgccgctt accggatacc tgtccgcctt tctcccttcg    8280
ggaagcgtgg cgctttctca tagctcacgc tgtaggtatc tcagttcggt gtaggtcgtt    8340
cgctccaagc tgggctgtgt gcacgaaccc cccgttcagc ccgaccgctg cgccttatcc    8400
ggtaactatc gtcttgagtc caacccggta agacacgact tatcgccact ggcagcagcc    8460
actggtaaca ggattagcag agcgaggtat gtaggcggtg ctacagagtt cttgaagtgg    8520
tggcctaact acggctacac tagaagaaca gtatttggta tctgcgctct gctgaagcca    8580
gttaccttcg gaaaaagagt tggtagctct tgatccggca aacaaaccac cgctggtagc    8640
ggtttttttg tttgcaagca gcagattacg cgcagaaaaa aaggatctca agaagatcct    8700
ttgatctttt ctacggggtc tgacgctcag tggaacgaaa actcacgtta agggattttg    8760
gtcatgagat tatcaaaaag gatcttcacc tagatccttt taaattaaaa atgaagtttt    8820
aaatcaatct aaagtatata tgagtaaact tggtctgaca gttaccaatg cttaatcagt    8880
gaggcaccta tctcagcgat ctgtctattt cgttcatcca tagttgcctg actccccgtc    8940
gtgtagataa ctacgatacg ggagggctta ccatctggcc ccagtgctgc aatgataccg    9000
cgagacccac gctcaccggc tccagattta tcagcaataa accagccagc cggaagggcc    9060
```

-continued

```
gagcgcagaa gtggtcctgc aactttatcc gcctccatcc agtctattaa ttgttgccgg      9120
gaagctagag taagtagttc gccagttaat agtttgcgca acgttgttgc cattgctaca      9180
ggcatcgtgg tgtcacgctc gtcgtttggt atggcttcat tcagctccgg ttcccaacga      9240
tcaaggcgag ttacatgatc ccccatgttg tgcaaaaaag cggttagctc cttcggtcct      9300
ccgatcgttg tcagaagtaa gttggccgca gtgttatcac tcatggttat ggcagcactg      9360
cataattctc ttactgtcat gccatccgta agatgctttt ctgtgactgg tgagtactca      9420
accaagtcat tctgagaata gtgtatgcgg cgaccgagtt gctcttgccc ggcgtcaata      9480
cgggataata ccgcgccaca tagcagaact ttaaaagtgc tcatcattgg aaaacgttct      9540
tcggggcgaa aactctcaag gatcttaccg ctgttgagat ccagttcgat gtaacccact      9600
cgtgcaccca actgatcttc agcatctttt actttcacca gcgtttctgg gtgagcaaaa      9660
acaggaaggc aaaatgccgc aaaaaaggga ataagggcga cacggaaatg ttgaatactc      9720
atactcttcc tttttcaata ttattgaagc atttatcagg gttattgtct catgagcgga      9780
tacatatttg aatgtattta gaaaaataaa caaataggggg ttccgcgcac atttccccga      9840
aaagtgccac ctgacgtc                                                   9858
```

```
<210> SEQ ID NO 3
<211> LENGTH: 3642
<212> TYPE: DNA
<213> ORGANISM: Artificial Sequence
<220> FEATURE:
<223> OTHER INFORMATION: spike protein coding sequence in #1 vector

<400> SEQUENCE: 3
```

```
atgtttgtgt tcctggtgct gctgccactg gtgtccagcc agtgtgtgaa cctgaccacc        60
aggacccaac ttcctcctgc ctacaccaac tccttcacca ggggagtcta ctaccctgac       120
aaggtgttca ggtcctctgt gctgcacagc acccaggacc tgttcctgcc attcttcagc       180
aatgtgacct ggttccatgc catccatgtg tctggcacca atggcaccaa gaggtttgac       240
aaccctgtgc tgccattcaa tgatggagtc actttgcca gcacagagaa gagcaacatc        300
atcaggggct ggatttttgg caccaccctg gacagcaaga cccagtccct gctgattgtg       360
aacaatgcca ccaatgtggt gattaaggtg tgtgagttcc agttctgtaa tgacccattc       420
ctgggagtct actaccacaa gaacaacaag tcctggatgg agtctgagtt cagggtctac       480
tcctctgcca caactgtac ctttgaatat gtgagccaac cattcctgat ggacttggag        540
ggcaagcagg gcaacttcaa gaacctgagg gagtttgtgt tcaagaacat tgatggctac       600
ttcaagattt acagcaaaca cacaccaatc aacctggtga gggacctgcc acagggcttc       660
tctgccttgg aaccactggt ggacctgcca attggcatca acatcaccag gttccagacc       720
ctgctggctc tgcacaggtc ctacctgaca cctggagact cctcctctgg ctggacagca       780
ggagcagcag cctactatgt gggctacctc caaccaagga ccttcctgct gaaatacaat       840
gagaatggca ccatcacaga tgctgtggac tgtgccctgg acccactgtc tgagaccaag       900
tgtaccctga atccttcac agtggagaag ggcatctacc agaccagcaa cttcagggtc        960
caaccaacag agagcattgt gaggtttcca aacatcacca acctgtgtcc atttggagag      1020
gtgttcaatg ccaccaggtt tgcctctgtc tatgcctgga acaggaagag gattagcaac      1080
tgtgtggctg actactctgt gctctacaac tctgcctcct tcagcacctt caagtgttat      1140
ggagtgagcc caaccaaact gaatgacctg tgtttcacca atgtctatgc tgactccttt      1200
```

```
gtgattaggg gagatgaggt gagacagatt gcccctggac aaacaggcaa gattgctgac   1260
tacaactaca aactgcctga tgacttcaca ggctgtgtga ttgcctggaa cagcaacaac   1320
ctggacagca aggtgggagg caactacaac tacctctaca gactgttcag gaagagcaac   1380
ctgaaaccat ttgagaggga catcagcaca gagatttacc aggctggcag cacaccatgt   1440
aatggagtgg agggcttcaa ctgttacttt ccactccaat cctatggctt ccaaccaacc   1500
aatggagtgg gctaccaacc atacaggdtg gtggtgctgt cctttgaact gctccatgcc   1560
cctgccacag tgtgtggacc aaagaagagc accaacctgg tgaagaacaa gtgtgtgaac   1620
ttcaacttca atggactgac aggcacagga gtgctgacag agagcaacaa gaagttcctg   1680
ccattccaac agtttggcag ggacattgct gacaccacag atgctgtgag ggacccacag   1740
accttggaga ttctggacat cacaccatgt tcctttggag gagtgtctgt gattacacct   1800
ggcaccaaca ccagcaacca ggtggctgtg ctctaccagg atgtgaactg tactgaggtg   1860
cctgtggcta tccatgctga ccaacttaca ccaacctgga gggtctacag cacaggcagc   1920
aatgtgttcc agaccagggc tggctgtctg attggagcag agcatgtgaa caactcctat   1980
gagtgtgaca tcccaattgg agcaggcatc tgtgcctcct accagaccca gaccaacagc   2040
ccaaggaggg caaggtctgt ggcaagccag agcatcattg cctacacaat gagtctggga   2100
gcagagaact ctgtggctta cagcaacaac agcattgcca tcccaaccaa cttcaccatc   2160
tctgtgacca cagagattct gcctgtgagt atgaccaaga cctctgtgga ctgtacaatg   2220
tatatctgtg gagacagcac agagtgtagc aacctgctgc tccaatatgg ctccttctgt   2280
acccaactta caggggctct gacaggcatt gctgtggaac aggacaagaa cacccaggag   2340
gtgtttgccc aggtgaagca gatttacaag acacctccaa tcaaggactt tggaggcttc   2400
aacttcagcc agattctgcc tgacccaagc aagccaagca agaggtcctt cattgaggac   2460
ctgctgttca caaggtgac cctggctgat gctggcttca tcaagcaata tggagactgt   2520
ctgggagaca ttgctgccag ggacctgatt tgtgcccaga agttcaatgg actgacagtg   2580
ctgcctccac tgctgacaga tgagatgatt gcccaataca cctctgccct gctggctggc   2640
accatcacct ctggctggac ctttggagca ggagcagccc tccaaatccc atttgctatg   2700
cagatggctt acaggttcaa tggcattgga gtgacccaga atgtgctcta tgagaaccag   2760
aaactgattg ccaaccagtt caactctgcc attggcaaga ttcaggactc cctgtccagc   2820
acagcctctg ccctgggcaa actccaagat gtggtgaacc agaatgccca ggctctgaac   2880
accctggtga gcaactttc cagcaacttt ggagccatct cctctgtgct gaatgacatc   2940
ctgagcagac tggacaaggt ggaggctgag gtccagattg acagactgat tacaggcaga   3000
ctccaatccc tccaaaccta tgtgacccaa caacttatca gggctgctga gattagggca   3060
tctgccaacc tggctgccac caagatgagt gagtgtgtgc tgggacaaag caagagggtg   3120
gacttctgtg gcaagggcta ccacctgatg agttttccac agtctgcccc tcatggagtg   3180
gtgttcctgc atgtgaccta tgtgcctgcc caggagaaga cttcaccac agccctgcc    3240 atctgccatg atggcaaggc tcactttcca agggagggag tgtttgtgag caatggcacc   3300
cactggtttg tgacccagag gaacttctat gaaccacaga ttatcaccac agacaacacc   3360
tttgtgtctg gcaactgtga tgtggtgatt ggcattgtga caacacagt ctatgaccca    3420 ctccaacctg aactggactc cttcaaggag gaactggaca aatacttcaa gaaccacacc   3480
agccctgatg tggacctggg agacatctct ggcatcaatg cctctgtggt gaacatccag   3540
aaggagattg acagactgaa tgaggtggct aagaacctga atgagtccct gattgacctc   3600
```

```
caagaactgg gcaaatatga acaatacatc aagtggccat ga                    3642

<210> SEQ ID NO 4
<211> LENGTH: 37
<212> TYPE: DNA
<213> ORGANISM: Artificial Sequence
<220> FEATURE:
<223> OTHER INFORMATION: spike protein ending gene forward primer

<400> SEQUENCE: 4
tccagcctcc gatttgccac catgtttgtg ttcctgg                         37

<210> SEQ ID NO 5
<211> LENGTH: 39
<212> TYPE: DNA
<213> ORGANISM: Artificial Sequence
<220> FEATURE:
<223> OTHER INFORMATION: spike protein ending gene reverse primer

<400> SEQUENCE: 5
gattatgatc aattttcatg gccacttgat gtattgttc                       39

<210> SEQ ID NO 6
<211> LENGTH: 24
<212> TYPE: DNA
<213> ORGANISM: Artificial Sequence
<220> FEATURE:
<223> OTHER INFORMATION: S1/S2 cleavage site

<400> SEQUENCE: 6
acgaattctc ctcggcgggc acgt                                       24

<210> SEQ ID NO 7
<211> LENGTH: 12
<212> TYPE: DNA
<213> ORGANISM: Artificial Sequence
<220> FEATURE:
<223> OTHER INFORMATION: linker

<400> SEQUENCE: 7
acgatcctcc gt                                                    12

<210> SEQ ID NO 8
<211> LENGTH: 3630
<212> TYPE: DNA
<213> ORGANISM: Artificial Sequence
<220> FEATURE:
<223> OTHER INFORMATION: spike protein coding sequence in #2 vector

<400> SEQUENCE: 8
atgtttgtgt tcctggtgct gctgccactg gtgtccagcc agtgtgtgaa cctgaccacc    60
aggacccaac ttcctcctgc ctacaccaac tccttcacca ggggagtcta ctaccctgac   120
aaggtgttca ggtcctctgt gctgcacagc acccaggacc tgttcctgcc attcttcagc   180
aatgtgacct ggttccatgc catccatgtg tctggcacca atggcaccaa gaggtttgac   240
aaccctgtgc tgccattcaa tgatggagtc tactttgcca gcacagagaa gagcaacatc   300 atcagggggct ggatttttgg caccaccctg gacagcaaga cccagtccct gctgattgtg   360
aacaatgcca ccaatgtggt gattaaggtg tgtgagttcc agttctgtaa tgacccattc   420
ctgggagtct actaccacaa gaacaacaag tcctggatgg agtctgagtt cagggtctac   480
tcctctgcca caactgtac ctttgaatat gtgagccaac cattcctgat ggacttggag   540
```

-continued

```
ggcaagcagg gcaacttcaa gaacctgagg gagtttgtgt tcaagaacat tgatggctac      600
ttcaagattt acagcaaaca cacaccaatc aacctggtga gggacctgcc acagggcttc      660
tctgccttgg aaccactggt ggacctgcca attggcatca acatcaccag gttccagacc      720
ctgctggctc tgcacaggtc ctacctgaca cctggagact cctcctctgg ctggacagca      780
ggagcagcag cctactatgt gggctacctc caaccaagga ccttcctgct gaaatacaat      840
gagaatggca ccatcacaga tgctgtggac tgtgccctgg acccactgtc tgagaccaag      900
tgtaccctga aatccttcac agtggagaag ggcatctacc agaccagcaa cttcagggtc      960
caaccaacag agagcattgt gaggtttcca aacatcacca acctgtgtcc atttggagag     1020
gtgttcaatg ccaccaggtt tgcctctgtc tatgcctgga acaggaagag gattagcaac     1080
tgtgtggctg actactctgt gctctacaac tctgcctcct tcagcacctt caagtgttat     1140
ggagtgagcc caaccaaact gaatgacctg tgtttcacca atgtctatgc tgactccttt     1200
gtgattaggg gagatgaggt gagacagatt gcccctggac aaacaggcaa gattgctgac     1260
tacaactaca aactgcctga tgacttcaca ggctgtgtga ttgcctggaa cagcaacaac     1320
ctggacagca aggtgggagg caactacaac tacctctaca gactgttcag gaagagcaac     1380
ctgaaaccat ttgagaggga catcagcaca gagatttacc aggctggcag cacaccatgt     1440
aatggagtgg agggcttcaa ctgttacttt ccactccaat cctatggctt ccaaccaacc     1500
aatggagtgg gctaccaacc atacagggtg gtggtgctgt cctttgaact gctccatgcc     1560
cctgccacag tgtgtggacc aaagaagagc accaacctgg tgaagaacaa gtgtgtgaac     1620
ttcaacttca tggactgac aggcacagga gtgctgacag agagcaacaa gaagttcctg      1680
ccattccaac agtttggcag ggacattgct gacaccacag atgctgtgag ggacccacag     1740
accttggaga ttctggacat cacaccatgt tcctttggag gagtgtctgt gattacacct     1800
ggcaccaaca ccagcaacca ggtggctgtg ctctaccagg atgtgaactg tactgaggtg     1860
cctgtggcta tccatgctga ccaacttaca ccaacctgga gggtctacag cacaggcagc     1920
aatgtgttcc agaccagggc tggctgtctg attggagcag agcatgtgaa caactcctat     1980
gagtgtgaca tcccaattgg agcaggcatc tgtgcctcct accagaccca gaccatcctc     2040
aggtctgtgg caagccagag catcattgcc tacacaatga gtctgggagc agagaactct     2100
gtggcttaca gcaacaacag cattgccatc ccaaccaact tcaccatctc tgtgaccaca     2160
gagattctgc ctgtgagtat gaccaagacc tctgtggact gtacaatgta tatctgtgga     2220
gacagcacag agtgtagcaa cctgctgctc caatatggct ccttctgtac ccaacttaac     2280
agggctctga caggcattgc tgtggaacag gacaagaaca cccaggaggt gtttgcccag     2340
gtgaagcaga tttacaagac acctccaatc aaggactttg gaggcttcaa cttcagccag     2400
attctgcctg acccaagcaa gccaagcaag aggtccttca ttgaggacct gctgttcaac     2460
aaggtgaccc tggctgatgc tggcttcatc aagcaatatg gagactgtct gggagacatt     2520
gctgccaggg acctgatttg tgcccagaag ttcaatggac tgacagtgct gcctccactg     2580
ctgacagatg agatgattgc ccaatacacc tctgccctgc tggctggcac catcacctct     2640
ggctggacct ttggagcagg agcagccctc caaatcccat ttgctatgca gatggcttac     2700
aggttcaatg gcattggagt gacccagaat gtgctctatg agaaccagaa actgattgcc     2760
aaccagttca actctgccat tggcaagatt caggactccc tgtccagcac agcctctgcc     2820
ctgggcaaac tccaagatgt ggtgaaccag aatgcccagg ctctgaacac cctggtgaag     2880
caactttcca gcaactttgg agccatctcc tctgtgctga atgacatcct gagcagactg     2940
```

-continued

```
gacaaggtgg aggctgaggt ccagattgac agactgatta caggcagact ccaatccctc    3000
caaacctatg tgacccaaca acttatcagg gctgctgaga ttagggcatc tgccaacctg    3060
gctgccacca agatgagtga gtgtgtgctg ggacaaagca agagggtgga cttctgtggc    3120
aagggctacc acctgatgag ttttccacag tctgcccctc atggagtggt gttcctgcat    3180
gtgacctatg tgcctgccca ggagaagaac ttcaccacag cccctgccat ctgccatgat    3240
ggcaaggctc actttccaag ggagggagtg tttgtgagca atggcaccca ctggtttgtg    3300
acccagagga acttctatga accacagatt atcaccacag acaacacctt tgtgtctggc    3360
aactgtgatg tggtgattgg cattgtgaac aacacagtct atgacccact ccaacctgaa    3420
ctggactcct tcaaggagga actggacaaa tacttcaaga accacaccag ccctgatgtg    3480
gacctgggag acatctctgg catcaatgcc tctgtggtga acatccagaa ggagattgac    3540
agactgaatg aggtggctaa gaacctgaat gagtccctga ttgacctcca agaactgggc    3600
aaatatgaac aatacatcaa gtggccatga                                     3630
```

```
<210> SEQ ID NO 9
<211> LENGTH: 31
<212> TYPE: DNA
<213> ORGANISM: Artificial Sequence
<220> FEATURE:
<223> OTHER INFORMATION: forward primer

<400> SEQUENCE: 9
agaccatcct caggtctgtg gcaagccaga g                                     31
```

```
<210> SEQ ID NO 10
<211> LENGTH: 30
<212> TYPE: DNA
<213> ORGANISM: Artificial Sequence
<220> FEATURE:
<223> OTHER INFORMATION: reverse primer

<400> SEQUENCE: 10
cctcctacca gacccagacc atcctcaggt                                       30
```

```
<210> SEQ ID NO 11
<211> LENGTH: 27
<212> TYPE: DNA
<213> ORGANISM: Artificial Sequence
<220> FEATURE:
<223> OTHER INFORMATION: linker

<400> SEQUENCE: 11
accggtggcg gtgggtcgag gtctgtg                                          27
```

```
<210> SEQ ID NO 12
<211> LENGTH: 3639
<212> TYPE: DNA
<213> ORGANISM: Artificial Sequence
<220> FEATURE:
<223> OTHER INFORMATION: spike protein coding sequence in #3 vector

<400> SEQUENCE: 12
atgtttgtgt tcctggtgct gctgccactg gtgtccagcc agtgtgtgaa cctgaccacc     60
aggacccaac ttcctcctgc ctacaccaac tccttcacca ggggagtcta ctaccctgac    120
aaggtgttca ggtcctctgt gctgcacagc acccaggacc tgttcctgcc attcttcagc    180
aatgtgacct ggttccatgc catccatgtg tctggcacca atggcaccaa gaggtttgac    240
```

-continued

```
aaccctgtgc tgccattcaa tgatggagtc tactttgcca gcacagagaa gagcaacatc    300
atcaggggct ggatttttgg caccaccctg gacagcaaga cccagtccct gctgattgtg    360
aacaatgcca ccaatgtggt gattaaggtg tgtgagttcc agttctgtaa tgacccattc    420
ctgggagtct actaccacaa gaacaacaag tcctggatgg agtctgagtt cagggtctac    480
tcctctgcca acaactgtac ctttgaatat gtgagccaac cattcctgat ggacttggag    540
ggcaagcagg gcaacttcaa gaacctgagg gagtttgtgt tcaagaacat tgatggctac    600
ttcaagattt acagcaaaca cacaccaatc aacctggtga gggacctgcc acagggcttc    660
tctgccttgg aaccactggt ggacctgcca attggcatca acatcaccag gttccagacc    720
ctgctggctc tgcacaggtc ctacctgaca cctggagact cctcctctgg ctggacagca    780
ggagcagcag cctactatgt gggctacctc caaccaagga ccttcctgct gaaatacaat    840
gagaatggca ccatcacaga tgctgtggac tgtgccctgg acccactgtc tgagaccaag    900
tgtaccctga aatccttcac agtggagaag ggcatctacc agaccagcaa cttcagggtc    960
caaccaacag agagcattgt gaggtttcca aacatcacca acctgtgtcc atttggagag   1020
gtgttcaatg ccaccaggtt tgcctctgtc tatgcctgga acaggaagag gattagcaac   1080
tgtgtggctg actactctgt gctctacaac tctgcctcct tcagcacctt caagtgttat   1140
ggagtgagcc caaccaaact gaatgacctg tgtttcacca atgtctatgc tgactccttt   1200
gtgattaggg gagatgaggt gagacagatt gcccctggac aaacaggcaa gattgctgac   1260
tacaactaca aactgcctga tgacttcaca ggctgtgtga ttgcctggaa cagcaacaac   1320
ctggacagca aggtgggagg caactacaac tacctctaca gactgttcag gaagagcaac   1380
ctgaaaccat ttgagaggga catcagcaca gagatttacc aggctggcag cacaccatgt   1440
aatggagtgg agggcttcaa ctgttacttt ccactccaat cctatggctt ccaaccaacc   1500
aatggagtgg gctaccaacc atacagggtg gtggtgctgt cctttgaact gctccatgcc   1560
cctgccacag tgtgtggacc aaagaagagc accaacctgg tgaagaacaa gtgtgtgaac   1620
ttcaacttca atggactgac aggcacagga gtgctgacag agagcaacaa gaagttcctg   1680
ccattccaac agtttggcag ggacattgct gacaccacag atgctgtgag ggacccacag   1740
accttggaga ttctggacat cacaccatgt tcctttggag gagtgtctgt gattacacct   1800
ggcaccaaca ccagcaacca ggtggctgtg ctctaccagg atgtgaactg tactgaggtg   1860
cctgtggcta tccatgctga ccaacttaca ccaacctgga gggtctacag cacaggcagc   1920
aatgtgttcc agaccagggc tggctgtctg attggagcag agcatgtgaa caactcctat   1980
gagtgtgaca tcccaattgg agcaggcatc tgtgcctcct accagaccca gaccggtggc   2040
ggtgggtcga ggtctgtggc aagccagagc atcattgcct acacaatgag tctgggagca   2100
gagaactctg tggcttacag caacaacagc attgccatcc caaccaactt caccatctct   2160
gtgaccacag agattctgcc tgtgagtatg accaagaccc tgtggactg tacaatgtat   2220 atctgtggag acagcacaga gtgtagcaac ctgctgctcc aatatggctc cttctgtacc   2280
caacttaaca gggctctgac aggcattgct gtggaacagg acaagaacac ccaggaggtg   2340
tttgcccagt gaagcagat ttacaagaca cctccaatca aggactttgg aggcttcaac   2400
ttcagccaga ttctgcctga cccaagcaag ccaagcaaga ggtccttcat tgaggacctg   2460
ctgttcaaca aggtgaccct ggctgatgct ggcttcatca gcaatatgg agactgtctg   2520 ggagacattg ctgccaggga cctgatttgt gcccagaagt tcaatggact gacagtgctg   2580
cctccactgc tgacagatga gatgattgcc caatacacct ctgccctgct ggctggcacc   2640
```

-continued

```
atcacctctg gctggacctt tggagcagga gcagccctcc aaatcccatt tgctatgcag      2700
atggcttaca ggttcaatgg cattggagtg acccagaatg tgctctatga gaaccagaaa      2760
ctgattgcca accagttcaa ctctgccatt ggcaagattc aggactccct gtccagcaca      2820
gcctctgccc tgggcaaact ccaagatgtg gtgaaccaga atgcccaggc tctgaacacc      2880
ctggtgaagc aactttccag caactttgga gccatctcct ctgtgctgaa tgacatcctg      2940
agcagactgg acaaggtgga ggctgaggtc agattgaca gactgattac aggcagactc      3000
caatccctcc aaacctatgt gacccaacaa cttatcaggg ctgctgagat tagggcatct      3060
gccaacctgg ctgccaccaa gatgagtgag tgtgtgctgg acaaagcaa gagggtggac      3120 ttctgtggca agggctacca cctgatgagt tttccacagt ctgcccctca tggagtggtg      3180
ttcctgcatg tgacctatgt gcctgcccag gagaagaact tcaccacagc ccctgccatc      3240
tgccatgatg gcaaggctca ctttccaagg gagggagtgt ttgtgagcaa tggcacccac      3300
tggtttgtga cccagaggaa cttctatgaa ccacagatta tcaccacaga caacacctttt    3360 gtgtctggca actgtgatgt ggtgattggc attgtgaaca acacagtcta tgacccactc      3420
caacctgaac tggactcctt caaggaggaa ctggacaaat acttcaagaa ccacaccagc      3480
cctgatgtgg acctgggaga catctctggc atcaatgcct ctgtggtgaa catccagaag      3540
gagattgaca gactgaatga ggtggctaag aacctgaatg agtccctgat tgacctccaa      3600
gaactgggca aatatgaaca atacatcaag tggccatga                            3639
```

<210> SEQ ID NO 13
<211> LENGTH: 36
<212> TYPE: DNA
<213> ORGANISM: Artificial Sequence
<220> FEATURE:
<223> OTHER INFORMATION: forward primer

<400> SEQUENCE: 13

```
cggtggcggt gggtcgaggt ctgtggcaag ccagag                                36
```

<210> SEQ ID NO 14
<211> LENGTH: 34
<212> TYPE: DNA
<213> ORGANISM: Artificial Sequence
<220> FEATURE:
<223> OTHER INFORMATION: reverse primer

<400> SEQUENCE: 14

```
gacccaccgc caccggtctg ggtctggtag gagg                                  34
```

<210> SEQ ID NO 15
<211> LENGTH: 57
<212> TYPE: DNA
<213> ORGANISM: Artificial Sequence
<220> FEATURE:
<223> OTHER INFORMATION: linker

<400> SEQUENCE: 15

```
accggtggcg gtgggtcggg cggtggtggg tcgggtggcg gcggttccag gtctgtg         57
```

<210> SEQ ID NO 16
<211> LENGTH: 3669
<212> TYPE: DNA
<213> ORGANISM: Artificial Sequence
<220> FEATURE:
<223> OTHER INFORMATION: spike protein coding sequence in #4 vector -continued

```
<400> SEQUENCE: 16
atgtttgtgt tcctggtgct gctgccactg gtgtccagcc agtgtgtgaa cctgaccacc      60
aggacccaac ttcctcctgc ctacaccaac tccttcacca ggggagtcta ctaccctgac     120
aaggtgttca ggtcctctgt gctgcacagc acccaggacc tgttcctgcc attcttcagc     180
aatgtgacct ggttccatgc catccatgtg tctggcacca atggcaccaa gaggtttgac     240
aaccctgtgc tgccattcaa tgatggagtc tactttgcca gcacagagaa gagcaacatc     300
atcaggggct ggattttggg caccaccctg gacagcaaga cccagtccct gctgattgtg     360
aacaatgcca ccaatgtggt gattaaggtg tgtgagttcc agttctgtaa tgacccattc     420
ctgggagtct actaccacaa gaacaacaag tcctggatgg agtctgagtt cagggtctac     480
tcctctgcca caactgtac ctttgaatat gtgagccaac cattcctgat ggacttggag     540
ggcaagcagg gcaacttcaa gaacctgagg gagtttgtgt tcaagaacat tgatggctac     600
ttcaagattt acagcaaaca cacaccaatc aacctggtga gggacctgcc acagggcttc     660
tctgccttgg aaccactggt ggacctgcca attggcatca acatcaccag gttccagacc     720
ctgctggctc tgcacaggtc ctacctgaca cctggagact cctcctctgg ctggacagca     780
ggagcagcag cctactatgt gggctacctc caaccaagga ccttcctgct gaaatacaat     840
gagaatggca ccatcacaga tgctgtggac tgtgccctgg acccactgtc tgagaccaag     900
tgtaccctga atccttcac agtggagaag ggcatctacc agaccagcaa cttcagggtc     960
caaccaacag agagcattgt gaggtttcca aacatcacca acctgtgtcc atttggagag    1020
gtgttcaatg ccaccaggtt tgcctctgtc tatgcctgga acaggaagag gattagcaac    1080
tgtgtggctg actactctgt gctctacaac tctgcctcct tcagcacctt caagtgttat    1140
ggagtgagcc caaccaaact gaatgacctg tgtttcacca atgtctatgc tgactccttt    1200
gtgattaggg gagatgaggt gagacagatt gcccctggac aaacaggcaa gattgctgac    1260
tacaactaca aactgcctga tgacttcaca ggctgtgtga ttgcctggaa cagcaacaac    1320
ctggacagca aggtgggagg caactacaac tacctctaca gactgttcag gaagagcaac    1380
ctgaaaccat ttgagaggga catcagcaca gagatttacc aggctggcag cacaccatgt    1440
aatggagtgg agggcttcaa ctgttacttt ccactccaat cctatggctt ccaaccaacc    1500
aatggagtgg ctaccaacc atacagggtg gtggtgctgt cctttgaact gctccatgcc    1560
cctgccacag tgtgtggacc aaagaagagc accaacctgg tgaagaacaa gtgtgtgaac    1620
ttcaacttca tggactgac aggcacagga gtgctgacag agagcaacaa gaagttcctg    1680
ccattccaac agtttggcag ggacattgct gacaccacag atgctgtgag ggacccacag    1740
accttggaga ttctggacat cacaccatgt tcctttggag gagtgtctgt gattacacct    1800
ggcaccaaca ccagcaacca ggtggctgtg ctctaccagg atgtgaactg tactgaggtg    1860
cctgtggcta tccatgctga ccaacttaca ccaacctgga gggtctacag cacaggcagc    1920
aatgtgttcc agaccagggc tggctgtctg attggagcag agcatgtgaa caactcctat    1980
gagtgtgaca tcccaattgg agcaggcatc tgtgcctcct accagaccca gaccggtggc    2040
ggtgggtcgg gcggtggtgg gtcgggtggc ggcggttcca ggtctgtggc aagccagagc    2100
atcattgcct acacaatgag tctgggagca gagaactctg tggcttacag caacaacagc    2160
attgccatcc caaccaactt caccatctct gtgaccacag agattctgcc tgtgagtatg    2220
accaagacct ctgtggactg tacaatgtat atctgtggag acagcacaga gtgtagcaac    2280
ctgctgctcc aatatggctc cttctgtacc caacttaaca gggctctgac aggcattgct    2340
```

-continued

```
gtggaacagg acaagaacac ccaggaggtg tttgcccagg tgaagcagat ttacaagaca      2400
cctccaatca aggactttgg aggcttcaac ttcagccaga ttctgcctga cccaagcaag      2460
ccaagcaaga ggtccttcat tgaggacctg ctgttcaaca aggtgaccct ggctgatgct      2520
ggcttcatca agcaatatgg agactgtctg ggagacattg ctgccaggga cctgatttgt      2580
gcccagaagt tcaatggact gacagtgctg cctccactgc tgacagatga gatgattgcc      2640
caatacacct ctgccctgct ggctggcacc atcacctctg ctggacctt tggagcagga       2700 gcagccctcc aaatcccatt tgctatgcag atggcttaca ggttcaatgg cattggagtg      2760
acccagaatg tgctctatga gaaccagaaa ctgattgcca accagttcaa ctctgccatt      2820
ggcaagattc aggactccct gtccagcaca gcctctgccc tgggcaaact ccaagatgtg      2880
gtgaaccaga atgcccaggc tctgaacacc ctggtgaagc aactttccag caactttgga      2940
gccatctcct ctgtgctgaa tgacatcctg agcagactgg acaaggtgga ggctgaggtc      3000
cagattgaca gactgattac aggcagactc caatccctcc aaacctatgt gacccaacaa      3060
cttatcaggg ctgctgagat tagggcatct gccaacctgg ctgccaccaa gatgagtgag      3120
tgtgtgctgg gacaaagcaa gagggtggac ttctgtggca agggctacca cctgatgagt      3180
tttccacagt ctgcccctca tggagtggtg ttcctgcatg tgacctatgt gcctgcccag      3240
gagaagaact tcaccacagc ccctgccatc tgccatgatg gcaaggctca ctttccaagg      3300
gagggagtgt ttgtgagcaa tggcacccac tggtttgtga cccagaggaa cttctatgaa      3360
ccacagatta tcaccacaga caacaccttt gtgtctggca actgtgatgt ggtgattggc      3420
attgtgaaca acacagtcta tgacccactc caacctgaac tggactcctt caaggaggaa      3480
ctggacaaat acttcaagaa ccacaccagc cctgatgtgg acctgggaga catctctggc      3540
atcaatgcct ctgtggtgaa catccagaag gagattgaca gactgaatga ggtggctaag      3600
aacctgaatg agtccctgat tgacctccaa gaactgggca aatatgaaca atacatcaag      3660
tggccatga                                                             3669
```

```
<210> SEQ ID NO 17
<211> LENGTH: 51
<212> TYPE: DNA
<213> ORGANISM: Artificial Sequence
<220> FEATURE:
<223> OTHER INFORMATION: forward primer

<400> SEQUENCE: 17
gggcggtggt gggtcgggtg gcggcggttc caggtctgtg gcaagccaga g              51

<210> SEQ ID NO 18
<211> LENGTH: 49
<212> TYPE: DNA
<213> ORGANISM: Artificial Sequence
<220> FEATURE:
<223> OTHER INFORMATION: reverse primer

<400> SEQUENCE: 18
gacccaccac cgcccgaccc accgccaccg gtctgggtct ggtaggagg                 49

<210> SEQ ID NO 19
<211> LENGTH: 7
<212> TYPE: PRT
<213> ORGANISM: Artificial Sequence
<220> FEATURE:
<223> OTHER INFORMATION: #3 linker
```

```
<400> SEQUENCE: 19

Thr Gly Gly Gly Gly Ser Arg
1               5

<210> SEQ ID NO 20
<211> LENGTH: 9
<212> TYPE: PRT
<213> ORGANISM: Artificial Sequence
<220> FEATURE:
<223> OTHER INFORMATION: #4 linker

<400> SEQUENCE: 20

Thr Gly Gly Gly Gly Ser Arg Arg Arg
1               5

<210> SEQ ID NO 21
<211> LENGTH: 31091
<212> TYPE: DNA
<213> ORGANISM: Artificial Sequence
<220> FEATURE:
<223> OTHER INFORMATION: Adk35F

<400> SEQUENCE: 21
catcatcaat aatatacctt attttggatt gaagccaata tgataatgag ggggtggagt        60
ttgtgacgtg gcgcggggcg tgggaacggg gcgggtgacg tagtagtgtg gcggaagtgt       120
gatgttgcaa gtgtggcgga acacatgtaa gcgacggatg tggcaaaagt gacgtttttg       180
gtgtgcgccg gtgtacacag gaagtgacaa ttttcgcgcg gttttaggcg gatgttgtag       240
taaatttggg cgtaaccgag taagatttgg ccattttcgc gggaaaactg aataagagga       300
agtgaaatct gaataatttt gtgttactca tagcgcgtaa tactgtaata gtaatcaatt       360
acggggtcat tagttcatag cccatatatg gagttccgcg ttacataact tacggtaaat       420
ggcccgcctg gctgaccgcc caacgacccc cgcccattga cgtcaataat gacgtatgtt       480
cccatagtaa cgccaatagg gactttccat tgacgtcaat gggtggagta tttacggtaa       540
actgcccact tggcagtaca tcaagtgtat catatgccaa gtacgccccc tattgacgtc       600
aatgacggta aatggcccgc ctggcattat gcccagtaca tgaccttatg ggactttcct       660
acttggcagt acatctacgt attagtcatc gctattacca tggtgatgcg gttttggcag       720
tacatcaatg ggcgtggata gcggtttgac tcacggggat ttccaagtct ccaccccatt       780
gacgtcaatg ggagtttgtt ttggcaccaa aatcaacggg actttccaaa atgtcgtaac       840
aactccgccc cattgacgca aatgggcggt aggcgtgtac ggtgggaggt ctatataagc       900
agagctctcc ctatcagtga tagagatctc cctatcagtg atagagatcg tcgacgagct       960
cgtttagtga accgtcagat cgcctggaga cgccatccac gctgttttga cctccataga      1020
agacaccggg accgatccag cctccgattt aaattgatca taatcagcca taccacattt      1080
gtagaggttt tacttgcttt aaaaaacctc ccacacctcc ccctgaacct gaaacataaa      1140
atgaatgcaa ttgttgttgt taacttgttt attgcagctt ataatggtta caaataaagc      1200
aatagcatca caaatttcac aaataaagca ttttttttcac tgcattctag ttgtggtttg      1260
tccaaactca tcaatgtatc ttaacgcgga tctgggcgtg gttaagggtg ggaaagaata      1320
tataaggtgg gggtcttatg tagttttgta tctgttttgc agcagccgcc gccgccatga      1380
gcaccaactc gtttgatgga agcattgtga gctcatattt gacaacgcgc atgcccccat      1440
gggccggggt gcgtcagaat gtgatgggct ccagcattga tggtcgcccc gtcctgcccg      1500
caaactctac taccttgacc tacgagaccg tgtctggaac gccgttggag actgcagcct      1560
```

-continued

```
ccgccgccgc ttcagccgct gcagccaccg cccgcgggat tgtgactgac tttgctttcc    1620
tgagcccgct tgcaagcagt gcagcttccc gttcatccgc ccgcgatgac aagttgacgg    1680
ctcttttggc acaattggat tctttgaccc gggaacttaa tgtcgtttct cagcagctgt    1740
tggatctgcg ccagcaggtt tctgccctga aggcttcctc ccctcccaat gcggtttaaa    1800
acataaataa aaaaccagac tctgtttgga tttggatcaa gcaagtgtct tgctgtcttt    1860
atttaggggt tttgcgcgcg cggtaggccc gggaccagcg gtctcggtcg ttgagggtcc    1920
tgtgtatttt ttccaggacg tggtaaaggt gactctggat gttcagatac atgggcataa    1980
gcccgtctct ggggtggagg tagcaccact gcagagcttc atgctgcggg gtggtgttgt    2040
agatgatcca gtcgtagcag gagcgctggg cgtggtgcct aaaaatgtct ttcagtagca    2100
agctgattgc caggggcagg cccttggtgt aagtgtttac aaagcggtta agctgggatg    2160
ggtgcatacg tggggatatg agatgcatct tggactgtat ttttaggttg gctatgttcc    2220
cagccatatc cctccgggga ttcatgttgt gcagaaccac cagcacagtg tatccggtgc    2280
acttgggaaa tttgtcatgt agcttagaag gaaatgcgtg gaagaacttg gagacgccct    2340
tgtgacctcc aagattttcc atgcattcgt ccataatgat ggcaatgggc ccacgggcgg    2400
cggcctgggc gaagatattt ctgggatcac taacgtcata gttgtgttcc aggatgagat    2460
cgtcataggc catttttaca aagcgcgggc ggagggtgcc agactgcggt ataatggttc    2520
catccggccc aggggcgtag ttaccctcac agatttgcat ttcccacgct ttgagttcag    2580
atggggggat catgtctacc tgcggggcga tgaagaaaac ggtttccggg gtaggggaga    2640
tcagctggga agaaagcagg ttcctgagca gctgcgactt accgcagccg gtgggcccgt    2700
aaatcacacc tattaccggc tgcaactggt agttaagaga gctgcagctg ccgtcatccc    2760
tgagcagggg ggccacttcg ttaagcatgt ccctgactcg catgttttcc ctgaccaaat    2820
ccgccagaag gcgctcgccg cccagcgata gcagttcttg caaggaagca aagtttttca    2880
acggtttgag accgtccgcc gtaggcatgc ttttgagcgt ttgaccaagc agttccaggc    2940
ggtcccacag ctcggtcacc tgctctacgg catctcgatc cagcatatct cctcgtttcg    3000
cgggttgggg cggctttcgc tgtacggcag tagtcggtgc tcgtccagac gggccagggt    3060
catgtctttc cacgggcgca gggtcctcgt cagcgtagtc tgggtcacgg tgaaggggtg    3120
cgctccgggc tgcgcgctgg ccagggtgcg cttgaggctg gtcctgctgg tgctgaagcg    3180
ctgccggtct tcgccctgcg cgtcggccag gtagcatttg accatggtgt catagtccag    3240
cccctccgcg gcgtggccct tggcgcgcag cttgcccttg gaggaggcgc cgcacgaggg    3300
gcagtgcaga cttttgaggg cgtagagctt gggcgcgaga ataccgatt ccggggagta    3360 ggcatccgcg ccgcaggccc cgcagacggt ctcgcattcc acgagccagg tgagctctgg    3420
ccgttcgggg tcaaaaacca ggtttccccc atgcttttg atgcgtttct tacctctggt    3480
ttccatgagc cggtgtccac gctcggtgac gaaaaggctg tccgtgtccc cgtatacaga    3540
cttgagaggc ctgtcctcga gcggtgttcc gcggtcctcc tcgtatagaa actcggacca    3600
ctctgagaca aaggctcgcg tccaggccag cacgaaggag gctaagtggg aggggtagcg    3660
gtcgttgtcc actagggggt ccactcgctc cagggtgtga agacacatgt cgccctcttc    3720
ggcatcaagg aaggtgattg gtttgtaggt gtaggccacg tgaccgggtg ttcctgaagg    3780
ggggctataa aaggggtgg gggcgcgttc gtcctcactc tcttccgcat cgctgtctgc    3840
gagggccagc tgttggggtg agtactccct ctgaaaagcg ggcatgactt ctgcgctaag    3900
```

-continued

```
attgtcagtt tccaaaaacg aggaggattt gatattcacc tggcccgcgg tgatgccttt    3960
gagggtggcc gcatccatct ggtcagaaaa gacaatcttt ttgttgtcaa gcttggtggc    4020
aaacgacccg tagagggcgt tggacagcaa cttggcgatg gagcgcaggg tttggttttt    4080
gtcgcgatcg gcgcgctcct tggccgcgat gtttagctgc acgtattcgc gcgcaacgca    4140
ccgccattcg ggaaagacgg tggtgcgctc gtcgggcacc aggtgcacgc gccaaccgcg    4200
gttgtgcagg gtgacaaggt caacgctggt ggctacctct ccgcgtaggc gctcgttggt    4260
ccagcagagg cggccgccct tgcgcgagca gaatggcggt aggggtctca gctgcgtctc    4320
gtccgggggg tctgcgtcca cggtaaagac cccgggcagc aggcgcgcgt cgaagtagtc    4380
tatcttgcat ccttgcaagt ctagcgcctg ctgccatgcg cgggcggcaa gcgcgcgctc    4440
gtatgggttg agtgggggac cccatggcat ggggtgggtg agcgcggagg cgtacatgcc    4500
gcaaatgtcg taaacgtaga ggggctctct gagtattcca agatatgtag ggtagcatct    4560
tccaccgcgg atgctggcgc gcacgtaatc gtatagttcg tgcgagggag cgaggaggtc    4620
gggaccgagg ttgctacggg cgggctgctc tgctcggaag actatctgcc tgaagatggc    4680
atgtgagttg gatgatatgg ttggacgctg gaagacgttg aagctggcgt ctgtgagacc    4740
taccgcgtca cgcacgaagg aggcgtagga gtcgcgcagc ttgttgacca gctcggcggt    4800
gacctgcacg tctagggcgc agtagtccag ggtttccttg atgatgtcat acttatcctg    4860
tccctttttt ttccacagct cgcggttgag gacaaactct tcgcggtctt tccagtactc    4920
ttggatcgga aacccgtcgg cctccgaacg gtaagagcct agcatgtaga actggttgac    4980
ggcctggtag gcgcagcatc cctttttctac gggtagcgcg tatgcctgcg cggccttccg    5040
gagcgaggtg tgggtgagcg caaaggtgtc cctgaccatg actttgaggt actggtattt    5100
gaagtcagtg tcgtcgcatc cgccctgctc ccagagcaaa aagtccgtgc gcttttttgga   5160 acgcggattt ggcagggcga aggtgacatc gttgaagagt atctttcccg cgcgaggcat    5220
aaagttgcgt gtgatgcgga agggtcccgg cacctcggaa cggttgttaa ttacctgggc    5280
ggcgagcacg atctcgtcaa agccgttgat gttgtggccc acaatgtaaa gttccaagaa    5340
gcgcgggatg cccttgatgg aaggcaattt tttaagttcc tcgtaggtga gctcttcagg    5400
ggagctgagc ccgtgctctg aaagggccca gtctgcaaga tgagggttgg aagcgacgaa    5460
tgagctccac aggtcacggg ccattagcat ttgcaggtgg tcgcgaaagg tcctaaactg    5520
gcgacctatg gccattttttt ctggggtgat gcagtagaag gtaagcgggt cttgttccca    5580
gcggtcccat ccaaggttcg cggctaggtc tcgcgcggca gtcactagag gctcatctcc    5640
gccgaacttc atgaccagca tgaagggcac gagctgcttc ccaaaggccc ccatccaagt    5700
ataggtctct acatcgtagg tgacaaagag acgctcggtg cgaggatgcg agccgatcgg    5760
gaagaactgg atctcccgcc accaattgga ggagtggcta ttgatgtggt gaaagtagaa    5820
gtccctgcga cgggccgaac actcgtgctg gcttttgtaa aaacgtgcgc agtactggca    5880
gcggtgcacg ggctgtacat cctgcacgag gttgacctga cgaccgcgca caaggaagca    5940
gagtgggaat ttgagcccct cgcctggcgg gtttggctgg tggtcttcta cttcggctgc    6000
ttgtccttga ccgtctggct gctcgagggg agttacggtg gatcggacca ccacgccgcg    6060
cgagcccaaa gtccagatgt ccgcgcgcgg cggtcggagc ttgatgacaa catcgcgcag    6120
atgggagctg tccatggtct ggagctcccg cggcgtcagg tcaggcggga gctcctgcag    6180
gtttacctcg catagacggg tcaggcgcgc ggctagatcc aggtgatacc taatttccag    6240
gggctggttg gtggcggcgt cgatggcttg caagaggccg catccccgcg gcgcgactac    6300
```

-continued

```
ggtaccgcgc ggcgggcggt gggccgcggg ggtgtccttg gatgatgcat ctaaaagcgg      6360
tgacgcgggc gagcccccgg aggtaggggg ggctccggac ccgccgggag aggggggcagg      6420 ggcacgtcgg cgccgcgcgc gggcaggagc tggtgctgcg cgcgtaggtt gctggcgaac      6480
gcgacgacgg ggcggttgat ctcctgaatc tggcgcctct gcgtgaagac gacgggcccg      6540
gtgagcttga acctgaaaga gagttcgaca gaatcaattt cggtgtcgtt gacggcggcc      6600
tggcgcaaaa tctcctgcac gtctcctgag ttgtcttgat aggcgatctc ggccatgaac      6660
tgctcgatct cttcctcctg gagatctccg cgtccggctc gctccacggt ggcggcgagg      6720
tcgttggaaa tgcgggccat gagctgcgag aaggcgttga ggcctccctc gttccagacg      6780
cggctgtaga ccacgccccc ttcggcatcg cgggcgcgca tgaccacctg cgcgagattg      6840
agctccacgt gccgggcgaa gacggcgtag tttcgcaggc gctgaaagag gtagttgagg      6900
gtggtggcgg tgtgttctgc cacgaagaag tacataaccc agcgtcgcaa cgtggattcg      6960
ttgatatccc ccaaggcctc aaggcgctcc atggcctcgt agaagtccac ggcgaagttg      7020
aaaaactggg agttgcgcgc cgacacggtt aactcctcct ccagaagacg gatgagctcg      7080
gcgacagtgt cgcgcacctc gcgctcaaag gctacagggg cctcttcttc ttcttcaatc      7140
tcctcttcca taagggcctc cccttcttct tcttctggcg gcggtggggg aggggggaca      7200
cggcggcgac gacggcgcac cgggaggcgg tcgacaaagc gctcgatcat ctccccgcgg      7260
cgacggcgca tggtctcggt gacggcgcgg ccgttctcgc ggggcgcag ttggaagacg      7320 ccgcccgtca tgtcccggtt atgggttggc ggggggctgc catgcggcag ggatacggcg      7380
ctaacgatgc atctcaacaa ttgttgtgta ggtactccgc cgccgaggga cctgagcgag      7440
tccgcatcga ccggatcgga aaacctctcg agaaaggcgt ctaaccagtc acagtcgcaa      7500
ggtaggctga gcaccgtggc gggcggcagc gggcggcggt cggggttgtt tctgcggag      7560 gtgctgctga tgatgtaatt aaagtaggcg gtcttgagac ggcggatggt cgacagaagc      7620
accatgtcct tgggtccggc ctgctgaatg cgcaggcggt cggccatgcc ccaggcttcg      7680
ttttgacatc ggcgcaggtc tttgtagtag tcttgcatga gcctttctac cggcacttct      7740
tcttctcctt cctcttgtcc tgcatctctt gcatctatcg ctgcggcggc ggcggagttt      7800
ggccgtaggt ggcgccctct tcctcccatg cgtgtgaccc cgaagcccct catcggctga      7860
agcagggcta ggtcggcgac aacgcgctcg gctaatatgg cctgctgcac ctgcgtgagg      7920
gtagactgga agtcatccat gtccacaaag cggtggtatg cgcccgtgtt gatggtgtaa      7980
gtgcagttgg ccataacgga ccagttaacg gtctggtgac ccggctgcga gagctcggtg      8040
tacctgagac gcgagtaagc cctcgagtca aatacgtagt cgttgcaagt ccgcaccagg      8100
tactggtatc ccaccaaaaa gtgcggcggc ggctggcggt agaggggcca gcgtaggggtg      8160 gccgggggctc cggggggcgag atcttccaac ataaggcgat gatatccgta gatgtacctg      8220
gacatccagg tgatgccggc ggcggtggtg gaggcgcgcg gaaagtcgcg gacgcggttc      8280
cagatgttgc gcagcggcaa aaagtgctcc atggtcggga cgctctggcc ggtcaggcgc      8340
gcgcaatcgt tgacgctcta gcgtgcaaaa ggagagcctg taagcgggca ctcttccgtg      8400
gtctggtgga taaattcgca agggtatcat ggcggacgac cggggttcga gccccgtatc      8460
cggccgtccg ccgtgatcca tgcggttacc gcccgcgtgt cgaacccagg tgtgcgacgt      8520
cagacaacgg gggagtgctc cttttggctt ccttccaggc gcggcggctg ctgcgctagc      8580
ttttttggcc actggccgcg cgcagcgtaa gcggttaggc tggaaagcga aagcattaag      8640
```

-continued

```
tggctcgctc cctgtagccg gagggttatt ttccaagggt tgagtcgcgg gacccccggt    8700
tcgagtctcg gaccggccgg actgcggcga acgggggttt gcctccccgt catgcaagac    8760
cccgcttgca aattcctccg gaaacaggga cgagcccctt ttttgctttt cccagatgca    8820
tccggtgctg cggcagatgc gcccccctcc tcagcagcgg caagagcaag agcagcggca    8880
gacatgcagg gcaccctccc ctcctcctac cgcgtcagga ggggcgacat ccgcggttga    8940
cgcggcagca gatggtgatt acgaaccccc gcggcgccgg gcccggcact acctggactt    9000
ggaggagggc gagggcctgg cgcggctagg agcgccctct cctgagcggc acccaagggt    9060
gcagctgaag cgtgatacgc gtgaggcgta cgtgccgcgg cagaacctgt ttcgcgaccg    9120
cgagggagag gagcccgagg agatgcggga tcgaaagttc cacgcagggc gcgagctgcg    9180
gcatggcctg aatcgcgagc ggttgctgcg cgaggaggac tttgagcccg acgcgcgaac    9240
cgggattagt cccgcgcgcg cacacgtggc ggccgccgac ctggtaaccg catacgagca    9300
gacggtgaac caggagatta actttcaaaa aagctttaac aaccacgtgc gtacgcttgt    9360
ggcgcgcgag gaggtggcta taggactgat gcatctgtgg gactttgtaa gcgcgctgga    9420
gcaaaaccca aatagcaagc cgctcatggc gcagctgttc cttatagtgc agcacagcag    9480
ggacaacgag gcattcaggg atgcgctgct aaacatagta gagcccgagg gccgctggct    9540
gctcgatttg ataaacatcc tgcagagcat agtggtgcag gagcgcagct tgagcctggc    9600
tgacaaggtg gccgccatca actattccat gcttagcctg ggcaagtttt acgcccgcaa    9660
gatataccat accccttacg ttcccataga caaggaggta aagatcgagg ggttctacat    9720
gcgcatggcg ctgaaggtgc ttaccttgag cgacgacctg ggcgtttatc gcaacgagcg    9780
catccacaag gccgtgagcg tgagccggcg gcgcgagctc agcgaccgcg agctgatgca    9840
cagcctgcaa agggccctgg ctggcacggg cagcggcgat agagaggccg agtcctactt    9900
tgacgcgggc gctgacctgc gctgggcccc aagccgacgc gccctggagg cagctggggc    9960
cggacctggg ctggcggtgg cacccgcgcg cgctggcaac gtcggcggcg tggaggaata   10020
tgacgaggac gatgagtacg agccagagga cggcgagtac taagcggtga tgtttctgat   10080
cagatgatga agacgcaac ggaccccggcg gtgcgggcgg cgctgcagag ccagccgtcc   10140
ggccttaact ccacggacga ctggcgccag gtcatggacc gcatcatgtc gctgactgcg   10200
cgcaatcctg acgcgttccg gcagcagccg caggccaacc ggctctccgc aattctggaa   10260
gcggtggtcc cggcgcgcgc aaaccccacg cacgagaagg tgctggcgat cgtaaacgcg   10320
ctggccgaaa acagggccat ccggcccgac gaggccggcc tggtctacga cgcgctgctt   10380
cagcgcgtgg ctcgttacaa cagcggcaac gtgcagacca acctggaccg gctggtgggg   10440
gatgtgcgcg aggccgtggc gcagcgtgag cgcgcgcagc agcagggcaa cctgggctcc   10500
atggttgcac taaacgcctt cctgagtaca cagcccgcca acgtgccgcg gggacaggag   10560
gactacacca actttgtgag cgcactgcgg ctaatggtga ctgagacacc gcaaagtgag   10620
gtgtaccagt ctgggccaga ctattttttc cagaccagta gacaaggcct gcagaccgta   10680
aacctgagcc aggctttcaa aaacttgcag gggctgtggg gggtgcgggc tcccacaggc   10740
gaccgcgcga ccgtgtctag cttgctgacg cccaactcgc gcctgttgct gctgctaata   10800
gcgcccttca cggacagtgg cagcgtgtcc cgggacacat acctaggtca cttgctgaca   10860
ctgtaccgcg aggccatagg tcaggcgcat gtggacgagc atactttcca ggagattaca   10920
agtgtcagcc gcgcgctggg gcaggaggac acgggcagcc tggaggcaac cctaaactac   10980
ctgctgacca accggcggca gaagatcccc tcgttgcaca gtttaaacag cgaggaggag   11040
```

-continued

```
cgcattttgc gctacgtgca gcagagcgtg agccttaacc tgatgcgcga cggggtaacg    11100
cccagcgtgg cgctggacat gaccgcgcgc aacatggaac cgggcatgta tgcctcaaac    11160
cggccgttta tcaaccgcct aatggactac ttgcatcgcg cggccgccgt gaaccccgag    11220
tatttcacca atgccatctt gaacccgcac tggctaccgc cccctggttt ctacaccggg    11280
ggattcgagg tgcccgaggg taacgatgga ttcctctggg acgacataga cgacagcgtg    11340
ttttccccgc aaccgcagac cctgctagag ttgcaacagc gcgagcaggc agaggcggcg    11400
ctgcgaaagg aaagcttccg caggccaagc agcttgtccg atctaggcgc tgcggccccg    11460
cggtcagatg ctagtagccc atttccaagc ttgatagggt ctcttaccag cactcgcacc    11520
acccgcccgc gcctgctggg cgaggaggag tacctaaaca actcgctgct gcagccgcag    11580
cgcgaaaaaa acctgcctcc ggcatttccc aacaacggga tagagagcct agtggacaag    11640
atgagtagat ggaagacgta cgcgcaggag cacagggacg tgccaggccc gcgcccgccc    11700
acccgtcgtc aaaggcacga ccgtcagcgg ggtctggtgt gggaggacga tgactcggca    11760
gacgacagca gcgtcctgga tttgggaggg agtggcaacc cgtttgcgca ccttcgcccc    11820
aggctgggga gaatgtttta aaaaaaaaa agcatgatgc aaaataaaaa actcaccaag    11880
gccatggcac cgagcgttgg ttttcttgta ttcccttag tatgcggcgc gcggcgatgt    11940
atgaggaagg tcctcctccc tcctacgaga gtgtggtgag cgcggcgcca gtggcggcgg    12000
cgctgggttc tcccttcgat gctcccctgg acccgccgtt tgtgcctccg cggtacctgc    12060
ggcctaccgg ggggagaaac agcatccgtt actctgagtt ggcaccccta ttcgacacca    12120
cccgtgtgta cctggtggac aacaagtcaa cggatgtggc atccctgaac taccagaacg    12180
accacagcaa ctttctgacc acggtcattc aaaacaatga ctacagcccg ggggaggcaa    12240
gcacacagac catcaatctt gacgaccggt cgcactgggg cggcgacctg aaaaccatcc    12300
tgcataccaa catgccaaat gtgaacgagt tcatgtttac caataagttt aaggcgcggg    12360
tgatggtgtc gcgcttgcct actaaggaca atcaggtgga gctgaaatac gagtgggtgg    12420
agttcacgct gcccgagggc aactactccg agaccatgac catagacctt atgaacaacg    12480
cgatcgtgga gcactacttg aaagtgggca gacagaacgg ggttctggaa agcgacatcg    12540
gggtaaagtt tgacacccgc aacttcagac tggggtttga ccccgtcact ggtcttgtca    12600
tgcctggggt atatacaaac gaagccttcc atccagacat cattttgctg ccaggatgcg    12660
gggtggactt cacccacagc cgcctgagca acttgttggg catccgcaag cggcaaccct    12720
tccaggaggg ctttaggatc acctacgatg atctggaggt tggtaacatt cccgcactgt    12780
tggatgtgga cgcctaccag gcgagcttga agatgacac cgaacagggc gggggtggcg    12840
caggcggcag caacagcagt ggcagcggcg cggaagagaa ctccaacgcg gcagccgcgg    12900
caatgcagcc ggtggaggac atgaacgatc atgccattcg cggcgacacc tttgccacac    12960
gggctgagga gaagcgcgct gaggccgaag cagcggccga agctgccgcc cccgctgcgc    13020
aacccgaggt cgagaagcct cagaagaaac cggtgatcaa acccctgaca gaggacagca    13080
agaaacgcag ttacaaccta ataagcaatg acagcaccct tcacccagtac cgcagctggt    13140 accttgcata caactacggc gaccctcaga ccggaatccg ctcatggacc ctgctttgca    13200
ctcctgacgt aacctgcggc tcggagcagg tctactggtc gttgccagac atgatgcaag    13260
accccgtgac cttccgctcc acgcgccaga tcagcaactt tccggtggtg ggcgccgagc    13320
tgttgcccgt gcactccaag agcttctaca acgaccaggc cgtctactcc caactcatcc    13380
```

-continued

```
gccagtttac ctctctgacc cacgtgttca atcgctttcc cgagaaccag attttggcgc   13440
gcccgccagc ccccaccatc accaccgtca gtgaaaacgt tcctgctctc acagatcacg   13500
ggacgctacc gctgcgcaac agcatcggag gagtccagcg agtgaccatt actgacgcca   13560
gacgccgcac ctgcccctac gtttacaagg ccctgggcat agtctcgccg cgcgtcctat   13620
cgagccgcac tttttgagca agcatgtcca tccttatatc gcccagcaat aaacacaggct   13680 ggggcctgcg cttcccaagc aagatgtttg gcggggccaa gaagcgctcc gaccaacacc   13740
cagtgcgcgt gcgcgggcac taccgcgcgc cctggggcgc gcacaaacgc ggccgcactg   13800
ggcgcaccac cgtcgatgac gccatcgacg cggtggtgga ggaggcgcgc aactacacgc   13860
ccacgccgcc accagtgtcc acagtggacg cggccattca gaccgtggtg cgcggagccc   13920
ggcgctatgc taaaatgaag agacggcgga ggcgcgtagc acgtcgccac cgccgccgac   13980
ccggcactgc cgcccaacgc gcggcggcgg ccctgcttaa ccgcgcacgt cgcaccggcc   14040
gacgggcggc catgcgggcc gctcgaaggc tggccgcggg tattgtcact gtgcccccca   14100
ggtccaggcg acgagcggcc gccgcagcag ccgcggccat tagtgctatg actcagggtc   14160
gcaggggcaa cgtgtattgg gtgcgcgact cggttagcgg cctgcgcgtg cccgtgcgca   14220
cccgcccccc gcgcaactag attgcaagaa aaaactactt agactcgtac tgttgtatgt   14280
atccagcggc ggcggcgcgc aacgaagcta tgtccaagcg caaaatcaaa gaagagatgc   14340
tccaggtcat cgcgccggag atctatggcc ccccgaagaa ggaagagcag gattacaagc   14400
cccgaaagct aaagcgggtc aaaaagaaaa agaaagatga tgatgatgaa cttgacgacg   14460
aggtggaact gctgcacgct accgcgccca ggcgacgggt acagtggaaa ggtcgacgcg   14520
taaaacgtgt tttgcgaccc ggcaccaccg tagtctttac gcccggtgag cgctccaccc   14580
gcacctacaa gcgcgtgtat gatgaggtgt acggcgacga ggacctgctt gagcaggcca   14640
acgagcgcct cggggagttt gcctacggaa agcggcataa ggacatgctg gcgttgccgc   14700
tggacgaggg caacccaaca cctagcctaa agcccgtaac actgcagcag gtgctgcccg   14760
cgcttgcacc gtccgaagaa aagcgcggcc taaagcgcga gtctggtgac ttggcaccca   14820
ccgtgcagct gatggtaccc aagcgccagc gactggaaga tgtcttggaa aaaatgaccg   14880
tggaacctgg gctggagccc gaggtccgcg tgcggccaat caagcaggtg gcgccgggac   14940
tgggcgtgca gaccgtggac gttcagatac ccactaccag tagcaccagt attgccaccg   15000
ccacagaggg catggagaca caaacgtccc cggttgcctc agcggtggcg gatgccgcgg   15060
tgcaggcggt cgctgcggcc gcgtccaaga cctctacgga ggtgcaaacg gacccgtgga   15120
tgtttcgcgt ttcagccccc cggcgcccgc gccgttcgag gaagtacggc gccgccagcg   15180
cgctactgcc cgaatatgcc ctacatcctt ccattgcgcc tacccccggc tatcgtggct   15240
acacctaccg ccccagaaga cgagcaacta cccgacgccg aaccaccact ggaacccgcc   15300
gccgccgtcg ccgtcgccag cccgtgctgg ccccgatttc cgtgcgcagg gtggctcgcg   15360
aaggaggcag gaccctggtg ctgccaacag cgcgctacca ccccagcatc gtttaaaagc   15420
cggtctttgt ggttcttgca gatatggccc tcacctgccg cctccgtttc ccggtgccgg   15480
gattccgagg aagaatgcac cgtaggaggg gcatggccgg ccacggcctg acgggcggca   15540
tgcgtcgtgc gcaccaccgg cggcggcgcg cgtcgcaccg tcgcatgcgc ggcggtatcc   15600
tgcccctcct tattccactg atcgccgcgg cgattggcgc cgtgcccgga attgcatccg   15660
tggccttgca ggcgcagaga cactgattaa aaacaagttg catgtggaaa aatcaaaata   15720
aaaagtctgg actctcacgc tcgcttggtc ctgtaactat tttgtagaat ggaagacatc   15780
```

-continued

```
aactttgcgt ctctggcccc gcgacacggc tcgcgcccgt tcatgggaaa ctggcaagat   15840
atcggcacca gcaatatgag cggtggcgcc ttcagctggg gctcgctgtg gagcggcatt   15900
aaaaatttcg gttccaccgt taagaactat ggcagcaagg cctggaacag cagcacaggc   15960
cagatgctga gggataagtt gaaagagcaa aatttccaac aaaaggtggt agatggcctg   16020
gcctctggca ttagcggggt ggtggacctg gccaaccagg cagtgcaaaa taagattaac   16080
agtaagcttg atccccgccc tcccgtagag gagcctccac cggccgtgga gacagtgtct   16140
ccagaggggc gtggcgaaaa gcgtccgcgc cccgacaggg aagaaactct ggtgacgcaa   16200
atagacgagc ctccctcgta cgaggaggca ctaaagcaag gcctgcccac cacccgtccc   16260
atcgcgccca tggctaccgg agtgctgggc cagcacacac ccgtaacgct ggacctgcct   16320 cccccgccg acacccagca gaaacctgtg ctgccaggcc cgaccgccgt tgttgtaacc   16380
cgtcctagcc gcgcgtccct gcgccgcgcc gccagcggtc cgcgatcgtt gcggcccgta   16440
gccagtggca actggcaaag cacactgaac agcatcgtgg gtctgggggt gcaatccctg   16500
aagcgccgac gatgcttctg atagctaacg tgtcgtatgt gtgtcatgta tgcgtccatg   16560
tcgccgccag aggagctgct gagccgccgc gcgcccgctt tccaagatgg ctacccttc   16620 gatgatgccg cagtggtctt acatgcacat ctcgggccag gacgcctcgg agtacctgag   16680 cccccgggctg gtgcagtttg cccgcgccac cgagacgtac ttcagcctga ataacaagtt   16740
tagaaacccc acggtggcgc ctacgcacga cgtgaccaca gaccggtccc agcgtttgac   16800
gctgcggttc atccctgtgg accgtgagga tactgcgtac tcgtacaagg cgcggttcac   16860
cctagctgtg ggtgataacc gtgtgctgga catggcttcc acgtactttg acatccgcgg   16920
cgtgctggac aggggcccta cttttaagcc ctactctggc actgcctaca acgccctggc   16980
tcccaagggt gccccaaatc cttgcgaatg ggatgaagct gctactgctc ttgaaataaa   17040
cctagaagaa gaggacgatg acaacgaaga cgaagtagac gagcaagctg agcagcaaaa   17100
aactcacgta tttgggcagg cgccttattc tggtataaat attacaaagg agggtattca   17160
aataggtgtc gaaggtcaaa cacctaaata tgccgataaa acatttcaac ctgaacctca   17220
aataggagaa tctcagtggt acgaaacaga aattaatcat gcagctggga gagtcctaaa   17280
aaagactacc ccaatgaaac catgttacgg ttcatatgca aaacccacaa atgaaaatgg   17340
agggcaaggc attcttgtaa agcaacaaaa tggaaagcta gaaagtcaag tggaaatgca   17400 attttttctca actactgagg cagccgcagg caatggtgat aacttgactc ctaaagtggt   17460
attgtacagt gaagatgtag atatagaaac cccagacact catatttctt acatgcccac   17520
tattaaggaa ggtaactcac gagaactaat gggccaacaa tctatgccca acaggcctaa   17580
ttacattgct tttaggggaca atttta ttgg tctaatgtat tacaacagca cgggtaatat   17640
gggtgttctg gcgggccaag catcgcagtt gaatgctgtt gtagatttgc aagacagaaa   17700
cacagagctt tcataccagc ttttgcttga ttccattggt gatagaacca ggtacttttc   17760
tatgtggaat caggctgttg acagctatga tccagatgtt agaattattg aaaatcatgg   17820
aactgaagat gaacttccaa attactgctt tccactggga ggtgtgatta atacagagac   17880
tcttaccaag gtaaaaccta aaacaggtca ggaaaatgga tgggaaaaag atgctacaga   17940
attttcagat aaaaatgaaa taagagttgg aaataatttt gccatggaaa tcaatctaaa   18000
tgccaacctg tggagaaatt tcctgtactc caacatagcg ctgtatttgc ccgacaagct   18060
aaagtacagt ccttccaacg taaaaatttc tgataaccca aacacctacg actacatgaa   18120
```

-continued

```
caagcgagtg gtggctcccg ggctagtgga ctgctacatt aaccttggag cacgctggtc   18180
ccttgactat atggacaacg tcaacccatt taaccaccac cgcaatgctg gcctgcgcta   18240
ccgctcaatg ttgctgggca atggtcgcta tgtgcccttc cacatccagg tgcctcagaa   18300
gttctttgcc attaaaaacc tccttctcct gccgggctca tacacctacg agtggaactt   18360
caggaaggat gttaacatgg ttctgcagag ctccctagga aatgacctaa gggttgacgg   18420
agccagcatt aagtttgata gcatttgcct ttacgccacc ttcttcccca tggcccacaa   18480
caccgcctcc acgcttgagg ccatgcttag aaacgacacc aacgaccagt cctttaacga   18540
ctatctctcc gccgccaaca tgctctaccc tatacccgcc aacgctacca acgtgcccat   18600
atccatcccc tcccgcaact gggcggcttt ccgcggctgg gccttcacgc gccttaagac   18660
taaggaaacc ccatcactgg gctcgggcta cgacccttat tacacctact ctggctctat   18720
accctaccta gatggaacct tttacctcaa ccacaccttt aagaaggtgg ccattacctt   18780
tgactcttct gtcagctggc ctggcaatga ccgcctgctt accccaaacg agtttgaaat   18840
taagcgctca gttgacgggg agggttacaa cgttgcccag tgtaacatga ccaaagactg   18900
gttcctggta caaatgctag ctaactataa cattggctac cagggcttct atatcccaga   18960
gagctacaag gaccgcatgt actccttctt tagaaacttc cagcccatga gccgtcaggt   19020
ggtggatgat actaaataca aggactacca acaggtgggc atcctacacc aacacaacaa   19080
ctctggattt gttggctacc ttgccccac catgcgcgaa ggacaggcct accctgctaa   19140
cttcccctat ccgcttatag gcaagaccgc agttgacagc attacccaga aaaagtttct   19200
ttgcgatcgc accctttggc gcatcccatt ctccagtaac tttatgtcca tgggcgcact   19260
cacagacctg ggccaaaacc ttctctacgc caactccgcc cacgcgctag acatgacttt   19320
tgaggtggat cccatggacg agcccaccct tctttatgtt ttgtttgaag tctttgacgt   19380
ggtccgtgtg caccagccgc accgcggcgt catcgaaacc gtgtacctgc gcacgccctt   19440
ctcggccggc aacgccacaa cataaagaag caagcaacat caacaacagc tgccgccatg   19500
ggctccagtg agcaggaact gaaagccatt gtcaaagatc ttggttgtgg gccatatttt   19560
ttgggcacct atgacaagcg ctttccaggc tttgtttctc cacacaagct cgcctgcgcc   19620
atagtcaata cggccggtcg cgagactggg ggcgtacact ggatggcctt tgcctggaac   19680
ccgcactcaa aaacatgcta cctctttgag ccctttggct tttctgacca gcgactcaag   19740
caggtttacc agtttgagta cgagtcactc ctgcgccgta gcgccattgc ttcttccccc   19800
gaccgctgta taacgctgga aaagtccacc caaagcgtac aggggcccaa ctcggccgcc   19860
tgtggactat tctgctgcat gtttctccac gcctttgcca actggcccca aactcccatg   19920
gatcacaacc ccaccatgaa ccttattacc ggggtaccca actccatgct caacagtccc   19980
caggtacagc ccaccctgcg tcgcaaccag gaacagctct acagcttcct ggagcgccac   20040
tcgccctact tccgcagcca cagtgcgcag attaggagcg ccacttcttt ttgtcacttg   20100
aaaaacatgt aaaaataatg tactagagac actttcaata aaggcaaatg cttttatttg   20160
tacactctcg ggtgattatt taccccccacc cttgccgtct gcgccgttta aaaatcaaag   20220
gggttctgcc gcgcatcgct atgcgccact ggcagggaca cgttgcgata ctggtgttta   20280
gtgctccact taaactcagg cacaaccatc cgcggcagct cggtgaagtt ttcactccac   20340
aggctgcgca ccatcaccaa cgcgtttagc aggtcgggcg ccgatatctt gaagtcgcag   20400 ttgggggcctc cgccctgcgc gcgcgagttg cgatacacag ggttgcagca ctggaacact   20460
atcagcgccg ggtggtgcac gctggccagc acgctcttgt cggagatcag atccgcgtcc   20520
```

-continued

```
aggtcctccg cgttgctcag ggcgaacgga gtcaactttg gtagctgcct tcccaaaaag   20580
ggcgcgtgcc caggctttga gttgcactcg caccgtagtg gcatcaaaag gtgaccgtgc   20640
ccggtctggg cgttaggata cagcgcctgc ataaaagcct tgatctgctt aaaagccacc   20700
tgagcctttg cgccttcaga gaagaacatg ccgcaagact tgccggaaaa ctgattggcc   20760
ggacaggccg cgtcgtgcac gcagcacctt gcgtcggtgt tggagatctg caccacattt   20820
cggccccacc ggttcttcac gatcttggcc ttgctagact gctccttcag cgcgcgctgc   20880
ccgttttcgc tcgtcacatc catttcaatc acgtgctcct tatttatcat aatgcttccg   20940
tgtagacact taagctcgcc ttcgatctca gcgcagcggt gcagccacaa cgcgcagccc   21000
gtgggctcgt gatgcttgta ggtcacctct gcaaacgact gcaggtacgc ctgcaggaat   21060
cgccccatca tcgtcacaaa ggtcttgttg ctggtgaagg tcagctgcaa cccgcggtgc   21120
tcctcgttca gccaggtctt gcatacggcc gccagagctt ccacttggtc aggcagtagt   21180
ttgaagttcg cctttagatc gttatccacg tggtacttgt ccatcagcgc gcgcgcagcc   21240
tccatgccct tctcccacgc agacacgatc ggcacactca gcgggttcat caccgtaatt   21300
tcactttccg cttcgctggg ctcttcctct tcctcttgcg tccgcatacc acgcgccact   21360
gggtcgtctt cattcagccg ccgcactgtg cgcttacctc ctttgccatg cttgattagc   21420
accggtgggt tgctgaaacc caccatttgt agcgccacat cttctctttc ttcctcgctg   21480
tccacgatta cctctggtga tggcgggcgc tcgggcttgg gagaagggcg cttctttttc   21540
ttcttgggcg caatggccaa atccgccgcc gaggtcgatg gccgcgggct gggtgtgcgc   21600
ggcaccagcg cgtcttgtga tgagtcttcc tcgtcctcgg actcgatacg ccgcctcatc   21660
cgcttttttg ggggcgcccg gggaggcggc ggcgacgggg acgggacga cacgtcctcc   21720 atggttgggg gacgtcgcgc cgcaccgcgt ccgcgctcgg gggtggtttc gcgctgctcc   21780
tcttcccgac tggccatttc cttctcctat aggcagaaaa agatcatgga gtcagtcgag   21840
aagaaggaca gcctaaccgc cccctctgag ttcgccacca ccgcctccac cgatgccgcc   21900
aacgcgccta ccaccttccc cgtcgaggca ccccgcttg aggaggagga agtgattatc   21960
gagcaggacc caggttttgt aagcgaagac gacgaggacc gctcagtacc aacagaggat   22020
aaaaagcaag accaggacaa cgcagaggca aacgaggaac aagtcgggcg gggggacgaa   22080
aggcatggcg actacctaga tgtgggagac gacgtgctgt tgaagcatct gcagcgccag   22140
tgcgccatta tctgcgacgc gttgcaagag cgcagcgatg tgccctcgc catagcggat   22200 gtcagccttg cctacgaacg ccacctattc tcaccgcgcg taccccccaa acgccaagaa   22260
aacggcacat gcgagcccaa cccgcgcctc aacttctacc ccgtatttgc cgtgccagag   22320
gtgcttgcca cctatcacat cttttttccaa aactgcaaga tacccctatc ctgccgtgcc   22380
aaccgcagcc gagcggacaa gcagctggcc ttgcggcagg gcgctgtcat acctgatatc   22440
gcctcgctca acgaagtgcc aaaaatcttt gaggggtcttg gacgcgacga gaagcgcgcg   22500
gcaaacgctc tgcaacagga aaacagcgaa aatgaaagtc actctggagt gttggtggaa   22560
ctcgagggtg acaacgcgcg cctagccgta ctaaaacgca gcatcgaggt cacccacttt   22620
gcctacccgg cacttaacct accccccaag gtcatgagca cagtcatgag tgagctgatc   22680
gtgcgccgtg cgcagcccct ggagagggat gcaaatttgc aagaacaaac agaggagggc   22740
ctacccgcag ttggcgacga gcagctagcg cgctggcttc aaacgcgcga gcctgccgac   22800
ttggaggagc gacgcaaact aatgatggcc gcagtgctcg ttaccgtgga gcttgagtgc   22860
```

-continued

```
atgcagcggt tctttgctga cccggagatg cagcgcaagc tagaggaaac attgcactac   22920
acctttcgac agggctacgt acgccaggcc tgcaagatct ccaacgtgga gctctgcaac   22980
ctggtctcct accttggaat tttgcacgaa aaccgccttg ggcaaaacgt gcttcattcc   23040
acgctcaagg gcgaggcgcg ccgcgactac gtccgcgact gcgtttactt atttctatgc   23100
tacacctggc agacggccat gggcgtttgg cagcagtgct tggaggagtg caacctcaag   23160
gagctgcaga aactgctaaa gcaaaacttg aaggacctat ggacggcctt caacgagcgc   23220
tccgtggccg cgcacctggc ggacatcatt ttccccgaac gcctgcttaa aaccctgcaa   23280
cagggtctgc cagacttcac cagtcaaagc atgttgcaga actttaggaa ctttatccta   23340
gagcgctcag gaatcttgcc cgccacctgc tgtgcacttc ctagcgactt tgtgcccatt   23400
aagtaccgcg aatgccctcc gccgctttgg ggccactgct accttctgca gctagccaac   23460
taccttgcct accactctga cataatggaa gacgtgagcg gtgacggtct actggagtgt   23520
cactgtcgct gcaacctatg cacccgcac cgctccctgg tttgcaattc gcagctgctt   23580
aacgaaagtc aaattatcgg tacctttgag ctgcagggtc cctcgcctga cgaaaagtcc   23640
gcggctccgg ggttgaaact cactccgggg ctgtggacgt cggcttacct tcgcaaattt   23700
gtacctgagg actaccacgc ccacgagatt aggttctacg aagaccaatc ccgcccgcct   23760
aatgcggagc ttaccgcctg cgtcattacc cagggccaca ttcttggcca attgcaagcc   23820
atcaacaaag cccgccaaga gtttctgcta cgaaagggac gggggtttta cttggacccc   23880
cagtccggcg aggagctcaa cccaatcccc ccgccgccgc agccctatca gcagcagccg   23940
cgggcccttg cttcccagga tggcacccaa aaagaagctg cagctgccgc cgccacccac   24000
ggacgaggag gaatactggg acagtcaggc agaggaggtt ttggacgagg aggaggagga   24060
catgatggaa gactgggaga gcctagacga ggaagcttcc gaggtcgaag aggtgtcaga   24120
cgaaacaccg tcaccctcgg tcgcattccc ctcgccggcg ccccagaaat cggcaaccgg   24180
ttccagcatg gctacaacct ccgctcctca ggcgccgccg gcactgcccg ttcgccgacc   24240
caaccgtaga tgggacacca ctggaaccag ggccggtaag tccaagcagc cgccgccgtt   24300
agcccaagag caacaacagc gccaaggcta ccgctcatgg cgcgggcaca agaacgccat   24360
agttgcttgc ttgcaagact gtggggcaa catctccttc gcccgccgct ttcttctcta   24420
ccatcacggc gtggccttcc cccgtaacat cctgcattac taccgtcatc tctacagccc   24480
atactgcacc ggcggcagcg gcagcaacag cagcggccac acagaagcaa aggcgaccgg   24540
atagcaagac tctgacaaag cccaagaaat ccacagcggc ggcagcagca ggaggaggag   24600
cgctgcgtct ggcgcccaac gaacccgtat cgacccgcga gcttagaaac aggattttc   24660 ccactctgta tgctatattt caacagagca ggggccaaga acaagagctg aaaataaaaa   24720
acaggtctct gcgatccctc acccgcagct gcctgtatca caaaagcgaa gatcagcttc   24780
ggcgcacgct ggaagacgcg gaggctctct tcagtaaata ctgcgcgctg actcttaagg   24840
actagtttcg cgccctttct caaatttaag cgcgaaaact acgtcatctc cagcggccac   24900
acccggcgcc agcacctgtt gtcagcgcca ttatgagcaa ggaaattccc acgccctaca   24960
tgtggagtta ccagccacaa atgggacttg cggctggagc tgcccaagac tactcaaccc   25020
gaataaacta catgagcgcg ggaccccaca tgatatcccg ggtcaacgga atacgcgccc   25080
accgaaaccg aattctcctg gaacaggcgg ctattaccac cacacctcgt aataacctta   25140
atccccgtag ttggcccgct gccctggtgt accaggaaag tcccgctccc accactgtgg   25200
tacttcccag agacgcccag gccgaagttc agatgactaa ctcaggggcg cagcttgcgg   25260
```

```
gcggctttcg tcacagggtg cggtcgcccg ggcagggtat aactcacctg acaatcagag   25320
ggcgaggtat tcagctcaac gacgagtcgg tgagctcctc gcttggtctc cgtccggacg   25380
ggacatttca gatcggcggc gccggccgct cttcattcac gcctcgtcag gcaatcctaa   25440
ctctgcagac ctcgtcctct gagccgcgct ctggaggcat tggaactctg caatttattg   25500
aggagtttgt gccatcggtc tactttaacc ccttctcggg acctcccggc cactatccgg   25560
atcaatttat tcctaacttt gacgcggtaa aggactcggc ggacggctac gactgaatgt   25620
taagtggaga ggcagagcaa ctgcgcctga aacacctggt ccactgtcgc cgccacaagt   25680
gctttgcccg cgactccggt gagttttgct actttgaatt gcccgaggat catatcgagg   25740
gcccggcgca cggcgtccgg cttaccgccc agggagagct tgcccgtagc ctgattcggg   25800
agttacccca gcgccccctg ctagttgagc gggacagggg accctgtgtt ctcactgtga   25860
tttgcaactg tcctaaccct ggattacatc aagatcctct agttaatgtc aggtcgccta   25920
agtcgattaa ctagagtacc cggggatctt attcccttta actaataaaa aaaaataata   25980
aagcatcact tacttaaaat cagttagcaa atttctgtcc agtttattca gcagcacctc   26040
cttgccctcc tcccagctct ggtattgcag cttcctcctg gctgcaaact ttctccacaa   26100
tctaaatgga atgtcagttt cctcctgttc ctgtccatcc gcacccacta tcttcatgtt   26160
gttgcagatg aagcgcgcaa gaccgtctga agataccttc aaccccgtgt atccatatga   26220
cacggaaacc ggtcctccaa ctgtgccttt tcttactcct ccctttgtat cccccaatgg   26280
gtttcaagag agtccccctg gggtactctc tttgcgccta tccgaacctc tagttacctc   26340
caatggcatg cttgcgctca aaatgggcaa cggcctctct ctggacgagg ccggcaacct   26400
tacctcccaa aatgtaacca ctgtgagccc acctctcaaa aaaaccaagt caaacataaa   26460
cctggaaata tctgcacccc tcacagttac ctcagaagcc ctaactgtgg ctgccgccgc   26520
acctctaatg gtcgcgggca acacactcac catgcaatca caggccccgc taaccgtgca   26580
cgactccaaa cttagcattg ccacccaagg acccctcaca gtgtcagaag gaaagctagc   26640
cctgcaaaca tcaggccccc tcaccaccac cgatagcagt acccttacta tcactgcctc   26700 acccctcta actactgcca ctggtagctt gggcattgac ttgaaagagc ccatttatac   26760
acaaaatgga aaactaggac taaagtacgg ggctcctttg catgtaacag acgacctaaa   26820
cactttgacc gtagcaactg gtccaggtgt gactattaat aatacttcct tgcaaactaa   26880
agttactgga gccttgggtt ttgattcaca aggcaatatg caacttaatg tagcaggagg   26940
actaaggatt gattctcaaa acagacgcct tatacttgat gttagttatc cgtttgatgc   27000
tcaaaaccaa ctaaatctaa gactaggaca gggccctctt tttataaact cagcccacaa   27060
cttggatatt aactacaaca aaggccttta cttgtttaca gcttcaaaca attccaaaaa   27120
gcttgaggtt aacctaagca ctgccaaggg gttgatgttt gacgctacag ccatagccat   27180
taatgcagga gatgggcttg aatttggttc acctaatgca ccaaacacaa atcccctcaa   27240
aacaaaaatt ggccatggcc tagaatttga ttcaaacaag gctatggttc ctaaactagg   27300
aactggcctt agttttgaca gcacaggtgc cattacagta ggaaacaaaa ataatgataa   27360
gctaactttg tggaccggaa taaaccctcc acctaactgt caaattgtgg aaaacactaa   27420
tacaaatgat ggcaaactta ctttagtatt agtaaaaaat ggagggcttg ttaatggcta   27480
cgtgtctcta gttggtgtat cagacactgt gaaccaaatg ttcacacaaa agacagcaaa   27540
catccaatta agattatatt ttgactcttc tggaaatcta ttaactgagg aatcagactt   27600
```

-continued

```
aaaaattcca cttaaaaata aatcttctac agcgaccagt gaaactgtag ccagcagcaa   27660
agcctttatg ccaagtacta cagcttatcc cttcaacacc actactaggg atagtgaaaa   27720
ctacattcat ggaatatgtt actacatgac tagttatgat agaagtctat ttcccttgaa   27780
catttctata atgctaaaca gccgtatgat ttcttccaat gttgcctatg ccatacaatt   27840
tgaatggaat ctaaatgcaa gtgaatctcc agaaagcaac atagctacgc tgaccacatc   27900 ccccttttttc ttttcttaca ttacagaaga cgacaactaa agaatcgttt gtgttatgtt   27960
tcaacgtgtt tattttttcaa ttgcagaaaa tttcaagtca tttttcattc agtagtatag   28020
ccccaccacc acatagctta tacagatcac cgtaccttaa tcaaactcac agaaccctag   28080
tattcaacct gccacctccc tcccaacaca cagagtacac agtcctttct ccccggctgg   28140
ccttaaaaag catcatatca tgggtaacag acatattctt aggtgttata ttccacacgg   28200
tttcctgtcg agccaaacgc tcatcagtga tattaataaa ctccccgggc agctcactta   28260
agttcatgtc gctgtccagc tgctgagcca caggctgctg tccaacttgc ggttgcttaa   28320
cgggcggcga aggagaagtc cacgcctaca tgggggtaga gtcataatcg tgcatcagga   28380
tagggcggtg gtgctgcagc agcgcgcgaa taaactgctg ccgccgccgc tccgtcctgc   28440
aggaatacaa catggcagtg gtctcctcag cgatgattcg caccgcccgc agcataaggc   28500
gccttgtcct ccgggcacag cagcgcaccc tgatctcact aaaatcagca cagtaactgc   28560
agcacagcac cacaatattg ttcaaaatcc cacagtgcaa ggcgctgtat ccaaagctca   28620
tggcggggac cacagaaccc acgtggccat cataccacaa gcgcaggtag attaagtggc   28680 gaccctcat aaacacgctg gacataaaca ttacctcttt tggcatgttg taattcacca   28740
cctcccggta ccatataaac ctctgattaa acatggcgcc atccaccacc atcctaaacc   28800
agctggccaa aacctgcccg ccggctatac actgcaggga accgggactg gaacaatgac   28860
agtggagagc ccaggactcg taaccatgga tcatcatgct cgtcatgata tcaatgttgg   28920
cacaacacag gcacacgtgc atacacttcc tcaggattac aagctcctcc cgcgttagaa   28980
ccatatccca gggaacaacc cattcctgaa tcagcgtaaa tcccacactg cagggaagac   29040
ctcgcacgta actcacgttg tgcattgtca aagtgttaca ttcgggcagc agcggatgat   29100
cctccagtat ggtagcgcgg gtttctgtct caaaaggagg tagacgatcc ctactgtacg   29160
gagtgcgccg agacaaccga gatcgtgttg gtcgtagtgt catgccaaat ggaacgccgg   29220
acgtagtcat atttcctgaa gcaaaaccag gtgcgggcgt gacaaacaga tctgcgtctc   29280
cggtctcgcc gcttagatcg ctctgtgtag tagttgtagt atatccactc tctcaaagca   29340
tccaggcgcc ccctggcttc gggttctatg taaactcctt catgcgccgc tgccctgata   29400
acatccacca ccgcagaata agccacaccc agccaaccta cacattcgtt ctgcgagtca   29460
cacacgggag gagcgggaag agctggaaga accatgtttt ttttttttatt ccaaaagatt   29520 atccaaaacc tcaaaatgaa gatctattaa gtgaacgcgc tccctccgg tggcgtggtc   29580 aaactctaca gccaaagaac agataatggc atttgtaaga tgttgcacaa tggcttccaa   29640
aaggcaaacg gccctcacgt ccaagtggac gtaaaggcta aacccttcag ggtgaatctc   29700
ctctataaac attccagcac cttcaaccat gcccaaataa ttctcatctc gccaccttct   29760
caatatatct ctaagcaaat cccgaatatt aagtccggcc attgtaaaaa tctgctccag   29820
agcgccctcc accttcagcc tcaagcagcg aatcatgatt gcaaaaattc aggttcctca   29880
cagacctgta taagattcaa aagcggaaca ttaacaaaaa taccgcgatc ccgtaggtcc   29940
cttcgcaggg ccagctgaac ataatcgtgc aggtctgcac ggaccagcgc ggccacttcc   30000
```

-continued

```
ccgccaggaa ccatgacaaa agaacccaca ctgattatga cacgcatact cggagctatg    30060
ctaaccagcg tagccccgat gtaagcttgt tgcatgggcg gcgatataaa atgcaaggtg    30120
ctgctcaaaa aatcaggcaa agcctcgcgc aaaaaagaaa gcacatcgta gtcatgctca    30180
tgcagataaa ggcaggtaag ctccggaacc accacagaaa aagacaccat tttctctca    30240 aacatgtctg cgggtttctg cataaacaca aaataaaata acaaaaaaac atttaaacat    30300
tagaagcctg tcttacaaca ggaaaaacaa cccttataag cataagacgg actacggcca    30360
tgccggcgtg accgtaaaaa aactggtcac cgtgattaaa aagcaccacc gacagctcct    30420
cggtcatgtc cggagtcata atgtaagact cggtaaacac atcaggttga ttcacatcgg    30480
tcagtgctaa aaagcgaccg aaatagcccg ggggaataca tacccgcagg cgtagagaca    30540
acattacagc ccccatagga ggtataacaa aattaatagg agagaaaaac acataaacac    30600
ctgaaaaacc ctcctgccta ggcaaaatag caccctcccg ctccagaaca acatacagcg    30660
cttccacagc ggcagccata acagtcagcc ttaccagtaa aaaagaaaac ctattaaaaa    30720
aacaccactc gacacggcac cagctcaatc agtcacagtg taaaaaaggg ccaagtgcag    30780
agcgagtata tataggacta aaaaatgacg taacggttaa agtccacaaa aaacacccag    30840
aaaaccgcac gcgaacctac gcccagaaac gaaagccaaa aaacccacaa cttcctcaaa    30900
tcgtcacttc cgttttccca cgttacgtca cttcccattt taagaaaact acaattccca    30960
acacatacaa gttactccgc cctaaaacct acgtcacccg ccccgttccc acgccccgcg    31020
ccacgtcaca aactccaccc cctcattatc atattggctt caatccaaaa taaggtatat    31080
tattgatgat g                                                        31091
```

<210> SEQ ID NO 22
<211> LENGTH: 37678
<212> TYPE: DNA
<213> ORGANISM: Artificial Sequence
<220> FEATURE:
<223> OTHER INFORMATION: plasmid #1 vector

<400> SEQUENCE: 22

```
ttaattaaca tgcatggatc catatgcggt gtgaaatacc gcacagatgc gtaaggagaa      60
aataccgcat caggcgctct tccgcttcct cgctcactga ctcgctgcgc tcggtcgttc     120
ggctgcggcg agcggtatca gctcactcaa aggcggtaat acggttatcc acagaatcag     180
gggataacgc aggaaagaac atgtgagcaa aaggccagca aaaggccagg aaccgtaaaa     240
aggccgcgtt gctggcgttt ttccataggc tccgcccccc tgacgagcat cacaaaaatc     300
gacgctcaag tcagaggtgg cgaaacccga caggactata aagataccag gcgtttcccc     360
ctggaagctc cctcgtgcgc tctcctgttc cgaccctgcc gcttaccgga tacctgtccg     420
cctttctccc ttcgggaagc gtggcgcttt ctcatagctc acgctgtagg tatctcagtt     480
cggtgtaggt cgttcgctcc aagctgggct gtgtgcacga accccccgtt cagcccgacc     540
gctgcgcctt atccggtaac tatcgtcttg agtccaaccc ggtaagacac gacttatcgc     600
cactggcagc agccactggt aacaggatta gcagagcgag gtatgtaggc ggtgctacag     660
agttcttgaa gtggtggcct aactacggct acactagaag gacagtattt ggtatctgcg     720
ctctgctgaa gccagttacc ttcggaaaaa gagttggtag ctcttgatcc ggcaaacaaa     780
ccaccgctgg tagcggtggt ttttttgttt gcaagcagca gattacgcgc agaaaaaaag     840
gatctcaaga agatcctttg atctttttcta cggggtctga cgctcagtgg aacgaaaact     900
```

-continued

```
cacgttaagg gattttggtc atgagattat caaaaaggat cttcacctag atccttttaa     960
attaaaaatg aagttttaaa tcaatctaaa gtatatatga gtaaacttgg tctgacagtt    1020
accaatgctt aatcagtgag gcacctatct cagcgatctg tctatttcgt tcatccatag    1080
ttgcctgact ccccgtcgtg tagataacta cgatacggga gggcttacca tctggcccca    1140
gtgctgcaat gataccgcga gacccacgct caccggctcc agatttatca gcaataaacc    1200
agccagccgg aagggccgag cgcagaagtg gtcctgcaac tttatccgcc tccatccagt    1260
ctattaattg ttgccgggaa gctagagtaa gtagttcgcc agttaatagt ttgcgcaacg    1320
ttgttgccat tgctgcagcc atgagattat caaaaaggat cttcacctag atccttttca    1380
cgtagaaagc cagtccgcag aaacggtgct gaccccggat gaatgtcagc tactgggcta    1440
tctggacaag ggaaaacgca agcgcaaaga gaaagcaggt agcttgcagt gggcttacat    1500
ggcgatagct agactgggcg gttttatgga cagcaagcga accggaattg ccagctgggg    1560
cgccctctgg taaggttggg aagccctgca aagtaaactg gatggctttc ttgccgccaa    1620
ggatctgatg gcgcagggga tcaagctctg atcaagagac aggatgagga tcgtttcgca    1680
tgattgaaca agatggattg cacgcaggtt ctccggccgc ttgggtggag aggctattcg    1740
gctatgactg ggcacaacag acaatcggct gctctgatgc cgccgtgttc cggctgtcag    1800
cgcaggggcg cccggttctt tttgtcaaga ccgacctgtc cggtgccctg aatgaactgc    1860
aagacgagga gcgcggcta tcgtggctgg ccacgacggg cgttccttgc gcagctgtgc    1920
tcgacgttgt cactgaagcg ggaagggact ggctgctatt gggcgaagtg ccggggcagg    1980
atctcctgtc atctcacctt gctcctgccg agaaagtatc catcatggct gatgcaatgc    2040
ggcggctgca tacgcttgat ccggctacct gcccattcga ccaccaagcg aaacatcgca    2100
tcgagcgagc acgtactcgg atggaagccg gtcttgtcga tcaggatgat ctggacgaag    2160
agcatcaggg gctcgcgcca gccgaactgt tcgccaggct caaggcgagc atgcccgacg    2220
gcgaggatct cgtcgtgacc catggcgatg cctgcttgcc gaatatcatg gtggaaaatg    2280
gccgcttttc tggattcatc gactgtggcc ggctgggtgt ggcggaccgc tatcaggaca    2340
tagcgttggc tacccgtgat attgctgaag agcttggcgg cgaatgggct gaccgcttcc    2400
tcgtgcttta cggtatcgcc gctcccgatt cgcagcgcat cgccttctat cgccttcttg    2460
acgagttctt ctgaatttg ttaaaatttt tgttaaatca gctcattttt taaccaatag    2520
gccgaaatcg gcaaaatccc ttataaatca aaagaataga ccgagatagg gttgagtgtt    2580
gttccagttt ggaacaagag tccactatta aagaacgtgg actccaacgt caaagggcga    2640
aaaaccgtct atcagggcga tggcccacta cgtgaaccat caccctaatc aagttttttg    2700
gggtcgaggt gccgtaaagc actaaatcgg aaccctaaag ggagcccccg atttagagct    2760
tgacggggaa agccggcgaa cgtggcgaga aaggaaggga agaaagcgaa aggagcgggc    2820
gctagggcgc tggcaagtgt agcggtcacg ctgcgcgtaa ccaccacacc cgccgcgctt    2880
aatgcgccgc tacagggcgc gtccattcgc cattcaggat cgaattaatt cttaattaac    2940
atcatcaata atatacctta ttttggattg aagccaatat gataatgagg gggtggagtt    3000
tgtgacgtgg cgcggggcgt gggaacgggc cgggtgacgt agtagtgtgg cggaagtgtg    3060
atgttgcaag tgtggcggaa cacatgtaag cgacggatgt ggcaaaagtg acgtttttgg    3120
tgtgcgccgg tgtacacagg aagtgacaat tttcgcgcgg ttttaggcgg atgttgtagt    3180
aaatttgggc gtaaccgagt aagatttggc cattttcgcg ggaaaactga ataagaggaa    3240
gtgaaatctg aataattttg tgttactcat agcgcgtaat actgtaatag taatcaatta    3300
```

-continued

```
cggggtcatt agttcatagc ccatatatgg agttccgcgt tacataactt acggtaaatg   3360
gcccgcctgg ctgaccgccc aacgacccc gcccattgac gtcaataatg acgtatgttc    3420
ccatagtaac gccaataggg actttccatt gacgtcaatg ggtggagtat ttacggtaaa    3480
ctgcccactt ggcagtacat caagtgtatc atatgccaag tacgcccct attgacgtca     3540 atgacggtaa atggcccgcc tggcattatg cccagtacat gaccttatgg gactttccta    3600
cttggcagta catctacgta ttagtcatcg ctattaccat ggtgatgcgg ttttggcagt    3660
acatcaatgg gcgtggatag cggtttgact cacgggatt tccaagtctc cacccattg     3720 acgtcaatgg gagtttgttt tggcaccaaa atcaacggga ctttccaaaa tgtcgtaaca    3780
actccgcccc attgacgcaa atgggcggta ggcgtgtacg gtgggaggtc tatataagca    3840
gagctctccc tatcagtgat agagatctcc ctatcagtga tagagatcgt cgacgagctc    3900
gtttagtgaa ccgtcagatc gcctggagac gccatccacg ctgttttgac ctccatagaa    3960
gacaccggga ccgatccagc ctccgatttg ccaccatgtt tgtgttcctg gtgctgctgc    4020
cactggtgtc cagccagtgt gtgaacctga ccaccaggac ccaacttcct cctgcctaca    4080
ccaactcctt caccagggga gtctactacc ctgacaaggt gttcaggtcc tctgtgctgc    4140
acagcaccca ggacctgttc ctgccattct tcagcaatgt gacctggttc catgccatcc    4200
atgtgtctgg caccaatggc accaagaggt ttgacaaccc tgtgctgcca ttcaatgatg    4260
gagtctactt tgccagcaca gagaagagca acatcatcag gggctggatt tttggcacca    4320
ccctggacag caagacccag tccctgctga ttgtgaacaa tgccaccaat gtggtgatta    4380
aggtgtgtga gttccagttc tgtaatgacc cattcctggg agtctactac cacaagaaca    4440
acaagtcctg gatggagtct gagttcaggg tctactcctc tgccaacaac tgtacctttg    4500
aatatgtgag ccaaccattc ctgatggact tggagggcaa gcagggcaac ttcaagaacc    4560
tgagggagtt tgtgttcaag aacattgatg gctacttcaa gatttacagc aaacacacac    4620
caatcaacct ggtgagggac ctgccacagg gcttctctgc cttggaacca ctggtggacc    4680
tgccaattgg catcaacatc accaggttcc agaccctgct ggctctgcac aggtcctacc    4740
tgacacctgg agactcctcc tctggctgga cagcaggagc agcagcctac tatgtgggct    4800
acctccaacc aaggaccttc ctgctgaaat acaatgagaa tggcaccatc acagatgctg    4860
tggactgtgc cctggaccca ctgtctgaga ccaagtgtac cctgaaatcc ttcacagtgg    4920
agaagggcat ctaccagacc agcaacttca gggtccaacc aacagagagc attgtgaggt    4980
ttccaaacat caccaacctg tgtccatttg gagaggtgtt caatgccacc aggtttgcct    5040
ctgtctatgc ctggaacagg aagaggatta gcaactgtgt ggctgactac tctgtgctct    5100
acaactctgc ctccttcagc accttcaagt gttatggagt gagcccaacc aaactgaatg    5160
acctgtgttt caccaatgtc tatgctgact cctttgtgat taggggagat gaggtgagac    5220
agattgcccc tggacaaaca ggcaagattg ctgactacaa ctacaaactg cctgatgact    5280
tcacaggctg tgtgattgcc tggaacagca acaacctgga cagcaaggtg ggaggcaact    5340
acaactacct ctacagactg ttcaggaaga gcaacctgaa accatttgag agggacatca    5400
gcacagagat ttaccaggct ggcagcacac catgtaatgg agtggagggc ttcaactgtt    5460
actttccact ccaatcctat ggcttccaac aaccaatgg agtgggctac caaccataca    5520
gggtggtggt gctgtccttt gaactgctcc atgcccctgc cacagtgtgt ggaccaaaga    5580
agagcaccaa cctggtgaag aacaagtgtg tgaacttcaa cttcaatgga ctgacaggca    5640
```

-continued

```
caggagtgct gacagagagc aacaagaagt tcctgccatt ccaacagttt ggcagggaca    5700
ttgctgacac cacagatgct gtgagggacc cacagacctt ggagattctg gacatcacac    5760
catgttcctt tggaggagtg tctgtgatta cacctggcac caacaccagc aaccaggtgg    5820
ctgtgctcta ccaggatgtg aactgtactg aggtgcctgt ggctatccat gctgaccaac    5880
ttacaccaac ctggagggtc tacagcacag gcagcaatgt gttccagacc agggctggct    5940
gtctgattgg agcagagcat gtgaacaact cctatgagtg tgacatccca attggagcag    6000
gcatctgtgc ctcctaccag acccagacca acagcccaag gagggcaagg tctgtggcaa    6060
gccagagcat cattgcctac acaatgagtc tgggagcaga gaactctgtg gcttacagca    6120
acaacagcat tgccatccca accaacttca ccatctctgt gaccacagag attctgcctg    6180
tgagtatgac caagacctct gtggactgta caatgtatat ctgtggagac agcacagagt    6240
gtagcaacct gctgctccaa tatggctcct tctgtaccca acttaacagg gctctgacag    6300
gcattgctgt ggaacaggac aagaacaccc aggaggtgtt tgcccaggtg aagcagattt    6360
acaagacacc tccaatcaag gactttggag cttcaactt cagccagatt ctgcctgacc    6420
caagcaagcc aagcaagagg tccttcattg aggacctgct gttcaacaag gtgaccctgg    6480
ctgatgctgg cttcatcaag caatatggag actgtctggg agacattgct gccagggacc    6540
tgatttgtgc ccagaagttc aatggactga cagtgctgcc tccactgctg acagatgaga    6600
tgattgccca atacacctct gccctgctgg ctggcaccat cacctctggc tggacctttg    6660
gagcaggagc agccctccaa atcccatttg ctatgcagat ggcttacagg ttcaatggca    6720
ttggagtgac ccagaatgtg ctctatgaga accagaaact gattgccaac cagttcaact    6780
ctgccattgg caagattcag gactccctgt ccagcacagc ctctgccctg ggcaaactcc    6840
aagatgtggt gaaccagaat gcccaggctc tgaacaccct ggtgaagcaa ctttccagca    6900
actttggagc catctcctct gtgctgaatg acatcctgag cagactggac aaggtggagg    6960
ctgaggtcca gattgacaga ctgattacag gcagactcca atccctccaa acctatgtga    7020
cccaacaact tatcagggct gctgagatta gggcatctgc caacctggct gccaccaaga    7080
tgagtgagtg tgtgctggga caaagcaaga gggtggactt ctgtggcaag ggctaccacc    7140
tgatgagttt tccacagtct gcccctcatg gagtggtgtt cctgcatgtg acctatgtgc    7200
ctgcccagga gaagaacttc accacagccc ctgccatctg ccatgatggc aaggctcact    7260
ttccaaggga gggagtgttt gtgagcaatg gcacccactg gtttgtgacc cagaggaact    7320
tctatgaacc acagattatc accacagaca acacctttgt gtctggcaac tgtgatgtgg    7380
tgattggcat tgtgaacaac acagtctatg acccactcca acctgaactg gactccttca    7440
aggaggaact ggacaaatac ttcaagaacc acaccagccc tgatgtggac ctgggagaca    7500
tctctggcat caatgcctct gtggtgaaca tccagaagga gattgacaga ctgaatgagg    7560
tggctaagaa cctgaatgag tccctgattg acctccaaga actgggcaaa tatgaacaat    7620
acatcaagtg gccatgaaaa ttgatcataa tcagccatac cacatttgta gaggttttac    7680
ttgctttaaa aaacctccca cacctccccc tgaacctgaa acataaaatg aatgcaattg    7740
ttgttgttaa cttgtttatt gcagcttata atggttacaa ataaagcaat agcatcacaa    7800
atttcacaaa taaagcattt ttttcactgc attctagttg tggtttgtcc aaactcatca    7860
atgtatctta acgcggatct gggcgtggtt aagggtggga agaatatat aaggtggggg    7920 tcttatgtag ttttgtatct gttttgcagc agccgccgcc gccatgagca ccaactcgtt    7980
tgatggaagc attgtgagct catatttgac aacgcgcatg cccccatggg ccggggtgcg    8040
```

-continued

```
tcagaatgtg atgggctcca gcattgatgg tcgccccgtc ctgcccgcaa actctactac      8100
cttgacctac gagaccgtgt ctggaacgcc gttggagact gcagcctccg ccgccgcttc      8160
agccgctgca gccaccgccc gcgggattgt gactgacttt gctttcctga gcccgcttgc      8220
aagcagtgca gcttcccgtt catccgcccg cgatgacaag ttgacggctc ttttggcaca      8280
attggattct ttgacccggg aacttaatgt cgtttctcag cagctgttgg atctgcgcca      8340
gcaggtttct gccctgaagg cttcctcccc tcccaatgcg gtttaaaaca taaataaaaa      8400
accagactct gtttggattt ggatcaagca agtgtcttgc tgtctttatt tagggggtttt     8460 gcgcgcgcgg taggcccggg accagcggtc tcggtcgttg agggtcctgt gtatttttc       8520 caggacgtgg taaaggtgac tctggatgtt cagatacatg ggcataagcc cgtctctggg      8580
gtggaggtag caccactgca gagcttcatg ctgcggggtg gtgttgtaga tgatccagtc      8640
gtagcaggag cgctgggcgt ggtgcctaaa aatgtctttc agtagcaagc tgattgccag      8700
gggcaggccc ttggtgtaag tgtttacaaa gcggttaagc tgggatgggt gcatacgtgg      8760
ggatatgaga tgcatcttgg actgtatttt taggttggct atgttcccag ccatatccct      8820
ccggggattc atgttgtgca gaaccaccag cacagtgtat ccggtgcact tgggaaattt      8880
gtcatgtagc ttagaaggaa atgcgtggaa gaacttggag acgcccttgt gacctccaag      8940
attttccatg cattcgtcca taatgatggc aatgggccca cgggcggcgg cctgggcgaa      9000
gatatttctg ggatcactaa cgtcatagtt gtgttccagg atgagatcgt cataggccat      9060
ttttacaaag cgcgggcgga gggtgccaga ctgcggtata atggttccat ccggcccagg      9120
ggcgtagtta ccctcacaga tttgcatttc ccacgctttg agttcagatg gggggatcat      9180
gtctacctgc ggggcgatga agaaaacggt ttccggggta ggggagatca gctgggaaga      9240
aagcaggttc ctgagcagct gcgacttacc gcagccggtg ggcccgtaaa tcacacctat      9300
taccggctgc aactggtagt taagagagct gcagctgccg tcatccctga gcaggggggc      9360
cacttcgtta agcatgtccc tgactcgcat gtttttccctg accaaatccg ccagaaggcg     9420
ctcgccgccc agcgatagca gttcttgcaa ggaagcaaag tttttcaacg gtttgagacc      9480
gtccgccgta ggcatgcttt tgagcgtttg accaagcagt tccaggcggt cccacagctc      9540
ggtcacctgc tctacggcat ctcgatccag catatctcct cgtttcgcgg gttggggcgg      9600
ctttcgctgt acggcagtag tcggtgctcg tccagacggg ccaggtcat gtctttccac       9660 gggcgcaggg tcctcgtcag cgtagtctgg gtcacggtga aggggtgcgc tccgggctgc      9720
gcgctggcca gggtgcgctt gaggctggtc ctgctggtgc tgaagcgctg ccggtcttcg      9780
ccctgcgcgt cggccaggta gcatttgacc atggtgtcat agtccagccc ctccgcggcg      9840
tggcccttgg cgcgcagctt gcccttggag gaggcgccgc acgaggggca gtgcagactt      9900
ttgagggcgt agagcttggg cgcgagaaat accgattccg gggagtaggc atccgcgccg      9960
caggccccgc agacggtctc gcattccacg agccaggtga gctctggccg ttcgggtca      10020 aaaaccaggt ttcccccatg cttttttgatg cgtttcttac ctctggtttc catgagccgg     10080
tgtccacgct cggtgacgaa aaggctgtcc gtgtccccgt atacagactt gagaggcctg     10140
tcctcgagcg gtgttccgcg gtcctcctcg tatagaaact cggaccactc tgagacaaag     10200
gctcgcgtcc aggccagcac gaaggaggct aagtgggagg ggtagcggtc gttgtccact     10260 aggggtgtcca ctcgctccag ggtgtgaaga cacatgtcgc cctcttcggc atcaaggaag    10320
gtgattggtt tgtaggtgta ggccacgtga ccgggtgttc ctgaaggggg gctataaaag     10380
```

-continued

```
ggggtggggg cgcgttcgtc ctcactctct tccgcatcgc tgtctgcgag ggccagctgt   10440
tggggtgagt actccctctg aaaagcgggc atgacttctg cgctaagatt gtcagtttcc   10500
aaaaacgagg aggatttgat attcacctgg cccgcggtga tgcctttgag ggtggccgca   10560
tccatctggt cagaaaagac aatctttttg ttgtcaagct tggtggcaaa cgacccgtag   10620
agggcgttgg acagcaactt ggcgatggag cgcagggttt ggttttttgtc gcgatcggcg   10680 cgctccttgg ccgcgatgtt tagctgcacg tattcgcgcg caacgcaccg ccattcggga   10740
aagacggtgg tgcgctcgtc gggcaccagg tgcacgcgcc aaccgcggtt gtgcagggtg   10800
acaaggtcaa cgctggtggc tacctctccg cgtaggcgct cgttggtcca gcagaggcgg   10860
ccgcccttgc gcgagcagaa tggcggtagg gggtctagct gcgtctcgtc cggggggtct   10920
gcgtccacgg taaagacccc gggcagcagg cgcgcgtcga agtagtctat cttgcatcct   10980
tgcaagtcta gcgcctgctg ccatgcgcgg gcggcaagcg cgcgctcgta tgggttgagt   11040
gggggacccc atggcatggg gtgggtgagc gcggaggcgt acatgccgca aatgtcgtaa   11100
acgtagaggg gctctctgag tattccaaga tatgtagggt agcatcttcc accgcggatg   11160
ctggcgcgca cgtaatcgta tagttcgtgc gagggagcga ggaggtcggg accgaggttg   11220
ctacgggcgg gctgctctgc tcggaagact atctgcctga agatggcatg tgagttggat   11280
gatatggttg gacgctggaa gacgttgaag ctggcgtctg tgagacctac cgcgtcacgc   11340
acgaaggagg cgtaggagtc gcgcagcttg ttgaccagct cggcggtgac ctgcacgtct   11400
agggcgcagt agtccagggt ttccttgatg atgtcatact tatcctgtcc cttttttttc   11460
cacagctcgc ggttgaggac aaactcttcg cggtctttcc agtactcttg gatcggaaac   11520
ccgtcggcct ccgaacggta agagcctagc atgtagaact ggttgacggc ctggtaggcg   11580
cagcatccct tttctacggg tagcgcgtat gcctgcgcgg ccttccggag cgaggtgtgg   11640
gtgagcgcaa aggtgtccct gaccatgact ttgaggtact ggtatttgaa gtcagtgtcg   11700
tcgcatccgc cctgctccca gagcaaaaag tccgtgcgct ttttggaacg cggatttggc   11760
agggcgaagg tgacatcgtt gaagagtatc tttcccgcgc gaggcataaa gttgcgtgtg   11820
atgcggaagg gtcccggcac ctcggaacgg ttgttaatta cctgggcggc gagcacgatc   11880
tcgtcaaagc cgttgatgtt gtggcccaca atgtaaagtt ccaagaagcg cgggatgccc   11940
ttgatggaag gcaattttttt aagttcctcg taggtgagct cttcagggga gctgagcccg   12000
tgctctgaaa gggcccagtc tgcaagatga gggttggaag cgacgaatga gctccacagg   12060
tcacgggcca ttagcatttg caggtggtcg cgaaaggtcc taaactggcg acctatggcc   12120
attttttctg gggtgatgca gtagaaggta agcgggtctt gttcccagcg gtcccatcca   12180
aggttcgcgg ctaggtctcg cgcggcagtc actagaggct catctccgcc gaacttcatg   12240
accagcatga agggcacgag ctgcttccca aaggcccca tccaagtata ggtctctaca   12300
tcgtaggtga caaagagacg ctcggtgcga ggatgcgagc cgatcgggaa gaactggatc   12360
tcccgccacc aattggagga gtggctattg atgtggtgaa agtagaagtc cctgcgacgg   12420
gccgaacact cgtgctggct tttgtaaaaa cgtgcgcagt actggcagcg gtgcacgggc   12480
tgtacatcct gcacgaggtt gacctgacga ccgcgcacaa ggaagcagag tgggaatttg   12540
agcccctcgc ctggcgggtt tggctggtgg tcttctactt cggctgcttg tccttgaccg   12600
tctggctgct cgaggggagt tacggtggat cggaccacca cgccgcgcga gcccaaagtc   12660
cagatgtccg cgcgcggcgg tcggagcttg atgacaacat cgcgcagatg ggagctgtcc   12720
atggtctgga gctcccgcgg cgtcaggtca ggcgggagct cctgcaggtt tacctcgcat   12780
```

-continued

```
agacgggtca  gggcgcgggc  tagatccagg  tgatacctaa  tttccagggg  ctggttggtg  12840
gcggcgtcga  tggcttgcaa  gaggccgcat  ccccgcggcg  cgactacggt  accgcgcggc  12900
gggcggtggg  ccgcgggggt  gtccttggat  gatgcatcta  aaagcggtga  cgcgggcgag  12960
cccccggagg  taggggggc   tccggacccg  ccgggagagg  gggcaggggc  acgtcggcgc  13020
cgcgcgcggg  caggagctgg  tgctgcgcgc  gtaggttgct  ggcgaacgcg  acgacgcggc  13080
ggttgatctc  ctgaatctgg  cgcctctgcg  tgaagacgac  gggcccggtg  agcttgaacc  13140
tgaaagagag  ttcgacagaa  tcaatttcgg  tgtcgttgac  ggcggcctgg  cgcaaaatct  13200
cctgcacgtc  tcctgagttg  tcttgatagg  cgatctcggc  catgaactgc  tcgatctctt  13260
cctcctggag  atctccgcgt  ccggctcgct  ccacggtggc  ggcgaggtcg  ttggaaatgc  13320
gggccatgag  ctgcgagaag  gcgttgaggc  ctccctcgtt  ccagacgcgg  ctgtagacca  13380 cgccccttc   ggcatcgcgg  gcgcgcatga  ccacctgcgc  gagattgagc  tccacgtgcc  13440
gggcgaagac  ggcgtagttt  cgcaggcgct  gaaagaggta  gttgagggtg  gtggcggtgt  13500
gttctgccac  gaagaagtac  ataacccagc  gtcgcaacgt  ggattcgttg  atatccccca  13560
aggcctcaag  gcgctccatg  gcctcgtaga  agtccacggc  gaagttgaaa  aactgggagt  13620
tgcgcgccga  cacggttaac  tcctcctcca  gaagacggat  gagctcggcg  acagtgtcgc  13680
gcacctcgcg  ctcaaaggct  acaggggcct  cttcttcttc  ttcaatctcc  tcttccataa  13740
gggcctcccc  ttcttcttct  tctggcggcg  gtgggggagg  ggggacacgg  cggcgacgac  13800
ggcgcaccgg  gaggcggtcg  acaaagcgct  cgatcatctc  cccgcggcga  cggcgcatgg  13860
tctcggtgac  ggcgcggccg  ttctcgcggg  ggcgcagttg  gaagacgccg  cccgtcatgt  13920
cccggttatg  ggttggcggg  gggctgccat  gcggcaggga  tacggcgcta  acgatgcatc  13980
tcaacaattg  ttgtgtaggt  actccgccgc  cgagggacct  gagcgagtcc  gcatcgaccg  14040
gatcggaaaa  cctctcgaga  aaggcgtcta  accagtcaca  gtcgcaaggt  aggctgagca  14100
ccgtggcggg  cggcagcggg  cggcggtcgg  ggttgtttct  ggcggaggtg  ctgctgatga  14160
tgtaattaaa  gtaggcggtc  ttgagacggc  ggatggtcga  cagaagcacc  atgtccttgg  14220
gtccggcctg  ctgaatgcgc  aggcggtcgg  ccatgcccca  ggcttcgttt  tgacatcggc  14280
gcaggtcttt  gtagtagtct  tgcatgagcc  tttctaccgg  cacttcttct  tctccttcct  14340
cttgtcctgc  atctcttgca  tctatcgctg  cggcggcggc  ggagtttggc  cgtaggtggc  14400
gccctcttcc  tcccatgcgt  gtgaccccga  agccctcat   cggctgaagc  agggctaggt  14460
cggcgacaac  gcgctcggct  aatatggcct  gctgcacctg  cgtgagggta  gactggaagt  14520
catccatgtc  cacaaagcgg  tggtatgcgc  ccgtgttgat  ggtgtaagtg  cagttggcca  14580
taacggacca  gttaacggtc  tggtgacccg  gctgcgagag  ctcggtgtac  ctgagacgcg  14640
agtaagccct  cgagtcaaat  acgtagtcgt  tgcaagtccg  caccaggtac  tggtatccca  14700
ccaaaaagtg  cggcggcggc  tggcggtaga  ggggccagcg  tagggtggcc  ggggctccgg  14760
gggcgagatc  ttccaacata  aggcgatgat  atccgtagat  gtacctggac  atccaggtga  14820
tgccggcggc  ggtggtggag  gcgcgcggaa  agtcgcggac  gcggttccag  atgttgcgca  14880
gcggcaaaaa  gtgctccatg  gtcgggacgc  tctggccggt  caggcgcgcg  caatcgttga  14940
cgctctagcg  tgcaaaagga  gagcctgtaa  gcgggcactc  ttccgtggtc  tggtggataa  15000
attcgcaagg  gtatcatggc  ggacgaccgg  ggttcgagcc  ccgtatccgg  ccgtccgccg  15060
tgatccatgc  ggttaccgcc  cgcgtgtcga  acccaggtgt  gcgacgtcag  acaacggggg  15120
```

-continued

```
agtgctcctt ttggcttcct tccaggcgcg gcggctgctg cgctagcttt tttggccact   15180
ggccgcgcgc agcgtaagcg gttaggctgg aaagcgaaag cattaagtgg ctcgctccct   15240
gtagccggag ggttattttc caagggttga gtcgcgggac ccccggttcg agtctcggac   15300
cggccggact gcggcgaacg ggggtttgcc tccccgtcat gcaagacccc gcttgcaaat   15360
tcctccggaa acagggacga gccccttttt tgctttccc agatgcatcc ggtgctgcgg    15420
cagatgcgcc cccctcctca gcagcggcaa gagcaagagc agcggcagac atgcagggca   15480
ccctcccctc ctcctaccgc gtcaggaggg gcgacatccg cggttgacgc ggcagcagat   15540
ggtgattacg aaccccgcg gcgccgggcc cggcactacc tggacttgga ggagggcgag    15600
ggcctggcgc ggctaggagc gccctctcct gagcggcacc caagggtgca gctgaagcgt   15660
gatacgcgtg aggcgtacgt gccgcggcag aacctgtttc gcgaccgcga gggagaggag   15720
cccgaggaga tgcgggatcg aaagttccac gcagggcgcg agctgcggca tggcctgaat   15780
cgcgagcggt tgctgcgcga ggaggacttt gagcccgacg cgcgaaccgg gattagtccc   15840
gcgcgcgcac acgtggcggc cgccgacctg gtaaccgcat acgagcagac ggtgaaccag   15900
gagattaact ttcaaaaaag ctttaacaac cacgtgcgta cgcttgtggc gcgcgaggag   15960
gtggctatag gactgatgca tctgtgggac tttgtaagcg cgctggagca aaacccaaat   16020
agcaagccgc tcatggcgca gctgttcctt atagtgcagc acagcaggga caacgaggca   16080
ttcagggatg cgctgctaaa catagtagag cccgagggcc gctggctgct cgatttgata   16140
aacatcctgc agagcatagt ggtgcaggag cgcagcttga gcctggctga caaggtggcc   16200
gccatcaact attccatgct tagcctgggc aagtttttacg cccgcaagat ataccatacc   16260
ccttacgttc ccatagacaa ggaggtaaag atcgaggggt tctacatgcg catggcgctg   16320
aaggtgctta ccttgagcga cgacctgggc gtttatcgca acgagcgcat ccacaaggcc   16380
gtgagcgtga gccggcggcg cgagctcagc accgcgagc tgatgcacag cctgcaaagg    16440
gccctggctg gcacgggcag cggcgataga gaggccgagt cctactttga cgcgggcgct   16500
gacctgcgct gggccccaag ccgacgcgcc ctggaggcag ctggggccgg acctgggctg   16560
gcggtggcac ccgcgcgcgc tggcaacgtc ggcggcgtgg aggaatatga cgaggacgat   16620
gagtacgagc cagaggacgg cgagtactaa gcggtgatgt ttctgatcag atgatgcaag   16680
acgcaacgga cccggcggtg cgggcggcgc tgcagagcca gccgtccggc cttaactcca   16740
cggacgactg gcgccaggtc atggaccgca tcatgtcgct gactgcgcgc aatcctgacg   16800
cgttccggca gcagccgcag gccaaccggc tctccgcaat tctggaagcg gtggtcccgg   16860
cgcgcgcaaa ccccacgcac gagaaggtgc tggcgatcgt aaacgcgctg gccgaaaaca   16920
gggccatccg gcccgacgag gccggcctgg tctacgacgc gctgcttcag cgcgtggctc   16980
gttacaacag cggcaacgtg cagaccaacc tggaccggct ggtggggggat gtgcgcgagg   17040 ccgtggcgca gcgtgagcgc gcgcagcagc agggcaacct gggctccatg ttgcactaa    17100 acgccttcct gagtacacag cccgccaacg tgccgcgggg acaggaggac tacaccaact   17160
ttgtgagcgc actgcggcta atggtgactg agacaccgca aagtgaggtg taccagtctg   17220
ggccagacta ttttttccag accagtgaga aaggcctgca gaccgtaaac ctgagccagg   17280 cttttcaaaaa cttgcagggg ctgtgggggg tgcgggctcc cacaggcgac cgcgcgaccg   17340
tgtctagctt gctgacgccc aactcgcgcc tgttgctgct gctaatagcg cccttcacgg   17400
acagtggcag cgtgtcccgg gacacatacc taggtcactt gctgacactg taccgcgagg   17460
ccataggtca ggcgcatgtg gacgagcata ctttccagga gattacaagt gtcagccgcg   17520
```

```
cgctggggca ggaggacacg ggcagcctgg aggcaaccct aaactacctg ctgaccaacc   17580
ggcggcagaa gatcccctcg ttgcacagtt taaacagcga ggaggagcgc attttgcgct   17640
acgtgcagca gagcgtgagc cttaacctga tgcgcgacgg ggtaacgccc agcgtggcgc   17700
tggacatgac cgcgcgcaac atggaaccgg gcatgtatgc ctcaaaccgg ccgtttatca   17760
accgcctaat ggactacttg catcgcgcgg ccgccgtgaa ccccgagtat ttcaccaatg   17820
ccatcttgaa cccgcactgg ctaccgcccc ctggtttcta caccgggggga ttcgaggtgc   17880 ccgagggtaa cgatggattc ctctgggacg acatagacga cagcgtgttt tccccgcaac   17940
cgcagaccct gctagagttg caacagcgcg agcaggcaga ggcggcgctg cgaaaggaaa   18000
gcttccgcag gccaagcagc ttgtccgatc taggcgctgc ggccccgcgg tcagatgcta   18060
gtagcccatt tccaagcttg atagggtctc ttaccagcac tcgcaccacc cgcccgcgcc   18120
tgctgggcga ggaggagtac ctaaacaact cgctgctgca gccgcagcgc gaaaaaaacc   18180
tgcctccggc atttcccaac aacgggatag agagcctagt ggacaagatg agtagatgga   18240
agacgtacgc gcaggagcac agggacgtgc caggcccgcg cccgcccacc cgtcgtcaaa   18300
ggcacgaccg tcagcggggt ctggtgtggg aggacgatga ctcggcagac gacagcagcg   18360
tcctggattt gggagggagt ggcaacccgt ttgcgcacct tcgccccagg ctggggagaa   18420
tgttttaaaa aaaaaaagc atgatgcaaa ataaaaaact caccaaggcc atggcaccga   18480
gcgttggttt tcttgtattc cccttagtat gcggcgcgcg gcgatgtatg aggaaggtcc   18540
tcctccctcc tacgagagtg tggtgagcgc ggcgccagtg gcggcggcgc tgggttctcc   18600
cttcgatgct cccctggacc cgccgtttgt gcctccgcgg tacctgcggc ctaccggggg   18660
gagaaacagc atccgttact ctgagttggc acccctattc gacaccaccc gtgtgtacct   18720
ggtggacaac aagtcaacgg atgtggcatc cctgaactac cagaacgacc acagcaactt   18780
tctgaccacg gtcattcaaa acaatgacta cagcccgggg gaggcaagca cacagaccat   18840
caatcttgac gaccggtcgc actggggcgg cgacctgaaa accatcctgc ataccaacat   18900
gccaaatgtg aacgagttca tgtttaccaa taagtttaag gcgcgggtga tggtgtcgcg   18960
cttgcctact aaggacaatc aggtggagct gaaatacgag tgggtggagt tcacgctgcc   19020
cgagggcaac tactccgaga ccatgaccat agaccttatg aacaacgcga tcgtggagca   19080
ctacttgaaa gtgggcagac agaacggggt tctggaaagc gacatcgggg taaagtttga   19140
cacccgcaac ttcagactgg ggtttgaccc cgtcactggt cttgtcatgc ctggggtata   19200
tacaaacgaa gccttccatc cagacatcat tttgctgcca ggatgcgggg tggacttcac   19260
ccacagccgc ctgagcaact tgttgggcat ccgcaagcgg caacccttcc aggagggctt   19320
taggatcacc tacgatgatc tggagggtgg taacattccc gcactgttgg atgtggacgc   19380
ctaccaggcg agcttgaaag atgacaccga acagggcggg ggtggcgcag gcggcagcaa   19440
cagcagtggc agcggcgcgg aagagaactc caacgcggca gccgcggcaa tgcagccggt   19500
ggaggacatg aacgatcatg ccattcgcgg cgacacctt gccacacggg ctgaggagaa   19560
gcgcgctgag gccgaagcag cggccgaagc tgccgccccc gctgcgcaac ccgaggtcga   19620
gaagcctcag aagaaaccgg tgatcaaacc cctgacagag gacagcaaga aacgcagtta   19680
caacctaata agcaatgaca gcaccttcac ccagtaccgc agctggtacc ttgcatacaa   19740
ctacggcgac cctcagaccg gaatccgctc atggaccctg ctttgcactc ctgacgtaac   19800
ctgcggctcg gagcaggtct actggtcgtt gccagacatg atgcaagacc ccgtgacctt   19860
```

-continued

```
ccgctccacg cgccagatca gcaactttcc ggtggtgggc gccgagctgt tgcccgtgca   19920
ctccaagagc ttctacaacg accaggccgt ctactcccaa ctcatccgcc agtttacctc   19980
tctgacccac gtgttcaatc gctttcccga gaaccagatt ttggcgcgcc cgccagcccc   20040
caccatcacc accgtcagtg aaaacgttcc tgctctcaca gatcacggga cgctaccgct   20100
gcgcaacagc atcggaggag tccagcgagt gaccattact gacgccagac gccgcacctg   20160
cccctacgtt tacaaggccc tgggcatagt ctcgccgcgc gtcctatcga gccgcacttt   20220
ttgagcaagc atgtccatcc ttatatcgcc cagcaataac acaggctggg gcctgcgctt   20280
cccaagcaag atgtttggcg gggccaagaa gcgctccgac caacacccag tgcgcgtgcg   20340
cgggcactac cgcgcgccct ggggcgcgca caaacgcggc cgcactgggc gcaccaccgt   20400
cgatgacgcc atcgacgcgg tggtggagga ggcgcgcaac tacacgccca cgccgccacc   20460
agtgtccaca gtggacgcgg ccattcagac cgtggtgcgc ggagcccggc gctatgctaa   20520
aatgaagaga cggcggaggc gcgtagcacg tcgccaccgc cgccgacccg gcactgccgc   20580
ccaacgcgcg gcggcggccc tgcttaaccg cgcacgtcgc accggccgac gggcggccat   20640
gcgggccgct cgaaggctgg ccgcgggtat tgtcactgtg cccccaggt ccaggcgacg     20700 agcggccgcc gcagcagccg cggccattag tgctatgact cagggtcgca ggggcaacgt   20760
gtattgggtg cgcgactcgg ttagcggcct gcgcgtgccc gtgcgcaccc gccccccgcg   20820
caactagatt gcaagaaaaa actacttaga ctcgtactgt tgtatgtatc cagcggcggc   20880
ggcgcgcaac gaagctatgt ccaagcgcaa aatcaaagaa gagatgctcc aggtcatcgc   20940
gccggagatc tatggcccc cgaagaagga agagcaggat tacaagcccc gaaagctaaa    21000
gcgggtcaaa aagaaaaaga aagatgatga tgatgaactt gacgacgagg tggaactgct   21060
gcacgctacc gcgcccaggc gacgggtaca gtggaaaggt cgacgcgtaa aacgtgtttt   21120
gcgacccggc accaccgtag tctttacgcc cggtgagcgc tccacccgca cctacaagcg   21180
cgtgtatgat gaggtgtacg gcgacgagga cctgcttgag caggccaacg agcgcctcgg   21240
ggagtttgcc tacggaaagc ggcataagga catgctggcg ttgccgctgg acgagggcaa   21300
cccaacacct agcctaaagc ccgtaacact gcagcaggtg ctgcccgcgc ttgcaccgtc   21360
cgaagaaaag cgcggcctaa agcgcgagtc tggtgacttg gcacccaccg tgcagctgat   21420
ggtacccaag cgccagcgac tggaagatgt cttggaaaaa atgaccgtgg aacctgggct   21480
ggagcccgag gtccgcgtgc ggccaatcaa gcaggtggcg ccgggactgg gcgtgcagac   21540
cgtggacgtt cagatacca ctaccagtag caccagtatt gccaccgcca cagagggcat    21600
ggagacacaa acgtccccgg ttgcctcagc ggtggcggat gccgcggtgc aggcggtcgc   21660
tgcggccgcg tccaagacct ctacggaggt gcaaacggac ccgtggatgt ttcgcgtttc   21720
agccccccgg cgcccgcgcc gttcgaggaa gtacggcgcc gccagcgcgc tactgcccga   21780
atatgcccta catccttcca ttgcgcctac ccccggctat cgtggctaca cctaccgccc   21840
cagaagacga gcaactaccc gacgccgaac caccactgga acccgccgcc gccgtcgccg   21900
tcgccagccc gtgctggccc cgatttccgt gcgcagggtg gctcgcgaag gaggcaggac   21960
cctggtgctg ccaacagcgc gctaccaccc cagcatcgtt taaaagccgg tctttgtggt   22020
tcttgcagat atggccctca cctgccgcct ccgtttcccg gtgccgggat tccgaggaag   22080
aatgcaccgt aggaggggca tggccggcca cggcctgacg ggcggcatgc gtcgtgcgca   22140
ccaccggcgg cggcgcgcgt cgcaccgtcg catgcgcggc ggtatcctgc ccctccttat   22200
tccactgatc gccgcggcga ttggcgccgt gcccggaatt gcatccgtgg ccttgcaggc   22260
```

-continued

```
gcagagacac tgattaaaaa caagttgcat gtggaaaaat caaaataaaa agtctggact  22320
ctcacgctcg cttggtcctg taactatttt gtagaatgga agacatcaac tttgcgtctc  22380
tggccccgcg acacggctcg cgcccgttca tgggaaactg gcaagatatc ggcaccagca  22440
atatgagcgg tggcgccttc agctggggct cgctgtggag cggcattaaa aatttcggtt  22500
ccaccgttaa gaactatggc agcaaggcct ggaacagcag cacaggccag atgctgaggg  22560
ataagttgaa agagcaaaat ttccaacaaa aggtggtaga tggcctggcc tctggcatta  22620
gcggggtggt ggacctggcc aaccaggcag tgcaaaataa gattaacagt aagcttgatc  22680
cccgccctcc cgtagaggag cctccaccgg ccgtgggagac agtgtctcca gaggggcgtg  22740
gcgaaaagcg tccgcgcccc gacagggaag aaactctggt gacgcaaata gacgagcctc  22800
cctcgtacga ggaggcacta aagcaaggcc tgcccaccac ccgtcccatc gcgcccatgg  22860
ctaccggagt gctgggccag cacacacccg taacgctgga cctgcctccc cccgccgaca  22920
cccagcagaa acctgtgctg ccaggcccga ccgccgttgt tgtaacccgt cctagccgcg  22980
cgtccctgcg ccgcgccgcc agcggtccgc gatcgttgcg gcccgtagcc agtggcaact  23040
ggcaaagcac actgaacagc atcgtgggtc tggggtgca atccctgaag cgccgacgat  23100
gcttctgata gctaacgtgt cgtatgtgtg tcatgtatgc gtccatgtcg ccgccagagg  23160
agctgctgag ccgccgcgcg cccgctttcc aagatggcta ccccttcgat gatgccgcag  23220
tggtcttaca tgcacatctc gggccaggac gcctcggagt acctgagccc cgggctggtg  23280
cagtttgccc gcgccaccga gacgtacttc agcctgaata acaagtttag aaaccccacg  23340
gtggcgccta cgcacgacgt gaccacagac cggtcccagc gtttgacgct gcggttcatc  23400
cctgtggacc gtgaggatac tgcgtactcg tacaaggcgc ggttcaccct agctgtgggt  23460
gataaccgtg tgctggacat ggcttccacg tactttgaca tccgcggcgt gctggacagg  23520
ggccctactt ttaagcccta ctctggcact gcctacaacg ccctggctcc caagggtgcc  23580
ccaaatcctt gcgaatggga tgaagctgct actgctcttg aaataaacct agaagaagag  23640
gacgatgaca acgaagacga agtagacgag caagctgagc agcaaaaaac tcacgtattt  23700
gggcaggcgc cttattctgg tataaatatt acaaaggagg gtattcaaat aggtgtcgaa  23760
ggtcaaacac ctaaatatgc cgataaaaca tttcaacctg aacctcaaat aggagaatct  23820
cagtggtacg aaacagaaat taatcatgca gctgggagag tcctaaaaaa gactacccca  23880
atgaaaccat gttacggttc atatgcaaaa cccacaaatg aaaatggagg gcaaggcatt  23940
cttgtaaagc aacaaaatgg aaagctagaa agtcaagtgg aaatgcaatt tttctcaact  24000
actgaggcag ccgcaggcaa tggtgataac ttgactccta agtggtatt gtacagtgaa  24060 gatgtagata tagaaacccc agacactcat atttcttaca tgcccactat taaggaaggt  24120
aactcacgag aactaatggg ccaacaatct atgcccaaca ggcctaatta cattgctttt  24180
agggacaatt ttattggtct aatgtattac aacagcacgg gtaatatggg tgttctggcg  24240
ggccaagcat cgcagttgaa tgctgttgta gatttgcaag acagaaacac agagctttca  24300
taccagcttt tgcttgattc cattggtgat agaaccaggt acttttctat gtggaatcag  24360
gctgttgaca gctatgatcc agatgttaga attattgaaa tcatggaac tgaagatgaa  24420 cttccaaatt actgctttcc actgggaggt gtgattaata cagagactct taccaaggta  24480
aaacctaaaa caggtcagga aaatggatgg gaaaaagatg ctacagaatt ttcagataaa  24540
aatgaaataa gagttggaaa taattttgcc atggaaatca atctaaatgc caacctgtgg  24600
```

-continued

```
agaaatttcc tgtactccaa catagcgctg tatttgcccg acaagctaaa gtacagtcct    24660
tccaacgtaa aaatttctga taacccaaac acctacgact acatgaacaa gcgagtggtg    24720
gctcccgggc tagtggactg ctacattaac cttggagcac gctggtccct tgactatatg    24780
gacaacgtca acccatttaa ccaccaccgc aatgctggcc tgcgctaccg ctcaatgttg    24840
ctgggcaatg gtcgctatgt gcccttccac atccaggtgc ctcagaagtt ctttgccatt    24900
aaaaacctcc ttctcctgcc gggctcatac acctacgagt ggaacttcag gaaggatgtt    24960
aacatggttc tgcagagctc cctaggaaat gacctaaggg ttgacggagc cagcattaag    25020
tttgatagca tttgcctta cgccaccttc ttccccatgg cccacaacac cgcctccacg    25080
cttgaggcca tgcttagaaa cgacaccaac gaccagtcct ttaacgacta tctctccgcc    25140
gccaacatgc tctaccctat acccgccaac gctaccaacg tgcccatatc catcccctcc    25200
cgcaactggg cggctttccg cggctgggcc ttcacgcgcc ttaagactaa ggaaacccca    25260
tcactgggct cgggctacga cccttattac acctactctg gctctatacc ctacctagat    25320
ggaacctttt acctcaacca caccttaag aaggtggcca ttacctttga ctcttctgtc    25380
agctggcctg gcaatgaccg cctgcttacc cccaacgagt ttgaaattaa gcgctcagtt    25440 gacgggagg gttacaacgt tgcccagtgt aacatgacca aagactggtt cctggtacaa    25500
atgctagcta actataacat tggctaccag ggcttctata tcccagagag ctacaaggac    25560
cgcatgtact ccttctttag aaacttccag cccatgagcc gtcaggtggt ggatgatact    25620
aaatacaagg actaccaaca ggtgggcatc ctacaccaac acaacaactc tggatttgtt    25680
ggctaccttg cccccaccat gcgcgaagga caggcctacc ctgctaactt cccctatccg    25740
cttataggca agaccgcagt tgacagcatt acccagaaaa agtttctttg cgatcgcacc    25800
ctttggcgca tcccattctc cagtaacttt atgtccatgg gcgcactcac agacctgggc    25860
caaaaccttc tctacgccaa ctccgcccac gcgctagaca tgactttga ggtggatccc    25920 atggacgagc ccacccttct ttatgttttg tttgaagtct ttgacgtggt ccgtgtgcac    25980
cagccgcacc gcggcgtcat cgaaaccgtg tacctgcgca cgcccttctc ggccggcaac    26040
gccacaacat aaagaagcaa gcaacatcaa caacagctgc cgccatgggc tccagtgagc    26100
aggaactgaa agccattgtc aaagatcttg gttgtgggcc atatttttg ggcacctatg    26160 acaagcgctt tccaggcttt gtttctccac acaagctcgc ctgcgccata gtcaatacgg    26220
ccggtcgcga gactgggggc gtacactgga tggcctttgc ctggaacccg cactcaaaaa    26280
catgctacct cttttgagccc tttggctttt ctgaccagcg actcaagcag gtttaccagt    26340
ttgagtacga gtcactcctg cgccgtagcg ccattgcttc ttccccgac cgctgtataa    26400 cgctggaaaa gtccacccaa agcgtacagg ggcccaactc ggccgcctgt ggactattct    26460
gctgcatgtt tctccacgcc tttgccaact ggccccaaac tcccatggat cacaacccca    26520
ccatgaacct tattaccggg gtacccaact ccatgctcaa cagtcccag gtacagccca    26580 ccctgcgtcg caaccaggaa cagctctaca gcttcctgga gcgccactcg ccctacttcc    26640
gcagccacag tgcgcagatt aggagcgcca cttcttttg tcacttgaaa aacatgtaaa    26700
aataatgtac tagagacact ttcaataaag gcaaatgctt ttatttgtac actctcgggt    26760
gattatttac ccccacccctt gccgtctgcg ccgtttaaaa atcaaagggg ttctgccgcg    26820
catcgctatg cgccactggc agggacacgt tgcgatactg gtgtttagtg ctccacttaa    26880
actcaggcac aaccatccgc ggcagctcgg tgaagtttc actccacagg ctgcgcacca    26940
tcaccaacgc gtttagcagg tcgggcgccg atatcttgaa gtcgcagttg gggcctccgc    27000
```

-continued

```
cctgcgcgcg cgagttgcga tacacagggt tgcagcactg gaacactatc agcgccgggt   27060
ggtgcacgct ggccagcacg ctcttgtcgg agatcagatc cgcgtccagg tcctccgcgt   27120
tgctcagggc gaacggagtc aactttggta gctgccttcc caaaaagggc gcgtgcccag   27180
gctttgagtt gcactcgcac cgtagtggca tcaaaaggtg accgtgcccg gtctgggcgt   27240
taggatacag cgcctgcata aaagccttga tctgcttaaa agccacctga gcctttgcgc   27300
cttcagagaa gaacatgccg caagacttgc cggaaaactg attggccgga caggccgcgt   27360
cgtgcacgca gcaccttgcg tcggtgttgg agatctgcac cacatttcgg ccccaccggt   27420
tcttcacgat cttggccttg ctagactgct ccttcagcgc gcgctgcccg ttttcgctcg   27480
tcacatccat ttcaatcacg tgctccttat ttatcataat gcttccgtgt agacacttaa   27540
gctcgccttc gatctcagcg cagcggtgca gccacaacgc gcagcccgtg ggctcgtgat   27600
gcttgtaggt cacctctgca aacgactgca ggtacgcctg caggaatcgc cccatcatcg   27660
tcacaaaggt cttgttgctg gtgaaggtca gctgcaaccc gcggtgctcc tcgttcagcc   27720
aggtcttgca tacggccgcc agagcttcca cttggtcagg cagtagtttg aagttcgcct   27780
ttagatcgtt atccacgtgg tacttgtcca tcagcgcgcg cgcagcctcc atgcccttct   27840
cccacgcaga cacgatcggc acactcagcg ggttcatcac cgtaatttca ctttccgctt   27900
cgctgggctc ttcctcttcc tcttgcgtcc gcataccacg cgccactggg tcgtcttcat   27960
tcagccgccg cactgtgcgc ttacctcctt tgccatgctt gattagcacc ggtgggttgc   28020
tgaaacccac catttgtagc gccacatctt ctctttcttc ctcgctgtcc acgattacct   28080
ctggtgatgg cgggcgctcg ggcttgggag aagggcgctt ctttttcttc ttgggcgcaa   28140
tggccaaatc cgccgccgag gtcgatggcc gcgggctggg tgtgcgcggc accagcgcgt   28200
cttgtgatga gtcttcctcg tcctcggact cgatacgccg cctcatccgc ttttttgggg   28260
gcgcccgggg aggcggcggc gacggggacg gggacgacac gtcctccatg gttgggggac   28320
gtcgcgccgc accgcgtccg cgctcggggg tggtttcgcg ctgctcctct tcccgactgg   28380
ccatttcctt ctcctatagg cagaaaaaga tcatggagtc agtcgagaag aaggacagcc   28440
taaccgcccc ctctgagttc gccaccaccg cctccaccga tgccgccaac gcgcctacca   28500
ccttccccgt cgaggcaccc ccgcttgagg aggaggaagt gattatcgag caggacccag   28560
gttttgtaag cgaagacgac gaggaccgct cagtaccaac agaggataaa aagcaagacc   28620
aggacaacgc agaggcaaac gaggaacaag tcgggcgggg ggacgaaagg catggcgact   28680
acctagatgt gggagacgac gtgctgttga agcatctgca gcgccagtgc gccattatct   28740
gcgacgcgtt gcaagagcgc agcgatgtgc ccctcgccat agcggatgtc agccttgcct   28800
acgaacgcca cctattctca ccgcgcgtac cccccaaacg ccaagaaaac ggcacatgcg   28860
agcccaaccc gcgcctcaac ttctaccccg tatttgccgt gccagaggtg cttgccacct   28920
atcacatctt tttccaaaac tgcaagatac ccctatcctg ccgtgccaac cgcagccgag   28980
cggacaagca gctggccttg cggcagggcg ctgtcatacc tgatatcgcc tcgctcaacg   29040
aagtgccaaa aatctttgag ggtcttggac gcgacgagaa gcgcgcggca aacgctctgc   29100
aacaggaaaa cagcgaaaat gaaagtcact ctggagtgtt ggtggaactc gagggtgaca   29160
acgcgcgcct agccgtacta aaacgcagca tcgaggtcac ccactttgcc tacccggcac   29220
ttaacctacc ccccaaggtc atgagcacag tcatgagtga gctgatcgtg cgccgtgcgc   29280
agcccctgga gagggatgca aatttgcaag aacaaacaga ggagggccta cccgcagttg   29340
```

-continued

```
gcgacgagca gctagcgcgc tggcttcaaa cgcgcgagcc tgccgacttg gaggagcgac   29400
gcaaactaat gatggccgca gtgctcgtta ccgtggagct tgagtgcatg cagcggttct   29460
ttgctgaccc ggagatgcag cgcaagctag aggaaacatt gcactacacc tttcgacagg   29520
gctacgtacg ccaggcctgc aagatctcca acgtggagct ctgcaacctg gtctcctacc   29580
ttggaatttt gcacgaaaac cgccttgggc aaaacgtgct tcattccacg ctcaagggcg   29640
aggcgcgccg cgactacgtc cgcgactgcg tttacttatt tctatgctac acctggcaga   29700
cggccatggg cgtttggcag cagtgcttgg aggagtgcaa cctcaaggag ctgcagaaac   29760
tgctaaagca aaacttgaag gacctatgga cggccttcaa cgagcgctcc gtggccgcgc   29820
acctggcgga catcatttc cccgaacgcc tgcttaaaac cctgcaacag ggtctgccag   29880
acttcaccag tcaaagcatg ttgcagaact ttaggaactt tatcctagag cgctcaggaa   29940
tcttgcccgc cacctgctgt gcacttccta gcgactttgt gcccattaag taccgcgaat   30000
gccctccgcc gctttggggc cactgctacc ttctgcagct agccaactac cttgcctacc   30060
actctgacat aatggaagac gtgagcggtg acggtctact ggagtgtcac tgtcgctgca   30120
acctatgcac cccgcaccgc tccctggttt gcaattcgca gctgcttaac gaaagtcaaa   30180
ttatcggtac ctttgagctg cagggtccct cgcctgacga aaagtccgcg gctccggggt   30240
tgaaactcac tccgggggctg tggacgtcgg cttaccttcg caaatttgta cctgaggact   30300
accacgccca cgagattagg ttctacgaag accaatcccg cccgcctaat gcggagctta   30360
ccgcctgcgt cattacccag ggccacattc ttggccaatt gcaagccatc aacaaagccc   30420
gccaagagtt tctgctacga aagggacggg gggtttactt ggacccccag tccggcgagg   30480
agctcaaccc aatcccccccg ccgccgcagc cctatcagca gcagccgcgg gcccttgctt   30540
cccaggatgg cacccaaaaa gaagctgcag ctgccgccgc cacccacgga cgaggaggaa   30600
tactgggaca gtcaggcaga ggaggttttg gacgaggagg aggaggacat gatggaagac   30660 tgggagagc tagacgagga agcttccgag gtcgaagagt gtcagacga aacaccgtca   30720 ccctcggtcg cattcccctc gccggcgccc cagaaatcgg caaccggttc cagcatggct   30780
acaacctccg ctcctcaggc gccgccggca ctgcccgttc gccgaccaa ccgtagatgg   30840 gacaccactg gaaccagggc cggtaagtcc aagcagccgc cgccgttagc ccaagagcaa   30900
caacagcgcc aaggctaccg ctcatggcgc gggcacaaga acgccatagt tgcttgcttg   30960
caagactgtg ggggcaacat ctccttcgcc cgccgctttc ttctctacca tcacggcgtg   31020
gccttccccc gtaacatcct gcattactac cgtcatctct acagcccata ctgcaccggc   31080
ggcagcggca gcaacagcag cggccacaca gaagcaaagg cgaccggata gcaagactct   31140
gacaaagccc aagaaatcca cagcggcggc agcagcagga ggaggagcgc tgcgtctggc   31200
gcccaacgaa cccgtatcga cccgcgagct tagaaacagg attttttccca ctctgtatgc   31260 tatatttcaa cagagcaggg gccaagaaca agagctgaaa ataaaaaaca ggtctctgcg   31320
atccctcacc cgcagctgcc tgtatcacaa aagcgaagat cagcttcggc gcacgctgga   31380
agacgcggag gctctcttca gtaaatactg cgcgctgact cttaaggact agtttcgcgc   31440
cctttctcaa atttaagcgc gaaaactacg tcatctccag cggccacacc cggcgccagc   31500
acctgttgtc agcgccatta tgagcaagga aattcccacg ccctacatgt ggagttacca   31560
gccacaaatg ggacttgcgg ctggagctgc ccaagactac tcaacccgaa taaactacat   31620
gagcgcggga ccccacatga tatcccgggt caacggaata cgcgcccacc gaaaccgaat   31680
tctcctggaa caggcggcta ttaccaccac acctcgtaat aaccttaatc cccgtagttg   31740
```

-continued

```
gcccgctgcc ctggtgtacc aggaaagtcc cgctcccacc actgtggtac ttcccagaga   31800
cgcccaggcc gaagttcaga tgactaactc aggggcgcag cttgcgggcg gctttcgtca   31860
cagggtgcgg tcgcccgggc agggtataac tcacctgaca atcagagggc gaggtattca   31920
gctcaacgac gagtcggtga gctcctcgct tggtctccgt ccggacggga catttcagat   31980
cggcggcgcc ggccgctctt cattcacgcc tcgtcaggca atcctaactc tgcagacctc   32040
gtcctctgag ccgcgctctg gaggcattgg aactctgcaa tttattgagg agtttgtgcc   32100
atcggtctac tttaacccct tctcgggacc tcccggccac tatccggatc aatttattcc   32160
taactttgac gcggtaaagg actcggcgga cggctacgac tgaatgttaa gtggagaggc   32220
agagcaactg cgcctgaaac acctggtcca ctgtcgccgc cacaagtgct ttgcccgcga   32280
ctccggtgag ttttgctact ttgaattgcc cgaggatcat atcgagggcc cggcgcacgg   32340
cgtccggctt accgcccagg gagagcttgc ccgtagcctg attcgggagt ttacccagcg   32400
ccccctgcta gttgagcggg acaggggacc ctgtgttctc actgtgattt gcaactgtcc   32460
taaccctgga ttacatcaag atcctctagt taatgtcagg tcgcctaagt cgattaacta   32520
gagtacccgg ggatcttatt ccctttaact aataaaaaaa aataataaag catcacttac   32580
ttaaaatcag ttagcaaatt tctgtccagt ttattcagca gcacctcctt gccctcctcc   32640 cagtctggt attgcagctt cctcctggct gcaaactttc tccacaatct aaatggaatg   32700
tcagtttcct cctgttcctg tccatccgca cccactatct tcatgttgtt gcagatgaag   32760
cgcgcaagac cgtctgaaga taccttcaac cccgtgtatc catatgacac ggaaaccggt   32820
cctccaactg tgcctttct tactcctccc tttgtatccc ccaatgggtt tcaagagagt   32880
cccctggggg tactctcttt gcgcctatcc gaacctctag ttacctccaa tggcatgctt   32940
gcgctcaaaa tgggcaacgg cctctctctg gacgaggccg gcaaccttac ctcccaaaat   33000
gtaaccactg tgagcccacc tctcaaaaaa accaagtcaa acataaacct ggaaatatct   33060
gcacccctca cagttacctc agaagcccta actgtggctg ccgccgcacc tctaatggtc   33120
gcgggcaaca cactcaccat gcaatcacag gccccgctaa ccgtgcacga ctccaaactt   33180
agcattgcca cccaaggacc cctcacagtg tcagaaggaa agctagccct gcaaacatca   33240 ggcccccctca ccaccaccga tagcagtacc cttactatca ctgcctcacc ccctctaact   33300
actgccactg gtagcttggg cattgacttg aaagagccca tttatacaca aaatggaaaa   33360
ctaggactaa agtacggggc tcctttgcat gtaacagacg acctaaacac tttgaccgta   33420
gcaactggtc caggtgtgac tattaataat acttccttgc aaactaaagt tactggagcc   33480
ttgggttttg attcacaagg caatatgcaa cttaatgtag caggaggact aaggattgat   33540
tctcaaaaca gacgccttat acttgatgtt agttatccgt ttgatgctca aaaccaacta   33600
aatctaagac taggacaggg ccctcttttt ataaactcag cccacaactt ggatattaac   33660
tacaacaaag gcctttactt gtttacagct tcaaacaatt ccaaaaagct tgaggttaac   33720
ctaagcactg ccaagggggtt gatgtttgac gctacagcca tagccattaa tgcaggagat   33780
gggcttgaat ttggttcacc taatgcacca aacacaaatc ccctcaaaac aaaaattggc   33840
catggcctag aatttgattc aaacaaggct atggttccta aactaggaac tggccttagt   33900
tttgacagca caggtgccat tacagtagga aacaaaaata tgataagct aactttgtgg   33960 accggaataa accctccacc taactgtcaa attgtggaaa acactaatac aaatgatggc   34020
aaacttactt tagtattagt aaaaaatgga gggcttgtta atggctacgt gtctctagtt   34080
```

-continued

```
ggtgtatcag acactgtgaa ccaaatgttc acacaaaaga cagcaaacat ccaattaaga   34140
ttatattttg actcttctgg aaatctatta actgaggaat cagacttaaa aattccactt   34200
aaaaataaat cttctacagc gaccagtgaa actgtagcca gcagcaaagc ctttatgcca   34260
agtactacag cttatccctt caacaccact actagggata gtgaaaacta cattcatgga   34320
atatgttact acatgactag ttatgataga agtctatttc ccttgaacat ttctataatg   34380
ctaaacagcc gtatgatttc ttccaatgtt gcctatgcca tacaatttga atggaatcta   34440
aatgcaagtg aatctccaga aagcaacata gctacgctga ccacatcccc cttttttcttt   34500 tcttacatta cagaagacga caactaaaga atcgtttgtg ttatgtttca acgtgtttat   34560
ttttcaattg cagaaaattt caagtcattt ttcattcagt agtatagccc caccaccaca   34620
tagcttatac agatcaccgt accttaatca aactcacaga accctagtat tcaacctgcc   34680
acctccctcc caacacacag agtacacagt cctttctccc cggctggcct taaaaagcat   34740
catatcatgg gtaacagaca tattcttagg tgttatattc cacacggttt cctgtcgagc   34800
caaacgctca tcagtgatat taataaaactc cccgggcagc tcacttaagt tcatgtcgct   34860
gtccagctgc tgagccacag gctgctgtcc aacttgcggt tgcttaacgg gcggcgaagg   34920
agaagtccac gcctacatgg gggtagagtc ataatcgtgc atcaggatag ggcggtggtg   34980
ctgcagcagc gcgcgaataa actgctgccg ccgccgctcc gtcctgcagg aatacaacat   35040
ggcagtggtc tcctcagcga tgattcgcac cgcccgcagc ataaggcgcc ttgtcctccg   35100
ggcacagcag cgcaccctga tctcacttaa atcagcacag taactgcagc acagcaccac   35160
aatattgttc aaaatcccac agtgcaaggc gctgtatcca aagctcatgg cggggaccac   35220
agaacccacg tggccatcat accacaagcg caggtagatt aagtggcgac ccctcataaa   35280
cacgctggac ataaacatta cctcttttgg catgttgtaa ttcaccacct cccggtacca   35340
tataaacctc tgattaaaca tggcgccatc caccaccatc ctaaaccagc tggccaaaac   35400
ctgcccgccg gctatacact gcagggaacc gggactggaa caatgacagt ggagagccca   35460
ggactcgtaa ccatggatca tcatgctcgt catgatatca atgttggcac aacacaggca   35520
cacgtgcata cacttcctca ggattacaag ctcctcccgc gttagaacca tatcccaggg   35580
aacaacccat tcctgaatca gcgtaaatcc cacactgcag ggaagacctc gcacgtaact   35640
cacgttgtgc attgtcaaag tgttacattc gggcagcagc ggatgatcct ccagtatggt   35700
agcgcgggtt tctgtctcaa aaggaggtag acgatcccta ctgtacggag tgcgccgaga   35760
caaccgagat cgtgttggtc gtagtgtcat gccaaatgga acgccggacg tagtcatatt   35820
tcctgaagca aaaccaggtg cgggcgtgac aaacagatct gcgtctccgg tctcgccgct   35880
tagatcgctc tgtgtagtag ttgtagtata tccactctct caaagcatcc aggcgccccc   35940
tggcttcggg ttctatgtaa actccttcat gcgccgctgc cctgataaca tccaccaccg   36000
cagaataagc cacacccagc caacctacac attcgttctg cgagtcacac acgggaggag   36060
cgggaagagc tggaagaacc atgttttttt ttttattcca aaagattatc caaaacctca   36120
aaatgaagat ctattaagtg aacgcgctcc cctccggtgg cgtggtcaaa ctctacagcc   36180
aaagaacaga taatggcatt tgtaagatgt tgcacaatgg cttccaaaag gcaaacggcc   36240
ctcacgtcca agtggacgta aaggctaaac ccttcagggt gaatctcctc tataaacatt   36300
ccagcacctt caaccatgcc caaataattc tcatctcgcc accttctcaa tatatctcta   36360
agcaaatccc gaatattaag tccggccatt gtaaaaatct gctccagagc gccctccacc   36420
ttcagcctca agcagcgaat catgattgca aaaattcagg ttcctcacag acctgtataa   36480
```

```
gattcaaaag cggaacatta acaaaaatac cgcgatcccg taggtccctt cgcagggcca   36540
gctgaacata atcgtgcagg tctgcacgga ccagcgcggc cacttccccg ccaggaacca   36600
tgacaaaaga acccacactg attatgacac gcatactcgg agctatgcta accagcgtag   36660
ccccgatgta agcttgttgc atgggcggcg atataaaatg caaggtgctg ctcaaaaaat   36720
caggcaaagc ctcgcgcaaa aaagaaagca catcgtagtc atgctcatgc agataaaggc   36780
aggtaagctc cggaaccacc acagaaaaag acaccatttt tctctcaaac atgtctgcgg   36840
gtttctgcat aaacacaaaa taaaataaca aaaaaacatt taaacattag aagcctgtct   36900
tacaacagga aaaacaaccc ttataagcat aagacggact acggccatgc cggcgtgacc   36960
gtaaaaaaac tggtcaccgt gattaaaaag caccaccgac agctcctcgg tcatgtccgg   37020
agtcataatg taagactcgg taaacacatc aggttgattc acatcggtca gtgctaaaaa   37080
gcgaccgaaa tagcccgggg gaatacatac ccgcaggcgt agagacaaca ttacagcccc   37140
cataggaggt ataacaaaat taataggaga gaaaaacaca taaacacctg aaaaaccctc   37200
ctgcctaggc aaaatagcac cctcccgctc cagaacaaca tacagcgctt ccacagcggc   37260
agccataaca gtcagcctta ccagtaaaaa agaaaaccta ttaaaaaaac accactcgac   37320
acggcaccag ctcaatcagt cacagtgtaa aaaagggcca agtgcagagc gagtatatat   37380
aggactaaaa aatgacgtaa cggttaaagt ccacaaaaaa cacccagaaa accgcacgcg   37440
aacctacgcc cagaaacgaa agccaaaaaa cccacaactt cctcaaatcg tcacttccgt   37500
tttcccacgt tacgtcactt cccattttaa gaaaactaca attcccaaca catacaagtt   37560
actccgccct aaaacctacg tcacccgccc cgttcccacg ccccgcgcca cgtcacaaac   37620
tccaccccct cattatcata ttggcttcaa tccaaaataa ggtatattat tgatgatg     37678
```

```
<210> SEQ ID NO 23
<211> LENGTH: 34739
<212> TYPE: DNA
<213> ORGANISM: Artificial Sequence
<220> FEATURE:
<223> OTHER INFORMATION: #1 vector

<400> SEQUENCE: 23
```

```
catcatcaat aatatacctt attttggatt gaagccaata tgataatgag ggggtggagt      60
ttgtgacgtg gcgcggggcg tgggaacggg gcgggtgacg tagtagtgtg gcggaagtgt     120
gatgttgcaa gtgtggcgga acacatgtaa gcgacggatg tggcaaaagt gacgtttttg     180
gtgtgcgccg gtgtacacag gaagtgacaa ttttcgcgcg gttttaggcg gatgttgtag     240
taaatttggg cgtaaccgag taagatttgg ccattttcgc gggaaaactg aataagagga     300
agtgaaatct gaataatttt gtgttactca tagcgcgtaa tactgtaata gtaatcaatt     360
acggggtcat tagttcatag cccatatatg gagttccgcg ttacataact tacggtaaat     420
ggcccgcctg gctgaccgcc caacgacccc cgcccattga cgtcaataat gacgtatgtt     480
cccatagtaa cgccaatagg gactttccat tgacgtcaat gggtggagta tttacggtaa     540
actgcccact tggcagtaca tcaagtgtat catatgccaa gtacgccccc tattgacgtc     600
aatgacggta aatggcccgc ctggcattat gcccagtaca tgaccttatg gactttcct     660 acttggcagt acatctacgt attagtcatc gctattacca tggtgatgcg gttttggcag     720
tacatcaatg ggcgtggata gcggtttgac tcacggggat ttccaagtct ccaccccatt     780
gacgtcaatg ggagtttgtt ttggcaccaa aatcaacggg actttccaaa atgtcgtaac     840
```

-continued

```
aactccgccc cattgacgca aatgggcggt aggcgtgtac ggtgggaggt ctatataagc      900
agagctctcc ctatcagtga tagagatctc cctatcagtg atagagatcg tcgacgagct      960
cgtttagtga accgtcagat cgcctggaga cgccatccac gctgttttga cctccataga     1020
agacaccggg accgatccag cctccgattt gccaccatgt ttgtgttcct ggtgctgctg     1080
ccactggtgt ccagccagtg tgtgaacctg accaccagga cccaacttcc tcctgcctac     1140
accaactcct tcaccagggg agtctactac cctgacaagg tgttcaggtc ctctgtgctg     1200
cacagcaccc aggacctgtt cctgccattc ttcagcaatg tgacctggtt ccatgccatc     1260
catgtgtctg gcaccaatgg caccaagagg tttgacaacc ctgtgctgcc attcaatgat     1320
ggagtctact ttgccagcac agagaagagc aacatcatca ggggctggat ttttggcacc     1380
accctggaca gcaagaccca gtccctgctg attgtgaaca atgccaccaa tgtggtgatt     1440
aaggtgtgtg agttccagtt ctgtaatgac ccattcctgg gagtctacta ccacaagaac     1500
aacaagtcct ggatggagtc tgagttcagg gtctactcct ctgccaacaa ctgtaccttt     1560
gaatatgtga gccaaccatt cctgatggac ttggagggca agcagggcaa cttcaagaac     1620
ctgagggagt ttgtgttcaa gaacattgat ggctacttca gatttacaag caaacacaca     1680
ccaatcaacc tggtgaggga cctgccacag ggcttctctg ccttggaacc actggtggac     1740
ctgccaattg gcatcaacat caccaggttc cagaccctgc tggctctgca caggtcctac     1800
ctgacacctg gagactcctc ctctggctgg acagcaggag cagcagccta ctatgtgggc     1860
tacctccaac caaggacctt cctgctgaaa tacaatgaga atggcaccat cacagatgct     1920
gtggactgtg ccctggaccc actgtctgag accaagtgta ccctgaaatc cttcacagtg     1980
gagaagggca tctaccagac cagcaacttc agggtccaac caacagagag cattgtgagg     2040
tttccaaaca tcaccaacct gtgtccattt ggagaggtgt tcaatgccac caggtttgcc     2100
tctgtctatg cctggaacag gaagaggatt agcaactgtg tggctgacta ctctgtgctc     2160
tacaactctg cctccttcag caccttcaag tgttatggag tgagcccaac caaactgaat     2220
gacctgtgtt tcaccaatgt ctatgctgac tcctttgtga ttaggggaga tgaggtgaga     2280
cagattgccc ctggacaaac aggcaagatt gctgactaca actacaaact gcctgatgac     2340
ttcacaggct gtgtgattgc ctggaacagc aacaacctgg acagcaaggt gggaggcaac     2400
tacaactacc tctacagact gttcaggaag agcaacctga aaccatttga gagggacatc     2460
agcacagaga tttaccaggc tggcagcaca ccatgtaatg gagtggaggg cttcaactgt     2520
tactttccac tccaatccta tggcttccaa ccaaccaatg gagtgggcta ccaaccatac     2580
agggtggtgg tgctgtcctt tgaactgctc catgcccctg ccacagtgtg tggaccaaag     2640
aagagcacca acctggtgaa gaacaagtgt gtgaacttca acttcaatgg actgacaggc     2700
acaggagtgc tgacagagag caacaagaag ttcctgccat ccaacagtt tggcagggac     2760 attgctgaca ccacagatgc tgtgagggac ccacagacct ggagattct ggacatcaca     2820 ccatgttcct ttggaggagt gtctgtgatt acacctggca ccaacaccag caaccaggtg     2880
gctgtgctct accaggatgt gaactgtact gaggtgcctg tggctatcca tgctgaccaa     2940
cttacaccaa cctggagggt ctacagcaca ggcagcaatg tgttccagac cagggctggc     3000
tgtctgattg gagcagagca tgtgaacaac tcctatgagt gtgacatccc aattggagca     3060
ggcatctgtg cctcctacca gacccagacc aacagcccaa ggagggcaag gtctgtggca     3120
agccagagca tcattgccta cacaatgagt ctggagcag agaactctgt ggcttacagc     3180
aacaacagca ttgccatccc aaaccaacttc accatctctg tgaccacaga gattctgcct     3240
```

-continued

```
gtgagtatga ccaagacctc tgtggactgt acaatgtata tctgtggaga cagcacagag   3300
tgtagcaacc tgctgctcca atatggctcc ttctgtaccc aacttaacag ggctctgaca   3360
ggcattgctg tggaacagga caagaacacc caggaggtgt ttgcccaggt gaagcagatt   3420
tacaagacac ctccaatcaa ggactttgga ggcttcaact tcagccagat tctgcctgac   3480
ccaagcaagc caagcaagag gtccttcatt gaggacctgc tgttcaacaa ggtgaccctg   3540
gctgatgctg gcttcatcaa gcaatatgga gactgtctgg gagacattgc tgccagggac   3600
ctgatttgtg cccagaagtt caatggactg acagtgctgc ctccactgct gacagatgag   3660
atgattgccc aatacacctc tgccctgctg gctggcacca tcacctctgg ctggaccttt   3720
ggagcaggag cagccctcca aatcccattt gctatgcaga tggcttacag gttcaatggc   3780
attggagtga cccagaatgt gctctatgag aaccagaaac tgattgccaa ccagttcaac   3840
tctgccattg gcaagattca ggactccctg tccagcacag cctctgccct gggcaaactc   3900
caagatgtgt tgaaccagaa tgcccaggct ctgaacaccc tggtgaagca actttccagc   3960
aactttggag ccatctcctc tgtgctgaat gacatcctga gcagactgga caaggtggag   4020
gctgaggtcc agattgacag actgattaca ggcagactcc aatccctcca aacctatgtg   4080
acccaacaac ttatcagggc tgctgagatt agggcatctg ccaacctggc tgccaccaag   4140
atgagtgagt gtgtgctggg acaaagcaag agggtggact tctgtggcaa gggctaccac   4200
ctgatgagtt ttccacagtc tgcccctcat ggagtggtgt tcctgcatgt gacctatgtg   4260
cctgcccagg agaagaactt caccacagcc cctgccatct gccatgatgg caaggctcac   4320
tttccaaggg agggagtgtt tgtgagcaat ggcacccact ggtttgtgac ccagaggaac   4380
ttctatgaac cacagattat caccacagac aacacctttg tgtctggcaa ctgtgatgtg   4440
gtgattggca ttgtgaacaa cacagtctat gacccactcc aacctgaact ggactccttc   4500
aaggaggaac tggacaaata cttcaagaac cacaccagcc ctgatgtgga cctgggagac   4560
atctctggca tcaatgcctc tgtggtgaac atccagaagg agattgacag actgaatgag   4620
gtggctaaga acctgaatga gtccctgatt gacctccaag aactgggcaa atatgaacaa   4680
tacatcaagt ggccatgaaa attgatcata atcagccata ccacatttgt agaggtttta   4740
cttgctttaa aaaacctccc acacctcccc ctgaacctga aacataaaat gaatgcaatt   4800
gttgttgtta acttgtttat tgcagcttat aatggttaca aataaagcaa tagcatcaca   4860
aatttcacaa ataaagcatt tttttcactg cattctagtt gtggtttgtc caaactcatc   4920
aatgtatctt aacgcggatc tgggcgtggt taagggtggg aaagaatata taaggtgggg   4980
gtcttatgta gttttgtatc tgtttttgcag cagccgccgc cgccatgagc accaactcgt   5040
ttgatggaag cattgtgagc tcatatttga caacgcgcat gccccatgg gccggggtgc   5100 gtcagaatgt gatgggctcc agcattgatg gtcgccccgt cctgcccgca aactctacta   5160
ccttgaccta cgagaccgtg tctggaacgc cgttggagac tgcagcctcc gccgccgctt   5220
cagccgctgc agccaccgcc cgcgggattg tgactgactt tgctttcctg agcccgcttg   5280
caagcagtgc agcttcccgt tcatccgccc gcgatgacaa gttgacggct cttttggcac   5340
aattggattc tttgacccgg gaacttaatg tcgtttctca gcagctgttg gatctgcgcc   5400
agcaggtttc tgccctgaag gcttcctccc ctcccaatgc ggtttaaaac ataaataaaa   5460
aaccagactc tgtttggatt tggatcaagc aagtgtcttg ctgtctttat ttaggggttt   5520
tgcgcgcgcg gtaggcccgg gaccagcggt ctcggtcgtt gagggtcctg tgtatttttt   5580
```

-continued

```
ccaggacgtg gtaaaggtga ctctggatgt tcagatacat gggcataagc ccgtctctgg      5640
ggtggaggta gcaccactgc agagcttcat gctgcggggt ggtgttgtag atgatccagt      5700
cgtagcagga gcgctgggcg tggtgcctaa aaatgtcttt cagtagcaag ctgattgcca      5760
ggggcaggcc cttggtgtaa gtgtttacaa agcggttaag ctgggatggg tgcatacgtg      5820
gggatatgag atgcatcttg gactgtattt ttaggttggc tatgttccca gccatatccc      5880
tccggggatt catgttgtgc agaaccacca gcacagtgta tccggtgcac ttgggaaatt      5940
tgtcatgtag cttagaagga aatgcgtgga agaacttgga gacgcccttg tgacctccaa      6000
gattttccat gcattcgtcc ataatgatgg caatgggccc acgggcggcg gcctgggcga      6060
agatatttct gggatcacta acgtcatagt tgtgttccag gatgagatcg tcataggcca      6120
tttttacaaa gcgcgggcgg agggtgccag actgcggtat aatggttcca tccggcccag      6180
gggcgtagtt accctcacag atttgcattt cccacgcttt gagttcagat ggggggggatca      6240 tgtctacctg cggggcgatg aagaaaacgg tttccggggt aggggagatc agctgggaag      6300
aaagcaggtt cctgagcagc tgcgacttac cgcagccggt gggcccgtaa atcacaccta      6360
ttaccggctg caactggtag ttaagagagc tgcagctgcc gtcatccctg agcagggggg      6420
ccacttcgtt aagcatgtcc ctgactcgca tgttttccct gaccaaatcc gccagaaggc      6480
gctcgccgcc cagcgatagc agttcttgca aggaagcaaa gtttttcaac ggtttgagac      6540
cgtccgccgt aggcatgctt ttgagcgttt gaccaagcag ttccaggcgg tcccacagct      6600
cggtcacctg ctctacggca tctcgatcca gcatatctcc tcgtttcgcg ggttggggcg      6660
gctttcgctg tacggcagta gtcggtgctc gtccagacgg gccagggtca tgtctttcca      6720
cgggcgcagg gtcctcgtca gcgtagtctg ggtcacggtg aaggggtgcg ctccgggctg      6780
cgcgctggcc agggtgcgct tgaggctggt cctgctggtg ctgaagcgct gccggtcttc      6840
gccctgcgcg tcggccaggt agcatttgac catggtgtca tagtccagcc cctccgcggc      6900
gtggcccttg gcgcgcagct tgcccttgga ggaggcgccg cacgaggggc agtgcagact      6960
tttgagggcg tagagcttgg gcgcgagaaa taccgattcc ggggagtagg catccgcgcc      7020
gcaggccccg cagacggtct cgcattccac gagccaggtg agctctggcc gttcggggtc      7080
aaaaaccagg tttcccccat gctttttgat gcgtttctta cctctggttt ccatgagccg      7140
gtgtccacgc tcggtgacga aaaggctgtc cgtgtccccg tatacagact tgagaggcct      7200
gtcctcgagc ggtgttccgc ggtcctcctc gtatagaaac tcggaccact ctgagacaaa      7260
ggctcgcgtc caggccagca cgaaggaggc taagtgggag gggtagcggt cgttgtccac      7320
tagggggtcc actcgctcca gggtgtgaag acacatgtcg ccctcttcgg catcaaggaa      7380
ggtgattggt ttgtaggtgt aggccacgtg accgggtgtt cctgaagggg ggctataaaa      7440
gggggtgggg gcgcgttcgt cctcactctc ttccgcatcg ctgtctgcga gggccagctg      7500
ttggggtgag tactccctct gaaaagcggg catgacttct gcgctaagat tgtcagtttc      7560
caaaaacgag gaggatttga tattcacctg ccccgcggtg atgcctttga gggtggccgc      7620
atccatctgg tcagaaaaga caatcttttt gttgtcaagc ttggtggcaa acgacccgta      7680
gagggcgttg gacagcaact ggcgatgga gcgcaggggt tggttttttgt cgcgatcggc      7740 gcgctccttg gccgcgatgt ttagctgcac gtattcgcgc gcaacgcacc gccattcggg      7800
aaagacggtg gtgcgctcgt cgggcaccag gtgcacgcgc caaccgcggt tgtgcagggt      7860
gacaaggtca acgctggtgg ctacctctcc gcgtaggcgc tcgttggtcc agcagaggcg      7920
gccgcccttg cgcgagcaga atggcggtag ggggtctagc tgcgtctcgt ccggggggtc      7980
```

-continued

```
tgcgtccacg gtaaagaccc cgggcagcag gcgcgcgtcg aagtagtcta tcttgcatcc     8040
ttgcaagtct agcgcctgct gccatgcgcg ggcggcaagc gcgcgctcgt atgggttgag     8100
tgggggaccc catggcatgg ggtgggtgag cgcggaggcg tacatgccgc aaatgtcgta     8160
aacgtagagg ggctctctga gtattccaag atatgtaggg tagcatcttc caccgcggat     8220
gctggcgcgc acgtaatcgt atagttcgtg cgagggagcg aggaggtcgg gaccgaggtt     8280
gctacgggcg ggctgctctg ctcggaagac tatctgcctg aagatggcat gtgagttgga     8340
tgatatggtt ggacgctgga agacgttgaa gctggcgtct gtgagaccta ccgcgtcacg     8400
cacgaaggag gcgtaggagt cgcgcagctt gttgaccagc tcggcggtga cctgcacgtc     8460
tagggcgcag tagtccaggg tttccttgat gatgtcatac ttatcctgtc cctttttttt     8520
ccacagctcg cggttgagga caaactcttc gcggtctttc cagtactctt ggatcggaaa     8580
cccgtcggcc tccgaacggt aagagcctag catgtagaac tggttgacgg cctggtaggc     8640
gcagcatccc tttctacgg gtagcgcgta tgcctgcgcg gccttccgga gcgaggtgtg     8700
ggtgagcgca aaggtgtccc tgaccatgac tttgaggtac tggtatttga agtcagtgtc     8760
gtcgcatccg ccctgctccc agagcaaaaa gtccgtgcgc tttttggaac gcggatttgg     8820
cagggcgaag gtgacatcgt tgaagagtat ctttcccgcg cgaggcataa agttgcgtgt     8880
gatgcggaag ggtcccggca cctcggaacg gttgttaatt acctgggcgg cgagcacgat     8940
ctcgtcaaag ccgttgatgt tgtggcccac aatgtaaagt tccaagaagc gcgggatgcc     9000
cttgatggaa ggcaattttt taagttcctc gtaggtgagc tcttcagggg agctgagccc     9060
gtgctctgaa agggcccagt ctgcaagatg agggttggaa gcgacgaatg agctccacag     9120
gtcacgggcc attagcattt gcaggtggtc gcgaaaggtc ctaaactggc gacctatggc     9180
cattttttct ggggtgatgc agtagaaggt aagcgggtct tgttcccagc ggtcccatcc     9240
aaggttcgcg gctaggtctc gcgcggcagt cactagaggc tcatctccgc cgaacttcat     9300
gaccagcatg aagggcacga gctgcttccc aaaggccccc atccaagtat aggtctctac     9360
atcgtaggtg acaaagagac gctcggtgcg aggatgcgag ccgatcggga agaactggat     9420
ctcccgccac caattggagg agtggctatt gatgtggtga aagtagaagt ccctgcgacg     9480
ggccgaacac tcgtgctggc ttttgtaaaa acgtgcgcag tactggcagc ggtgcacggg     9540
ctgtacatcc tgcacgaggt tgacctgacg accgcgcaca aggaagcaga gtgggaattt     9600
gagcccctcg cctggcgggt ttggctggtg gtcttctact tcggctgctt gtccttgacc     9660
gtctggctgc tcgaggggag ttacggtgga tcggaccacc acgccgcgcg agcccaaagt     9720
ccagatgtcc gcgcgcggcg gtcggagctt gatgacaaca tcgcgcagat gggagctgtc     9780
catggtctga agctcccgcg gcgtcaggtc aggcgggagc tcctgcaggt ttacctcgca     9840
tagacgggtc agggcgcggg ctagatccag gtgatgccta atttccaggg gctggttggt     9900
ggcggcgtcg atggcttgca agaggccgca tccccgcggc gcgactacgg taccgcgcgg     9960
cgggcggtgg gccgcggggg tgtccttgga tgatgcatct aaaagcggtg acgcgggcga    10020
gcccccggag gtaggggggg ctccggaccc gccgggagag ggggcagggg cacgtcggcg    10080 ccgcgcgcg gcaggagctg gtgctgcgcg cgtaggttgc tggcgaacgc gacgacgcgg    10140
cggttgatct cctgaatctg gcgcctctgc gtgaagacga cgggcccggt gagcttgaac    10200
ctgaaagaga gttcgacaga atcaatttcg gtgtcgttga cggcggcctg gcgcaaaatc    10260
tcctgcacgt ctcctgagtt gtcttgatag gcgatctcgg ccatgaactg ctcgatctct    10320
```

-continued

```
tcctcctgga gatctccgcg tccggctcgc tccacggtgg cggcgaggtc gttggaaatg    10380
cgggccatga gctgcgagaa ggcgttgagg cctccctcgt tccagacgcg gctgtagacc    10440 acgcccccctt cggcatcgcg ggcgcgcatg accacctgcg cgagattgag ctccacgtgc    10500
cgggcgaaga cggcgtagtt tcgcaggcgc tgaaagaggt agttgagggt ggtggcggtg    10560
tgttctgcca cgaagaagta cataacccag cgtcgcaacg tggattcgtt gatatccccc    10620
aaggcctcaa ggcgctccat ggcctcgtag aagtccacgg cgaagttgaa aaactgggag    10680
ttgcgcgccg acacggttaa ctcctcctcc agaagacgga tgagctcggc gacagtgtcg    10740
cgcacctcgc gctcaaaggc tacaggggcc tcttcttctt cttcaatctc ctcttccata    10800
agggcctccc cttcttcttc ttctggcggc ggtgggggag gggggacacg gcggcgacga    10860
cggcgcaccg ggaggcggtc gacaaagcgc tcgatcatct ccccgcggcg acggcgcatg    10920
gtctcggtga cggcgcggcc gttctcgcgg gggcgcagtt ggaagacgcc gcccgtcatg    10980
tcccggttat gggttggcgg ggggctgcca tgcggcaggg atacggcgct aacgatgcat    11040
ctcaacaatt gttgtgtagg tactccgccg ccgaggacc tgagcgagtc cgcatcgacc      11100
ggatcggaaa acctctcgag aaaggcgtct aaccagtcac agtcgcaagg taggctgagc    11160
accgtggcgg gcggcagcgg gcggcggtcg gggttgtttc tggcggaggt gctgctgatg    11220
atgtaattaa agtaggcggt cttgagacgg cggatggtcg acagaagcac catgtccttg    11280
ggtccggcct gctgaatgcg caggcggtcg gccatgcccc aggcttcgtt ttgacatcgg    11340
cgcaggtctt tgtagtagtc ttgcatgagc ctttctaccg gcacttcttc ttctccttcc    11400
tcttgtcctg catctcttgc atctatcgct gcggcggcgg cggagtttgg ccgtaggtgg    11460
cgccctcttc ctcccatgcg tgtgaccccg aagcccctca tcggctgaag cagggctagg    11520
tcggcgacaa cgcgctcggc taatatggcc tgctgcacct gcgtgagggt agactggaag    11580
tcatccatgt ccacaaagcg gtggtatgcg cccgtgttga tggtgtaagt gcagttggcc    11640
ataacggacc agttaacggt ctggtgaccc ggctgcgaga gctcggtgta cctgagacgc    11700
gagtaagccc tcgagtcaaa tacgtagtcg ttgcaagtcc gcaccaggta ctggtatccc    11760
accaaaaagt gcggcggcgg ctggcggtag aggggccagc gtaggtggc cggggctccg      11820 ggggcgagat cttccaacat aaggcgatga tatccgtaga tgtacctgga catccaggtg    11880
atgccggcgg cggtggtgga ggcgcgcgga aagtcgcgga cgcggttcca gatgttgcgc    11940
agcggcaaaa agtgctccat ggtcgggacg ctctggccgg tcaggcgcgc gcaatcgttg    12000
acgctctagc gtgcaaaagg agagcctgta agcgggcact cttccgtggt ctggtggata    12060
aattcgcaag ggtatcatgg cggacgaccg gggttcgagc cccgtatccg gccgtccgcc    12120
gtgatccatg cggttaccgc ccgcgtgtcg aacccaggtg tgcgacgtca dacaacgggg    12180
gagtgctcct tttggcttcc ttccaggcgc ggcggctgct gcgctagctt ttttggccac    12240
tggccgcgcg cagcgtaagc ggttaggctg aaaagcgaaa gcattaagtg gctcgctccc    12300
tgtagccgga gggttatttt ccaagggttg agtcgcggga ccccggttc gagtctcgga      12360 ccggccggac tgcggcgaac gggggtttgc ctccccgtca tgcaagaccc cgcttgcaaa    12420
ttcctccgga aacagggacg agccccttttt ttgcttttcc cagatgcatc cggtgctgcg    12480 gcagatcgc cccccctcctc agcagcggca agagcaagag cagcggcaga catgcagggc      12540
accctcccct cctcctaccg cgtcaggagg ggcgacatcc gcggttgacg cggcagcaga    12600
tggtgattac gaaccccgc ggcgccgggc ccggcactac ctggacttgg aggagggcga      12660
gggcctggcg cggctaggag cgccctctcc tgagcggcac ccaagggtgc agctgaagcg    12720
```

-continued

```
tgatacgcgt gaggcgtacg tgccgcggca gaacctgttt cgcgaccgcg agggagagga   12780
gcccgaggag atgcgggatc gaaagttcca cgcagggcgc gagctgcggc atggcctgaa   12840
tcgcgagcgg ttgctgcgcg aggaggactt tgagcccgac gcgcgaaccg ggattagtcc   12900
cgcgcgcgca cacgtggcgg ccgccgacct ggtaaccgca tacgagcaga cggtgaacca   12960
ggagattaac tttcaaaaaa gctttaacaa ccacgtgcgt acgcttgtgg cgcgcgagga   13020
ggtggctata ggactgatgc atctgtggga ctttgtaagc gcgctggagc aaaacccaaa   13080
tagcaagccg ctcatggcgc agctgttcct tatagtgcag cacagcaggg acaacgaggc   13140
attcagggat gcgctgctaa acatagtaga gcccgagggc cgctggctgc tcgatttgat   13200
aaacatcctg cagagcatag tggtgcagga gcgcagcttg agcctggctg acaaggtggc   13260
cgccatcaac tattccatgc ttagcctggg caagttttac gcccgcaaga tataccatac   13320
cccttacgtt cccatagaca aggaggtaaa gatcgagggg ttctacatgc gcatggcgct   13380
gaaggtgctt accttgagcg acgacctggg cgtttatcgc aacgagcgca tccacaaggc   13440
cgtgagcgtg agccggcggc gcgagctcag cgaccgcgag ctgatgcaca gcctgcaaag   13500
ggccctggct ggcacgggca gcggcgatag agaggccgag tcctactttg acgcgggcgc   13560
tgacctgcgc tgggccccaa gccgacgcgc cctggaggca gctggggccg gacctgggct   13620
ggcggtggca cccgcgcgcg ctggcaacgt cggcggcgtg gaggaatatg acgaggacga   13680
tgagtacgag ccagaggacg gcgagtacta agcggtgatg tttctgatca gatgatgcaa   13740
gacgcaacgg accggcggt gcgggcggcg ctgcagagcc agccgtccgg ccttaactcc   13800
acggacgact ggcgccaggt catggaccgc atcatgtcgc tgactgcgcg caatcctgac   13860
gcgttccggc agcagccgca ggccaaccgg ctctccgcaa ttctggaagc ggtggtcccg   13920
gcgcgcgcaa accccacgca cgagaaggtg ctggcgatcg taaacgcgct ggccgaaaac   13980
agggccatcc ggcccgacga ggccggcctg gtctacgacg cgctgcttca gcgcgtggct   14040
cgttacaaca gcggcaacgt gcagaccaac ctggaccggc tggtggggga tgtgcgcgag   14100
gccgtggcgc agcgtgagcg cgcgcagcag cagggcaacc tgggctccat ggttgcacta   14160
aacgccttcc tgagtacaca gcccgccaac gtgccgcggg gacaggagga ctacaccaac   14220
tttgtgagcg cactgcggct aatggtgact gagacaccgc aaagtgaggt gtaccagtct   14280
gggccagact attttttcca gaccagtaga caaggcctgc agaccgtaaa cctgagccag   14340
gctttcaaaa acttgcaggg gctgtggggg gtgcgggctc ccacaggcga ccgcgcgacc   14400
gtgtctagct tgctgacgcc caactcgcgc ctgttgctgc tgctaatagc gcccttcacg   14460
gacagtggca gcgtgtcccg ggacacatac ctaggtcact tgctgacact gtaccgcgag   14520
gccataggtc aggcgcatgt ggacgagcat actttccagg agattacaag tgtcagccgc   14580
gcgctggggc aggaggacac gggcagcctg gaggcaaccc taaactacct gctgaccaac   14640
cggcggcaga agatcccctc gttgcacagt ttaaacagcg aggaggagcg cattttcgcg   14700
tacgtgcagc agagcgtgag ccttaacctg atgcgcgacg gggtaacgcc cagcgtggcg   14760
ctggacatga ccgcgcgcaa catggaaccg ggcatgtatg cctcaaaccg gccgtttatc   14820
aaccgcctaa tggactactt gcatcgcgcg ccgccgtga accccgagta tttcaccaat   14880
gccatcttga acccgcactg gctaccgccc cctggtttct acaccggggg attcgaggtg   14940
cccgagggta acgatggatt cctctgggac gacatagacg acagcgtgtt ttcccgcaa   15000 ccgcagaccc tgctagagtt gcaacagcgc gagcaggcag aggcggcgct gcgaaaggaa   15060
```

```
agcttccgca ggccaagcag cttgtccgat ctaggcgctg cggccccgcg gtcagatgct   15120
agtagcccat ttccaagctt gatagggtct cttaccagca ctcgcaccac ccgcccgcgc   15180
ctgctgggcg aggaggagta cctaaacaac tcgctgctgc agccgcagcg cgaaaaaaac   15240
ctgcctccgg catttcccaa caacgggata gagagcctag tggacaagat gagtagatgg   15300
aagacgtacg cgcaggagca cagggacgtg ccaggcccgc gcccgcccac ccgtcgtcaa   15360
aggcacgacc gtcagcgggg tctggtgtgg gaggacgatg actcggcaga cgacagcagc   15420
gtcctggatt tgggagggag tggcaacccg tttgcgcacc ttcgccccag gctggggaga   15480 atgtttaaa aaaaaaaaag catgatgcaa aataaaaaac tcaccaaggc catggcaccg    15540
agcgttggtt ttcttgtatt ccccttagta tgcggcgcgc ggcgatgtat gaggaaggtc   15600
ctcctccctc ctacgagagt gtggtgagcg cggcgccagt ggcggcggcg ctgggttctc   15660
ccttcgatgc tcccctggac ccgccgtttg tgcctccgcg gtacctgcgg cctaccgggg   15720
ggagaaacag catccgttac tctgagttgg cacccctatt cgacaccacc cgtgtgtacc   15780
tggtggacaa caagtcaacg gatgtggcat ccctgaacta ccagaacgac cacagcaact   15840
ttctgaccac ggtcattcaa aacaatgact acagcccggg ggaggcaagc acacagacca   15900
tcaatcttga cgaccggtcg cactgggcg gcgacctgaa aaccatcctg cataccaaca    15960
tgccaaatgt gaacgagttc atgtttacca ataagtttaa ggcgcgggtg atggtgtcgc   16020
gcttgcctac taaggacaat caggtggagc tgaaatacga gtgggtggag ttcacgctgc   16080
ccgagggcaa ctactccgag accatgacca tagaccttat gaacaacgcg atcgtggagc   16140
actacttgaa agtgggcaga cagaacgggg ttctggaaag cgacatcggg gtaaagtttg   16200
acacccgcaa cttcagactg gggtttgacc ccgtcactgg tcttgtcatg cctggggtat   16260
atacaaacga agccttccat ccagacatca ttttgctgcc aggatgcggg gtggacttca   16320
cccacagccg cctgagcaac ttgttgggca tccgcaagcg gcaacccttc caggagggct   16380
ttaggatcac ctacgatgat ctggagggtg gtaacattcc cgcactgttg gatgtggacg   16440
cctaccaggc gagcttgaaa gatgacaccg aacagggcgg gggtggcgca ggcggcagca   16500
acagcagtgg cagcggcgcg gaagagaact ccaacgcggc agccgcggca atgcagccgg   16560
tggaggacat gaacgatcat gccattcgcg gcgacacctt tgccacacgg gctgaggaga   16620
agcgcgctga ggccgaagca gcggccgaag ctgccgcccc cgctgcgcaa cccgaggtcg   16680
agaagcctca gaagaaaccg gtgatcaaac ccctgacaga ggacagcaag aaacgcagtt   16740
acaacctaat aagcaatgac agcaccttca cccagtaccg cagctggtac cttgcataca   16800
actacggcga ccctcagacc ggaatccgct catggaccct gctttgcact cctgacgtaa   16860
cctgcggctc ggagcaggtc tactggtcgt tgccagacat gatgcaagac cccgtgacct   16920
tccgctccac gcgccagatc agcaactttc cggtggtggg cgccgagctg ttgcccgtgc   16980
actccaagag cttctacaac gaccaggccg tctactccca actcatccgc cagtttacct   17040
ctctgaccca cgtgttcaat cgctttcccg agaaccagat tttggcgcgc ccgccagccc   17100
ccaccatcac caccgtcagt gaaaacgttc ctgctctcac agatcacggg acgctaccgc   17160
tgcgcaacag catcggagga gtccagcgag tgaccattac tgacgccaga cgccgcacct   17220 gccectacgt ttacaaggcc ctgggcatag tctcgccgcg cgtcctatcg agccgcactt   17280
tttgagcaag catgtccatc cttatatcgc ccagcaataa cacaggctgg ggcctgcgct   17340
tcccaagcaa gatgtttggc ggggccaaga agcgctccga ccaacaccca gtgcgcgtgc   17400
gcgggcacta ccgcgcgccc tggggcgcgc acaaacgcgg ccgcactggg cgcaccaccg   17460
```

-continued

```
tcgatgacgc catcgacgcg gtggtggagg aggcgcgcaa ctacacgccc acgccgccac    17520
cagtgtccac agtggacgcg gccattcaga ccgtggtgcg cggagcccgg cgctatgcta    17580
aaatgaagag acggcggagg cgcgtagcac gtcgccaccg ccgccgaccc ggcactgccg    17640
cccaacgcgc ggcggcggcc ctgcttaacc gcgcacgtcg caccggccga cgggcggcca    17700
tgcgggccgc tcgaaggctg gccgcgggta ttgtcactgt gccccccagg tccaggcgac    17760
gagcggccgc cgcagcagcc gcggccatta gtgctatgac tcagggtcgc aggggcaacg    17820
tgtattgggt gcgcgactcg gttagcggcc tgcgcgtgcc cgtgcgcacc cgccccccgc    17880
gcaactagat tgcaagaaaa aactacttag actcgtactg ttgtatgtat ccagcggcgg    17940
cggcgcgcaa cgaagctatg tccaagcgca aaatcaaaga agagatgctc caggtcatcg    18000
cgccggagat ctatggcccc ccgaagaagg aagagcagga ttacaagccc cgaaagctaa    18060
agcgggtcaa aaagaaaaag aaagatgatg atgatgaact tgacgacgag gtggaactgc    18120
tgcacgctac cgcgcccagg cgacgggtac agtggaaagg tcgacgcgta aaacgtgttt    18180
tgcgacccgg caccaccgta gtctttacgc ccggtgagcg ctccacccgc acctacaagc    18240
gcgtgtatga tgaggtgtac ggcgacgagg acctgcttga gcaggccaac gagcgcctcg    18300
gggagtttgc ctacggaaag cggcataagg acatgctggc gttgccgctg gacgagggca    18360
acccaacacc tagcctaaag cccgtaacac tgcagcaggt gctgcccgcg cttgcaccgt    18420
ccgaagaaaa gcgcggccta agcgcgagt ctggtgactt ggcacccacc gtgcagctga    18480
tggtacccaa gcgccagcga ctggaagatg tcttggaaaa aatgaccgtg gaacctgggc    18540
tggagcccga ggtccgcgtg cggccaatca agcaggtggc gccgggactg ggcgtgcaga    18600
ccgtggacgt tcagataccc actaccagta gcaccagtat tgccaccgcc acagagggca    18660
tggagacaca aacgtccccg gttgcctcag cggtggcgga tgccgcggtg caggcggtcg    18720
ctgcggccgc gtccaagacc tctacggagg tgcaaacgga cccgtggatg tttcgcgttt    18780 cagcccccg gcgcccgcgc cgttcgagga agtacggcgc cgccagcgcg ctactgcccg    18840
aatatgccct acatccttcc attgcgccta cccccggcta tcgtggctac acctaccgcc    18900
ccagaagacg agcaactacc cgacgccgaa ccaccactgg aacccgccgc cgccgtcgcc    18960
gtcgccagcc cgtgctggcc ccgatttccg tgcgcagggt ggctcgcgaa ggaggcagga    19020
ccctggtgct gccaacagcg cgctaccacc ccagcatcgt ttaaaagccg gtctttgtgg    19080
ttcttgcaga tatggccctc acctgccgcc tccgtttccc ggtgccggga ttccgaggaa    19140
gaatgcaccg taggaggggc atggccggcc acggcctgac gggcggcatg cgtcgtgcgc    19200
accaccggcg gcggcgcgcg tcgcaccgtc gcatgcgcgg cggtatcctg ccctcctta    19260 ttccactgat cgccgcggcg attggcgccg tgcccggaat tgcatccgtg gccttgcagg    19320
cgcagagaca ctgattaaaa acaagttgca tgtggaaaaa tcaaaataaa agtctggac    19380 tctcacgctc gcttggtcct gtaactattt tgtagaatgg aagacatcaa ctttgcgtct    19440
ctggccccgc gacacggctc gcgcccgttc atgggaaact ggcaagatat cggcaccagc    19500
aatatgagcg gtggcgcctt cagctggggc tcgctgtgga gcggcattaa aaatttcggt    19560
tccaccgtta agaactatgg cagcaaggcc tggaacagca gcacaggcca gatgctgagg    19620
gataagttga agagcaaaa tttccaacaa aaggtggtag atggcctggc ctctggcatt    19680 agcgggggtgg tggacctggc caaccaggca gtgcaaaata agattaacag taagcttgat    19740
ccccgccctc ccgtagagga gcctccaccg gccgtggaga cagtgtctcc agagggggcgt    19800
```

-continued

```
ggcgaaaagc gtccgcgccc cgacagggaa gaaactctgg tgacgcaaat agacgagcct    19860
ccctcgtacg aggaggcact aaagcaaggc ctgcccacca cccgtcccat cgcgcccatg    19920
gctaccggag tgctgggcca gcacacaccc gtaacgctgg acctgcctcc ccccgccgac    19980
acccagcaga aacctgtgct gccaggcccg accgccgttg ttgtaacccg tcctagccgc    20040
gcgtccctgc gccgcgccgc cagcggtccg cgatcgttgc ggcccgtagc cagtggcaac    20100
tggcaaagca cactgaacag catcgtgggt ctggggggtgc aatccctgaa gcgccgacga    20160
tgcttctgat agctaacgtg tcgtatgtgt gtcatgtatg cgtccatgtc gccgccagag    20220
gagctgctga gccgccgcgc gcccgctttc caagatggct accccttcga tgatgccgca    20280
gtggtcttac atgcacatct cgggccagga cgcctcggag tacctgagcc ccgggctggt    20340
gcagtttgcc cgcgccaccg agacgtactt cagcctgaat aacaagttta gaaaccccac    20400
ggtggcgcct acgcacgacg tgaccacaga ccggtcccag cgtttgacgc tgcggttcat    20460
ccctgtggac cgtgaggata ctgcgtactc gtacaaggcg cggttcaccc tagctgtggg    20520
tgataaccgt gtgctggaca tggcttccac gtactttgac atccgcggcg tgctggacag    20580
gggccctact tttaagccct actctggcac tgcctacaac gccctggctc ccaagggtgc    20640
cccaaatcct tgcgaatggg atgaagctgc tactgctctt gaaataaacc tagaagaaga    20700
ggacgatgac aacgaagacg aagtagacga gcaagctgag cagcaaaaaa ctcacgtatt    20760
tgggcaggcg ccttattctg gtataaatat tacaaaggag ggtattcaaa taggtgtcga    20820
aggtcaaaca cctaaatatg ccgataaaac atttcaacct gaacctcaaa taggagaatc    20880
tcagtggtac gaaacagaaa ttaatcatgc agctgggaga gtcctaaaaa agactacccc    20940
aatgaaacca tgttacggtt catatgcaaa acccacaaat gaaaatggag ggcaaggcat    21000
tcttgtaaag caacaaaatg gaaagctaga aagtcaagtg gaaatgcaat ttttctcaac    21060
tactgaggca gccgcaggca atggtgataa cttgactcct aaaagtggtat tgtacagtga    21120 agatgtagat atagaaaccc cagacactca tatttcttac atgcccacta ttaaggaagg    21180
taactcacga gaactaatgg ccaacaatc tatgcccaac aggcctaatt acattgcttt    21240
tagggacaat tttattggtc taatgtatta caacagcacg ggtaatatgg gtgttctggc    21300
gggccaagca tcgcagttga atgctgttgt agatttgcaa gacagaaaca cagagctttc    21360
ataccagctt ttgcttgatt ccattggtga tagaaccagg tacttttcta tgtggaatca    21420
ggctgttgac agctatgatc cagatgttag aattattgaa aatcatggaa ctgaagatga    21480
acttccaaat tactgctttc cactgggagg tgtgattaat acagagactc ttaccaaggt    21540
aaaacctaaa acaggtcagg aaaatggatg ggaaaaagat gctacagaat tttcagataa    21600
aaatgaaata agagttggaa ataattttgc catggaaatc aatctaaatg ccaacctgtg    21660
gagaaatttc ctgtactcca acatagcgct gtatttgccc gacaagctaa agtacagtcc    21720
ttccaacgta aaaatttctg ataacccaaa cacctacgac tacatgaaca agcgagtggt    21780
ggctcccggg ctagtggact gctacattaa ccttggagca cgctggtccc ttgactatat    21840
ggacaacgtc aacccatttta accaccaccg caatgctggc ctgcgctacc gctcaatgtt    21900
gctgggcaat ggtcgctatg tgcccttcca catccaggtg cctcagaagt ctctttgccat    21960 taaaaacctc cttctcctgc cgggctcata cacctacgag tggaacttca ggaaggatgt    22020
taacatggtt ctgcagagct ccctaggaaa tgacctaagg gttgacggag ccagcattaa    22080
gtttgatagc atttgccttt acgccacctt cttccccatg gcccacaaca ccgcctccac    22140
gcttgaggcc atgcttagaa acgacaccaa cgaccagtcc tttaacgact atctctccgc    22200
```

-continued

```
cgccaacatg ctctacccta tacccgccaa cgctaccaac gtgcccatat ccatcccctc   22260
ccgcaactgg gcggctttcc gcggctgggc cttcacgcgc cttaagacta aggaaacccc   22320
atcactgggc tcgggctacg acccttatta cacctactct ggctctatac cctacctaga   22380
tggaaccttt tacctcaacc acacctttaa gaaggtggcc attacctttg actcttctgt   22440
cagctggcct ggcaatgacc gcctgcttac ccccaacgag tttgaaatta agcgctcagt   22500
tgacggggag ggttacaacg ttgcccagtg taacatgacc aaagactggt cctggtaca    22560 aatgctagct aactataaca ttggctacca gggcttctat atcccagaga gctacaagga   22620
ccgcatgtac tccttcttta gaaacttcca gcccatgagc cgtcaggtgg tggatgatac   22680
taaatacaag gactaccaac aggtgggcat cctacaccaa cacaacaact ctggatttgt   22740
tggctacctt gcccccacca tgcgcgaagg acaggcctac cctgctaact tcccctatcc   22800
gcttataggc aagaccgcag ttgacagcat tacccagaaa aagtttcttt gcgatcgcac   22860
cctttggcgc atcccattct ccagtaactt tatgtccatg ggcgcactca cagacctggg   22920
ccaaaacctt ctctacgcca actccgccca cgcgctagac atgacttttg aggtggatcc   22980
catggacgag cccacccttc tttatgtttt gtttgaagtc tttgacgtgg tccgtgtgca   23040
ccagccgcac cgcggcgtca tcgaaaccgt gtacctgcgc acgcccttct cggccggcaa   23100
cgccacaaca taaagaagca agcaacatca acaacagctg ccgccatggg ctccagtgag   23160
caggaactga aagccattgt caaagatctt ggttgtgggc catatttttt gggcacctat   23220
gacaagcgct ttccaggctt tgtttctcca cacaagctcg cctgcgccat agtcaatacg   23280
gccggtcgcg agactggggg cgtacactgg atggcctttg cctggaaccc gcactcaaaa   23340
acatgctacc tctttgagcc ctttggcttt tctgaccagc gactcaagca ggtttaccag   23400
tttgagtacg agtcactcct gcgccgtagc gccattgctt cttcccccga ccgctgtata   23460
acgctggaaa agtccaccca aagcgtacag gggcccaact cggccgcctg tggactattc   23520
tgctgcatgt ttctccacgc ctttgccaac tggccccaaa ctcccatgga tcacaacccc   23580
accatgaacc ttattaccgg ggtacccaac tccatgctca acagtcccca ggtacagccc   23640
accctgcgtc gcaaccagga acagctctac agcttcctgg agcgccactc gccctacttc   23700
cgcagccaca gtgcgcagat taggagcgcc acttcttttt gtcacttgaa aaacatgtaa   23760
aaataatgta ctagagacac tttcaataaa ggcaaatgct tttatttgta cactctcggg   23820 tgattatta ccccccaccct tgccgtctgc gccgtttaaa aatcaaaggg gttctgccgc   23880
gcatcgctat gcgccactgg cagggacacg ttgcgatact ggtgtttagt gctccactta   23940
aactcaggca caaccatccg cggcagctcg gtgaagtttt cactccacag gctgcgcacc   24000
atcaccaacg cgtttagcag gtcgggcgcc gatatcttga agtcgcagtt ggggcctccg   24060
ccctgcgcgc gcgagttgcg atacacaggg ttgcagcact ggaacactat cagcgccggg   24120
tggtgcacgc tggccagcac gctcttgtcg gagatcagat ccgcgtccag gtcctccgcg   24180
ttgctcaggg cgaacggagt caactttggt agctgccttc ccaaaaaggg cgcgtgccca   24240
ggctttgagt tgcactcgca ccgtagtggc atcaaaaggt gaccgtgccc ggtctgggcg   24300
ttaggataca gcgcctgcat aaaagccttg atctgcttaa aagccacctg agcctttgcg   24360
ccttcagaga agaacatgcc gcaagacttg ccggaaaact gattggccgg acaggccgcg   24420
tcgtgcacga gcaccttgc gtcggtgttg gagatctgca ccacatttcg gccccaccgg   24480
ttcttcacga tcttggcctt gctagactgc tccttcagcg cgcgctgccc gttttcgctc   24540
```

-continued

```
gtcacatcca tttcaatcac gtgctcctta tttatcataa tgcttccgtg tagacactta   24600
agctcgcctt cgatctcagc gcagcggtgc agccacaacg cgcagcccgt gggctcgtga   24660
tgcttgtagg tcacctctgc aaacgactgc aggtacgcct gcaggaatcg ccccatcatc   24720
gtcacaaagg tcttgttgct ggtgaaggtc agctgcaacc cgcggtgctc ctcgttcagc   24780
caggtcttgc atacggccgc cagagcttcc acttggtcag gcagtagttt gaagttcgcc   24840
tttagatcgt tatccacgtg gtacttgtcc atcagcgcgc gcgcagcctc catgcccttc   24900
tcccacgcag acacgatcgg cacactcagc gggttcatca ccgtaatttc actttccgct   24960
tcgctgggct cttcctcttc ctcttgcgtc cgcataccac gcgccactgg gtcgtcttca   25020
ttcagccgcc gcactgtgcg cttacctcct ttgccatgct tgattagcac cggtgggttg   25080
ctgaaaccca ccatttgtag cgccacatct tctctttctt cctcgctgtc cacgattacc   25140
tctggtgatg gcgggcgctc gggcttggga gaagggcgct tctttttctt cttgggcgca   25200
atggccaaat ccgccgccga ggtcgatggc cgcgggctgg gtgtgcgcgg caccagcgcg   25260
tcttgtgatg agtcttcctc gtcctcggac tcgatacgcc gcctcatccg cttttttggg   25320
ggcgcccggg gaggcggcgg cgacggggac ggggacgaca cgtcctccat ggttggggga   25380
cgtcgcgccg caccgcgtcc gcgctcgggg gtggtttcgc gctgctcctc ttcccgactg   25440
gccatttcct tctcctatag gcagaaaaag atcatggagt cagtcgagaa gaaggacagc   25500
ctaaccgccc cctctgagtt cgccaccacc gcctccaccg atgccgccaa cgcgcctacc   25560
accttccccg tcgaggcacc cccgcttgag gaggaggaag tgattatcga gcaggaccca   25620
ggttttgtaa gcgaagacga cgaggaccgc tcagtaccaa cagaggataa aaagcaagac   25680
caggacaacg cagaggcaaa cgaggaacaa gtcgggcggg gggacgaaag gcatggcgac   25740
tacctagatg tgggagacga cgtgctgttg aagcatctgc agcgccagtg cgccattatc   25800
tgcgacgcgt tgcaagagcg cagcgatgtg cccctcgcca tagcggatgt cagccttgcc   25860
tacgaacgcc accattctc accgcgcgta ccccccaaac gccaagaaaa cggcacatgc   25920
gagcccaacc cgcgcctcaa cttctacccc gtatttgccg tgccagaggt gcttgccacc   25980
tatcacatct tttccaaaa ctgcaagata cccctatcct gccgtgccaa ccgcagccga   26040
gcggacaagc agctggcctt gcggcagggc gctgtcatac ctgatatcgc ctcgctcaac   26100
gaagtgccaa aaatctttga gggtcttgga cgcgacgaga agcgcgcggc aaacgctctg   26160
caacaggaaa acagcgaaaa tgaaagtcac tctggagtgt tggtggaact cgagggtgac   26220
aacgcgcgcc tagccgtact aaaacgcagc atcgaggtca cccactttgc ctacccggca   26280
cttaacctac cccccaaggt catgagcaca gtcatgagtg agctgatcgt gcgccgtgcg   26340 cagccctgg agagggatgc aaatttgcaa gaacaaacag aggagggcct acccgcagtt   26400
ggcgacgagc agctagcgcg ctggcttcaa acgcgcgagc ctgccgactt ggaggagcga   26460
cgcaaactaa tgatggccgc agtgctcgtt accgtggagc ttgagtgcat gcagcggttc   26520
tttgctgacc cggagatgca gcgcaagcta gaggaaacat tgcactacac ctttcgacag   26580
ggctacgtac gccaggcctg caagatctcc aacgtggagc tctgcaacct ggtctcctac   26640
cttgaatttt tgcacgaaaa ccgccttggg caaaacgtgc ttcattccac gctcaagggc   26700
gaggcgcgcc gcgactacgt ccgcgactgc gtttacttat ttctatgcta cacctggcag   26760
acggccatgg gcgtttggca gcagtgcttg gaggagtgca acctcaagga gctgcagaaa   26820
ctgctaaagc aaaacttgaa ggaccatatg gacggcctca cgagcgctc cgtggccgcg   26880 cacctggcgg acatcatttt ccccgaacgc ctgcttaaaa ccctgcaaca gggtctgcca   26940
```

-continued

```
gacttcacca gtcaaagcat gttgcagaac tttaggaact ttatcctaga gcgctcagga   27000
atcttgcccg ccacctgctg tgcacttcct agcgactttg tgcccattaa gtaccgcgaa   27060
tgccctccgc cgctttgggg ccactgctac cttctgcagc tagccaacta ccttgcctac   27120
cactctgaca taatggaaga cgtgagcggt gacggtctac tggagtgtca ctgtcgctgc   27180
aacctatgca ccccgcaccg ctccctggtt tgcaattcgc agctgcttaa cgaaagtcaa   27240
attatcggta cctttgagct gcagggtccc tcgcctgacg aaaagtccgc ggctccgggg   27300
ttgaaactca ctccggggct gtggacgtcg gcttaccttc gcaaatttgt acctgaggac   27360
taccacgccc acgagattag gttctacgaa gaccaatccc gcccgcctaa tgcggagctt   27420
accgcctgcg tcattaccca gggccacatt cttggccaat tgcaagccat caacaaagcc   27480
cgccaagagt ttctgctacg aaagggacgg ggggtttact tggaccccca gtccggcgag   27540
gagctcaacc caatcccccc gccgccgcag ccctatcagc agcagccgcg ggcccttgct   27600
tcccaggatg gcacccaaaa agaagctgca gctgccgccg ccacccacgg acgaggagga   27660
atactgggac agtcaggcag aggaggtttt ggacgaggag gaggaggaca tgatggaaga   27720
ctgggagagc ctagacgagg aagcttccga ggtcgaagag gtgtcagacg aaacaccgtc   27780
accctcggtc gcattcccct cgccggcgcc ccagaaatcg gcaaccggtt ccagcatggc   27840
tacaacctcc gctcctcagg cgccgccggc actgcccgtt cgccgaccca accgtagatg   27900
ggacaccact ggaaccaggg ccggtaagtc caagcagccg ccgccgttag cccaagagca   27960 acaacgcgc caaggctacc gctcatggcg cgggcacaag aacgccatag ttgcttgctt   28020
gcaagactgt gggggcaaca tctccttcgc ccgccgcttt cttctctacc atcacggcgt   28080
ggccttcccc cgtaacatcc tgcattacta ccgtcatctc tacagcccat actgcaccgg   28140
cggcagcggc agcaacagca gcggccacac agaagcaaag gcgaccggat agcaagactc   28200
tgacaaagcc caagaaatcc acagcggcgg cagcagcagg aggaggagcg ctgcgtctgg   28260
cgcccaacga acccgtatcg acccgcgagc ttagaaacag gatttttccc actctgtatg   28320
ctatatttca acagagcagg ggccaagaac aagagctgaa aataaaaaac aggtctctgc   28380
gatccctcac ccgcagctgc ctgtatcaca aaagcgaaga tcagcttcgg cgcacgctgg   28440
aagacgcgga ggctctcttc agtaaatact gcgcgctgac tcttaaggac tagtttcgcg   28500
ccctttctca aatttaagcg cgaaaactac gtcatctcca gcggcacac ccggcgccag   28560 cacctgttgt cagcgccatt atgagcaagg aaattcccac gccctacatg tggagttacc   28620
agccacaaat gggacttgcg gctggagctg cccaagacta ctcaacccga ataaactaca   28680
tgagcgcggg accccacatg atatcccggg tcaacggaat acgcgccac cgaaaccgaa   28740 ttctcctgga acaggcggct attaccacca cacctcgtaa taaccttaat ccccgtagtt   28800
ggcccgctgc cctggtgtac caggaaagtc ccgctcccac cactgtggta cttcccagag   28860 acgcccagc cgaagttcag atgactaact caggggcgca gcttgcgggc ggctttcgtc   28920
acagggtgcg gtcgcccggg cagggtataa ctcacctgac aatcagaggg cgaggtattc   28980
agctcaacga cgagtcggtg agctcctcgc ttggtctccg tccggacggg acatttcaga   29040
tcggcggcgc cggccgctct tcattcacgc ctcgtcagga aatcctaact ctgcagacct   29100
cgtcctctga gccgcgctct ggaggcattg gaactctgca atttattgag gagtttgtgc   29160
catcggtcta ctttaacccc ttctcgggac ctcccggcca ctatccggat caatttattc   29220
ctaactttga cgcggtaaag gactcggcgg acggctacga ctgaatgtta agtggagagg   29280
```

-continued

```
cagagcaact gcgcctgaaa cacctggtcc actgtcgccg ccacaagtgc tttgcccgcg   29340
actccggtga gttttgctac tttgaattgc ccgaggatca tatcgagggc ccggcgcacg   29400
gcgtccggct taccgcccag ggagagcttg cccgtagcct gattcgggag tttacccagc   29460
gccccctgct agttgagcgg gacaggggac cctgtgttct cactgtgatt tgcaactgtc   29520
ctaaccctgg attacatcaa gatcctctag ttaatgtcag gtcgcctaag tcgattaact   29580
agagtacccg gggatcttat tccctttaac taataaaaaa aaataataaa gcatcactta   29640
cttaaaatca gttagcaaat ttctgtccag tttattcagc agcacctcct tgccctcctc   29700
ccagctctgg tattgcagct tcctcctggc tgcaaacttt ctccacaatc taaatggaat   29760
gtcagtttcc tcctgttcct gtccatccgc acccactatc ttcatgttgt tgcagatgaa   29820
gcgcgcaaga ccgtctgaag ataccttcaa ccccgtgtat ccatatgaca cggaaaccgg   29880
tcctccaact gtgccttttc ttactcctcc ctttgtatcc cccaatgggt ttcaagagag   29940 tcccctggg gtactctctt tgcgcctatc cgaacctcta gttacctcca atggcatgct   30000
tgcgctcaaa atgggcaacg gcctctctct ggacgaggcc ggcaacctta cctcccaaaa   30060
tgtaaccact gtgagcccac ctctcaaaaa aaccaagtca aacataaacc tggaaatatc   30120
tgcacccctc acagttacct cagaagccct aactgtggct gccgccgcac ctctaatggt   30180
cgcgggcaac acactcacca tgcaatcaca ggccccgcta accgtgcacg actccaaact   30240
tagcattgcc acccaaggac ccctcacagt gtcagaagga aagctagccc tgcaaacatc   30300 aggcccctc accaccaccg atagcagtac ccttactatc actgcctcac cccctctaac   30360
tactgccact ggtagcttgg gcattgactt gaaagagccc atttatacac aaaatggaaa   30420
actaggacta aagtacgggg ctcctttgca tgtaacagac gacctaaaca ctttgaccgt   30480
agcaactggt ccaggtgtga ctattaataa tacttccttg caaactaaag ttactggagc   30540
cttgggtttt gattcacaag gcaatatgca acttaatgta gcaggaggac taaggattga   30600
ttctcaaaac agacgcctta tacttgatgt tagttatccg tttgatgctc aaaaccaact   30660
aaatctaaga ctaggacagg gccctctttt tataaactca gcccacaact tggatattaa   30720
ctacaacaaa ggcctttact tgtttacagc ttcaaacaat tccaaaaagc ttgaggttaa   30780
cctaagcact gccaaggggt tgatgtttga cgctacagcc atagccatta atgcaggaga   30840
tgggcttgaa tttggttcac ctaatgcacc aaacacaaat cccctcaaaa caaaaattgg   30900
ccatggccta gaatttgatt caaacaaggc tatggttcct aaaactaggaa ctggccttag   30960 ttttgacagc acaggtgcca ttacagtagg aaacaaaaat aatgataagc taactttgtg   31020
gaccggaata aaccctccac ctaactgtca aattgtggaa aacactaata caaatgatgg   31080
caaacttact ttagtattag taaaaaatgg agggcttgtt aatggctacg tgtctctagt   31140
tggtgtatca gacactgtga accaaatgtt cacacaaaag acagcaaaca tccaattaag   31200
attatatttt gactcttctg gaaatctatt aactgaggaa tcagacttaa aaattccact   31260
taaaaataaa tcttctacag cgaccagtga aactgtagcc agcagcaaag cctttatgcc   31320
aagtactaca gcttatccct tcaacaccac tactagggat agtgaaaact acattcatgg   31380
aatatgttac tacatgacta gttatgatag aagtctatt cccttgaaca tttctataat   31440
gctaaacagc cgtatgattt cttccaatgt tgcctatgcc atacaatttg aatggaatct   31500
aaatgcaagt gaatctccag aaaagcaacat agctacgctg accacatccc ccttttttctt   31560 ttcttacatt acagaagacg acaactaaag aatcgtttgt gttatgtttc aacgtgttta   31620
tttttcaatt gcagaaaatt tcaagtcatt tttcattcag tagtatagcc ccaccaccac   31680
```

-continued

```
atagcttata cagatcaccg taccttaatc aaactcacag aaccctagta ttcaacctgc   31740
cacctccctc ccaacacaca gagtacacag tcctttctcc ccggctggcc ttaaaaagca   31800
tcatatcatg ggtaacagac atattcttag gtgttatatt ccacacggtt tcctgtcgag   31860
ccaaacgctc atcagtgata ttaataaact ccccgggcag ctcacttaag ttcatgtcgc   31920
tgtccagctg ctgagccaca ggctgctgtc caacttgcgg ttgcttaacg ggcggcgaag   31980
gagaagtcca cgcctacatg ggggtagagt cataatcgtg catcaggata gggcggtggt   32040
gctgcagcag cgcgcgaata aactgctgcc gccgccgctc cgtcctgcag gaatacaaca   32100
tggcagtggt ctcctcagcg atgattcgca ccgcccgcag cataaggcgc cttgtcctcc   32160
gggcacagca gcgcaccctg atctcactta aatcagcaca gtaactgcag cacagcacca   32220
caatattgtt caaaatccca cagtgcaagg cgctgtatcc aaagctcatg gcggggacca   32280
cagaacccac gtggccatca taccacaagc gcaggtagat taagtggcga cccctcataa   32340
acacgctgga cataaacatt acctcttttg gcatgttgta attcaccacc tcccggtacc   32400
atataaacct ctgattaaac atggcgccat ccaccaccat cctaaaccag ctggccaaaa   32460
cctgcccgcc ggctatacac tgcagggaac cgggactgga acaatgacag tggagagccc   32520
aggactcgta accatggatc atcatgctcg tcatgatatc aatgttggca caacacaggc   32580
acacgtgcat acacttcctc aggattacaa gctcctcccg cgttagaacc atatcccagg   32640
gaacaaccca ttcctgaatc agcgtaaatc ccacactgca gggaagacct cgcacgtaac   32700
tcacgttgtg cattgtcaaa gtgttacatt cgggcagcag cggatgatcc tccagtatgg   32760
tagcgcgggt ttctgtctca aaaggaggta gacgatccct actgtacgga gtgcgccgag   32820
acaaccgaga tcgtgttggt cgtagtgtca tgccaaatgg aacgccggac gtagtcatat   32880
ttcctgaagc aaaaccaggt gcgggcgtga caaacagatc tgcgtctccg gtctcgccgc   32940
ttagatcgct ctgtgtagta gttgtagtat atccactctc tcaaagcatc caggcgcccc   33000
ctggcttcgg gttctatgta aactccttca tgcgccgctg ccctgataac atccaccacc   33060
gcagaataag ccacacccag ccaacctaca cattcgttct gcgagtcaca cacgggagga   33120
gcgggaagag ctggaagaac catgtttttt tttttattcc aaaagattat ccaaaacctc   33180
aaaatgaaga tctattaagt gaacgcgctc ccctccggtg gcgtggtcaa actctacagc   33240
caaagaacag ataatggcat ttgtaagatg ttgcacaatg gcttccaaaa ggcaaacggc   33300
cctcacgtcc aagtggacgt aaaggctaaa cccttcaggg tgaatctcct ctataaacat   33360
tccagcacct tcaaccatgc ccaaataatt ctcatctcgc caccttctca atatatctct   33420
aagcaaatcc cgaatattaa gtccggccat tgtaaaaatc tgctccagag cgccctccac   33480
cttcagcctc aagcagcgaa tcatgattgc aaaaattcag gttcctcaca gacctgtata   33540
agattcaaaa gcggaacatt aacaaaaata ccgcgatccc gtaggtccct tcgcagggcc   33600
agctgaacat aatcgtgcag gtctgcacgg accagcgcgg ccacttcccc gccaggaacc   33660
atgacaaaag aacccacact gattatgaca cgcatactcg gagctatgct aaccagcgta   33720
gccccgatgt aagcttgttg catgggcggc gatataaaat gcaaggtgct gctcaaaaaa   33780
tcaggcaaag cctcgcgcaa aaagaaagc acatcgtagt catgctcatg cagataaagg   33840
caggtaagct ccggaaccac cacagaaaaa gacaccattt ttctctcaaa catgtctgcg   33900
ggtttctgca taaacacaaa ataaaataac aaaaaaacat ttaaacatta gaagcctgtc   33960
ttacaacagg aaaaacaacc cttataagca taagacggac tacggccatg ccggcgtgac   34020
```

-continued

```
cgtaaaaaaa ctggtcaccg tgattaaaaa gcaccaccga cagctcctcg gtcatgtccg   34080
gagtcataat gtaagactcg gtaaacacat caggttgatt cacatcggtc agtgctaaaa   34140
agcgaccgaa atagcccggg ggaatacata cccgcaggcg tagagacaac attacagccc   34200
ccataggagg tataacaaaa ttaataggag agaaaaacac ataaacacct gaaaaaccct   34260
cctgcctagg caaaatagca ccctcccgct ccagaacaac atacagcgct tccacagcgg   34320
cagccataac agtcagcctt accagtaaaa aagaaaacct attaaaaaaa caccactcga   34380
cacggcacca gctcaatcag tcacagtgta aaaaggggcc aagtgcagag cgagtatata   34440
taggactaaa aaatgacgta acggttaaag tccacaaaaa acacccagaa aaccgcacgc   34500
gaacctacgc ccagaaacga aagccaaaaa acccacaact tcctcaaatc gtcacttccg   34560
ttttcccacg ttacgtcact tcccatttta agaaaactac aattcccaac acatacaagt   34620
tactccgccc taaaacctac gtcacccgcc ccgttcccac gccccgcgcc acgtcacaaa   34680
ctccaccccc tcattatcat attggcttca atccaaaata aggtatatta ttgatgatg    34739
```

```
<210> SEQ ID NO 24
<211> LENGTH: 37666
<212> TYPE: DNA
<213> ORGANISM: Artificial Sequence
<220> FEATURE:
<223> OTHER INFORMATION: plasmid #2 vector

<400> SEQUENCE: 24
ttaattaaca tgcatggatc catatgcggt gtgaaatacc gcacagatgc gtaaggagaa     60
aataccgcat caggcgctct tccgcttcct cgctcactga ctcgctgcgc tcggtcgttc    120
ggctgcggcg agcggtatca gctcactcaa aggcggtaat acggttatcc acagaatcag    180
gggataacgc aggaaagaac atgtgagcaa aaggccagca aaaggccagg aaccgtaaaa    240
aggccgcgtt gctggcgttt ttccataggc tccgcccccc tgacgagcat cacaaaaatc    300
gacgctcaag tcagaggtgg cgaaacccga caggactata aagataccag gcgtttcccc    360
ctggaagctc cctcgtgcgc tctcctgttc cgaccctgcc gcttaccgga tacctgtccg    420
cctttctccc ttcgggaagc gtggcgcttt ctcatagctc acgctgtagg tatctcagtt    480
cggtgtaggt cgttcgctcc aagctgggct gtgtgcacga accccccgtt cagcccgacc    540
gctgcgcctt atccggtaac tatcgtcttg agtccaaccc ggtaagacac gacttatcgc    600
cactggcagc agccactggt aacaggatta gcagagcgag gtatgtaggc ggtgctacag    660
agttcttgaa gtggtggcct aactacggct acactagaag gacagtattt ggtatctgcg    720
ctctgctgaa gccagttacc ttcggaaaaa gagttggtag ctcttgatcc ggcaaacaaa    780
ccaccgctgg tagcggtggt ttttttgttt gcaagcagca gattacgcgc agaaaaaaag    840
gatctcaaga agatcctttg atcttttcta cggggtctga cgctcagtgg aacgaaaact    900
cacgttaagg gattttggtc atgagattat caaaaaggat cttcacctag atccttttaa    960
attaaaaatg aagttttaaa tcaatctaaa gtatatatga gtaaacttgg tctgacagtt   1020
accaatgctt aatcagtgag gcacctatct cagcgatctg tctatttcgt tcatccatag   1080
ttgcctgact ccccgtcgtg tagataacta cgatacggga gggcttacca tctggcccca   1140
gtgctgcaat gataccgcga gacccacgct caccggctcc agatttatca gcaataaacc   1200
agccagccgg aagggccgag cgcagaagtg gtcctgcaac tttatccgcc tccatccagt   1260
ctattaattg ttgccgggaa gctagagtaa gtagttcgcc agttaatagt ttgcgcaacg   1320
ttgttgccat tgctgcagcc atgagattat caaaaaggat cttcacctag atccttttca   1380
```

-continued

```
cgtagaaagc cagtccgcag aaacggtgct gaccccggat gaatgtcagc tactgggcta      1440
tctggacaag ggaaaacgca agcgcaaaga gaaagcaggt agcttgcagt gggcttacat      1500
ggcgatagct agactgggcg gttttatgga cagcaagcga accggaattg ccagctgggg      1560
cgccctctgg taaggttggg aagccctgca aagtaaactg gatggctttc ttgccgccaa      1620
ggatctgatg gcgcagggga tcaagctctg atcaagagac aggatgagga tcgtttcgca      1680
tgattgaaca agatggattg cacgcaggtt ctccggccgc ttgggtggag aggctattcg      1740
gctatgactg ggcacaacag acaatcggct gctctgatgc cgccgtgttc cggctgtcag      1800
cgcaggggcg cccggttctt tttgtcaaga ccgacctgtc cggtgccctg aatgaactgc      1860
aagacgaggc agcgcggcta tcgtggctgg ccacgacggg cgttccttgc gcagctgtgc      1920
tcgacgttgt cactgaagcg ggaagggact ggctgctatt gggcgaagtg ccggggcagg      1980
atctcctgtc atctcacctt gctcctgccg agaaagtatc catcatggct gatgcaatgc      2040
ggcggctgca tacgcttgat ccggctacct gcccattcga ccaccaagcg aaacatcgca      2100
tcgagcgagc acgtactcgg atggaagccg gtcttgtcga tcaggatgat ctggacgaag      2160
agcatcaggg gctcgcgcca gccgaactgt tcgccaggct caaggcgagc atgcccgacg      2220
gcgaggatct cgtcgtgacc catggcgatg cctgcttgcc gaatatcatg gtggaaaatg      2280
gccgcttttc tggattcatc gactgtggcc ggctgggtgt ggcggaccgc tatcaggaca      2340
tagcgttggc tacccgtgat attgctgaag agcttggcgg cgaatgggct gaccgcttcc      2400
tcgtgcttta cggtatcgcc gctcccgatt cgcagcgcat cgccttctat cgccttcttg      2460
acgagttctt ctgaattttg ttaaaatttt tgttaaatca gctcattttt taaccaatag      2520
gccgaaatcg gcaaaatccc ttataaatca aagaataga ccgagatagg gttgagtgtt      2580
gttccagttt ggaacaagag tccactatta aagaacgtgg actccaacgt caaagggcga      2640
aaaaccgtct atcagggcga tggcccacta cgtgaaccat caccctaatc aagttttttg      2700
gggtcgaggt gccgtaaagc actaaatcgg aaccctaaag ggagccccg atttagagct      2760 tgacggggaa agccggcgaa cgtggcgaga aggaaggga agaaagcgaa aggagcgggc      2820
gctagggcgc tggcaagtgt agcggtcacg ctgcgcgtaa ccaccacacc cgccgcgctt      2880
aatgcgccgc tacagggcgc gtccattcgc cattcaggat cgaattaatt cttaattaac      2940
atcatcaata atataccta ttttggattg aagccaatat gataatgagg gggtggagtt      3000
tgtgacgtgg cgcggggcgt gggaacgggg cgggtgacgt agtagtgtgg cggaagtgtg      3060
atgttgcaag tgtggcggaa cacatgtaag cgacggatgg ggcaaaagtg acgttttgg      3120 tgtgcgccgg tgtacacagg aagtgacaat tttcgcgcgg ttttaggcgg atgttgtagt      3180
aaatttgggc gtaaccgagt aagatttggc cattttcgcg ggaaaactga ataagaggaa      3240
gtgaaatctg aataattttg tgttactcat agcgcgtaat actgtaatag taatcaatta      3300
cggggtcatt agttcatagc ccatatatgg agttccgcgt tacataactt acggtaaatg      3360
gcccgcctgg ctgaccgccc aacgacccc gcccattgac gtcaataatg acgtatgttc      3420
ccatagtaac gccaataggg actttccatt gacgtcaatg ggtggagtat ttacggtaaa      3480
ctgcccactt ggcagtacat caagtgtatc atatgccaag tacgccccct attgacgtca      3540
atgacggtaa atggcccgcc tggcattatg cccagtacat gaccttatgg gactttccta      3600
cttggcagta catctacgta ttagtcatcg ctattaccat ggtgatgcgg ttttggcagt      3660
acatcaatgg gcgtggatag cggtttgact cacggggatt tccaagtctc cacccattg      3720
```

-continued

```
acgtcaatgg gagtttgttt tggcaccaaa atcaacggga ctttccaaaa tgtcgtaaca    3780
actccgcccc attgacgcaa atgggcggta ggcgtgtacg gtgggaggtc tatataagca    3840
gagctctccc tatcagtgat agagatctcc ctatcagtga tagagatcgt cgacgagctc    3900
gtttagtgaa ccgtcagatc gcctggagac gccatccacg ctgttttgac ctccatagaa    3960
gacaccggga ccgatccagc ctccgatttg ccaccatgtt tgtgttcctg gtgctgctgc    4020
cactggtgtc cagccagtgt gtgaacctga ccaccaggac ccaacttcct cctgcctaca    4080
ccaactcctt caccaggggga gtctactacc ctgacaaggt gttcaggtcc tctgtgctgc    4140
acagcaccca ggacctgttc ctgccattct tcagcaatgt gacctggttc catgccatcc    4200
atgtgtctgg caccaatggc accaagaggt ttgacaaccc tgtgctgcca ttcaatgatg    4260
gagtctactt tgccagcaca gagaagagca acatcatcag gggctggatt tttggcacca    4320
ccctggacag caagacccag tccctgctga ttgtgaacaa tgccaccaat gtggtgatta    4380
aggtgtgtga gttccagttc tgtaatgacc cattcctggg agtctactac cacaagaaca    4440
acaagtcctg gatggagtct gagttcaggg tctactcctc tgccaacaac tgtacctttg    4500
aatatgtgag ccaaccattc ctgatggact tggagggcaa gcagggcaac ttcaagaacc    4560
tgagggagtt tgtgttcaag aacattgatg gctacttcaa gatttacagc aaacacacac    4620
caatcaacct ggtgagggac ctgccacagg gcttctctgc cttggaacca ctggtggacc    4680
tgccaattgg catcaacatc accaggttcc agaccctgct ggctctgcac aggtcctacc    4740
tgacacctgg agactcctcc tctggctgga cagcaggagc agcagcctac tatgtgggct    4800
acctccaacc aaggaccttc ctgctgaaat acaatgagaa tggcaccatc acagatgctg    4860
tggactgtgc cctggaccca ctgtctgaga ccaagtgtac cctgaaatcc ttcacagtgg    4920
agaagggcat ctaccagacc agcaacttca gggtccaacc aacagagagc attgtgaggt    4980
ttccaaacat caccaacctg tgtccatttg agaggtgtt caatgccacc aggtttgcct    5040
ctgtctatgc ctggaacagg aagaggatta gcaactgtgt ggctgactac tctgtgctct    5100
acaactctgc ctccttcagc accttcaagt gttatggagt gagcccaacc aaactgaatg    5160
acctgtgttt caccaatgtc tatgctgact cctttgtgat taggggagat gaggtgagac    5220
agattgcccc tggacaaaca ggcaagattg ctgactacaa ctacaaactg cctgatgact    5280
tcacaggctg tgtgattgcc tggaacagca acaacctgga cagcaaggtg ggaggcaact    5340
acaactacct ctacagactg ttcaggaaga gcaacctgaa accatttgag agggacatca    5400
gcacagagat ttaccaggct ggcagcacac catgtaatgg agtggagggc ttcaactgtt    5460
actttccact ccaatcctat ggcttccaac caaccaatgg agtgggctac caaccataca    5520
gggtggtggt gctgtccttt gaactgctcc atgcccctgc cacagtgtgt ggaccaaaga    5580
agagcaccaa cctggtgaag aacaagtgtg tgaacttcaa cttcaatgga ctgacaggca    5640
caggagtgct gacagagagc aacaagaagt tcctgccatt ccaacagttt ggcagggaca    5700
ttgctgacac cacagatgct gtgagggacc cacagaccct ggagattctg gacatcacac    5760
catgttcctt tggaggagtg tctgtgatta cacctggcac caacaccagc aaccaggtgg    5820
ctgtgctcta ccaggatgtg aactgtactg aggtgcctgt ggctatccat gctgaccaac    5880
ttacaccaac ctggagggtc tacagcacag gcagcaatgt gttccagacc agggctggct    5940
gtctgattgg agcagagcat gtgaacaact cctatgagtg tgacatccca attggagcag    6000
gcatctgtgc ctcctaccag acccagacca tcctcaggtc tgtggcaagc cagagcatca    6060
ttgcctacac aatgagtctg ggagcagaga actctgtggc ttacagcaac aacagcattg    6120
```

-continued

```
ccatcccaac caacttcacc atctctgtga ccacagagat tctgcctgtg agtatgacca      6180
agacctctgt ggactgtaca atgtatatct gtggagacag cacagagtgt agcaacctgc      6240
tgctccaata tggctccttc tgtacccaac ttaacagggc tctgacaggc attgctgtgg      6300
aacaggacaa gaacacccag gaggtgtttg cccaggtgaa gcagatttac aagacacctc      6360
caatcaagga ctttggaggc ttcaacttca gccagattct gcctgaccca agcaagccaa      6420
gcaagaggtc cttcattgag gacctgctgt tcaacaaggt gaccctggct gatgctggct      6480
tcatcaagca atatggagac tgtctgggag acattgctgc cagggacctg atttgtgccc      6540
agaagttcaa tggactgaca gtgctgcctc cactgctgac agatgagatg attgcccaat      6600
acacctctgc cctgctggct ggcaccatca cctctggctg gacctttgga gcaggagcag      6660
ccctccaaat cccatttgct atgcagatgg cttacaggtt caatggcatt ggagtgaccc      6720
agaatgtgct ctatgagaac cagaaactga ttgccaacca gttcaactct gccattggca      6780
agattcagga ctccctgtcc agcacagcct ctgccctggg caaactccaa gatgtggtga      6840
accagaatgc ccaggctctg aacaccctgg tgaagcaact ttccagcaac tttggagcca      6900
tctcctctgt gctgaatgac atcctgagca gactggacaa ggtggaggct gaggtccaga      6960
ttgacagact gattacaggc agactccaat ccctccaaac ctatgtgacc caacaactta      7020
tcagggctgc tgagattagg gcatctgcca acctggctgc caccaagatg agtgagtgtg      7080
tgctgggaca aagcaagagg gtggacttct gtggcaaggg ctaccacctg atgagttttc      7140
cacagtctgc ccctcatgga gtggtgttcc tgcatgtgac ctatgtgcct gcccaggaga      7200
agaacttcac cacagcccct gccatctgcc atgatggcaa ggctcacttt ccaagggagg      7260
gagtgtttgt gagcaatggc acccactggt ttgtgaccca gaggaacttc tatgaaccac      7320
agattatcac cacagacaac accttttgtgt ctggcaactg tgatgtggtg attggcattg      7380
tgaacaacac agtctatgac ccactccaac ctgaactgga ctccttcaag gaggaactgg      7440
acaaatactt caagaaccac accagccctg atgtggacct gggagacatc tctggcatca      7500
atgcctctgt ggtgaacatc cagaaggaga ttgacagact gaatgaggtg gctaagaacc      7560
tgaatgagtc cctgattgac ctccaagaac tgggcaaata tgaacaatac atcaagtggc      7620
catgaaaatt gatcataatc agccatacca catttgtaga ggttttactt gctttaaaaa      7680
acctcccaca cctcccctg aacctgaaac ataaaatgaa tgcaattgtt gttgttaact      7740
tgtttattgc agcttataat ggttacaaat aaagcaatag catcacaaat ttcacaaata      7800
aagcattttt ttcactgcat tctagttgtg gtttgtccaa actcatcaat gtatcttaac      7860
gcggatctgg gcgtggttaa gggtgggaaa gaatatataa ggtgggggtc ttatgtagtt      7920
ttgtatctgt tttgcagcag ccgccgccgc catgagcacc aactcgtttg atggaagcat      7980
tgtgagctca tatttgacaa cgcgcatgcc cccatgggcc ggggtgcgtc agaatgtgat      8040
gggctccagc attgatggtc gccccgtcct gcccgcaaac tctactacct tgacctacga      8100
gaccgtgtct ggaacgccgt tggagactgc agcctccgcc gccgcttcag ccgctgcagc      8160
caccgcccgc gggattgtga ctgactttgc tttcctgagc ccgcttgcaa gcagtgcagc      8220
ttcccgttca tccgcccgcg atgacaagtt gacggctctt ttggcacaat ggattctttt      8280
gacccgggaa cttaatgtcg tttctcagca gctgttggat ctgcgccagc aggtttctgc      8340
cctgaaggct cctcccctc ccaatgcggt ttaaaacata aataaaaaac cagactctgt      8400
ttggatttgg atcaagcaag tgtcttgctg tctttatttta ggggtttttgc gcgcgcggta      8460
```

-continued

```
ggcccgggac cagcggtctc ggtcgttgag ggtcctgtgt attttttcca ggacgtggta   8520
aaggtgactc tggatgttca gatacatggg cataagcccg tctctggggt ggaggtagca   8580
ccactgcaga gcttcatgct gcggggtggt gttgtagatg atccagtcgt agcaggagcg   8640
ctgggcgtgg tgcctaaaaa tgtctttcag tagcaagctg attgccaggg gcaggccctt   8700
ggtgtaagtg tttacaaagc ggttaagctg ggatgggtgc atacgtgggg atatgagatg   8760
catcttggac tgtattttta ggttggctat gttcccagcc atatccctcc ggggattcat   8820
gttgtgcaga accaccagca cagtgtatcc ggtgcacttg ggaaatttgt catgtagctt   8880
agaaggaaat gcgtggaaga acttggagac gcccttgtga cctccaagat tttccatgca   8940
ttcgtccata atgatggcaa tgggcccacg ggcggcggcc tgggcgaaga tatttctggg   9000
atcactaacg tcatagttgt gttccaggat gagatcgtca taggccattt ttacaaagcg   9060
cgggcggagg gtgccagact gcggtataat ggttccatcc ggcccagggg cgtagttacc   9120
ctcacagatt tgcatttccc acgctttgag ttcagatggg gggatcatgt ctacctgcgg   9180
ggcgatgaag aaaacggttt ccggggtagg ggagatcagc tgggaagaaa gcaggttcct   9240
gagcagctgc gacttaccgc agccggtggg cccgtaaatc acacctatta ccggctgcaa   9300
ctggtagtta agagagctgc agctgccgtc atccctgagc aggggggcca cttcgttaag   9360
catgtccctg actcgcatgt tttccctgac caaatccgcc agaaggcgct cgccgcccag   9420
cgatagcagt tcttgcaagg aagcaaagtt tttcaacggt ttgagaccgt ccgccgtagg   9480
catgcttttg agcgtttgac caagcagttc caggcggtcc cacagctcgg tcacctgctc   9540
tacggcatct cgatccagca tatctcctcg tttcgcgggt tggggcggct ttcgctgtac   9600
ggcagtagtc ggtgctcgtc cagacgggcc agggtcatgt ctttccacgg gcgcagggtc   9660
ctcgtcagcg tagtctgggt cacggtgaag gggtgcgctc cgggctgcgc gctggccagg   9720
gtgcgcttga ggctggtcct gctggtgctg aagcgctgcc ggtcttcgcc ctgcgcgtcg   9780
gccaggtagc atttgaccat ggtgtcatag tccagcccct ccgcggcgtg gcccttggcg   9840
cgcagcttgc ccttggagga ggcgccgcac gaggggcagt gcagactttt gagggcgtag   9900
agcttgggcg cgagaaatac cgattccggg gagtaggcat ccgcgccgca ggccccgcag   9960
acggtctcgc attccacgag ccaggtgagc tctggccgtt cggggtcaaa aaccaggttt  10020
cccccatgct ttttgatgcg tttcttacct ctggtttcca tgagccggtg tccacgctcg  10080
gtgacgaaaa ggctgtccgt gtccccgtat acagacttga gaggcctgtc ctcgagcggt  10140
gttccgcggt cctcctcgta tagaaactcg gaccactctg agacaaaggc tcgcgtccag  10200
gccagcacga aggaggctaa gtgggagggg tagcggtcgt tgtccactag ggggtccact  10260
cgctccaggg tgtgaagaca catgtcgccc tcttcggcat caaggaaggt gattggtttg  10320
taggtgtagg ccacgtgacc gggtgttcct gaaggggggc tataaaaggg ggtgggggcg  10380
cgttcgtcct cactctcttc cgcatcgctg tctgcgaggg ccagctgttg gggtgagtac  10440
tccctctgaa aagcgggcat gacttctgcg ctaagattgt cagtttccaa aaacgaggag  10500
gatttgatat tcacctggcc cgcggtgatg cctttgaggg tggccgcatc catctggtca  10560
gaaaagacaa tctttttgtt gtcaagcttg gtggcaaacg acccgtagag ggcgttggac  10620
agcaacttgg cgatggagcg cagggtttgg tttttgtcgc gatcggcgcg ctccttggcc  10680
gcgatgttta gctgcacgta ttcgcgcgca acgcaccgcc attcgggaaa gacggtggtg  10740
cgctcgtcgg gcaccaggtg cacgcgccaa ccgcggttgt gcaggtgac aaggtcaacg  10800 ctggtggcta cctctccgcg taggcgctcg ttggtccagc agaggcggcc gcccttgcgc  10860
```

-continued

```
gagcagaatg gcggtagggg gtctagctgc gtctcgtccg gggggtctgc gtccacggta    10920
aagaccccgg gcagcaggcg cgcgtcgaag tagtctatct tgcatccttg caagtctagc    10980
gcctgctgcc atgcgcgggc ggcaagcgcg cgctcgtatg ggttgagtgg gggacccat     11040 ggcatggggt gggtgagcgc ggaggcgtac atgccgcaaa tgtcgtaaac gtagaggggc    11100
tctctgagta ttccaagata tgtagggtag catcttccac cgcggatgct ggcgcgcacg    11160
taatcgtata gttcgtgcga gggagcgagg aggtcgggac cgaggttgct acgggcgggc    11220
tgctctgctc ggaagactat ctgcctgaag atggcatgtg agttggatga tatggttgga    11280
cgctggaaga cgttgaagct ggcgtctgtg agacctaccg cgtcacgcac gaaggaggcg    11340
taggagtcgc gcagcttgtt gaccagctcg gcggtgacct gcacgtctag ggcgcagtag    11400
tccagggttt ccttgatgat gtcatactta tcctgtccct ttttttttcca cagctcgcgg   11460 ttgaggacaa actcttcgcg gtctttccag tactcttgga tcggaaaccc gtcggcctcc    11520
gaacggtaag agcctagcat gtagaactgg ttgacggcct ggtaggcgca gcatcccttt    11580
tctacgggta gcgcgtatgc ctgcgcggcc ttccggagcg aggtgtgggt gagcgcaaag    11640
gtgtccctga ccatgacttt gaggtactgg tatttgaagt cagtgtcgtc gcatccgccc    11700
tgctcccaga gcaaaaagtc cgtgcgcttt ttggaacgcg gatttggcag ggcgaaggtg    11760
acatcgttga agagtatctt tcccgcgcga ggcataaagt tgcgtgtgat gcggaagggt    11820
cccggcacct cggaacggtt gttaattacc tgggcggcga gcacgatctc gtcaaagccg    11880
ttgatgttgt ggcccacaat gtaaagttcc aagaagcgcg ggatgccctt gatggaaggc    11940 aatttttttaa gttcctcgta ggtgagctct tcaggggagc tgagcccgtg ctctgaaagg    12000
gcccagtctg caagatgagg gttggaagcg acgaatgagc tccacaggtc acgggccatt    12060
agcatttgca ggtggtcgcg aaaggtccta aactggcgac ctatggccat tttttctggg    12120
gtgatgcagt agaaggtaag cgggtcttgt tcccagcggt cccatccaag gttcgcggct    12180
aggtctcgcg cggcagtcac tagaggctca tctccgccga acttcatgac cagcatgaag    12240
ggcacgagct gcttcccaaa ggcccccatc caagtatagg tctctacatc gtaggtgaca    12300
aagagacgct cggtgcgagg atgcgagccg atcgggaaga actggatctc ccgccaccaa    12360
ttggaggagt ggctattgat gtggtgaaag tagaagtccc tgcgacgggc cgaacactcg    12420
tgctggcttt tgtaaaaacg tgcgcagtac tggcagcggt gcacgggctg tacatcctgc    12480
acgaggttga cctgacgacc gcgcacaagg aagcagagtg ggaatttgag cccctcgcct    12540
ggcgggtttg gctggtggtc ttctacttcg gctgcttgtc cttgaccgtc tggctgctcg    12600
aggggagtta cggtggatcg gaccaccacg ccgcgcgagc ccaaagtcca gatgtccgcg    12660
cgcggcggtc ggagcttgat gacaacatcg cgcagatggg agctgtccat ggtctggagc    12720
tcccgcggcg tcaggtcagg cgggagctcc tgcaggttta cctcgcatag acgggtcagg    12780
gcgcgggcta gatccaggtg atacctaatt tccaggggct ggttggtggc ggcgtcgatg    12840
gcttgcaaga ggccgcatcc ccgcggcgcg actacggtac cgcgcggcgg gcggtgggcc    12900
gcgggggtgt ccttggatga tgcatctaaa agcggtgacg cgggcgagcc cccggaggta    12960 ggggggctc cggacccgcc gggagagggg gcaggggcac gtcggcgccg cgcgcgggca     13020
ggagctggtg ctgcgcgcgt aggttgctgg cgaacgcgac gacgcggcgg ttgatctcct    13080
gaatctggcg cctctgcgtg aagacgacgg gcccggtgag cttgaacctg aaagagagtt    13140
cgacagaatc aatttcggtg tcgttgacgg cggcctggcg caaaatctcc tgcacgtctc    13200
```

-continued

```
ctgagttgtc ttgataggcg atctcggcca tgaactgctc gatctcttcc tcctggagat   13260
ctccgcgtcc ggctcgctcc acggtggcgg cgaggtcgtt ggaaatgcgg gccatgagct   13320
gcgagaaggc gttgaggcct ccctcgttcc agacgcggct gtagaccacg ccccccttcgg  13380 catcgcgggc gcgcatgacc acctgcgcga gattgagctc cacgtgccgg gcgaagacgg   13440
cgtagtttcg caggcgctga aagaggtagt tgagggtggt ggcggtgtgt tctgccacga   13500
agaagtacat aacccagcgt cgcaacgtgg attcgttgat atcccccaag gcctcaaggc   13560
gctccatggc ctcgtagaag tccacggcga agttgaaaaa ctgggagttg cgcgccgaca   13620
cggttaactc ctcctccaga agacggatga gctcggcgac agtgtcgcgc acctcgcgct   13680
caaaggctac aggggcctct tcttcttctt caatctcctc ttccataagg gcctcccctt   13740
cttcttcttc tggcggcggt gggggagggg ggacacggcg gcgacgacgg cgcaccggga   13800
ggcggtcgac aaagcgctcg atcatctccc cgcggcgacg gcgcatggtc tcggtgacgg   13860
cgcggccgtt ctcgcggggg cgcagttgga agacgccgcc cgtcatgtcc cggttatggg   13920
ttggcggggg gctgccatgc ggcagggata cggcgctaac gatgcatctc aacaattgtt   13980
gtgtaggtac tccgccgccg agggacctga gcgagtccgc atcgaccgga tcggaaaacc   14040
tctcgagaaa ggcgtctaac cagtcacagt cgcaaggtag gctgagcacc gtggcgggcg   14100
gcagcgggcg gcggtcgggg ttgtttctgg cggaggtgct gctgatgatg taattaaagt   14160
aggcggtctt gagacggcgg atggtcgaca gaagcaccat gtccttgggt ccggcctgct   14220
gaatgcgcag gcggtcggcc atgccccagg cttcgttttg acatcggcgc aggtctttgt   14280
agtagtcttg catgagcctt tctaccggca cttcttcttc tccttcctct tgtcctgcat   14340
ctcttgcatc tatcgctgcg gcggcggcgg agtttggccg taggtggcgc cctcttcctc   14400
ccatgcgtgt gaccccgaag cccctcatcg gctgaagcag ggctaggtcg cgacaacgc    14460 gctcggctaa tatggcctgc tgcacctgcg tgagggtaga ctggaagtca tccatgtcca   14520
caaagcggtg gtatgcgccc gtgttgatgg tgtaagtgca gttggccata acggaccagt   14580
taacggtctg gtgacccggc tgcgagagct cggtgtacct gagacgcgag taagccctcg   14640
agtcaaatac gtagtcgttg caagtccgca ccaggtactg gtatcccacc aaaaagtgcg   14700
gcggcggctg gcggtagagg ggccagcgta gggtggccgg ggctccgggg gcgagatctt   14760
ccaacataag gcgatgatat ccgtagatgt acctggacat ccaggtgatg ccggcggcgg   14820
tggtggaggc gcgcggaaag tcgcggacgc ggttccagat gttgcgcagc ggcaaaaagt   14880
gctccatggt cgggacgctc tggccggtca ggcgcgcgca atcgttgacg ctctagcgtg   14940
caaaaggaga gcctgtaagc gggcactctt ccgtggtctg gtggataaat cgcaagggt    15000 atcatggcgg acgaccgggg ttcgagcccc gtatccggcc gtccgccgtg atccatgcgg   15060
ttaccgcccg cgtgtcgaac ccaggtgtgc gacgtcagac aacgggggag tgctcctttt   15120
ggcttccttc caggcgcggc ggctgctgcg ctagcttttt tggccactgg ccgcgcgcag   15180
cgtaagcggt taggctggaa agcgaaagca ttaagtggct cgctccctgt agccggaggg   15240
ttattttcca agggttgagt cgcgggaccc ccggttcgag tctcggaccg gccggactgc   15300
ggcgaacggg ggtttgcctc cccgtcatgc aagaccccgc ttgcaaattc ctccggaaac   15360
agggacgagc ccctttttttg cttttcccag atgcatccgg tgctgcggca gatgcgcccc   15420
cctcctcagc agcggcaaga gcaagagcag cggcagacat gcaggcacc ctcccctcct    15480 cctaccgcgt caggaggggc gacatccgcg gttgacgcgg cagcagatgg tgattacgaa   15540
cccccgcggc gccgggcccg gcactacctg gacttggagg agggcgaggg cctggcgcgg   15600
```

-continued

```
ctaggagcgc cctctcctga gcggcaccca agggtgcagc tgaagcgtga tacgcgtgag   15660
gcgtacgtgc cgcggcagaa cctgtttcgc daccgcgagg gagaggagcc cgaggagatg   15720
cgggatcgaa agttccacgc agggcgcgag ctgcggcatg gcctgaatcg cgagcggttg   15780
ctgcgcgagg aggactttga gcccgacgcg cgaaccggga ttagtcccgc gcgcgcacac   15840
gtggcggccg ccgacctggt aaccgcatac gagcagacgg tgaaccagga gattaacttt   15900
caaaaaagct ttaacaacca cgtgcgtacg cttgtggcgc gcgaggaggt ggctatagga   15960
ctgatgcatc tgtgggactt tgtaagcgcg ctggagcaaa acccaaatag caagccgctc   16020
atggcgcagc tgttccttat agtgcagcac agcagggaca acgaggcatt cagggatgcg   16080
ctgctaaaca tagtagagcc cgagggccgc tggctgctcg atttgataaa catcctgcag   16140
agcatagtgg tgcaggagcg cagcttgagc ctggctgaca aggtggccgc catcaactat   16200
tccatgctta gcctgggcaa gttttacgcc cgcaagatat accataCCCC ttacgttccc   16260
atagacaagg aggtaaagat cgagggttc tacatgcgca tggcgctgaa ggtgcttacc   16320
ttgagcgacg acctgggcgt ttatcgcaac gagcgcatcc acaaggccgt gagcgtgagc   16380
cggcggcgcg agctcagcga ccgcgagctg atgcacagcc tgcaaagggc cctggctggc   16440
acgggcagcg gcgatagaga ggccgagtcc tactttgacg cgggcgctga cctgcgctgg   16500
gccccaagcc gacgcgccct ggaggcagct ggggccggac ctgggctggc ggtggcaccc   16560
gcgcgcgctg gcaacgtcgg cggcgtggag gaatatgacg aggacgatga gtacgagcca   16620
gaggacggca gtactaagc ggtgatgttt ctgatcagat gatgcaagac gcaacggacc   16680
cggcggtgcg ggcggcgctg cagagccagc cgtccggcct taactccacg gacgactggc   16740
gccaggtcat ggaccgcatc atgtcgctga ctgcgcgcaa tcctgacgcg ttccggcagc   16800
agccgcaggc caaccggctc tccgcaattc tggaagcggt ggtcccggcg cgcgcaaacc   16860
ccacgcacga gaaggtgctg gcgatcgtaa acgcgctggc cgaaaacagg gccatccggc   16920
ccgacgaggc cggcctggtc tacgacgcgc tgcttcagcg cgtggctcgt tacaacagcg   16980
gcaacgtgca gaccaacctg gaccggctgg tgggggatgt gcgcgaggcc gtggcgcagc   17040
gtgagcgcgc gcagcagcag ggcaacctgg gctccatggt tgcactaaac gccttcctga   17100
gtacacagcc cgccaacgtg ccgcgggggac aggaggacta caccaacttt gtgagcgcac   17160
tgcggctaat ggtgactgag acaccgcaaa gtgaggtgta ccagtctggg ccagactatt   17220
ttttccagac cagtagacaa ggcctgcaga ccgtaaacct gagccaggct ttcaaaaact   17280
tgcaggggct gtgggggggtg cgggctccca caggcgaccg cgcgaccgtg tctagcttgc   17340
tgacgcccaa ctcgcgcctg ttgctgctgc taatagcgcc cttcacggac agtggcagcg   17400
tgtcccggga cacataccta ggtcacttgc tgacactgta ccgcgaggcc ataggtcagg   17460
cgcatgtgga cgagcatact ttccaggaga ttacaagtgt cagccgcgcg ctggggcagg   17520
aggacacggg cagcctggag gcaaccctaa actacctgct gaccaaccgg cggcagaaga   17580 tccccctcgtt gcacagttta aacagcgagg aggagcgcat tttgcgctac gtgcagcaga   17640
gcgtgagcct taacctgatg cgcgacgggg taacgcccag cgtggcgctg gacatgaccg   17700
cgcgcaacat ggaaccgggc atgtatgcct caaaccggcc gttatcaac cgcctaatgg   17760 actacttgca tcgcgcggcc gccgtgaacc ccgagtattt caccaatgcc atcttgaacc   17820
cgcactggct accgcccect ggtttctaca ccggggggatt cgaggtgccc gagggtaacg   17880
atggattcct ctgggacgac atagacgaca gcgtgtttttc cccgcaaccg cagaccctgc   17940
```

-continued

```
tagagttgca acagcgcgag caggcagagg cggcgctgcg aaaggaaagc ttccgcaggc    18000
caagcagctt gtccgatcta ggcgctgcgg ccccgcggtc agatgctagt agcccatttc    18060
caagcttgat agggtctctt accagcactc gcaccacccg cccgcgcctg ctgggcgagg    18120
aggagtacct aaacaactcg ctgctgcagc cgcagcgcga aaaaaacctg cctccggcat    18180
ttcccaacaa cgggatagag agcctagtgg acaagatgag tagatggaag acgtacgcgc    18240
aggagcacag ggacgtgcca ggcccgcgcc cgcccacccg tcgtcaaagg cacgaccgtc    18300
agcggggtct ggtgtgggag gacgatgact cggcagacga cagcagcgtc ctggatttgg    18360
gagggagtgg caacccgttt gcgcaccttc gccccaggct ggggagaatg ttttaaaaaa    18420
aaaaaagcat gatgcaaaat aaaaaactca ccaaggccat ggcaccgagc gttggttttc    18480
ttgtattccc cttagtatgc ggcgcgcggc gatgtatgag gaaggtcctc ctccctccta    18540
cgagagtgtg gtgagcgcgg cgccagtggc ggcggcgctg ggttctccct tcgatgctcc    18600
cctggacccg ccgtttgtgc ctccgcggta cctgcggcct accgggggga gaaacagcat    18660
ccgttactct gagttggcac ccctattcga caccacccgt gtgtacctgg tggacaacaa    18720
gtcaacggat gtggcatccc tgaactacca gaacgaccac agcaactttc tgaccacggt    18780
cattcaaaac aatgactaca gcccggggga ggcaagcaca cagaccatca atcttgacga    18840
ccggtcgcac tggggcggcg acctgaaaac catcctgcat accaacatgc caaatgtgaa    18900
cgagttcatg tttaccaata gtttaaggc gcgggtgatg gtgtcgcgct tgcctactaa    18960
ggacaatcag gtggagctga aatacgagtg ggtggagttc acgctgcccg agggcaacta    19020
ctccgagacc atgaccatag accttatgaa caacgcgatc gtggagcact acttgaaagt    19080
gggcagacag aacggggttc tggaaagcga catcggggta aagtttgaca cccgcaactt    19140
cagactgggg tttgaccccg tcactggtct tgtcatgcct ggggtatata caaacgaagc    19200
cttccatcca gacatcattt tgctgccagg atgcgggggtg gacttcaccc acagccgcct    19260
gagcaacttg ttgggcatcc gcaagcggca acccttccag gagggcttta ggatcaccta    19320
cgatgatctg gagggtggta acattcccgc actgttggat gtggacgcct accaggcgag    19380
cttgaaagat gacaccgaac agggcggggg tggcgcaggc ggcagcaaca gcagtggcag    19440
cggcgcggaa gagaactcca acgcggcagc cgcggcaatg cagccggtgg aggacatgaa    19500
cgatcatgcc attcgcggcg acacctttgc cacacgggct gaggagaagc gcgctgaggc    19560
cgaagcagcg gccgaagctg ccgcccccgc tgcgcaaccc gaggtcgaga agcctcagaa    19620
gaaaccggtg atcaaacccc tgacagagga cagcaagaaa cgcagttaca acctaataag    19680
caatgacagc accttcaccc agtaccgcag ctggtacctt gcatacaact acggcgaccc    19740
tcagaccgga atccgctcat ggaccctgct ttgcactcct gacgtaacct gcggctcgga    19800
gcaggtctac tggtcgttgc cagacatgat gcaagacccc gtgaccttcc gctccacgcg    19860
ccagatcagc aactttccgg tggtgggcgc cgagctgttg cccgtgcact ccaagagctt    19920
ctacaacgac caggccgtct actcccaact catccgccag tttacctctc tgacccacgt    19980
gttcaatcgc tttcccgaga accagatttt ggcgcgcccg ccagcccca ccatcaccac    20040 cgtcagtgaa aacgttcctg ctctcacaga tcacgggacg ctaccgctgc gcaacagcat    20100
cggaggagtc cagcgagtga ccattactga cgccagacgc cgcacctgcc cctacgttta    20160
caaggccctg ggcatagtct cgccgcgcgt cctatcgagc cgcacttttt gagcaagcat    20220
gtccatcctt atatcgccca gcaataacac aggctggggc ctgcgcttcc caagcaagat    20280
gtttggcggg gccaagaagc gctccgacca acacccagtg cgcgtgcgcg ggcactaccg    20340
```

-continued

```
cgcgccctgg ggcgcgcaca aacgcggccg cactgggcgc accaccgtcg atgacgccat  20400
cgacgcggtg gtggaggagg cgcgcaacta cacgcccacg ccgccaccag tgtccacagt  20460
ggacgcggcc attcagaccg tggtgcgcgg agcccggcgc tatgctaaaa tgaagagacg  20520
gcggaggcgc gtagcacgtc gccaccgccg ccgacccggc actgccgccc aacgcgcggc  20580
ggcggccctg cttaaccgcg cacgtcgcac cggccgacgg gcggccatgc gggccgctcg  20640
aaggctggcc gcgggtattg tcactgtgcc ccccaggtcc aggcgacgag cggccgccgc  20700
agcagccgcg gccattagtg ctatgactca gggtcgcagg ggcaacgtgt attgggtgcg  20760
cgactcggtt agcggcctgc gcgtgcccgt gcgcacccgc cccccgcgca actagattgc  20820
aagaaaaaac tacttagact cgtactgttg tatgtatcca gcggcggcgg cgcgcaacga  20880
agctatgtcc aagcgcaaaa tcaaagaaga gatgctccag gtcatcgcgc cggagatcta  20940
tggccccccg aagaaggaag agcaggatta caagccccga aagctaaagc gggtcaaaaa  21000
gaaaaagaaa gatgatgatg atgaacttga cgacgaggtg gaactgctgc acgctaccgc  21060
gcccaggcga cgggtacagt ggaaaggtcg acgcgtaaaa cgtgttttgc gacccggcac  21120
caccgtagtc tttacgcccg gtgagcgctc caccctcacc tacaagcgcg tgtatgatga  21180
ggtgtacggc gacgaggacc tgcttgagca ggccaacgag cgcctcgggg agtttgccta  21240
cggaaagcgg cataaggaca tgctggcgtt gccgctggac gagggcaacc caacacctag  21300
cctaaagccc gtaacactgc agcaggtgct gcccgcgctt gcaccgtccg aagaaaagcg  21360
cggcctaaag cgcgagtctg gtgacttggc acccaccgtg cagctgatgg tacccaagcg  21420
ccagcgactg gaagatgtct tggaaaaaat gaccgtggaa cctgggctgg agcccgaggt  21480
ccgcgtgcgg ccaatcaagc aggtggcgcc gggactgggc gtgcagaccg tggacgttca  21540 gataccccact accagtagca ccagtattgc caccgccaca gagggcatgg agacacaaac  21600
gtccccggtt gcctcagcgg tggcggatgc cgcggtgcag gcggtcgctg cggccgcgtc  21660
caagacctct acggaggtgc aaacggaccc gtggatgttt cgcgtttcag cccccggcg   21720 cccgcgccgt tcgaggaagt acggcgccgc cagcgcgcta ctgcccgaat atgccctaca  21780
tccttccatt gcgcctaccc ccggctatcg tggctacacc taccgcccca gaagacgagc  21840
aactacccga cgccgaacca ccactggaac ccgccgccgc cgtcgccgtc gccagcccgt  21900
gctggccccg atttccgtgc gcaggtggc tcgcgaagga ggcaggaccc tggtgctgcc  21960
aacagcgcgc taccacccca gcatcgtta aaagccggtc tttgtggttc ttgcagatat  22020 ggcctcacc tgccgcctcc gtttcccggt gccgggattc cgaggaagaa tgcaccgtag  22080
gaggggcatg gccggccacg gcctgacggg cggcatgcgt cgtgcgcacc accggcggcg  22140
gcgcgcgtcg caccgtcgca tgcgcggcgg tatcctgccc ctccttattc cactgatcgc  22200
cgcggcgatt ggcgccgtgc ccggaattgc atccgtggcc ttgcaggcgc agagacactg  22260
attaaaaaca agttgcatgt ggaaaaatca aaataaaaag tctggactct cacgctcgct  22320
tggtcctgta actattttgt agaatggaag acatcaactt tgcgtctctg gccccgcgac  22380
acggctcgcg cccgttcatg ggaaactggc aagatatcgg caccagcaat atgagcggtg  22440
gcgccttcag ctggggctcg ctgtggagcg gcattaaaaa tttcggttcc accgttaaga  22500
actatggcag caaggcctgg aacagcagca caggccagat gctgagggat aagttgaaag  22560
agcaaaattt ccaacaaaag gtggtagatg gcctggcctc tggcattagc ggggtggtgg  22620
acctggccaa ccaggcagtg caaaataaga ttaacagtaa gcttgatccc cgccctcccg  22680
```

-continued

```
tagaggagcc tccaccggcc gtggagacag tgtctccaga ggggcgtggc gaaaagcgtc    22740
cgcgccccga cagggaagaa actctggtga cgcaaataga cgagcctccc tcgtacgagg    22800
aggcactaaa gcaaggcctg cccaccaccc gtcccatcgc gcccatggct accggagtgc    22860
tgggccagca cacacccgta acgctggacc tgcctccccc cgccgacacc cagcagaaac    22920
ctgtgctgcc aggcccgacc gccgttgttg taacccgtcc tagccgcgcg tccctgcgcc    22980
gcgccgccag cggtccgcga tcgttgcggc ccgtagccag tggcaactgg caaagcacac    23040
tgaacagcat cgtgggtctg ggggtgcaat ccctgaagcg ccgacgatgc ttctgatagc    23100
taacgtgtcg tatgtgtgtc atgtatgcgt ccatgtcgcc gccagaggag ctgctgagcc    23160
gccgcgcgcc cgctttccaa gatggctacc ccttcgatga tgccgcagtg gtcttacatg    23220
cacatctcgg gccaggacgc ctcggagtac ctgagccccg ggctggtgca gtttgcccgc    23280
gccaccgaga cgtacttcag cctgaataac aagtttagaa accccacggt ggcgcctacg    23340
cacgacgtga ccacagaccg gtcccagcgt ttgacgctgc ggttcatccc tgtggaccgt    23400
gaggatactg cgtactcgta caaggcgcgg ttcaccctag ctgtgggtga taaccgtgtg    23460
ctggacatgg cttccacgta ctttgacatc cgcggcgtgc tggacagggg ccctactttt    23520
aagccctact ctggcactgc ctacaacgcc ctggctccca agggtgcccc aaatccttgc    23580
gaatgggatg aagctgctac tgctcttgaa ataaacctag aagaagagga cgatgacaac    23640
gaagacgaag tagacgagca agctgagcag caaaaaactc acgtatttgg gcaggcgcct    23700
tattctggta taaatattac aaaggagggt attcaaatag gtgtcgaagg tcaaacacct    23760
aaatatgccg ataaaacatt tcaacctgaa cctcaaatag gagaatctca gtggtacgaa    23820
acagaaatta atcatgcagc tgggagagtc ctaaaaaaga ctaccccaat gaaaccatgt    23880
tacggttcat atgcaaaacc cacaaatgaa aatggagggc aaggcattct tgtaaagcaa    23940
caaaatggaa agctagaaag tcaagtggaa atgcaatttt tctcaactac tgaggcagcc    24000
gcaggcaatg gtgataactt gactcctaaa gtggtattgt acagtgaaga tgtagatata    24060
gaaaccccag acactcatat ttcttacatg cccactatta aggaaggtaa ctcacgagaa    24120
ctaatgggcc aacaatctat gcccaacagg cctaattaca ttgctttttag ggacaatttt    24180 attggtctaa tgtattacaa cagcacgggt aatatgggtg ttctggcggg ccaagcatcg    24240
cagttgaatg ctgttgtaga tttgcaagac agaaacacag agctttcata ccagcttttg    24300
cttgattcca ttggtgatag aaccaggtac ttttctatgt ggaatcaggc tgttgacagc    24360
tatgatccag atgttagaat tattgaaaat catggaactg aagatgaact tccaaattac    24420
tgctttccac tgggaggtgt gattaataca gagactctta ccaaggtaaa acctaaaaca    24480
ggtcaggaaa atggatggga aaaagatgct acagaatttt cagataaaaa tgaaataaga    24540
gttggaaata attttgccat ggaaatcaat ctaaatgcca acctgtggag aaatttcctg    24600
tactccaaca tagcgctgta tttgcccgac aagctaaagt acagtccttc caacgtaaaa    24660
atttctgata acccaaacac ctacgactac atgaacaagc gagtggtggc tcccgggcta    24720
gtggactgct acattaacct tggagcacgc tggtcccttg actatatgga caacgtcaac    24780
ccatttaacc accaccgcaa tgctggcctg cgctaccgct caatgttgct gggcaatggt    24840
cgctatgtgc ccttccacat ccaggtgcct cagaagttct ttgccattaa aaacctcctt    24900
ctcctgccgg gctcatacac ctacgagtgg aacttcagga aggatgttaa catggttctg    24960
cagagctccc taggaaatga cctaagggtt gacggagcca gcattaagtt tgatagcatt    25020
tgcctttacg ccaccttctt ccccatggcc cacaacaccg cctccacgct tgaggccatg    25080
```

-continued

```
cttagaaacg acaccaacga ccagtccttt aacgactatc tctccgccgc caacatgctc   25140
taccctatac ccgccaacgc taccaacgtg cccatatcca tcccctcccg caactgggcg   25200
gctttccgcg gctgggcctt cacgcgcctt aagactaagg aaaccccatc actgggctcg   25260
ggctacgacc cttattacac ctactctggc tctataccct acctagatgg aaccttttac   25320
ctcaaccaca cctttaagaa ggtggccatt acctttgact cttctgtcag ctggcctggc   25380
aatgaccgcc tgcttacccc caacgagttt gaaattaagc gctcagttga cggggagggt   25440
tacaacgttg cccagtgtaa catgaccaaa gactggttcc tggtacaaat gctagctaac   25500
tataacattg gctaccaggg cttctatatc ccagagagct acaaggaccg catgtactcc   25560
ttctttagaa acttccagcc catgagccgt caggtggtgg atgatactaa atacaaggac   25620
taccaacagg tgggcatcct acaccaacac aacaactctg gatttgttgg ctaccttgcc   25680
cccaccatgc gcgaaggaca ggcctaccct gctaacttcc cctatccgct tataggcaag   25740
accgcagttg acagcattac ccagaaaaag tttctttgcg atcgcaccct ttggcgcatc   25800
ccattctcca gtaactttat gtccatgggc gcactcacag acctgggcca aaaccttctc   25860
tacgccaact ccgcccacgc gctagacatg acttttgagg tggatcccat ggacgagccc   25920
acccttcttt atgttttgtt tgaagtcttt gacgtggtcc gtgtgcacca gccgcaccgc   25980
ggcgtcatcg aaaccgtgta cctgcgcacg cccttctcgg ccggcaacgc cacaacataa   26040
agaagcaagc aacatcaaca acagctgccg ccatgggctc cagtgagcag gaactgaaag   26100
ccattgtcaa agatcttggt tgtgggccat attttttggg cacctatgac aagcgctttc   26160
caggctttgt ttctccacac aagctcgcct gcgccatagt caatacggcc ggtcgcgaga   26220
ctgggggcgt acactggatg gcctttgcct ggaacccgca ctcaaaaaca tgctacctct   26280
ttgagccctt tggcttttct gaccagcgac tcaagcaggt ttaccagttt gagtacgagt   26340
cactcctgcg ccgtagcgcc attgcttctt cccccgaccg ctgtataacg ctggaaaagt   26400
ccacccaaag cgtacagggg cccaactcgg ccgcctgtgg actattctgc tgcatgtttc   26460
tccacgcctt tgccaactgg ccccaaactc ccatggatca caaccccacc atgaaccttc  26520
ttaccggggt acccaactcc atgctcaaca gtccccaggt acagcccacc ctgcgtcgca   26580
accaggaaca gctctacagc ttcctggagc gccactcgcc ctacttccgc agccacagtg   26640
cgcagattag gagcgccact tctttttgtc acttgaaaaa catgtaaaaa taatgtacta   26700
gagacacttt caataaaggc aaatgctttt atttgtacac tctcgggtga ttatttaccc   26760
ccacccttgc cgtctgcgcc gtttaaaaat caaaggggtt ctgccgcgca tcgctatgcg   26820
ccactggcag ggacacgttg cgatactggt gtttagtgct ccacttaaac tcaggcacaa   26880
ccatccgcgc cagctcggtg aagttttcac tccacaggct gcgcaccatc accaacgcgt   26940
ttagcaggtc gggcgccgat atcttgaagt cgcagttggg gcctccgccc tgcgcgcgcg   27000
agttgcgata cacagggttg cagcactgga acactatcag cgccgggtgg tgcacgctgg   27060
ccagcacgct cttgtcggag atcagatccg cgtccaggtc ctccgcgttg ctcagggcga   27120
acggagtcaa ctttggtagc tgccttccca aaaagggcgc gtgcccaggc tttgagttgc   27180
actcgcaccg tagtggcatc aaaaggtgac cgtgcccgt ctgggcgtta ggatacagcg   27240
cctgcataaa agccttgatc tgcttaaaag ccacctgagc ctttgcgcct tcagagaaga   27300
acatgccgca agacttgccg gaaaactgat tggccgacag gccgcgtcg tgcacgcagc   27360 accttgcgtc ggtgttggag atctgcacca catttcggcc ccaccggttc ttcacgatct   27420
```

-continued

```
tggccttgct agactgctcc ttcagcgcgc gctgcccgtt ttcgctcgtc acatccattt   27480
caatcacgtg ctccttattt atcataatgc ttccgtgtag acacttaagc tcgccttcga   27540
tctcagcgca gcggtgcagc cacaacgcgc agcccgtggg ctcgtgatgc ttgtaggtca   27600
cctctgcaaa cgactgcagg tacgcctgca ggaatcgccc catcatcgtc acaaaggtct   27660
tgttgctggt gaaggtcagc tgcaacccgc ggtgctcctc gttcagccag gtcttgcata   27720
cggccgccag agcttccact tggtcaggca gtagtttgaa gttcgccttt agatcgttat   27780
ccacgtggta cttgtccatc agcgcgcgcg cagcctccat gcccttctcc cacgcagaca   27840
cgatcggcac actcagcggg ttcatcaccg taatttcact ttccgcttcg ctgggctctt   27900
cctcttcctc ttgcgtccgc ataccacgcg ccactgggtc gtcttcattc agccgccgca   27960
ctgtgcgctt acctcctttg ccatgcttga ttagcaccgg tgggttgctg aaacccacca   28020
tttgtagcgc cacatcttct ctttcttcct cgctgtccac gattacctct ggtgatggcg   28080
ggcgctcggg cttgggagaa gggcgcttct ttttcttctt gggcgcaatg gccaaatccg   28140
ccgccgaggt cgatggccgc gggctgggtg tgcgcggcac cagcgcgtct tgtgatgagt   28200
cttcctcgtc ctcggactcg atacgccgcc tcatccgctt ttttgggggc gcccggggag   28260
gcggcggcga cggggacggg gacgacacgt cctccatggt tgggggacgt cgcgccgcac   28320
cgcgtccgcg ctcgggggtg gtttcgcgct gctcctcttc ccgactggcc atttccttct   28380
cctataggca gaaaaagatc atggagtcag tcgagaagaa ggacagccta accgccccct   28440
ctgagttcgc caccaccgcc tccaccgatg ccgccaacgc gcctaccacc ttccccgtcg   28500 aggcacccc gcttgaggag gaggaagtga ttatcgagca ggacccaggt tttgtaagcg   28560
aagacgacga ggaccgctca gtaccaacag aggataaaaa gcaagaccag gacaacgcag   28620
aggcaaacga ggaacaagtc gggcggggg acgaaaggca tggcgactac ctagatgtgg   28680
gagacgacgt gctgttgaag catctgcagc gccagtgcgc cattatctgc gacgcgttgc   28740
aagagcgcag cgatgtgccc ctcgccatag cggatgtcag ccttgcctac gaacgccacc   28800
tattctcacc gcgcgtaccc cccaaacgcc aagaaacgg cacatgcgag cccaacccgc   28860
gcctcaactt ctaccccgta tttgccgtgc cagaggtgct tgccacctat cacatctttt   28920
tccaaaactg caagataccc ctatcctgcc gtgccaaccg cagccgagcg gacaagcagc   28980
tggccttgcg gcagggcgct gtcatacctg atatcgcctc gctcaacgaa gtgccaaaaa   29040
tctttgaggg tcttggacgc gacgagaagc gcgcggcaaa cgctctgcaa caggaaaaca   29100
gcgaaaatga aagtcactct ggagtgttgg tggaactcga gggtgacaac gcgcgcctag   29160
ccgtactaaa acgcagcatc gaggtcaccc actttgccta cccggcactt aacctacccc   29220
ccaaggtcat gagcacagtc atgagtgagc tgatcgtgcg ccgtgcgcag cccctggaga   29280
gggatgcaaa tttgcaagaa caaacagagg agggcctacc cgcagttggc gacgagcagc   29340
tagcgcgctg gcttcaaacg cgcgagcctg ccgacttgga ggagcgacgc aaactaatga   29400
tggccgcagt gctcgttacc gtggagcttg agtgcatgca gcggttcttt gctgacccgg   29460
agatgcagcg caagctagag gaaacattgc actacacctt tcgacagggc tacgtacgcc   29520
aggcctgcaa gatctccaac gtggagctct gcaacctggt ctcctacctt ggaattttgc   29580
acgaaaaccg ccttgggcaa aacgtgcttc attccacgct caagggcgag gcgcgccgcg   29640
actacgtccg cgactgcgtt tacttatttc tatgctacac ctggcagacg gccatgggcg   29700
tttggcagca gtgcttggag gagtgcaacc tcaaggagct gcagaaactg ctaaagcaaa   29760
acttgaagga cctatggacg gccttcaacg agcgctccgt ggccgcgcac ctggcggaca   29820
```

```
tcattttccc cgaacgcctg cttaaaaccc tgcaacaggg tctgccagac ttcaccagtc   29880
aaagcatgtt gcagaacttt aggaacttta tcctagagcg ctcaggaatc ttgcccgcca   29940
cctgctgtgc acttcctagc gactttgtgc ccattaagta ccgcgaatgc cctccgccgc   30000
tttgggccca ctgctacctt ctgcagctag ccaactacct tgcctaccac tctgacataa   30060
tggaagacgt gagcggtgac ggtctactgg agtgtcactg tcgctgcaac ctatgcaccc   30120
cgcaccgctc cctggtttgc aattcgcagc tgcttaacga aagtcaaatt atcggtacct   30180
ttgagctgca gggtccctcg cctgacgaaa agtccgcggc tccggggttg aaactcactc   30240
cggggctgtg gacgtcggct taccttcgca aatttgtacc tgaggactac cacgcccacg   30300
agattaggtt ctacgaagac caatcccgcc cgcctaatgc ggagcttacc gcctgcgtca   30360
ttacccaggg ccacattctt ggccaattgc aagccatcaa caaagcccgc caagagtttc   30420
tgctacgaaa gggacggggg gtttacttgg accccagtc cggcgaggag ctcaacccaa   30480 tcccccgcc gccgcagccc tatcagcagc agccgcgggc ccttgcttcc caggatggca   30540
cccaaaaaga agctgcagct gccgccgcca cccacggacg aggaggaata ctgggacagt   30600
caggcagagg aggttttgga cgaggaggag gaggacatga tggaagactg ggagagccta   30660
gacgaggaag cttccgaggt cgaagaggtg tcagacgaaa caccgtcacc ctcggtcgca   30720
ttcccctcgc cggcgcccca gaaatcggca accggttcca gcatggctac aacctccgct   30780
cctcaggcgc cgccggcact gcccgttcgc cgacccaacc gtagatggga caccactgga   30840
accagggccg gtaagtccaa gcagccgccg ccgttagccc aagagcaaca acagcgccaa   30900
ggctaccgct catggcgcgg gcacaagaac gccatagttg cttgcttgca agactgtggg   30960
ggcaacatct ccttcgcccg ccgctttctt ctctaccatc acggcgtggc cttcccccgt   31020
aacatcctgc attactaccg tcatctctac agcccatact gcaccggcgg cagcggcagc   31080
aacagcagcg gccacacaga agcaaaggcg accggatagc aagactctga caaagcccaa   31140
gaaatccaca gcggcggcag cagcaggagg aggagcgctg cgtctggcgc ccaacgaacc   31200
cgtatcgacc cgccgagctta gaaacaggat ttttcccact ctgtatgcta tatttcaaca   31260
gagcaggggc caagaacaag agctgaaaat aaaaaacagg tctctgcgat ccctcacccg   31320
cagctgcctg tatcacaaaa gcgaagatca gcttcggcgc acgctggaag acgcggaggc   31380
tctcttcagt aaatactgcg cgctgactct taaggactag tttcgcgccc tttctcaaat   31440
ttaagcgcga aaactacgtc atctccagcg gccacacccg gcgccagcac ctgttgtcag   31500
cgccattatg agcaaggaaa ttcccacgcc ctacatgtgg agttaccagc cacaaatggg   31560
acttgcggct ggagctgccc aagactactc aacccgaata aactacatga gcgcgggacc   31620
ccacatgata tcccgggtca acggaatacg cgccaccga aaccgaattc tcctggaaca   31680
ggcggctatt accaccacac ctcgtaataa ccttaatccc cgtagttggc ccgctgccct   31740
ggtgtaccag gaaagtcccg ctcccaccac tgtggtactt cccagagacg cccaggccga   31800
agttcagatg actaactcag gggcgcagct tgcgggcggc tttcgtcaca gggtgcggtc   31860
gcccgggcag ggtataactc acctgacaat cagagggcga ggtattcagc tcaacgacga   31920
gtcggtgagc tcctcgcttg gtctccgtcc ggacgggaca tttcagatcg gcggcgccgg   31980
ccgctcttca ttcacgcctc gtcaggcaat cctaactctg cagacctcgt cctctgagcc   32040
gcgctctgga ggcattggaa ctctgcaatt tattgaggag tttgtgccat cggtctactt   32100
taaccccttc tcgggacctc ccggccacta tccggatcaa tttattccta actttgacgc   32160
```

-continued

```
ggtaaaggac tcggcggacg gctacgactg aatgttaagt ggagaggcag agcaactgcg    32220
cctgaaacac ctggtccact gtcgccgcca caagtgcttt gcccgcgact ccggtgagtt    32280
ttgctacttt gaattgcccg aggatcatat cgagggcccg gcgcacggcg tccggcttac    32340
cgcccaggga gagcttgccc gtagcctgat tcgggagttt acccagcgcc ccctgctagt    32400
tgagcgggac aggggaccct gtgttctcac tgtgatttgc aactgtccta accctggatt    32460
acatcaagat cctctagtta atgtcaggtc gcctaagtcg attaactaga gtacccgggg    32520
atcttattcc ctttaactaa taaaaaaaaa taataaagca tcacttactt aaaatcagtt    32580
agcaaatttc tgtccagttt attcagcagc acctccttgc cctcctccca gctctggtat    32640
tgcagcttcc tcctggctgc aaactttctc cacaatctaa atggaatgtc agtttcctcc    32700
tgttcctgtc catccgcacc cactatcttc atgttgttgc agatgaagcg cgcaagaccg    32760
tctgaagata ccttcaaccc cgtgtatcca tatgacacgg aaaccggtcc tccaactgtg    32820
ccttttctta ctcctccctt tgtatccccc aatgggtttc aagagagtcc ccctggggta    32880
ctctctttgc gcctatccga acctctagtt acctccaatg gcatgcttgc gctcaaaatg    32940
ggcaacggcc tctctctgga cgaggccggc aaccttacct cccaaaatgt aaccactgtg    33000
agcccacctc tcaaaaaaac caagtcaaac ataaacctgg aaatatctgc acccctcaca    33060
gttacctcag aagccctaac tgtggctgcc gccgcacctc taatggtcgc gggcaacaca    33120
ctcaccatgc aatcacaggc cccgctaacc gtgcacgact ccaaacttag cattgccacc    33180
caaggacccc tcacagtgtc agaaggaaag ctagccctgc aaacatcagg ccccctcacc    33240
accaccgata gcagtaccct tactatcact gcctcacccc ctctaactac tgccactggt    33300
agcttgggca ttgacttgaa agagcccatt tatacacaaa atggaaaact aggactaaag    33360 tacgggggctc ctttgcatgt aacagacgac ctaaacactt tgaccgtagc aactggtcca    33420
ggtgtgacta ttaataatac ttccttgcaa actaaagtta ctggagcctt gggttttgat    33480
tcacaaggca atatgcaact taatgtagca ggaggactaa ggattgattc tcaaaacaga    33540
cgccttatac ttgatgttag ttatccgttt gatgctcaaa accaactaaa tctaagacta    33600 ggacagggc ctcttttttat aaactcagcc cacaacttgg atattaacta caacaaaggc    33660
ctttacttgt ttacagcttc aaacaattcc aaaaagcttg aggttaacct aagcactgcc    33720
aaggggttga tgtttgacgc tacagccata gccattaatg caggagatgg gcttgaattt    33780
ggttcaccta atgcaccaaa cacaaatccc ctcaaaacaa aaattggcca tggcctagaa    33840
tttgattcaa acaaggctat ggttcctaaa ctaggaactg gccttagttt tgacagcaca    33900
ggtgccatta cagtaggaaa caaaaataat gataagctaa ctttgtggac cggaataaac    33960
cctccaccta actgtcaaat tgtggaaaac actaatacaa atgatggcaa acttactttta    34020 gtattagtaa aaaatggagg gcttgttaat ggctacgtgt ctctagttgg tgtatcagac    34080
actgtgaacc aaatgttcac acaaaagaca gcaaacatcc aattaagatt atattttgac    34140
tcttctggaa atctattaac tgaggaatca gacttaaaaa ttccacttaa aaataaatct    34200
tctacagcga ccagtgaaac tgtagccagc agcaaagcct ttatgccaag tactacagct    34260 tatccttca acaccactac tagggatagt gaaaactaca ttcatggaat atgttactac    34320
atgactagtt atgatagaag tctatttccc ttgaacattt ctataatgct aaacagccgt    34380
atgatttctt ccaatgttgc ctatgccata caatttgaat ggaatctaaa tgcaagtgaa    34440 tctcagaaa gcaacatagc tacgctgacc acatcccccct ttttcttttc ttacattaca    34500
gaagacgaca actaaagaat cgtttgtgtt atgtttcaac gtgtttattt ttcaattgca    34560
```

-continued

```
gaaaatttca agtcattttt cattcagtag tatagcccca ccaccacata gcttatacag    34620
atcaccgtac cttaatcaaa ctcacagaac cctagtattc aacctgccac ctccctccca    34680
acacacagag tacacagtcc tttctccccg gctggcctta aaaagcatca tatcatgggt    34740
aacagacata ttcttaggtg ttatattcca cacggtttcc tgtcgagcca aacgctcatc    34800
agtgatatta ataaactccc cgggcagctc acttaagttc atgtcgctgt ccagctgctg    34860
agccacaggc tgctgtccaa cttgcggttg cttaacgggc ggcgaaggag aagtccacgc    34920
ctacatgggg gtagagtcat aatcgtgcat caggatagggg cggtggtgct gcagcagcgc    34980
gcgaataaac tgctgccgcc gccgctccgt cctgcaggaa tacaacatgg cagtggtctc    35040
ctcagcgatg attcgcaccg cccgcagcat aaggcgcctt gtcctccggg cacagcagcg    35100
caccctgatc tcacttaaat cagcacagta actgcagcac agcaccacaa tattgttcaa    35160
aatcccacag tgcaaggcgc tgtatccaaa gctcatggcg gggaccacag aacccacgtg    35220
gccatcatac cacaagcgca ggtagattaa gtggcgaccc ctcataaaca cgctggacat    35280
aaacattacc tcttttggca tgttgtaatt caccacctcc cggtaccata taaacctctg    35340
attaaacatg gcgccatcca ccaccatcct aaaccagctg gccaaaacct gcccgccggc    35400
tatacactgc agggaaccgg gactggaaca atgacagtgg agagcccagg actcgtaacc    35460
atggatcatc atgctcgtca tgatatcaat gttggcacaa cacaggcaca cgtgcataca    35520
cttcctcagg attacaagct cctcccgcgt tagaaccata tcccagggaa caacccattc    35580
ctgaatcagc gtaaatccca cactgcaggg aagacctcgc acgtaactca cgttgtgcat    35640
tgtcaaagtg ttacattcgg gcagcagcgg atgatcctcc agtatggtag cgcgggtttc    35700
tgtctcaaaa ggaggtagac gatccctact gtacggagtg cgccgagaca accgagatcg    35760
tgttggtcgt agtgtcatgc caaatggaac gccggacgta gtcatatttc ctgaagcaaa    35820
accaggtgcg ggcgtgacaa acagatctgc gtctccggtc tcgccgctta gatcgctctg    35880
tgtagtagtt gtagtatatc cactctctca aagcatccag gcgcccctg gcttcgggtt    35940 ctatgtaaac tccttcatgc gccgctgccc tgataacatc caccaccgca gaataagcca    36000
cacccagcca acctacacat tcgttctgcg agtcacacac gggaggagcg ggaagagctg    36060
gaagaaccat gttttttttt ttattccaaa agattatcca aaacctcaaa atgaagatct    36120
attaagtgaa cgcgctcccc tccggtggcg tggtcaaact ctacagccaa agaacagata    36180
atggcatttg taagatgttg cacaatggct tccaaaaggc aaacggccct cacgtccaag    36240
tggacgtaaa ggctaaaccc ttcagggtga atctcctcta taaacattcc agcaccttca    36300
accatgccca aataattctc atctcgccac cttctcaata tatctctaag caaatcccga    36360
atattaagtc cggccattgt aaaaatctgc tccagagcgc cctccacctt cagcctcaag    36420
cagcgaatca tgattgcaaa aattcaggtt cctcacagac ctgtataaga ttcaaaagcg    36480
gaacattaac aaaaataccg cgatcccgta ggtcccttcg cagggccagc tgaacataat    36540
cgtgcaggtc tgcacggacc agcgcggcca cttccccgcc aggaaccatg acaaaagaac    36600
ccacactgat tatgacacgc atactcggag ctatgctaac cagcgtagcc ccgatgtaag    36660
cttgttgcat gggcggcgat ataaaatgca aggtgctgct caaaaaatca ggcaaagcct    36720
cgcgcaaaaa agaaagcaca tcgtagtcat gctcatgcag ataaaggcag gtaagctccg    36780
gaaccaccac agaaaaagac accatttttc tctcaaacat gtctgcgggt ttctgcataa    36840
acacaaaata aaataacaaa aaaacattta aacattagaa gcctgtctta caacaggaaa    36900
```

-continued

```
aacaacccct ataagcataa gacggactac ggccatgccg gcgtgaccgt aaaaaaactg    36960
gtcaccgtga ttaaaaagca ccaccgacag ctcctcggtc atgtccggag tcataatgta    37020
agactcggta aacacatcag gttgattcac atcggtcagt gctaaaaagc gaccgaaata    37080
gcccggggga atacataccc gcaggcgtag agacaacatt acagccccca taggaggtat    37140
aacaaaatta ataggagaga aaaacacata aacacctgaa aaaccctcct gcctaggcaa    37200
aatagcaccc tcccgctcca gaacaacata cagcgcttcc acagcggcag ccataacagt    37260
cagccttacc agtaaaaaag aaaacctatt aaaaaaacac cactcgacac ggcaccagct    37320
caatcagtca cagtgtaaaa aagggccaag tgcagagcga gtatatatag gactaaaaaa    37380
tgacgtaacg gttaaagtcc acaaaaaaca cccagaaaac cgcacgcgaa cctacgccca    37440
gaaacgaaag ccaaaaaacc cacaacttcc tcaaatcgtc acttccgttt tcccacgtta    37500
cgtcacttcc cattttaaga aaactacaat tcccaacaca tacaagttac tccgccctaa    37560
aacctacgtc acccgccccg ttcccacgcc ccgcgccacg tcacaaactc caccccctca    37620
ttatcatatt ggcttcaatc caaaataagg tatattattg atgatg              37666
```

<210> SEQ ID NO 25
<211> LENGTH: 34727
<212> TYPE: DNA
<213> ORGANISM: Artificial Sequence
<220> FEATURE:
<223> OTHER INFORMATION: #2 vector

<400> SEQUENCE: 25

```
catcatcaat aatatacctt attttggatt gaagccaata tgataatgag ggggtggagt      60
ttgtgacgtg gcgcggggcg tgggaacggg gcgggtgacg tagtagtgtg gcggaagtgt     120
gatgttgcaa gtgtggcgga acacatgtaa gcgacggatg tggcaaaagt gacgtttttg     180
gtgtgcgccg gtgtacacag gaagtgacaa ttttcgcgcg gttttaggcg gatgttgtag     240
taaatttggg cgtaaccgag taagatttgg ccatttttcgc gggaaaactg aataagagga     300
agtgaaatct gaataatttt gtgttactca tagcgcgtaa tactgtaata gtaatcaatt     360
acggggtcat tagttcatag cccatatatg gagttccgcg ttacataact tacggtaaat     420
ggcccgcctg gctgaccgcc caacgacccc cgcccattga cgtcaataat gacgtatgtt     480
cccatagtaa cgccaatagg gactttccat tgacgtcaat gggtggagta tttacggtaa     540
actgcccact tggcagtaca tcaagtgtat catatgccaa gtacgccccc tattgacgtc     600
aatgacggta aatggcccgc ctggcattat gcccagtaca tgaccttatg gactttcct     660 acttggcagt acatctacgt attagtcatc gctattacca tggtgatgcg gttttggcag     720
tacatcaatg ggcgtggata gcggtttgac tcacggggat ttccaagtct ccacccccatt     780 gacgtcaatg ggagtttgtt ttggcaccaa aatcaacggg actttccaaa atgtcgtaac     840
aactccgccc cattgacgca aatgggcggt aggcgtgtac ggtgggaggt ctatataagc     900
agagctctcc ctatcagtga tagagatctc cctatcagtg atagagatcg tcgacgagct     960
cgtttagtga accgtcagat cgcctggaga cgccatccac gctgttttga cctccataga    1020
agacaccggg accgatccag cctccgattt gccaccatgt tgtgttcct ggtgctgctg    1080 ccactggtgt ccagccagtg tgtgaacctg accaccagga cccaacttcc tcctgcctac    1140
accaactcct tcaccagggg agtctactac cctgacaagg tgttcaggtc ctctgtgctg    1200
cacagcaccc aggacctgtt cctgccattc ttcagcaatg tgacctggtt ccatgccatc    1260
catgtgtctg gcaccaatgg caccaagagg tttgacaacc ctgtgctgcc attcaatgat    1320
```

```
ggagtctact ttgccagcac agagaagagc aacatcatca ggggctggat ttttggcacc    1380
accctggaca gcaagaccca gtccctgctg attgtgaaca atgccaccaa tgtggtgatt    1440
aaggtgtgtg agttccagtt ctgtaatgac ccattcctgg gagtctacta ccacaagaac    1500
aacaagtcct ggatggagtc tgagttcagg gtctactcct ctgccaacaa ctgtaccttt    1560
gaatatgtga gccaaccatt cctgatggac ttggagggca agcagggcaa cttcaagaac    1620
ctgagggagt ttgtgttcaa gaacattgat ggctacttca agatttacag caaacacaca    1680
ccaatcaacc tggtgaggga cctgccacag ggcttctctg ccttggaacc actggtggac    1740
ctgccaattg gcatcaacat caccaggttc cagaccctgc tggctctgca caggtcctac    1800
ctgacacctg agactcctc ctctggctgg acagcaggag cagcagccta ctatgtgggc    1860
tacctccaac caaggacctt cctgctgaaa tacaatgaga atggcaccat cacagatgct    1920
gtggactgtg ccctggaccc actgtctgag accaagtgta ccctgaaatc cttcacagtg    1980
gagaagggca tctaccagac cagcaacttc agggtccaac caacagagag cattgtgagg    2040
tttccaaaca tcaccaacct gtgtccattt ggagaggtgt tcaatgccac caggtttgcc    2100
tctgtctatg cctggaacag gaagaggatt agcaactgtg tggctgacta ctctgtgctc    2160
tacaactctg cctccttcag caccttcaag tgttatggag tgagcccaac caaactgaat    2220
gacctgtgtt tcaccaatgt ctatgctgac tcctttgtga ttaggggaga tgaggtgaga    2280
cagattgccc ctggacaaac aggcaagatt gctgactaca actacaaact gcctgatgac    2340
ttcacaggct gtgtgattgc ctggaacagc aacaacctgg acagcaaggt gggaggcaac    2400
tacaactacc tctacagact gttcaggaag agcaacctga aaccatttga gagggacatc    2460
agcacagaga tttaccaggc tggcagcaca ccatgtaatg gagtggaggg cttcaactgt    2520
tactttccac tccaatccta tggcttccaa ccaaccaatg gagtgggcta ccaaccatac    2580
agggtggtgg tgctgtcctt tgaactgctc catgccctg ccacagtgtg tggaccaaag    2640
aagagcacca acctggtgaa gaacaagtgt gtgaacttca acttcaatgg actgacaggc    2700
acaggagtgc tgacagagag caacaagaag ttcctgccat tccaacagtt tggcagggac    2760
attgctgaca ccacagatgc tgtgagggac ccacagacct tggagattct ggacatcaca    2820
ccatgttcct ttggaggagt gtctgtgatt acacctggca ccaacaccag caaccaggtg    2880
gctgtgctct accaggatgt gaactgtact gaggtgcctg tggctatcca tgctgaccaa    2940
cttacaccaa cctggagggt ctacagcaca ggcagcaatg tgttccagac cagggctggc    3000
tgtctgattg gagcagagca tgtgaacaac tcctatgagt gtgacatccc aattggagca    3060
ggcatctgtg cctcctacca gacccagacc atcctcaggt ctgtggcaag ccagagcatc    3120
attgcctaca caatgagtct gggagcagag aactctgtgg cttacagcaa caacagcatt    3180
gccatcccaa ccaacttcac catctctgtg accacagaga ttctgcctgt gagtatgacc    3240
aagacctctg tggactgtac aatgtatatc tgtggagaca gcacagagtg tagcaacctg    3300
ctgctccaat atggctcctt ctgtacccaa cttaacaggg ctctgacagg cattgctgtg    3360
gaacaggaca gaacaccca ggaggtgttt gcccaggtga agcagattta caagacacct    3420
ccaatcaagg actttggagg cttcaacttc agccagattc tgcctgaccc aagcaagcca    3480
agcaagaggt ccttcattga ggacctgctg ttcaacaagg tgaccctggc tgatgctggc    3540
ttcatcaagc aatatggaga ctgtctggga gacattgctg ccaggaccct gatttgtgcc    3600
cagaagttca atggactgac agtgctgcct ccactgctga cagatgagat gattgcccaa    3660
```

-continued

```
tacacctctg ccctgctggc tggcaccatc acctctggct ggacctttgg agcaggagca      3720
gccctccaaa tcccatttgc tatgcagatg gcttacaggt tcaatggcat tggagtgacc      3780
cagaatgtgc tctatgagaa ccagaaactg attgccaacc agttcaactc tgccattggc      3840
aagattcagg actccctgtc cagcacagcc tctgccctgg gcaaactcca agatgtggtg      3900
aaccagaatg cccaggctct gaacaccctg gtgaagcaac tttccagcaa ctttggagcc      3960
atctcctctg tgctgaatga catcctgagc agactggaca aggtggaggc tgaggtccag      4020
attgacagac tgattacagg cagactccaa tccctccaaa cctatgtgac ccaacaactt      4080
atcagggctg ctgagattag ggcatctgcc aacctggctg ccaccaagat gagtgagtgt      4140
gtgctgggac aaagcaagag ggtggacttc tgtggcaagg ctaccacct gatgagtttt      4200 ccacagtctg cccctcatgg agtggtgttc ctgcatgtga cctatgtgcc tgcccaggag      4260
aagaacttca ccacagcccc tgccatctgc catgatggca aggctcactt tccaagggag      4320
ggagtgtttg tgagcaatgg cacccactgg tttgtgaccc agaggaactt ctatgaacca      4380
cagattatca ccacagacaa cacctttgtg tctggcaact gtgatgtggt gattggcatt      4440
gtgaacaaca cagtctatga cccactccaa cctgaactgg actccttcaa ggaggaactg      4500
gacaaatact tcaagaacca caccagccct gatgtggacc tgggagacat ctctggcatc      4560
aatgcctctg tggtgaacat ccagaaggag attgacagac tgaatgaggt ggctaagaac      4620
ctgaatgagt ccctgattga cctccaagaa ctgggcaaat atgaacaata catcaagtgg      4680
ccatgaaaat tgatcataat cagccatacc acatttgtag aggtttttact tgctttaaaa      4740 aacctcccac acctccccct gaacctgaaa cataaaatga atgcaattgt tgttgttaac      4800
ttgtttattg cagcttataa tggttacaaa taaagcaata gcatcacaaa tttcacaaat      4860
aaagcatttt tttcactgca ttctagttgt ggtttgtcca aactcatcaa tgtatcttaa      4920
cgcggatctg ggcgtggtta agggtgggaa agaatatata aggtgggggt cttatgtagt      4980
tttgtatctg ttttgcagca gccgccgccg ccatgagcac caactcgttt gatggaagca      5040
ttgtgagctc atatttgaca acgcgcatgc ccccatgggc cggggtgcgt cagaatgtga      5100
tgggctccag cattgatggt cgccccgtcc tgcccgcaaa ctctactacc ttgacctacg      5160
agaccgtgtc tggaacgccg ttggagactg cagcctccgc cgccgcttca gccgctgcag      5220
ccaccgcccg cgggattgtg actgactttg cttttcctgag cccgcttgca agcagtgcag      5280
cttcccgttc atccgcccgc gatgacaagt tgacggctct tttggcacaa ttggattctt      5340
tgacccggga acttaatgtc gtttctcagc agctgttgga tctgcgccag caggtttctg      5400
ccctgaaggc ttcctcccct cccaatgcgg tttaaaacat aaataaaaaa ccagactctg      5460
tttggatttg gatcaagcaa gtgtcttgct gtctttattt aggggtttttg cgcgcgcggt      5520 aggcccggga ccagcggtct cggtcgttga gggtcctgtg tatttttttcc aggacgtggt      5580 aaaggtgact ctggatgttc agatacatgg gcataagccc gtctctgggg tggaggtagc      5640
accactgcag agcttcatgc tgcggggtgg tgttgtagat gatccagtcg tagcaggagc      5700
gctgggcgtg gtgcctaaaa atgtctttca gtagcaagct gattgccagg ggcaggccct      5760
tggtgtaagt gtttacaaag cggttaagct gggatgggtg catacgtggg gatatgagat      5820
gcatcttgga ctgtattttt aggttggcta tgttcccagc catatccctc cggggattca      5880
tgttgtgcag aaccaccagc acagtgtatc cggtgcactt gggaaatttg tcatgtagct      5940
tagaaggaaa tgcgtggaag aacttggaga cgcccttgtg acctccaaga ttttccatgc      6000
attcgtccat aatgatggca atgggcccac gggcggcggc ctgggcgaag atatttctgg      6060
```

-continued

```
gatcactaac gtcatagttg tgttccagga tgagatcgtc ataggccatt tttacaaagc    6120
gcgggcggag ggtgccagac tgcggtataa tggttccatc cggcccaggg gcgtagttac    6180
cctcacagat ttgcatttcc cacgctttga gttcagatgg ggggatcatg tctacctgcg    6240
gggcgatgaa gaaaacggtt tccggggtag gggagatcag ctgggaagaa agcaggttcc    6300
tgagcagctg cgacttaccg cagccggtgg gcccgtaaat cacacctatt accggctgca    6360
actggtagtt aagagagctg cagctgccgt catccctgag cagggggggcc acttcgttaa    6420 gcatgtccct gactcgcatg ttttccctga ccaaatccgc cagaaggcgc tcgccgccca    6480
gcgatagcag ttcttgcaag gaagcaaagt ttttcaacgg tttgagaccg tccgccgtag    6540
gcatgctttt gagcgtttga ccaagcagtt ccaggcggtc ccacagctcg gtcacctgct    6600
ctacggcatc tcgatccagc atatctcctc gtttcgcggg ttggggcggc tttcgctgta    6660
cggcagtagt cggtgctcgt ccagacgggc caggtcatg tctttccacg ggcgcagggt     6720
cctcgtcagc gtagtctggg tcacggtgaa ggggtgcgct ccgggctgcg cgctggccag    6780
ggtgcgcttg aggctggtcc tgctggtgct gaagcgctgc cggtcttcgc cctgcgcgtc    6840
ggccaggtag catttgacca tggtgtcata gtccagcccc tccgcggcgt ggcccttggc    6900
gcgcagcttg cccttggagg aggcgccgca cgaggggcag tgcagacttt tgagggcgta    6960
gagcttgggc gcgagaaata ccgattccgg ggagtaggca tccgcgccgc aggccccgca    7020
gacggtctcg cattccacga gccaggtgag ctctggccgt tcgggtcaa aaaccaggtt     7080 tcccccatgc tttttgatgc gtttcttacc tctggtttcc atgagccggt gtccacgctc    7140
ggtgacgaaa aggctgtccg tgtccccgta tacagacttg agaggcctgt cctcgagcgg    7200
tgttccgcgg tcctcctcgt atagaaactc ggaccactct gagacaaagg ctcgcgtcca    7260
ggccagcacg aaggaggcta agtgggaggg gtagcggtcg ttgtccacta gggggtccac    7320
tcgctccagg gtgtgaagac acatgtcgcc ctcttcggca tcaaggaagg tgattggttt    7380
gtaggtgtag gccacgtgac cgggtgttcc tgaagggggg ctataaaagg gggtgggggc    7440
gcgttcgtcc tcactctctt ccgcatcgct gtctgcgagg gccagctgtt ggggtgagta    7500
ctccctctga aaagcgggca tgacttctgc gctaagattg tcagtttcca aaaacgagga    7560
ggatttgata ttcacctggc ccgcggtgat gcctttgagg gtggccgcat ccatctggtc    7620
agaaaagaca atcttttttgt tgtcaagctt ggtggcaaac gacccgtaga gggcgttgga    7680
cagcaacttg gcgatggagc gcagggtttg gtttttgtcg cgatcggcgc gctccttggc    7740
cgcgatgttt agctgcacgt attcgcgcgc aacgcaccgc cattcgggaa agacggtggt    7800
gcgctcgtcg ggcaccaggt gcacgcgcca accgcggttg tgcagggtga caaggtcaac    7860
gctggtggct acctctccgc gtaggcgctc gttggtccag cagaggcggc cgcccttgcg    7920
cgagcagaat ggcggtaggg ggtctagctg cgtctcgtcc ggggggtctg cgtccacggt    7980
aaagaccccg ggcagcaggc gcgcgtcgaa gtagtctatc ttgcatcctt gcaagtctag    8040
cgcctgctgc catgcgcggg cggcaagcgc gcgctcgtat gggttgagtg ggggacccca    8100
tggcatgggg tgggtgagcg cggaggcgta catgccgcaa atgtcgtaaa cgtagagggg    8160
ctctctgagt attccaagat atgtaggggta gcatcttcca ccgcggatgc tggcgcgcac    8220
gtaatcgtat agttcgtgcg agggagcgag gaggtcggga ccgaggttgc tacgggcggg    8280
ctgctctgct cggaagacta tctgcctgaa gatggcatgt gagttggatg atatggttgg    8340
acgctggaag acgttgaagc tggcgtctgt gagacctacc gcgtcacgca cgaaggaggc    8400
```

-continued

```
gtaggagtcg cgcagcttgt tgaccagctc ggcggtgacc tgcacgtcta gggcgcagta   8460
gtccagggtt tccttgatga tgtcatactt atcctgtccc tttttttttcc acagctcgcg   8520 gttgaggaca aactcttcgc ggtctttcca gtactcttgg atcggaaacc cgtcggcctc   8580
cgaacggtaa gagcctagca tgtagaactg gttgacggcc tggtaggcgc agcatccctt   8640
ttctacgggt agcgcgtatg cctgcgcggc cttccggagc gaggtgtggg tgagcgcaaa   8700
ggtgtccctg accatgactt tgaggtactg gtatttgaag tcagtgtcgt cgcatccgcc   8760
ctgctcccag agcaaaaagt ccgtgcgctt tttggaacgc ggatttggca gggcgaaggt   8820
gacatcgttg aagagtatct ttcccgcgcg aggcataaag ttgcgtgtga tgcggaaggg   8880
tcccggcacc tcggaacggt tgttaattac ctgggcggcg agcacgatct cgtcaaagcc   8940
gttgatgttg tggcccacaa tgtaaagttc caagaagcgc gggatgccct tgatggaagg   9000 caattttttta agttcctcgt aggtgagctc ttcaggggag ctgagcccgt gctctgaaag   9060
ggcccagtct gcaagatgag ggttggaagc gacgaatgag ctccacaggt cacgggccat   9120
tagcatttgc aggtggtcgc gaaaggtcct aaactggcga cctatggcca tttttctgg   9180 ggtgatgcag tagaaggtaa gcgggtcttg ttcccagcgg tcccatccaa ggttcgcggc   9240
taggtctcgc gcggcagtca ctagaggctc atctccgccg aacttcatga ccagcatgaa   9300
gggcacgagc tgcttcccaa aggcccccat ccaagtatag gtctctacat cgtaggtgac   9360
aaagagacgc tcggtgcgag gatgcgagcc gatcgggaag aactggatct cccgccacca   9420
attggaggag tggctattga tgtggtgaaa gtagaagtcc ctgcgacggg ccgaacactc   9480
gtgctggctt ttgtaaaaac gtgcgcagta ctggcagcgg tgcacgggct gtacatcctg   9540
cacgaggttg acctgacgac cgcgcacaag gaagcagagt gggaatttga gccctcgcc   9600 tggcgggttt ggctggtggt cttctacttc ggctgcttgt ccttgaccgt ctggctgctc   9660
gaggggagtt acggtggatc ggaccaccac gccgcgcgag cccaaagtcc agatgtccgc   9720
gcgcggcggc cggagcttga tgacaacatc gcgcagatgg gagctgtcca tggtctggag   9780
ctcccgcggc gtcaggtcag gcgggagctc ctgcaggttt acctcgcata gacgggtcag   9840
ggcgcgggct agatccaggt gatacctaat ttccaggggc tggttggtgg cggcgtcgat   9900
ggcttgcaag aggccgcatc cccgcggcgc gactacggta ccgcgcggcg ggcggtgggc   9960
cgcgggggtg tccttggatg atgcatctaa aagcggtgac gcgggcgagc ccccggaggt   10020
agggggggct ccggacccgc cgggagaggg ggcaggggca cgtcggcgcc gcgcgcgggc   10080
aggagctggt gctgcgcgcg taggttgctg gcgaacgcga cgacgcggcg gttgatctcc   10140
tgaatctggc gcctctgcgt gaagacgacg ggcccggtga gcttgaacct gaaagagagt   10200
tcgacagaat caatttcggt gtcgttgacg gcggcctggc gcaaaatctc ctgcacgtct   10260
cctgagttgt cttgataggc gatctcggcc atgaactgct cgatctcttc ctcctggaga   10320
tctccgcgtc cggctcgctc cacggtggcg gcgaggtcgt tggaaatgcg ggccatgagc   10380
tgcgagaagg cgttgaggcc tccctcgttc cagacgcggc tgtagaccac gcccccttcg   10440
gcatcgcggg cgcgcatgac cacctgcgcg agattgagct ccacgtgccg ggcgaagacg   10500
gcgtagtttc gcaggcgctg aaagaggtag ttgaggtgg tggcggtgtg ttctgccacg   10560
aagaagtaca taacccagcg tcgcaacgtg gattcgttga tatcccccaa ggcctcaagg   10620
cgctccatgg cctcgtagaa gtccacggcg aagttgaaaa actgggagtt gcgcgccgac   10680
acggttaact cctcctccag aagacggatg agctcggcga cagtgtcgcg cacctcgcgc   10740
tcaaaggcta caggggcctc ttcttcttct tcaatctcct cttccataag ggcctcccct   10800
```

```
tcttcttctt ctggcggcgg tgggggaggg gggacacggc ggcgacgacg gcgcaccggg    10860
aggcggtcga caaagcgctc gatcatctcc ccgcggcgac ggcgcatggt ctcggtgacg    10920
gcgcggccgt tctcgcgggg gcgcagttgg aagacgccgc ccgtcatgtc ccggttatgg    10980
gttggcgggg ggctgccatg cggcaggat acggcgctaa cgatgcatct caacaattgt     11040
tgtgtaggta ctccgccgcc gagggacctg agcgagtccg catcgaccgg atcggaaaac    11100
ctctcgagaa aggcgtctaa ccagtcacag tcgcaaggta ggctgagcac cgtggcgggc    11160
ggcagcgggc ggcggtcggg gttgtttctg gcggaggtgc tgctgatgat gtaattaaag    11220
taggcggtct tgagacggcg gatggtcgac agaagcacca tgtccttggg tccggcctgc    11280
tgaatgcgca ggcggtcggc catgccccag gcttcgtttt gacatcggcg caggtctttg    11340
tagtagtctt gcatgagcct ttctaccggc acttcttctt ctccttcctc ttgtcctgca    11400
tctcttgcat ctatcgctgc ggcggcggcg gagtttggcc gtaggtggcg ccctcttcct    11460
cccatgcgtg tgaccccgaa gcccctcatc ggctgaagca gggctaggtc ggcgacaacg    11520
cgctcggcta atatggcctg ctgcacctgc gtgagggtag actggaagtc atccatgtcc    11580
acaaagcggt ggtatgcgcc cgtgttgatg gtgtaagtgc agttggccat aacggaccag    11640
ttaacggtct ggtgacccgg ctgcgagagc tcggtgtacc tgagacgcga gtaagccctc    11700
gagtcaaata cgtagtcgtt gcaagtccgc accaggtact ggtatcccac caaaaagtgc    11760
ggcggcggct ggcggtagag gggccagcgt agggtggccg gggctccggg ggcgagatct    11820
tccaacataa ggcgatgata tccgtagatg tacctggaca tccaggtgat gccggcggcg    11880
gtggtggagg cgcgcggaaa gtcgcggacg cggttccaga tgttgcgcag cggcaaaaag    11940
tgctccatgg tcgggacgct ctggccggtc aggcgcgcgc aatcgttgac gctctagcgt    12000
gcaaaaggag agcctgtaag cgggcactct tccgtggtct ggtggataaa ttcgcaaggg    12060
tatcatggcg gacgaccggg gttcgagccc cgtatccggc cgtccgccgt gatccatgcg    12120
gttaccgccc gcgtgtcgaa cccaggtgtg cgacgtcaga caacgggga gtgctccttt     12180 tggcttcctt ccaggcgcgg cggctgctgc gctagctttt ttggccactg gccgcgcgca    12240
gcgtaagcgg ttaggctgga aagcgaaagc attaagtggc tcgctccctg tagccggagg    12300
gttattttcc aagggttgag tcgcgggacc cccggttcga gtctcggacc ggccggactg    12360
cggcgaacgg gggtttgcct ccccgtcatg caagaccccg cttgcaaatt cctccggaaa    12420
cagggacgag cccctttttt gcttttccca gatgcatccg gtgctgcggc agatgcgccc    12480
ccctcctcag cagcggcaag agcaagagca gcggcagaca tgcagggcac cctcccctcc    12540
tcctaccgcg tcaggagggg cgacatccgc ggttgacgcg gcagcagatg gtgattacga    12600
accccgcgcg cgccgggccc ggcactacct ggacttggag gagggcgagg gcctggcgcg    12660
gctaggagcg ccctctcctg agcggcaccc aagggtgcag ctgaagcgtg atacgcgtga    12720
ggcgtacgtg ccgcggcaga acctgtttcg cgaccgcgag ggagaggagc ccgaggagat    12780
gcgggatcga aagttccacg cagggcgcga gctgcggcat ggcctgaatc gcgagcggtt    12840
gctgcgcgag gaggactttg agcccgacgc gcgaaccggg attagtcccg cgcgcgcaca    12900
cgtggcggcc gccgacctgg taaccgcata cgagcagacg gtgaaccagg agattaactt    12960
tcaaaaaagc tttaacaacc acgtgcgtac gcttgtggcg cgcgaggagg tggctatagg    13020
actgatgcat ctgtgggact ttgtaagcgc gctggagcaa aacccaaata gcaagccgct    13080
catggcgcag ctgttcctta tagtgcagca cagcagggac aacgaggcat tcaggggatgc   13140
```

-continued

```
gctgctaaac atagtagagc ccgagggccg ctggctgctc gatttgataa acatcctgca   13200
gagcatagtg gtgcaggagc gcagcttgag cctggctgac aaggtggccg ccatcaacta   13260
ttccatgctt agcctgggca agttttacgc ccgcaagata taccataccc cttacgttcc   13320
catagacaag gaggtaaaga tcgaggggtt ctacatgcgc atggcgctga aggtgcttac   13380
cttgagcgac gacctgggcg tttatcgcaa cgagcgcatc cacaaggccg tgagcgtgag   13440
ccggcggcgc gagctcagcg accgcgagct gatgcacagc ctgcaaaggg ccctggctgg   13500
cacgggcagc ggcgatagag aggccgagtc ctactttgac gcgggcgctg acctgcgctg   13560
ggccccaagc cgacgcgccc tggaggcagc tggggccgga cctgggctgg cggtggcacc   13620
cgcgcgcgct ggcaacgtcg gcggcgtgga ggaatatgac gaggacgatg agtacgagcc   13680
agaggacggc gagtactaag cggtgatgtt tctgatcaga tgatgcaaga cgcaacggac   13740
ccggcggtgc gggcggcgct gcagagccag ccgtccggcc ttaactccac ggacgactgg   13800
cgccaggtca tggaccgcat catgtcgctg actgcgcgca atcctgacgc gttccggcag   13860
cagccgcagg ccaaccggct ctccgcaatt ctggaagcgg tggtcccggc gcgcgcaaac   13920
cccacgcacg agaaggtgct ggcgatcgta aacgcgctgg ccgaaaacag ggccatccgg   13980
cccgacgagg ccggcctggt ctacgacgcg ctgcttcagc gcgtggctcg ttacaacagc   14040
ggcaacgtgc agaccaacct ggaccggctg gtgggggatg tgcgcgaggc cgtggcgcag   14100
cgtgagcgcg cgcagcagca gggcaacctg ggctccatgg ttgcactaaa cgccttcctg   14160
agtacacagc ccgccaacgt gccgcgggga caggaggact acaccaactt tgtgagcgca   14220
ctgcggctaa tggtgactga gacaccgcaa agtgaggtgt accagtctgg gccagactat   14280
tttttccaga ccagtagaca aggcctgcag accgtaaacc tgagccaggc tttcaaaaac   14340
ttgcaggggc tgtggggggt gcgggctccc acaggcgacc gcgcgaccgt gtctagcttg   14400
ctgacgccca actcgcgcct gttgctgctg ctaatagcgc ccttcacgga cagtggcagc   14460
gtgtcccggg acacatacct aggtcacttg ctgacactgt accgcgaggc cataggtcag   14520
gcgcatgtgg acgagcatac tttccaggag attacaagtg tcagccgcgc gctggggcag   14580
gaggacacgg gcagcctgga ggcaaccta aactacctgc tgaccaaccg gcggcagaag   14640
atcccctcgt tgcacagttt aaacagcgag gaggagcgca ttttgcgcta cgtgcagcag   14700
agcgtgagcc ttaacctgat gcgcgacggg gtaacgccca gcgtggcgct ggacatgacc   14760
gcgcgcaaca tggaaccggg catgtatgcc tcaaaccggc cgtttatcaa ccgcctaatg   14820
gactacttgc atcgcgcggc cgccgtgaac cccgagtatt tcaccaatgc catcttgaac   14880
ccgcactggc taccgccccc tggtttctac accgggggat tcgaggtgcc cgagggtaac   14940
gatggattcc tctgggacga catagacgac agcgtgtttt ccccgcaacc gcagaccctg   15000
ctagagttgc aacagcgcga gcaggcagag gcggcgctgc gaaaggaaag cttccgcagg   15060
ccaagcagct tgtccgatct aggcgctgcg gccccgcgt cagatgctag tagcccattt   15120
ccaagcttga tagggtctct taccagcact cgcaccaccc gcccgcgcct gctgggcgag   15180
gaggagtacc taaacaactc gctgctgcag ccgcagcgcg aaaaaaacct gcctccggca   15240
tttcccaaca cgggdataga gagcctagtg gacaagatga gtagatggaa gacgtacgcg   15300
caggagcaca gggacgtgcc aggcccgcgc cgcccaccc gtcgtcaaag gcacgaccgt   15360
cagcggggtc tggtgtggga ggacgatgac tcggcagacg acagcagcgt cctggatttg   15420
ggagggagtg gcaacccgtt tgcgcacctt cgccccaggc tggggagaat gttttaaaaa   15480
aaaaaaagca tgatgcaaaa taaaaaactc accaaggcca tggcaccgag cgttggtttt   15540
```

-continued

```
cttgtattcc ccttagtatg cggcgcgcgg cgatgtatga ggaaggtcct cctccctcct    15600
acgagagtgt ggtgagcgcg gcgccagtgg cggcggcgct gggttctccc ttcgatgctc    15660
ccctggaccc gccgtttgtg cctccgcggt acctgcggcc taccgggggg agaaacagca    15720
tccgttactc tgagttggca cccctattcg acaccacccg tgtgtacctg gtggacaaca    15780
agtcaacgga tgtggcatcc ctgaactacc agaacgacca cagcaacttt ctgaccacgg    15840
tcattcaaaa caatgactac agcccggggg aggcaagcac acagaccatc aatcttgacg    15900
accggtcgca ctggggcggc gacctgaaaa ccatcctgca taccaacatg ccaaatgtga    15960
acgagttcat gtttaccaat aagtttaagg cgcgggtgat ggtgtcgcgc ttgcctacta    16020
aggacaatca ggtggagctg aaatacgagt gggtggagtt cacgctgccc gagggcaact    16080
actccgagac catgaccata gaccttatga acaacgcgat cgtggagcac tacttgaaag    16140
tgggcagaca gaacgggggt ctggaaagcg acatcggggt aaagtttgac acccgcaact    16200
tcagactggg gtttgacccc gtcactggtc ttgtcatgcc tggggtatat acaaacgaag    16260
ccttccatcc agacatcatt ttgctgccag gatgcggggt ggacttcacc cacagccgcc    16320
tgagcaactt gttgggcatc cgcaagcggc aaccccttcca ggagggcttt aggatcacct    16380
acgatgatct ggagggtggt aacattcccg cactgttgga tgtggacgcc taccaggcga    16440
gcttgaaaga tgacaccgaa cagggcgggg gtggcgcagg cggcagcaac agcagtggca    16500
gcggcgcgga agagaactcc aacgcggcag ccgcggcaat gcagccggtg gaggacatga    16560
acgatcatgc cattcgcggc gacacctttg ccacacgggc tgaggagaag cgcgctgagg    16620
ccgaagcagc ggccgaagct gccgcccccg ctgcgcaacc cgaggtcgag aagcctcaga    16680
agaaaccggt gatcaaaccc ctgacagagg acagcaagaa acgcagttac aacctaataa    16740
gcaatgacag caccttcacc cagtaccgca gctggtacct tgcatacaac tacggcgacc    16800
ctcagaccgg aatccgctca tggacccctgc tttgcactcc tgacgtaacc tgcggctcgg    16860
agcaggtcta ctggtcgttg ccagacatga tgcaagaccc cgtgaccttc cgctccacgc    16920
gccagatcag caactttccg gtggtgggcg ccgagctgtt gcccgtgcac tccaagagct    16980
tctacaacga ccaggccgtc tactcccaac tcatccgcca gtttacctct ctgacccacg    17040
tgttcaatcg cttttcccgag aaccagattt tggcgcgccc gccagccccc accatcacca    17100
ccgtcagtga aaacgttcct gctctcacag atcacgggac gctaccgctg cgcaacagca    17160
tcggaggagt ccagcgagtg accattactg acgccagacg ccgcacctgc ccctacgttt    17220
acaaggccct gggcatagtc tcgccgcgcg tcctatcgag ccgcactttt tgagcaagca    17280
tgtccatcct tatatcgccc agcaataaca caggctgggg cctgcgcttc ccaagcaaga    17340
tgtttggcgg ggccaagaag cgctccgacc aacacccagt gcgcgtgcgc gggcactacc    17400
gcgcgccctg gggcgcgcac aaacgcggcc gcactgggcg caccaccgtc gatgacgcca    17460
tcgacgcggt ggtggaggag gcgcgcaact acacgcccac gccgccacca gtgtccacag    17520
tggacgcggc cattcagacc gtggtgcgcg agcccggcg ctatgctaaa atgaagagac    17580
ggcggaggcg cgtagcacgt cgccaccgcc gccgacccgg cactccgccc caacgcgcgg    17640
cggcggccct gcttaaccgc gcacgtcgca ccggccgacg ggcggccatg cgggccgctc    17700
gaaggctggc cgcgggtatt gtcactgtgc ccccaggtc caggcgacga gcggccgccg    17760
cagcagccgg ggccattagt gctatgactc agggtcgcag gggcaacgtg tattgggtgc    17820
gcgactcggt tagcggcctg cgcgtgcccg tgcgcacccg ccccccgcgc aactagattg    17880
```

-continued

```
caagaaaaaa ctacttagac tcgtactgtt gtatgtatcc agcggcggcg gcgcgcaacg    17940
aagctatgtc caagcgcaaa atcaaagaag agatgctcca ggtcatcgcg ccggagatct    18000
atggcccccc gaagaaggaa gagcaggatt acaagccccg aaagctaaag cgggtcaaaa    18060
agaaaaagaa agatgatgat gatgaacttg acgacgaggt ggaactgctg cacgctaccg    18120
cgcccaggcg acgggtacag tggaaaggtc gacgcgtaaa acgtgttttg cgacccggca    18180
ccaccgtagt ctttacgccc ggtgagcgct ccacccgcac ctacaagcgc gtgtatgatg    18240
aggtgtacgg cgacgaggac ctgcttgagc aggccaacga gcgcctcggg gagtttgcct    18300
acggaaagcg gcataaggac atgctggcgt tgccgctgga cgagggcaac ccaacaccta    18360
gcctaaagcc cgtaacactg cagcaggtgc tgcccgcgct tgcaccgtcc gaagaaaagc    18420
gcggcctaaa gcgcgagtct ggtgacttgg cacccaccgt gcagctgatg gtacccaagc    18480
gccagcgact ggaagatgtc ttggaaaaaa tgaccgtgga acctgggctg gagcccgagg    18540
tccgcgtgcg gccaatcaag caggtggcgc cgggactggg cgtgcagacc gtggacgttc    18600
agatacccac taccagtagc accagtattg ccaccgccac agagggcatg gagacacaaa    18660
cgtccccggt tgcctcagcg gtggcggatg ccgcggtgca ggcggtcgct gcggccgcgt    18720
ccaagacctc tacggaggtg caaacggacc cgtggatgtt tcgcgtttca gcccccccggc    18780 gcccgcgccg ttcgaggaag tacggcgccg ccagcgcgct actgcccgaa tatgccctac    18840
atccttccat tgcgcctacc cccggctatc gtggctacac ctaccgcccc agaagacgag    18900
caactacccg acgccgaacc accactggaa cccgccgccg ccgtcgccgt cgccagcccg    18960
tgctggcccc gatttccgtg cgcagggtgg ctcgcgaagg aggcaggacc ctggtgctgc    19020
caacagcgcg ctaccacccc agcatcgttt aaaagccggt ctttgtggtt cttgcagata    19080
tggccctcac ctgccgcctc cgtttcccgg tgccgggatt ccgaggaaga atgcaccgta    19140
ggaggggcat ggccggccac ggcctgacgg cgggcatgcg tcgtgcgcac caccggcggc    19200
ggcgcgcgtc gcaccgtcgc atgcgcggcg gtatcctgcc cctccttatt ccactgatcg    19260
ccgcggcgat tggcgccgtg cccggaattg catccgtggc cttgcaggcg cagagacact    19320
gattaaaaac aagttgcatg tggaaaaatc aaaataaaaa gtctggactc tcacgctcgc    19380
ttggtcctgt aactattttg tagaatggaa gacatcaact ttgcgtctct ggccccgcga    19440
cacggctcgc gcccgttcat gggaaactgg caagatatcg gcaccagcaa tatgagcggt    19500
ggcgccttca gctggggctc gctgtggagc ggcattaaaa atttcggttc caccgttaag    19560
aactatggca gcaaggcctg gaacagcagc acaggccaga tgctgagggga taagttgaaa    19620 gagcaaaatt tccaacaaaa ggtggtagat ggcctggcct ctggcattag cggggtggtg    19680
gacctggcca accaggcagt gcaaaataag attaacagta agcttgatcc ccgccctccc    19740
gtagaggagc ctccaccggc cgtggagaca gtgtctccag aggggcgtgg cgaaaagcgt    19800
ccgcgccccg acagggaaga aactctggtg acgcaaatag acgagcctcc ctcgtacgag    19860
gaggcactaa agcaaggcct gcccaccacc cgtcccatcg cgcccatggc taccggagtg    19920
ctgggccagc acacacccgt aacgctggac ctgcctcccc ccgccgacac ccagcagaaa    19980
cctgtgctgc aggcccgac cgccgttgtt gtaacccgtc ctagccgcgc gtccctcgcgc    20040 cgcgccgcca gcggtccgcg atcgttgcgg cccgtagcca gtggcaactg gcaaagcaca    20100
ctgaacagca tcgtgggtct gggggtgcaa tccctgaagc gccgacgatg cttctgatag    20160
ctaacgtgtc gtatgtgtgt catgtatgcg tccatgtcgc cgccagagga ctgctgagc    20220 cgccgcgcgc ccgctttcca agatggctac ccccttcgatg atgccgcagt ggtcttacat    20280
```

-continued

```
gcacatctcg ggccaggacg cctcggagta cctgagcccc gggctggtgc agtttgcccg   20340
cgccaccgag acgtacttca gcctgaataa caagtttaga aaccccacgg tggcgcctac   20400
gcacgacgtg accacagacc ggtcccagcg tttgacgctg cggttcatcc ctgtggaccg   20460
tgaggatact gcgtactcgt acaaggcgcg gttcacccta gctgtgggtg ataaccgtgt   20520
gctggacatg gcttccacgt actttgacat ccgcggcgtg ctggacaggg gccctacttt   20580
taagccctac tctggcactg cctacaacgc cctggctccc aagggtgccc caaatccttg   20640
cgaatgggat gaagctgcta ctgctcttga aataaaccta gaagaagagg acgatgacaa   20700
cgaagacgaa gtagacgagc aagctgagca gcaaaaaact cacgtatttg ggcaggcgcc   20760
ttattctggt ataaatatta caaggagggg tattcaaata ggtgtcgaag gtcaaacacc   20820
taaatatgcc gataaaacat ttcaacctga acctcaaata ggagaatctc agtggtacga   20880
aacagaaatt aatcatgcag ctgggagagt cctaaaaaag actaccccaa tgaaaccatg   20940
ttacggttca tatgcaaaac ccacaaatga aaatggaggg caaggcattc ttgtaaagca   21000
acaaaatgga aagctagaaa gtcaagtgga aatgcaattt ttctcaacta ctgaggcagc   21060
cgcaggcaat ggtgataact tgactcctaa agtggtattg tacagtgaag atgtagatat   21120
agaaacccca gacactcata tttcttacat gcccactatt aaggaaggta actcacgaga   21180
actaatgggc caacaatcta tgcccaacag gcctaattac attgctttta gggacaattt   21240
tattggtcta atgtattaca acagcacggg taatatgggt gttctggcgg gccaagcatc   21300
gcagttgaat gctgttgtag atttgcaaga cagaaacaca gagctttcat accagctttt   21360
gcttgattcc attggtgata gaaccaggta cttttctatg tggaatcagg ctgttgacag   21420
ctatgatcca gatgttagaa ttattgaaaa tcatggaact gaagatgaac ttccaaatta   21480
ctgctttcca ctgggaggtg tgattaatac agagactctt accaaggtaa aacctaaaac   21540
aggtcaggaa aatggatggg aaaaagatgc tacagaattt tcagataaaa atgaaataag   21600
agttggaaat aattttgcca tggaaatcaa tctaaatgcc aacctgtgga gaaatttcct   21660
gtactccaac atagcgctgt atttgcccga caagctaaag tacagtcctt ccaacgtaaa   21720
aatttctgat aacccaaaca cctacgacta catgaacaag cgagtggtgg ctcccgggct   21780
agtggactgc tacattaacc ttggagcacg ctggtccctt gactatatgg acaacgtcaa   21840
cccatttaac caccaccgca atgctggcct gcgctaccgc tcaatgttgc tgggcaatgg   21900
tcgctatgtg cccttccaca tccaggtgcc tcagaagttc tttgccatta aaaacctcct   21960
tctcctgccg ggctcataca cctacgagtg gaacttcagg aaggatgtta acatggttct   22020
gcagagctcc ctaggaaatg acctaagggt tgacggagcc agcattaagt ttgatagcat   22080
ttgcctttac gccaccttct tccccatggc ccacaacacc gcctccacgc ttgaggccat   22140
gcttagaaac gacaccaacg accagtcctt taacgactat ctctccgccg ccaacatgct   22200
ctaccctata cccgccaacg ctaccaacgt gcccatatcc atccctccc gcaactgggc   22260 ggctttccgc ggctgggcct tcacgcgcct taagactaag gaaaccccat cactgggctc   22320
gggctacgac ccttattaca cctactctgg ctctataccc tacctagatg gaacctttta   22380
cctcaaccac acctttaaga aggtggccat taccttttgac tcttctgtca gctggcctgg   22440
caatgaccgc ctgcttaccc ccaacgagtt tgaaattaag cgctcagttg acggggaggg   22500
ttacaacgtt gcccagtgta acatgaccaa agactggttc ctggtacaaa tgctagctaa   22560
ctataacatt ggctaccagg gcttctatat cccagagagc tacaaggacc gcatgtactc   22620
```

-continued

```
cttctttaga aacttccagc ccatgagccg tcaggtggtg gatgatacta aatacaagga   22680
ctaccaacag gtgggcatcc tacaccaaca caacaactct ggatttgttg gctaccttgc   22740
ccccaccatg cgcgaaggac aggcctaccc tgctaacttc ccctatccgc ttataggcaa   22800
gaccgcagtt gacagcatta cccagaaaaa gtttctttgc gatcgcaccc tttggcgcat   22860
cccattctcc agtaacttta tgtccatggg cgcactcaca gacctgggcc aaaaccttct   22920
ctacgccaac tccgcccacg cgctagacat gacttttgag gtggatccca tggacgagcc   22980
cacccttctt tatgttttgt ttgaagtctt tgacgtggtc cgtgtgcacc agccgcaccg   23040
cggcgtcatc gaaaccgtgt acctgcgcac gcccttctcg gccggcaacg ccacaacata   23100
aagaagcaag caacatcaac aacagctgcc gccatgggct ccagtgagca ggaactgaaa   23160
gccattgtca aagatcttgg ttgtgggcca tattttttgg gcacctatga caagcgcttt   23220
ccaggctttg tttctccaca caagctcgcc tgcgccatag tcaatacggc cggtcgcgag   23280
actgggggcg tacactggat ggcctttgcc tggaacccgc actcaaaaac atgctacctc   23340
tttgagccct ttggcttttc tgaccagcga ctcaagcagg tttaccagtt tgagtacgag   23400
tcactcctgc gccgtagcgc cattgcttct tcccccgacc gctgtataac gctggaaaag   23460
tccacccaaa gcgtacaggg gcccaactcg gccgcctgtg gactattctg ctgcatgttt   23520
ctccacgcct ttgccaactg gcccaaact cccatggatc acaaccccac catgaacctt   23580
attaccgggg tacccaactc catgctcaac agtcccagg tacagcccac cctgcgtcgc   23640
aaccaggaac agctctacag cttcctggag cgccactcgc cctacttccg cagccacagt   23700
gcgcagatta ggagcgccac ttcttttttgt cacttgaaaa acatgtaaaa ataatgtact   23760
agagacactt tcaataaagg caaatgcttt tatttgtaca ctctcgggtg attatttacc   23820
cccacccttg ccgtctgcgc cgtttaaaaa tcaaaggggt tctgccgcgc atcgctatgc   23880
gccactggca gggacacgtt gcgatactgg tgtttagtgc tccacttaaa ctcaggcaca   23940
accatccgcg gcagctcggt gaagttttca ctccacaggc tgcgcaccat caccaacgcg   24000
tttagcaggt cgggcgccga tatcttgaag tcgcagttgg ggcctccgcc ctgcgcgcgc   24060
gagttgcgat acacagggtt gcagcactgg aacactatca gcgccgggtg gtgcacgctg   24120
gccagcacgc tcttgtcgga gatcagatcc gcgtccaggt cctccgcgtt gctcagggcg   24180
aacggagtca actttggtag ctgccttccc aaaaagggcg cgtgcccagg ctttgagttg   24240
cactcgcacc gtagtggcat caaaaggtga ccgtgcccgg tctgggcgtt aggatacagc   24300
gcctgcataa aagccttgat ctgcttaaaa gccacctgag cctttgcgcc ttcagagaag   24360
aacatgccgc aagacttgcc ggaaaactga ttggccggac aggccgcgtc gtgcacgcag   24420
caccttgcgt cggtgttgga gatctgcacc acatttcggc cccaccggtt cttcacgatc   24480
ttggccttgc tagactgctc cttcagcgcg cgctgcccgt tttcgctcgt cacatccatt   24540
tcaatcacgt gctccttatt tatcataatg cttccgtgta gacacttaag ctcgccttcg   24600
atctcagcgc agcggtgcag ccacaacgcg cagcccgtgg gctcgtgatg cttgtaggtc   24660
acctctgcaa acgactgcag gtacgcctgc aggaatcgcc ccatcatcgt cacaaaggtc   24720
ttgttgctgg tgaaggtcag ctgcaacccg cggtgctcct cgttcagcca ggtcttgcat   24780
acggccgcca gagcttccac ttggtcaggc agtagtttga agttcgcctt tagatcgtta   24840
tccacgtggt acttgtccat cagcgcgcgc gcagcctcca tgcccttctc ccacgcagac   24900
acgatcggca cactcagcgg gttcatcacc gtaatttcac tttccgcttc gctgggctct   24960
tcctcttcct cttgcgtccg cataccacgc gccactgggt cgtcttcatt cagccgccgc   25020
```

-continued

```
actgtgcgct tacctccttt gccatgcttg attagcaccg gtgggttgct gaaacccacc    25080
atttgtagcg ccacatcttc tctttcttcc tcgctgtcca cgattacctc tggtgatggc    25140
gggcgctcgg gcttgggaga agggcgcttc tttttcttct tgggcgcaat ggccaaatcc    25200
gccgccgagg tcgatggccg cgggctgggt gtgcgcggca ccagcgcgtc ttgtgatgag    25260
tcttcctcgt cctcggactc gatacgccgc ctcatccgct tttttggggg cgcccgggga    25320
ggcggcggcg acggggacgg ggacgacacg tcctccatgg ttgggggacg tcgcgccgca    25380
ccgcgtccgc gctcgggggt ggtttcgcgc tgctcctctt cccgactggc catttccttc    25440
tcctataggc agaaaaagat catggagtca gtcgagaaga aggacagcct aaccgccccc    25500
tctgagttcg ccaccaccgc ctccaccgat gccgccaacg cgcctaccac cttccccgtc    25560
gaggcacccc cgcttgagga ggaggaagtg attatcgagc aggacccagg tttttgtaagc    25620 gaagacgacg aggaccgctc agtaccaaca gaggataaaa agcaagacca ggacaacgca    25680
gaggcaaacg aggaacaagt cgggcggggg gacgaaaggc atggcgacta cctagatgtg    25740
ggagacgacg tgctgttgaa gcatctgcag cgccagtgcg ccattatctg cgacgcgttg    25800
caagagcgca gcgatgtgcc cctcgccata gcggatgtca gccttgccta cgaacgccac    25860
ctattctcac cgcgcgtacc ccccaaacgc caagaaaacg gcacatgcga gcccaacccg    25920
cgcctcaact tctaccccgt atttgccgtg ccagaggtgc ttgccaccta tcacatcttt    25980
ttccaaaact gcaagatacc cctatcctgc cgtgccaacc gcagccgagc ggacaagcag    26040
ctggccttgc ggcagggcgc tgtcatacct gatatcgcct cgctcaacga agtgccaaaa    26100
atctttgagg gtcttggacg cgacgagaag cgcgcggcaa acgctctgca acaggaaaac    26160
agcgaaaatg aaagtcactc tggagtgttg gtggaactcg agggtgacaa cgcgcgccta    26220
gccgtactaa aacgcagcat cgaggtcacc cactttgcct acccggcact taacctaccc    26280
cccaaggtca tgagcacagt catgagtgag ctgatcgtgc gccgtgcgca gcccctggag    26340
agggatgcaa atttgcaaga acaaacagag gagggcctac ccgcagttgg cgacgagcag    26400
ctagcgcgct ggcttcaaac gcgcgagcct gccgacttgg aggagcgacg caaactaatg    26460
atggccgcag tgctcgttac cgtggagctt gagtgcatga gcggttctt tgctgacccg    26520 gagatgcagc gcaagctaga ggaaacattg cactacacct ttcgacaggg ctacgtacgc    26580
caggcctgca agatctccaa cgtggagctc tgcaacctgg tctcctacct tggaattttg    26640
cacgaaaacc gccttgggca aaacgtgctt cattccacgc tcaagggcga ggcgcgccgc    26700
gactacgtcc gcgactgcgt ttacttattt ctatgctaca cctggcagac ggccatgggc    26760
gtttggcagc agtgcttgga ggagtgcaac ctcaaggagc tgcagaaact gctaaagcaa    26820
aacttgaagg acctatggac ggccttcaac gagcgctccg tggccgcgca cctggcggac    26880 atcatttttcc ccgaacgcct gcttaaaacc ctgcaacagg gtctgccaga cttcaccagt    26940
caaagcatgt tgcagaactt taggaacttt atcctagagc gctcaggaat cttgcccgcc    27000
acctgctgtg cacttcctag cgactttgtg cccattaagt accgcgaatg ccctccgccg    27060
ctttggggcc actgctacct tctgcagcta gccaactacc ttgcctacca ctctgacata    27120
atggaagacg tgagcggtga cggtctactg gagtgtcact gtcgctgcaa cctatgcacc    27180
ccgcaccgct ccctggtttg caattcgcag ctgcttaacg aaagtcaaat tatcggtacc    27240
tttgagctgc agggtccctc gcctgacgaa aagtccgcgg ctccggggtt gaaactcact    27300
ccggggctgt ggacgtcggc ttaccttcgc aaatttgtac ctgaggacta ccacgcccac    27360
```

-continued

```
gagattaggt tctacgaaga ccaatcccgc ccgcctaatg cggagcttac cgcctgcgtc    27420
attacccagg gccacattct tggccaattg caagccatca acaaagcccg ccaagagttt    27480
ctgctacgaa agggacgggg ggtttacttg gaccccagt ccggcgagga gctcaaccca     27540
atccccccgc cgccgcagcc ctatcagcag cagccgcggg cccttgcttc ccaggatggc    27600
acccaaaaag aagctgcagc tgccgccgcc acccacggac gaggaggaat actgggacag    27660
tcaggcagag gaggtttgg acgaggagga ggaggacatg atggaagact gggagagcct     27720
agacgaggaa gcttccgagg tcgaagaggt gtcagacgaa acaccgtcac cctcggtcgc    27780
attcccctcg ccggcgcccc agaaatcggc aaccggttcc agcatggcta caacctccgc    27840
tcctcaggcg ccgccggcac tgcccgttcg ccgacccaac cgtagatggg acaccactgg    27900
aaccagggcc ggtaagtcca agcagccgcc gccgttagcc caagagcaac aacagcgcca    27960
aggctaccgc tcatggcgcg ggcacaagaa cgccatagtt gcttgcttgc aagactgtgg    28020
gggcaacatc tccttcgccc gccgctttct tctctaccat cacggcgtgg ccttcccccg    28080
taacatcctg cattactacc gtcatctcta cagcccatac tgcaccggcg gcagcggcag    28140
caacagcagc ggccacacag aagcaaaggc gaccggatag caagactctg acaaagccca    28200
agaaatccac agcggcggca gcagcaggag gaggagcgct gcgtctggcg cccaacgaac    28260
ccgtatcgac ccgcgagctt agaaacagga ttttccac tctgtatgct atatttcaac      28320
agagcagggg ccaagaacaa gagctgaaaa taaaaaacag gtctctgcga tccctcaccc    28380
gcagctgcct gtatcacaaa agcgaagatc agcttcggcg cacgctggaa gacgcggagg    28440
ctctcttcag taaatactgc gcgctgactc ttaaggacta gtttcgcgcc ctttctcaaa    28500
tttaagcgcg aaaactacgt catctccagc ggccacaccc ggcgccagca cctgttgtca    28560
gcgccattat gagcaaggaa attcccacgc cctacatgtg gagttaccag ccacaaatgg    28620
gacttgcggc tggagctgcc caagactact caacccgaat aaactacatg agcgcgggac    28680
cccacatgat atcccgggtc aacggaatac gcgcccaccg aaaccgaatt ctcctggaac    28740
aggcggctat taccaccaca cctcgtaata accttaatcc ccgtagttgg cccgctgccc    28800
tggtgtacca ggaaagtccc gctcccacca ctgtggtact tcccagagac gcccaggccg    28860
aagttcagat gactaactca ggggcgcagc ttgcgggcgg ctttcgtcac agggtgcggt    28920
cgcccgggca gggtataact cacctgacaa tcagagggcg aggtattcag ctcaacgacg    28980
agtcggtgag ctcctcgctt ggtctccgtc cggacgggac atttcagatc ggcggcgccg    29040
gccgctcttc attcacgcct cgtcaggcaa tcctaactct gcagacctcg tcctctgagc    29100
cgcgctctgg aggcattgga actctgcaat ttattgagga gtttgtgcca tcggtctact    29160
ttaacccctt ctcgggacct cccgccact atccggatca atttattcct aactttgacg     29220
cggtaaagga ctcggcggac ggctacgact gaatgttaag tggagaggca gagcaactgc    29280
gcctgaaaca cctggtccac tgtcgccgcc acaagtgctt tgcccgcgac tccggtgagt    29340
tttgctactt tgaattgccc gaggatcata tcgagggccc ggcgcacggc gtccggctta    29400
ccgcccaggg agagcttgcc cgtagcctga ttcgggagtt tacccagcgc cccctgctag    29460
ttgagcggga caggggaccc tgtgttctca ctgtgatttg caactgtcct aaccctggat    29520
tacatcaaga tcctctagtt aatgtcaggt cgcctaagtc gattaactag agtacccggg    29580
gatcttattc cctttaacta ataaaaaaa ataataaagc atcacttact taaaatcagt      29640
tagcaaattt ctgtccagtt tattcagcag cacctccttg ccctcctccc agctctggta    29700
ttgcagcttc ctcctggctg caaactttct ccacaatcta aatggaatgt cagtttcctc    29760
```

```
ctgttcctgt ccatccgcac ccactatctt catgttgttg cagatgaagc gcgcaagacc   29820
gtctgaagat accttcaacc ccgtgtatcc atatgacacg gaaaccggtc ctccaactgt   29880
gccttttctt actcctccct ttgtatcccc caatgggttt caagagagtc ccctggggt    29940 actctctttg cgcctatccg aacctctagt tacctccaat ggcatgcttg cgctcaaaat   30000
gggcaacggc ctctctctgg acgaggccgg caaccttacc tcccaaaatg taaccactgt   30060
gagcccacct ctcaaaaaaa ccaagtcaaa cataaacctg gaaatatctg caccectcac   30120 agttacctca gaagccctaa ctgtggctgc cgccgcacct ctaatggtcg cgggcaacac   30180
actcaccatg caatcacagg ccccgctaac cgtgcacgac tccaaactta gcattgccac   30240
ccaaggaccc ctcacagtgt cagaaggaaa gctagccctg caaacatcag gccccctcac   30300
caccaccgat agcagtaccc ttactatcac tgcctcaccc cctctaacta ctgccactgg   30360
tagcttgggc attgacttga aagagcccat ttatacacaa aatggaaaac taggactaaa   30420
gtacggggct cctttgcatg taacagacga cctaaacact ttgaccgtag caactggtcc   30480
aggtgtgact attaataata cttccttgca aactaaagtt actggagcct tgggttttga    30540
ttcacaaggc aatatgcaac ttaatgtagc aggaggacta aggattgatt ctcaaaacag   30600
acgccttata cttgatgtta gttatccgtt tgatgctcaa aaccaactaa atctaagact   30660
aggacagggc cctctttta taaactcagc ccacaacttg gatattaact acaacaaagg    30720
cctttacttg tttacagctt caaacaattc caaaaagctt gaggttaacc taagcactgc   30780
caaggggttg atgtttgacg ctacagccat agccattaat gcaggagatg ggcttgaatt   30840
tggttcacct aatgcaccaa acacaaatcc cctcaaaaca aaaattggcc atggcctaga   30900
atttgattca aacaaggcta tggttcctaa actaggaact ggccttagtt ttgacagcac   30960
aggtgccatt acagtaggaa acaaaaataa tgataagcta actttgtgga ccggaataaa   31020
ccctccacct aactgtcaaa ttgtggaaaa cactaataca aatgatggca aacttacttt   31080
agtattagta aaaaatggag ggcttgttaa tggctacgtg tctctagttg gtgtatcaga   31140
cactgtgaac caaatgttca cacaaaagac agcaaacatc caattaagat tatattttga   31200
ctcttctgga aatctattaa ctgaggaatc agacttaaaa attccactta aaaataaatc   31260
ttctacagcg accagtgaaa ctgtagccag cagcaaagcc tttatgccaa gtactacagc   31320
ttatcccttc aacaccacta ctagggatag tgaaaactac attcatggaa tatgttacta   31380
catgactagt tatgatagaa gtctatttcc cttgaacatt tctataatgc taaacagccg   31440
tatgatttct tccaatgttg cctatgccat acaatttgaa tggaatctaa atgcaagtga   31500
atctccagaa agcaacatag ctacgctgac cacatccccc ttttctttt cttacattac    31560 agaagacgac aactaaagaa tcgtttgtgt tatgtttcaa cgtgtttatt tttcaattgc   31620
agaaaatttc aagtcatttt tcattcagta gtatagcccc accaccacat agcttataca   31680
gatcaccgta ccttaatcaa actcacagaa ccctagtatt caacctgcca cctccctccc   31740
aacacacaga gtacacagtc ctttctcccc ggctggcctt aaaaagcatc atatcatggg   31800
taacagacat attcttaggt gttatattcc acacggtttc ctgtcgagcc aaacgctcat   31860
cagtgatatt aataaactcc ccgggcagct cacttaagtt catgtcgctg tccagctgct   31920
gagccacagg ctgctgtcca acttgcggtt gcttaacggg cggcgaagga gaagtccacg   31980
cctacatggg ggtagagtca taatcgtgca tcaggatagg gcggtggtgc tgcagcagcg   32040
cgcgaataaa ctgctgccgc cgccgctccg tcctgcagga atacaacatg gcagtggtct   32100
```

```
cctcagcgat gattcgcacc gcccgcagca taaggcgcct tgtcctccgg gcacagcagc   32160
gcaccctgat ctcacttaaa tcagcacagt aactgcagca cagcaccaca atattgttca   32220
aaatcccaca gtgcaaggcg ctgtatccaa agctcatggc ggggaccaca gaacccacgt   32280
ggccatcata ccacaagcgc aggtagatta agtggcgacc cctcataaac acgctggaca   32340
taaacattac ctcttttggc atgttgtaat tcaccacctc ccggtaccat ataaacctct   32400
gattaaacat ggcgccatcc accaccatcc taaaccagct ggccaaaacc tgcccgccgg   32460
ctatacactg cagggaaccg ggactggaac aatgacagtg gagagcccag gactcgtaac   32520
catggatcat catgctcgtc atgatatcaa tgttggcaca acacaggcac acgtgcatac   32580
acttcctcag gattacaagc tcctcccgcg ttagaaccat atcccaggga acaacccatt   32640
cctgaatcag cgtaaatccc acactgcagg gaagacctcg cacgtaactc acgttgtgca   32700
ttgtcaaagt gttacattcg ggcagcagcg gatgatcctc cagtatggta gcgcgggttt   32760
ctgtctcaaa aggaggtaga cgatccctac tgtacggagt gcgccgagac aaccgagatc   32820
gtgttggtcg tagtgtcatg ccaaatggaa cgccggacgt agtcatattt cctgaagcaa   32880
aaccaggtgc gggcgtgaca aacagatctg cgtctccggt ctcgccgctt agatcgctct   32940
gtgtagtagt tgtagtatat ccactctctc aaagcatcca ggcgcccct ggcttcgggt   33000 tctatgtaaa ctccttcatg cgccgctgcc ctgataacat ccaccaccgc agaataagcc   33060
acacccagcc aacctacaca ttcgttctgc gagtcacaca cgggaggagc gggaagagct   33120
ggaagaacca tgttttttttt tttattccaa aagattatcc aaaacctcaa aatgaagatc   33180
tattaagtga acgcgctccc ctccggtggc gtggtcaaac tctacagcca aagaacagat   33240
aatggcattt gtaagatgtt gcacaatggc ttccaaaagg caaacggccc tcacgtccaa   33300
gtggacgtaa aggctaaacc cttcagggtg aatctcctct ataaacattc cagcaccttc   33360
aaccatgccc aaataattct catctcgcca ccttctcaat atatctctaa gcaaatcccg   33420
aatattaagt ccggccattg taaaaatctg ctccagagcg ccctccacct tcagcctcaa   33480
gcagcgaatc atgattgcaa aaattcaggt tcctcacaga cctgtataag attcaaaagc   33540
ggaacattaa caaaaatacc gcgatcccgt aggtcccttc gcagggccag ctgaacataa   33600
tcgtgcaggt ctgcacggac cagcgcggcc acttccccgc caggaaccat gacaaaagaa   33660
cccacactga ttatgacacg catactcgga gctatgctaa ccagcgtagc cccgatgtaa   33720
gcttgttgca tgggcggcga tataaaatgc aaggtgctgc tcaaaaaatc aggcaaagcc   33780
tcgcgcaaaa aagaaagcac atcgtagtca tgctcatgca gataaaggca ggtaagctcc   33840
ggaaccacca cagaaaaaga caccattttt ctctcaaaca tgtctgcggg tttctgcata   33900
aacacaaaat aaaataacaa aaaaacattt aaacattaga agcctgtctt acaacaggaa   33960
aaacaaccct tataagcata agacggacta cggccatgcc ggcgtgaccg taaaaaaact   34020
ggtcaccgtg attaaaaagc accaccgaca gctcctcggt catgtccgga gtcataatgt   34080
aagactcggt aaacacatca ggttgattca catcggtcag tgctaaaaag cgaccgaaat   34140 agcccgggggg aatacatacc cgcaggcgta gagacaacat tacagcccccc ataggaggta   34200 taacaaaatt aataggagag aaaaacacat aaacacctga aaaaccctcc tgcctaggca   34260
aaatagcacc ctcccgctcc agaacaacat acagcgcttc cacagcggca gccataacag   34320
tcagccttac cagtaaaaaa gaaaacctat taaaaaaaca ccactcgaca cggcaccagc   34380
tcaatcagtc acagtgtaaa aaagggccaa gtgcagagcg agtatatata ggactaaaaa   34440
atgacgtaac ggttaaagtc cacaaaaaac acccagaaaa ccgcacgcga acctacgccc   34500
```

-continued

```
agaaacgaaa gccaaaaaac ccacaacttc ctcaaatcgt cacttccgtt ttcccacgtt    34560
acgtcacttc ccattttaag aaaactacaa ttcccaacac atacaagtta ctccgcccta    34620
aaacctacgt cacccgcccc gttcccacgc cccgcgccac gtcacaaact ccacccctc     34680 attatcatat tggcttcaat ccaaaataag gtatattatt gatgatg                  34727
```

<210> SEQ ID NO 26
<211> LENGTH: 37675
<212> TYPE: DNA
<213> ORGANISM: Artificial Sequence
<220> FEATURE:
<223> OTHER INFORMATION: plasmid #3 vector

<400> SEQUENCE: 26

```
ttaattaaca tgcatggatc catatgcggt gtgaaatacc gcacagatgc gtaaggagaa     60
aataccgcat caggcgctct tccgcttcct cgctcactga ctcgctgcgc tcggtcgttc    120
ggctgcggcg agcggtatca gctcactcaa aggcggtaat acggttatcc acagaatcag    180
gggataacgc aggaaagaac atgtgagcaa aaggccagca aaaggccagg aaccgtaaaa    240
aggccgcgtt gctggcgttt ttccataggc tccgcccccc tgacgagcat cacaaaaatc    300
gacgctcaag tcagaggtgg cgaaacccga caggactata aagataccag gcgtttcccc    360
ctggaagctc cctcgtgcgc tctcctgttc cgaccctgcc gcttaccgga tacctgtccg    420
cctttctccc ttcgggaagc gtggcgcttt ctcatagctc acgctgtagg tatctcagtt    480
cggtgtaggt cgttcgctcc aagctgggct gtgtgcacga accccccgtt cagcccgacc    540
gctgcgcctt atccggtaac tatcgtcttg agtccaaccc ggtaagacac gacttatcgc    600
cactggcagc agccactggt aacaggatta gcagagcgag gtatgtaggc ggtgctacag    660
agttcttgaa gtggtggcct aactacggct acactagaag gacagtattt ggtatctgcg    720
ctctgctgaa gccagttacc ttcggaaaaa gagttggtag ctcttgatcc ggcaaacaaa    780
ccaccgctgg tagcggtggt ttttttgttt gcaagcagca gattacgcgc agaaaaaaag    840
gatctcaaga agatcctttg atcttttcta cggggtctga cgctcagtgg aacgaaaact    900
cacgttaagg gattttggtc atgagattat caaaaaggat cttcacctag atccttttaa    960
attaaaaatg aagttttaaa tcaatctaaa gtatatatga gtaaacttgg tctgacagtt   1020
accaatgctt aatcagtgag gcacctatct cagcgatctg tctatttcgt tcatccatag   1080
ttgcctgact ccccgtcgtg tagataacta cgatacggga gggcttacca tctggcccca   1140
gtgctgcaat gataccgcga gacccacgct caccggctcc agatttatca gcaataaacc   1200
agccagccgg aagggccgag cgcagaagtg gtcctgcaac tttatccgcc tccatccagt   1260
ctattaattg ttgccgggaa gctagagtaa gtagttcgcc agttaatagt ttgcgcaacg   1320
ttgttgccat tgctgcagcc atgagattat caaaaaggat cttcacctag atccttttca   1380
cgtagaaagc cagtccgcag aaacggtgct gaccccggat gaatgtcagc tactgggcta   1440
tctggacaag ggaaaacgca gcgcaaaga gaaagcaggt agcttgcagt gggcttacat   1500
ggcgatagct agactgggcg gttttatgga cagcaagcga accggaattg ccagctgggg   1560
cgccctctgg taaggttggg aagccctgca aagtaaactg gatggctttc ttgccgccaa   1620
ggatctgatg gcgcagggga tcaagctctg atcaagagac aggatgagga tcgtttcgca   1680
tgattgaaca agatggattg cacgcaggtt ctccggccgc ttgggtggag aggctattcg   1740
gctatgactg ggcacaacag acaatcggct gctctgatgc cgccgtgttc cggctgtcag   1800
```

-continued

```
cgcaggggcg cccggttctt tttgtcaaga ccgacctgtc cggtgccctg aatgaactgc    1860
aagacgaggc agcgcggcta tcgtggctgg ccacgacggg cgttccttgc gcagctgtgc    1920
tcgacgttgt cactgaagcg ggaagggact ggctgctatt gggcgaagtg ccggggcagg    1980
atctcctgtc atctcacctt gctcctgccg agaaagtatc catcatggct gatgcaatgc    2040
ggcggctgca tacgcttgat ccggctacct gcccattcga ccaccaagcg aaacatcgca    2100
tcgagcgagc acgtactcgg atggaagccg gtcttgtcga tcaggatgat ctggacgaag    2160
agcatcaggg gctcgcgcca gccgaactgt tcgccaggct caaggcgagc atgcccgacg    2220
gcgaggatct cgtcgtgacc catggcgatg cctgcttgcc gaatatcatg gtggaaaatg    2280
gccgcttttc tggattcatc gactgtggcc ggctgggtgt ggcggaccgc tatcaggaca    2340
tagcgttggc tacccgtgat attgctgaag agcttggcgg cgaatgggct gaccgcttcc    2400
tcgtgcttta cggtatcgcc gctcccgatt cgcagcgcat cgccttctat cgccttcttg    2460
acgagttctt ctgaatttttg ttaaaatttt tgttaaatca gctcattttt taaccaatag    2520
gccgaaatcg gcaaatccc ttataaatca aaagaataga ccgagatagg gttgagtgtt    2580
gttccagttt ggaacaagag tccactatta aagaacgtgg actccaacgt caaagggcga    2640
aaaaccgtct atcagggcga tggcccacta cgtgaaccat caccctaatc aagttttttg    2700
gggtcgaggt gccgtaaagc actaaatcgg aaccctaaag ggagccccg atttagagct    2760 tgacggggaa agccggcgaa cgtggcgaga aggaaggga agaaagcgaa aggagcgggc    2820
gctagggcgc tggcaagtgt agcggtcacg ctgcgcgtaa ccaccacacc cgccgcgctt    2880
aatgcgccgc tacagggcgc gtccattcgc cattcaggat cgaattaatt cttaattaac    2940
atcatcaata atataccta ttttggattg aagccaatat gataatgagg gggtggagtt    3000
tgtgacgtgg cgcggggcgt gggaacgggg cgggtgacgt agtagtgtgg cggaagtgtg    3060
atgttgcaag tgtggcggaa cacatgtaag cgacggatgt ggcaaaagtg acgtttttgg    3120
tgtgcgccgg tgtacacagg aagtgacaat tttcgcgcgg ttttaggcgg atgttgtagt    3180
aaatttgggc gtaaccgagt aagatttggc cattttcgcg ggaaaactga ataagaggaa    3240
gtgaaatctg aataattttg tgttactcat agcgcgtaat actgtaatag taatcaatta    3300
cggggtcatt agttcatagc ccatatatgg agttccgcgt tacataactt acggtaaatg    3360
gcccgcctgg ctgaccgccc aacgacccc gcccattgac gtcaataatg acgtatgttc    3420
ccatagtaac gccaataggg actttccatt gacgtcaatg ggtggagtat ttacggtaaa    3480
ctgcccactt ggcagtacat caagtgtatc atatgccaag tacgcccct attgacgtca    3540 atgacggtaa atggcccgcc tggcattatg cccagtacat gaccttatgg gactttccta    3600
cttggcagta catctacgta ttagtcatcg ctattaccat ggtgatgcgg ttttggcagt    3660
acatcaatgg gcgtggatag cggtttgact cacggggatt tccaagtctc caccccattg    3720
acgtcaatgg gagtttgttt tggcaccaaa atcaacggga ctttccaaaa tgtcgtaaca    3780
actccgcccc attgacgcaa atgggcggta ggcgtgtacg gtgggaggtc tatataagca    3840
gagctctccc tatcagtgat agagatctcc ctatcagtga tagagatcgt cgacgagctc    3900
gtttagtgaa ccgtcagatc gcctggagac gccatccacg ctgttttgac ctccatagaa    3960
gacaccggga ccgatccagc ctccgatttg ccaccatgtt tgtgttcctg gtgctgctgc    4020
cactggtgtc cagccagtgt gtgaacctga ccaccaggac ccaacttcct cctgcctaca    4080
ccaactcctt caccaggggga gtctactacc ctgacaaggt gttcaggtcc tctgtgctgc    4140
acagcaccca ggacctgttc ctgccattct tcagcaatgt gacctggttc catgccatcc    4200
```

-continued

```
atgtgtctgg caccaatggc accaagaggt ttgacaaccc tgtgctgcca ttcaatgatg      4260
gagtctactt tgccagcaca gagaagagca acatcatcag gggctggatt tttggcacca      4320
ccctggacag caagacccag tccctgctga ttgtgaacaa tgccaccaat gtggtgatta      4380
aggtgtgtga gttccagttc tgtaatgacc cattcctggg agtctactac cacaagaaca      4440
acaagtcctg gatggagtct gagttcaggg tctactcctc tgccaacaac tgtacctttg      4500
aatatgtgag ccaaccattc ctgatggact ggaggcaa gcagggcaac ttcaagaacc      4560
tgagggagtt tgtgttcaag aacattgatg gctacttcaa gatttacagc aaacacacac      4620
caatcaacct ggtgagggac ctgccacagg gcttctctgc cttggaacca ctggtggacc      4680
tgccaattgg catcaacatc accaggttcc agaccctgct ggctctgcac aggtcctacc      4740
tgacacctgg agactcctcc tctggctgga cagcaggagc agcagcctac tatgtgggct      4800
acctccaacc aaggaccttc ctgctgaaat acaatgagaa tggcaccatc acagatgctg      4860
tggactgtgc cctggaccca ctgtctgaga ccaagtgtac cctgaaatcc ttcacagtgg      4920
agaagggcat ctaccagacc agcaacttca gggtccaacc aacagagagc attgtgaggt      4980
ttccaaacat caccaacctg tgtccatttg gagaggtgtt caatgccacc aggtttgcct      5040
ctgtctatgc ctggaacagg aagaggatta gcaactgtgt ggctgactac tctgtgctct      5100
acaactctgc ctccttcagc accttcaagt gttatggagt gagcccaacc aaactgaatg      5160
acctgtgttt caccaatgtc tatgctgact cctttgtgat taggggagat gaggtgagac      5220
agattgcccc tggacaaaca ggcaagattg ctgactacaa ctacaaactg cctgatgact      5280
tcacaggctg tgtgattgcc tggaacagca acaacctgga cagcaaggtg ggaggcaact      5340
acaactacct ctacagactg ttcaggaaga gcaacctgaa accatttgag agggacatca      5400
gcacagagat ttaccaggct ggcagcacac catgtaatgg agtggagggc ttcaactgtt      5460
actttccact ccaatcctat ggcttccaac caaccaatgg agtgggctac caaccataca      5520
gggtggtggt gctgtccttt gaactgctcc atgcccctgc cacagtgtgt ggaccaaaga      5580
agagcaccaa cctggtgaag aacaagtgtg tgaacttcaa cttcaatgga ctgacaggca      5640
caggagtgct gacagagagc aacaagaagt tcctgccatt ccaacagttt ggcagggaca      5700
ttgctgacac cacagatgct gtgagggacc cacagacctt ggagattctg gacatcacac      5760
catgttcctt tggaggagtg tctgtgatta cacctggcac caacaccagc aaccaggtgg      5820
ctgtgctcta ccaggatgtg aactgtactg aggtgcctgt ggctatccat gctgaccaac      5880
ttacaccaac ctggagggtc tacagcacag gcagcaatgt gttccagacc agggctggct      5940
gtctgattgg agcagagcat gtgaacaact cctatgagtg tgacatccca attggagcag      6000
gcatctgtgc ctcctaccag acccagaccg tggcggtgg tcgaggtct gtggcaagcc      6060 agagcatcat tgcctacaca atgagtctgg gagcagagaa ctctgtggct tacagcaaca      6120
acagcattgc catcccaacc aacttccacc tctctgtgac cacagagatt ctgcctgtga      6180
gtatgaccaa gacctctgtg gactgtacaa tgtatatctg tggagacagc acagagtgta      6240
gcaacctgct gctccaatat ggctccttct gtacccaact taacagggct ctgacaggca      6300
ttgctgtgga acaggacaag aacacccagg aggtgtttgc ccaggtgaag cagatttaca      6360
agacacctcc aatcaaggac tttggaggct tcaacttcag ccagattctg cctgacccaa      6420
gcaagccaag caagaggtcc ttcattgagg acctgctgtt caacaaggtg accctggctg      6480
atgctggctt catcaagcaa tatggagact gtctgggaga cattgctgcc agggacctga      6540
```

-continued

```
tttgtgccca gaagttcaat ggactgacag tgctgcctcc actgctgaca gatgagatga    6600
ttgcccaata cacctctgcc ctgctggctg gcaccatcac ctctggctgg acctttggag    6660
caggagcagc cctccaaatc ccatttgcta tgcagatggc ttacaggttc aatggcattg    6720
gagtgaccca gaatgtgctc tatgagaacc agaaactgat tgccaaccag ttcaactctg    6780
ccattggcaa gattcaggac tccctgtcca gcacagcctc tgccctgggc aaactccaag    6840
atgtggtgaa ccagaatgcc caggctctga cacccctggt gaagcaactt ccagcaact    6900 ttggagccat ctcctctgtg ctgaatgaca tcctgagcag actggacaag gtggaggctg    6960
aggtccagat tgacagactg attacaggca gactccaatc cctccaaacc tatgtgaccc    7020
aacaacttat cagggctgct gagattaggg catctgccaa cctggctgcc accaagatga    7080
gtgagtgtgt gctgggacaa agcaagaggg tggacttctg tggcaagggc taccacctga    7140 tgagtttttcc acagtctgcc cctcatggag tggtgttcct gcatgtgacc tatgtgcctg    7200
cccaggagaa gaacttcacc acagcccctg ccatctgcca tgatggcaag gctcactttc    7260
caagggaggg agtgtttgtg agcaatggca cccactggtt tgtgacccag aggaacttct    7320
atgaaccaca gattatcacc acagacaaca cctttgtgtc tggcaactgt gatgtggtga    7380
ttggcattgt gaacaacaca gtctatgacc cactccaacc tgaactggac tccttcaagg    7440
aggaactgga caaatacttc aagaaccaca ccagccctga tgtggacctg ggagacatct    7500
ctggcatcaa tgcctctgtg gtgaacatcc agaaggagat tgacagactg aatgaggtgg    7560
ctaagaacct gaatgagtcc ctgattgacc tccaagaact gggcaaatat gaacaataca    7620
tcaagtggcc atgaaaattg atcataatca gccataccac atttgtagag gttttacttg    7680
ctttaaaaaa cctcccacac ctccccctga acctgaaaca taaaatgaat gcaattgttg    7740
ttgttaactt gtttattgca gcttataatg gttacaaata aagcaatagc atcacaaatt    7800
tcacaaataa agcattttttt tcactgcatt ctagttgtgg tttgtccaaa ctcatcaatg    7860
tatcttaacg cggatctggg cgtggttaag ggtgggaaag aatatataag gtgggggtct    7920
tatgtagttt tgtatctgtt ttgcagcagc cgccgccgcc atgagcacca actcgtttga    7980
tggaagcatt gtgagctcat atttgacaac gcgcatgccc ccatgggccg gggtgcgtca    8040
gaatgtgatg ggctccagca ttgatggtcg ccccgtcctg cccgcaaact ctactacctt    8100
gacctacgag accgtgtctg gaacgccgtt ggagactgca gcctccgccg ccgcttcagc    8160
cgctgcagcc accgccgcg ggattgtgac tgactttgct ttcctgagcc cgcttgcaag    8220
cagtgcagct tcccgttcat ccgcccgcga tgacaagttg acggctcttt tggcacaatt    8280
ggattctttg acccgggaac ttaatgtcgt ttctcagcag ctgttggatc tgcgccagca    8340
ggtttctgcc ctgaaggctt cctcccctcc caatgcggtt taaaacataa ataaaaaacc    8400
agactctgtt tggatttgga tcaagcaagt gtcttgctgt ctttatttag gggttttgcg    8460
cgcgcggtag gcccgggacc agcggtctcg gtcgttgagg tcctgtgtta ttttttccag    8520
gacgtggtaa aggtgactct ggatgttcag atacatgggc ataagcccgt ctctggggtg    8580
gaggtagcac cactgcagag cttcatgctg cggggtggtg ttgtagatga tccagtcgta    8640
gcaggagcgc tgggcgtggt gcctaaaaat gtctttcagt agcaagctga ttgccagggg    8700
caggcccttg gtgtaagtgt ttacaaagcg gttaagctgg gatgggtgca tacgtgggga    8760
tatgagatgc atcttggact gtattttttag gttggctatg ttcccagcca tatccctccg    8820
gggattcatg ttgtgcagaa ccaccagcac agtgtatccg gtgcacttgg gaaatttgtc    8880
atgtagctta gaaggaaatg cgtggaagaa cttggagacg cccttgtgac ctccaagatt    8940
```

-continued

```
ttccatgcat tcgtccataa tgatggcaat gggcccacgg gcggcggcct gggcgaagat    9000
atttctggga tcactaacgt catagttgtg ttccaggatg agatcgtcat aggccatttt    9060
tacaaagcgc gggcggaggg tgccagactg cggtataatg gttccatccg gcccaggggc    9120
gtagttaccc tcacagattt gcatttccca cgctttgagt tcagatgggg ggatcatgtc    9180
tacctgcggg gcgatgaaga aaacggtttc cggggtaggg gagatcagct gggaagaaag    9240
caggttcctg agcagctgcg acttaccgca gccggtgggc ccgtaaatca cacctattac    9300
cggctgcaac tggtagttaa gagagctgca gctgccgtca tccctgagca gggggggccac    9360 ttcgttaagc atgtccctga ctcgcatgtt ttccctgacc aaatccgcca gaaggcgctc    9420
gccgcccagc gatagcagtt cttgcaagga agcaaagttt ttcaacggtt tgagaccgtc    9480
cgccgtaggc atgcttttga gcgtttgacc aagcagttcc aggcggtccc acagctcggt    9540
cacctgctct acggcatctc gatccagcat atctcctcgt ttcgcgggtt ggggcggctt    9600
tcgctgtacg gcagtagtcg gtgctcgtcc agacgggcca gggtcatgtc tttccacggg    9660
cgcagggtcc tcgtcagcgt agtctgggtc acggtgaagg ggtgcgctcc gggctgcgcg    9720
ctggccaggt tgcgcttgag gctggtcctg ctggtgctga agcgctgccg gtcttcgccc    9780
tgcgcgtcgg ccaggtagca tttgaccatg gtgtcatagt ccagcccctc cgcggcgtgg    9840
cccttggcgc gcagcttgcc cttggaggag gcgccgcacg aggggcagtg cagacttttg    9900
agggcgtaga gcttgggcgc gagaaatacc gattccgggg agtaggcatc cgcgccgcag    9960
gccccgcaga cggtctcgca ttccacgagc caggtgagct ctggccgttc ggggtcaaaa    10020
accaggtttc ccccatgctt tttgatgcgt ttcttacctc tggtttccat gagccggtgt    10080
ccacgctcgg tgacgaaaag gctgtccgtg tccccgtata cagacttgag aggcctgtcc    10140
tcgagcggtg ttccgcggtc ctcctcgtat agaaactcgg accactctga gacaaaggct    10200
cgcgtccagg ccagcacgaa ggaggctaag tgggaggggt agcggtcgtt gtccactagg    10260
gggtccactc gctccagggt gtgaagacac atgtcgccct cttcggcatc aaggaaggtg    10320
attggtttgt aggtgtaggc cacgtgaccg ggtgttcctg aagggggget ataaaagggg    10380 gtgggggcgc gttcgtcctc actctcttcc gcatcgctgt ctgcgagggc cagctgttgg    10440
ggtgagtact ccctctgaaa agcgggcatg acttctgcgc taagattgtc agtttccaaa    10500
aacgaggagg atttgatatt cacctggccc gcggtgatgc ctttgagggt ggccgcatcc    10560
atctggtcag aaaagacaat cttttttgttg tcaagcttgg tggcaaacga cccgtagagg    10620
gcgttggaca gcaacttggc gatggagcgc agggtttggt ttttgtcgcg atcggcgcgc    10680
tccttggccg cgatgtttag ctgcacgtat tcgcgcgcaa cgcaccgcca ttcgggaaag    10740
acggtggtgc gctcgtcggg caccaggtgc acgcgccaac cgcggttgtg cagggtgaca    10800
aggtcaacgc tggtggctac ctctccgcgt aggcgctcgt tggtccagca gaggcggccg    10860
cccttgcgcg agcagaatgg cggtagggggg tctagctgcg tctcgtccgg ggggtctgcg    10920
tccacggtaa agaccccggg cagcaggcgc gcgtcgaagt agtctatctt gcatccttgc    10980
aagtctagcg cctgctgcca tgcgcggggcg gcaagcgcgc gctcgtatgg gttgagtggg    11040
ggaccccatg gcatggggtg ggtgagcgcg gaggcgtaca tgccgcaaat gtcgtaaacg    11100
tagaggggct ctctgagtat tccaagatat gtagggtagc atcttccacc gcggatgctg    11160
gcgcgcacgt aatcgtatag ttcgtgcgag ggagcgagga ggtcgggacc gaggttgcta    11220
cgggcgggct gctctgctcg gaagactatc tgcctgaaga tggcatgtga gttggatgat    11280
```

-continued

```
atggttggac gctggaagac gttgaagctg gcgtctgtga gacctaccgc gtcacgcacg    11340
aaggaggcgt aggagtcgcg cagcttgttg accagctcgg cggtgacctg cacgtctagg    11400
gcgcagtagt ccagggtttc cttgatgatg tcatacttat cctgtccctt tttttttccac   11460 agctcgcggt tgaggacaaa ctcttcgcgg tctttccagt actcttggat cggaaacccg    11520
tcggcctccg aacggtaaga gcctagcatg tagaactggt tgacggcctg gtaggcgcag    11580
catccctttt ctacgggtag cgcgtatgcc tgcgcggcct tccggagcga ggtgtgggtg    11640
agcgcaaagg tgtccctgac catgactttg aggtactggt atttgaagtc agtgtcgtcg    11700
catccgccct gctcccagag caaaaagtcc gtgcgctttt tggaacgcgg atttggcagg    11760
gcgaaggtga catcgttgaa gagtatcttt cccgcgcgag gcataaagtt gcgtgtgatg    11820
cggaagggtc ccggcacctc ggaacggttg ttaattacct gggcggcgag cacgatctcg    11880
tcaaagccgt tgatgttgtg gcccacaatg taaagttcca agaagcgcgg gatgcccttg    11940
atggaaggca attttttaag ttcctcgtag gtgagctctt caggggagct gagcccgtgc    12000
tctgaaaggg cccagtctgc aagatgaggg ttggaagcga cgaatgagct ccacaggtca    12060
cgggccatta gcatttgcag gtggtcgcga aaggtcctaa actggcgacc tatggccatt    12120
ttttctgggg tgatgcagta gaaggtaagc gggtcttgtt cccagcggtc ccatccaagg    12180
ttcgcggcta ggtctcgcgc ggcagtcact agaggctcat ctccgccgaa cttcatgacc    12240
agcatgaagg gcacgagctg cttcccaaag gcccccatcc aagtataggt ctctacatcg    12300
taggtgacaa agagacgctc ggtgcgagga tgcgagccga tcgggaagaa ctggatctcc    12360
cgccaccaat tggaggagtg gctattgatg tggtgaaagt agaagtccct gcgacgggcc    12420
gaacactcgt gctggctttt gtaaaaacgt gcgcagtact ggcagcggtg cacgggctgt    12480
acatcctgca cgaggttgac ctgacgaccg cgcacaagga agcagagtgg gaatttgagc    12540
ccctcgcctg gcgggtttgg ctggtggtct tctacttcgg ctgcttgtcc ttgaccgtct    12600
ggctgctcga ggggagttac ggtggatcgg accaccacgc cgcgcgagcc caaagtccag    12660
atgtccgcgc gcggcggtcg gagcttgatg acaacatcgc gcagatggga gctgtccatg    12720
gtctggagct cccgcggcgt caggtcaggc gggagctcct gcaggtttac ctcgcataga    12780
cgggtcaggg cgcgggctag atccaggtga tacctaattt ccaggggctg gttggtggcg    12840
gcgtcgatgg cttgcaagag gccgcatccc cgcggcgcga ctacggtacc gcgcggcggg    12900
cggtgggccg cgggggtgtc cttggatgat gcatctaaaa gcggtgacgc gggcgagccc    12960
ccggaggtag ggggggctcc ggacccgccg ggagagggg cagggcacg tcggcgccgc     13020 gcgcgggcag gagctggtgc tgcgcgcgta ggttgctggc gaacgcgacg acgcggcggt    13080
tgatctcctg aatctggcgc ctctgcgtga agacgacggg cccggtgagc ttgaacctga    13140
aagagagttc gacagaatca atttcggtgt cgttgacggc ggcctggcgc aaaatctcct    13200
gcacgtctcc tgagttgtct tgataggcga tctcggccat gaactgctcg atctcttcct    13260
cctggagatc tccgcgtccg gctcgctcca cggtggcggc gaggtcgttg gaaatgcggg    13320
ccatgagctg cgagaaggcg ttgaggcctc cctcgttcca gacgcggctg tagaccacgc    13380
ccccttcggc atcgcgggcg cgcatgacca cctgcgcgag attgagctcc acgtgccggg    13440
cgaagacggc gtagtttcgc aggcgctgaa agaggtagtt gagggtggtg gcggtgtgtt    13500
ctgccacgaa gaagtacata acccagcgtc gcaacgtgga ttcgttgata tcccccaagg    13560
cctcaaggcg ctccatggcc tcgtagaagt ccacggcgaa gttgaaaaac tgggagttgc    13620
gcgccgacac ggttaactcc tcctccagaa gacggatgag ctcggcgaca gtgtcgcgca    13680
```

```
cctcgcgctc aaaggctaca ggggcctctt cttcttcttc aatctcctct tccataaggg   13740
cctccccttc ttcttcttct ggcggcggtg ggggagggg gacacggcgg cgacgacggc    13800
gcaccgggag gcggtcgaca aagcgctcga tcatctcccc gcggcgacgg cgcatggtct    13860
cggtgacggc gcggccgttc tcgcggggc gcagttggaa gacgccgccc gtcatgtccc     13920
ggttatgggt tggcggggg ctgccatgcg gcagggatac ggcgctaacg atgcatctca     13980
acaattgttg tgtaggtact ccgccgccga gggacctgag cgagtccgca tcgaccggat     14040
cggaaaacct ctcgagaaag gcgtctaacc agtcacagtc gcaaggtagg ctgagcaccg    14100
tggcgggcgg cagcgggcgg cggtcggggt tgtttctggc ggaggtgctg ctgatgatgt    14160
aattaaagta ggcggtcttg agacggcgga tggtcgacag aagcaccatg tccttgggtc    14220
cggcctgctg aatgcgcagg cggtcggcca tgccccaggc ttcgttttga catcggcgca    14280
ggtctttgta gtagtcttgc atgagccttt ctaccggcac ttcttcttct ccttcctctt    14340
gtcctgcatc tcttgcatct atcgctgcg cggcggcgga gtttggccgt aggtggcgcc     14400
ctcttcctcc catgcgtgtg accccgaagc ccctcatcgg ctgaagcagg gctaggtcgg    14460
cgacaacgcg ctcggctaat atggcctgct gcacctgcgt gagggtagac tggaagtcat    14520
ccatgtccac aaagcggtgg tatgcgcccg tgttgatggt gtaagtgcag ttggccataa    14580
cggaccagtt aacggtctgg tgacccggct gcgagagctc ggtgtacctg agacgcgagt    14640
aagccctcga gtcaaatacg tagtcgttgc aagtccgcac caggtactgg tatcccacca    14700
aaaagtgcgg cggcggctgg cggtagaggg gccagcgtag ggtggccggg gctccggggg    14760
cgagatcttc caacataagg cgatgatatc cgtagatgta cctggacatc caggtgatgc    14820
cggcggcggt ggtggaggcg cgcggaaagt cgcggacgcg gttccagatg ttgcgcagcg    14880
gcaaaaagtg ctccatggtc gggacgctct ggccggtcag gcgcgcgcaa tcgttgacgc    14940
tctagcgtgc aaaaggagag cctgtaagcg ggcactcttc cgtggtctgg tggataaatt    15000
cgcaagggta tcatggcgga cgaccggggt tcgagccccg tatccggccg tccgccgtga    15060
tccatgcggt taccgcccgc gtgtcgaacc caggtgtgcg acgtcagaca acggggagt     15120 gctccttttg gcttccttcc aggcgcggcg gctgctgcgc tagctttttt ggccactggc    15180
cgcgcgcagc gtaagcggtt aggctggaaa gcgaaagcat taagtggctc gctccctgta    15240
gccggagggt tattttccaa gggttgagtc gcgggacccc cggttcgagt ctcggaccgg    15300
ccggactgcg gcgaacgggg gtttgcctcc ccgtcatgca agaccccgct tgcaaattcc    15360
tccggaaaca gggacgagcc ccttttttgc ttttcccaga tgcatccggt gctgcggcag    15420
atgcgccccc ctcctcagca gcggcaagag caagagcagc ggcagacatg cagggcaccc    15480
tcccctcctc ctaccgcgtc aggaggggcg acatccgcgg ttgacgcggc agcagatggt    15540
gattacgaac ccccgcggcg ccgggcccgg cactacctgg acttggagga gggcgagggc    15600
ctggcgcggc taggagcgcc ctctcctgag cggcacccaa gggtgcagct gaagcgtgat    15660
acgcgtgagg cgtacgtgcc gcggcagaac ctgtttcgcg accgcgaggg agaggagccc    15720
gaggagatgc gggatcgaaa gttccacgca gggcgcgagc tgcggcatgg cctgaatcgc    15780
gagcggttgc tgcgcgagga ggactttgag cccgacgcg gaaccgggat tagtcccgcg     15840
cgcgcacacg tggcggccgc cgacctggta accgcatacg agcagacggt gaaccaggag    15900
attaactttc aaaaaagctt taacaaccac gtgcgtacgc ttgtggcgcg cgaggaggtg    15960
gctataggac tgatgcatct gtgggacttt gtaagcgcgc tggagcaaaa cccaaatagc    16020
```

-continued

```
aagccgctca tggcgcagct gttccttata gtgcagcaca gcagggacaa cgaggcattc   16080
agggatgcgc tgctaaacat agtagagccc gagggccgct ggctgctcga tttgataaac   16140
atcctgcaga gcatagtggt gcaggagcgc agcttgagcc tggctgacaa ggtggccgcc   16200
atcaactatt ccatgcttag cctgggcaag ttttacgccc gcaagatata ccatacccct   16260
tacgttccca tagacaagga ggtaaagatc gaggggttct acatgcgcat ggcgctgaag   16320
gtgcttacct tgagcgacga cctgggcgtt tatcgcaacg agcgcatcca caaggccgtg   16380
agcgtgagcc ggcggcgcga gctcagcgac cgcgagctga tgcacagcct gcaaagggcc   16440
ctggctggca cgggcagcgg cgatagagag gccgagtcct actttgacgc gggcgctgac   16500
ctgcgctggg ccccaagccg acgcgccctg gaggcagctg gggccggacc tgggctggcg   16560
gtggcacccg cgcgcgctgg caacgtcggc ggcgtggagg aatatgacga ggacgatgag   16620
tacgagccag aggacggcga gtactaagcg gtgatgtttc tgatcagatg atgcaagacg   16680
caacggaccc ggcggtgcgg gcggcgctgc agagccagcc gtccggcctt aactccacgg   16740
acgactggcg ccaggtcatg gaccgcatca tgtcgctgac tgcgcgcaat cctgacgcgt   16800
tccggcagca gccgcaggcc aaccggctct ccgcaattct ggaagcggtg gtcccggcgc   16860
gcgcaaaccc cacgcacgag aaggtgctgg cgatcgtaaa cgcgctggcc gaaaacaggg   16920
ccatccggcc cgacgaggcc ggcctggtct acgacgcgct gcttcagcgc gtggctcgtt   16980
acaacagcgg caacgtgcag accaacctgg accggctggt gggggatgtg cgcgaggccg   17040
tggcgcagcg tgagcgcgcg cagcagcagg gcaacctggg ctccatggtt gcactaaacg   17100
ccttcctgag tacacagccc gccaacgtgc cgcggggaca ggaggactac accaactttg   17160
tgagcgcact gcggctaatg gtgactgaga caccgcaaag tgaggtgtac cagtctgggc   17220
cagactattt tttccagacc agtagacaag gcctgcagac cgtaaacctg agccaggctt   17280
tcaaaaactt gcagggggctg tgggggggtgc gggctcccac aggcgaccgc gcgaccgtgt   17340
ctagcttgct gacgcccaac tcgcgcctgt tgctgctgct aatagcgccc ttcacggaca   17400
gtggcagcgt gtcccgggac acataccctag gtcacttgct gacactgtac cgcgaggcca   17460
taggtcaggc gcatgtggac gagcatactt tccaggagat tacaagtgtc agccgcgcgc   17520
tggggcagga ggacacgggc agcctggagg caaccctaaa ctacctgctg accaaccggc   17580
ggcagaagat cccctcgttg cacagtttaa acagcgagga ggagcgcatt ttgcgctacg   17640
tgcagcagag cgtgagcctt aacctgatgc gcgacggggt aacgcccagc gtggcgctgg   17700
acatgaccgc gcgcaacatg gaaccgggca tgtatgcctc aaaccggccg tttatcaacc   17760
gcctaatgga ctacttgcat cgcgcggccg ccgtgaaccc cgagtatttc accaatgcca   17820
tcttgaaccc gcactggcta ccgcccctg gtttctacac cggggattc gaggtgcccg   17880 agggtaacga tggattcctc tgggacgaca tagacgacag cgtgtttttcc ccgcaaccgc   17940 agacctgct agagttgcaa cagcgcgagc aggcagaggc ggcgctgcga aaggaaagct   18000
tccgcaggcc aagcagcttg tccgatctag cgctgcggc cccgcggtca gatgctagta   18060
gcccatttcc aagcttgata gggtctctta ccagcactcg caccacccgc ccgcgcctgc   18120
tgggcgagga ggagtaccta aacaactcgc tgctgcagcc gcagcgcgaa aaaaacctgc   18180
ctccggcatt tcccaacaac gggatagaga gcctagtgga caagatgagt agatggaaga   18240
cgtacgcgca ggagcacagg gacgtgccag gcccgcgccc gcccacccgt cgtcaaaggc   18300
acgaccgtca gcggggtctg gtgtgggagg acgatgactc ggcagacgac agcagcgtcc   18360
tggatttggg agggagtggc aacccgtttg cgcaccttcg ccccaggctg gggagaatgt   18420
```

-continued

```
tttaaaaaaa aaaaagcatg atgcaaaata aaaaactcac caaggccatg gcaccgagcg   18480 ttggtttttct tgtattcccc ttagtatgcg gcgcgcggcg atgtatgagg aaggtcctcc   18540
tccctcctac gagagtgtgg tgagcgcggc gccagtggcg gcggcgctgg gttctccctt   18600
cgatgctccc ctggacccgc cgtttgtgcc tccgcggtac ctgcggccta ccggggggag   18660
aaacagcatc cgttactctg agttggcacc cctattcgac accacccgtg tgtacctggt   18720
ggacaacaag tcaacggatg tggcatccct gaactaccag aacgaccaca gcaactttct   18780
gaccacggtc attcaaaaca atgactacag cccggggggag gcaagcacac agaccatcaa   18840
tcttgacgac cggtcgcact ggggcggcga cctgaaaacc atcctgcata ccaacatgcc   18900
aaatgtgaac gagttcatgt ttaccaataa gtttaaggcg cgggtgatgg tgtcgcgctt   18960
gcctactaag gacaatcagg tggagctgaa atacgagtgg gtggagttca cgctgcccga   19020
gggcaactac tccgagacca tgaccataga ccttatgaac aacgcgatcg tggagcacta   19080
cttgaaagtg ggcagacaga acggggttct ggaaagcgac atcggggtaa agtttgacac   19140
ccgcaacttc agactggggt ttgaccccgt cactggtctt gtcatgcctg gggtatatac   19200
aaacgaagcc ttccatccag acatcatttt gctgccagga tgcggggtgg acttcaccca   19260
cagccgcctg agcaacttgt tgggcatccg caagcggcaa cccttccagg agggctttag   19320
gatcacctac gatgatctgg agggtggtaa cattcccgca ctgttggatg tggacgccta   19380
ccaggcgagc ttgaaagatg acaccgaaca gggcgggggt ggcgcaggcg gcagcaacag   19440
cagtggcagc ggcgcggaag agaactccaa cgcggcagcc gcggcaatgc agccggtgga   19500
ggacatgaac gatcatgcca ttcgcggcga caccttttgcc acacgggctg aggagaagcg   19560
cgctgaggcc gaagcagcgg ccgaagctgc cgcccccgct gcgcaacccg aggtcgagaa   19620
gcctcagaag aaaccggtga tcaaacccct gacagaggac agcaagaaac gcagttacaa   19680
cctaataagc aatgacagca ccttcacccca gtaccgcagc tggtaccttg catacaacta   19740
cggcgaccct cagaccggaa tccgctcatg gaccctgctt tgcactcctg acgtaacctg   19800
cggctcggag caggtctact ggtcgttgcc agacatgatg caagaccccg tgaccttccg   19860
ctccacgcgc cagatcagca actttccggt ggtgggcgcc gagctgttgc ccgtgcactc   19920
caagagcttc tacaacgacc aggccgtcta ctcccaactc atccgccagt ttacctctct   19980
gacccacgtg ttcaatcgct ttcccgagaa ccagattttg gcgcgcccgc cagccccac   20040 catcaccacc gtcagtgaaa acgttcctgc tctcacagat cacgggacgc taccgctgcg   20100
caacagcatc ggaggagtcc agcgagtgac cattactgac gccagacgcc gcacctgccc   20160
ctacgtttac aaggccctgg gcatagtctc gccgcgcgtc ctatcgagcc gcacttttttg   20220 agcaagcatg tccatcctta tatcgcccag caataacaca ggctggggcc tgcgcttccc   20280
aagcaagatg tttggcgggg ccaagaagcg ctccgaccaa cacccagtgc gcgtgcgcgg   20340
gcactaccgc gcgccctggg gcgcgcacaa acgcggccgc actgggcgca ccaccgtcga   20400
tgacgccatc gacgcggtgg tggaggaggc gcgcaactac acgcccacgc cgccaccagt   20460
gtccacagtg gacgcggcca ttcagaccgt ggtgcgcgga gcccggcgct atgctaaaat   20520
gaagagacgg cggaggcgcg tagcacgtcg ccaccgccgc cgacccggca ctgccgccca   20580
acgcgcggcg gcggccctgc ttaaccgcgc acgtcgcacc ggccgacggg cggccatgcg   20640
ggccgctcga aggctggccg cgggtattgt cactgtgccc cccaggtcca ggcgacgagc   20700
ggccgccgca gcagccgcgg ccattagtgc tatgactcag ggtcgcaggg gcaacgtgta   20760
```

-continued

```
ttgggtgcgc gactcggtta gcggcctgcg cgtgcccgtg cgcacccgcc ccccgcgcaa   20820
ctagattgca agaaaaaact acttagactc gtactgttgt atgtatccag cggcggcggc   20880
gcgcaacgaa gctatgtcca agcgcaaaat caaagaagag atgctccagg tcatcgcgcc   20940
ggagatctat ggccccccga agaaggaaga gcaggattac aagccccgaa agctaaagcg   21000
ggtcaaaaag aaaaagaaag atgatgatga tgaacttgac gacgaggtgg aactgctgca   21060
cgctaccgcg cccaggcgac gggtacagtg gaaaggtcga cgcgtaaaac gtgttttgcg   21120
acccggcacc accgtagtct ttacgcccgg tgagcgctcc acccgcacct acaagcgcgt   21180
gtatgatgag gtgtacggcg acgaggacct gcttgagcag gccaacgagc gcctcgggga   21240
gtttgcctac ggaaagcggc ataaggacat gctggcgttg ccgctggacg agggcaaccc   21300
aacacctagc ctaaagcccg taacactgca gcaggtgctg cccgcgcttg caccgtccga   21360
agaaaagcgc ggcctaaagc gcgagtctgg tgacttggca cccaccgtgc agctgatggt   21420
acccaagcgc cagcgactgg aagatgtctt ggaaaaaatg accgtggaac ctgggctgga   21480
gcccgaggtc cgcgtgcggc caatcaagca ggtggcgccg ggactgggcg tgcagaccgt   21540
ggacgttcag ataccccacta ccagtagcac cagtattgcc accgccacag agggcatgga   21600
gacacaaacg tccccggttg cctcagcggt ggcggatgcc gcggtgcagg cggtcgctgc   21660
ggccgcgtcc aagacctcta cggaggtgca aacggacccg tggatgtttc gcgtttcagc   21720
cccccggcgc ccgcgccgtt cgaggaagta cggcgccgcc agcgcgctac tgcccgaata   21780
tgccctacat ccttccattg cgcctacccc cggctatcgt ggctacacct accgccccag   21840
aagacgagca actaccccgac gccgaaccac cactggaacc cgccgccgcc gtcgccgtcg   21900
ccagcccgtg ctggccccga tttccgtgcg cagggtggct cgcgaaggag gcaggaccct   21960
ggtgctgcca acagcgcgct accaccccag catcgtttaa aagccggtct ttgtggttct   22020
tgcagatatg gccctcacct gccgcctccg tttcccggtg ccgggattcc gaggaagaat   22080
gcaccgtagg aggggcatgg ccggccacgg cctgacgggc ggcatgcgtc gtgcgcacca   22140
ccggcggcgg cgcgcgtcgc accgtcgcat gcgcggcggt atcctgcccc tccttattcc   22200
actgatcgcc gcggcgattg gcgccgtgcc cggaattgca tccgtggcct tgcaggcgca   22260
gagacactga ttaaaaacaa gttgcatgtg gaaaaatcaa aataaaaagt ctggactctc   22320
acgctcgctt ggtcctgtaa ctattttgta gaatggaaga catcaacttt gcgtctctgg   22380
ccccgcgaca cggctcgcgc ccgttcatgg gaaactggca agatatcggc accagcaata   22440
tgagcggtgg cgccttcagc tggggctcgc tgtggagcgg cattaaaaat ttcggttcca   22500
ccgttaagaa ctatggcagc aaggcctgga acagcagcac aggccagatg ctgagggata   22560
agttgaaaga gcaaaatttc caacaaaagg tggtagatgg cctggcctct ggcattagcg   22620
gggtggtgga cctggccaac caggcagtgc aaaataagat taacagtaag cttgatcccc   22680
gccctcccgt agaggagcct ccaccggccg tggagacagt gtctccagag gggcgtggcg   22740
aaaagcgtcc gcgccccgac agggaagaaa ctctggtgac gcaaatagac gagcctccct   22800
cgtacgagga ggcactaaag caaggcctgc ccaccacccg tcccatcgcg cccatggcta   22860
ccggagtgct gggccagcac acacccgtaa cgctggacct gcctcccccc gccgacaccc   22920
agcagaaacc tgtgctgcca ggcccgaccg ccgttgttgt aacccgtcct agccgcgcgt   22980
ccctgcgccg cgccgccagc ggtccgcgat cgttgcggcc cgtagccagt ggcaactggc   23040
aaagcacact gaacagcatc gtgggtctgg gggtgcaatc cctgaagcgc cgacgatgct   23100
tctgatagct aacgtgtcgt atgtgtgtca tgtatgcgtc catgtcgccg ccagaggagc   23160
```

-continued

```
tgctgagccg ccgcgcgccc gctttccaag atggctaccc cttcgatgat gccgcagtgg    23220
tcttacatgc acatctcggg ccaggacgcc tcggagtacc tgagccccgg gctggtgcag    23280
tttgcccgcg ccaccgagac gtacttcagc ctgaataaca agtttagaaa ccccacggtg    23340
gcgcctacgc acgacgtgac cacagaccgg tcccagcgtt tgacgctgcg gttcatccct    23400
gtggaccgtg aggatactgc gtactcgtac aaggcgcggt tcaccctagc tgtgggtgat    23460
aaccgtgtgc tggacatggc ttccacgtac tttgacatcc gcggcgtgct ggacaggggc    23520
cctactttta agccctactc tggcactgcc tacaacgccc tggctcccaa gggtgcccca    23580
aatccttgcg aatgggatga agctgctact gctcttgaaa taaacctaga agaagaggac    23640
gatgacaacg aagacgaagt agacgagcaa gctgagcagc aaaaaactca cgtatttggg    23700
caggcgcctt attctggtat aaatattaca aaggagggta ttcaaatagg tgtcgaaggt    23760
caaacaccta aatatgccga taaaacattt caacctgaac ctcaaatagg agaatctcag    23820
tggtacgaaa cagaaattaa tcatgcagct gggagagtcc taaaaaagac taccccaatg    23880
aaaccatgtt acggttcata tgcaaaccc acaaatgaaa atggagggca aggcattctt    23940
gtaaagcaac aaaatggaaa gctagaaagt caagtggaaa tgcaattttt ctcaactact    24000
gaggcagccg caggcaatgg tgataacttg actcctaaag tggtattgta cagtgaagat    24060
gtagatatag aaaccccaga cactcatatt tcttacatgc ccactattaa ggaaggtaac    24120
tcacgagaac taatgggcca acaatctatg cccaacaggc ctaattacat tgctttttagg    24180 gacaatttta ttggtctaat gtattacaac agcacgggta atatgggtgt tctggcgggc    24240
caagcatcgc agttgaatgc tgttgtagat ttgcaagaca gaaacacaga gctttcatac    24300
cagcttttgc ttgattccat tggtgataga accaggtact tttctatgtg gaatcaggct    24360
gttgacagct atgatccaga tgttagaatt attgaaaatc atggaactga agatgaactt    24420
ccaaattact gctttccact gggaggtgtg attaatacag agactcttac caaggtaaaa    24480
cctaaaacag gtcaggaaaa tggatgggaa aaagatgcta cagaatttc agataaaaat    24540 gaaataagag ttggaaataa ttttgccatg gaaatcaatc taaatgccaa cctgtggaga    24600
aatttcctgt actccaacat agcgctgtat ttgcccgaca agctaaagta cagtccttcc    24660
aacgtaaaaa tttctgataa cccaaacacc tacgactaca tgaacaagcg agtggtggct    24720
cccgggctag tggactgcta cattaacctt ggagcacgct ggtcccttga ctatatggac    24780
aacgtcaacc catttaacca ccaccgcaat gctggcctgc gctaccgctc aatgttgctg    24840
ggcaatggtc gctatgtgcc cttccacatc caggtgcctc agaagttctt tgccattaaa    24900
aacctccttc tcctgccggg ctcatacacc tacgagtgga acttcaggaa ggatgttaac    24960
atggttctgc agagctccct aggaaatgac ctaaggggttg acggagccag cattaagttt    25020
gatagcattt gcctttacgc caccttcttc cccatggccc acaacaccgc ctccacgctt    25080
gaggccatgc ttagaaacga caccaacgac cagtcccttta acgactatct ctccgccgcc    25140
aacatgctct accctataccc cgccaacgct accaacgtgc ccatatccat cccctcccgc    25200
aactgggcgg ctttccgcgg ctgggccttc acgcgcctta agactaagga aaccccatca    25260
ctgggctcgg gctacgaccc ttattacacc tactctggct ctatacccta cctagatgga    25320 acctttttacc tcaaccacac ctttaagaag gtggccatta cctttgactc ttctgtcagc    25380
tggcctggca atgaccgcct gcttaccccc aacgagtttg aaattaagcg ctcagttgac    25440
ggggagggtt acaacgttgc ccagtgtaac atgaccaaag actggttcct ggtacaaatg    25500
```

-continued

```
ctagctaact ataacattgg ctaccagggc ttctatatcc cagagagcta caaggaccgc   25560
atgtactcct tctttagaaa cttccagccc atgagccgtc aggtggtgga tgatactaaa   25620
tacaaggact accaacaggt gggcatccta caccaacaca acaactctgg atttgttggc   25680
taccttgccc ccaccatgcg cgaaggacag gcctaccctg ctaacttccc ctatccgctt   25740
ataggcaaga ccgcagttga cagcattacc cagaaaaagt ttctttgcga tcgcaccctt   25800
tggcgcatcc cattctccag taactttatg tccatgggcg cactcacaga cctgggccaa   25860
aaccttctct acgccaactc cgcccacgcg ctagacatga cttttgaggt ggatcccatg   25920
gacgagccca cccttcttta tgtttttgttt gaagtctttg acgtggtccg tgtgcaccag   25980
ccgcaccgcg gcgtcatcga aaccgtgtac ctgcgcacgc ccttctcggc cggcaacgcc   26040
acaacataaa gaagcaagca acatcaacaa cagctgccgc catgggctcc agtgagcagg   26100
aactgaaagc cattgtcaaa gatcttggtt gtgggccata ttttttgggc acctatgaca   26160
agcgctttcc aggctttgtt tctccacaca agctcgcctg cgccatagtc aatacggccg   26220
gtcgcgagac tgggggcgta cactggatgg cctttgcctg gaacccgcac tcaaaaacat   26280
gctacctctt tgagcccttt ggcttttctg accagcgact caagcaggtt taccagtttg   26340
agtacgagtc actcctgcgc cgtagcgcca ttgcttcttc ccccgaccgc tgtataacgc   26400
tggaaaagtc cacccaaagc gtacaggggc ccaactcggc cgcctgtgga ctattctgct   26460
gcatgtttct ccacgccttt gccaactggc cccaaactcc catggatcac aaccccacca   26520
tgaaccttat taccggggta cccaactcca tgctcaacag tccccaggta cagcccaccc   26580
tgcgtcgcaa ccaggaacag ctctacagct tcctggagcg ccactcgccc tacttccgca   26640
gccacagtgc gcagattagg agcgccactt cttttgtca cttgaaaaac atgtaaaaat   26700
aatgtactag agacactttc aataaaggca aatgctttta tttgtacact ctcgggtgat   26760
tatttacccc caccccttgcc gtctgcgccg tttaaaaatc aaaggggttc tgccgcgcat   26820
cgctatgcgc cactggcagg gacacgttgc gatactggtg tttagtgctc cacttaaact   26880
caggcacaac catccgcggc agctcggtga agttttcact ccacaggctg cgcaccatca   26940
ccaacgcgtt tagcaggtcg ggcgccgata tcttgaagtc gcagttgggg cctccgccct   27000
gcgcgcgcga gttgcgatac acagggttgc agcactggaa cactatcagc gccgggtggt   27060
gcacgctggc cagcacgctc ttgtcggaga tcagatccgc gtccaggtcc tccgcgttgc   27120
tcagggcgaa cggagtcaac tttggtagct gccttcccaa aaagggcgcg tgcccaggct   27180
ttgagttgca ctcgcaccgt agtggcatca aaaggtgacc gtgcccggtc tgggcgttag   27240
gatacagcgc ctgcataaaa gccttgatct gcttaaaagc cacctgagcc tttgcgcctt   27300
cagagaagaa catgccgcaa gacttgccgg aaaactgatt ggccggacag gccgcgtcgt   27360
gcacgcagca ccttgcgtcg gtgttggaga tctgcaccac atttcggccc caccggttct   27420
tcacgatctt ggccttgcta gactgctcct tcagcgcgcg ctgcccgttt tcgctcgtca   27480
catccatttc aatcacgtgc tccttatttta tcataatgct tccgtgtaga cacttaagct   27540
cgccttcgat ctcagcgcag cggtgcagcc acaacgcgca gcccgtgggc tcgtgatgct   27600
tgtaggtcac ctctgcaaac gactgcaggt acgcctgcag gaatcgcccc atcatcgtca   27660
caaaggtctt gttgctggtg aaggtcagct gcaacccgcg gtgctcctcg ttcagccagg   27720
tcttgcatac ggccgccaga gcttccactt ggtcaggcag tagtttgaag ttcgccttta   27780
gatcgttatc cacgtggtac ttgtccatca gcgcgcgcgc agcctccatg cccttctccc   27840
acgcagacac gatcggcaca ctcagcgggt tcatcaccgt aatttcactt tccgcttcgc   27900
```

-continued

```
tgggctcttc ctcttcctct tgcgtccgca taccacgcgc cactgggtcg tcttcattca   27960
gccgccgcac tgtgcgctta cctcctttgc catgcttgat tagcaccggt gggttgctga   28020
aacccaccat ttgtagcgcc acatcttctc tttcttcctc gctgtccacg attacctctg   28080
gtgatggcgg gcgctcgggc ttgggagaag ggcgcttctt tttcttcttg ggcgcaatgg   28140
ccaaatccgc cgccgaggtc gatggccgcg ggctgggtgt gcgcggcacc agcgcgtctt   28200
gtgatgagtc ttcctcgtcc tcggactcga tacgccgcct catccgcttt tttgggggcg   28260
cccgggatgg cggcggcgac ggggacgggg acgacacgtc ctccatggtt gggggacgtc   28320
gcgccgcacc gcgtccgcgc tcgggggtgg tttcgcgctg ctcctcttcc cgactggcca   28380
tttccttctc ctataggcag aaaaagatca tggagtcagt cgagaagaag gacagcctaa   28440 ccgcccctc tgagttcgcc accaccgcct ccaccgatgc cgccaacgcg cctaccacct   28500
tccccgtcga ggcacccccg cttgaggagg aggaagtgat tatcgagcag gacccaggtt   28560
ttgtaagcga agacgacgag gaccgctcag taccaacaga ggataaaaag caagaccagg   28620
acaacgcaga ggcaaacgag gaacaagtcg ggcgggggga cgaaaggcat ggcgactacc   28680
tagatgtggg agacgacgtg ctgttgaagc atctgcagcg ccagtgcgcc attatctgcg   28740
acgcgttgca agagcgcagc gatgtgcccc tcgccatagc ggatgtcagc cttgcctacg   28800
aacgccacct attctcaccg cgcgtacccc ccaaacgcca agaaaacggc acatgcgagc   28860
ccaacccgcg cctcaacttc tacccgtat ttgccgtgcc agaggtgctt gccacctatc   28920
acatcttttt ccaaaactgc aagataccc tatcctgccg tgccaaccgc agccgagcgg   28980
acaagcagct ggccttgcgg cagggcgctg tcatacctga tatcgcctcg ctcaacgaag   29040
tgccaaaaat ctttgagggt cttggacgcg acgagaagcg cgcggcaaac gctctgcaac   29100
aggaaaacag cgaaaatgaa agtcactctg gagtgttggt ggaactcgag ggtgacaacg   29160
cgcgcctagc cgtactaaaa cgcagcatcg aggtcaccca ctttgcctac ccggcactta   29220
acctaccccc caaggtcatg agcacagtca tgagtgagct gatcgtgcgc cgtgcgcagc   29280
ccctggagag ggatgcaaat ttgcaagaac aaacagagga gggcctaccc gcagttggcg   29340
acgagcagct agcgcgctgg cttcaaacgc gcgagcctgc cgacttggag gagcgacgca   29400
aactaatgat ggccgcagtg ctcgttaccg tggagcttga gtgcatgcag cggttctttg   29460
ctgacccgga gatgcagcgc aagctagagg aaacattgca ctacacctt cgacagggct   29520 acgtacgcca ggcctgcaag atctccaacg tggagctctg caacctggtc tcctaccttg   29580
gaattttgca cgaaaaccgc cttgggcaaa acgtgcttca ttccacgctc aagggcgagg   29640
cgcgccgcga ctacgtccgc gactgcgttt acttatttct atgctacacc tggcagacgg   29700
ccatgggcgt ttggcagcag tgcttggagg agtgcaacct caaggagctg cagaaactgc   29760
taaagcaaaa cttgaaggac ctatggacgg ccttcaacga gcgctccgtg gccgcgcacc   29820
tggcggacat cattttcccc gaacgcctgc ttaaaaccct gcaacagggt ctgccagact   29880
tcaccagtca aagcatgttg cagaacttta ggaactttat cctagagcgc tcaggaatct   29940
tgcccgccac ctgctgtgca cttcctagcg actttgtgcc cattaagtac cgcgaatgcc   30000
ctccgccgct ttggggccac tgctaccttc tgcagctagc caactacctt gcctaccact   30060
ctgacataat ggaagacgtg agcggtgacg tctactgga gtgtcactgt cgctgcaacc   30120
tatgcacccc gcaccgctcc ctggtttgca attcgcagct gcttaacgaa agtcaaatta   30180
tcggtacctt tgagctgcag ggtccctcgc ctgacgaaaa gtccgcggct ccggggttga   30240
```

-continued

```
aactcactcc ggggctgtgg acgtcggctt accttcgcaa atttgtacct gaggactacc   30300
acgcccacga gattaggttc tacgaagacc aatcccgccc gcctaatgcg gagcttaccg   30360
cctgcgtcat tacccagggc cacattcttg gccaattgca agccatcaac aaagcccgcc   30420
aagagtttct gctacgaaag ggacgggggg tttacttgga cccccagtcc ggcgaggagc   30480
tcaacccaat cccccgccg ccgcagccct atcagcagca gccgcgggcc cttgcttccc   30540
aggatggcac ccaaaaagaa gctgcagctg ccgccgccac ccacggacga ggaggaatac   30600
tgggacagtc aggcagagga ggtttttggac gaggaggagg aggacatgat ggaagactgg   30660
gagagcctag acgaggaagc ttccgaggtc gaagaggtgt cagacgaaac accgtcaccc   30720
tcggtcgcat tcccctcgcc ggcgccccag aaatcggcaa ccggttccag catggctaca   30780
acctccgctc ctcaggcgcc gccggcactg cccgttcgcc gacccaaccg tagatgggac   30840
accactggaa ccagggccgg taagtccaag cagccgccgc cgttagccca agagcaacaa   30900
cagcgccaag gctaccgctc atggcgcggg cacaagaacg ccatagttgc ttgcttgcaa   30960
gactgtgggg gcaacatctc cttcgcccgc cgctttcttc tctaccatca cggcgtggcc   31020
ttcccccgta acatcctgca ttactaccgt catctctaca gcccatactg caccggcggc   31080
agcggcagca acagcagcgg ccacacagaa gcaaaggcga ccggatagca agactctgac   31140
aaagcccaag aaatccacag cggcggcagc agcaggagga ggagcgctgc gtctggcgcc   31200
caacgaaccc gtatcgaccc gcgagcttag aaacaggatt tttcccactc tgtatgctat   31260
atttcaacag agcaggggcc aagaacaaga gctgaaaata aaaaacaggt ctctgcgatc   31320
cctcacccgc agctgcctgt atcacaaaag cgaagatcag cttcggcgca cgctggaaga   31380
cgcggaggct ctcttcagta aatactgcgc gctgactctt aaggactagt ttcgcgccct   31440
ttctcaaatt taagcgcgaa aactacgtca tctccagcgg ccacacccgg cgccagcacc   31500
tgttgtcagc gccattatga gcaaggaaat tcccacgccc tacatgtgga gttaccagcc   31560
acaaatggga cttgcggctg gagctgccca agactactca acccgaataa actacatgag   31620
cgcgggaccc cacatgatat cccgggtcaa cggaatacgc gcccaccgaa accgaattct   31680
cctggaacag gcggctatta ccaccacacc tcgtaataac cttaatcccc gtagttggcc   31740
cgctgccctg gtgtaccagg aaagtcccgc tcccaccact gtggtacttc ccagagacgc   31800
ccaggccgaa gttcagatga ctaactcagg ggcgcagctt gcgggcggct ttcgtcacag   31860
ggtgcggtcg cccgggcagg gtataactca cctgacaatc agagggcgag gtattcagct   31920
caacgacgag tcggtgagct cctcgcttgg tctccgtccg gacgggacat ttcagatcgg   31980
cggcgccggc cgctcttcat tcacgcctcg tcaggcaatc ctaactctgc agacctcgtc   32040
ctctgagccg cgctctggag gcattggaac tctgcaattt attgaggagt ttgtgccatc   32100
ggtctacttt aaccccttct cgggacctcc cggccactat ccggatcaat ttattcctaa   32160
ctttgacgcg gtaaaggact cggcggacgg ctacgactga atgttaagtg gagaggcaga   32220
gcaactgcgc ctgaaacacc tggtccactg tcgccgccac aagtgctttg cccgcgactc   32280
cggtgagttt tgctactttg aattgcccga ggatcatatc gagggcccgg cgcacggcgt   32340
ccggcttacc gcccagggag agcttgcccg tagcctgatt cggagtttta cccagcgccc   32400
cctgctagtt gagcgggaca ggggaccctg tgttctcact gtgatttgca actgtcctaa   32460
ccctggatta catcaagatc ctctagttaa tgtcaggtcg cctaagtcga ttaactagag   32520
tacccgggga tcttattccc tttaactaat aaaaaaaaat aataaagcat cacttactta   32580
aaatcagtta gcaaatttct gtccagttta ttcagcagca cctccttgcc ctcctcccag   32640
```

-continued

```
ctctggtatt gcagcttcct cctggctgca aactttctcc acaatctaaa tggaatgtca   32700
gtttcctcct gttcctgtcc atccgcaccc actatcttca tgttgttgca gatgaagcgc   32760
gcaagaccgt ctgaagatac cttcaacccc gtgtatccat atgacacgga aaccggtcct   32820
ccaactgtgc ctttcttac tcctcccttt gtatcccca atgggtttca agagagtccc   32880
cctggggtac tctctttgcg cctatccgaa cctctagtta cctccaatgg catgcttgcg   32940
ctcaaaatgg gcaacggcct ctctctggac gaggccggca accttacctc ccaaaatgta   33000
accactgtga gcccacctct caaaaaaacc aagtcaaaca taaacctgga aatatctgca   33060
cccctcacag ttacctcaga agccctaact gtggctgccg ccgcacctct aatggtcgcg   33120
ggcaacacac tcaccatgca atcacaggcc ccgctaaccg tgcacgactc caaacttagc   33180
attgccaccc aaggacccct cacagtgtca gaaggaaagc tagccctgca aacatcaggc   33240
cccctcacca ccaccgatag cagtaccctt actatcactg cctcaccccc tctaactact   33300
gccactggta gcttgggcat tgacttgaaa gagcccattt atacacaaaa tggaaaaacta   33360 ggactaaagt acggggctcc tttgcatgta acagacgacc taaacacttt gaccgtagca   33420
actggtccag gtgtgactat taataatact tccttgcaaa ctaaagttac tggagccttg   33480
ggttttgatt cacaaggcaa tatgcaactt aatgtagcag gaggactaag gattgattct   33540
caaaacagac gccttatact tgatgttagt tatccgtttg atgctcaaaa ccaactaaat   33600
ctaagactag gacagggccc tcttttttata aactcagccc acaacttgga tattaactac   33660
aacaaaggcc tttacttgtt tacagcttca aacaattcca aaaagcttga ggttaaccta   33720
agcactgcca aggggttgat gtttgacgct acagccatag ccattaatgc aggagatggg   33780
cttgaatttg gttcacctaa tgcaccaaac acaaatcccc tcaaaacaaa aattggccat   33840
ggcctagaat ttgattcaaa caaggctatg gttcctaaac taggaactgg ccttagtttt   33900
gacagcacag gtgccattac agtaggaaac aaaaataatg ataagctaac tttgtggacc   33960
ggaataaacc ctccacctaa ctgtcaaatt gtggaaaaca ctaatacaaa tgatggcaaa   34020
cttactttag tattagtaaa aaatggaggg cttgttaatg gctacgtgtc tctagttggt   34080
gtatcagaca ctgtgaacca aatgttcaca caaaagacac caaacatcca attaagatta   34140
tattttgact cttctggaaa tctattaact gaggaatcag acttaaaaat tccacttaaa   34200
aataaatctt ctacagcgac cagtgaaact gtagccagca gcaaagcctt tatgccaagt   34260
actacagctt atcccttcaa caccactact agggatagtg aaaactacat tcatggaata   34320
tgttactaca tgactagtta tgatagaagt ctatttccct tgaacatttc tataatgcta   34380
aacagccgta tgatttcttc caatgttgcc tatgccatac aatttgaatg gaatctaaat   34440
gcaagtgaat ctcagaaaag caacatagct acgctgacca catccccctt tttctttttct   34500 tacattacag aagacgacaa ctaaagaatc gtttgtgtta tgtttcaacg tgtttatttt   34560
tcaattgcag aaaatttcaa gtcatttttc attcagtagt atagccccac caccacatag   34620
cttatacaga tcaccgtacc ttaatcaaac tcacagaacc ctagtattca acctgccacc   34680
tccctcccaa cacacagagt acacagtcct ttctccccgg ctggccttaa aaagcatcat   34740
atcatgggta acagacatat tcttaggtgt tatattccac acggtttcct gtcgagccaa   34800
acgctcatca gtgatattaa taaactcccc gggcagctca cttaagttca tgtcgctgtc   34860
cagctgctga gccacaggct gctgtccaac ttgcggttgc ttaacgggcg gcgaaggaga   34920
agtccacgcc tacatggggg tagagtcata atcgtgcatc aggatagggc ggtggtgctg   34980
```

-continued

```
cagcagcgcg cgaataaact gctgccgccg ccgctccgtc ctgcaggaat acaacatggc   35040
agtggtctcc tcagcgatga ttcgcaccgc ccgcagcata aggcgccttg tcctccgggc   35100
acagcagcgc accctgatct cacttaaatc agcacagtaa ctgcagcaca gcaccacaat   35160
attgttcaaa atcccacagt gcaaggcgct gtatccaaag ctcatggcgg ggaccacaga   35220
acccacgtgg ccatcatacc acaagcgcag gtagattaag tggcgacccc tcataaacac   35280
gctggacata aacattacct cttttggcat gttgtaattc accacctccc ggtaccatat   35340
aaacctctga ttaaacatgg cgccatccac caccatccta aaccagctgg ccaaaacctg   35400
cccgccggct atacactgca gggaaccggg actggaacaa tgacagtgga gagcccagga   35460
ctcgtaacca tggatcatca tgctcgtcat gatatcaatg ttggcacaac acaggcacac   35520
gtgcatacac ttcctcagga ttacaagctc ctcccgcgtt agaaccatat cccagggaac   35580
aacccattcc tgaatcagcg taaatcccac actgcaggga agacctcgca cgtaactcac   35640
gttgtgcatt gtcaaagtgt tacattcggg cagcagcgga tgatcctcca gtatggtagc   35700
gcgggtttct gtctcaaaag gaggtagacg atccctactg tacggagtgc gccgagacaa   35760
ccgagatcgt gttggtcgta gtgtcatgcc aaatggaacg ccggacgtag tcatatttcc   35820
tgaagcaaaa ccaggtgcgg gcgtgacaaa cagatctgcg tctccggtct cgccgcttag   35880
atcgctctgt gtagtagttg tagtatatcc actctctcaa agcatccagg cgcccctgg   35940 cttcgggttc tatgtaaact ccttcatgcg ccgctgccct gataacatcc accaccgcag   36000
aataagccac acccagccaa cctacacatt cgttctgcga gtcacacacg ggaggagcgg   36060
gaagagctgg aagaaccatg ttttttttt tattccaaaa gattatccaa aacctcaaaa   36120
tgaagatcta ttaagtgaac gcgctcccct ccggtggcgt ggtcaaactc tacagccaaa   36180
gaacagataa tggcatttgt aagatgttgc acaatggctt ccaaaaggca aacggccctc   36240
acgtccaagt ggacgtaaag gctaaaccct tcagggtgaa tctcctctat aaacattcca   36300
gcaccttcaa ccatgcccaa ataattctca tctcgccacc ttctcaatat atctctaagc   36360
aaatcccgaa tattaagtcc ggccattgta aaaatctgct ccagagcgcc ctccaccttc   36420
agcctcaagc agcgaatcat gattgcaaaa attcaggttc ctcacagacc tgtataagat   36480
tcaaaagcgg aacattaaca aaaataccgc gatcccgtag gtcccttcgc agggccagct   36540
gaacataatc gtgcaggtct gcacggacca gcgcggccac ttccccgcca ggaaccatga   36600
caaaagaacc cacactgatt atgacacgca tactcggagc tatgctaacc agcgtagccc   36660
cgatgtaagc ttgttgcatg ggcggcgata taaaatgcaa ggtgctgctc aaaaaatcag   36720
gcaaagcctc gcgcaaaaaa gaaagcacat cgtagtcatg ctcatgcaga taaaggcagg   36780
taagctccgg aaccaccaca gaaaaagaca ccatttttct ctcaaacatg tctgcgggtt   36840
tctgcataaa cacaaaataa aataacaaaa aaacatttaa acattagaag cctgtcttac   36900
aacaggaaaa acaaccctta taagcataag acggactacg gccatgccgg cgtgaccgta   36960
aaaaaactgg tcaccgtgat taaaaagcac caccgacagc tcctcggtca tgtccggagt   37020
cataatgtaa gactcggtaa acacatcagg ttgattcaca tcggtcagtg ctaaaaagcg   37080
accgaaatag cccggggggaa tacatacccg caggcgtaga gacaacatta cagcccccat   37140
aggaggtata acaaaattaa taggagagaa aaacacataa acacctgaaa aaccctcctg   37200
cctaggcaaa atagcaccct cccgctccag aacaacatac agcgcttcca cagcggcagc   37260
cataacagtc agccttacca gtaaaaaaga aaacctatta aaaaaacacc actcgacacg   37320
gcaccagctc aatcagtcac agtgtaaaaa agggccaagt gcagagcgag tatatatagg   37380
```
actaaaaaat gacgtaacgg ttaaagtcca caaaaaacac ccagaaaacc gcacgcgaac    37440
ctacgcccag aaacgaaagc caaaaaaccc acaacttcct caaatcgtca cttccgtttt    37500
cccacgttac gtcacttccc attttaagaa aactacaatt cccaacacat acaagttact    37560
ccgccctaaa acctacgtca cccgccccgt tcccacgccc cgcgccacgt cacaaactcc    37620
accccctcat tatcatattg gcttcaatcc aaaataaggt atattattga tgatg         37675

<210> SEQ ID NO 27
<211> LENGTH: 34736
<212> TYPE: DNA
<213> ORGANISM: Artificial Sequence
<220> FEATURE:
<223> OTHER INFORMATION: #3 vector

<400> SEQUENCE: 27
catcatcaat aatataccct attttggatt gaagccaata tgataatgag ggggtggagt      60
ttgtgacgtg gcgcggggcg tgggaacggg gcgggtgacg tagtagtgtg gcggaagtgt     120
gatgttgcaa gtgtggcgga acacatgtaa gcgacggatg tggcaaaagt gacgtttttg     180
gtgtgcgccg gtgtacacag gaagtgacaa ttttcgcgcg gttttaggcg gatgttgtag     240
taaatttggg cgtaaccgag taagatttgg ccattttcgc gggaaaactg aataagagga     300
agtgaaatct gaataatttt gtgttactca tagcgcgtaa tactgtaata gtaatcaatt     360
acggggtcat tagttcatag cccatatatg gagttccgcg ttacataact tacggtaaat     420
ggcccgcctg gctgaccgcc caacgacccc cgcccattga cgtcaataat gacgtatgtt     480
cccatagtaa cgccaatagg gactttccat tgacgtcaat gggtggagta tttacggtaa     540
actgcccact tggcagtaca tcaagtgtat catatgccaa gtacgccccc tattgacgtc     600
aatgacggta aatggcccgc ctggcattat gcccagtaca tgacctttatg gactttcct     660 acttggcagt acatctacgt attagtcatc gctattacca tggtgatgcg gttttggcag     720
tacatcaatg ggcgtggata gcggtttgac tcacggggat ttccaagtct ccacccatt     780 gacgtcaatg ggagtttgtt ttggcaccaa aatcaacggg actttccaaa atgtcgtaac     840
aactccgccc cattgacgca aatgggcggt aggcgtgtac ggtgggaggt ctatataagc     900
agagctctcc ctatcagtga tagagatctc cctatcagtg atagagatcg tcgacgagct     960
cgtttagtga accgtcagat cgcctggaga cgccatccac gctgttttga cctccataga    1020
agacaccggg accgatccag cctccgattt gccaccatgt ttgtgttcct ggtgctgctg    1080
ccactggtgt ccagccagtg tgtgaacctg accaccagga cccaacttcc tcctgcctac    1140
accaactcct tcaccagggg agtctactac cctgacaagg tgttcaggtc ctctgtgctg    1200
cacagcaccc aggacctgtt cctgccattc ttcagcaatg tgacctggtt ccatgccatc    1260
catgtgtctg gcaccaatgg caccaagagg tttgacaacc ctgtgctgcc attcaatgat    1320
ggagtctact tgccagcac agagaagagc aacatcatca ggggctggat ttttggcacc    1380
accctggaca gcaagaccca gtccctgctg attgtgaaca atgccaccaa tgtggtgatt    1440
aaggtgtgtg agttccagtt ctgtaatgac ccattcctgg gagtctacta ccacaagaac    1500
aacaagtcct ggatggagtc tgagttcagg gtctactcct ctgccaacaa ctgtaccttt    1560
gaatatgtga gccaaccatt cctgatggac ttggagggca gcagggcaa cttcaagaac    1620 ctgagggagt ttgtgttcaa gaacattgat ggctacttca gatttacag caaacacaca    1680 ccaatcaacc tggtgaggga cctgccacag ggcttctctg ccttggaacc actggtggac    1740

-continued

```
ctgccaattg gcatcaacat caccaggttc cagaccctgc tggctctgca caggtcctac      1800
ctgacacctg gagactcctc ctctggctgg acagcaggag cagcagccta ctatgtgggc      1860
tacctccaac caaggacctt cctgctgaaa tacaatgaga atggcaccat cacagatgct      1920
gtggactgtg ccctggaccc actgtctgag accaagtgta ccctgaaatc cttcacagtg      1980
gagaagggca tctaccagac cagcaacttc agggtccaac aacagagag cattgtgagg      2040 tttccaaaca tcaccaacct gtgtccattt ggagaggtgt tcaatgccac caggtttgcc      2100
tctgtctatg cctggaacag gaagaggatt agcaactgtg tggctgacta ctctgtgctc      2160
tacaactctg cctccttcag caccttcaag tgttatggag tgagcccaac caaactgaat      2220
gacctgtgtt tcaccaatgt ctatgctgac tcctttgtga ttaggggaga tgaggtgaga      2280
cagattgccc ctggacaaac aggcaagatt gctgactaca actacaaact gcctgatgac      2340
ttcacaggct gtgtgattgc ctggaacagc aacaacctgg acagcaaggt gggaggcaac      2400
tacaactacc tctacagact gttcaggaag agcaacctga aaccatttga gagggacatc      2460
agcacagaga tttaccaggc tggcagcaca ccatgtaatg gagtggaggg cttcaactgt      2520
tactttccac tccaatccta tggcttccaa ccaaccaatg gagtgggcta ccaaccatac      2580
agggtggtgg tgctgtcctt tgaactgctc catgcccctg ccacagtgtg tggaccaaag      2640
aagagcacca acctggtgaa gaacaagtgt gtgaacttca acttcaatgg actgacaggc      2700
acaggagtgc tgacagagag caacaagaag ttcctgccat tccaacagtt tggcagggac      2760
attgctgaca ccacagatgc tgtgagggac ccacagacct ggagattct ggacatcaca      2820 ccatgttcct ttggaggagt gtctgtgatt acacctggca ccaacaccag caaccaggtg      2880
gctgtgctct accaggatgt gaactgtact gaggtgcctg tggctatcca tgctgaccaa      2940
cttacaccaa cctggagggt ctacagcaca ggcagcaatg tgttccagac cagggctggc      3000
tgtctgattg gagcagagca tgtgaacaac tcctatgagt gtgacatccc aattggagca      3060
ggcatctgtg cctcctacca gacccagacc ggtggcggtg ggtcgaggtc tgtggcaagc      3120
cagagcatca ttgcctacac aatgagtctg ggagcagaga actctgtggc ttacagcaac      3180
aacagcattg ccatcccaac caacttcacc atctctgtga ccacagagat tctgcctgtg      3240
agtatgacca agacctctgt ggactgtaca atgtatatct gtggagacag cacagagtgt      3300
agcaacctgc tgctccaata tggctccttc tgtacccaac ttaacagggc tctgacaggc      3360
attgctgtgg aacaggacaa gaacacccag gaggtgtttg cccaggtgaa gcagatttac      3420
aagacacctc caatcaagga ctttggaggc ttcaacttca gccagattct gcctgaccca      3480
agcaagccaa gcaagaggtc cttcattgag gacctgctgt tcaacaaggt gaccctggct      3540
gatgctggct tcatcaagca atatggagac tgtctgggag acattgctgc cagggacctg      3600
atttgtgccc agaagttcaa tggactgaca gtgctgcctc cactgctgac agatgagatg      3660
attgcccaat acacctctgc cctgctggct ggcaccatca cctctggctg gacctttgga      3720
gcaggagcag ccctccaaat cccatttgct atgcagatgg cttacaggtt caatggcatt      3780
ggagtgaccc agaatgtgct ctatgagaac cagaaactga ttgccaacca gttcaactct      3840
gccattggca gattcagga ctccctgtcc agcacagcct ctgccctggg caaactccaa      3900
gatgtggtga accagaatgc ccaggctctg aacaccctgg tgaagcaact ttccagcaac      3960
tttggagcca tctcctctgt gctgaatgac atcctgagca gactggacaa ggtggaggct      4020
gaggtccaga ttgacagact gattacaggc agactccaat ccctccaaac ctatgtgacc      4080
caacaactta tcagggctgc tgagattagg gcatctgcca acctggctgc caccaagatg      4140
```

-continued

```
agtgagtgtg tgctgggaca aagcaagagg gtggacttct gtggcaaggg ctaccacctg    4200
atgagttttc cacagtctgc ccctcatgga gtggtgttcc tgcatgtgac ctatgtgcct    4260
gcccaggaga agaacttcac cacagcccct gccatctgcc atgatggcaa ggctcacttt    4320
ccaagggagg gagtgtttgt gagcaatggc acccactggt ttgtgaccca gaggaacttc    4380
tatgaaccac agattatcac cacagacaac acctttgtgt ctggcaactg tgatgtggtg    4440
attggcattg tgaacaacac agtctatgac ccactccaac ctgaactgga ctccttcaag    4500
gaggaactgg acaaatactt caagaaccac accagccctg atgtggacct gggagacatc    4560
tctggcatca atgcctctgt ggtgaacatc cagaaggaga ttgacagact gaatgaggtg    4620
gctaagaacc tgaatgagtc cctgattgac ctccaagaac tgggcaaata tgaacaatac    4680
atcaagtggc catgaaaatt gatcataatc agccatacca catttgtaga ggttttactt    4740
gctttaaaaa acctcccaca cctccccctg aacctgaaac ataaaatgaa tgcaattgtt    4800
gttgttaact tgtttattgc agcttataat ggttacaaat aaagcaatag catcacaaat    4860
ttcacaaata aagcattttt ttcactgcat tctagttgtg gtttgtccaa actcatcaat    4920
gtatcttaac gcggatctgg gcgtggttaa gggtgggaaa gaatatataa ggtgggggtc    4980
ttatgtagtt ttgtatctgt tttgcagcag ccgccgccgc catgagcacc aactcgtttg    5040
atggaagcat tgtgagctca tatttgacaa cgcgcatgcc cccatgggcc ggggtgcgtc    5100
agaatgtgat gggctccagc attgatggtc gccccgtcct gcccgcaaac tctactacct    5160
tgacctacga gaccgtgtct ggaacgccgt tggagactgc agcctccgcc gccgcttcag    5220
ccgctgcagc caccgcccgc gggattgtga ctgactttgc tttcctgagc ccgcttgcaa    5280
gcagtgcagc ttcccgttca tccgcccgcg atgacaagtt gacggctctt ttggcacaat    5340
tggattcttt gacccgggaa cttaatgtcg tttctcagca gctgttggat ctgcgccagc    5400
aggtttctgc cctgaaggct tcctcccctc ccaatgcggt ttaaaacata aataaaaaac    5460
cagactctgt ttggatttgg atcaagcaag tgtcttgctg tctttattta ggggtttttgc    5520 gcgcgcggta ggcccgggac cagcggtctc ggtcgttgag ggtcctgtgt attttttcca    5580
ggacgtggta aaggtgactc tggatgttca gatacatggg cataagcccg tctctggggt    5640
ggaggtagca ccactgcaga gcttcatgct gcggggtggt gttgtagatg atccagtcgt    5700
agcaggagcg ctgggcgtgg tgcctaaaaa tgtctttcag tagcaagctg attgccaggg    5760
gcaggcsctt ggtgtaagtg tttacaaagc ggttaagctg ggatgggtgc atacgtgggg    5820
atatgagatg catcttggac tgtatttta ggttggctat gttcccagcc atatccctcc    5880
ggggattcat gttgtgcaga accaccagca cagtgtatcc ggtgcacttg ggaaatttgt    5940
catgtagctt agaaggaaat gcgtggaaga acttggagac gcccttgtga cctccaagat    6000
tttccatgca ttcgtccata atgatggcaa tgggcccacg gcggcggcc tgggcgaaga    6060 tatttctggg atcactaacg tcatagttgt gttccaggat gagatcgtca taggccattt    6120
ttacaaagcg cgggcggagg gtgccagact gcggtataat ggttccatcc ggcccagggg    6180
cgtagttacc ctcacagatt tgcatttccc acgctttgag ttcagatggg gggatcatgt    6240
ctacctgcgg ggcgatgaag aaaacggttt ccggggtagg ggagatcagc tgggaagaaa    6300
gcaggttcct gagcagctgc gacttaccgc agccggtggg cccgtaaatc acacctatta    6360
ccggctgcaa ctggtagtta agagagctgc agctgccgtc atccctgagc aggggggcca    6420
cttcgttaag catgtccctg actcgcatgt tttccctgac caaatccgcc agaaggcgct    6480
```

-continued

```
cgccgcccag cgatagcagt tcttgcaagg aagcaaagtt tttcaacggt ttgagaccgt   6540
ccgccgtagg catgcttttg agcgtttgac caagcagttc caggcggtcc cacagctcgg   6600
tcacctgctc tacggcatct cgatccagca tatctcctcg tttcgcgggt tggggcggct   6660
ttcgctgtac ggcagtagtc ggtgctcgtc cagacgggcc agggtcatgt ctttccacgg   6720
gcgcagggtc ctcgtcagcg tagtctgggt cacggtgaag gggtgcgctc cgggctgcgc   6780
gctggccagg gtgcgcttga ggctggtcct gctggtgctg aagcgctgcc ggtcttcgcc   6840
ctgcgcgtcg gccaggtagc atttgaccat ggtgtcatag tccagcccct ccgcggcgtg   6900
gcccttggcg cgcagcttgc ccttggagga ggcgccgcac gaggggcagt gcagactttt   6960
gagggcgtag agcttgggcg cgagaaatac cgattccggg gagtaggcat ccgcgccgca   7020
ggccccgcag acggtctcgc attccacgag ccaggtgagc tctggccgtt cggggtcaaa   7080
aaccaggttt cccccatgct ttttgatgcg tttcttacct ctggtttcca tgagccggtg   7140
tccacgctcg gtgacgaaaa ggctgtccgt gtccccgtat acagacttga gaggcctgtc   7200
ctcgagcggt gttccgcggt cctcctcgta tagaaactcg gaccactctg agacaaaggc   7260
tcgcgtccag gccagcacga aggaggctaa gtgggagggg tagcggtcgt tgtccactag   7320
ggggtccact cgctccaggg tgtgaagaca catgtcgccc tcttcggcat caaggaaggt   7380
gattggtttg taggtgtagg ccacgtgacc gggtgttcct gaagggggc tataaaaggg   7440 ggtgggggcg cgttcgtcct cactctcttc cgcatcgctg tctgcgaggg ccagctgttg   7500
gggtgagtac tccctctgaa aagcgggcat gacttctgcg ctaagattgt cagtttccaa   7560
aaacgaggag gatttgatat tcacctggcc cgcggtgatg cctttgaggg tggccgcatc   7620
catctggtca gaaaagacaa tcttttttgtt gtcaagcttg gtggcaaacg acccgtagag   7680
ggcgttggac agcaacttgg cgatggagcg cagggtttgg tttttgtcgc gatcggcgcg   7740
ctccttggcc gcgatgttta gctgcacgta ttcgcgcgca acgcaccgcc attcgggaaa   7800
gacggtggtg cgctcgtcgg gcaccaggtg cacgcgccaa ccgcggttgt gcagggtgac   7860
aaggtcaacg ctggtggcta cctctccgcg taggcgctcg ttggtccagc agaggcggcc   7920
gcccttgcgc gagcagaatg gcggtagggg gtctagctgc gtctcgtccg gggggtctgc   7980
gtccacggta aagaccccgg gcagcaggcg cgcgtcgaag tagtctatct tgcatccttg   8040
caagtctagc gcctgctgcc atgcgcgggc ggcaagcgcg cgctcgtatg ggttgagtgg   8100 gggacccat ggcatggggt gggtgagcgc ggaggcgtac atgccgcaaa tgtcgtaaac   8160
gtagaggggc tctctgagta ttccaagata tgtagggtag catcttccac cgcgggatgct   8220 ggcgcgcacg taatcgtata gttcgtgcga gggagcgagg aggtcgggac cgaggttgct   8280
acgggcgggc tgctctgctc ggaagactat ctgcctgaag atggcatgtg agttggatga   8340
tatggttgga cgctggaaga cgttgaagct ggcgtctgtg agacctaccg cgtcacgcac   8400
gaaggaggcg taggagtcgc gcagcttgtt gaccagctcg gcggtgacct gcacgtctag   8460
ggcgcagtag tccagggttt ccttgatgat gtcatactta tcctgtccct ttttttttcca   8520 cagctcgcgg ttgaggacaa actcttcgcg gtctttccag tactcttgga tcggaaaccc   8580
gtcggcctcc gaacggtaag agcctagcat gtagaactgg ttgacggcct ggtaggcgca   8640
gcatcccttt tctacgggta gcgcgtatgc ctgcgcggcc ttccggagcg aggtgtgggt   8700
gagcgcaaag gtgtccctga ccatgacttt gaggtactgg tatttgaagt cagtgtcgtc   8760
gcatccgccc tgctcccaga gcaaaaagtc cgtgcgcttt ttggaacgcg gatttggcag   8820
ggcgaaggtg acatcgttga agagtatctt tcccgcgcga ggcataaagt tgcgtgtgat   8880
```

-continued

```
gcggaagggt cccggcacct cggaacggtt gttaattacc tgggcggcga gcacgatctc    8940
gtcaaagccg ttgatgttgt ggcccacaat gtaaagttcc aagaagcgcg ggatgccctt    9000
gatggaaggc aattttttaa gttcctcgta ggtgagctct tcaggggagc tgagcccgtg    9060
ctctgaaagg gcccagtctg caagatgagg gttggaagcg acgaatgagc tccacaggtc    9120
acgggccatt agcatttgca ggtggtcgcg aaaggtccta aactggcgac ctatggccat    9180
tttttctggg gtgatgcagt agaaggtaag cgggtcttgt tcccagcggt cccatccaag    9240
gttcgcggct aggtctcgcg cggcagtcac tagaggctca tctccgccga acttcatgac    9300
cagcatgaag ggcacgagct gcttcccaaa ggcccccatc caagtatagg tctctacatc    9360
gtaggtgaca aagagacgct cggtgcgagg atgcgagccg atcgggaaga actggatctc    9420
ccgccaccaa ttggaggagt ggctattgat gtggtgaaag tagaagtccc tgcgacgggc    9480
cgaacactcg tgctggcttt tgtaaaaacg tgcgcagtac tggcagcggt gcacgggctg    9540
tacatcctgc acgaggttga cctgacgacc gcgcacaagg aagcagagtg ggaatttgag    9600
cccctcgcct ggcgggtttg gctggtggtc ttctacttcg gctgcttgtc cttgaccgtc    9660
tggctgctcg aggggagtta cggtggatcg gaccaccacg ccgcgcgagc ccaaagtcca    9720
gatgtccgcg cgcggcggtc ggagcttgat gacaacatcg cgcagatggg agctgtccat    9780
ggtctggagc tcccgcggcg tcaggtcagg cgggagctcc tgcaggttta cctcgcatag    9840
acgggtcagg gcgcgggcta gatccaggtg atacctaatt tccagggget ggttggtggc    9900 ggcgtcgatg gcttgcaaga ggccgcatcc ccgcggcgcg actacggtac cgcgcggcgg    9960
gcggtgggcc gcggggggtgt ccttggatga tgcatctaaa agcggtgacg cgggcgagcc    10020
cccggaggta gggggggctc cggacccgcc gggagagggg gcaggggcac gtcggcgccg    10080
cgcgcgggca ggagctggtg ctgcgcgcgt aggttgctgg cgaacgcgac gacgcggcgg    10140
ttgatctcct gaatctggcg cctctgcgtg aagacgacgg gcccggtgag cttgaacctg    10200
aaagagagtt cgacagaatc aatttcggtg tcgttgacgg cggcctggcg caaaatctcc    10260
tgcacgtctc ctgagttgtc ttgataggcg atctcggcca tgaactgctc gatctcttcc    10320
tcctggagat ctccgcgtcc ggctcgctcc acggtggcgg cgaggtcgtt ggaaatgcgg    10380
gccatgagct gcgagaaggc gttgaggcct ccctcgttcc agacgcggct gtagaccacg    10440
cccccttcgg catcgcgggc gcgcatgacc acctgcgcga gattgagctc cacgtgccgg    10500
gcgaagacgg cgtagtttcg caggcgctga aagaggtagt tgagggtggt ggcggtgtgt    10560
tctgccacga agaagtacat aacccagcgt cgcaacgtgg attcgttgat atcccccaag    10620
gcctcaaggc gctccatggc ctcgtagaag tccacggcga agttgaaaaa ctgggagttg    10680
cgcgccgaca cggttaactc ctcctccaga agacggatga gctcggcgac agtgtcgcgc    10740
acctcgcgct caaaggctac aggggcctct tcttcttctt caatctcctc ttccataagg    10800 gcctccctt cttcttcttc tggcggcggt ggggggagggg ggacacggcg cgacgacgg    10860 cgcaccggga ggcggtcgac aaagcgctcg atcatctccc cgcggcgacg gcgcatggtc    10920
tcggtgacgg cgcggccgtt ctcgcgggg gcgcagttgga agacgccgcc cgtcatgtcc    10980
cggttatggg ttggcggggg gctgccatgc ggcaggggata cggcgctaac gatgcatctc    11040
aacaattgtt gtgtaggtac tccgccgccg agggacctga gcgagtccgc atcgaccgga    11100
tcggaaaacc tctcgagaaa ggcgtctaac cagtcacagt cgcaaggtag gctgagcacc    11160
gtggcgggcg gcagcgggcg gcggtcgggg ttgtttctgg cggaggtgct gctgatgatg    11220
```

-continued

```
taattaaagt aggcggtctt gagacggcgg atggtcgaca gaagcaccat gtccttgggt    11280
ccggcctgct gaatgcgcag gcggtcggcc atgccccagg cttcgttttg acatcggcgc    11340
aggtctttgt agtagtcttg catgagcctt tctaccggca cttcttcttc tccttcctct    11400
tgtcctgcat ctcttgcatc tatcgctgcg gcggcggcgg agtttggccg taggtggcgc    11460
cctcttcctc ccatgcgtgt gaccccgaag cccctcatcg gctgaagcag ggctaggtcg    11520
gcgacaacgc gctcggctaa tatggcctgc tgcacctgcg tgagggtaga ctggaagtca    11580
tccatgtcca caaagcggtg gtatgcgccc gtgttgatgg tgtaagtgca gttggccata    11640
acggaccagt taacggtctg gtgacccggc tgcgagagct cggtgtacct gagacgcgag    11700
taagccctcg agtcaaatac gtagtcgttg caagtccgca ccaggtactg gtatcccacc    11760
aaaaagtgcg gcggcggctg gcggtagagg ggccagcgta gggtggccgg ggctccgggg    11820
gcgagatctt ccaacataag gcgatgatat ccgtagatgt acctggacat ccaggtgatg    11880
ccggcggcgg tggtggaggc gcgcggaaag tcgcggacgc ggttccagat gttgcgcagc    11940
ggcaaaaagt gctccatggt cgggacgctc tggccggtca ggcgcgcgca atcgttgacg    12000
ctctagcgtg caaaaggaga gcctgtaagc gggcactctt ccgtggtctg gtggataaat    12060
tcgcaagggt atcatggcgg acgaccgggg ttcgagcccc gtatccggcc gtccgccgtg    12120
atccatgcgg ttaccgcccg cgtgtcgaac ccaggtgtgc gacgtcagac aacgggggag    12180
tgctcctttt ggcttccttc caggcgcggc ggctgctgcg ctagcttttt tggccactgg    12240
ccgcgcgcag cgtaagcggt taggctggaa agcgaaagca ttaagtggct cgctccctgt    12300
agccggaggg ttattttcca agggttgagt cgcgggaccc ccggttcgag tctcggaccg    12360
gccggactgc ggcgaacggg ggtttgcctc cccgtcatgc aagacccgc ttgcaaattc    12420 ctccggaaac agggacgagc ccctttttg cttttcccag atgcatccgg tgctgcggca    12480
gatgcgcccc cctcctcagc agcggcaaga gcaagagcag cggcagacat gcagggcacc    12540
ctcccctcct cctaccgcgt caggaggggc gacatccgcg gttgacgcgg cagcagatgg    12600
tgattacgaa cccccgcggc gccgggcccg gcactacctg gacttggagg agggcgaggg    12660
cctggcgcgg ctaggagcgc cctctcctga gcggcaccca agggtgcagc tgaagcgtga    12720
tacgcgtgag gcgtacgtgc cgcggcagaa cctgtttcgc gaccgcgagg gagaggagcc    12780
cgaggagatg cgggatcgaa agttccacgc agggcgcgag ctgcggcatg gcctgaatcg    12840
cgagcggttg ctgcgcgagg aggactttga gcccgacgcg cgaaccggga ttagtcccgc    12900
gcgcgcacac gtggcggccg ccgacctggt aaccgcatac gagcagacgg tgaaccagga    12960
gattaacttt caaaaaagct ttaacaacca cgtgcgtacg cttgtggcgc gcgaggaggt    13020
ggctatagga ctgatgcatc tgtgggactt tgtaagcgcg ctggagcaaa acccaaatag    13080
caagccgctc atggcgcagc tgttccttat agtgcagcac agcagggaca acgaggcatt    13140
cagggatgcg ctgctaaaca tagtagagcc cgagggccgc tggctgctcg atttgataaa    13200
catcctgcag agcatagtgg tgcaggagcg cagcttgagc ctggctgaca aggtggccgc    13260
catcaactat tccatgctta gcctgggcaa gttttacgcc cgcaagatat accataccccc    13320 ttacgttccc atagacaagg aggtaaagat cgaggggttc tacatgcgca tggcgctgaa    13380
ggtgcttacc ttgagcgacg acctgggcgt ttatcgcaac gagcgcatcc acaaggccgt    13440
gagcgtgagc cggcggcgcg agctcagcga ccgcgagctg atgcacagcc tgcaaagggc    13500
cctggctggc acgggcagcg gcgatagaga ggccgagtcc tactttgacg cgggcgctga    13560
cctgcgctgg gccccaagcc gacgcgccct ggaggcagct ggggccggac ctgggctggc    13620
```

-continued

```
ggtggcaccc gcgcgcgctg gcaacgtcgg cggcgtggag gaatatgacg aggacgatga   13680
gtacgagcca gaggacggcg agtactaagc ggtgatgttt ctgatcagat gatgcaagac   13740
gcaacggacc cggcggtgcg ggcggcgctg cagagccagc cgtccggcct taactccacg   13800
gacgactggc gccaggtcat ggaccgcatc atgtcgctga ctgcgcgcaa tcctgacgcg   13860
ttccggcagc agccgcaggc caaccggctc tccgcaattc tggaagcggt ggtcccggcg   13920
cgcgcaaacc ccacgcacga gaaggtgctg gcgatcgtaa acgcgctggc cgaaaacagg   13980
gccatccggc ccgacgaggc cggcctggtc tacgacgcgc tgcttcagcg cgtggctcgt   14040
tacaacagcg gcaacgtgca gaccaacctg gaccggctgg tggggatgt gcgcgaggcc   14100 gtggcgcagc gtgagcgcgc gcagcagcag ggcaacctgg gctccatggt tgcactaaac   14160
gccttcctga gtacacagcc cgccaacgtg ccgcggggac aggaggacta caccaacttt   14220
gtgagcgcac tgcggctaat ggtgactgag acaccgcaaa gtgaggtgta ccagtctggg   14280
ccagactatt ttttccagac cagtagacaa ggcctgcaga ccgtaaacct gagccaggct   14340
ttcaaaaact tgcaggggct gtggggggtg cgggctccca caggcgaccg cgcgaccgtg   14400
tctagcttgc tgacgcccaa ctcgcgcctg ttgctgctgc taatagcgcc cttcacggac   14460
agtggcagcg tgtcccggga cacataccta ggtcacttgc tgacactgta ccgcgaggcc   14520
ataggtcagg cgcatgtgga cgagcatact ttccaggaga ttacaagtgt cagccgcgcg   14580
ctggggcagg aggacacggg cagcctggag gcaaccctaa actacctgct gaccaaccgg   14640
cggcagaaga tcccctcgtt gcacagttta aacagcgagg aggagcgcat tttgcgctac   14700
gtgcagcaga gcgtgagcct taacctgatg cgcgacgggg taacgcccag cgtggcgctg   14760
gacatgaccg cgcgcaacat ggaaccgggc atgtatgcct caaaccggcc gtttatcaac   14820
cgcctaatgg actacttgca tcgcgcggcc gccgtgaacc ccgagtattt caccaatgcc   14880
atcttgaacc cgcactggct accgcccccct ggtttctaca ccgggggatt cgaggtgccc   14940
gagggtaacg atggattcct ctgggacgac atagacgaca gcgtgttttc cccgcaaccg   15000
cagaccctgc tagagttgca acagcgcgag caggcagagg cggcgctgcg aaaggaaagc   15060
ttccgcaggc caagcagctt gtccgatcta ggcgctgcgg ccccgcggtc agatgctagt   15120
agcccatttc caagcttgat agggtctctt accagcactc gcaccacccg cccgcgcctg   15180
ctgggcgagg aggagtacct aaacaactcg ctgctgcagc cgcagcgcga aaaaaacctg   15240
cctccggcat ttcccaacaa cgggatagag agcctagtgg acaagatgag tagatggaag   15300
acgtacgcgc aggagcacag ggacgtgcca ggcccgcgcc cgcccacccg tcgtcaaagg   15360
cacgaccgtc agcgggggtct ggtgtgggag gacgatgact cggcagacga cagcagcgtc   15420
ctggatttgg gagggagtgg caacccgttt gcgcaccttc gccccaggct ggggagaatg   15480
ttttaaaaaa aaaaaagcat gatgcaaaat aaaaaactca ccaaggccat ggcaccgagc   15540
gttggttttc ttgtattccc cttagtatgc ggcgcgcggc gatgtatgag gaaggtcctc   15600
ctccctccta cgagagtgtg gtgagcgcgg cgccagtggc ggcggcgctg ggttctccct   15660
tcgatgctcc cctggacccg ccgtttgtgc ctccgcggta cctgcggcct accgggggga   15720
gaaacagcat ccgttactct gagttggcac ccctattcga caccacccgt gtgtacctgg   15780
tggacaacaa gtcaacggat gtggcatccc tgaactacca gaacgaccac agcaactttc   15840
tgaccacggt cattcaaaac aatgactaca gcccgggggga ggcaagcaca cagaccatca   15900
atcttgacga ccgggtcgcac tggggcggcg acctgaaaac catcctgcat accaacatgc   15960
```

-continued

```
caaatgtgaa cgagttcatg tttaccaata agtttaaggc gcgggtgatg gtgtcgcgct   16020
tgcctactaa ggacaatcag gtggagctga aatacgagtg ggtggagttc acgctgcccg   16080
agggcaacta ctccgagacc atgaccatag accttatgaa caacgcgatc gtggagcact   16140
acttgaaagt gggcagacag aacggggttc tggaaagcga catcgggta aagtttgaca   16200 cccgcaactt cagactgggg tttgacccg tcactggtct tgtcatgcct ggggtatata   16260
caaacgaagc cttccatcca gacatcattt tgctgccagg atgcggggtg gacttcaccc   16320
acagccgcct gagcaacttg ttgggcatcc gcaagcggca acccttccag gagggctta   16380 ggatcaccta cgatgatctg gagggtggta acattcccgc actgttggat gtggacgcct   16440
accaggcgag cttgaaagat gacaccgaac agggcgggg tggcgcaggc ggcagcaaca   16500
gcagtggcag cggcgcggaa gagaactcca acgcggcagc cgcggcaatg cagccggtgg   16560
aggacatgaa cgatcatgcc attcgcggcg acacctttgc cacacgggct gaggagaagc   16620
gcgctgaggc cgaagcagcg gccgaagctg ccgcccccgc tgcgcaaccc gaggtcgaga   16680
agcctcagaa gaaaccggtg atcaaacccc tgacagagga cagcaagaaa cgcagttaca   16740
acctaataag caatgacagc accttcaccc agtaccgcag ctggtacctt gcatacaact   16800
acggcgaccc tcagaccgga atccgctcat ggaccctgct ttgcactcct gacgtaacct   16860
gcggctcgga gcaggtctac tggtcgttgc cagacatgat gcaagacccc gtgaccttcc   16920
gctccacgcg ccagatcagc aactttccgg tggtgggcgc cgagctgttg cccgtgcact   16980
ccaagagctt ctacaacgac caggccgtct actcccaact catccgccag tttacctctc   17040
tgacccacgt gttcaatcgc tttcccgaga accagatttt ggcgcgcccg ccagcccca   17100 ccatcaccac cgtcagtgaa aacgttcctg ctctcacaga tcacgggacg ctaccgctgc   17160
gcaacagcat cggaggagtc cagcgagtga ccattactga cgccagacgc cgcacctgcc   17220
cctacgttta caaggccctg ggcatagtct cgccgcgcgt cctatcgagc cgcacttttt   17280
gagcaagcat gtccatcctt atatcgccca gcaataacac aggctggggc ctgcgcttcc   17340
caagcaagat gtttggcggg gccaagaagc gctccgacca acacccagtg cgcgtgcgcg   17400
ggcactaccg cgcgccctgg ggcgcgcaca aacgcggccg cactgggcgc accaccgtcg   17460
atgacgccat cgacgcggtg gtggaggagg cgcgcaacta cacgcccacg ccgccaccag   17520
tgtccacagt ggacgcggcc attcagaccg tggtgcgcgg agcccggcgc tatgctaaaa   17580
tgaagagacg gcggaggcgc gtagcacgtc gccaccgccg ccgacccggc actgccgccc   17640
aacgcgcggc ggcggccctg cttaaccgcg cacgtcgcac cggccgacgg gcggccatgc   17700
gggccgctcg aaggctggcc gcgggtattg tcactgtgcc ccccaggtcc aggcgacgag   17760
cggccgccgc agcagccgcg gccattagtg ctatgactca gggtcgcagg ggcaacgtgt   17820
attgggtgcg cgactcggtt agcggcctgc gcgtgcccgt gcgcacccgc cccccgcgca   17880
actagattgc aagaaaaaac tacttagact cgtactgttg tatgtatcca gcggcggcgg   17940
cgcgcaacga agctatgtcc aagcgcaaaa tcaaagaaga gatgctccag gtcatcgcgc   18000
cggagatcta tggccccccg aagaaggaag agcaggatta caagccccga aagctaaagc   18060
gggtcaaaaa gaaaaagaaa gatgatgatg atgaacttga cgacgaggtg gaactgctgc   18120
acgctaccgc gcccaggcga cgggtacagt ggaaaggtcg acgcgtaaaa cgtgtttttgc   18180 gaccccggcac caccgtagtc tttacgcccg gtgagcgctc caccgcacc tacaagcgcg   18240 tgtatgatga ggtgtacggc gacgaggacc tgcttgagca ggccaacgag cgcctcgggg   18300
agtttgccta cggaaagcgg cataaggaca tgctggcgtt gccgctggac gagggcaacc   18360
```

-continued

```
caacacctag cctaaagccc gtaacactgc agcaggtgct gcccgcgctt gcaccgtccg   18420
aagaaaagcg cggcctaaag cgcgagtctg gtgacttggc acccaccgtg cagctgatgg   18480
tacccaagcg ccagcgactg gaagatgtct tggaaaaaat gaccgtggaa cctgggctgg   18540
agcccgaggt ccgcgtgcgg ccaatcaagc aggtggcgcc gggactgggc gtgcagaccg   18600
tggacgttca gatacccact accagtagca ccagtattgc caccgccaca gagggcatgg   18660
agacacaaac gtccccggtt gcctcagcgg tggcggatgc cgcggtgcag gcggtcgctg   18720
cggccgcgtc caagacctct acggaggtgc aaacggaccc gtggatgttt cgcgtttcag   18780 cccccccggcg cccgcgccgt tcgaggaagt acggcgccgc cagcgcgcta ctgcccgaat   18840
atgccctaca tccttccatt gcgcctaccc ccggctatcg tggctacacc taccgcccca   18900
gaagacgagc aactacccga cgccgaacca ccactggaac ccgccgccgc cgtcgccgtc   18960
gccagcccgt gctggccccg atttccgtgc gcagggtggc tcgcgaagga ggcaggaccc   19020
tggtgctgcc aacagcgcgc taccacccca gcatcgttta aaagccggtc tttgtggttc   19080
ttgcagatat ggccctcacc tgccgcctcc gtttcccggt gccgggattc cgaggaagaa   19140
tgcaccgtag gaggggcatg gccggccacg gcctgacggg cggcatgcgt cgtgcgcacc   19200
accggcggcg gcgcgcgtcg caccgtcgca tgcgcggcgg tatcctgccc ctccttattc   19260
cactgatcgc cgcggcgatt ggcgccgtgc ccggaattgc atccgtggcc ttgcaggcgc   19320
agagacactg attaaaaaca agttgcatgt ggaaaaatca aaataaaaag tctggactct   19380
cacgctcgct tggtcctgta actattttgt agaatggaag acatcaactt tgcgtctctg   19440
gccccgcgac acggctcgcg cccgttcatg ggaaactggc aagatatcgg caccagcaat   19500
atgagcggtg gcgccttcag ctggggctcg ctgtggagcg gcattaaaaa tttcggttcc   19560
accgttaaga actatggcag caaggcctgg aacagcagca caggccagat gctgagggat   19620
aagttgaaag agcaaaattt ccaacaaaag gtggtagatg gcctggcctc tggcattagc   19680
ggggtggtgg acctggccaa ccaggcagtg caaaataaga ttaacagtaa gcttgatccc   19740
cgccctcccg tagaggagcc tccaccggcc gtggagacag tgtctccaga ggggcgtggc   19800
gaaaagcgtc cgcgccccga cagggaagaa actctggtga cgcaaataga cgagcctccc   19860
tcgtacgagg aggcactaaa gcaaggcctg cccaccaccc gtcccatcgc gcccatggct   19920
accggagtgc tgggccagca cacacccgta acgctggacc tgcctccccc cgccgacacc   19980
cagcagaaac ctgtgctgcc aggcccgacc gccgttgttg taacccgtcc tagccgcgcg   20040
tccctgcgcc gcgccgccag cggtccgcga tcgttgcggc ccgtagccag tggcaactgg   20100
caaagcacac tgaacagcat cgtgggtctg ggggtgcaat ccctgaagcg ccgacgatgc   20160
ttctgatagc taacgtgtcg tatgtgtgtc atgtatgcgt ccatgtcgcc gccagaggag   20220
ctgctgagcc gccgcgcgcc cgctttccaa gatggctacc ccttcgatga tgccgcagtg   20280
gtcttacatg cacatctcgg gccaggacgc ctcggagtac ctgagccccg ggctggtgca   20340
gtttgcccgc gccaccgaga cgtacttcag cctgaataac aagtttagaa accccacggt   20400
ggcgcctacg cacgacgtga ccacagaccg gtcccagcgt ttgacgctgc ggttcatccc   20460
tgtggaccgt gaggatactg cgtactcgta caaggcgcgg ttcacccctag ctgtgggtga   20520 taaccgtgtg ctggacatgg cttccacgta ctttgacatc cgcggcgtgc tggacagggg   20580
ccctactttt aagccctact ctggcactgc ctacaacgcc ctggctccca gggggtgcccc   20640 aaatccttgc gaatgggatg aagctgctac tgctcttgaa ataaacctag aagaagagga   20700
```

-continued

```
cgatgacaac gaagacgaag tagacgagca agctgagcag caaaaaactc acgtatttgg   20760
gcaggcgcct tattctggta taaatattac aaaggagggt attcaaatag gtgtcgaagg   20820
tcaaacacct aaatatgccg ataaaacatt tcaacctgaa cctcaaatag gagaatctca   20880
gtggtacgaa acagaaatta atcatgcagc tgggagagtc ctaaaaaaga ctaccccaat   20940
gaaaccatgt tacggttcat atgcaaaacc cacaaatgaa aatggagggc aaggcattct   21000
tgtaaagcaa caaaatggaa agctagaaag tcaagtggaa atgcaatttt tctcaactac   21060
tgaggcagcc gcaggcaatg gtgataactt gactcctaaa gtggtattgt acagtgaaga   21120
tgtagatata gaaaccccag acactcatat ttcttacatg cccactatta aggaaggtaa   21180
ctcacgagaa ctaatgggcc aacaatctat gcccaacagg cctaattaca ttgctttttag   21240 ggacaatttt attggtctaa tgtattacaa cagcacgggt aatatgggtg ttctggcggg   21300
ccaagcatcg cagttgaatg ctgttgtaga tttgcaagac agaaacacag agctttcata   21360
ccagcttttg cttgattcca ttggtgatag aaccaggtac ttttctatgt ggaatcaggc   21420
tgttgacagc tatgatccag atgttagaat tattgaaaat catggaactg aagatgaact   21480
tccaaattac tgctttccac tgggaggtgt gattaataca gagactctta ccaaggtaaa   21540
acctaaaaca ggtcaggaaa atggatggga aaaagatgct acagaatttt cagataaaaa   21600
tgaaataaga gttggaaata attttgccat ggaaatcaat ctaaatgcca acctgtggag   21660
aaatttcctg tactccaaca tagcgctgta tttgcccgac aagctaaagt acagtccttc   21720
caacgtaaaa atttctgata acccaaacac ctacgactac atgaacaagc gagtggtggc   21780
tcccgggcta gtggactgct acattaacct tggagcacgc tggtcccttg actatatgga   21840
caacgtcaac ccatttaacc accaccgcaa tgctggcctg cgctaccgct caatgttgct   21900
gggcaatggt cgctatgtgc ccttccacat ccaggtgcct cagaagttct ttgccattaa   21960
aaacctcctt ctcctgccgg gctcatacac ctacgagtgg aacttcagga aggatgttaa   22020
catggttctg cagagctccc taggaaatga cctaagggtt gacggagcca gcattaagtt   22080
tgatagcatt tgcctttacg ccaccttctt ccccatggcc cacaacaccg cctccacgct   22140
tgaggccatg cttagaaacg acaccaacga ccagtccttt aacgactatc tctccgccgc   22200
caacatgctc taccctatac ccgccaacgc taccaacgtg cccatatcca tcccctcccg   22260
caactgggcg gctttccgcg gctgggccct cacgcgcctt aagactaagg aaaccccatc   22320
actgggctcg ggctacgacc cttattacac ctactctggc tctataccct acctagatgg   22380
aaccttttac ctcaaccaca cctttaagaa ggtggccatt accttttgact cttctgtcag   22440 ctggcctggc aatgaccgcc tgcttacccc caacgagttt gaaattaagc gctcagttga   22500 cgggagggt tacaacgttg cccagtgtaa catgaccaaa gactggttcc tggtacaaat   22560
gctagctaac tataacattg ctaccagggg cttctatatc ccagagagct acaaggaccg   22620
catgtactcc ttctttagaa acttccagcc catgagccgt caggtggtgg atgatactaa   22680
atacaaggac taccaacagg tgggcatcct acaccaacac aacaactctg gatttgttgg   22740
ctaccttgcc cccaccatgc gcgaaggaca ggcctaccct gctaacttcc cctatccgct   22800
tataggcaag accgcagttg acagcattac ccagaaaaag tttctttgcg atcgcaccct   22860
ttggcgcatc ccattctcca gtaactttat gtccatgggc gcactcacag acctgggcca   22920
aaaccttctc tacgccaact ccgcccacgc gctagacatg acttttgagg tggatcccat   22980
ggacgagccc accttctttt atgtttttgt tgaagtcttt gacgtggtcc gtgtgcacca   23040
gccgcaccgc ggcgtcatcg aaaccgtgta cctgcgcacg cccttctcgg ccggcaacgc   23100
```

-continued

```
cacaacataa agaagcaagc aacatcaaca acagctgccg ccatgggctc cagtgagcag    23160
gaactgaaag ccattgtcaa agatcttggt tgtgggccat attttttggg cacctatgac    23220
aagcgctttc caggctttgt ttctccacac aagctcgcct gcgccatagt caatacggcc    23280
ggtcgcgaga ctgggggcgt acactggatg gcctttgcct ggaacccgca ctcaaaaaca    23340
tgctacctct ttgagccctt tggcttttct gaccagcgac tcaagcaggt ttaccagttt    23400
gagtacgagt cactcctgcg ccgtagcgcc attgcttctt cccccgaccg ctgtataacg    23460
ctggaaaagt ccacccaaag cgtacagggg cccaactcgg ccgcctgtgg actattctgc    23520
tgcatgtttc tccacgcctt tgccaactgg ccccaaactc ccatggatca caaccccacc    23580
atgaacctta ttaccggggt acccaactcc atgctcaaca gtccccaggt acagcccacc    23640
ctgcgtcgca accaggaaca gctctacagc ttcctggagc gccactcgcc ctacttccgc    23700
agccacagtg cgcagattag gagcgccact tctttttgtc acttgaaaaa catgtaaaaa    23760
taatgtacta gagacacttt caataaaggc aaatgctttt atttgtacac tctcgggtga    23820
ttatttaccc ccacccttgc cgtctgcgcc gtttaaaaat caaaggggtt ctgccgcgca    23880
tcgctatgcg ccactggcag ggacacgttg cgatactggt gtttagtgct ccacttaaac    23940
tcaggcacaa ccatccgcgg cagctcggtg aagtttttcac tccacaggct gcgcaccatc    24000
accaacgcgt ttagcaggtc gggcgccgat atcttgaagt cgcagttggg gcctccgccc    24060
tgcgcgcgcg agttgcgata cacagggttg cagcactgga acactatcag cgccgggtgg    24120
tgcacgctgg ccagcacgct cttgtcggag atcagatccg cgtccaggtc ctccgcgttg    24180
ctcagggcga acggagtcaa ctttggtagc tgccttccca aaaagggcgc gtgcccaggc    24240
tttgagttgc actcgcaccg tagtggcatc aaaaggtgac cgtgcccggt ctgggcgtta    24300
ggatacagcg cctgcataaa agccttgatc tgcttaaaag ccacctgagc ctttgcgcct    24360
tcagagaaga acatgccgca agacttgccg gaaaactgat tggccggaca ggccgcgtcg    24420
tgcacgcagc accttgcgtc ggtgttggag atctgcacca catttcggcc ccaccggttc    24480
ttcacgatct tggccttgct agactgctcc ttcagcgcgc gctgcccgtt ttcgctcgtc    24540
acatccattt caatcacgtg ctccttattt atcataatgc ttccgtgtag acacttaagc    24600
tcgccttcga tctcagcgca gcggtgcagc cacaacgcgc agcccgtggg ctcgtgatgc    24660
ttgtaggtca cctctgcaaa cgactgcagg tacgcctgca ggaatcgccc catcatcgtc    24720
acaaaggtct tgttgctggt gaaggtcagc tgcaacccgc ggtgctcctc gttcagccag    24780
gtcttgcata cggccgccag agcttccact tggtcaggca gtagtttgaa gttcgccttt    24840
agatcgttat ccacgtggta cttgtccatc agcgcgcgcg cagcctccat gcccttctcc    24900
cacgcagaca cgatcggcac actcagcggg ttcatcaccg taatttcact ttccgcttcg    24960
ctgggctctt cctcttcctc ttgcgtccgc ataccacgcg ccactgggtc gtcttcattc    25020
agccgccgca ctgtgcgctt acctcctttg ccatgcttga ttagcaccgg tgggttgctg    25080
aaacccacca tttgtagcgc cacatcttct ctttcttcct cgctgtccac gattacctct    25140
ggtgatggcg ggcgctcggg cttgggagaa gggcgcttct ttttcttctt gggcgcaatg    25200
gccaaatccg ccgccgaggt cgatggccgc gggctgggtg tgcgcggcac cagcgcgtct    25260
tgtgatgagt cttcctcgtc ctcggactcg atacgccgcc tcatccgctt ttttgggggc    25320
gcccggggag gcgcggccga cggggacggg gacgacacgt cctccatggt ggggggacgt    25380
cgcgccgcac cgcgtccgcg ctcggggggtg gtttcgcgct gctcctcttc ccgactggcc    25440
```

-continued

```
atttccttct cctataggca gaaaaagatc atggagtcag tcgagaagaa ggacagccta   25500 accgcccccct ctgagttcgc caccaccgcc tccaccgatg ccgccaacgc gcctaccacc   25560
ttccccgtcg aggcacccccc gcttgaggag gaggaagtga ttatcgagca ggacccaggt   25620
tttgtaagcg aagacgacga ggaccgctca gtaccaacag aggataaaaa gcaagaccag   25680
gacaacgcag aggcaaacga ggaacaagtc gggcgggggg acgaaaggca tggcgactac   25740
ctagatgtgg gagacgacgt gctgttgaag catctgcagc gccagtgcgc cattatctgc   25800
gacgcgttgc aagagcgcag cgatgtgccc ctcgccatag cggatgtcag ccttgcctac   25860
gaacgccacc tattctcacc gcgcgtaccc cccaaacgcc aagaaaacgg cacatgcgag   25920
cccaacccgc gcctcaactt ctaccccgta tttgccgtgc cagaggtgct tgccacctat   25980
cacatctttt tccaaaactg caagataccc ctatcctgcc gtgccaaccg cagccgagcg   26040
gacaagcagc tggccttgcg gcagggcgct gtcatacctg atatcgcctc gctcaacgaa   26100
gtgccaaaaa tctttgaggg tcttggacgc gacgagaagc gcgcggcaaa cgctctgcaa   26160
caggaaaaca gcgaaaatga aagtcactct ggagtgttgg tggaactcga gggtgacaac   26220
gcgcgcctag ccgtactaaa acgcagcatc gaggtcaccc actttgccta cccggcactt   26280
aacctacccc ccaaggtcat gagcacagtc atgagtgagc tgatcgtgcg ccgtgcgcag   26340
cccctggaga gggatgcaaa tttgcaagaa caaacagagg agggcctacc cgcagttggc   26400
gacgagcagc tagcgcgctg gcttcaaacg cgcgagcctg ccgacttgga ggagcgacgc   26460
aaactaatga tggccgcagt gctcgttacc gtggagcttg agtgcatgca gcggttcttt   26520
gctgacccgg agatgcagcg caagctagag gaaacattgc actacacctt tcgacagggc   26580
tacgtacgcc aggcctgcaa gatctccaac gtggagctct gcaacctggt ctcctacctt   26640
ggaattttgc acgaaaaccg ccttgggcaa aacgtgcttc attccacgct caagggcgag   26700
gcgcgccgcg actacgtccg cgactgcgtt tacttatttc tatgctacac ctggcagacg   26760
gccatgggcg tttggcagca gtgcttggag gagtgcaacc tcaaggagct gcagaaactg   26820
ctaaagcaaa acttgaagga cctatggacg gccttcaacg agcgctccgt ggccgcgcac   26880
ctggcggaca tcattttccc cgaacgcctg cttaaaaccc tgcaacaggg tctgccagac   26940
ttcaccagtc aaagcatgtt gcagaacttt aggaacttta tcctagagcg ctcaggaatc   27000
ttgcccgcca cctgctgtgc acttcctagc gactttgtgc ccattaagta ccgcgaatgc   27060
cctccgccgc tttggggcca ctgctacctt ctgcagctag ccaactacct tgcctaccac   27120
tctgacataa tggaagacgt gagcggtgac ggtctactgg agtgtcactg tcgctgcaac   27180
ctatgcaccc cgcaccgctc cctggtttgc aattcgcagc tgcttaacga aagtcaaatt   27240
atcggtacct ttgagctgca gggtccctcg cctgacgaaa agtccgcggc tccggggttg   27300
aaactcactc cggggctgtg gacgtcggct taccttcgca aatttgtacc tgaggactac   27360
cacgcccacg agattaggtt ctacgaagac caatcccgcc cgcctaatgc ggagcttacc   27420
gcctgcgtca ttacccaggg ccacattctt ggccaattgc aagccatcaa caaagcccgc   27480
caagagtttc tgctacgaaa gggacggggg gtttacttgg accccccagtc cggcgaggag   27540 ctcaacccaa tccccccgcc gccgcagccc tatcagcagc agccgcgggc ccttgcttcc   27600
caggatggca cccaaaaaga agctgcagct gccgccgcca cccacggacg aggaggaata   27660
ctgggacagt caggcagagg aggtttttgga cgaggaggag gaggacatga tggaagactg   27720
ggagagccta gacgaggaag cttccgaggt cgaagaggtg tcagacgaaa caccgtcacc   27780
ctcggtcgca ttcccctcgc cggcgcccca gaaatcggca accggttcca gcatggctac   27840
```

-continued

```
aacctccgct cctcaggcgc cgccggcact gcccgttcgc cgacccaacc gtagatggga   27900
caccactgga accagggccg gtaagtccaa gcagccgccg ccgttagccc aagagcaaca   27960
acagcgccaa ggctaccgct catggcgcgg gcacaagaac gccatagttg cttgcttgca   28020
agactgtggg ggcaacatct ccttcgcccg ccgctttctt ctctaccatc acggcgtggc   28080
cttcccccgt aacatcctgc attactaccg tcatctctac agcccatact gcaccggcgg   28140
cagcggcagc aacagcagcg gccacacaga agcaaaggcg accggatagc aagactctga   28200
caaagcccaa gaaatccaca gcggcggcag cagcaggagg aggagcgctg cgtctggcgc   28260
ccaacgaacc cgtatcgacc cgcgagctta gaaacaggat ttttcccact ctgtatgcta   28320
tatttcaaca gagcaggggc caagaacaag agctgaaaat aaaaaacagg tctctgcgat   28380
ccctcacccg cagctgcctg tatcacaaaa gcgaagatca gcttcggcgc acgctggaag   28440
acgcggaggc tctcttcagt aaatactgcg cgctgactct taaggactag tttcgcgccc   28500
tttctcaaat ttaagcgcga aaactacgtc atctccagcg gccacacccg gcgccagcac   28560
ctgttgtcag cgccattatg agcaaggaaa ttcccacgcc ctacatgtgg agttaccagc   28620
cacaaatggg acttgcggct ggagctgccc aagactactc aacccgaata aactacatga   28680
gcgcgggacc ccacatgata tcccgggtca acggaatacg cgcccaccga aaccgaattc   28740
tcctggaaca ggcggctatt accaccacac ctcgtaataa ccttaatccc cgtagttggc   28800
ccgctgccct ggtgtaccag gaaagtcccg ctcccaccac tgtggtactt cccagagacg   28860
cccaggccga agttcagatg actaactcag gggcgcagct tgcgggcggc tttcgtcaca   28920
gggtgcggtc gcccgggcag ggtataactc acctgacaat cagagggcga ggtattcagc   28980
tcaacgacga gtcggtgagc tcctcgcttg gtctccgtcc ggacgggaca tttcagatcg   29040
gcggcgccgg ccgctcttca ttcacgcctc gtcaggcaat cctaactctg cagacctcgt   29100
cctctgagcc gcgctctgga ggcattggaa ctctgcaatt tattgaggag tttgtgccat   29160
cggtctactt taaccccttc tcgggacctc ccggccacta tccggatcaa tttattccta   29220
actttgacgc ggtaaaggac tcggcggacg gctacgactg aatgttaagt ggagaggcag   29280
agcaactgcg cctgaaacac ctggtccact gtcgccgcca caagtgcttt gcccgcgact   29340
ccggtgagtt ttgctacttt gaattgcccg aggatcatat cgagggcccg gcgcacggcg   29400
tccggcttac cgcccaggga gagcttgccc gtagcctgat tcgggagttt acccagcgcc   29460
ccctgctagt tgagcgggac aggggaccct gtgttctcac tgtgatttgc aactgtccta   29520
accctggatt acatcaagat cctctagtta atgtcaggtc gcctaagtcg attaactaga   29580
gtacccgggg atcttattcc ctttaactaa taaaaaaaaa taataaagca tcacttactt   29640
aaaatcagtt agcaaatttc tgtccagttt attcagcagc acctccttgc cctcctccca   29700
gctctggtat tgcagcttcc tcctggctgc aaactttctc cacaatctaa atggaatgtc   29760 agttcctcc tgttcctgtc catccgcacc cactatcttc atgttgttgc agatgaagcg   29820
cgcaagaccg tctgaagata ccttcaaccc cgtgtatcca tatgacacgg aaaccggtcc   29880
tccaactgtg cctttttctta ctcctccctt tgtatccccc aatgggtttc aagagagtcc   29940
ccctggggta ctctctttgc gcctatccga acctctagtt acctccaatg gcatgcttgc   30000
gctcaaaatg ggcaacggcc tctctctgga cgaggccggc aaccttacct cccaaaatgt   30060
aaccactgtg agcccaccctc tcaaaaaaac caagtcaaac ataaacctgg aaatatctgc   30120 accctcaca gttacctcag aagccctaac tgtggctgcc gccgcacctc taatggtcgc   30180
```

-continued

```
gggcaacaca ctcaccatgc aatcacaggc cccgctaacc gtgcacgact ccaaacttag   30240
cattgccacc caaggacccc tcacagtgtc agaaggaaag ctagccctgc aaacatcagg   30300
ccccctcacc accaccgata gcagtaccct tactatcact gcctcacccc ctctaactac   30360
tgccactggt agcttgggca ttgacttgaa agagcccatt tatacacaaa atggaaaact   30420
aggactaaag tacggggctc ctttgcatgt aacagacgac ctaaacactt tgaccgtagc   30480
aactggtcca ggtgtgacta ttaataatac ttccttgcaa actaaagtta ctggagcctt   30540 gggtttttgat tcacaaggca atatgcaact taatgtagca ggaggactaa ggattgattc   30600
tcaaaacaga cgccttatac ttgatgttag ttatccgttt gatgctcaaa accaactaaa   30660
tctaagacta ggacagggcc ctctttttat aaactcagcc cacaacttgg atattaacta   30720
caacaaaggc ctttacttgt ttacagcttc aaacaattcc aaaaagcttg aggttaacct   30780
aagcactgcc aaggggttga tgtttgacgc tacagccata gccattaatg caggagatgg   30840
gcttgaattt ggttcaccta atgcaccaaa cacaaatccc ctcaaaacaa aaattggcca   30900
tggcctagaa tttgattcaa acaaggctat ggttcctaaa ctaggaactg gccttagttt   30960
tgacagcaca ggtgccatta cagtaggaaa caaaaataat gataagctaa ctttgtggac   31020
cggaataaac cctccaccta actgtcaaat tgtggaaaac actaatacaa atgatggcaa   31080
acttacttta gtattagtaa aaaatggagg gcttgttaat ggctacgtgt ctctagttgg   31140
tgtatcagac actgtgaacc aaatgttcac acaaaagaca gcaaacatcc aattaagatt   31200
atattttgac tcttctggaa atctattaac tgaggaatca gacttaaaaa ttccacttaa   31260
aaataaatct tctacagcga ccagtgaaac tgtagccagc agcaaagcct ttatgccaag   31320
tactacagct tatcccttca acaccactac tagggatagt gaaaactaca ttcatggaat   31380
atgttactac atgactagtt atgatagaag tctatttccc ttgaacattt ctataatgct   31440
aaacagccgt atgatttctt ccaatgttgc ctatgccata caatttgaat ggaatctaaa   31500
tgcaagtgaa tctccagaaa gcaacatagc tacgctgacc acatccccct ttttcttttc   31560
ttacattaca gaagacgaca actaaagaat cgtttgtgtt atgtttcaac gtgtttattt   31620
ttcaattgca gaaaatttca agtcattttt cattcagtag tatagcccca ccaccacata   31680
gcttatacag atcaccgtac cttaatcaaa ctcacagaac cctagtattc aacctgccac   31740
ctccctccca acacacagag tacacagtcc tttctccccg gctggcctta aaaagcatca   31800
tatcatgggt aacagacata ttcttaggtg ttatattcca cacggtttcc tgtcgagcca   31860
aacgctcatc agtgatatta ataaactccc cgggcagctc acttaagttc atgtcgctgt   31920
ccagctgctg agccacaggc tgctgtccaa cttgcggttg cttaacgggc ggcgaaggag   31980
aagtccacgc ctacatgggg gtagagtcat aatcgtgcat caggataggg cggtggtgct   32040
gcagcagcgc gcgaataaac tgctgccgcc gccgctccgt cctgcaggaa tacaacatgg   32100
cagtggtctc ctcagcgatg attcgcaccg cccgcagcat aaggcgcctt gtcctccggg   32160
cacagcagcg caccctgatc tcacttaaat cagcacagta actgcagcac agcaccacaa   32220
tattgttcaa aatcccacag tgcaaggcgc tgtatccaaa gctcatggcg gggaccacag   32280
aacccacgtg gccatcatac cacaagcgca ggtagattaa gtggcgaccc ctcataaaca   32340
cgctggacat aaacattacc tcttttggca tgttgtaatt caccacctcc cggtaccata   32400
taaacctctg attaaacatg gcgccatcca ccaccatcct aaaccagctg gccaaaacct   32460
gcccgccggc tatacactgc agggaaccgg gactggaaca atgacagtgg agagcccagg   32520
actcgtaacc atggatcatc atgctcgtca tgatatcaat gttggcacaa cacaggcaca   32580
```

-continued

```
cgtgcataca cttcctcagg attacaagct cctcccgcgt tagaaccata tcccagggaa    32640
caacccattc ctgaatcagc gtaaatccca cactgcaggg aagacctcgc acgtaactca    32700
cgttgtgcat tgtcaaagtg ttacattcgg gcagcagcgg atgatcctcc agtatggtag    32760
cgcgggtttc tgtctcaaaa ggaggtagac gatccctact gtacggagtg cgccgagaca    32820
accgagatcg tgttggtcgt agtgtcatgc caaatggaac gccggacgta gtcatatttc    32880
ctgaagcaaa accaggtgcg ggcgtgacaa acagatctgc gtctccggtc tcgccgctta    32940
gatcgctctg tgtagtagtt gtagtatatc cactctctca aagcatccag gcgccccctg    33000
gcttcgggtt ctatgtaaac tccttcatgc gccgctgccc tgataacatc caccaccgca    33060
gaataagcca cacccagcca acctacacat tcgttctgcg agtcacacac gggaggagcg    33120
ggaagagctg gaagaaccat gtttttttt ttattccaaa agattatcca aaacctcaaa     33180
atgaagatct attaagtgaa cgcgctcccc tccggtggcg tggtcaaact ctacagccaa    33240
agaacagata atggcatttg taagatgttg cacaatggct tccaaaaggc aaacggccct    33300
cacgtccaag tggacgtaaa ggctaaaccc ttcagggtga atctcctcta taaacattcc    33360
agcaccttca accatgccca aataattctc atctcgccac cttctcaata tatctctaag    33420
caaatcccga atattaagtc cggccattgt aaaaatctgc tccagagcgc cctccacctt    33480
cagcctcaag cagcgaatca tgattgcaaa aattcaggtt cctcacagac ctgtataaga    33540
ttcaaaagcg gaacattaac aaaaataccg cgatcccgta ggtcccttcg cagggccagc    33600
tgaacataat cgtgcaggtc tgcacggacc agcgcggcca cttccccgcc aggaaccatg    33660
acaaaagaac ccacactgat tatgacacgc atactcggag ctatgctaac cagcgtagcc    33720
ccgatgtaag cttgttgcat gggcggcgat ataaaatgca aggtgctgct caaaaaatca    33780
ggcaaagcct cgcgcaaaaa agaaagcaca tcgtagtcat gctcatgcag ataaaggcag    33840
gtaagctccg gaaccaccac agaaaaagac accatttttc tctcaaacat gtctgcgggt    33900
ttctgcataa acacaaaata aaataacaaa aaaacattta aacattagaa gcctgtctta    33960
caacaggaaa aacaacccct ataagcataa gacggactac ggccatgccg gcgtgaccgt    34020
aaaaaaactg gtcaccgtga ttaaaaagca ccaccgacag ctcctcggtc atgtccggag    34080
tcataatgta agactcggta aacacatcag gttgattcac atcggtcagt gctaaaaagc    34140
gaccgaaata gcccggggga atacataccc gcaggcgtag agacaacatt acagccccca    34200
taggaggtat aacaaaatta ataggagaga aaaacacata aacacctgaa aaaccctcct    34260
gcctaggcaa aatagcaccc tcccgctcca gaacaacata cagcgcttcc acagcggcag    34320
ccataacagt cagccttacc agtaaaaaag aaaacctatt aaaaaaacac cactcgacac    34380
ggcaccagct caatcagtca cagtgtaaaa aagggccaag tgcagagcga gtatatatag    34440
gactaaaaaa tgacgtaacg gttaaagtcc acaaaaaaca cccagaaaac cgcacgcgaa    34500
cctacgccca gaaacgaaag ccaaaaaacc cacaacttcc tcaaatcgtc acttccgttt    34560
tcccacgtta cgtcacttcc cattttaaga aaactacaat tcccaacaca tacaagttac    34620
tccgccctaa aacctacgtc acccgccccg ttcccacgcc ccgcgccacg tcacaaactc    34680 cacccctca ttatcatatt ggcttcaatc caaaataagg tatattattg atgatg        34736
```

<210> SEQ ID NO 28
<211> LENGTH: 37705
<212> TYPE: DNA
<213> ORGANISM: Artificial Sequence
<220> FEATURE:

-continued

<223> OTHER INFORMATION: plasmid #4 vector

<400> SEQUENCE: 28

```
ttaattaaca tgcatggatc catatgcggt gtgaaatacc gcacagatgc gtaaggagaa        60
aataccgcat caggcgctct tccgcttcct cgctcactga ctcgctgcgc tcggtcgttc       120
ggctgcggcg agcggtatca gctcactcaa aggcggtaat acggttatcc acagaatcag       180
gggataacgc aggaaagaac atgtgagcaa aaggccagca aaaggccagg aaccgtaaaa       240
aggccgcgtt gctggcgttt ttccataggc tccgcccccc tgacgagcat cacaaaaatc       300
gacgctcaag tcagaggtgg cgaaacccga caggactata aagataccag gcgtttcccc       360
ctggaagctc cctcgtgcgc tctcctgttc cgaccctgcc gcttaccgga tacctgtccg       420
cctttctccc ttcgggaagc gtggcgcttt ctcatagctc acgctgtagg tatctcagtt       480
cggtgtaggt cgttcgctcc aagctgggct gtgtgcacga accccccgtt cagcccgacc       540
gctgcgcctt atccggtaac tatcgtcttg agtccaaccc ggtaagacac gacttatcgc       600
cactggcagc agccactggt aacaggatta gcagagcgag gtatgtaggc ggtgctacag       660
agttcttgaa gtggtggcct aactacggct acactagaag gacagtattt ggtatctgcg       720
ctctgctgaa gccagttacc ttcggaaaaa gagttggtag ctcttgatcc ggcaaacaaa       780
ccaccgctgg tagcggtggt ttttttgttt gcaagcagca gattacgcgc agaaaaaaag       840
gatctcaaga agatcctttg atcttttcta cggggtctga cgctcagtgg aacgaaaact       900
cacgttaagg gattttggtc atgagattat caaaaaggat cttcacctag atccttttaa       960
attaaaaatg aagttttaaa tcaatctaaa gtatatatga gtaaacttgg tctgacagtt      1020
accaatgctt aatcagtgag gcacctatct cagcgatctg tctatttcgt tcatccatag      1080
ttgcctgact ccccgtcgtg tagataacta cgatacggga gggcttacca tctggcccca      1140
gtgctgcaat gataccgcga gacccacgct caccggctcc agatttatca gcaataaacc      1200
agccagccgg aagggccgag cgcagaagtg gtcctgcaac tttatccgcc tccatccagt      1260
ctattaattg ttgccgggaa gctagagtaa gtagttcgcc agttaatagt ttgcgcaacg      1320
ttgttgccat tgctgcagcc atgagattat caaaaaggat cttcacctag atccttttca      1380
cgtagaaagc cagtccgcag aaacggtgct gaccccggat gaatgtcagc tactgggcta      1440
tctggacaag ggaaaacgca agcgcaaaga gaaagcaggt agcttgcagt gggcttacat      1500
ggcgatagct agactgggcg gttttatgga cagcaagcga accggaattg ccagctgggg      1560
cgccctctgg taaggttggg aagccctgca aagtaaactg gatggctttc ttgccgccaa      1620
ggatctgatg gcgcagggga tcaagctctg atcaagagac aggatgagga tcgtttcgca      1680
tgattgaaca agatggattg cacgcaggtt ctccggccgc ttgggtggag aggctattcg      1740
gctatgactg ggcacaacag acaatcggct gctctgatgc cgccgtgttc cggctgtcag      1800
cgcaggggcg cccggttctt tttgtcaaga ccgacctgtc cggtgccctg aatgaactgc      1860
aagacgaggc agcgcggcta tcgtggctgg ccacgacggg cgttccttgc gcagctgtgc      1920
tcgacgttgt cactgaagcg ggaagggact ggctgctatt gggcgaagtg ccggggcagg      1980
atctcctgtc atctcacctt gctcctgccg agaaagtatc catcatggct gatgcaatgc      2040
ggcggctgca tacgcttgat ccggctacct gcccattcga ccaccaagcg aaacatcgca      2100
tcgagcgagc acgtactcgg atggaagccg gtcttgtcga tcaggatgat ctggacgaag      2160
agcatcaggg gctcgcgcca gccgaactgt tcgccaggct caaggcgagc atgcccgacg      2220
gcgaggatct cgtcgtgacc catggcgatg cctgcttgcc gaatatcatg gtggaaaatg      2280
```

-continued

```
gccgctttc tggattcatc gactgtggcc ggctgggtgt ggcggaccgc tatcaggaca     2340
tagcgttggc tacccgtgat attgctgaag agcttggcgg cgaatgggct gaccgcttcc     2400
tcgtgcttta cggtatcgcc gctcccgatt cgcagcgcat cgccttctat cgccttcttg     2460
acgagttctt ctgaattttg ttaaaatttt tgttaaatca gctcattttt taaccaatag     2520
gccgaaatcg gcaaaatccc ttataaatca aaagaataga ccgagatagg gttgagtgtt     2580
gttccagttt ggaacaagag tccactatta aagaacgtgg actccaacgt caaagggcga     2640
aaaaccgtct atcagggcga tggcccacta cgtgaaccat caccctaatc aagttttttg     2700
gggtcgaggt gccgtaaagc actaaatcgg aaccctaaag ggagccccg atttagagct     2760 tgacggggaa agccggcgaa cgtggcgaga aggaaggga agaaagcgaa aggagcgggc     2820 gctaggcgc tggcaagtgt agcggtcacg ctgcgcgtaa ccaccacacc cgccgcgctt     2880
aatgcgccgc tacagggcgc gtccattcgc cattcaggat cgaattaatt cttaattaac     2940
atcatcaata atataccta tttttggattg aagccaatat gataatgagg gggtggagtt     3000
tgtgacgtgg cgcggggcgt gggaacgggg cgggtgacgt agtagtgtgg cggaagtgtg     3060
atgttgcaag tgtggcggaa cacatgtaag cgacggatgg ggcaaaagtg acgttttttg     3120
tgtgcgccgg tgtacacagg aagtgacaat tttcgcgcgg ttttaggcgg atgttgtagt     3180
aaatttgggc gtaaccgagt aagatttggc cattttcgcg ggaaaactga ataagaggaa     3240
gtgaaatctg aataatttttg tgttactcat agcgcgtaat actgtaatag taatcaatta     3300
cggggtcatt agttcatagc ccatatatgg agttccgcgt tacataactt acggtaaatg     3360
gcccgcctgg ctgaccgccc aacgaccccc gcccattgac gtcaataatg acgtatgttc     3420
ccatagtaac gccaataggg actttccatt gacgtcaatg ggtggagtat ttacggtaaa     3480
ctgcccactt ggcagtacat caagtgtatc atatgccaag tacgcccct attgacgtca     3540 atgacggtaa atggcccgcc tggcattatg cccagtacat gaccttatgg actttcctta     3600
cttggcagta catctacgta ttagtcatcg ctattaccat ggtgatgcgg ttttggcagt     3660
acatcaatgg gcgtggatag cggtttgact cacggggatt tccaagtctc caccccattg     3720
acgtcaatgg gagtttgttt tggcaccaaa atcaacggga ctttccaaaa tgtcgtaaca     3780
actccgcccc attgacgcaa atgggcggta ggcgtgtacg gtgggaggtc tatataagca     3840
gagctctccc tatcagtgat agagatctcc ctatcagtga tagagatcgt cgacgagctc     3900
gtttagtgaa ccgtcagatc gcctggagac gccatccacg ctgttttgac ctccatagaa     3960
gacaccggga ccgatccagc ctccgatttg ccaccatgtt tgtgttcctg gtgctgctgc     4020
cactggtgtc cagccagtgt gtgaacctga ccaccaggac ccaacttcct cctgcctaca     4080
ccaactcctt caccaggga gtctactacc ctgacaaggt gttcaggtcc tctgtgctgc     4140
acagcaccca ggacctgttc ctgccattct tcagcaatgt gacctggttc catgccatcc     4200
atgtgtctgg caccaatggc accaagaggt ttgacaaccc tgtgctgcca ttcaatgatg     4260
gagtctactt tgccagcaca gagaagagca acatcatcag gggctggatt tttggcacca     4320
ccctggacag caagacccag tccctgctga ttgtgaacaa tgccaccaat gtggtgatta     4380
aggtgtgtga gttccagttc tgtaatgacc cattcctggg agtctactac cacaagaaca     4440
acaagtcctg gatggagtct gagttcaggg tctactcctc tgccaacaac tgtacctttg     4500
aatatgtgag ccaaccattc ctgatggact ggagggcaa gcaggcaac ttcaagaacc     4560 tgagggagtt tgtgttcaag aacattgatg gctacttcaa gatttacagc aaacacacac     4620
```

-continued

```
caatcaacct ggtgagggac ctgccacagg gcttctctgc cttggaacca ctggtggacc     4680
tgccaattgg catcaacatc accaggttcc agaccctgct ggctctgcac aggtcctacc     4740
tgacacctgg agactcctcc tctggctgga cagcaggagc agcagcctac tatgtgggct     4800
acctccaacc aaggaccttc ctgctgaaat acaatgagaa tggcaccatc acagatgctg     4860
tggactgtgc cctggaccca ctgtctgaga ccaagtgtac cctgaaatcc ttcacagtgg     4920
agaagggcat ctaccagacc agcaacttca gggtccaacc aacagagagc attgtgaggt     4980
ttccaaacat caccaacctg tgtccatttg gagaggtgtt caatgccacc aggtttgcct     5040
ctgtctatgc ctggaacagg aagaggatta gcaactgtgt ggctgactac tctgtgctct     5100
acaactctgc ctccttcagc accttcaagt gttatggagt gagcccaacc aaactgaatg     5160
acctgtgttt caccaatgtc tatgctgact cctttgtgat tagggagat gaggtgagac     5220 agattgcccc tggacaaaca ggcaagattg ctgactacaa ctacaaactg cctgatgact     5280
tcacaggctg tgtgattgcc tggaacagca caacctgga cagcaaggtg ggaggcaact     5340
acaactacct ctacagactg ttcaggaaga gcaacctgaa accatttgag agggacatca     5400
gcacagagat ttaccaggct ggcagcacac catgtaatgg agtggagggc ttcaactgtt     5460
actttccact ccaatcctat ggcttccaac caaccaatgg agtgggctac caaccataca     5520
gggtggtggt gctgtccttt gaactgctcc atgcccctgc cacagtgtgt ggaccaaaga     5580
agagcaccaa cctggtgaag aacaagtgtg tgaacttcaa cttcaatgga ctgacaggca     5640
caggagtgct gacagagagc aacaagaagt tcctgccatt ccaacagttt ggcagggaca     5700
ttgctgacac cacagatgct gtgagggacc cacagacctt ggagattctg gacatcacac     5760
catgttcctt tggaggagtg tctgtgatta cacctggcac caacaccagc aaccaggtgg     5820
ctgtgctcta ccaggatgtg aactgtactg aggtgcctgt ggctatccat gctgaccaac     5880
ttacaccaac ctggagggtc tacagcacag gcagcaatgt gttccagacc agggctggct     5940
gtctgattgg agcagagcat gtgaacaact cctatgagtg tgacatccca attggagcag     6000
gcatctgtgc ctcctaccag acccagaccg gtggcggtgg gtcgggcggt ggtgggtcgg     6060
gtggcggcgg ttccaggtct gtggcaagcc agagcatcat tgcctacaca atgagtctgg     6120
gagcagagaa ctctgtggct tacagcaaca acagcattgc catcccaacc aacttcacca     6180
tctctgtgac cacagagatt ctgcctgtga gtatgaccaa gacctctgtg gactgtacaa     6240
tgtatatctg tggagacagc acagagtgta gcaacctgct gctccaatat ggctccttct     6300
gtacccaact taacagggct ctgacaggca ttgctgtgga acaggacaag aacacccagg     6360
aggtgtttgc ccaggtgaag cagatttaca gacacctcc aatcaaggac tttggaggct     6420
tcaacttcag ccagattctg cctgacccaa gcaagccaag caagaggtcc ttcattgagg     6480
acctgctgtt caacaaggtg accctggctg atgctggctt catcaagcaa tatggagact     6540
gtctgggaga cattgctgcc agggacctga tttgtgccca gaagttcaat ggactgacag     6600
tgctgcctcc actgctgaca gatgagatga ttgcccaata cacctctgcc ctgctggctg     6660
gcaccatcac ctctggctgg acctttggag caggagcagc cctccaaatc ccatttgcta     6720
tgcagatggc ttacaggttc aatggcattg gagtgaccca gaatgtgctc tatgagaacc     6780
agaaactgat tgccaaccag ttcaactctg ccattggcaa gattcaggac tccctgtcca     6840
gcacagcctc tgccctgggc aaactccaag atgtggtgaa ccagaatgcc caggctctga     6900
acaccctggt gaagcaactt tccagcaact ttggagccat ctcctctgtg ctgaatgaca     6960
tcctgagcag actggacaag gtggaggctg aggtccagat tgacagactg attacaggca     7020
```

-continued

```
gactccaatc cctccaaacc tatgtgaccc aacaacttat cagggctgct gagattaggg   7080
catctgccaa cctggctgcc accaagatga gtgagtgtgt gctgggacaa agcaagaggg   7140
tggacttctg tggcaagggc taccacctga tgagttttcc acagtctgcc cctcatggag   7200
tggtgttcct gcatgtgacc tatgtgcctg cccaggagaa gaacttcacc acagcccctg   7260
ccatctgcca tgatggcaag gctcactttc caagggaggg agtgtttgtg agcaatggca   7320
cccactggtt tgtgacccag aggaacttct atgaaccaca gattatcacc acagacaaca   7380
cctttgtgtc tggcaactgt gatgtggtga ttggcattgt gaacaacaca gtctatgacc   7440
cactccaacc tgaactggac tccttcaagg aggaactgga caaatacttc aagaaccaca   7500
ccagccctga tgtggacctg ggagacatct ctggcatcaa tgcctctgtg gtgaacatcc   7560
agaaggagat tgacagactg aatgaggtgg ctaagaacct gaatgagtcc ctgattgacc   7620
tccaagaact gggcaaatat gaacaataca tcaagtggcc atgaaaattg atcataatca   7680
gccataccac atttgtagag gttttacttg ctttaaaaaa cctcccacac ctccccctga   7740
acctgaaaca taaaatgaat gcaattgttg ttgttaactt gtttattgca gcttataatg   7800
gttacaaata aagcaatagc atcacaaatt tcacaaataa agcatttttt tcactgcatt   7860
ctagttgtgg tttgtccaaa ctcatcaatg tatcttaacg cggatctggg cgtggttaag   7920
ggtgggaaag aatatataag gtgggggtct tatgtagttt tgtatctgtt ttgcagcagc   7980
cgccgccgcc atgagcacca actcgtttga tggaagcatt gtgagctcat atttgacaac   8040
gcgcatgccc ccatgggccg gggtgcgtca gaatgtgatg ggctccagca ttgatggtcg   8100
ccccgtcctg cccgcaaact ctactacctt gacctacgag accgtgtctg gaacgccgtt   8160
ggagactgca gcctccgccg ccgcttcagc cgctgcagcc accgcccgcg ggattgtgac   8220
tgactttgct ttcctgagcc cgcttgcaag cagtgcagct tcccgttcat ccgcccgcga   8280
tgacaagttg acggctcttt tggcacaatt ggattctttg acccgggaac ttaatgtcgt   8340
ttctcagcag ctgttggatc tgcgccagca ggtttctgcc ctgaaggctt cctcccctcc   8400
caatgcggtt taaaacataa ataaaaaacc agactctgtt tggatttgga tcaagcaagt   8460
gtcttgctgt ctttatttag gggttttgcg cgcgcggtag gcccgggacc agcggtctcg   8520
gtcgttgagg gtcctgtgta ttttttccag gacgtggtaa aggtgactct ggatgttcag   8580
atacatgggc ataagcccgt ctctggggtg gaggtagcac cactgcagag cttcatgctg   8640
cggggtggtg ttgtagatga tccagtcgta gcaggagcgc tgggcgtggt gcctaaaaat   8700
gtctttcagt agcaagctga ttgccagggg caggcccttg gtgtaagtgt ttacaaagcg   8760
gttaagctgg gatgggtgca tacgtgggga tatgagatgc atcttggact gtattttag   8820 gttggctatg ttcccagcca tatccctccg gggattcatg ttgtgcagaa ccaccagcac   8880
agtgtatccg gtgcacttgg gaaatttgtc atgtagctta gaaggaaatg cgtggaagaa   8940
cttggagacg ccccttgtgac ctccaagatt ttccatgcat tcgtccataa tgatggcaat   9000
gggcccacgg gcggcggcct gggcgaagat atttctggga tcactaacgt catagttgtg   9060
ttccaggatg agatcgtcat aggccatttt tacaaagcgc gggcggaggg tgccagactg   9120
cggtataatg gttccatccg gcccaggggc gtagttaccc tcacagattt gcatttccca   9180
cgctttgagt tcagatgggg gatcatgtc tacctgcggg gcgatgaaga aaacggtttc   9240
cggggtaggg gagatcagct gggaagaaag caggttcctg agcagctgcg acttaccgca   9300
gccggtgggc ccgtaaatca cacctattac cggctgcaac tggtagttaa gagagctgca   9360
```

-continued

```
gctgccgtca tccctgagca ggggggccac ttcgttaagc atgtccctga ctcgcatgtt    9420
ttccctgacc aaatccgcca gaaggcgctc gccgcccagc gatagcagtt cttgcaagga    9480
agcaaagttt ttcaacggtt tgagaccgtc cgccgtaggc atgcttttga gcgtttgacc    9540
aagcagttcc aggcggtccc acagctcggt cacctgctct acggcatctc gatccagcat    9600
atctcctcgt ttcgcgggtt ggggcggctt tcgctgtacg gcagtagtcg gtgctcgtcc    9660
agacgggcca gggtcatgtc tttccacggg cgcaggtcc tcgtcagcgt agtctgggtc    9720
acggtgaagg ggtgcgctcc gggctgcgcg ctggccaggg tgcgcttgag gctggtcctg    9780
ctggtgctga agcgctgccg gtcttcgccc tgcgcgtcgg ccaggtagca tttgaccatg    9840
gtgtcatagt ccagcccctc cgcggcgtgg cccttggcgc gcagcttgcc cttggaggag    9900
gcgccgcacg aggggcagtg cagacttttg agggcgtaga gcttgggcgc gagaaatacc    9960
gattccgggg agtaggcatc cgcgccgcag gccccgcaga cggtctcgca ttccacgagc    10020
caggtgagct ctggccgttc ggggtcaaaa accaggtttc ccccatgctt tttgatgcgt    10080
ttcttacctc tggtttccat gagccggtgt ccacgctcgg tgacgaaaag gctgtccgtg    10140
tccccgtata cagacttgag aggcctgtcc tcgagcggtg ttccgcggtc ctcctcgtat    10200
agaaactcgg accactctga dacaaaggct cgcgtccagg ccagcacgaa ggaggctaag    10260
tgggaggggt agcggtcgtt gtccactagg gggtccactc gctccagggt gtgaagacac    10320
atgtcgccct cttcggcatc aaggaaggtg attggtttgt aggtgtaggc cacgtgaccg    10380
ggtgttcctg aagggggggct ataaaagggg gtggggcgc gttcgtcctc actctcttcc    10440
gcatcgctgt ctgcgagggc cagctgttgg ggtgagtact ccctctgaaa agcgggcatg    10500
acttctgcgc taagattgtc agtttccaaa aacgaggagg atttgatatt cacctggccc    10560
gcggtgatgc ctttgagggt ggccgcatcc atctggtcag aaaagacaat cttttttgttg    10620 tcaagcttgg tggcaaacga cccgtagagg gcgttggaca gcaacttggc gatggagcgc    10680
agggtttggt ttttgtcgcg atcggcgcgc tccttggccg cgatgtttag ctgcacgtat    10740
tcgcgcgcaa cgcaccgcca ttcgggaaag acggtggtgc gctcgtcggg caccaggtgc    10800
acgcgccaac cgcggttgtg cagggtgaca aggtcaacgc tggtggctac ctctccgcgt    10860
aggcgctcgt tggtccagca gaggcggccg cccttgcgcg agcagaatgg cggtaggggg    10920
tctagctgcg tctcgtccgg ggggtctgcg tccacggtaa agaccccggg cagcaggcgc    10980
gcgtcgaagt agtctatctt gcatccttgc aagtctagcg cctgctgcca tgcgcgggcg    11040
gcaagcgcgc gctcgtatgg gttgagtggg ggaccccatg gcatggggtg ggtgagcgcg    11100
gaggcgtaca tgccgcaaat gtcgtaaacg tagaggggct ctctgagtat tccaagatat    11160
gtagggtagc atcttccacc gcggatgctg gcgcgcacgt aatcgtatag ttcgtgcgag    11220
ggagcgagga ggtcgggacc gaggttgcta cgggcgggct gctctgctcg gaagactatc    11280
tgcctgaaga tggcatgtga gttggatgat atggttggac gctggaagac gttgaagctg    11340
gcgtctgtga gacctaccgc gtcacgcacg aaggaggcgt aggagtcgcg cagcttgttg    11400
accagctcgg cggtgacctg cacgtctagg gcgcagtagt ccagggtttc cttgatgatg    11460
tcatacttat cctgtccctt ttttttccac agctcgcggt tgaggacaaa ctcttcgcgg    11520
tctttccagt actcttggat cggaaacccg tcggcctccg aacggtaaga gcctagcatg    11580
tagaactggt tgacgccctg gtaggcgcag catccctttt ctacgggtag cgcgtatgcc    11640
tgcgcggcct tccggagcga ggtgtgggtg agcgcaaagg tgtccctgac catgactttg    11700
aggtactggt atttgaagtc agtgtcgtcg catccgccct gctcccagag caaaaagtcc    11760
```

-continued

```
gtgcgctttt tggaacgcgg atttggcagg gcgaaggtga catcgttgaa gagtatcttt   11820
cccgcgcgag gcataaagtt gcgtgtgatg cggaagggtc ccggcacctc ggaacggttg   11880
ttaattacct gggcggcgag cacgatctcg tcaaagccgt tgatgttgtg gcccacaatg   11940
taaagttcca agaagcgcgg gatgcccttg atggaaggca attttttaag ttcctcgtag   12000
gtgagctctt caggggagct gagcccgtgc tctgaaaggg cccagtctgc aagatgaggg   12060
ttggaagcga cgaatgagct ccacaggtca cgggccatta gcatttgcag gtggtcgcga   12120
aaggtcctaa actggcgacc tatggccatt ttttctgggg tgatgcagta gaaggtaagc   12180
gggtcttgtt cccagcggtc ccatccaagg ttcgcggcta ggtctcgcgc ggcagtcact   12240
agaggctcat ctccgccgaa cttcatgacc agcatgaagg gcacgagctg cttcccaaag   12300
gcccccatcc aagtataggt ctctacatcg taggtgacaa agagacgctc ggtgcgagga   12360
tgcgagccga tcgggaagaa ctggatctcc cgccaccaat tggaggagtg gctattgatg   12420
tggtgaaagt agaagtccct gcgacgggcc gaacactcgt gctggctttt gtaaaaacgt   12480
gcgcagtact ggcagcggtg cacgggctgt acatcctgca cgaggttgac ctgacgaccg   12540
cgcacaagga agcagagtgg gaatttgagc ccctcgcctg gcgggtttgg ctggtggtct   12600
tctacttcgg ctgcttgtcc ttgaccgtct ggctgctcga ggggagttac ggtggatcgg   12660
accaccacgc cgcgcgagcc caaagtccag atgtccgcgc gcggcggtcg gagcttgatg   12720
acaacatcgc gcagatggga gctgtccatg gtctggagct cccgcggcgt caggtcaggc   12780
gggagctcct gcaggtttac ctcgcataga cgggtcaggg cgcgggctag atccaggtga   12840
tacctaattt ccaggggctg gttggtggcg gcgtcgatgg cttgcaagag gccgcatccc   12900
cgcggcgcga ctacggtacc gcgcggcggg cggtgggccg cggggggtgtc cttggatgat   12960 gcatctaaaa gcggtgacgc gggcgagccc ccggaggtag gggggggctcc ggacccgccg   13020 ggagaggggg caggggcacg tcggcgccgc gcgcgggcag gagctggtgc tgcgcgcgta   13080
ggttgctggc gaacgcgacg acgcggcggt tgatctcctg aatctggcgc ctctgcgtga   13140
agacgacggg cccggtgagc ttgaacctga aagagagttc gacagaatca atttcggtgt   13200
cgttgacggc ggcctggcgc aaaatctcct gcacgtctcc tgagttgtct tgataggcga   13260
tctcggccat gaactgctcg atctcttcct cctggagatc tccgcgtccg gctcgctcca   13320
cggtggcggc gaggtcgttg gaaatgcggg ccatgagctg cgagaaggcg ttgaggcctc   13380
cctcgttcca gacgcggctg tagaccacgc ccccttcggc atcgcgggcg cgcatgacca   13440
cctgcgcgag attgagctcc acgtgccggg cgaagacggc gtagtttcgc aggcgctgaa   13500
agaggtagtt gagggtggtg gcggtgtgtt ctgccacgaa gaagtacata acccagcgtc   13560
gcaacgtgga ttcgttgata tcccccaagg cctcaaggcg ctccatggcc tcgtagaagt   13620
ccacggcgaa gttgaaaaac tgggagttgc gcgccgacac ggttaactcc tcctccagaa   13680
gacggatgag ctcggcgaca gtgtcgcgca cctcgcgctc aaaggctaca ggggcctctt   13740
cttcttcttc aatctcctct tccataaggg cctccccttc ttcttcttct ggcggcggtg   13800 ggggagggggg gacacggcgg cgacgacggc gcaccgggag gcggtcgaca aagcgctcga   13860
tcatctcccc gcggcgacgg cgcatggtct cggtgacggc gcggccgttc tcgcggggggc   13920 gcagttggaa gacgccgccc gtcatgtccc ggttatgggt tggcgggggg ctgccatgcg   13980
gcagggatac ggcgctaacg atgcatctca acaattgttg tgtaggtact ccgccgccga   14040
gggacctgag cgagtccgca tcgaccggat cggaaaacct ctcgagaaag gcgtctaacc   14100
```

-continued

```
agtcacagtc gcaaggtagg ctgagcaccg tggcgggcgg cagcgggcgg cggtcggggt   14160
tgtttctggc ggaggtgctg ctgatgatgt aattaaagta ggcggtcttg agacggcgga   14220
tggtcgacag aagcaccatg tccttgggtc cggcctgctg aatgcgcagg cggtcggcca   14280
tgccccaggc ttcgttttga catcggcgca ggtctttgta gtagtcttgc atgagccttt   14340
ctaccggcac ttcttcttct ccttcctctt gtcctgcatc tcttgcatct atcgctgcgg   14400
cggcggcgga gtttggccgt aggtggcgcc ctcttcctcc catgcgtgtg accccgaagc   14460
ccctcatcgg ctgaagcagg gctaggtcgg cgacaacgcg ctcggctaat atggcctgct   14520
gcacctgcgt gagggtagac tggaagtcat ccatgtccac aaagcggtgg tatgcgcccg   14580
tgttgatggt gtaagtgcag ttggccataa cggaccagtt aacggtctgg tgacccggct   14640
gcgagagctc ggtgtacctg agacgcgagt aagccctcga gtcaaatacg tagtcgttgc   14700
aagtccgcac caggtactgg tatcccacca aaaagtgcgg cggcggctgg cggtagaggg   14760
gccagcgtag ggtggccggg gctccggggg cgagatcttc caacataagg cgatgatatc   14820
cgtagatgta cctggacatc caggtgatgc cggcggcggt ggtggaggcg cgcggaaagt   14880
cgcggacgcg gttccagatg ttgcgcagcg gcaaaaagtg ctccatggtc gggacgctct   14940
ggccggtcag gcgcgcgcaa tcgttgacgc tctagcgtgc aaaaggagag cctgtaagcg   15000
ggcactcttc cgtggtctgg tggataaatt cgcaagggta tcatggcgga cgaccggggt   15060
tcgagccccg tatccggccg tccgccgtga tccatgcggt taccgcccgc gtgtcgaacc   15120
caggtgtgcg acgtcagaca acgggggagt gctccttttg gcttccttcc aggcgcggcg   15180
gctgctgcgc tagctttttt ggccactggc cgcgcgcagc gtaagcggtt aggctggaaa   15240
gcgaaagcat taagtggctc gctccctgta gccggagggt tattttccaa gggttgagtc   15300
gcgggacccc cggttcgagt ctcggaccgg ccggactgcg cgaacgggg gtttgcctcc   15360 ccgtcatgca agaccccgct tgcaaattcc tccggaaaca gggacgagcc ccttttttgc   15420
ttttcccaga tgcatccggt gctgcggcag atgcgccccc ctcctcagca gcggcaagag   15480
caagagcagc ggcagacatg cagggcaccc tcccctcctc ctaccgcgtc aggaggggcg   15540
acatccgcgt ttgacgcggc agcagatggt gattacgaac ccccgcggcg ccgggcccgg   15600
cactacctgg acttggagga gggcgagggc ctggcgcggc taggagcgcc ctctcctgag   15660
cggcacccaa gggtgcagct gaagcgtgat acgcgtgagg cgtacgtgcc gcggcagaac   15720
ctgtttcgcg accgcgaggg agaggagccc gaggagatgc gggatcgaaa gttccacgca   15780
gggcgcgagc tgcggcatgg cctgaatcgc gagcggttgc tgcgcgagga ggactttgag   15840
cccgacgcgc gaaccgggat tagtcccgcg cgcgcacacg tggcggccgc cgacctggta   15900
accgcatacg agcagacggt gaaccaggag attaactttc aaaaaagctt taacaaccac   15960
gtgcgtacgc ttgtggcgcg cgaggaggtg gctataggac tgatgcatct gtgggacttt   16020
gtaagcgcgc tggagcaaaa cccaaatagc aagccgctca tggcgcagct gttccttata   16080
gtgcagcaca gcagggacaa cgaggcattc agggatgcgc tgctaaacat agtagagccc   16140
gagggccgct ggctgctcga tttgataaac atcctgcaga gcatagtggt gcaggagcgc   16200
agcttgagcc tggctgacaa ggtggccgcc atcaactatt ccatgcttag cctgggcaag   16260
ttttacgccc gcaagatata ccatacccct tacgttccca tagacaagga ggtaaagatc   16320
gaggggttct acatgcgcat ggcgctgaag gtgcttacct tgagcgacga cctgggcgtt   16380
tatcgcaacg agcgcatcca caaggccgtg agcgtgagcc ggcggcgcga gctcagcgac   16440
cgcgagctga tgcacagcct gcaaagggcc ctggctggca cgggcagcgg cgatagagag   16500
```

-continued

```
gccgagtcct actttgacgc gggcgctgac ctgcgctggg ccccaagccg acgcgccctg    16560
gaggcagctg gggccggacc tgggctggcg gtggcacccg cgcgcgctgg caacgtcggc    16620
ggcgtggagg aatatgacga ggacgatgag tacgagccag aggacggcga gtactaagcg    16680
gtgatgtttc tgatcagatg atgcaagacg caacggaccc ggcggtgcgg cgggcgctgc    16740
agagccagcc gtccggcctt aactccacgg acgactggcg ccaggtcatg gaccgcatca    16800
tgtcgctgac tgcgcgcaat cctgacgcgt tccggcagca gccgcaggcc aaccggctct    16860
ccgcaattct ggaagcggtg gtcccggcgc gcgcaaaccc cacgcacgag aaggtgctgg    16920
cgatcgtaaa cgcgctggcc gaaaacaggg ccatccggcc cgacgaggcc ggcctggtct    16980
acgacgcgct gcttcagcgc gtggctcgtt acaacagcgg caacgtgcag accaacctgg    17040
accggctggt gggggatgtg cgcgaggccg tggcgcagcg tgagcgcgcg cagcagcagg    17100
gcaacctggg ctccatggtt gcactaaacg ccttcctgag tacacagccc gccaacgtgc    17160
cgcggggaca ggaggactac accaactttg tgagcgcact gcggctaatg gtgactgaga    17220
caccgcaaag tgaggtgtac cagtctgggc cagactattt tttccagacc agtagacaag    17280
gcctgcagac cgtaaacctg agccaggctt tcaaaaactt gcaggggctg tggggggtgc    17340
gggctcccac aggcgaccgc gcgaccgtgt ctagcttgct gacgcccaac tcgcgcctgt    17400
tgctgctgct aatagcgccc ttcacggaca gtggcagcgt gtcccgggac acatacctag    17460
gtcacttgct gacactgtac cgcgaggcca taggtcaggc gcatgtggac gagcatactt    17520
tccaggagat tacaagtgtc agccgcgcgc tggggcagga ggacacgggc agcctggagg    17580
caaccctaaa ctacctgctg accaaccggc ggcagaagat cccctcgttg cacagtttaa    17640
acagcgagga ggagcgcatt ttgcgctacg tgcagcagag cgtgagcctt aacctgatgc    17700
gcgacggggt aacgcccagc gtggcgctgg acatgaccgc gcgcaacatg gaaccgggca    17760
tgtatgcctc aaaccggccg tttatcaacc gcctaatgga ctacttgcat cgcgcgcgccg   17820 ccgtgaaccc cgagtatttc accaatgcca tcttgaaccc gcactggcta ccgcccctg     17880 gtttctacac cgggggattc gaggtgcccg agggtaacga tggattcctc tgggacgaca    17940
tagacgacag cgtgttttcc ccgcaaccgc agacctgct agagttgcaa cagcgcgagc     18000
aggcagaggc ggcgctgcga aaggaaagct tccgcaggcc aagcagcttg tccgatctag    18060
gcgctgcggc cccgcggtca gatgctagta gcccatttcc aagcttgata gggtctctta    18120
ccagcactcg caccacccgc ccgcgcctgc tgggcgagga ggagtaccta aacaactcgc    18180
tgctgcagcc gcagcgcgaa aaaaacctgc ctccggcatt tcccaacaac gggatagaga    18240
gcctagtgga caagatgagt agatggaaga cgtacgcgca ggagcacagg acgtgccag     18300 gcccgcgccc gcccacccgt cgtcaaaggc acgaccgtca cgcgggtctg gtgtgggagg    18360
acgatgactc ggcagacgac agcagcgtcc tggatttggg agggagtggc aacccgtttg    18420
cgcaccttcg ccccaggctg gggagaatgt tttaaaaaaa aaaaagcatg atgcaaaata    18480
aaaaactcac caaggccatg gcaccgagcg ttggtttttct tgtattcccc ttagtatgcg    18540
gcgcgcggcg atgtatgagg aaggtcctcc tccctcctac gagagtgtgg tgagcgcggc    18600
gccagtggcg gcggcgctgg gttctcccct cgatgctccc ctggaccgc cgtttgtgcc    18660 tccgcggtac ctgcggccta ccggggggag aaacagcatc cgttactctg agttggcacc    18720
cctattcgac accaccgtg tgtacctggt ggacaacaag tcaacggatg tggcatccct     18780
gaactaccag aacgaccaca gcaactttct gaccacggtc attcaaaaca atgactacag    18840
```

-continued

```
cccgggggag gcaagcacac agaccatcaa tcttgacgac cggtcgcact ggggcggcga   18900
cctgaaaacc atcctgcata ccaacatgcc aaatgtgaac gagttcatgt ttaccaataa   18960
gtttaaggcg cgggtgatgg tgtcgcgctt gcctactaag gacaatcagg tggagctgaa   19020
atacgagtgg gtggagttca cgctgcccga gggcaactac tccgagacca tgaccataga   19080
ccttatgaac aacgcgatcg tggagcacta cttgaaagtg ggcagacaga acggggttct   19140
ggaaagcgac atcggggtaa agtttgacac ccgcaacttc agactggggt ttgaccccgt   19200
cactggtctt gtcatgcctg gggtatatac aaacgaagcc ttccatccag acatcatttt   19260
gctgccagga tgcggggtgg acttcacccca cagccgcctg agcaacttgt tgggcatccg   19320
caagcggcaa cccttccagg agggctttag gatcacctac gatgatctgg agggtggtaa   19380
cattcccgca ctgttggatg tggacgccta ccaggcgagc ttgaaagatg acaccgaaca   19440 gggcggggt ggcgcaggcg gcagcaacag cagtggcagc ggcgcggaag agaactccaa   19500
cgcggcagcc gcggcaatgc agccggtgga ggacatgaac gatcatgcca ttcgcggcga   19560
cacctttgcc acacgggctg aggagaagcg cgctgaggcc gaagcagcgg ccgaagctgc   19620
cgcccccgct gcgcaacccg aggtcgagaa gcctcagaag aaaccggtga tcaaacccct   19680
gacagaggac agcaagaaac gcagttacaa cctaataagc aatgacagca ccttcaccca   19740
gtaccgcagc tggtaccttg catacaacta cggcgaccct cagaccggaa tccgctcatg   19800 gacccctgctt tgcactcctg acgtaacctg cggctcggag caggtctact ggtcgttgcc   19860
agacatgatg caagaccccg tgaccttccg ctccacgcgc cagatcagca actttccggt   19920
ggtgggcgcc gagctgttgc ccgtgcactc caagagcttc tacaacgacc aggccgtcta   19980
ctcccaactc atccgccagt ttacctctct gacccacgtg ttcaatcgct ttcccgagaa   20040
ccagattttg gcgcgcccgc cagcccccac catcaccacc gtcagtgaaa acgttcctgc   20100
tctcacagat cacgggacgc taccgctgcg caacagcatc ggaggagtcc agcgagtgac   20160
cattactgac gccagacgcc gcacctgccc ctacgtttac aaggccctgg gcatagtctc   20220
gccgcgcgtc ctatcgagcc gcactttttg agcaagcatg tccatcctta tatcgcccag   20280
caataacaca ggctggggcc tgcgcttccc aagcaagatg tttggcgggg ccaagaagcg   20340
ctccgaccaa cacccagtgc gcgtgcgcgg gcactaccgc gcgccctggg gcgcgcacaa   20400
acgcggccgc actgggcgca ccaccgtcga tgacgccatc gacgcggtgg tggaggaggc   20460
gcgcaactac acgcccacgc cgccaccagt gtccacagtg gacgcggcca ttcagaccgt   20520
ggtgcgcgga gcccggcgct atgctaaaat gaagagacgg cggaggcgcg tagcacgtcg   20580
ccaccgccgc cgacccggca ctgccgccca acgcgcggcg gcggccctgc ttaaccgcgc   20640
acgtcgcacc ggccgacggg cggccatgcg ggccgctcga aggctggccg cgggtattgt   20700
cactgtgccc cccaggtcca ggcgacgagc ggccgccgca gcagccgcgg ccattagtgc   20760
tatgactcag ggtcgcaggg gcaacgtgta ttgggtgcgc gactcggtta gcggcctgcg   20820
cgtgcccgtg cgcacccgcc ccccgcgcaa ctagattgca agaaaaaact acttagactc   20880
gtactgttgt atgtatccag cggcggcggc gcgcaacgaa gctatgtcca agcgcaaaat   20940
caaagaagag atgctccagg tcatcgcgcc ggagatctat ggccccccga agaaggaaga   21000
gcaggattac aagcccgaa agctaaagcg ggtcaaaaag aaaaagaaag atgatgatga   21060
tgaacttgac gacgaggtgg aactgctgca cgctaccgcg cccaggcgac gggtacagtg   21120
gaaaggtcga cgcgtaaaac gtgttttgcg acccggcacc accgtagtct ttacgcccgg   21180
tgagcgctcc acccgcacct acaagcgcgt gtatgatgag gtgtacggcg acgaggacct   21240
```

-continued

```
gcttgagcag gccaacgagc gcctcgggga gtttgcctac ggaaagcggc ataaggacat   21300
gctggcgttg ccgctggacg agggcaaccc aacacctagc ctaaagcccg taacactgca   21360
gcaggtgctg cccgcgcttg caccgtccga agaaaagcgc ggcctaaagc gcgagtctgg   21420
tgacttggca cccaccgtgc agctgatggt acccaagcgc cagcgactgg aagatgtctt   21480
ggaaaaaatg accgtggaac ctgggctgga gcccgaggtc cgcgtgcggc caatcaagca   21540
ggtggcgccg ggactgggcg tgcagaccgt ggacgttcag atacccacta ccagtagcac   21600
cagtattgcc accgccacag agggcatgga gacacaaacg tccccggttg cctcagcggt   21660
ggcggatgcc gcggtgcagg cggtcgctgc ggccgcgtcc aagacctcta cggaggtgca   21720
aacggacccg tggatgtttc gcgtttcagc cccccggcgc ccgcgccgtt cgaggaagta   21780
cggcgccgcc agcgcgctac tgcccgaata tgccctacat ccttccattg cgcctacccc   21840
cggctatcgt ggctacacct accgcccag aagacgagca actacccgac gccgaaccac   21900
cactggaacc cgccgccgcc gtcgccgtcg ccagcccgtg ctggccccga tttccgtgcg   21960
cagggtggct cgcgaaggag gcaggaccct ggtgctgcca acagcgcgct accaccccag   22020
catcgtttaa aagccggtct ttgtggttct tgcagatatg gccctcacct gccgcctccg   22080
tttcccggtg ccgggattcc gaggaagaat gcaccgtagg aggggcatgg ccggccacgg   22140
cctgacgggc ggcatgcgtc gtgcgcacca ccggcggcgg cgcgcgtcgc accgtcgcat   22200
gcgcggcggt atcctgcccc tccttattcc actgatcgcc gcggcgattg cgccgtgcc   22260 cggaattgca tccgtggcct tgcaggcgca gagacactga ttaaaaacaa gttgcatgtg   22320
gaaaaatcaa aataaaaagt ctggactctc acgctcgctt ggtcctgtaa ctattttgta   22380
gaatggaaga catcaacttt gcgtctctgg ccccgcgaca cggctcgcgc ccgttcatgg   22440
gaaactggca agatatcggc accagcaata tgagcggtgg cgccttcagc tggggctcgc   22500
tgtggagcgg cattaaaaat ttcggttcca ccgttaagaa ctatggcagc aaggcctgga   22560
acagcagcac aggccagatg ctgagggata agttgaaaga gcaaaatttc caacaaaagg   22620
tggtagatgg cctggcctct ggcattagcg gggtggtgga cctggccaac caggcagtgc   22680
aaaataagat taacagtaag cttgatcccc gccctcccgt agaggagcct ccaccggccg   22740
tggagacagt gtctccagag gggcgtggcg aaaagcgtcc gcgccccgac agggaagaaa   22800
ctctggtgac gcaaatagac gagcctccct cgtacgagga ggcactaaag caaggcctgc   22860
ccaccacccg tcccatcgcg cccatggcta ccggagtgct gggccagcac acacccgtaa   22920
cgctggacct gcctcccccc gccgacaccc agcagaaacc tgtgctgcca ggcccgaccg   22980
ccgttgttgt aacccgtcct agccgcgcgt ccctgcgccg cgccgccagc ggtccgcgat   23040
cgttgcggcc cgtagccagt ggcaactggc aaagcacact gaacagcatc gtgggtctgg   23100
gggtgcaatc cctgaagcgc cgacgatgct tctgatagct aacgtgtcgt atgtgtgtca   23160
tgtatgcgtc catgtcgccg ccagaggagc tgctgagccg ccgcgcgccc gctttccaag   23220
atggctaccc cttcgatgat gccgcagtgg tcttacatgc acatctcggg ccaggacgcc   23280
tcggagtacc tgagccccgg gctggtgcag tttgcccgcg ccaccgagac gtacttcagc   23340
ctgaataaca agtttagaaa ccccacggtg gcgcctacgc acgacgtgac cacagaccgg   23400
tcccagcgtt tgacgctgcg gttcatccct gtggaccgtg aggatactgc gtactcgtac   23460
aaggcgcggt tcaccctagc tgtgggtgat aaccgtgtgc tggacatggc ttccacgtac   23520
tttgacatcc gcggcgtgct ggacaggggc cctactttta agccctactc tggcactgcc   23580
```

-continued

```
tacaacgccc tggctcccaa gggtgcccca aatccttgcg aatgggatga agctgctact   23640
gctcttgaaa taaacctaga agaagaggac gatgacaacg aagacgaagt agacgagcaa   23700
gctgagcagc aaaaaactca cgtatttggg caggcgcctt attctggtat aaatattaca   23760
aaggagggta ttcaaatagg tgtcgaaggt caaacaccta aatatgccga taaaacattt   23820
caacctgaac ctcaaatagg agaatctcag tggtacgaaa cagaaattaa tcatgcagct   23880
gggagagtcc taaaaaagac taccccaatg aaaccatgtt acggttcata tgcaaaaccc   23940
acaaatgaaa atggagggca aggcattctt gtaaagcaac aaaatggaaa gctagaaagt   24000
caagtggaaa tgcaattttt ctcaactact gaggcagccg caggcaatgg tgataacttg   24060
actcctaaag tggtattgta cagtgaagat gtagatatag aaacccaga cactcatatt   24120 tcttacatgc ccactattaa ggaaggtaac tcacgagaac taatgggcca acaatctatg   24180
cccaacaggc ctaattacat tgcttttagg gacaattttta ttggtctaat gtattacaac   24240
agcacgggta atatgggtgt tctggcgggc caagcatcgc agttgaatgc tgttgtagat   24300
ttgcaagaca gaaacacaga gctttcatac cagcttttgc ttgattccat tggtgataga   24360
accaggtact tttctatgtg gaatcaggct gttgacagct atgatccaga tgttagaatt   24420
attgaaaatc atggaactga agatgaactt ccaaattact gctttccact gggaggtgtg   24480
attaatacag agactcttac caaggtaaaa cctaaaacag gtcaggaaaa tggatgggaa   24540
aaagatgcta cagaatttttc agataaaaat gaaataagag ttggaaataa ttttgccatg   24600
gaaatcaatc taaatgccaa cctgtggaga aatttcctgt actccaacat agcgctgtat   24660
ttgcccgaca agctaaagta cagtccttcc aacgtaaaaa tttctgataa cccaaacacc   24720
tacgactaca tgaacaagcg agtggtggct cccgggctag tggactgcta cattaacctt   24780
ggagcacgct ggtcccttga ctatatggac aacgtcaacc catttaacca ccaccgcaat   24840
gctggcctgc gctaccgctc aatgttgctg ggcaatggtc gctatgtgcc cttccacatc   24900
caggtgcctc agaagttctt tgccattaaa aacctccttc tcctgccggg ctcatacacc   24960
tacgagtgga acttcaggaa ggatgttaac atggttctgc agagctccct aggaaatgac   25020 ctaaggggttg acggagccag cattaagttt gatagcattt gcctttacgc caccttcttc   25080
cccatggccc acaacaccgc ctccacgctt gaggccatgc ttagaaacga caccaacgac   25140 cagtcctttta acgactatct ctccgccgcc aacatgctct accctatacc cgccaacgct   25200
accaacgtgc ccatatccat ccctcccgc aactgggcgg ctttcgcgg ctgggccttc   25260 acgcgcctta agactaagga aaccccatca ctgggctcgg gctacgaccc ttattacacc   25320
tactctggct ctatacccta cctagatgga accttttacc tcaaccacac ctttaagaag   25380
gtggccatta ccttttgactc ttctgtcagc tggcctggca atgaccgcct gcttacccc   25440 aacgagtttg aaattaagcg ctcagttgac ggggagggtt acaacgttgc ccagtgtaac   25500
atgaccaaag actggttcct ggtacaaatg ctagctaact ataacattgg ctaccagggc   25560
ttctatatcc cagagagcta caaggaccgc atgtactcct tcttttagaaa cttccagccc   25620 atgagccgtc aggtggtgga tgatactaaa tacaaggact accaacaggt gggcatccta   25680
caccaacaca caactctgg atttgttggc taccttgccc ccaccatgcg cgaaggacag   25740
gcctaccctg ctaacttccc ctatccgctt ataggcaaga ccgcagttga cagcattacc   25800
cagaaaaagt ttctttgcga tcgcaccctt tggcgcatcc cattctccag taactttatg   25860
tccatgggcg cactcacaga cctgggccaa aaccttctct acgccaactc cgcccacgcg   25920
ctagacatga cttttgaggt ggatcccatg gacgagccca cccttctttta tgttttgttt   25980
```

-continued

```
gaagtctttg acgtggtccg tgtgcaccag ccgcaccgcg gcgtcatcga aaccgtgtac    26040
ctgcgcacgc ccttctcggc cggcaacgcc acaacataaa gaagcaagca acatcaacaa    26100
cagctgccgc catgggctcc agtgagcagg aactgaaagc cattgtcaaa gatcttggtt    26160
gtgggccata tttttggggc acctatgaca agcgctttcc aggctttgtt tctccacaca    26220
agctcgcctg cgccatagtc aatacggccg gtcgcgagac tgggggcgta cactggatgg    26280
cctttgcctg gaacccgcac tcaaaaacat gctacctctt tgagcccttt ggcttttctg    26340
accagcgact caagcaggtt taccagtttg agtacgagtc actcctgcgc cgtagcgcca    26400
ttgcttcttc ccccgaccgc tgtataacgc tggaaaagtc cacccaaagc gtacaggggc    26460
ccaactcggc cgcctgtgga ctattctgct gcatgtttct ccacgccttt gccaactggc    26520
cccaaactcc catggatcac aaccccacca tgaaccttat taccggggta cccaactcca    26580
tgctcaacag tccccaggta cagcccaccc tgcgtcgcaa ccaggaacag ctctacagct    26640
tcctggagcg ccactcgccc tacttccgca gccacagtgc gcagattagg agcgccactt    26700 cttttttgtca cttgaaaaac atgtaaaaat aatgtactag agacactttc aataaaggca    26760
aatgctttta tttgtacact ctcgggtgat tatttacccc cacccttgcc gtctgcgccg    26820
tttaaaaatc aaaggggttc tgccgcgcat cgctatgcgc cactggcagg gacacgttgc    26880
gatactggtg tttagtgctc cacttaaact caggcacaac catccgcggc agctcggtga    26940 agtttttcact ccacaggctg cgcaccatca ccaacgcgtt tagcaggtcg ggcgccgata    27000
tcttgaagtc gcagttgggg cctccgccct gcgcgcgcga gttgcgatac acagggttgc    27060
agcactggaa cactatcagc gccgggtggt gcacgctggc cagcacgctc ttgtcggaga    27120
tcagatccgc gtccaggtcc tccgcgttgc tcagggcgaa cggagtcaac tttggtagct    27180
gccttcccaa aaagggcgcg tgcccaggct ttgagttgca ctcgcaccgt agtggcatca    27240
aaaggtgacc gtgcccggtc tgggcgttag gatacagcgc ctgcataaaa gccttgatct    27300
gcttaaaagc cacctgagcc tttgcgcctt cagagaagaa catgccgcaa gacttgccgg    27360
aaaactgatt ggccggacag gccgcgtcgt gcacgcagca ccttgcgtcg gtgttggaga    27420
tctgcaccac atttcggccc caccggttct tcacgatctt ggccttgcta gactgctcct    27480
tcagcgcgcg ctgcccgttt cgctcgtca catccatttc aatcacgtgc tccttatta    27540 tcataatgct tccgtgtaga cacttaagct cgccttcgat ctcagcgcag cggtgcagcc    27600
acaacgcgca gcccgtgggc tcgtgatgct tgtaggtcac ctctgcaaac gactgcaggt    27660
acgcctgcag gaatcgcccc atcatcgtca caaaggtctt gttgctggtg aaggtcagct    27720
gcaacccgcg gtgctcctcg ttcagccagg tcttgcatac ggccgccaga gcttccactt    27780
ggtcaggcag tagtttgaag ttcgccttta gatcgttatc cacgtggtac ttgtccatca    27840
gcgcgcgcgc agcctccatg cccttctccc acgcagacac gatcggcaca ctcagcgggt    27900
tcatcaccgt aatttcactt tccgcttcgc tgggctcttc ctcttcctct tgcgtccgca    27960
taccacgcgc cactgggtcg tcttcattca gccgccgcac tgtgcgctta cctcctttgc    28020
catgcttgat tagcaccggt gggttgctga aacccaccat ttgtagcgcc acatcttctc    28080
tttcttcctc gctgtccacg attacctctg gtgatggcgg gcgctcgggc ttgggagaag    28140
ggcgcttctt tttcttcttg ggcgcaatgg ccaaatccgc cgccgaggtc gatggccgcg    28200
ggctgggtgt gcgcggcacc agcgcgtctt gtgatgagtc ttcctcgtcc tcggactcga    28260
tacgccgcct catccgcttt tttggggggcg cccgggggagg cggcggcgac ggggacgggg    28320
```

-continued

```
acgacacgtc ctccatggtt gggggacgtc gcgccgcacc gcgtccgcgc tcggggtgg    28380 tttcgcgctg ctcctcttcc cgactggcca tttccttctc ctataggcag aaaaagatca    28440
tggagtcagt cgagaagaag gacagcctaa ccgcccctc tgagttcgcc accaccgcct    28500
ccaccgatgc cgccaacgcg cctaccacct tccccgtcga ggcacccccg cttgaggagg    28560
aggaagtgat tatcgagcag gacccaggtt ttgtaagcga agacgacgag gaccgctcag    28620
taccaacaga ggataaaaag caagaccagg acaacgcaga ggcaaacgag gaacaagtcg    28680 ggcggggga cgaaaggcat ggcgactacc tagatgtggg agacgacgtg ctgttgaagc    28740
atctgcagcg ccagtgcgcc attatctgcg acgcgttgca agagcgcagc gatgtgcccc    28800
tcgccatagc ggatgtcagc cttgcctacg aacgccacct attctcaccg cgcgtaccc    28860 ccaaacgcca agaaacggc acatgcgagc ccaacccgcg cctcaacttc taccccgtat    28920
ttgccgtgcc agaggtgctt gccacctatc acatctttt ccaaaactgc aagataccc    28980 tatcctgccg tgccaaccgc agccgagcgg acaagcagct ggccttgcgg cagggcgctg    29040
tcatacctga tatcgcctcg ctcaacgaag tgccaaaaat cttttgagggt cttggacgcg    29100 acgagaagcg cgcggcaaac gctctgcaac aggaaaacag cgaaaatgaa agtcactctg    29160
gagtgttggt ggaactcgag ggtgacaacg cgcgcctagc cgtactaaaa cgcagcatcg    29220
aggtcaccca ctttgcctac ccggcactta acctaccccc caaggtcatg agcacagtca    29280
tgagtgagct gatcgtgcgc cgtgcgcagc ccctggagag ggatgcaaat ttgcaagaac    29340
aaacagagga gggcctaccc gcagttggcg acgagcagct agcgcgctgg cttcaaacgc    29400
gcgagcctgc cgacttggag gagcgacgca aactaatgat ggccgcagtg ctcgttaccg    29460
tggagcttga gtgcatgcag cggttctttg ctgacccgga gatgcagcgc aagctagagg    29520
aaacattgca ctacaccttt cgacagggct acgtacgcca ggcctgcaag atctccaacg    29580
tggagctctg caacctggtc tcctaccttg gaatttttgca cgaaaaccgc cttgggcaaa    29640
acgtgcttca ttccacgctc aagggcgagg cgcgccgcga ctacgtccgc gactgcgttt    29700
acttatttct atgctacacc tggcagacgg ccatgggcgt ttggcagcag tgcttggagg    29760
agtgcaacct caaggagctg cagaaactgc taaagcaaaa cttgaaggac ctatggacgg    29820
ccttcaacga gcgctccgtg gccgcgcacc tggcggacat cattttcccc gaacgcctgc    29880 ttaaaacct gcaacagggt ctgccagact tcaccagtca aagcatgttg cagaacttta    29940
ggaactttat cctagagcgc tcaggaatct tgcccgccac ctgctgtgca cttcctagcg    30000
actttgtgcc cattaagtac cgcgaatgcc ctccgccgct ttggggccac tgctaccttc    30060
tgcagctagc caactacctt gcctaccact ctgacataat ggaagacgtg agcggtgacg    30120
gtctactgga gtgtcactgt cgctgcaacc tatgcacccc gcaccgctcc ctggtttgca    30180
attcgcagct gcttaacgaa agtcaaatta tcggtacctt tgagctgcag ggtccctcgc    30240
ctgacgaaaa gtccgcggct ccggggttga aactcactcc ggggctgtgg acgtcggctt    30300
accttcgcaa atttgtacct gaggactacc acgcccacga gattaggttc tacgaagacc    30360
aatcccgccc gcctaatgcg gagcttaccg cctgcgtcat tacccagggc cacattcttg    30420
gccaattgca gagccatcaac aaagcccgcc aagagtttct gctacgaaag ggacgggggg    30480
tttacttgga ccccagtcc ggcgaggagc tcaacccaat cccccgccg ccgcagccct    30540 atcagcagca gccgcgggcc cttgcttccc aggatggcac ccaaaaagaa gctgcagctg    30600
ccgccgccac ccacgacga ggaggaatac tgggacagtc aggcagagga ggttttggac    30660
gaggaggagg aggacatgat ggaagactgg gagagcctag acgaggaagc ttccgaggtc    30720
```

-continued

```
gaagaggtgt cagacgaaac accgtcaccc tcggtcgcat tcccctcgcc ggcgccccag   30780
aaatcggcaa ccggttccag catggctaca acctccgctc ctcaggcgcc gccggcactg   30840
cccgttcgcc gacccaaccg tagatgggac accactggaa ccagggccgg taagtccaag   30900
cagccgccgc cgttagccca agagcaacaa cagcgccaag gctaccgctc atggcgcggg   30960
cacaagaacg ccatagttgc ttgcttgcaa gactgtgggg gcaacatctc cttcgcccgc   31020
cgctttcttc tctaccatca cggcgtggcc ttcccccgta acatcctgca ttactaccgt   31080
catctctaca gcccatactg caccggcggc agcggcagca acagcagcgg ccacacagaa   31140
gcaaaggcga ccgatagca agactctgac aaagcccaag aaatccacag cggcggcagc   31200
agcaggagga ggagcgctgc gtctggcgcc caacgaaccc gtatcgaccc gcgagcttag   31260
aaacaggatt tttcccactc tgtatgctat atttcaacag agcaggggcc aagaacaaga   31320
gctgaaaata aaaaacaggt ctctgcgatc cctcacccgc agctgcctgt atcacaaaag   31380
cgaagatcag cttcggcgca cgctggaaga cgcggaggct ctcttcagta aatactgcgc   31440
gctgactctt aaggactagt ttcgcgccct ttctcaaatt taagcgcgaa aactacgtca   31500
tctccagcgg ccacacccgg cgccagcacc tgttgtcagc gccattatga gcaaggaaat   31560
tcccacgccc tacatgtgga gttaccagcc acaaatggga cttgcggctg gagctgccca   31620
agactactca acccgaataa actacatgag cgcgggaccc cacatgatat cccgggtcaa   31680
cggaatacgc gcccaccgaa accgaattct cctggaacag gcggctatta ccaccacacc   31740
tcgtaataac cttaatcccc gtagttggcc cgctgccctg gtgtaccagg aaagtcccgc   31800
tcccaccact gtggtacttc ccagagacgc ccaggccgaa gttcagatga ctaactcagg   31860
ggcgcagctt gcgggcggct ttcgtcacag ggtgcggtcg cccggcagg gtataactca   31920 cctgacaatc agagggcgag gtattcagct caacgacgag tcggtgagct cctcgcttgg   31980
tctccgtccg gacgggacat ttcagatcgg cggcgccggc cgctcttcat tcacgcctcg   32040
tcaggcaatc ctaactctgc agacctcgtc ctctgagccg cgctctggag gcattggaac   32100
tctgcaattt attgaggagt ttgtgccatc ggtctacttt aaccccttct cgggacctcc   32160
cggccactat ccggatcaat ttattcctaa ctttgacgcg gtaaaggact cggcggacgg   32220
ctacgactga atgttaagtg gagaggcaga gcaactgcgc ctgaaacacc tggtccactg   32280
tcgccgccac aagtgctttg cccgcgactc cggtgagttt tgctactttg aattgcccga   32340
ggatcatatc gagggcccgg cgcacggcgt ccggcttacc gcccagggag agcttgcccg   32400
tagcctgatt cgggagttta cccagcgccc cctgctagtt gagcgggaca ggggaccctg   32460
tgttctcact gtgatttgca actgtcctaa ccctggatta catcaagatc ctctagttaa   32520
tgtcaggtcg cctaagtcga ttaactagag tacccgggga tcttattccc tttaactaat   32580
aaaaaaaaat aataaagcat cacttactta aaatcagtta gcaaatttct gtccagttta   32640
ttcagcagca cctccttgcc ctcctcccag ctctggtatt gcagcttcct cctggctgca   32700
aactttctcc acaatctaaa tggaatgtca gtttcctcct gttcctgtcc atccgcaccc   32760
actatcttca tgttgttgca gatgaagcgc gcaagaccgt ctgaagatac cttcaacccc   32820
gtgtatccat atgacacgga aaccggtcct ccaactgtgc cttttcttac tcctcccttt   32880
gtatccccca atgggtttca agagagtccc cctggggtac tctctttgcg cctatccgaa   32940
cctctagtta cctccaatgg catgcttgcg ctcaaaatgg caacggcct ctctctggac   33000 gaggccggca accttacctc ccaaaatgta accactgtga gcccacctct caaaaaaacc   33060
```

-continued

```
aagtcaaaca taaacctgga aatatctgca cccctcacag ttacctcaga agccctaact   33120
gtggctgccg ccgcacctct aatggtcgcg ggcaacacac tcaccatgca atcacaggcc   33180
ccgctaaccg tgcacgactc caaacttagc attgccaccc aaggacccct cacagtgtca   33240
gaaggaaagc tagccctgca aacatcaggc cccctcacca ccaccgatag cagtaccctt   33300
actatcactg cctcacccc tctaactact gccactggta gcttgggcat tgacttgaaa   33360
gagcccattt atacacaaaa tggaaaacta ggactaaagt acggggctcc tttgcatgta   33420
acagacgacc taaacacttt gaccgtagca actggtccag gtgtgactat taataatact   33480
tccttgcaaa ctaaagttac tggagccttg ggttttgatt cacaaggcaa tatgcaactt   33540
aatgtagcag gaggactaag gattgattct caaaacagac gccttatact tgatgttagt   33600
tatccgtttg atgctcaaaa ccaactaaat ctaagactag dacagggccc tcttttttata   33660 aactcagccc acaacttgga tattaactac aacaaaggcc tttacttgtt tacagcttca   33720
aacaattcca aaaagcttga ggttaaccta agcactgcca agggggttgat gtttgacgct   33780 acagccatag ccattaatgc aggagatggg cttgaatttg gttcacctaa tgcaccaaac   33840
acaaatcccc tcaaaacaaa aattggccat ggcctagaat ttgattcaaa caaggctatg   33900
gttcctaaac taggaactgg ccttagtttt gacagcacag gtgccattac agtaggaaac   33960
aaaaataatg ataagctaac tttgtggacc ggaataaacc ctccacctaa ctgtcaaatt   34020
gtggaaaaca ctaatacaaa tgatggcaaa cttactttag tattagtaaa aaatggaggg   34080
cttgttaatg gctacgtgtc tctagttggt gtatcagaca ctgtgaacca aatgttcaca   34140
caaaagacag caaacatcca attaagaatta tattttgact cttctggaaa tctattaact   34200
gaggaatcag acttaaaaat tccacttaaa aataaatctt ctacagcgac cagtgaaact   34260
gtagccagca gcaaagcctt tatgccaagt actacagctt atcccttcaa caccactact   34320
agggatagtg aaaactacat tcatggaata tgttactaca tgactagtta tgatagaagt   34380
ctatttccct tgaacatttc tataatgcta aacagccgta tgatttcttc caatgttgcc   34440
tatgccatac aatttgaatg gaatctaaat gcaagtgaat ctccagaaag caacatagct   34500
acgctgacca catccccctt tttctttttct tacattacag aagacgacaa ctaaagaatc   34560
gtttgtgtta tgtttcaacg tgtttatttt tcaattgcag aaaatttcaa gtcatttttc   34620
attcagtagt atagccccac caccacatag cttatacaga tcaccgtacc ttaatcaaac   34680
tcacagaacc ctagtattca acctgccacc tccctcccaa cacacagagt acacagtcct   34740
ttctccccgg ctggccttaa aaagcatcat atcatgggta acagacatat tcttaggtgt   34800
tatattccac acggtttcct gtcgagccaa acgctcatca gtgatattaa taaactcccc   34860
gggcagctca cttaagttca tgtcgctgtc cagctgctga gccacaggct gctgtccaac   34920
ttgcggttgc ttaacgggcg gcgaaggaga agtccacgcc tacatggggg tagagtcata   34980
atcgtgcatc aggatagggc ggtggtgctg cagcagcgcg cgaataaact gctgccgccg   35040
ccgctccgtc ctgcaggaat acaacatggc agtggtctcc tcagcgatga ttcgcaccgc   35100
ccgcagcata aggcgccttg tcctccgggc acagcagcgc accctgatct cacttaaatc   35160
agcacagtaa ctgcagcaca gcaccacaat attgttcaaa atcccacagt gcaaggcgct   35220
gtatccaaag ctcatggcgg ggaccacaga acccacgtgg ccatcatacc acaagcgcag   35280
gtagattaag tggcgacccc tcataaacac gctggacata aacattacct ctttttggcat   35340 gttgtaattc accacctccc ggtaccatat aaacctctga ttaaacatgg cgccatccac   35400
caccatccta aaccagctgg ccaaaacctg cccgccggct atacactgca gggaaccggg   35460
```

-continued

```
actggaacaa tgacagtgga gagcccagga ctcgtaacca tggatcatca tgctcgtcat    35520
gatatcaatg ttggcacaac acaggcacac gtgcatacac ttcctcagga ttacaagctc    35580
ctcccgcgtt agaaccatat cccagggaac aacccattcc tgaatcagcg taaatcccac    35640
actgcaggga agacctcgca cgtaactcac gttgtgcatt gtcaaagtgt tacattcggg    35700
cagcagcgga tgatcctcca gtatggtagc gcgggtttct gtctcaaaag gaggtagacg    35760
atccctactg tacggagtgc gccgagacaa ccgagatcgt gttggtcgta gtgtcatgcc    35820
aaatggaacg ccggacgtag tcatatttcc tgaagcaaaa ccaggtgcgg gcgtgacaaa    35880
cagatctgcg tctccggtct cgccgcttag atcgctctgt gtagtagttg tagtatatcc    35940
actctctcaa agcatccagg cgcccctgg cttcgggttc tatgtaaact ccttcatgcg    36000
ccgctgccct gataacatcc accaccgcag aataagccac acccagccaa cctacacatt    36060
cgttctgcga gtcacacacg ggaggagcgg gaagagctgg aagaaccatg ttttttttt    36120 tattccaaaa gattatccaa aacctcaaaa tgaagatcta ttaagtgaac gcgctcccct    36180
ccggtggcgt ggtcaaactc tacagccaaa gaacagataa tggcatttgt aagatgttgc    36240
acaatggctt ccaaaaggca aacggccctc acgtccaagt ggacgtaaag gctaaaccct    36300
tcagggtgaa tctcctctat aaacattcca gcaccttcaa ccatgcccaa ataattctca    36360
tctcgccacc ttctcaatat atctctaagc aaatcccgaa tattaagtcc ggccattgta    36420
aaaatctgct ccagagcgcc ctccaccttc agcctcaagc agcgaatcat gattgcaaaa    36480
attcaggttc ctcacagacc tgtataagat tcaaaagcgg aacattaaca aaaataccgc    36540
gatcccgtag gtcccttcgc agggccagct gaacataatc gtgcaggtct gcacggacca    36600
gcgcggccac ttccccgcca ggaaccatga caaaagaacc cacactgatt atgacacgca    36660
tactcggagc tatgctaacc agcgtagccc cgatgtaagc ttgttgcatg ggcggcgata    36720
taaaatgcaa ggtgctgctc aaaaaatcag gcaaagcctc gcgcaaaaaa gaaagcacat    36780
cgtagtcatg ctcatgcaga taaaggcagg taagctccgg aaccaccaca gaaaaagaca    36840
ccatttttct ctcaaacatg tctgcgggtt tctgcataaa cacaaaataa aataacaaaa    36900
aaacatttaa acattagaag cctgtcttac aacaggaaaa acaaccctta taagcataag    36960
acggactacg gccatgccgg cgtgaccgta aaaaaactgg tcaccgtgat taaaaagcac    37020
caccgacagc tcctcggtca tgtccggagt cataatgtaa gactcggtaa acacatcagg    37080
ttgattcaca tcggtcagtg ctaaaaagcg accgaaatag cccgggggaa tacatacccg    37140
caggcgtaga gacaacatta cagccccat aggaggtata acaaaattaa taggagagaa    37200
aaacacataa acacctgaaa aaccctcctg cctaggcaaa atagcaccct cccgctccag    37260
aacaacatac agcgcttcca cagcggcagc cataacagtc agccttacca gtaaaaaaga    37320
aaacctatta aaaaacacc actcgacacg gcaccagctc aatcagtcac agtgtaaaaa    37380
agggccaagt gcagagcgag tatatatagg actaaaaaat gacgtaacgg ttaaagtcca    37440
caaaaaacac ccagaaaacc gcacgcgaac ctacgcccag aaacgaaagc caaaaaaccc    37500
acaacttcct caaatcgtca cttccgtttt cccacgttac gtcacttccc attttaagaa    37560
aactacaatt cccaacacat acaagttact ccgccctaaa acctacgtca cccgcccgt    37620 tcccacgccc cgcgccacgt cacaaactcc acccctcat tatcatattg gcttcaatcc    37680
aaaataaggt atattattga tgatg                                          37705
```

<210> SEQ ID NO 29

-continued

```
<211> LENGTH: 34766
<212> TYPE: DNA
<213> ORGANISM: Artificial Sequence
<220> FEATURE:
<223> OTHER INFORMATION: #4 vector
```

```
<400> SEQUENCE: 29
catcatcaat aatatacctt attttggatt gaagccaata tgataatgag ggggtggagt      60
ttgtgacgtg gcgcggggcg tgggaacggg gcgggtgacg tagtagtgtg gcggaagtgt     120
gatgttgcaa gtgtggcgga acacatgtaa gcgacggatg tggcaaaagt gacgtttttg     180
gtgtgcgccg gtgtacacag gaagtgacaa ttttcgcgcg gttttaggcg gatgttgtag     240
taaatttggg cgtaaccgag taagatttgg ccattttcgc gggaaaactg aataagagga     300
agtgaaatct gaataatttt gtgttactca tagcgcgtaa tactgtaata gtaatcaatt     360
acggggtcat tagttcatag cccatatatg gagttccgcg ttacataact tacggtaaat     420
ggcccgcctg gctgaccgcc caacgacccc cgcccattga cgtcaataat gacgtatgtt     480
cccatagtaa cgccaatagg gactttccat tgacgtcaat gggtggagta tttacggtaa     540
actgcccact tggcagtaca tcaagtgtat catatgccaa gtacgccccc tattgacgtc     600
aatgacggta aatggcccgc ctggcattat gcccagtaca tgaccttatg gactttcct      660 acttggcagt acatctacgt attagtcatc gctattacca tggtgatgcg gttttggcag     720
tacatcaatg ggcgtggata gcggtttgac tcacggggat ttccaagtct ccacccccatt    780 gacgtcaatg ggagtttgtt ttggcaccaa aatcaacggg actttccaaa atgtcgtaac     840
aactccgccc cattgacgca aatgggcggt aggcgtgtac ggtgggaggt ctatataagc     900
agagctctcc ctatcagtga tagagatctc cctatcagtg atagagatcg tcgacgagct     960
cgtttagtga accgtcagat cgcctggaga cgccatccac gctgttttga cctccataga    1020
agacaccggg accgatccag cctccgattt gccaccatgt ttgtgttcct ggtgctgctg    1080
ccactggtgt ccagccagtg tgtgaacctg accaccagga cccaacttcc tcctgcctac    1140
accaactcct tcaccagggg agtctactac cctgacaagg tgttcaggtc ctctgtgctg    1200
cacagcaccc aggacctgtt cctgccattc ttcagcaatg tgacctggtt ccatgccatc    1260
catgtgtctg gcaccaatgg caccaagagg tttgacaacc ctgtgctgcc attcaatgat    1320
ggagtctact ttgccagcac agagaagagc aacatcatca ggggctggat tttttggcacc    1380 accctggaca gcaagaccca gtccctgctg attgtgaaca atgccaccaa tgtggtgatt    1440
aaggtgtgtg agttccagtt ctgtaatgac ccattcctgg gagtctacta ccacaagaac    1500
aacaagtcct ggatggagtc tgagttcagg gtctactcct ctgccaacaa ctgtacctttt   1560 gaatatgtga gccaaccatt cctgatggac ttggagggca gcagggcaa cttcaagaac    1620 ctgagggagt ttgtgttcaa gaacattgat ggctacttca gatttacag caaacacaca     1680 ccaatcaacc tggtgaggga cctgccacag ggcttctctg ccttggaacc actggtggac    1740
ctgccaattg gcatcaacat caccaggttc cagaccctgc tggctctgca caggtcctac    1800
ctgacacctg agactcctc ctctggctgg acagcaggag cagcagccta ctatgtgggc     1860
tacctccaac caaggacctt cctgctgaaa tacaatgaga atggcaccat cacagatgct    1920
gtggactgtg ccctggaccc actgtctgag accaagtgta ccctgaaatc cttcacagtg    1980
gagaagggca tctaccagac cagcaacttc agggtccaac caacagagag cattgtgagg    2040
tttccaaaca tcaccaacct gtgtccattt ggagaggtgt tcaatgccac caggtttgcc    2100
tctgtctatg cctggaacag gaagaggatt agcaactgtg tggctgacta ctctgtgctc    2160
```

-continued

```
tacaactctg cctccttcag caccttcaag tgttatggag tgagcccaac caaactgaat     2220
gacctgtgtt tcaccaatgt ctatgctgac tcctttgtga ttaggggaga tgaggtgaga     2280
cagattgccc ctggacaaac aggcaagatt gctgactaca actacaaact gcctgatgac     2340
ttcacaggct gtgtgattgc ctggaacagc aacaacctgg acagcaaggt gggaggcaac     2400
tacaactacc tctacagact gttcaggaag agcaacctga aaccatttga gagggacatc     2460
agcacagaga tttaccaggc tggcagcaca ccatgtaatg gagtggaggg cttcaactgt     2520
tactttccac tccaatccta tggcttccaa ccaaccaatg gagtgggcta ccaaccatac     2580
agggtggtgg tgctgtcctt tgaactgctc catgcccctg ccacagtgtg tggaccaaag     2640
aagagcacca acctggtgaa gaacaagtgt gtgaacttca acttcaatgg actgacaggc     2700
acaggagtgc tgacagagag caacaagaag ttcctgccat tccaacagtt ggcagggac      2760 attgctgaca ccacagatgc tgtgagggac ccacagacct tggagattct ggacatcaca     2820
ccatgttcct ttggaggagt gtctgtgatt acacctggca ccaacaccag caaccaggtg     2880
gctgtgctct accaggatgt gaactgtact gaggtgcctg tggctatcca tgctgaccaa     2940
cttacaccaa cctggagggt ctacagcaca ggcagcaatg tgttccagac cagggctggc     3000
tgtctgattg gagcagagca tgtgaacaac tcctatgagt gtgacatccc aattggagca     3060
ggcatctgtg cctcctacca gacccagacc ggtggcggtg ggtcgggcgg tggtgggtcg     3120
ggtggcggcg gttccaggtc tgtggcaagc cagagcatca ttgcctacac aatgagtctg     3180
ggagcagaga actctgtggc ttacagcaac aacagcattg ccatcccaac caacttcacc     3240
atctctgtga ccacagagat tctgcctgtg agtatgacca gacctctgt  ggactgtaca      3300 atgtatatct gtggagacag cacagagtgt agcaacctgc tgctccaata tggctccttc     3360
tgtacccaac ttaacagggc tctgacaggc attgctgtgg aacaggacaa gaacacccag     3420
gaggtgtttg cccaggtgaa gcagatttac aagacacctc caatcaagga ctttggaggc     3480
ttcaacttca gccagattct gcctgaccca agcaagccaa gcaagaggtc cttcattgag     3540
gacctgctgt tcaacaaggt gaccctggct gatgctggct tcatcaagca atatggagac     3600
tgtctgggag acattgctgc cagggacctg atttgtgccc agaagttcaa tggactgaca     3660
gtgctgcctc cactgctgac agatgagatg attgcccaat acacctctgc cctgctggct     3720
ggcaccatca cctctggctg gacctttgga gcaggagcag ccctccaaat cccatttgct     3780
atgcagatgg cttacaggtt caatggcatt ggagtgaccc agaatgtgct ctatgagaac     3840
cagaaactga ttgccaacca gttcaactct gccattggca agattcagga ctccctgtcc     3900
agcacagcct ctgccctggg caaactccaa gatgtggtga accagaatgc ccaggctctg     3960
aacaccctgg tgaagcaact ttccagcaac tttggagcca tctcctctgt gctgaatgac     4020
atcctgagca gactggacaa ggtggaggct gaggtccaga ttgacagact gattacaggc     4080
agactccaat ccctccaaac ctatgtgacc caacaactta tcaggctgc  tgagattagg      4140 gcatctgcca acctggctgc caccaagatg agtgagtgtg tgctgggaca aagcaagagg     4200
gtggacttct gtggcaaggg ctaccaccctg atgagtttc  cacagtctgc ccctcatgga      4260
gtggtgttcc tgcatgtgac ctatgtgcct gcccaggaga gaacttcac  cacagcccct      4320 gccatctgcc atgatggcaa ggctcacttt ccaagggagg gagtgtttgt gagcaatggc     4380
acccactggt ttgtgaccca gaggaacttc tatgaaccac agattatcac cacagacaac     4440 accttttgtgt ctggcaactg tgatgtggtg attggcattg tgaacaacac agtctatgac     4500
```

-continued

```
ccactccaac ctgaactgga ctccttcaag gaggaactgg acaaatactt caagaaccac   4560
accagccctg atgtggacct gggagacatc tctggcatca atgcctctgt ggtgaacatc   4620
cagaaggaga ttgacagact gaatgaggtg gctaagaacc tgaatgagtc cctgattgac   4680
ctccaagaac tgggcaaata tgaacaatac atcaagtggc catgaaaatt gatcataatc   4740
agccatacca catttgtaga ggttttactt gctttaaaaa acctcccaca cctcccctg    4800 aacctgaaac ataaaatgaa tgcaattgtt gttgttaact tgtttattgc agcttataat   4860
ggttacaaat aaagcaatag catcacaaat ttcacaaata aagcatttttt ttcactgcat   4920 tctagttgtg gtttgtccaa actcatcaat gtatcttaac gcggatctgg gcgtggttaa   4980
gggtgggaaa gaatatataa ggtggggggtc ttatgtagtt ttgtatctgt tttgcagcag   5040
ccgccgccgc catgagcacc aactcgtttg atggaagcat tgtgagctca tatttgacaa   5100
cgcgcatgcc cccatgggcc ggggtgcgtc agaatgtgat gggctccagc attgatggtc   5160
gccccgtcct gcccgcaaac tctactacct tgacctacga accgtgtct ggaacgccgt    5220 tggagactgc agcctccgcc gccgcttcag ccgctgcagc caccgcccgc gggattgtga   5280
ctgactttgc tttcctgagc ccgcttgcaa gcagtgcagc ttcccgttca tccgcccgcg   5340
atgacaagtt gacggctctt ttggcacaat tggattcttt gacccgggaa cttaatgtcg   5400
tttctcagca gctgttggat ctgcgccagc aggtttctgc cctgaaggct tcctcccctc   5460
ccaatgcggt ttaaaacata aataaaaaac cagactctgt ttggatttgg atcaagcaag   5520
tgtcttgctg tctttatttta ggggtttttgc gcgcgcggta ggcccgggac cagcggtctc   5580
ggtcgttgag ggtcctgtgt attttttcca ggacgtggta aaggtgactc tggatgttca   5640
gatacatggg cataagcccg tctctggggt ggaggtagca ccactgcaga gcttcatgct   5700
gcggggtggt gttgtagatg atccagtcgt agcaggagcg ctgggcgtgg tgcctaaaaa   5760
tgtctttcag tagcaagctg attgccaggg gcaggcctt ggtgtaagtg tttacaaagc     5820
ggttaagctg ggatgggtgc atacgtgggg atatgagatg catcttggac tgtattttta   5880
ggttggctat gttcccagcc atatccctcc ggggattcat gttgtgcaga accaccagca   5940
cagtgtatcc ggtgcacttg ggaaatttgt catgtagctt agaaggaaat gcgtggaaga   6000
acttggagac gcccttgtga cctccaagat tttccatgca ttcgtccata atgatggcaa   6060
tgggcccacg ggcggcggcc tgggcgaaga tatttctggg atcactaacg tcatagttgt   6120
gttccaggat gagatcgtca taggccattt ttacaaagcg cgggcggagg gtgccagact   6180
gcggtataat ggttccatcc ggcccagggg cgtagttacc ctcacagatt tgcatttccc   6240
acgctttgag ttcagatggg gggatcatgt ctacctgcgg ggcgatgaag aaaacggttt   6300
ccggggtagg ggagatcagc tgggaagaaa gcaggttcct gagcagctgc gacttaccgc   6360
agccggtggg cccgtaaatc acacctatta ccggctgcaa ctggtagtta agagagctgc   6420
agctgccgtc atccctgagc aggggggcca cttcgttaag catgtccctg actcgcatgt   6480
tttccctgac caaatccgcc agaaggcgct cgccgcccag cgatagcagt tcttgcaagg   6540
aagcaaagtt tttcaacggt ttgagaccgt ccgccgtagg catgctttttg agcgtttgac   6600 caagcagttc caggcggtcc cacagctcgg tcacctgctc tacggcatct cgatccagca   6660
tatctcctcg tttcgcgggt tggggcggct ttcgctgtac ggcagtagtc ggtgctcgtc   6720
cagacgggcc aggtcatgt ctttccacgg gcgcagggtc ctcgtcagcg tagtctgggt     6780
cacggtgaag gggtgcgctc cgggctgcgc gctggccagg gtgcgcttga ggctggtcct   6840
gctggtgctg aagcgctgcc ggtcttcgcc ctgcgcgtcg gccaggtagc atttgaccat   6900
```

-continued

```
ggtgtcatag tccagccct ccgcggcgtg gcccttggcg cgcagcttgc ccttggagga   6960
ggcgccgcac gagggcagt gcagactttt gagggcgtag agcttgggcg cgagaaatac   7020
cgattccggg gagtaggcat ccgcgccgca ggccccgcag acggtctcgc attccacgag   7080
ccaggtgagc tctggccgtt cggggtcaaa aaccaggttt cccccatgct ttttgatgcg   7140
tttcttacct ctggtttcca tgagccggtg tccacgctcg gtgacgaaaa ggctgtccgt   7200
gtccccgtat acagacttga gaggcctgtc ctcgagcggt gttccgcggt cctcctcgta   7260
tagaaactcg gaccactctg agacaaaggc tcgcgtccag gccagcacga aggaggctaa   7320
gtgggagggg tagcggtcgt tgtccactag ggggtccact cgctccaggg tgtgaagaca   7380
catgtcgccc tcttcggcat caaggaaggt gattggtttg taggtgtagg ccacgtgacc   7440
gggtgttcct gaagggggc tataaaaggg ggtgggggcg cgttcgtcct cactctcttc   7500
cgcatcgctg tctgcgaggg ccagctgttg gggtgagtac tccctctgaa aagcgggcat   7560
gacttctgcg ctaagattgt cagtttccaa aaacgaggag gatttgatat tcacctggcc   7620
cgcggtgatg cctttgaggg tggccgcatc catctggtca gaaaagacaa tctttttgtt   7680
gtcaagcttg gtggcaaacg acccgtagag ggcgttggac agcaacttgg cgatggagcg   7740
cagggtttgg tttttgtcgc gatcggcgcg ctccttggcc gcgatgttta gctgcacgta   7800
ttcgcgcgca acgcaccgcc attcgggaaa gacggtggtg cgctcgtcgg gcaccaggtg   7860
cacgcgccaa ccgcggttgt gcagggtgac aaggtcaacg ctggtggcta cctctccgcg   7920
taggcgctcg ttggtccagc agaggcggcc gcccttgcgc gagcagaatg gcggtagggg   7980
gtctagctgc gtctcgtccg gggggtctgc gtccacggta aagaccccgg gcagcaggcg   8040
cgcgtcgaag tagtctatct tgcatccttg caagtctagc gcctgctgcc atgcgcgggc   8100
ggcaagcgcg cgctcgtatg ggttgagtgg gggacccat ggcatgggt gggtgagcgc   8160 ggaggcgtac atgccgcaaa tgtcgtaaac gtagaggggc tctctgagta ttccaagata   8220
tgtagggtag catcttccac cgcggatgct ggcgcgcacg taatcgtata gttcgtgcga   8280
gggagcgagg aggtcgggac cgaggttgct acgggcgggc tgctctgctc ggaagactat   8340
ctgcctgaag atggcatgtg agttggatga tatggttgga cgctggaaga cgttgaagct   8400
ggcgtctgtg agacctaccg cgtcacgcac gaaggaggcg taggagtcgc gcagcttgtt   8460
gaccagctcg gcggtgacct gcacgtctag ggcgcagtag tccagggttt ccttgatgat   8520
gtcatactta tcctgtccct ttttttttcca cagctcgcgg ttgaggacaa actcttcgcg   8580
gtctttccag tactcttgga tcggaaaccc gtcggcctcc gaacggtaag agcctagcat   8640
gtagaactgg ttgacggcct ggtaggcgca gcatcccttt tctacgggta gcgcgtatgc   8700
ctgcgcggcc ttccggagcg aggtgtgggt gagcgcaaag gtgtccctga ccatgacttt   8760
gaggtactgg tatttgaagt cagtgtcgtc gcatccgccc tgctcccaga gcaaaaagtc   8820
cgtgcgcttt ttggaacgcg gatttggcag ggcgaaggtg acatcgttga agagtatctt   8880
tcccgcgcga ggcataaagt tgcgtgtgat gcggaagggt cccggcacct cggaacggtt   8940
gttaattacc tgggcggcga gcacgatctc gtcaaagccg ttgatgttgt ggcccacaat   9000
gtaaagttcc aagaagcgcg ggatgccctt gatggaaggc aattttttaa gttcctcgta   9060
ggtgagctct tcaggggagc tgagcccgtg ctctgaaagg gcccagtctg caagatgagg   9120
gttggaagcg acgaatgagc tccacaggtc acgggccatt agcatttgca ggtggtcgcg   9180
aaaggtccta aactggcgac ctatggccat tttttctggg gtgatgcagt agaaggtaag   9240
```

-continued

```
cgggtcttgt tcccagcggt cccatccaag gttcgcggct aggtctcgcg cggcagtcac   9300
tagaggctca tctccgccga acttcatgac cagcatgaag ggcacgagct gcttcccaaa   9360
ggcccccatc caagtatagg tctctacatc gtaggtgaca aagagacgct cggtgcgagg   9420
atgcgagccg atcgggaaga actggatctc ccgccaccaa ttggaggagt ggctattgat   9480
gtggtgaaag tagaagtccc tgcgacgggc cgaacactcg tgctggcttt tgtaaaaacg   9540
tgcgcagtac tggcagcggt gcacgggctg tacatcctgc acgaggttga cctgacgacc   9600
gcgcacaagg aagcagagtg ggaatttgag cccctcgcct ggcgggtttg gctggtggtc   9660
ttctacttcg gctgcttgtc cttgaccgtc tggctgctcg aggggagtta cggtggatcg   9720
gaccaccacg ccgcgcgagc ccaaagtcca gatgtccgcg cgcggcggtc ggagcttgat   9780
gacaacatcg cgcagatggg agctgtccat ggtctggagc tcccgcggcg tcaggtcagg   9840
cgggagctcc tgcaggttta cctcgcatag acgggtcagg gcgcgggcta gatccaggtg   9900
atacctaatt tccaggggct ggttggtggc ggcgtcgatg gcttgcaaga ggccgcatcc   9960
ccgcggcgcg actacggtac cgcgcggcgg gcggtgggcc gcggggtgt ccttggatga  10020 tgcatctaaa agcggtgacg cgggcgagcc cccggaggta gggggggctc cggacccgcc  10080
gggagagggg gcagggcac gtcggcgccg cgcgcgggca ggagctggtg ctgcgcgcgt  10140
aggttgctgg cgaacgcgac gacgcggcgg ttgatctcct gaatctggcg cctctgcgtg  10200
aagacgacgg gcccggtgag cttgaacctg aaagagagtt cgacagaatc aatttcggtg  10260
tcgttgacgg cggcctggcg caaaatctcc tgcacgtctc ctgagttgtc ttgataggcg  10320
atctcggcca tgaactgctc gatctcttcc tcctggagat ctccgcgtcc ggctcgctcc  10380
acggtggcgg cgaggtcgtt ggaaatgcgg gccatgagct gcgagaaggc gttgaggcct  10440
ccctcgttcc agacgcggct gtagaccacg ccccccttcgg catcgcgggc gcgcatgacc  10500
acctgcgcga gattgagctc cacgtgccgg gcgaagacgg cgtagtttcg caggcgctga  10560
aagaggtagt tgagggtggt ggcggtgtgt tctgccacga agaagtacat aacccagcgt  10620
cgcaacgtgg attcgttgat atcccccaag gcctcaaggc gctccatggc ctcgtagaag  10680 tccacggcgca agttgaaaaa ctgggagttg cgcgccgaca cggttaactc ctcctccaga  10740
agacggatga gctcggcgac agtgtcgcgc acctcgcgct caaaggctac aggggcctct  10800
tcttcttctt caatctcctc ttccataagg gcctccccctt cttcttcttc tggcggcggt  10860
gggggagggg ggacacggcg gcgacgacgg cgcaccggga ggcggtcgac aaagcgctcg  10920
atcatctccc cgcggcgacg gcgcatggtc tcggtgacgg cgcggccgtt ctcgcggggg  10980
cgcagttgga agacgccgcc cgtcatgtcc cggttatggg ttggcggggg gctgccatgc  11040
ggcagggata cggcgctaac gatgcatctc aacaattgtt gtgtaggtac tccgccgccg  11100
agggacctga gcgagtccgc atcgaccgga tcggaaaacc tctcgagaaa ggcgtctaac  11160
cagtcacagt cgcaaggtag gctgagcacc gtggcgggcg gcagcgggcg gcggtcgggg  11220
ttgtttctgg cggaggtgct gctgatgatg taattaaagt aggcggtctt gagacggcgg  11280
atggtcgaca gaagcaccat gtccttgggt ccggcctgct gaatgcgcag gcggtcggcc  11340 atgcccagg cttcgtttgt acatcggcgc aggtctttgt agtagtcttg catgagcctt  11400
tctaccggca cttcttcttc tccttcctct tgtcctgcat ctcttgcatc tatcgctgcg  11460 gcggcggcg agtttggccg taggtggcgc cctcttcctc ccatgcgtgt gaccccgaag  11520
cccctcatcg gctgaagcag ggctaggtcg gcgcacaacgc gctcggctaa tatggcctgc  11580
tgcacctgcg tgagggtaga ctggaagtca tccatgtcca caaagcggtg gtatgcgccc  11640
```

-continued

```
gtgttgatgg tgtaagtgca gttggccata acggaccagt taacggtctg gtgacccggc   11700
tgcgagagct cggtgtacct gagacgcgag taagccctcg agtcaaatac gtagtcgttg   11760
caagtccgca ccaggtactg gtatcccacc aaaaagtgcg gcggcggctg gcggtagagg   11820
ggccagcgta gggtggccgg ggctccgggg gcgagatctt ccaacataag gcgatgatat   11880
ccgtagatgt acctggacat ccaggtgatg ccggcggcgg tggtggaggc gcgcggaaag   11940
tcgcggacgc ggttccagat gttgcgcagc ggcaaaaagt gctccatggt cgggacgctc   12000
tggccggtca ggcgcgcgca atcgttgacg ctctagcgtg caaaaggaga gcctgtaagc   12060
gggcactctt ccgtggtctg gtggataaat tcgcaagggt atcatggcgg acgaccgggg   12120
ttcgagcccc gtatccggcc gtccgccgtg atccatgcgg ttaccgcccg cgtgtcgaac   12180
ccaggtgtgc gacgtcagac aacgggggag tgctcctttt ggcttccttc caggcgcggc   12240
ggctgctgcg ctagcttttt tggccactgg ccgcgcgcag cgtaagcggt taggctggaa   12300
agcgaaagca ttaagtggct cgctccctgt agccggaggg ttattttcca agggttgagt   12360
cgcgggaccc ccggttcgag tctcggaccg gccggactgc ggcgaacggg ggtttgcctc   12420
cccgtcatgc aagaccccgc ttgcaaattc ctccggaaac agggacgagc cccttttttg   12480
cttttcccag atgcatccgg tgctgcggca gatgcgcccc cctcctcagc agcggcaaga   12540
gcaagagcag cggcagacat gcagggcacc ctcccctcct cctaccgcgt caggaggggc   12600
gacatccgcg gttgacgcgg cagcagatgg tgattacgaa cccccgcggc gccgggcccg   12660
gcactacctg gacttggagg agggcgaggg cctggcgcgg ctaggagcgc cctctcctga   12720
gcggcaccca agggtgcagc tgaagcgtga tacgcgtgag gcgtacgtgc cgcggcagaa   12780
cctgtttcgc gaccgcgagg gagaggagcc cgaggagatg cgggatcgaa agttccacgc   12840
agggcgcgag ctgcggcatg gcctgaatcg cgagcggttg ctgcgcgagg aggactttga   12900
gcccgacgcg cgaaccggga ttagtcccgc gcgcgcacac gtggcggccg ccgacctggt   12960
aaccgcatac gagcagacgg tgaaccagga gattaacttt caaaaaagct ttaacaacca   13020
cgtgcgtacg cttgtggcgc gcgaggaggt ggctatagga ctgatgcatc tgtgggactt   13080
tgtaagcgcg ctggagcaaa acccaaatag caagccgctc atggcgcagc tgttccttat   13140
agtgcagcac agcagggaca acgaggcatt cagggatgcg ctgctaaaca tagtagagcc   13200
cgagggccgc tggctgctcg atttgataaa catcctgcag agcatagtgg tgcaggagcg   13260
cagcttgagc ctggctgaca aggtggccgc catcaactat tccatgctta gcctgggcaa   13320
gttttacgcc cgcaagatat accatacccc ttacgttccc atagacaagg aggtaaagat   13380
cgaggggttc tacatgcgca tggcgctgaa ggtgcttacc ttgagcgacg acctgggcgt   13440
ttatcgcaac gagcgcatcc acaaggccgt gagcgtgagc cggcggcgcg agctcagcga   13500
ccgcgagctg atgcacagcc tgcaaagggc cctggctggc acgggcagcg gcgatagaga   13560
ggccgagtcc tactttgacg cgggcgctga cctgcgctgg gccccaagcc gacgcgccct   13620
ggaggcagct ggggccggac ctgggctggc ggtggcaccc gcgcgcgctg gcaacgtcgg   13680
cggcgtggag gaatatgacg aggacgatga gtacgagcca gaggacggcg agtactaagc   13740
ggtgatgttt ctgatcagat gatgcaagac gcaacggacc cggcggtgcg ggcggcgctg   13800
cagagccagc cgtccggcct taactccacg gacgactggc gccaggtcat ggaccgcatc   13860
atgtcgctga ctgcgcgcaa tcctgacgcg ttccggcagc agccgcaggc caaccggctc   13920
tccgcaattc tggaagcggt ggtcccggcg cgcgcaaacc ccacgcacga gaaggtgctg   13980
```

-continued

```
gcgatcgtaa acgcgctggc cgaaaacagg gccatccggc ccgacgaggc cggcctggtc   14040
tacgacgcgc tgcttcagcg cgtggctcgt tacaacagcg gcaacgtgca gaccaacctg   14100
gaccggctgg tgggggatgt gcgcgaggcc gtggcgcagc gtgagcgcgc gcagcagcag   14160
ggcaacctgg gctccatggt tgcactaaac gccttcctga gtacacagcc cgccaacgtg   14220
ccgcggggac aggaggacta caccaacttt gtgagcgcac tgcggctaat ggtgactgag   14280
acaccgcaaa gtgaggtgta ccagtctggg ccagactatt ttttccagac cagtagacaa   14340
ggcctgcaga ccgtaaacct gagccaggct ttcaaaaact tgcaggggct gtggggggtg   14400
cgggctccca caggcgaccg cgcgaccgtg tctagcttgc tgacgcccaa ctcgcgcctg   14460
ttgctgctgc taatagcgcc cttcacggac agtggcagcg tgtcccggga cacataccta   14520
ggtcacttgc tgacactgta ccgcgaggcc ataggtcagg cgcatgtgga cgagcatact   14580
ttccaggaga ttacaagtgt cagccgcgcg ctggggcagg aggacacggg cagcctggag   14640
gcaaccctaa actacctgct gaccaaccgg cggcagaaga tcccctcgtt gcacagttta   14700
aacagcgagg aggagcgcat tttgcgctac gtgcagcaga gcgtgagcct taacctgatg   14760
cgcgacgggg taacgcccag cgtggcgctg gacatgaccg cgcgcaacat ggaaccgggc   14820
atgtatgcct caaaccggcc gtttatcaac cgcctaatgg actacttgca tcgcgcggcc   14880
gccgtgaacc ccgagtattt caccaatgcc atcttgaacc cgcactggct accgcccct   14940 ggtttctaca ccgggggatt cgaggtgccc gagggtaacg atggattcct ctgggacgac   15000
atagacgaca gcgtgttttc cccgcaaccg cagaccctgc tagagttgca acagcgcgag   15060
caggcagagg cggcgctgcg aaaggaaagc ttccgcaggc caagcagctt gtccgatcta   15120
ggcgctgcgg ccccgcggtc agatgctagt agcccatttc caagcttgat agggtctctt   15180
accagcactc gcaccacccg cccgcgcctg ctgggcgagg aggagtacct aaacaactcg   15240
ctgctgcagc cgcagcgcga aaaaaacctg cctccggcat ttcccaacaa cgggatagag   15300
agcctagtgg acaagatgag tagatggaag acgtacgcgc aggagcacag ggacgtgcca   15360
ggcccgcgcc cgcccacccg tcgtcaaagg cacgaccgtc agcggggtct ggtgtgggag   15420
gacgatgact cggcagacga cagcagccgtc ctggatttgg gagggagtgg caacccgttt   15480
gcgcaccttc gccccaggct ggggagaatg ttttaaaaaa aaaaaagcat gatgcaaaat   15540 aaaaaaactca ccaaggccat ggcaccgagc gttggttttc ttgtattccc cttagtatgc   15600
ggcgcgcggc gatgtatgag gaaggtcctc ctccctccta cgagagtgtg gtgagcgcgg   15660
cgccagtggc ggcggcgctg ggttctccct tcgatgctcc cctggacccg ccgtttgtgc   15720
ctccgcggta cctgcggcct accggggggga gaaacagcat ccgttactct gagttggcac   15780
ccctattcga caccacccgt gtgtacctgg tggacaacaa gtcaacggat gtggcatccc   15840
tgaactacca gaacgaccac agcaactttc tgaccacggt cattcaaaac aatgactaca   15900
gcccggggga ggcaagcaca cagaccatca atcttgacga ccggtcgcac tggggcggcg   15960
acctgaaaac catcctgcat accaacatgc caaatgtgaa cgagttcatg tttaccaata   16020
agtttaaggc gcgggtgatg gtgtcgcgct tgcctactaa ggacaatcag gtggagctga   16080
aatacgagtg ggtggagttc acgctgcccg agggcaacta ctccgagacc atgaccatag   16140
accttatgaa caacgcgatc gtggagcact acttgaaagt gggcagacag aacgggggttc   16200 tggaaagcga catcggggta aagtttgaca cccgcaactt cagactgggg tttgaccccg   16260
tcactggtct tgtcatgcct ggggtatata caaaacgaagc cttccatcca gacatcattt   16320
tgctgccagg atgcgggggtg gacttcaccc acagccgcct gagcaacttg ttgggcatcc   16380
```

-continued

```
gcaagcggca acccttccag gagggcttta ggatcaccta cgatgatctg gagggtggta  16440
acattcccgc actgttggat gtggacgcct accaggcgag cttgaaagat gacaccgaac  16500
agggcggggg tggcgcaggc ggcagcaaca gcagtggcag cggcgcggaa gagaactcca  16560
acgcggcagc cgcggcaatg cagccggtgg aggacatgaa cgatcatgcc attcgcggcg  16620
acacctttgc cacacgggct gaggagaagc gcgctgaggc cgaagcagcg gccgaagctg  16680
ccgcccccgc tgcgcaaccc gaggtcgaga agcctcagaa gaaaccggtg atcaaacccc  16740
tgacagagga cagcaagaaa cgcagttaca acctaataag caatgacagc accttcaccc  16800
agtaccgcag ctggtacctt gcatacaact acggcgaccc tcagaccgga atccgctcat  16860
ggaccctgct ttgcactcct gacgtaacct gcggctcgga gcaggtctac tggtcgttgc  16920
cagacatgat gcaagacccc gtgaccttcc gctccacgcg ccagatcagc aactttccgg  16980
tggtgggcgc cgagctgttg cccgtgcact ccaagagctt ctacaacgac caggccgtct  17040
actcccaact catccgccag tttacctctc tgacccacgt gttcaatcgc tttcccgaga  17100
accagatttt ggcgcgcccg ccagccccca ccatcaccac cgtcagtgaa aacgttcctg  17160
ctctcacaga tcacgggacg ctaccgctgc gcaacagcat cggaggagtc cagcgagtga  17220
ccattactga cgccagacgc cgcacctgcc cctacgttta caaggccctg ggcatagtct  17280
cgccgcgcgt cctatcgagc cgcactttt gagcaagcat gtccatcctt atatcgccca  17340
gcaataacac aggctggggc ctgcgcttcc caagcaagat gtttggcggg gccaagaagc  17400
gctccgacca acacccagtg cgcgtgcgcg ggcactaccg cgcgccctgg ggcgcgcaca  17460
aacgcggccg cactgggcgc accaccgtcg atgacgccat cgacgcggtg gtggaggagg  17520
cgcgcaacta cacgcccacg ccgccaccag tgtccacagt ggacgcggcc attcagaccg  17580
tggtgcgcgg agcccggcgc tatgctaaaa tgaagagacg gcggaggcgc gtagcacgtc  17640
gccaccgccg ccgacccggc actgccgccc aacgcgcggc ggcggccctg cttaaccgcg  17700
cacgtcgcac cggccgacgg gcggccatgc gggccgctcg aaggctggcc gcgggtattg  17760
tcactgtgcc ccccaggtcc aggcgacgag cggccgccgc agcagccgcg gccattagtg  17820
ctatgactca gggtcgcagg ggcaacgtgt attgggtgcg cgactcggtt agcggcctgc  17880
gcgtgcccgt gcgcacccgc cccccgcgca actagattgc aagaaaaaac tacttagact  17940
cgtactgttg tatgtatcca gcggcggcgg cgcgcaacga agctatgtcc aagcgcaaaa  18000
tcaaagaaga gatgctccag gtcatcgcgc cggagatcta tggccccccg aagaaggaag  18060
agcaggatta caagccccga aagctaaagc gggtcaaaaa gaaaaagaaa gatgatgatg  18120
atgaacttga cgacgaggtg gaactgctgc acgctaccgc gcccaggcga cgggtacagt  18180
ggaaaggtcg acgcgtaaaa cgtgttttgc gacccggcac caccgtagtc tttacgcccg  18240
gtgagcgctc caccccgcac ctacaagcgcg tgtatgatga ggtgtacggc gacgaggacc  18300
tgcttgagca ggccaacgag cgcctcgggg agtttgccta cggaaagcgg cataaggaca  18360
tgctggcgtt gccgctggac gagggcaacc caacacctag cctaaagccc gtaacactgc  18420
agcaggtgct gcccgcgctt gcaccgtccg aagaaaagcg cggcctaaag cgcgagtctg  18480
gtgacttggc acccaccgtg cagctgatgg tacccaagcg ccagcgactg gaagatgtct  18540
tggaaaaaat gaccgtggaa cctgggctgg agcccgaggt ccgcgtgcgg ccaatcaagc  18600
aggtggcgcc gggactgggc gtgcagaccg tggacgttca gataccccact accagtagca  18660 ccagtattgc caccgccaca gagggcatgg agacacaaac gtccccggtt gcctcagcgg  18720
```

-continued

```
tggcggatgc cgcggtgcag gcggtcgctg cggccgcgtc caagacctct acggaggtgc   18780
aaacggaccc gtggatgttt cgcgtttcag cccccggcg cccgcgccgt tcgaggaagt    18840
acggcgccgc cagcgcgcta ctgcccgaat atgccctaca tccttccatt gcgcctaccc   18900
ccggctatcg tggctacacc taccgcccca gaagacgagc aactacccga cgccgaacca   18960
ccactggaac ccgccgccgc cgtcgccgtc gccagccgt gctggccccg atttccgtgc     19020
gcagggtggc tcgcgaagga ggcaggaccc tggtgctgcc aacagcgcgc taccacccca   19080
gcatcgttta aaagccggtc tttgtggttc ttgcagatat ggccctcacc tgccgcctcc   19140
gtttcccggt gccgggattc cgaggaagaa tgcaccgtag gaggggcatg gccggccacg   19200
gcctgacggg cggcatgcgt cgtgcgcacc accggcggcg gcgcgcgtcg caccgtcgca   19260
tgcgcggcgg tatcctgccc ctccttattc cactgatcgc cgcggcgatt ggcgccgtgc   19320
ccggaattgc atccgtggcc ttgcaggcgc agagacactg attaaaaaca agttgcatgt   19380
ggaaaaatca aaataaaaag tctggactct cacgctcgct tggtcctgta actattttgt   19440
agaatggaag acatcaactt tgcgtctctg gccccgcgac acggctcgcg cccgttcatg   19500
ggaaactggc aagatatcgg caccagcaat atgagcggtg gcgccttcag ctggggctcg   19560
ctgtggagcg gcattaaaaa tttcggttcc accgttaaga actatggcag caaggcctgg    19620
aacagcagca caggccagat gctgagggat aagttgaaag agcaaaattt ccaacaaaag   19680
gtggtagatg gcctggcctc tggcattagc ggggtggtgg acctggccaa ccaggcagtg   19740
caaaataaga ttaacagtaa gcttgatccc cgccctcccg tagaggagcc tccaccggcc   19800
gtggagacag tgtctccaga ggggcgtggc gaaaagcgtc cgcgccccga cagggaagaa   19860
actctggtga cgcaaataga cgagcctccc tcgtacgagg aggcactaaa gcaaggcctg    19920
cccaccaccc gtcccatcgc gcccatggct accggagtgc tgggccagca cacacccgta   19980
acgctggacc tgcctccccc cgccgacacc cagcagaaac ctgtgctgcc aggcccgacc   20040
gccgttgttg taacccgtcc tagccgcgcg tccctgcgcc gcgccgccag cggtccgcga   20100
tcgttgcggc ccgtagccag tggcaactgg caaagcacac tgaacagcat cgtgggtctg    20160
ggggtgcaat ccctgaagcg ccgacgatgc ttctgatagc taacgtgtcg tatgtgtgtc   20220
atgtatgcgt ccatgtcgcc gccagaggag ctgctgagcc gccgcgcgcc cgctttccaa   20280
gatggctacc ccttcgatga tgccgcagtg gtcttacatg cacatctcgg gccaggacgc    20340
ctcggagtac ctgagccccg ggctggtgca gtttgcccgc gccaccgaga cgtacttcag   20400
cctgaataac aagtttagaa accccacggt ggcgcctacg cacgacgtga ccacagaccg   20460
gtcccagcgt ttgacgctgc ggttcatccc tgtggaccgt gaggatactg cgtactcgta   20520
caaggcgcgg ttcacccctag ctgtgggtga taaccgtgtg ctggacatgg cttccacgta   20580
ctttgacatc cgcggcgtgc tggacagggg ccctactttt aagccctact ctggcactgc   20640
ctacaacgcc ctggctccca agggtgcccc aaatccttgc gaatgggatg aagctgctac   20700
tgctcttgaa ataaacctag aagaagagga cgatgacaac gaagacgaag tagacgagca   20760
agctgagcag caaaaaactc acgtatttgg gcaggcgcct tattctggta taaatattac   20820
aaaggagggt attcaaatag gtgtcgaagg tcaaacacct aaatatgccg ataaaacatt   20880
tcaacctgaa cctcaaatag gagaatctca gtggtacgaa acagaaatta tcatgcagc     20940 tgggagagtc ctaaaaaaga ctaccccaat gaaaccatgt tacggttcat atgcaaaacc   21000
cacaaatgaa aatggagggc aaggcattct tgtaaagcaa caaaatggaa agctagaaag   21060
tcaagtggaa atgcaatttt tctcaactac tgaggcagcc gcaggcaatg gtgataactt   21120
```

-continued

```
gactcctaaa gtggtattgt acagtgaaga tgtagatata gaaaccccag acactcatat   21180
ttcttacatg cccactatta aggaaggtaa ctcacgagaa ctaatgggcc aacaatctat   21240
gcccaacagg cctaattaca ttgctttag ggacaatttt attggtctaa tgtattacaa   21300
cagcacgggt aatatgggtg ttctggcggg ccaagcatcg cagttgaatg ctgttgtaga   21360
tttgcaagac agaaacacag agctttcata ccagcttttg cttgattcca ttggtgatag   21420
aaccaggtac ttttctatgt ggaatcaggc tgttgacagc tatgatccag atgttagaat   21480
tattgaaaat catggaactg aagatgaact tccaaattac tgctttccac tgggaggtgt   21540
gattaataca gagactctta ccaaggtaaa acctaaaaca ggtcaggaaa atggatggga   21600
aaaagatgct acagaatttt cagataaaaa tgaaataaga gttggaaata attttgccat   21660
ggaaatcaat ctaaatgcca acctgtggag aaatttcctg tactccaaca tagcgctgta   21720
tttgcccgac aagctaaagt acagtccttc caacgtaaaa atttctgata acccaaacac   21780
ctacgactac atgaacaagc gagtggtggc tcccgggcta gtggactgct acattaacct   21840
tggagcacgc tggtcccttg actatatgga caacgtcaac ccatttaacc accaccgcaa   21900
tgctggcctg cgctaccgct caatgttgct gggcaatggt cgctatgtgc ccttccacat   21960
ccaggtgcct cagaagttct ttgccattaa aaacctcctt ctcctgccgg gctcatacac   22020
ctacgagtgg aacttcagga aggatgttaa catggttctg cagagctccc taggaaatga   22080
cctaagggtt gacggagcca gcattaagtt tgatagcatt tgcctttacg ccaccttctt   22140
ccccatggcc cacaacaccg cctccacgct tgaggccatg cttagaaacg acaccaacga   22200
ccagtccttt aacgactatc tctccgccgc caacatgctc taccctatac ccgccaacgc   22260
taccaacgtg cccatatcca tcccctcccg caactgggcg gctttccgcg gctgggcctt   22320
cacgcgcctt aagactaagg aaacccatc actgggctcg ggctacgacc cttattacac   22380
ctactctggc tctataccct acctagatgg aacctttac ctcaaccaca cctttaagaa   22440
ggtggccatt accttttgact cttctgtcag ctggcctggc aatgaccgcc tgcttacccc   22500
caacgagttt gaaattaagc gctcagttga cgggggagggt tacaacgttg cccagtgtaa   22560
catgaccaaa gactggttcc tggtacaaat gctagctaac tataacattg gctaccaggg   22620
cttctatatc ccagagagct acaaggaccg catgtactcc ttctttagaa acttccagcc   22680
catgagccgt caggtggtgg atgatactaa atacaaggac taccaacagg tgggcatcct   22740
acaccaacac aacaactctg gatttgttgg ctaccttgcc cccaccatgc gcgaaggaca   22800
ggcctaccct gctaacttcc cctatccgct tataggcaag accgcagttg acagcattac   22860
ccagaaaaag tttctttgcg atcgcaccct ttggcgcatc ccattctcca gtaactttat   22920
gtccatgggc gcactcacag acctgggcca aaaccttctc tacgccaact ccgcccacgc   22980
gctagacatg actttttgagg tggatcccat ggacgagccc acccttcttt atgtttttgtt   23040 tgaagtcttt gacgtggtcc gtgtgcacca gccgcaccgc ggcgtcatcg aaaccgtgta   23100
cctgcgcacg cccttctcgg ccggcaacgc cacaacataa agaagcaagc aacatcaaca   23160
acagctgccg ccatgggctc cagtgagcag gaactgaaag ccattgtcaa agatcttggt   23220
tgtgggccat attttttggg cacctatgac aagcgctttc caggctttgt ttctccacac   23280
aagctcgcct gcgccatagt caatacggcc ggtcgcgaga ctggggcgt acactggatg   23340 gcctttgcct ggaacccgca ctcaaaaaca tgctacctct ttgagcccct tggcttttct   23400
gaccagcgac tcaagcaggt ttaccagttt gagtacgagt cactcctgcg ccgtagcgcc   23460
```

-continued

```
attgcttctt cccccgaccg ctgtataacg ctggaaaagt ccacccaaag cgtacagggg   23520
cccaactcgg ccgcctgtgg actattctgc tgcatgtttc tccacgcctt tgccaactgg   23580
ccccaaactc ccatggatca caaccccacc atgaacctta ttaccggggt acccaactcc   23640
atgctcaaca gtccccaggt acagcccacc ctgcgtcgca accaggaaca gctctacagc   23700
ttcctggagc gccactcgcc ctacttccgc agccacagtg cgcagattag gagcgccact   23760 tcttttttgtc acttgaaaaa catgtaaaaa taatgtacta gagacacttt caataaaggc   23820
aaatgctttt atttgtacac tctcgggtga ttatttaccc ccaccctttgc cgtctgcgcc   23880 gtttaaaaat caaaggggtt ctgccgcgca tcgctatgcg ccactggcag ggacacgttg   23940
cgatactggt gtttagtgct ccacttaaac tcaggcacaa ccatccgcgg cagctcggtg   24000
aagttttcac tccacaggct gcgcaccatc accaacgcgt ttagcaggtc gggcgccgat   24060
atcttgaagt cgcagttggg gcctccgccc tgcgcgcgcg agttgcgata cacagggttg   24120
cagcactgga acactatcag cgccgggtgg tgcacgctgg ccagcacgct cttgtcggag   24180
atcagatccg cgtccaggtc ctccgcgttg ctcagggcga acggagtcaa ctttggtagc   24240
tgccttccca aaaagggcgc gtgcccaggc tttgagttgc actcgcaccg tagtggcatc   24300
aaaaggtgac cgtgcccggt ctgggcgtta ggatacagcg cctgcataaa agccttgatc   24360
tgcttaaaag ccacctgagc ctttgcgcct tcagagaaga acatgccgca agacttgccg   24420
gaaaactgat tggccggaca ggccgcgtcg tgcacgcagc accttgcgtc ggtgttggag   24480
atctgcacca catttcggcc ccaccggttc ttcacgatct tggccttgct agactgctcc   24540
ttcagcgcgc gctgcccgtt ttcgctcgtc acatccattt caatcacgtg ctccttattt   24600
atcataatgc ttccgtgtag acacttaagc tcgccttcga tctcagcgca gcggtgcagc   24660
cacaacgcgc agcccgtggg ctcgtgatgc ttgtaggtca cctctgcaaa cgactgcagg   24720
tacgcctgca ggaatcgccc catcatcgtc acaaaggtct tgttgctggt gaaggtcagc   24780
tgcaacccgc ggtgctcctc gttcagccag gtcttgcata cggccgccag agcttccact   24840
tggtcaggca gtagtttgaa gttcgccttt agatcgttat ccacgtggta cttgtccatc   24900
agcgcgcgcg cagcctccat gcccttctcc cacgcagaca cgatcggcac actcagcggg   24960
ttcatcaccg taatttcact ttccgcttcg ctgggctctt cctcttcctc ttgcgtccgc   25020
ataccacgcg ccactgggtc gtcttcattc agccgccgca ctgtgcgctt acctcctttg   25080
ccatgcttga ttagcaccgg tgggttgctg aaacccacca tttgtagcgc cacatcttct   25140
ctttcttcct cgctgtccac gattacctct ggtgatggcg ggcgctcggg cttgggagaa   25200
gggcgcttct ttttcttctt gggcgcaatg gccaaatccg ccgccgaggt cgatggccgc   25260
gggctgggtg tgcgcggcac cagcgcgtct tgtgatgagt cttcctcgtc ctcggactcg   25320
atacgccgcc tcatccgctt ttttgggggc gcccggggag gcggcggcga cggggacggg   25380
gacgacacgt cctccatggt tggggacgt cgcgccgcac cgcgtccgcg ctcggggtg   25440 gtttcgcgct gctcctcttc ccgactggcc atttccttct cctataggca gaaaaagatc   25500
atggagtcag tcgagaagaa ggacagccta accgcccct ctgagttcgc caccaccgcc   25560
tccaccgatg ccgccaacgc gcctaccacc ttccccgtcg aggcacccc gcttgaggag   25620 gaggaagtga ttatcgagca ggacccaggt tttgtaagcg aagacgacga ggaccgctca   25680
gtaccaacag aggataaaaa gcaagaccag gacaacgcag aggcaaacga ggaacaagtc   25740 gggcggggggg acgaaaggca tggcgactac ctagatgtgg gagacgacgt gctgttgaag   25800
catctgcagc gccagtgcgc cattatctgc gacgcgttgc aagagcgcag cgatgtgccc   25860
```

-continued

```
ctcgccatag cggatgtcag ccttgcctac gaacgccacc tattctcacc gcgcgtaccc   25920
cccaaacgcc aagaaaacgg cacatgcgag cccaacccgc gcctcaactt ctaccccgta   25980
tttgccgtgc cagaggtgct tgccacctat cacatctttt tccaaaactg caagataccc   26040
ctatcctgcc gtgccaaccg cagccgagcg dacaagcagc tggccttgcg gcagggcgct   26100
gtcatacctg atatcgcctc gctcaacgaa gtgccaaaaa tctttgaggg tcttggacgc   26160
gacgagaagc gcgcggcaaa cgctctgcaa caggaaaaca gcgaaaatga aagtcactct   26220
ggagtgttgg tggaactcga gggtgacaac gcgcgcctag ccgtactaaa acgcagcatc   26280
gaggtcaccc actttgccta cccggcactt aacctacccc ccaaggtcat gagcacagtc   26340
atgagtgagc tgatcgtgcg ccgtgcgcag cccctggaga gggatgcaaa tttgcaagaa   26400
caaacagagg agggcctacc cgcagttggc gacgagcagc tagcgcgctg gcttcaaacg   26460
cgcgagcctg ccgacttgga ggagcgacgc aaactaatga tggccgcagt gctcgttacc   26520
gtggagcttg agtgcatgca gcggttcttt gctgacccgg agatgcagcg caagctagag   26580
gaaacattgc actacacctt tcgacagggc tacgtacgcc aggcctgcaa gatctccaac   26640
gtggagctct gcaacctggt ctcctacctt ggaattttgc acgaaaaccg ccttgggcaa   26700
aacgtgcttc attccacgct caagggcgag gcgcgccgcg actacgtccg cgactgcgtt   26760
tacttatttc tatgctacac ctggcagacg gccatgggcg tttggcagca gtgcttggag   26820
gagtgcaacc tcaaggagct gcagaaactg ctaaagcaaa acttgaagga cctatggacg   26880
gccttcaacg agcgctccgt ggccgcgcac ctggcggaca tcattttccc cgaacgcctg   26940
cttaaaaccc tgcaacaggg tctgccagac ttcaccagtc aaagcatgtt gcagaacttt   27000
aggaacttta tcctagagcg ctcaggaatc ttgcccgcca cctgctgtgc acttcctagc   27060
gactttgtgc ccattaagta ccgcgaatgc cctccgccgc tttggggcca ctgctacctt   27120
ctgcagctag ccaactacct tgcctaccac tctgacataa tggaagacgt gagcggtgac   27180
ggtctactgg agtgtcactg tcgctgcaac ctatgcaccc cgcaccgctc cctggtttgc   27240
aattcgcagc tgcttaacga aagtcaaatt atcggtacct ttgagctgca gggtccctcg   27300
cctgacgaaa gtccgcggc tccggggttg aaactcactc cggggctgtg gacgtcggct   27360
taccttcgca aatttgtacc tgaggactac cacgcccacg agattaggtt ctacgaagac   27420
caatcccgcc cgcctaatgc ggagcttacc gcctgcgtca ttacccaggg ccacattctt   27480
ggccaattgc aagccatcaa caaagcccgc caagagtttc tgctacgaaa gggacggggg   27540
gtttacttgg accccagtc cggcgaggag ctcaacccaa tccccccgcc gccgcagccc   27600
tatcagcagc agccgcgggc ccttgcttcc caggatggca cccaaaaaga agctgcagct   27660
gccgccgcca cccacggacg aggaggaata ctgggacagt caggcagagg aggttttgga   27720
cgaggaggag gaggacatga tggaagactg ggagagccta gacgaggaag cttccgaggt   27780
cgaagaggtg tcagacgaaa caccgtcacc ctcggtcgca ttcccctcgc cggcgcccca   27840
gaaatcggca accggttcca gcatggctac aacctccgct cctcaggcgc cgccggcact   27900
gcccgttcgc cgacccaacc gtagatggga caccactgga accagggccg gtaagtccaa   27960
gcagccgccg ccgttagccc aagagcaaca acagcgccaa ggctaccgct catggcgcgg   28020
gcacaagaac gccatagttg cttgcttgca agactgtggg ggcaacatct ccttcgcccg   28080
ccgctttctt ctctaccatc acggcgtggc cttcccccgt aacatcctgc attactaccg   28140
tcatctctac agcccatact gcaccggcgg cagcggcagc aacagcagcg gccacacaga   28200
```

-continued

```
agcaaaggcg accggatagc aagactctga caaagcccaa gaaatccaca gcggcggcag   28260
cagcaggagg aggagcgctg cgtctggcgc ccaacgaacc cgtatcgacc cgcgagctta   28320
gaaacaggat tttttcccact ctgtatgcta tatttcaaca gagcaggggc caagaacaag   28380
agctgaaaat aaaaaacagg tctctgcgat ccctcacccg cagctgcctg tatcacaaaa   28440
gcgaagatca gcttcggcgc acgctggaag acgcggaggc tctcttcagt aaatactgcg   28500
cgctgactct taaggactag tttcgcgccc tttctcaaat ttaagcgcga aaactacgtc   28560
atctccagcg gccacacccg gcgccagcac ctgttgtcag cgccattatg agcaaggaaa   28620
ttcccacgcc ctacatgtgg agttaccagc cacaaatggg acttgcggct ggagctgccc   28680
aagactactc aacccgaata aactacatga gcgcgggacc ccacatgata tcccgggtca   28740
acggaatacg cgcccaccga aaccgaattc tcctggaaca ggcggctatt accaccacac   28800
ctcgtaataa ccttaatccc cgtagttggc ccgctgccct ggtgtaccag gaaagtcccg   28860
ctcccaccac tgtggtactt cccagagacg cccaggccga agttcagatg actaactcag   28920
gggcgcagct tgcgggcggc tttcgtcaca gggtgcggtc gcccgggcag ggtataactc   28980
acctgacaat cagagggcga ggtattcagc tcaacgacga gtcggtgagc tcctcgcttg   29040
gtctccgtcc ggacgggaca tttcagatcg gcggcgccgg ccgctcttca ttcacgcctc   29100
gtcaggcaat cctaactctg cagacctcgt cctctgagcc gcgctctgga ggcattggaa   29160
ctctgcaatt tattgaggag tttgtgccat cggtctactt taacccottc tcgggacctc   29220 ccggccacta tccggatcaa tttattccta actttgacgc ggtaaaggac tcggcggacg   29280
gctacgactg aatgttaagt ggagaggcag agcaactgcg cctgaaacac ctggtccact   29340
gtcgccgcca caagtgcttt gcccgcgact ccggtgagtt ttgctacttt gaattgcccg   29400
aggatcatat cgagggcccg gcgcacggcg tccggcttac cgcccaggga gagcttgccc   29460
gtagcctgat tcgggagttt acccagcgcc ccctgctagt tgagcgggac aggggaccct   29520
gtgttctcac tgtgatttgc aactgtccta accctggatt acatcaagat cctctagtta   29580
atgtcaggtc gcctaagtcg attaactaga gtacccgggg atcttattcc ctttaactaa   29640 taaaaaaaa taataaagca tcacttactt aaaatcagtt agcaaatttc tgtccagttt   29700
attcagcagc acctccttgc cctcctccca gctctggtat tgcagcttcc tcctggctgc   29760
aaactttctc cacaatctaa atggaatgtc agtttcctcc tgttcctgtc catccgcacc   29820
cactatcttc atgttgttgc agatgaagcg cgcaagaccg tctgaagata ccttcaaccc   29880
cgtgtatcca tatgacacgg aaaccggtcc tccaactgtg cctttttctta ctcctccctt   29940 tgtatccccc aatgggtttc aagagagtcc ccctggggta ctctcttttgc gcctatccga   30000 acctctagtt acctccaatg gcatgcttgc gctcaaaatg ggcaacggcc tctctctgga   30060
cgaggccggc aaccttacct cccaaaatgt aaccactgtg agcccacctc tcaaaaaaac   30120
caagtcaaac ataaacctgg aaatatctgc acccctcaca gttacctcag aagccctaac   30180
tgtggctgcc gccgcacctc taatggtcgc gggcaacaca ctcaccatgc aatcacaggc   30240
cccgctaacc gtgcacgact ccaaacttag cattgccacc caaggacccc tcacagtgtc   30300
agaaggaaag ctagccctgc aaacatcagg cccctcacc accaccgata gcagtaccct   30360
tactatcact gcctcaccccc ctctaactac tgccactggt agcttgggca ttgacttgaa   30420
agagcccatt tatacacaaa atggaaaact aggactaaag tacgggctc ctttgcatgt   30480 aacagacgac ctaaacactt tgaccgtagc aactggtcca ggtgtgacta ttaataatac   30540
ttccttgcaa actaaagtta ctggagcctt gggttttgat tcacaaggca atatgcaact   30600
```

-continued

```
taatgtagca ggaggactaa ggattgattc tcaaaacaga cgccttatac ttgatgttag   30660
ttatccgttt gatgctcaaa accaactaaa tctaagacta ggacagggcc ctcttttttat   30720 aaactcagcc cacaacttgg atattaacta caacaaaggc ctttacttgt ttacagcttc   30780
aaacaattcc aaaaagcttg aggttaacct aagcactgcc aaggggttga tgtttgacgc   30840
tacagccata gccattaatg caggagatgg gcttgaattt ggttcaccta atgcaccaaa   30900
cacaaatccc ctcaaaacaa aaattggcca tggcctagaa tttgattcaa acaaggctat   30960
ggttcctaaa ctaggaactg gccttagttt tgacagcaca ggtgccatta cagtaggaaa   31020
caaaaataat gataagctaa ctttgtggac cggaataaac cctccaccta actgtcaaat   31080
tgtggaaaac actaatacaa atgatggcaa acttacttta gtattagtaa aaaatggagg   31140
gcttgttaat ggctacgtgt ctctagttgg tgtatcagac actgtgaacc aaatgttcac   31200
acaaaagaca gcaaacatcc aattaagatt atattttgac tcttctggaa atctattaac   31260
tgaggaatca gacttaaaaa ttccacttaa aaataaatct tctacagcga ccagtgaaac   31320
tgtagccagc agcaaagcct ttatgccaag tactacagct tatcccttca acaccactac   31380
tagggatagt gaaaactaca ttcatggaat atgttactac atgactagtt atgatagaag   31440
tctatttccc ttgaacattt ctataatgct aaacagccgt atgatttctt ccaatgttgc   31500
ctatgccata caatttgaat ggaatctaaa tgcaagtgaa tctccagaaa gcaacatagc   31560
tacgctgacc acatccccct ttttctttc ttacattaca gaagacgaca actaaagaat   31620
cgtttgtgtt atgtttcaac gtgtttattt ttcaattgca gaaaatttca agtcatttt   31680 cattcagtag tatagcccca ccaccacata gcttatacag atcaccgtac cttaatcaaa   31740
ctcacagaac cctagtattc aacctgccac ctccctccca acacacagag tacacagtcc   31800 tttctcccg gctggcctta aaaagcatca tatcatgggt aacagacata ttcttaggtg   31860
ttatattcca cacggtttcc tgtcgagcca aacgctcatc agtgatatta ataaactccc   31920
cgggcagctc acttaagttc atgtcgctgt ccagctgctg agccacaggc tgctgtccaa   31980
cttgcggttg cttaacgggc ggcgaaggag aagtccacgc ctacatgggg gtagagtcat   32040
aatcgtgcat caggataggg cggtggtgct gcagcagcgc gcgaataaac tgctgccgcc   32100
gccgctccgt cctgcaggaa tacaacatgg cagtggtctc ctcagcgatg attcgcaccg   32160
cccgcagcat aaggcgcctt gtcctccggg cacagcagcg caccctgatc tcacttaaat   32220
cagcacagta actgcagcac agcaccacaa tattgttcaa aatcccacag tgcaaggcgc   32280
tgtatccaaa gctcatggcg gggaccacag aacccacgtg gccatcatac cacaagcgca   32340
ggtagattaa gtggcgaccc ctcataaaca cgctggacat aaacattacc tcttttggca   32400
tgttgtaatt caccacctcc cggtaccata taaacctctg attaaacatg gcgccatcca   32460
ccaccatcct aaaccagctg gccaaaacct gcccgccggc tatacactgc agggaaccgg   32520
gactggaaca atgacagtgg agagcccagg actcgtaacc atggatcatc atgctcgtca   32580
tgatatcaat gttggcacaa cacaggcaca cgtgcataca cttcctcagg attacaagct   32640
cctcccgcgt tagaaccata tcccagggaa caacccattc ctgaatcagc gtaaatccca   32700
cactgcaggg aagacctcgc acgtaactca cgttgtgcat tgtcaaagtg ttacattcgg   32760
gcagcagcgg atgatcctcc agtatggtag cgcgggtttc tgtctcaaaa ggaggtagac   32820
gatccctact gtacggagtg cgccgagaca accgagatcg tgttggtcgt agtgtcatgc   32880
caaatggaac gccggacgta gtcatatttc ctgaagcaaa accaggtgcg ggcgtgacaa   32940
```

-continued

```
acagatctgc gtctccggtc tcgccgctta gatcgctctg tgtagtagtt gtagtatatc    33000
cactctctca aagcatccag gcgcccccctg gcttcgggtt ctatgtaaac tccttcatgc    33060
gccgctgccc tgataacatc caccaccgca gaataagcca cacccagcca acctacacat    33120
tcgttctgcg agtcacacac gggaggagcg ggaagagctg gaagaaccat gtttttttt    33180 ttattccaaa agattatcca aaacctcaaa atgaagatct attaagtgaa cgcgctcccc    33240
tccggtggcg tggtcaaact ctacagccaa agaacagata atggcatttg taagatgttg    33300
cacaatggct tccaaaaggc aaacggccct cacgtccaag tggacgtaaa ggctaaaccc    33360
ttcagggtga atctcctcta taaacattcc agcaccttca accatgccca aataattctc    33420
atctcgccac cttctcaata tatctctaag caaatcccga atattaagtc cggccattgt    33480
aaaaatctgc tccagagcgc cctccacctt cagcctcaag cagcgaatca tgattgcaaa    33540
aattcaggtt cctcacagac ctgtataaga ttcaaaagcg gaacattaac aaaaataccg    33600
cgatcccgta ggtcccttcg cagggccagc tgaacataat cgtgcaggtc tgcacggacc    33660
agcgcggcca cttccccgcc aggaaccatg acaaaagaac ccacactgat tatgacacgc    33720
atactcggag ctatgctaac cagcgtagcc ccgatgtaag cttgttgcat gggcggcgat    33780
ataaaatgca aggtgctgct caaaaaatca ggcaaagcct cgcgcaaaaa agaaagcaca    33840
tcgtagtcat gctcatgcag ataaaggcag gtaagctccg gaaccaccac agaaaaagac    33900
accatttttc tctcaaacat gtctgcgggt ttctgcataa acacaaaata aaataacaaa    33960
aaaacattta aacattagaa gcctgtctta caacaggaaa aacaacccctt ataagcataa    34020 gacggactac ggccatgccg gcgtgaccgt aaaaaaactg gtcaccgtga ttaaaaagca    34080
ccaccgacag ctcctcggtc atgtccggag tcataatgta agactcggta aacacatcag    34140
gttgattcac atcggtcagt gctaaaaagc gaccgaaata gcccgggga atacatacccc    34200 gcaggcgtag agacaacatt acagccccca taggaggtat aacaaaatta ataggagaga    34260
aaaacacata aacacctgaa aaaccctcct gcctaggcaa aatagcaccc tcccgctcca    34320
gaacaacata cagcgcttcc acagcggcag ccataacagt cagccttacc agtaaaaaag    34380
aaaacctatt aaaaaaacac cactcgacac ggcaccagct caatcagtca cagtgtaaaa    34440
aagggccaag tgcagagcga gtatatatag gactaaaaaa tgacgtaacg gttaaagtcc    34500
acaaaaaaca cccagaaaac cgcacgcgaa cctacgccca gaaacgaaag ccaaaaaacc    34560
cacaacttcc tcaaatcgtc acttccgttt tcccacgtta cgtcacttcc cattttaaga    34620
aaactacaat tcccaacaca tacaagttac tccgccctaa aacctacgtc acccgccccg    34680
ttcccacgcc ccgcgccacg tcacaaactc cacccccttca ttatcatatt ggcttcaatc    34740
caaaataagg tatattattg atgatg                                         34766
```

```
<210> SEQ ID NO 30
<211> LENGTH: 35726
<212> TYPE: DNA
<213> ORGANISM: Artificial Sequence
<220> FEATURE:
<223> OTHER INFORMATION: Adk35F2-Spike/E4orf6(mPGK)-E4dl-711(E4re#29)

<400> SEQUENCE: 30
```

```
ttaattaaca tcatcaataa tatacccttat tttggattga agccaatatg ataatgaggg     60
ggtggagttt gtgacgtggc gcggggcgtg ggaacggggc gggtgacgta gtagtgtggc    120
ggaagtgtga tgttgcaagt gtggcggaac acatgtaagc gacggatgtg gcaaaagtga    180 cgttttggt gtgcgccggt gtacacagga agtgacaatt ttcgcgcggt tttaggcgga    240
```

-continued

```
tgttgtagta aatttgggcg taaccgagta agatttggcc attttcgcgg gaaaactgaa      300
taagaggaag tgaaatctga ataattttgt gttactcata gcgcgtaata atttctgtaa      360
tagtaatcaa ttacggggtc attagttcat agcccatata tggagttccg cgttacataa      420
cttacggtaa atggcccgcc tggctgaccg cccaacgacc cccgcccatt gacgtcaata      480
atgacgtatg ttcccatagt aacgccaata gggactttcc attgacgtca atgggtggag      540
tatttacggt aaactgccca cttggcagta catcaagtgt atcatatgcc aagtacgccc      600
cctattgacg tcaatgacgg taaatggccc gcctggcatt atgcccagta catgacctta      660
tgggactttc ctacttggca gtacatctac gtattagtca tcgctattac catggtgatg      720
cggttttggc agtacatcaa tgggcgtgga tagcggtttg actcacgggg atttccaagt      780
ctccacccca ttgacgtcaa tgggagtttg ttttggcacc aaaatcaacg ggactttcca      840
aaatgtcgta acaactccgc cccattgacg caaatgggcg gtaggcgtgt acggtgggag      900
gtctatataa gcagagctct ccctatcagt gatagagatc tccctatcag tgatagagat      960
cgtcgacgag ctcgtttagt gaaccgtcag atcgcctgga gacgccatcc acgctgtttt     1020
gacctccata gaagacaccg ggaccgatcc agcctccgat ttgccaccat gtttgtgttc     1080
ctggtgctgc tgccactggt gtccagccag tgtgtgaacc tgaccaccag acccaactt     1140 cctcctgcct acaccaactc cttcaccagg ggagtctact accctgacaa ggtgttcagg     1200
tcctctgtgc tgcacagcac ccaggacctg ttcctgccat tcttcagcaa tgtgacctgg     1260
ttccatgcca tccatgtgtc tggcaccaat ggcaccaaga ggtttgacaa ccctgtgctg     1320
ccattcaatg atggagtcta ctttgccagc acagagaaga gcaacatcat caggggctgg     1380 attttttggca ccaccctgga cagcaagacc cagtccctgc tgattgtgaa caatgccacc     1440
aatgtggtga ttaaggtgtg tgagttccag ttctgtaatg acccattcct gggagtctac     1500
taccacaaga caacaagtc ctggatggag tctgagttca gggtctactc ctctgccaac     1560
aactgtacct ttgaatatgt gagccaacca ttcctgatgg acttggaggg caagcagggc     1620
aacttcaaga acctgagggga gtttgtgttc aagaacattg atggctactt caagatttac     1680
agcaaacaca caccaatcaa cctggtgagg gacctgccac agggcttctc tgccttggaa     1740
ccactggtgg acctgccaat tggcatcaac atcaccaggt tccagaccct gctggctctg     1800
cacaggtcct acctgacacc tggagactcc tcctctggct ggacagcagg agcagcagcc     1860
tactatgtgg gctacctcca accaaggacc ttcctgctga aatacaatga gaatggcacc     1920
atcacagatg ctgtggactg tgccctggac ccactgtctg agaccaagtg taccctgaaa     1980
tccttcacag tggagaaggg catctaccag accagcaact tcagggtcca accaacagag     2040
agcattgtga ggtttccaaa catcaccaac ctgtgtccat ttggagaggt gttcaatgcc     2100
accaggtttg cctctgtcta tgcctggaac aggaagagga ttagcaactg tgtggctgac     2160
tactctgtgc tctacaactc tgcctccttc agcaccttca gtgttatgg agtgagccca     2220 accaaactga atgacctgtg tttcaccaat gtctatgctg actccttgt gattaggggga     2280 gatgaggtga cacagattgc ccctggacaa acaggcaaga ttgctgacta caactacaaa     2340
ctgcctgatg acttcacagg ctgtgtgatt gcctggaaca gcaacaacct ggacagcaag     2400
gtgggaggca actacaacta cctctacaga ctgttcagga gagcaacct gaaaccattt     2460 gagagggaca tcagcacaga gatttaccag gctggcagca caccatgtaa tggagtggag     2520
ggcttcaact gttactttcc actccaatcc tatggcttcc aaccaaccaa tggagtgggc     2580
```

-continued

```
taccaaccat acagggtggt ggtgctgtcc tttgaactgc tccatgcccc tgccacagtg    2640
tgtggaccaa agaagagcac caacctggtg aagaacaagt gtgtgaactt caacttcaat    2700
ggactgacag gcacaggagt gctgacagag agcaacaaga agttcctgcc attccaacag    2760
tttggcaggg acattgctga caccacagat gctgtgaggg acccacagac cttggagatt    2820
ctggacatca caccatgttc ctttggagga gtgtctgtga ttacacctgg caccaacacc    2880
agcaaccagg tggctgtgct ctaccaggat gtgaactgta ctgaggtgcc tgtggctatc    2940
catgctgacc aacttacacc aacctggagg gtctacagca caggcagcaa tgtgttccag    3000
accagggctg gctgtctgat tggagcagag catgtgaaca actcctatga gtgtgacatc    3060
ccaattggag caggcatctg tgcctcctac cagacccaga ccggtggcgg tgggtcgagg    3120
tctgtggcaa gccagagcat cattgcctac acaatgagtc tgggagcaga gaactctgtg    3180
gcttacagca acaacagcat tgccatccca accaacttca ccatctctgt gaccacagag    3240
attctgcctg tgagtatgac caagacctct gtggactgta caatgtatat ctgtggagac    3300
agcacagagt gtagcaacct gctgctccaa tatggctcct tctgtaccca acttaacagg    3360
gctctgacag gcattgctgt ggaacaggac aagaacaccc aggaggtgtt tgcccaggtg    3420
aagcagattt acaagacacc tccaatcaag gactttggag gcttcaactt cagccagatt    3480
ctgcctgacc caagcaagcc aagcaagagg tccttcattg aggacctgct gttcaacaag    3540
gtgaccctgg ctgatgctgg cttcatcaag caatatggag actgtctggg agacattgct    3600
gccagggacc tgatttgtgc ccagaagttc aatggactga cagtgctgcc tccactgctg    3660
acagatgaga tgattgccca atacacctct gccctgctgg ctggcaccat cacctctggc    3720
tggacctttg gagcaggagc agccctccaa atcccatttg ctatgcagat ggcttacagg    3780
ttcaatggca ttggagtgac ccagaatgtg ctctatgaga accagaaact gattgccaac    3840
cagttcaact ctgccattgg caagattcag gactccctgt ccagcacagc ctctgccctg    3900
ggcaaactcc aagatgtggt gaaccagaat gcccaggctc tgaacaccct ggtgaagcaa    3960
ctttccagca ctttggagc catctcctct gtgctgaatg acatcctgag cagactggac    4020
aaggtggagg ctgaggtcca gattgacaga ctgattacag gcagactcca atccctccaa    4080
acctatgtga cccaacaact tatcagggct gctgagatta gggcatctgc caacctggct    4140
gccaccaaga tgagtgagtg tgtgctggga caaagcaaga gggtggactt ctgtggcaag    4200
ggctaccacc tgatgagttt tccacagtct gcccctcatg gagtggtgtt cctgcatgtg    4260
acctatgtgc ctgcccagga gaagaacttc accacagccc ctgccatctg ccatgatggc    4320
aaggctcact ttccaaggga gggagtgttt gtgagcaatg gcacccactg gtttgtgacc    4380
cagaggaact tctatgaacc acagattatc accacagaca caccctttgt gtctggcaac    4440
tgtgatgtgg tgattggcat tgtgaacaac acagtctatg acccactcca acctgaactg    4500
gactccttca aggaggaact ggacaaatac ttcaagaacc acaccagccc tgatgtggac    4560
ctgggagaca tctctggcat caatgcctct gtggtgaaca tccagaagga gattgacaga    4620
ctgaatgagg tggctaagaa cctgaatgag tccctgattg acctccaaga actgggcaaa    4680
tatgaacaat acatcaagtg gccatgaaaa ttgatcataa tcagccatac acatttgta    4740 gaggttttac ttgctttaaa aaacctccca cacctccccc tgaacctgaa acataaaatg    4800
aatgcaattg ttgttgttaa cttgtttatt gcagcttata atggttacaa ataaagcaat    4860
agcatcacaa atttcacaaa taaagcattt ttttcactgc attctagttg tggtttgtcc    4920
aaactcatca atgtatctta acgcggatcg ggtaggggag gcgcttttcc caaggcagtc    4980
```

-continued

```
tggagcatgc gctttagcag ccccgctggg cacttggcgc tacacaagtg gcctctggcc       5040
tcgcacacat tccacatcca ccggtaggcg ccaaccggct ccgttctttg gtggcccctt       5100
cgcgccacct tctactcctc ccctagtcag gaagttcccc cccgccccgc agctcgcgtc       5160
gtgcaggacg tgacaaatgg aagtagcacg tctcactagt ctcgtgcaga tggacagcac       5220
cgctgagcaa tggaagcggg taggcctttg gggcagcggc caatagcagc tttgctcctt       5280
cgctttctgg gctcagaggc tgggaagggg tgggtccggg ggcgggctca ggggcgggct       5340
caggggcggg gcgggcgccc gaaggtcctc cggaggcccg gcattctgca cgcttcaaaa       5400
gcgcacgtct gccgcgctgt tctcctcttc ctcatctccg ggcctttcga aactacccca       5460
agctggccac catgactacg tccggcgttc catttggcat gacactacga ccaacacgat       5520
ctcggttgtc tcggcgcact ccgtacagta gggatcgtct acctcctttt gagacagaaa       5580
cccgcgctac catactggag gatcatccgc tgctgcccga atgtaacact ttgacaatgc       5640
acaacgtgag ttacgtgcga ggtcttccct gcagtgtggg atttacgctg attcaggaat       5700
gggttgttcc ctgggatatg gttctaacgc gggaggagct tgtaatcctg aggaagtgta       5760
tgcacgtgtg cctgtgttgt gccaacattg atatcatgac gagcatgatg atccatggtt       5820
acgagtcctg ggctctccac tgtcattgtt ccagtcccgg ttccctgcag tgtatagccg       5880
gcgggcaggt tttggccagc tggtttagga tggtggtgga tggcgccatg tttaatcaga       5940
ggtttatatg gtaccgggag gtggtgaatt acaacatgcc aaaagaggta atgtttatgt       6000
ccagcgtgtt tatgaggggt cgccacttaa tctacctgcg cttgtggtat gatggccacg       6060
tgggttctgt ggtccccgcc atgagctttg gatacagcgc cttgcactgt gggattttga       6120
acaatattgt ggtgctgtgc tgcagttact gtgctgattt aagtgagatc agggtgcgct       6180
gctgtgcccg gaggacaagg cgccttatgc tgcgggcggt gcgaatcatc gctgaggaga       6240
ccactgccat gttgtattcc tgcaggacgg agcggcggcg gcagcagttt attcgcgcgc       6300
tgctgcagca ccaccgccct atcctgatgc acgattatga ctctacccccc atgtagaagc       6360 ttggggatca attctctaga gctcgctgat cagcctcgac tgtgccttct agttgccagc       6420
catctgttgt ttgcccctcc cccgtgcctt ccttgacccT ggaaggtgcc actcccactg       6480
tcctttccta ataaaatgag gaaattgcat cgcattgtct gagtaggtgt cattctattc       6540
tggggggtgg ggtggggcag gacagcaagg gggaggattg ggaagacaat agcaggcatg       6600
ctggggatgc ggtgggctct atggcttctg aggaaattgg gcgtggctta agggtgggaa       6660
agaatatata aggtggggggt cttatgtagt tttgtatctg ttttgcagca gccgccgccg       6720
ccatgagcac caactcgttt gatggaagca ttgtgagctc atatttgaca acgcgcatgc       6780
ccccatgggc cggggtgcgt cagaatgtga tgggctccag cattgatggt cgccccgtcc       6840
tgcccgcaaa ctctactacc ttgacctacg agaccgtgtc tggaacgccg ttggagactg       6900
cagcctccgc cgccgcttca gccgctgcag ccaccgcccg cggattgtg actgactttg       6960 ctttcctgag cccgcttgca agcagtgcag cttcccgttc atccgcccgc gatgacaagt       7020
tgacggctct tttggcacaa ttggattctt tgacccggga acttaatgtc gtttctcagc       7080
agctgttgga tctgcgccag caggtttctg ccctgaaggc ttcctcccct cccaatgcgg       7140
tttaaaacat aaataaaaaa ccagactctg tttggatttg gatcaagcaa gtgtcttgct       7200
gtctttattt aggggttttg cgcgcgcggt aggcccggga ccagcggtct cggtcgttga       7260
gggtcctgtg tattttttcc aggacgtggt aaaggtgact ctggatgttc agatacatgg       7320
```

-continued

```
gcataagccc gtctctgggg tggaggtagc accactgcag agcttcatgc tgcggggtgg      7380
tgttgtagat gatccagtcg tagcaggagc gctgggcgtg gtgcctaaaa atgtctttca      7440
gtagcaagct gattgccagg ggcaggccct tggtgtaagt gtttacaaag cggttaagct      7500
gggatgggtg catacgtggg gatatgagat gcatcttgga ctgtattttt aggttggcta      7560
tgttcccagc catatccctc cggggattca tgttgtgcag aaccaccagc acagtgtatc      7620
cggtgcactt gggaaatttg tcatgtagct tagaaggaaa tgcgtggaag aacttggaga      7680
cgcccttgtg acctccaaga ttttccatgc attcgtccat aatgatggca atgggcccac      7740
gggcggcggc ctgggcgaag atatttctgg gatcactaac gtcatagttg tgttccagga      7800
tgagatcgtc ataggccatt tttacaaagc gcgggcggag ggtgccagac tgcggtataa      7860
tggttccatc cggcccaggg gcgtagttac cctcacagat ttgcatttcc cacgctttga      7920
gttcagatgg ggggatcatg tctacctgcg gggcgatgaa gaaaacggtt tccggggtag      7980
gggagatcag ctgggaagaa agcaggttcc tgagcagctg cgacttaccg cagccggtgg      8040
gcccgtaaat cacacctatt accgggtgca actggtagtt aagagagctg cagctgccgt      8100
catccctgag caggggggcc acttcgttaa gcatgtccct gactcgcatg ttttccctga      8160
ccaaatccgc cagaaggcgc tcgccgccca gcgatagcag ttcttgcaag gaagcaaagt      8220
ttttcaacgg tttgagaccg tccgccgtag gcatgctttt gagcgtttga ccaagcagtt      8280
ccaggcggtc ccacagctcg gtcacctgct ctacggcatc tcgatccagc atatctcctc      8340
gtttcgcggg ttgggcggc tttcgctgta cggcagtagt cggtgctcgt ccagacgggc      8400
cagggtcatg tctttccacg ggcgcagggt cctcgtcagc gtagtctggg tcacggtgaa      8460
ggggtgcgct ccgggctgcg cgctggccag ggtgcgcttg aggctggtcc tgctggtgct      8520
gaagcgctgc cggtcttcgc cctgcgcgtc ggccaggtag catttgacca tggtgtcata      8580
gtccagcccc tccgcggcgt ggcccttggc gcgcagcttg cccttggagg aggcgccgca      8640
cgaggggcag tgcagacttt tgagggcgta gagcttgggc gcgagaaata ccgattccgg      8700
ggagtaggca tccgcgccgc aggccccgca gacggtctcg cattccacga gccaggtgag      8760
ctctggccgt tcggggtcaa aaaccaggtt tcccccatgc tttttgatgc gtttcttacc      8820
tctggtttcc atgagccggt gtccacgctc ggtgacgaaa aggctgtccg tgtccccgta      8880
tacagacttg agaggcctgt cctcgagcgg tgttccgcgg tcctcctcgt atagaaactc      8940
ggaccactct gagacaaagg ctcgcgtcca ggccagcacg aaggaggcta agtgggaggg      9000
gtagcggtcg ttgtccacta gggggtccac tcgctccagg gtgtgaagac acatgtcgcc      9060
ctcttcggca tcaaggaagg tgattggttt gtaggtgtag gccacgtgac cgggtgttcc      9120
tgaagggggg ctataaaagg gggtggggc gcgttcgtcc tcactctctt ccgcatcgct      9180
gtctgcgagg gccagctgtt ggggtgagta ctccctctga aaagcgggca tgacttctgc      9240
gctaagattg tcagtttcca aaaacgagga ggatttgata ttcacctggc ccgcggtgat      9300
gcctttgagg gtggccgcat ccatctggtc agaaaagaca atcttttttgt tgtcaagctt      9360 ggtggcaaac gacccgtaga gggcgttgga cagcaacttg gcgatggagc gcagggtttg      9420
gtttttgtcg cgatcggcgc gctccttggc cgcgatgttt agctgcacgt attcgcgcgc      9480
aacgcaccgc cattcgggaa agacggtggt gcgctcgtcg gcaccaggt gcacgcgcca      9540 accgcggttg tgcagggtga caaggtcaac gctggtggct acctctccgc gtaggcgctc      9600
gttggtccag cagaggcggc cgcccttgcg cgagcagaat ggcggtaggg ggtctagctg      9660
cgtctcgtcc gggggggtctg cgtccacggt aaagaccccg ggcagcaggc gcgcgtcgaa      9720
```

-continued

```
gtagtctatc ttgcatcctt gcaagtctag cgcctgctgc catgcgcggg cggcaagcgc   9780
gcgctcgtat gggttgagtg ggggacccca tggcatgggg tgggtgagcg cggaggcgta   9840
catgccgcaa atgtcgtaaa cgtagagggg ctctctgagt attccaagat atgtagggta   9900
gcatcttcca ccgcgcgatgc tggcgcgcac gtaatcgtat agttcgtgcg agggagcgag   9960
gaggtcggga ccgaggttgc tacgggcggg ctgctctgct cggaagacta tctgcctgaa  10020
gatggcatgt gagttggatg atatggttgg acgctggaag acgttgaagc tggcgtctgt  10080
gagacctacc gcgtcacgca cgaaggaggc gtaggagtcg cgcagcttgt tgaccagctc  10140
ggcggtgacc tgcacgtcta gggcgcagta gtccagggtt tccttgatga tgtcatactt  10200
atcctgtccc tttttttttcc acagctcgcg gttgaggaca aactcttcgc ggtctttcca  10260
gtactcttgg atcggaaacc cgtcggcctc cgaacggtaa gagcctagca tgtagaactg  10320
gttgacggcc tggtaggcgc agcatccctt ttctacgggt agcgcgtatg cctgcgcggc  10380
cttccggagc gaggtgtggg tgagcgcaaa ggtgtccctg accatgactt tgaggtactg  10440
gtatttgaag tcagtgtcgt cgcatccgcc ctgctcccag agcaaaaagt ccgtgcgctt  10500
tttggaacgc ggatttggca gggcgaaggt gacatcgttg aagagtatct ttcccgcgcg  10560
aggcataaag ttgcgtgtga tgcggaaggg tcccggcacc tcggaacggt tgttaattac  10620
ctgggcggcg agcacgatct cgtcaaagcc gttgatgttg tggcccacaa tgtaaagttc  10680
caagaagcgc gggatgccct tgatggaagg caatttttta agttcctcgt aggtgagctc  10740
ttcaggggag ctgagcccgt gctctgaaag ggcccagtct gcaagatgag ggttggaagc  10800
gacgaatgag ctccacaggt cacgggccat tagcatttgc aggtggtcgc gaaaggtcct  10860
aaactggcga cctatggcca ttttttctgg ggtgatgcag tagaaggtaa gcgggtcttg  10920
ttcccagcgg tcccatccaa ggttcgcggc taggtctcgc gcggcagtca ctagaggctc  10980
atctccgccg aacttcatga ccagcatgaa gggcacgagc tgcttcccaa aggcccccat  11040
ccaagtatag gtctctacat cgtaggtgac aaagagacgc tcggtgcgag gatgcgagcc  11100
gatcgggaag aactggatct cccgccacca attggaggag tggctattga tgtggtgaaa  11160
gtagaagtcc ctgcgacggg ccgaacactc gtgctggctt ttgtaaaaac gtgcgcagta  11220
ctggcagcgg tgcacgggct gtacatcctg cacgaggttg acctgacgac cgcgcacaag  11280
gaagcagagt gggaatttga gccctcgcc tggcgggttt ggctggtggt cttctacttc  11340
ggctgcttgt ccttgaccgt ctggctgctc gaggggagtt acggtggatc ggaccaccac  11400
gccgcgcgag cccaaagtcc agatgtccgc gcgcggcggt cggagcttga tgacaacatc  11460
gcgcagatgg gagctgtcca tggtctggag ctcccgcggc gtcaggtcag gcgggagctc  11520
ctgcaggttt acctcgcata gacgggtcag ggcgcgggct agatccaggt gatacctaat  11580
ttccaggggc tggttggtgg cggcgtcgat ggcttgcaag aggccgcatc cccgcggcgc  11640
gactacggta ccgcgcggcg ggcggtgggc gcgggggtg tccttggatg atgcatctaa  11700
aagcggtgac gcgggcgagc ccccggaggt aggggggget ccggacccgc cgggagaggg  11760
ggcaggggca cgtcggcgcc gcgcgcgggc aggagctggt gctgcgcgcg taggttgctg  11820
gcgaacgcga cgacgcggcg gttgatctcc tgaatctggc gcctctgcgt gaagacgacg  11880
ggcccggtga gcttgaacct gaaagagagt tcgacagaat caatttcggt gtcgttgacg  11940
gcggcctggc gcaaaatctc ctgcacgtct cctgagttgt cttgataggc gatctcggcc  12000
atgaactgct cgatctcttc ctcctggaga tctccgcgtc cggctcgctc cacggtggcg  12060
```

```
gcgaggtcgt tggaaatgcg ggccatgagc tgcgagaagg cgttgaggcc tccctcgttc   12120
cagacgcggc tgtagaccac gcccccttcg gcatcgcggg cgcgcatgac cacctgcgcg   12180
agattgagct ccacgtgccg ggcgaagacg gcgtagtttc gcaggcgctg aaagaggtag   12240
ttgagggtgg tggcggtgtg ttctgccacg aagaagtaca taacccagcg tcgcaacgtg   12300
gattcgttga tatcccccaa ggcctcaagg cgctccatgg cctcgtagaa gtccacggcg   12360
aagttgaaaa actgggagtt gcgcgccgac acggttaact cctcctccag aagacggatg   12420
agctcggcga cagtgtcgcg cacctcgcgc tcaaaggcta caggggcctc ttcttcttct   12480
tcaatctcct cttccataag ggcctcccct tcttcttctt ctggcggcgg tgggggaggg   12540
gggacacggc ggcgacgacg gcgcaccggg aggcggtcga caaagcgctc gatcatctcc   12600
ccgcggcgac ggcgcatggt ctcggtgacg gcgcggccgt tctcgcgggg gcgcagttgg   12660
aagacgccgc ccgtcatgtc ccggttatgg gttggcgggg ggctgccatg cggcagggat   12720
acggcgctaa cgatgcatct caacaattgt tgtgtaggta ctccgccgcc gagggacctg   12780
agcgagtccg catcgaccgg atcggaaaac ctctcgagaa aggcgtctaa ccagtcacag   12840
tcgcaaggta ggctgagcac cgtggcgggc ggcagcgggc ggcggtcggg gttgtttctg   12900
gcggaggtgc tgctgatgat gtaattaaag taggcggtct tgagacggcg gatggtcgac   12960
agaagcacca tgtccttggg tccggcctgc tgaatgcgca ggcggtcggc catgccccag   13020
gcttcgtttt gacatcggcg caggtctttg tagtagtctt gcatgagcct ttctaccggc   13080
acttcttctt ctccttcctc ttgtcctgca tctcttgcat ctatcgctgc ggcggcggcg   13140
gagtttggcc gtaggtggcg ccctcttcct cccatgcgtg tgaccccgaa gcccctcatc   13200
ggctgaagca gggctaggtc ggcgacaacg cgctcggcta atatggcctg ctgcacctgc   13260
gtgagggtag actggaagtc atccatgtcc acaaagcggt ggtatgcgcc cgtgttgatg   13320
gtgtaagtgc agttggccat aacggaccag ttaacggtct ggtgacccgg ctgcgagagc   13380
tcggtgtacc tgagacgcga gtaagccctc gagtcaaata cgtagtcgtt gcaagtccgc   13440
accaggtact ggtatcccac caaaaagtgc ggcggcggct ggcggtagag gggccagcgt   13500
agggtggccg gggctccggg ggcgagatct tccaacataa ggcgatgata tccgtagatg   13560
tacctggaca tccaggtgat gccggcggcg gtggtggagg cgcgcggaaa gtcgcggacg   13620
cggttccaga tgttgcgcag cggcaaaaag tgctccatgg tcgggacgct ctggccggtc   13680
aggcgcgcgc aatcgttgac gctctagcgt gcaaaaggag agcctgtaag cgggcactct   13740
tccgtggtct ggtggataaa ttcgcaaggg tatcatggcg gacgaccggg gttcgagccc   13800
cgtatccggc cgtccgccgt gatccatgcg gttaccgccc gcgtgtcgaa cccaggtgtg   13860
cgacgtcaga caacgggga gtgctccttt tggcttcctt ccaggcgcgg cggctgctgc   13920
gctagctttt ttggccactg gccgcgcgca gcgtaagcgg ttaggctgga aagcgaaagc   13980
attaagtggc tcgctccctg tagccggagg gttattttcc aagggttgag tcgcgggacc   14040
cccggttcga gtctcggacc ggccggactg cggcgaacgg gggtttgcct ccccgtcatg   14100
caagaccccg cttgcaaatt cctccggaaa cagggacgag cccctttttt gctttttccca  14160 gatgcatccg gtgctgcggc agatgcgccc ccctcctcag cagcggcaag agcaagagca   14220
gcggcagaca tgcagggcac cctcccctcc tcctaccgcg tcaggagggg cgacatccgc   14280
ggttgacgcg gcagcagatg gtgattacga accccgcgg cgccgggccc ggcactacct   14340
ggacttggag gagggcgagg gcctggcgcg gctaggagcg ccctctcctg agcggcaccc   14400
aagggtgcag ctgaagcgtg atacgcgtga ggcgtacgtg ccgcggcaga acctgtttcg   14460
```

-continued

```
cgaccgcgag ggagaggagc ccgaggagat gcgggatcga aagttccacg caggggcgcga   14520 gctgcggcat ggcctgaatc gcgagcggtt gctgcgcgag gaggactttg agcccgacgc   14580
gcgaaccggg attagtcccg cgcgcgcaca cgtggcggcc gccgacctgg taaccgcata   14640
cgagcagacg gtgaaccagg agattaactt tcaaaaaagc tttaacaacc acgtgcgtac   14700
gcttgtggcg cgcgaggagg tggctatagg actgatgcat ctgtgggact ttgtaagcgc   14760
gctggagcaa aacccaaata gcaagccgct catggcgcag ctgttcctta tagtgcagca   14820
cagcagggac aacgaggcat tcagggatgc gctgctaaac atagtagagc ccgagggccg   14880
ctggctgctc gatttgataa acatcctgca gagcatagtg gtgcaggagc gcagcttgag   14940
cctggctgac aaggtggccg ccatcaacta ttccatgctt agcctgggca agttttacgc   15000
ccgcaagata taccataccc cttacgttcc catagacaag gaggtaaaga tcgagggggtt   15060 ctacatgcgc atggcgctga aggtgcttac cttgagcgac gacctgggcg tttatcgcaa   15120
cgagcgcatc cacaaggccg tgagcgtgag ccggcggcgc gagctcagcg accgcgagct   15180
gatgcacagc ctgcaaaggg ccctggctgg cacgggcagc ggcgatagag aggccgagtc   15240
ctactttgac gcgggcgctg acctgcgctg ggccccaagc cgacgcgccc tggaggcagc   15300
tggggccgga cctgggctgg cggtggcacc cgcgcgcgct ggcaacgtcg cgggcgtgga   15360
ggaatatgac gaggacgatg agtacgagcc agaggacggc gagtactaag cggtgatgtt   15420
tctgatcaga tgatgcaaga cgcaacggac ccggcggtgc gggcggcgct gcagagccag   15480
ccgtccggcc ttaactccac ggacgactgg cgccaggtca tggaccgcat catgtcgctg   15540
actgcgcgca atcctgacgc gttccggcag cagccgcagg ccaaccggct ctccgcaatt   15600
ctggaagcgg tggtcccggc gcgcgcaaac cccacgcacg agaaggtgct ggcgatcgta   15660
aacgcgctgg ccgaaaacag ggccatccgg cccgacgagg ccggcctggt ctacgacgcg   15720
ctgcttcagc gcgtggctcg ttacaacagc ggcaacgtgc agaccaacct ggaccggctg   15780
gtgggggatg tgcgcgaggc cgtggcgcag cgtgagcgcg cgcagcagca gggcaacctg   15840
ggctccatgg ttgcactaaa cgccttcctg agtacacagc ccgccaacgt gccgcgggga   15900
caggaggact acaccaactt tgtgagcgca ctgcggctaa tggtgactga cacaccgcaa   15960
agtgaggtgt accagtctgg gccagactat tttttccaga ccagtagaca aggcctgcag   16020
accgtaaacc tgagccaggc tttcaaaaac ttgcaggggc tgtggggggt gcgggctccc   16080
acaggcgacc gcgcgaccgt gtctagcttg ctgacgccca actcgcgcct gttgctgctg   16140
ctaatagcgc ccttcacgga cagtggcagc gtgtcccggg acacatacct aggtcacttg   16200
ctgacactgt accgcgaggc cataggtcag gcgcatgtgg acgagcatac tttccaggag   16260
attacaagtg tcagccgcgc gctggggcag gaggacacgg gcagcctgga ggcaaccccta   16320 aactacctgc tgaccaaccg gcggcagaag atcccctcgt tgcacagttt aaacagcgag   16380
gaggagcgca ttttgcgcta cgtgcagcag agcgtgagcc ttaacctgat gcgcgacggg   16440
gtaacgccca gcgtggcgct ggacatgacc gcgcgcaaca tggaaccggg catgtatgcc   16500
tcaaaccggc cgtttatcaa ccgcctaatg gactacttgc atcgcgcggc cgccgtgaac   16560
cccgagtatt tcaccaatgc catcttgaac ccgcactggc taccgccccc tggtttctac   16620
accgggggat tcgaggtgcc cgagggtaac gatggattcc tctgggacga catagacgac   16680
agcgtgtttt ccccgcaacc gcagaccctg ctagagttgc aacagcgcga gcaggcagag   16740
gcggcgctgc gaaaggaaag cttccgcagg ccaagcagct tgtccgatct aggcgctgcg   16800
```

-continued

```
gccccgcggt cagatgctag tagcccattt ccaagcttga tagggtctct taccagcact   16860
cgcaccaccc gcccgcgcct gctgggcgag gaggagtacc taaacaactc gctgctgcag   16920
ccgcagcgcg aaaaaaacct gcctccggca tttcccaaca acgggataga gagcctagtg   16980
gacaagatga gtagatggaa gacgtacgcg caggagcaca gggacgtgcc aggcccgcgc   17040
ccgcccaccc gtcgtcaaag gcacgaccgt cagcggggtc tggtgtggga ggacgatgac   17100
tcggcagacg acagcagcgt cctggatttg ggagggagtg gcaacccgtt tgcgcacctt   17160
cgccccaggc tggggagaat gttttaaaaa aaaaaaagca tgatgcaaaa taaaaaactc   17220
accaaggcca tggcaccgag cgttggtttt cttgtattcc ccttagtatg cggcgcgcgg   17280
cgatgtatga ggaaggtcct cctccctcct acgagagtgt ggtgagcgcg cgcccagtgg   17340
cggcggcgct gggttctccc ttcgatgctc ccctggaccc gccgtttgtg cctccgcggt   17400
acctgcggcc taccggggggg agaaacagca tccgttactc tgagttggca cccctattcg   17460
acaccacccg tgtgtacctg gtggacaaca agtcaacgga tgtggcatcc ctgaactacc   17520
agaacgacca cagcaacttt ctgaccacgg tcattcaaaa caatgactac agcccggggg   17580
aggcaagcac acagaccatc aatcttgacg accggtcgca ctgggcgggc gacctgaaaa   17640
ccatcctgca taccaacatg ccaaatgtga acgagttcat gtttaccaat aagtttaagg   17700
cgcgggtgat ggtgtcgcgc ttgcctacta aggacaatca ggtggagctg aaatacgagt   17760
gggtggagtt cacgctgccc gagggcaact actccgagac catgaccata gaccttatga   17820
acaacgcgat cgtggagcac tacttgaaag tgggcagaca gaacgggggt ctggaaagcg   17880
acatcggggt aaagtttgac acccgcaact tcagactggg gtttgacccc gtcactggtc   17940
ttgtcatgcc tggggtatat acaaacgaag ccttccatcc agacatcatt ttgctgccag   18000
gatgcggggt ggacttcacc cacagccgcc tgagcaactt gttgggcatc cgcaagcggc   18060
aacccttcca ggagggcttt aggatcacct acgatgatct ggagggtggt aacattcccg   18120
cactgttgga tgtggacgcc taccaggcga gcttgaaaga tgacaccgaa cagggcgggg   18180
gtggcgcagg cggcagcaac agcagtggca gcggcgcgga agagaactcc aacgcggcag   18240
ccgcggcaat gcagccggtg gaggacatga acgatcatgc cattcgcggc gacacctttg   18300
ccacacgggc tgaggagaag cgcgctgagg ccgaagcagc ggccgaagct gccgcccccg   18360
ctgcgcaacc cgaggtcgag aagcctcaga gaaaccggt gatcaaaccc ctgacagagg   18420
acagcaagaa acgcagttac aacctaataa gcaatgacag caccttcacc cagtaccgca   18480
gctggtacct tgcatacaac tacggcgacc ctcagaccgg aatccgctca tggaccctgc   18540
tttgcactcc tgacgtaacc tgcggctcgg agcaggtcta ctggtcgttg ccagacatga   18600
tgcaagaccc cgtgaccttc cgctccacgc gccagatcag caactttccg gtggtgggcg   18660
ccgagctgtt gcccgtgcac tccaagagct tctacaacga ccaggccgtc tactcccaac   18720
tcatccgcca gttacctct ctgacccacg tgttcaatcg cttttcccgag aaccagattt   18780 tggcgcgccc gccagccccc accatcacca ccgtcagtga aaacgttcct gctctcacag   18840
atcacgggac gctaccgctg cgcaacagca tcggaggagt ccagcgagtg accattactg   18900
acgccagacg ccgcacctgc cctacgtttt acaaggccct gggcatagtc tcgccgcgcg   18960
tcctatcgag ccgcactttt tgagcaagca tgtccatcct tatatcgccc agcaataaca   19020
caggctgggg cctgcgcttc ccaagcaaga tgtttggcgg ggccaagaag cgctccgacc   19080
aacacccagt gcgcgtgcgc gggcactacc gcgcgccctg gggcgcgcac aaacgcggcc   19140
gcactgggcg caccaccgtc gatgacgcca tcgacgcggt ggtggaggag gcgcgcaact   19200
```

-continued

```
acacgcccac gccgccacca gtgtccacag tggacgcggc cattcagacc gtggtgcgcg   19260
gagcccggcg ctatgctaaa atgaagagac ggcggaggcg cgtagcacgt cgccaccgcc   19320
gccgacccgg cactgccgcc caacgcgcgg cggcggccct gcttaaccgc gcacgtcgca   19380
ccggccgacg ggcggccatg cgggccgctc gaaggctggc cgcgggtatt gtcactgtgc   19440
cccccaggtc caggcgacga gcggccgccg cagcagccgc ggccattagt gctatgactc   19500
agggtcgcag gggcaacgtg tattgggtgc gcgactcggt tagcggcctg cgcgtgcccg   19560
tgcgcacccg ccccccgcgc aactagattg caagaaaaaa ctacttagac tcgtactgtt   19620
gtatgtatcc agcggcggcg gcgcgcaacg aagctatgtc caagcgcaaa atcaaagaag   19680
agatgctcca ggtcatcgcg ccggagatct atggcccccc gaagaaggaa gagcaggatt   19740
acaagccccg aaagctaaag cgggtcaaaa agaaaaagaa agatgatgat gatgaacttg   19800
acgacgaggt ggaactgctg cacgctaccg cgcccaggcg acgggtacag tggaaaggtc   19860
gacgcgtaaa acgtgttttg cgacccggca ccaccgtagt ctttacgccc ggtgagcgct   19920
ccacccgcac ctacaagcgc gtgtatgatg aggtgtacgg cgacgaggac ctgcttgagc   19980
aggccaacga gcgcctcggg gagtttgcct acggaaagcg gcataaggac atgctggcgt   20040
tgccgctgga cgagggcaac ccaacaccta gcctaaagcc cgtaacactg cagcaggtgc   20100
tgcccgcgct tgcaccgtcc gaagaaaagc gcggcctaaa gcgcgagtct ggtgacttgg   20160
cacccaccgt gcagctgatg gtacccaagc gccagcgact ggaagatgtc ttggaaaaaa   20220
tgaccgtgga acctgggctg gagcccgagg tccgcgtgcg gccaatcaag caggtggcgc   20280
cgggactggg cgtgcagacc gtggacgttc agatacccac taccagtagc accagtattg   20340
ccaccgccac agagggcatg gagacacaaa cgtccccggt tgcctcagcg gtggcggatg   20400
ccgcggtgca ggcggtcgct gcggccgcgt ccaagacctc tacggaggtg caaacggacc   20460
cgtggatgtt tcgcgtttca gccccccggc gcccgcgccg ttcgaggaag tacggcgccg   20520
ccagcgcgct actgcccgaa tatgccctac atccttccat tgcgcctacc cccggctatc   20580
gtggctacac ctaccgcccc agaagacgag caactacccg acgccgaacc accactggaa   20640
cccgccgccg ccgtcgccgt cgccagcccg tgctggcccc gatttccgtg cgcagggtgg   20700
ctcgcgaagg aggcaggacc ctggtgctgc caacagcgcg ctaccacccc agcatcgttt   20760
aaaagccggt ctttgtggtt cttgcagata tggccctcac ctgccgcctc cgtttcccgg   20820
tgccgggatt ccgaggaaga atgcaccgta ggaggggcat ggccggccac ggcctgacgg   20880
gcggcatgcg tcgtgcgcac caccggcggc ggcgcgcgtc gcaccgtcgc atgcgcggcg   20940
gtatcctgcc cctccttatt ccactgatcg ccgcggcgat tggcgccgtg cccggaattg   21000
catccgtggc cttgcaggcg cagagacact gattaaaaac aagttgcatg tggaaaaatc   21060
aaaataaaaa gtctggactc tcacgctcgc ttggtcctgt aactattttg tagaatggaa   21120
gacatcaact ttgcgtctct ggccccgcga cacggctcgc gcccgttcat gggaaactgg   21180
caagatatcg gcaccagcaa tatgagcggt ggcgccttca gctggggctc gctgtggagc   21240
ggcattaaaa atttcggttc caccgttaag aactatggca gcaaggcctg aacagcagc   21300 acaggccaga tgctgaggga taagttgaaa gagcaaaatt tccaacaaaa ggtggtagat   21360
ggcctggcct ctggcattag cggggtggtg gacctggcca accaggcagt gcaaaataag   21420
attaacagta agcttgatcc ccgccctccc gtagaggagc ctccaccggc cgtggagaca   21480
gtgtctccag aggggcgtgg cgaaaagcgt ccgcgccccg acagggaaga aactctggtg   21540
```

-continued

```
acgcaaatag acgagcctcc ctcgtacgag gaggcactaa agcaaggcct gcccaccacc   21600
cgtcccatcg cgcccatggc taccggagtg ctgggccagc acacaccgt aacgctggac   21660 ctgcctcccc ccgccgacac ccagcagaaa cctgtgctgc caggcccgac cgccgttgtt   21720
gtaacccgtc ctagccgcgc gtccctgcgc cgcgccgcca gcggtccgcg atcgttgcgg   21780
cccgtagcca gtggcaactg gcaaagcaca ctgaacagca tcgtgggtct gggggtgcaa   21840
tccctgaagc gccgacgatg cttctgatag ctaacgtgtc gtatgtgtgt catgtatgcg   21900
tccatgtcgc cgccagagga gctgctgagc cgccgcgcgc ccgctttcca agatggctac   21960
cccttcgatg atgccgcagt ggtcttacat gcacatctcg ggccaggacg cctcggagta   22020
cctgagcccc gggctggtgc agtttgcccg cgccaccgag acgtacttca gcctgaataa   22080
caagtttaga aaccccacgg tggcgcctac gcacgacgtg accacagacc ggtcccagcg   22140
tttgacgctg cggttcatcc ctgtggaccg tgaggatact gcgtactcgt acaaggcgcg   22200
gttcacccta gctgtgggtg ataaccgtgt gctggacatg gcttccacgt actttgacat   22260
ccgcggcgtg ctggacaggg gccctacttt taagccctac tctggcactg cctacaacgc   22320
cctggctccc aagggtgccc caaatccttg cgaatgggat gaagctgcta ctgctcttga   22380
aataaaccta gaagaagagg acgatgacaa cgaagacgaa gtagacgagc aagctgagca   22440
gcaaaaaact cacgtatttg ggcaggcgcc ttattctggt ataaatatta caaggaggg   22500 tattcaaata ggtgtcgaag gtcaaacacc taaatatgcc gataaaacat ttcaacctga   22560
acctcaaata ggagaatctc agtggtacga aacagaaatt aatcatgcag ctgggagagt   22620
cctaaaaaag actaccccaa tgaaaccatg ttacggttca tatgcaaaac ccacaaatga   22680
aaatggaggg caaggcattc ttgtaaagca acaaaatgga aagctagaaa gtcaagtgga   22740
aatgcaattt ttctcaacta ctgaggcagc cgcaggcaat ggtgataact tgactcctaa   22800
agtggtattg tacagtgaag atgtagatat agaaacccca gacactcata tttcttacat   22860
gcccactatt aaggaaggta actcacgaga actaatgggc caacaatcta tgcccaacag   22920
gcctaattac attgctttta gggacaattt tattggtcta atgtattaca acagcacggg   22980
taatatgggt gttctggcgg gccaagcatc gcagttgaat gctgttgtag atttgcaaga   23040
cagaaacaca gagctttcat accagctttt gcttgattcc attggtgata gaaccaggta   23100
cttttctatg tggaatcagg ctgttgacag ctatgatcca gatgttagaa ttattgaaaa   23160
tcatggaact gaagatgaac ttccaaatta ctgctttcca ctgggaggtg tgattaatac   23220
agagactctt accaaggtaa aacctaaaac aggtcaggaa aatggatggg aaaaagatgc   23280
tacagaattt tcagataaaa atgaaataag agttggaaat aattttgcca tggaaatcaa   23340
tctaaatgcc aacctgtgga gaaatttcct gtactccaac atagcgctgt atttgcccga   23400
caagctaaag tacagtcctt ccaacgtaaa aatttctgat aacccaaaca cctacgacta   23460
catgaacaag cgagtggtgg ctcccgggct agtggactgc tacattaacc ttggagcacg   23520
ctggtcccct gactatatgg acaacgtcaa cccatttaac caccaccgca atgctggcct   23580
gcgctaccgc tcaatgttgc tgggcaatgg tcgctatgtg cccttccaca tccaggtgcc   23640
tcagaagttc tttgccatta aaaacctcct tctcctgccg ggctcataca cctacgagtg   23700
gaacttcagg aaggatgtta acatggttct gcagagctcc ctaggaaatg acctaagggt   23760
tgacggagcc agcattaagt ttgatagcat ttgcctttac gccaccttct tccccatggc   23820
ccacaacacc gcctccacgc ttgaggccat gcttagaaac gacaccaacg accagtcctt   23880
taacgactat ctctccgccg ccaacatgct ctaccctata cccgccaacg ctaccaacgt   23940
```

-continued

```
gcccatatcc atcccctccc gcaactgggc ggctttccgc ggctgggcct tcacgcgcct   24000
taagactaag gaaaccccat cactgggctc gggctacgac ccttattaca cctactctgg   24060
ctctataccc tacctagatg gaaccttta cctcaaccac acctttaaga aggtggccat   24120
tacctttgac tcttctgtca gctggcctgg caatgaccgc ctgcttaccc ccaacgagtt   24180
tgaaattaag cgctcagttg acggggaggg ttacaacgtt gcccagtgta acatgaccaa   24240
agactggttc ctggtacaaa tgctagctaa ctataacatt ggctaccagg gcttctatat   24300
cccagagagc tacaaggacc gcatgtactc cttctttaga aacttccagc ccatgagccg   24360
tcaggtggtg gatgatacta aatacaagga ctaccaacag gtgggcatcc tacaccaaca   24420
caacaactct ggatttgttg gctaccttgc ccccaccatg cgcgaaggac aggcctaccc   24480
tgctaacttc ccctatccgc ttataggcaa gaccgcagtt gacagcatta cccagaaaaa   24540
gtttctttgc gatcgcaccc tttggcgcat cccattctcc agtaacttta tgtccatggg   24600
cgcactcaca gacctgggcc aaaaccttct ctacgccaac tccgcccacg cgctagacat   24660
gacttttgag gtggatccca tggacgagcc caccccttctt tatgtttgt ttgaagtctt   24720 tgacgtggtc cgtgtgcacc agccgcaccg cggcgtcatc gaaaccgtgt acctgcgcac   24780
gcccttctcg gccggcaacg ccacaacata aagaagcaag caacatcaac aacagctgcc   24840
gccatgggct ccagtgagca ggaactgaaa gccattgtca aagatcttgg ttgtgggcca   24900
tattttttgg gcacctatga caagcgcttt ccaggctttg tttctccaca caagctcgcc   24960
tgcgccatag tcaatacggc cggtcgcgag actgggggcg tacactggat ggcctttgcc   25020
tggaacccgc actcaaaaac atgctacctc tttgagccct ttggctttc tgaccagcga   25080 ctcaagcagg tttaccagtt tgagtacgag tcactcctgc gccgtagcgc cattgcttct   25140
tcccccgacc gctgtataac gctggaaaag tccacccaaa gcgtacaggg gcccaactcg   25200
gccgcctgtg gactattctg ctgcatgttt ctccacgcct ttgccaactg gccccaaact   25260
cccatggatc acaaccccac catgaacctt attaccgggg tacccaactc catgctcaac   25320
agtccccagg tacagcccac cctgcgtcgc aaccaggaac agctctacag cttcctggag   25380
cgccactcgc cctacttccg cagccacagt gcgcagatta ggagcgccac ttctttttgt   25440
cacttgaaaa acatgtaaaa ataatgtact agagacactt tcaataaagg caaatgcttt   25500
tatttgtaca ctctcgggtg attatttacc cccacccttg ccgtctgcgc cgtttaaaaa   25560 tcaaagggt tctgccgcgc atcgctatgc gccactggca gggacacgtt gcgatactgg   25620
tgtttagtgc tccacttaaa ctcaggcaca accatccgcg gcagctcggt gaagttttca   25680
ctccacaggc tgcgcaccat caccaacgcg tttagcaggt cgggcgccga tatcttgaag   25740
tcgcagttgg ggcctccgcc ctgcgcgcgc gagttgcgat acacagggtt gcagcactgg   25800
aacactatca gcgccgggtg gtgcacgctg gccagcacgc tcttgtcgga gatcagatcc   25860
gcgtccaggt cctccgcgtt gctcaggbcg aacggagtca actttggtag ctgccttccc   25920
aaaaagggcg cgtgcccagg ctttgagttg cactcgcacc gtagtggcat caaaaggtga   25980
ccgtgcccgg tctgggcgtt aggatacagc gcctgcataa aagccttgat ctgcttaaaa   26040
gccacctgag cctttgcgcc ttcagagaag aacatgccgc aagacttgcc ggaaaactga   26100
ttggccggac aggccgcgtc gtgcacgcag caccttgcgt cggtgttgga gatctgcacc   26160
acatttcggc cccaccggtt cttcacgatc ttggccttgc tagactgctc cttcagcgcg   26220
cgctgcccgt tttcgctcgt cacatccatt tcaatcacgt gctccttatt tatcataatg   26280
```

-continued

```
cttccgtgta gacacttaag ctcgccttcg atctcagcgc agcggtgcag ccacaacgcg   26340
cagcccgtgg gctcgtgatg cttgtaggtc acctctgcaa acgactgcag gtacgcctgc   26400
aggaatcgcc ccatcatcgt cacaaaggtc ttgttgctgg tgaaggtcag ctgcaacccg   26460
cggtgctcct cgttcagcca ggtcttgcat acggccgcca gagcttccac ttggtcaggc   26520
agtagtttga agttcgcctt tagatcgtta tccacgtggt acttgtccat cagcgcgcgc   26580
gcagcctcca tgcccttctc ccacgcagac acgatcggca cactcagcgg gttcatcacc   26640
gtaatttcac tttccgcttc gctgggctct tcctcttcct cttgcgtccg cataccacgc   26700
gccactgggt cgtcttcatt cagccgccgc actgtgcgct tacctccttt gccatgcttg   26760
attagcaccg gtgggttgct gaaacccacc atttgtagcg ccacatcttc tctttcttcc   26820
tcgctgtcca cgattacctc tggtgatggc gggcgctcgg gcttgggaga agggcgcttc   26880 ttttcttct tgggcgcaat ggccaaatcc gccgccgagg tcgatggccg cgggctgggt   26940
gtgcgcggca ccagcgcgtc ttgtgatgag tcttcctcgt cctcggactc gatacgccgc   27000
ctcatccgct tttttggggg cgcccgggga ggcggcggcg acggggacgg ggacgacacg   27060
tcctccatgg ttgggggacg tcgcgccgca ccgcgtccgc gctcgggggt ggtttcgcgc   27120
tgctcctctt cccgactggc catttccttc tcctataggc agaaaaagat catggagtca   27180
gtcgagaaga aggacagcct aaccgcccc tctgagttcg ccaccaccgc ctccaccgat   27240
gccgccaacg cgcctaccac cttccccgtc gaggcacccc cgcttgagga ggaggaagtg   27300
attatcgagc aggacccagg ttttgtaagc gaagacgacg aggaccgctc agtaccaaca   27360
gaggataaaa agcaagacca ggacaacgca gaggcaaacg aggaacaagt cgggcggggg   27420
gacgaaaggc atggcgacta cctagatgtg ggagacgacg tgctgttgaa gcatctgcag   27480
cgccagtgcg ccattatctg cgacgcgttg caagagcgca gcgatgtgcc cctcgccata   27540
gcggatgtca gccttgccta cgaacgccac ctattctcac cgcgcgtacc ccccaaacgc   27600
caagaaaacg gcacatgcga gcccaacccg cgcctcaact tctaccccgt atttgccgtg   27660
ccagaggtgc ttgccaccta tcacatcttt ttccaaaact gcaagatacc cctatcctgc   27720
cgtgccaacc gcagccgagc ggacaagcag ctggccttgc ggcagggcgc tgtcatacct   27780
gatatcgcct cgctcaacga agtgccaaaa atctttgagg gtcttggacg cgacgagaag   27840
cgcgcggcaa acgctctgca acaggaaaac agcgaaaatg aaagtcactc tggagtgttg   27900
gtggaactcg agggtgacaa cgcgcgccta gccgtactaa aacgcagcat cgaggtcacc   27960
cactttgcct acccggcact taacctaccc cccaaggtca tgagcacagt catgagtgag   28020
ctgatcgtgc gccgtgcgca gcccctggag agggatgcaa atttgcaaga acaaacagag   28080
gagggcctac ccgcagttgg cgacgagcag ctagcgcgct ggcttcaaac gcgcgagcct   28140
gccgacttgg aggagcgacg caaactaatg atggccgcag tgctcgttac cgtggagctt   28200
gagtgcatgc agcggttctt tgctgacccg gagatgcagc gcaagctaga ggaaacattg   28260
cactacacct ttcgacaggg ctacgtacgc caggcctgca gatctccaa cgtggagctc   28320 tgcaacctgg tctcctacct tggaattttg cacgaaaacc gccttgggca aaacgtgctt   28380
cattccacgc tcaagggcga ggcgcgccgc gactacgtcc gcgactgcgt ttacttattt   28440
ctatgctaca cctggcagac ggccatgggc gtttggcagc agtgcttgga ggagtgcaac   28500
ctcaaggagc tgcagaaact gctaaagcaa aacttgaagg acctatggac ggccttcaac   28560
gagcgctccg tggccgcgca cctggcggac atcatttttcc ccgaacgcct gcttaaaacc   28620
ctgcaacagg gtctgccaga cttcaccagt caaagcatgt tgcagaactt taggaacttt   28680
```

-continued

```
atcctagagc gctcaggaat cttgcccgcc acctgctgtg cacttcctag cgactttgtg   28740
cccattaagt accgcgaatg ccctccgccg ctttggggcc actgctacct tctgcagcta   28800
gccaactacc ttgcctacca ctctgacata atggaagacg tgagcggtga cggtctactg   28860
gagtgtcact gtcgctgcaa cctatgcacc ccgcaccgct ccctggtttg caattcgcag   28920
ctgcttaacg aaagtcaaat tatcggtacc tttgagctgc agggtccctc gcctgacgaa   28980
aagtccgcgg ctccggggtt gaaactcact ccggggctgt ggacgtcggc ttaccttcgc   29040
aaatttgtac ctgaggacta ccacgcccac gagattaggt tctacgaaga ccaatcccgc   29100
ccgcctaatg cggagcttac cgcctgcgtc attacccagg gccacattct tggccaattg   29160
caagccatca acaaagcccg ccaagagttt ctgctacgaa agggacgggg ggtttacttg   29220 gaccccagt ccggcgagga gctcaaccca atccccccgc cgccgcagcc ctatcagcag   29280
cagccgcggg cccttgcttc ccaggatggc acccaaaaag aagctgcagc tgccgccgcc   29340
acccacggac gaggaggaat actgggacag tcaggcagag gaggttttgg acgaggagga   29400
ggaggacatg atggaagact gggagagcct agacgaggaa gcttccgagg tcgaagaggt   29460
gtcagacgaa acaccgtcac cctcggtcgc attcccctcg ccggcgcccc agaaatcggc   29520
aaccggttcc agcatggcta caacctccgc tcctcaggcg ccgccggcac tgcccgttcg   29580
ccgacccaac cgtagatggg acaccactgg aaccagggcc ggtaagtcca agcagccgcc   29640
gccgttagcc caagagcaac aacagcgcca aggctaccgc tcatggcgcg ggcacaagaa   29700
cgccatagtt gcttgcttgc aagactgtgg gggcaacatc tccttcgccc gccgctttct   29760
tctctaccat cacggcgtgg ccttcccccg taacatcctg cattactacc gtcatctcta   29820
cagcccatac tgcaccggcg gcagcggcag caacagcagc ggccacacag aagcaaaggc   29880
gaccggatag caagactctg acaaagccca agaaatccac agcggcggca gcagcaggag   29940
gaggagcgct gcgtctggcg cccaacgaac ccgtatcgac ccgcgagctt agaaacagga   30000
tttttcccac tctgtatgct atatttcaac agagcagggg ccaagaacaa gagctgaaaa   30060
taaaaaacag gtctctgcga tccctcaccc gcagctgcct gtatcacaaa agcgaagatc   30120
agcttcggcg cacgctggaa gacgcggagg ctctcttcag taaatactgc gcgctgactc   30180
ttaaggacta gtttcgcgcc ctttctcaaa tttaagcgcg aaaactacgt catctccagc   30240
ggccacaccc ggcgccagca cctgttgtca gcgccattat gagcaaggaa attcccacgc   30300
cctacatgtg gagttaccag ccacaaatgg gacttgcggc tggagctgcc caagactact   30360
caacccgaat aaactacatg agcgcgggac cccacatgat atcccgggtc aacggaatac   30420
gcgcccaccg aaaccgaatt ctcctggaac aggcggctat taccaccaca cctcgtaata   30480
accttaatcc ccgtagttgg cccgctgccc tggtgtacca ggaaagtccc gctcccacca   30540
ctgtggtact tcccagagac gcccaggccg aagttcagat gactaactca ggggcgcagc   30600 ttgcgggcg ctttcgtcac agggtgcggt cgccgggca gggtataact cacctgacaa   30660
tcagagggcg aggtattcag ctcaacgacg agtcggtgag ctcctcgctt ggtctccgtc   30720
cggacgggac atttcagatc ggcggcgccg gccgctcttc attcacgcct cgtcaggcaa   30780
tcctaactct gcagacctcg tcctctgagc cgcgctctgg aggcattgga actctgcaat   30840
ttattgagga gtttgtgcca tcggtctact ttaaccccctt ctcgggacct cccggccact   30900
atccggatca atttattcct aactttgacg cggtaaagga ctcggcggac ggctacgact   30960
gaatgttaag tggagaggca gagcaactgc gcctgaaaca cctggtccac tgtcgccgcc   31020
```

-continued

```
acaagtgctt tgcccgcgac tccggtgagt tttgctactt tgaattgccc gaggatcata   31080
tcgagggccc ggcgcacggc gtccggctta ccgcccaggg agagcttgcc cgtagcctga   31140
ttcgggagtt tacccagcgc cccctgctag ttgagcggga caggggaccc tgtgttctca   31200
ctgtgatttg caactgtcct aaccctggat tacatcaaga tcctctagtt aatgtcaggt   31260
cgcctaagtc gattaactag agtacccggg gatcttattc cctttaacta ataaaaaaaa   31320
ataataaagc atcacttact taaaatcagt tagcaaattt ctgtccagtt tattcagcag   31380
cacctccttg ccctcctccc agctctggta ttgcagcttc ctcctggctg caaactttct   31440
ccacaatcta aatggaatgt cagtttcctc ctgttcctgt ccatccgcac ccactatctt   31500
catgttgttg cagatgaagc gcgcaagacc gtctgaagat accttcaacc ccgtgtatcc   31560
atatgacacg gaaaccggtc ctccaactgt gccttttctt actcctccct ttgtatcccc   31620
caatgggttt caagagagtc cccctggggt actctctttg cgcctatccg aacctctagt   31680
tacctccaat ggcatgcttg cgctcaaaat gggcaacggc ctctctctgg acgaggccgg   31740
caaccttacc tcccaaaatg taaccactgt gagcccacct ctcaaaaaaa ccaagtcaaa   31800
cataaacctg gaaatatctg cacccctcac agttacctca gaagccctaa ctgtggctgc   31860
cgccgcacct ctaatggtcg cgggcaacac actcaccatg caatcacagg ccccgctaac   31920
cgtgcacgac tccaaactta gcattgccac ccaaggaccc ctcacagtgt cagaaggaaa   31980
gctagccctg caaacatcag gccccctcac caccaccgat agcagtaccc ttactatcac   32040
tgcctcaccc cctctaacta ctgccactgg tagcttgggc attgacttga aagagcccat   32100
ttatacacaa aatggaaaac taggactaaa gtacggggct cctttgcatg taacagacga   32160
cctaaacact ttgaccgtag caactggtcc aggtgtgact attaataata cttccttgca   32220
aactaaagtt actggagcct tgggttttga ttcacaaggc aatatgcaac ttaatgtagc   32280
aggaggacta aggattgatt ctcaaaacag acgccttata cttgatgtta gttatccgtt   32340
tgatgctcaa aaccaactaa atctaagact aggacagggc cctctttta taaactcagc   32400 ccacaacttg gatattaact acaacaaagg cctttacttg tttacagctt caaacaattc   32460
caaaaagctt gaggttaacc taagcactgc caaggggttg atgtttgacg ctacagccat   32520
agccattaat gcaggagatg ggcttgaatt tggttcacct aatgcaccaa acacaaatcc   32580
cctcaaaaca aaaattggcc atggcctaga atttgattca aacaaggcta tggttcctaa   32640
actaggaact ggccttagtt ttgacagcac aggtgccatt acagtaggaa acaaaaataa   32700
tgataagcta actttgtgga ccggaataaa ccctccacct aactgtcaaa ttgtggaaaa   32760
cactaataca aatgatggca aacttacttt agtattagta aaaaatggag ggcttgttaa   32820
tggctacgtg tctctagttg gtgtatcaga cactgtgaac caaatgttca cacaaaagac   32880
agcaaacatc caattaagat tatattttga ctcttctgga aatctattaa ctgaggaatc   32940
agacttaaaa attccactta aaaataaatc ttctacagcg accagtgaaa ctgtagccag   33000
cagcaaagcc tttatgccaa gtactacagc ttatcccttc aacaccacta ctaggggatag   33060 tgaaaactac attcatggaa tatgttacta catgactagt tatgatagaa gtctatttcc   33120
cttgaacatt tctataatgc taaacagccg tatgatttct tccaatgttg cctatgccat   33180
acaatttgaa tggaatctaa atgcaagtga atctccagaa agcaacatag ctacgctgac   33240
cacatccccc ttttttctttt cttacattac agaagacgac aactaaagaa tcgtttgtgt   33300
tatgtttcaa cgtgttatt tttcaattgc agaaaatttc aagtcatttt tcattcagta   33360
gtatagcccc accaccacat agcttataca gatcaccgta ccttaatcaa actcacagaa   33420
```

-continued

```
ccctagtatt caacctgcca cctccctccc aacacacaga gtacacagtc ctttctcccc   33480
ggctggcctt aaaaagcatc atatcatggg taacagacat attcttaggt gttatattcc   33540
acacggtttc ctgtcgagcc aaacgctcat cagtgatatt aataaactcc ccgggcagct   33600
cacttaagtt catgtcgctg tccagctgct gagccacagg ctgctgtcca acttgcggtt   33660
gcttaacggg cggcgaagga gaagtccacg cgttgtgcat tgtcaaagtg ttacattcgg   33720
gcagcagcgg atgatcctcc agtatggtag cgcgggtttc tgtctcaaaa ggaggtagac   33780
gatccctact gtacggagtg cgccgagaca accgagatcg tgttggtcgt agtgtcatgc   33840
caaatggaac gccggacgta gtcatatttc ctgaagcaaa accaggtgcg ggcgtgacaa   33900
acagatctgc gtctccggtc tcgccgctta gatcgctctg tgtagtagtt gtagtatatc   33960
cactctctca aagcatccag gcgcccctg gcttcgggtt ctatgtaaac tccttcatgc   34020
gccgctgccc tgataacatc caccaccgca gaataagcca cacccagcca acctacacat   34080
tcgttctgcg agtcacacac gggaggagcg ggaagagctg gaagaaccat gttttttttt   34140
ttattccaaa agattatcca aaacctcaaa atgaagatct attaagtgaa cgcgctcccc   34200
tccggtggcg tggtcaaact ctacagccaa agaacagata atggcatttg taagatgttg   34260
cacaatggct tccaaaaggc aaacggccct cacgtccaag tggacgtaaa ggctaaaccc   34320
ttcagggtga atctcctcta taaacattcc agcaccttca accatgccca aataattctc   34380
atctcgccac cttctcaata tatctctaag caaatcccga atattaagtc cggccattgt   34440
aaaaatctgc tccagagcgc cctccacctt cagcctcaag cagcgaatca tgattgcaaa   34500
aattcaggtt cctcacagac ctgtataaga ttcaaaagcg gaacattaac aaaaataccg   34560
cgatcccgta ggtcccttcg cagggccagc tgaacataat cgtgcaggtc tgcacggacc   34620
agcgcggcca cttccccgcc aggaaccatg acaaaagaac ccacactgat tatgacacgc   34680
atactcggag ctatgctaac cagcgtagcc ccgatgtaag cttgttgcat gggcggcgat   34740
ataaaatgca aggtgctgct caaaaaatca ggcaaagcct cgcgcaaaaa agaaagcaca   34800
tcgtagtcat gctcatgcag ataaaggcag gtaagctccg gaaccaccac agaaaaagac   34860
accatttttc tctcaaacat gtctgcgggt ttctgcataa acacaaaata aaataacaaa   34920
aaaacattta aacattagaa gcctgtctta caacaggaaa aacaacccct ataagcataa   34980
gacggactac ggccatgccg gcgtgaccgt aaaaaaactg gtcaccgtga ttaaaaagca   35040
ccaccgacag ctcctcggtc atgtccggag tcataatgta agactcggta aacacatcag   35100
gttgattcac atcggtcagt gctaaaaagc gaccgaaata gcccggggga atacataccc   35160
gcaggcgtag agacaacatt acagccccca taggaggtat aacaaaatta ataggagaga   35220
aaaacacata aacacctgaa aaaccctcct gcctaggcaa aatagcaccc tcccgctcca   35280
gaacaacata cagcgcttcc acagcggcag ccataacagt cagccttacc agtaaaaaag   35340
aaaacctatt aaaaaaacac cactcgacac ggcaccagct caatcagtca cagtgtaaaa   35400
aagggccaag tgcagagcga gtatatatag gactaaaaaa tgacgtaacg gttaaagtcc   35460
acaaaaaaca cccagaaaac cgcacgcgaa cctacgccca gaaacgaaag ccaaaaaacc   35520
cacaacttcc tcaaatcgtc acttccgttt tcccacgtta cgtcacttcc cattttaaga   35580
aaactacaat tcccaacaca tacaagttac tccgccctaa aacctacgtc acccgccccg   35640
ttcccacgcc ccgcgccacg tcacaaactc cacccctca ttatcatatt ggcttcaatc   35700
caaaataagg tatattattg atgatg                                       35726
```

```
<210> SEQ ID NO 31
<211> LENGTH: 5
<212> TYPE: PRT
<213> ORGANISM: Artificial Sequence
<220> FEATURE:
<223> OTHER INFORMATION: linker

<400> SEQUENCE: 31

Gly Gly Gly Gly Ser
1               5

<210> SEQ ID NO 32
<211> LENGTH: 8
<212> TYPE: PRT
<213> ORGANISM: Artificial Sequence
<220> FEATURE:
<223> OTHER INFORMATION: cleavage site

<400> SEQUENCE: 32

Thr Asn Ser Pro Arg Arg Ala Arg
1               5

<210> SEQ ID NO 33
<211> LENGTH: 4
<212> TYPE: PRT
<213> ORGANISM: Artificial Sequence
<220> FEATURE:
<223> OTHER INFORMATION: linker

<400> SEQUENCE: 33

Thr Ile Leu Arg
1

<210> SEQ ID NO 34
<211> LENGTH: 17
<212> TYPE: PRT
<213> ORGANISM: Artificial Sequence
<220> FEATURE:
<223> OTHER INFORMATION: linker

<400> SEQUENCE: 34

Thr Gly Gly Gly Gly Ser Gly Gly Gly Gly Ser Gly Gly Gly Gly Ser
1               5                   10                  15

Arg
```